US012428375B2

(12) United States Patent
Huang et al.

(10) Patent No.: US 12,428,375 B2
(45) Date of Patent: *Sep. 30, 2025

(54) COMPOUNDS AND COMPOSITIONS FOR TREATING CONDITIONS ASSOCIATED WITH LPA RECEPTOR ACTIVITY

(71) Applicant: Lhotse Bio, Inc., South San Francisco, CA (US)

(72) Inventors: Wei Huang, Shanghai (CN); Hui Lei, Shanghai (CN); Zhongmiao Xu, Shanghai (CN); Haizhen Zhang, Shanghai (CN); Qiong Zhang, Shanghai (CN)

(73) Assignee: Lhotse Bio, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/534,520

(22) Filed: Dec. 8, 2023

(65) Prior Publication Data

US 2024/0376054 A1  Nov. 14, 2024

Related U.S. Application Data

(63) Continuation of application No. 18/322,492, filed on May 23, 2023, now Pat. No. 11,884,627, which is a continuation of application No. PCT/CN2023/078288, filed on Feb. 25, 2023.

(30) Foreign Application Priority Data

Feb. 25, 2022 (WO) ................ PCT/CN2022/077844
May 25, 2022 (WO) ................ PCT/CN2022/094839
Sep. 8, 2022 (WO) ................ PCT/CN2022/117690

(51) Int. Cl.
*C07D 211/66* (2006.01)
*C07C 61/39* (2006.01)
*C07C 229/18* (2006.01)
*C07C 229/28* (2006.01)
*C07D 309/14* (2006.01)
*C07D 317/54* (2006.01)
*C07D 317/58* (2006.01)
*C07D 407/12* (2006.01)

(52) U.S. Cl.
CPC ............ *C07D 211/66* (2013.01); *C07C 61/39* (2013.01); *C07C 229/18* (2013.01); *C07C 229/28* (2013.01); *C07D 309/14* (2013.01); *C07D 317/54* (2013.01); *C07D 317/58* (2013.01); *C07D 407/12* (2013.01); *C07C 2601/02* (2017.05); *C07C 2601/04* (2017.05); *C07C 2601/08* (2017.05); *C07C 2602/08* (2017.05)

(58) Field of Classification Search
CPC ............................ C07D 211/66; C07D 407/12
USPC .................................................. 514/210.17
See application file for complete search history.

(56) References Cited

U.S. PATENT DOCUMENTS

| | | | |
|---|---|---|---|
| 8,124,645 B2 | 2/2012 | Terakado et al. | |
| 10,221,138 B2 | 3/2019 | Kim et al. | |
| 11,884,627 B2 * | 1/2024 | Huang | ................ C07C 229/18 |
| 2005/0256160 A1 | 11/2005 | Habashita et al. | |
| 2007/0032488 A1 | 2/2007 | Botyanszki et al. | |
| 2007/0149595 A1 | 6/2007 | Tanaka et al. | |
| 2013/0122297 A1 | 5/2013 | Grunder et al. | |
| 2018/0065909 A1 | 3/2018 | Ferreira et al. | |
| 2022/0073476 A1 | 3/2022 | Lou et al. | |
| 2022/0079928 A1 | 3/2022 | Lou et al. | |
| 2023/0097871 A1 | 3/2023 | Kuroda et al. | |

FOREIGN PATENT DOCUMENTS

| | | |
|---|---|---|
| CN | 114456157 A | 5/2022 |
| CN | 114456159 A | 5/2022 |
| CN | 114621135 A | 6/2022 |
| EP | 1695955 B1 | 10/2011 |
| EP | 3912975 A1 | 11/2021 |
| GB | 2466121 A | 6/2010 |
| JP | 4766384 B2 | 9/2011 |
| WO | WO 1999/041231 A1 | 8/1999 |
| WO | WO 2003/026587 A2 | 4/2003 |
| WO | WO 2003099765 A1 | 12/2003 |
| WO | WO 2004031118 A1 | 4/2004 |
| WO | WO 2005058790 A1 | 6/2005 |
| WO | WO 2006/018325 A1 | 2/2006 |
| WO | WO 2006/018326 A1 | 2/2006 |
| WO | WO 2010/077882 A2 | 7/2010 |
| WO | WO 2011/041462 A2 | 4/2011 |
| WO | WO 2011/041694 A2 | 4/2011 |
| WO | WO 2011041461 A2 | 4/2011 |
| WO | WO 2011053948 A1 | 5/2011 |
| WO | WO 2012/078593 A2 | 6/2012 |
| WO | WO 2012/138648 A1 | 10/2012 |
| WO | WO 2013/070879 A1 | 5/2013 |

(Continued)

OTHER PUBLICATIONS

International Search Report and Written Opinion for PCT/CN2021/125409 dated Jan. 20, 2022, 10 pages.

Ling et al., "A Molecular Torsion Balance Study: A Nearby Anionic Group Exerts Little Influence on Hydrophobic Interactions between Nonpolar Surfaces," A European Journal (2019), 25(61), 14010-14014.

Li et al., "Meta-Selective C—H Arylation of Aromatic Alcohols with a Readily Attachable and Cleavable Molecular Scaffold," A European Journal (2017), 23(48), 11519-11523.

Colombel et al., "Synthetic Approaches to Amino Analogues of N-Acetylcolchinol," Journal of Organic Chemistry (2009), 74(11), 4329-4335.

(Continued)

*Primary Examiner* — Kahsay Habte
(74) *Attorney, Agent, or Firm* — Sheppard Mullin Richter & Hampton LLP

(57) ABSTRACT

The present disclosure provides LPA antagonists, as well as pharmaceutical compositions comprising the compounds disclosed herein. Also provided are methods for treating LPA-associated diseases, disorders, and conditions.

15 Claims, No Drawings

(56) References Cited

FOREIGN PATENT DOCUMENTS

| | | | |
|---|---|---|---|
| WO | WO 2013/189864 A1 | 12/2013 |
| WO | WO 2014/145873 A2 | 9/2014 |
| WO | WO 2017/037146 A1 | 3/2017 |
| WO | WO 2017/223016 A1 | 12/2017 |
| WO | WO 2019041340 A1 | 3/2019 |
| WO | WO 2019126084 A1 | 6/2019 |
| WO | WO 2019126085 A1 | 6/2019 |
| WO | WO 2019126086 A1 | 6/2019 |
| WO | WO 2019126087 A1 | 6/2019 |
| WO | WO 2019126089 A1 | 6/2019 |
| WO | WO 2019126093 A1 | 6/2019 |
| WO | WO 2019126094 A1 | 6/2019 |
| WO | WO 2019126098 A1 | 6/2019 |
| WO | WO 2019126099 A1 | 6/2019 |
| WO | WO 2019126103 A1 | 6/2019 |
| WO | WO 2019/246109 A1 | 12/2019 |
| WO | WO 2020060914 A1 | 3/2020 |
| WO | WO 2020060915 A1 | 3/2020 |
| WO | WO 2020060916 A1 | 3/2020 |
| WO | WO 2020147739 A1 | 7/2020 |
| WO | WO 2020147740 A1 | 7/2020 |
| WO | WO 2020257135 A1 | 12/2020 |
| WO | WO 2020257138 A1 | 12/2020 |
| WO | WO 2020257139 A1 | 12/2020 |
| WO | WO 2021020429 A1 | 2/2021 |
| WO | WO 2021/116257 A1 | 6/2021 |
| WO | WO 2021/116259 A1 | 6/2021 |
| WO | WO 2022034568 A1 | 2/2022 |
| WO | WO 2022/083703 A1 | 4/2022 |
| WO | WO 2022/199815 A1 | 9/2022 |
| WO | WO 2023001177 A1 | 1/2023 |
| WO | WO 2023/066359 A1 | 4/2023 |
| WO | WO 2024/112895 A1 | 5/2024 |

OTHER PUBLICATIONS

Bhayana et al., "A minimal protein folding model to measure hydrophobic and CH-π effects on interactions between nonpolar surfaces in water," Angewandte Chemie, International Edition (2007), 46(36), 6833-6836.

STN Registry Database, Ref. No. 1026324-23-1, Etered STN: Jun. 8, 2008, 1 page.
STN Registry Database, Ref. No. 1181723-08-9, Etered STN: Sep. 9, 2009, 1 page.
STN Registry Database, Ref. No. 890534-53-9, Etered STN: Jul. 5, 2006, 1 page.
STN Registry Database, Ref. Nos. 1182241-89-9, 1182071-50-6, 1182253-77-5, 1182268-13-8, 1182026-98-7, Etered STN: Sep. 10, 2009, 2 pages.
STN Registry Database, Ref. Nos. 1182268-18-3, 1182245-58-4, 1182244-95-6, 1182222-49-6, Etered STN: Sep. 10, 2009, 2 pages.
Chrencik et al., "Crystal Structure of Antagonist Bound Human Lysophosphatidic Acid Receptor 1", Cell 161, Jun. 18, 2015, pp. 1633-1643.
Terakado et al., "Discovery of a Slow Tight Binding LPA1 Antagonist (ONO-0300302) for the Treatment of Benign Prostatic Hyperplasia", ACS Medicinal Chemistry Letters 2017, 8(12), 1281-1286.
Cheng et al., "Discovery of an Oxycyclohexyl Acid Lysophosphatidic Acid Receptor 1 ($LPA_1$) Antagonist BMS-986278 for the Treatment of Pulmonary Fibrotic Diseases", Journal of Medicinal Chemistry (2021), 64(21), 15549-15581.
Qian et al., "Discovery of Highly Selective and Orally Active Lysophosphatidic Acid Receptor-1 Antagonists with Potent Activity on Human Lung Fibroblasts" Journal of Medicinal Chemistry (2012), 55(17), 7920-7939.
Terakado et al., "Discovery of ONO-7300243 from a novel class of Lysophosphatidic Acid Receptor 1 antagonists: From hit to lead", ACS Medicinal Chemistry Letters, 2016 7 (10), 913-918.
Sakamoto et al., "Effect of ASP6432, a Novel Type 1 Lysophosphatidic Acid Receptor Antagonist, on Urethral Function and Prostate Cell Proliferations", Journal of Pharmacology and Experimental Therapeutics, 2018, 366 (2), 390-396.
Meduri et al., "Lysophosphatidic acid (LPA) receptor modulators: Structural features and recent development", European Journal of Medicinal Chemistry, (2021), 222, 113574.
Llona-Minguez, S. et al., "Lysophosphatidic acid receptor (LPAR) modulators: the current pharmacological toolbox", Progress in Lipid Research (2015), 58, 51-75.
Liu et al., "The development of modulators for lysophosphatidic acid receptors: A comprehensive review", Bioorganic Chemistry (2021), 117, 105386.

* cited by examiner

COMPOUNDS AND COMPOSITIONS FOR TREATING CONDITIONS ASSOCIATED WITH LPA RECEPTOR ACTIVITY

CROSS REFERENCE TO RELATED APPLICATIONS

The application is a Continuation of U.S. patent application Ser. No. 18/322,492 filed May 23. 2023, which is a continuation of International Patent Application Number PCT/CN2023/78288. filed Feb. 25, 2023, which claims the benefit of International Patent Application Number PCT/CN2022/077844, filed on Feb. 25, 2022, International Patent Application Number PCT/CN2022/094839, filed on May 25, 2022, and International Patent Application Number PCT/CN2022/117690, filed Sep. 8, 2022, each of which is incorporated herein by reference in its entirety.

FIELD

The present disclosure provides LPA antagonists, as well as pharmaceutical compositions comprising the compounds disclosed herein. Also provided are methods for treating LPA-associated diseases, disorders, and conditions.

BACKGROUND

Various lipid mediators, including eicosanoid and platelet activating factor (PAF) are produced by the activity of phospholipase from cell membranes. Lysophospholipids are one class of these membrane-derived bioactive lipid mediators and include lysophosphatidic acid (LPA). LPA is not a single molecular entity but a collection of endogenous structural variants with fatty acids of varied lengths and degrees of saturation. LPAs affect cellular functions that include cellular proliferation, differentiation, survival, migration, adhesion, invasion, and morphogenesis. These functions influence many biological processes that include neurogenesis, angiogenesis, wound healing, immunity, and carcinogenesis. LPA has a role as a biological effector molecule and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated. Activation of the LPA receptors ($LPA_1$, $LPA_2$, $LPA_3$, $LPA_4$, $LPA_5$, $LPA_6$) with LPA mediates a range of downstream signaling cascades.

SUMMARY

Antagonizing LPA receptors (such as the $LPA_1$ receptor) may be useful for the treatment of a variety of disorders, including fibrosis such as pulmonary fibrosis, hepatic fibrosis, renal fibrosis, arterial fibrosis and systemic sclerosis, and thus the diseases that result from fibrosis (e.g., pulmonary fibrosis, for example, Idiopathic Pulmonary Fibrosis (IPF), hepatic fibrosis, including Non-alcoholic Steatohepatitis (NASH), renal fibrosis, such as diabetic nephropathy, systemic sclerosis-scleroderma, etc.), COVID-19, chronic obstructive pulmonary disease (COPD), neuroinflammation, or multiple sclerosis. The present application describes LPA antagonists, as well as pharmaceutical compositions comprising the compounds disclosed herein. Also provided are methods for treating LPA-associated diseases, disorders, and conditions.

The present disclosure, in one embodiment, provides compounds of Formula I:

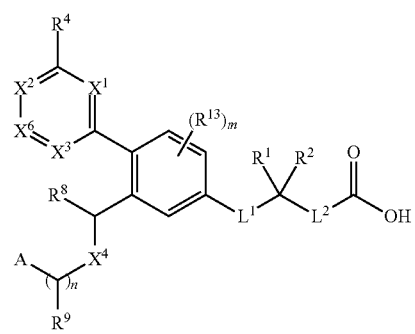

I or a pharmaceutically acceptable salt, stereoisomer, mixture of stereoisomers, tautomer, isotopically enriched analog, or solvate thereof, wherein:

A is $C_{1-6}$ alkyl, $C_{3-10}$ cycloalkyl, heterocyclyl, aryl, or heteroaryl; wherein each $C_{1-6}$ alkyl, $C_{3-10}$ cycloalkyl, heterocyclyl, aryl, or heteroaryl of A is independently optionally substituted with one to five $Z^1$;

$L^1$ is a bond, —O—, —S—, —S(O)—, —S(O)$_2$—, —$NR^{10}$—, $C_{1-3}$ alkylene, $C_{2-3}$ alkenylene, $C_{2-3}$ alkynylene, or $C_{1-3}$ heteroalkylene; wherein the $C_{1-3}$ alkylene, $C_{2-3}$ alkenylene, $C_{2-3}$ alkynylene, or $C_{1-3}$ heteroalkylene of $L^1$ is independently optionally substituted with one to five substituents independently selected from $C_{1-9}$ alkyl, halo, hydroxy, and cyano;

$L^2$ is a bond, $C_{1-3}$ alkylene, $C_{2-3}$ alkenylene, $C_{2-3}$ alkynylene, or $C_{1-3}$ heteroalkylene; wherein the $C_{1-3}$ alkylene, $C_{2-3}$ alkenylene, $C_{2-3}$ alkynylene, or $C_{1-3}$ heteroalkylene of $L^2$ is independently optionally substituted with one to five substituents independently selected from $C_{1-9}$ alkyl, halo, hydroxy, and cyano;

$X^1$ is N or $CR^3$;

$X^2$ is N or $CR^5$;

$X^3$ is N or $CR^7$;

$X^4$ is O or $CHR^{11}$; provided that when A is $C_{1-6}$ alkyl, then $X^4$ is O;

$X^6$ is N or $CR^6$;

n is 0, 1, or 2;

m is 0, 1, 2, or 3;

$R^1$ and $R^2$ are each independently hydrogen, $C_{1-9}$ alkyl, $C_{2-9}$ alkenyl, $C_{2-9}$ alkynyl, $C_{3-10}$ cycloalkyl, or heterocyclyl; wherein each $C_{1-9}$ alkyl, $C_{2-9}$ alkenyl, $C_{2-9}$ alkynyl, $C_{3-10}$ cycloalkyl, or heterocyclyl of $R^1$ and $R^2$ are independently optionally substituted with one to five $Z^1$;

or $R^1$ and $R^2$ are taken together with the atom to which they are attached to form a $C_{3-10}$ cycloalkyl or heterocyclyl; wherein the $C_{3-10}$ cycloalkyl or heterocyclyl is optionally substituted by one to five $Z^1$;

$R^3$ is hydrogen, halo, cyano, nitro, —OH, —SH, —$NH_2$, —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl; wherein the —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl of $R^3$ is independently optionally substituted with one to five substituents independently selected from halo, hydroxy, and cyano;

$R^4$ is halo, cyano, nitro, —OR$^{14}$, —N(R$^{14}$)$_2$, —SR$^{14}$, C$_{1-5}$ alkyl, C$_{2-5}$ alkenyl, C$_{2-5}$ alkynyl, C$_{3-5}$ cycloalkyl, or 3-5 membered heterocyclyl; wherein the C$_{1-5}$ alkyl, C$_{2-5}$ alkenyl, C$_{2-5}$ alkynyl, C$_{3-5}$ cycloalkyl, or 3-5 membered heterocyclyl of R is independently optionally substituted with one to five substituents independently selected from halo, hydroxy, C$_{1-5}$ alkoxy, and cyano;

or R$^3$ and R$^4$ are taken together with the atoms to which they are attached to form a cycloalkyl, aryl, heterocyclyl, or heteroaryl; wherein the cycloalkyl, aryl, heterocyclyl, or heteroaryl is optionally substituted with one to five substituents independently selected from halo, hydroxy, and cyano;

$R^5$ is hydrogen, halo, cyano, nitro, —OR$^{15}$, —N(R$^{15}$)$_2$, —SR$^{15}$, —C(O)R$^{15}$, —C(O)OR$^{15}$, C$_{1-5}$ alkyl, C$_{2-5}$ alkenyl, C$_{2-5}$ alkynyl, C$_{3-5}$ cycloalkyl, 3-5 membered heterocyclyl or 5 membered heteroaryl; wherein the C$_{1-5}$ alkyl, C$_{2-5}$ alkenyl, C$_{2-5}$ alkynyl, C$_{3-5}$ cycloalkyl, 3-5 membered heterocyclyl or 5 membered heteroaryl of R$^5$ is independently optionally substituted with one to five Z$^1$;

$R^6$ is hydrogen, halo, cyano, nitro, —OR$^{16}$, —N(R$^{16}$)$_2$, —SR$^{16}$, C$_{1-5}$ alkyl, C$_{2-5}$ alkenyl, C$_{2-5}$ alkynyl, C$_{3-5}$ cycloalkyl, or 3-5 membered heterocyclyl; wherein the C$_{1-5}$ alkyl, C$_{2-5}$ alkenyl, C$_{2-5}$ alkynyl, C$_{3-5}$ cycloalkyl, or 3-5 membered heterocyclyl of R$^6$ is independently optionally substituted with one to five substituents independently selected from halo, hydroxy, and cyano;

$R^7$ is hydrogen, halo, cyano, nitro, —OH, —SH, —NH$_2$, —NH—C$_{1-5}$ alkyl, —N(C$_{1-5}$ alkyl)$_2$, —S—C$_{1-5}$ alkyl, C$_{1-5}$ alkoxy, C$_{1-5}$ alkyl, C$_{2-5}$ alkenyl, C$_{2-5}$ alkynyl, C$_{3-5}$ cycloalkyl, or 3-5 membered heterocyclyl; wherein the —NH—C$_{1-5}$ alkyl, —N(C$_{1-5}$ alkyl)$_2$, —S—C$_{1-5}$ alkyl, C$_{1-5}$ alkoxy, C$_{1-5}$ alkyl, C$_{2-5}$ alkenyl, C$_{2-5}$ alkynyl, C$_{3-5}$ cycloalkyl, or 3-5 membered heterocyclyl of R is independently optionally substituted with one to five substituents independently selected from halo, hydroxy, and cyano;

or R$^6$ and R$^7$ are taken together with the atoms to which they are attached to form a cycloalkyl, aryl, heterocyclyl, or heteroaryl; wherein the cycloalkyl, aryl, heterocyclyl, or heteroaryl is optionally substituted with one to five substituents independently selected from halo, hydroxy, and cyano;

$R^8$ is hydrogen, C$_{1-9}$ alkyl, oxo, halo, hydroxy, or cyano;
$R^9$ is hydrogen, C$_{1-9}$ alkyl, oxo, halo, hydroxy, or cyano;
$R^{10}$ is hydrogen, C$_{1-5}$ alkyl, C$_{2-5}$ alkenyl, C$_{2-5}$ alkynyl, C$_{3-5}$ cycloalkyl, or 3-5 membered heterocyclyl; wherein the C$_{1-5}$ alkyl, C$_{2-5}$ alkenyl, C$_{2-5}$ alkynyl, C$_{3-5}$ cycloalkyl, or 3-5 membered heterocyclyl of R$^{10}$ is independently optionally substituted with one to five substituents independently selected from halo, hydroxy, and cyano;

$R^{11}$ is hydrogen, C$_{1-9}$ alkyl, oxo, halo, hydroxy, or cyano;
each $R^{13}$ is independently hydrogen, halo, cyano, nitro, —OH, —SH, —NH$_2$, —NH—C$_{1-9}$ alkyl, —N(C$_{1-9}$ alkyl)$_2$, —S—C$_{1-9}$ alkyl, C$_{1-9}$ alkoxy, C$_{1-9}$ alkyl, C$_{2-9}$ alkenyl, C$_{2-9}$ alkynyl, C$_{3-6}$ cycloalkyl, or 3 to 6-membered heterocyclyl; wherein each —NH—C$_{1-9}$ alkyl, —N(C$_{1-9}$ alkyl)$_2$, —S—C$_{1-9}$ alkyl, C$_{1-9}$ alkoxy, C$_{1-9}$ alkyl, C$_{2-9}$ alkenyl, C$_{2-9}$ alkynyl, C$_{3-6}$ cycloalkyl, or 3 to 6-membered heterocyclyl of R$^{13}$ is independently optionally substituted with one to five substituents independently selected from halo, hydroxy, and cyano;

$R^{14}$ is hydrogen, C$_{1-5}$ alkyl, C$_{2-5}$ alkenyl, C$_{2-5}$ alkynyl, C$_{3-5}$ cycloalkyl, or 3-5 membered heterocyclyl; wherein the C$_{1-5}$ alkyl, C$_{2-5}$ alkenyl, C$_{2-5}$ alkynyl, C$_{3-5}$ cycloalkyl, or 3-5 membered heterocyclyl of R$^{14}$ is independently optionally substituted with one to five substituents independently selected from halo, hydroxy, and cyano;

$R^{15}$ is hydrogen, C$_{1-5}$ alkyl, C$_{2-5}$ alkenyl, C$_{2-5}$ alkynyl, C$_{3-5}$ cycloalkyl, or 3-5 membered heterocyclyl; wherein the C$_{1-5}$ alkyl, C$_{2-5}$ alkenyl, C$_{2-5}$ alkynyl, C$_{3-5}$ cycloalkyl, or 3-5 membered heterocyclyl of R$^{15}$ is independently optionally substituted with one to five substituents independently selected from halo, hydroxy, and cyano;

$R^{16}$ is hydrogen, C$_{1-5}$ alkyl, C$_{2-5}$ alkenyl, C$_{2-5}$ alkynyl, C$_{3-5}$ cycloalkyl, or 3-5 membered heterocyclyl; wherein the C$_{1-5}$ alkyl, C$_{2-5}$ alkenyl, C$_{2-5}$ alkynyl, C$_{3-5}$ cycloalkyl, or 3-5 membered heterocyclyl of R$^{16}$ is independently optionally substituted with one to five substituents independently selected from halo, hydroxy, and cyano;

each $Z^1$ is independently halo, cyano, nitro, oxo, C$_{1-9}$ alkyl, C$_{2-9}$ alkenyl, C$_{2-9}$ alkynyl, C$_{3-10}$ cycloalkyl, heterocyclyl, aryl, heteroaryl, -L-H, -L-C$_{1-9}$ alkyl, -L-C$_{2-9}$ alkenyl, -L-C$_{2-9}$ alkynyl, -L-C$_{3-10}$ cycloalkyl, -L-heterocyclyl, -L-aryl, or -L-heteroaryl; wherein each C$_{1-9}$ alkyl, C$_{2-9}$ alkenyl, C$_{2-9}$ alkynyl, C$_{3-10}$ cycloalkyl, heterocyclyl, aryl, or heteroaryl of Z$^1$ is independently optionally substituted with one to five Z$^{1a}$;

each L is independently —O—, —S—, —NR$^{20}$—, —C(O)—, —C(O)O—, —OC(O)—, —OC(O)O—, —C(O)NR$^{20}$—, —NR$^{20}$C(O)—, —OC(O)NR$^{20}$—, —NR$^{20}$C(O)O—, —NR$^{20}$C(O)NR$^{21}$—, —S(O)—, —S(O)$_2$—, —S(O)NR$^{20}$—, —S(O)$_2$NR$^{20}$—, —NR$^{20}$S(O)—, —NR$^{20}$S(O)$_2$—, —NR$^{20}$S(O)NR$^{21}$—, or —NR$^{20}$S(O)$_2$NR$^{21}$—;

each $R^{20}$ and $R^{21}$ is independently hydrogen, C$_{1-9}$ alkyl, C$_{2-9}$ alkenyl, C$_{2-9}$ alkynyl, C$_{3-10}$ cycloalkyl, heterocyclyl, aryl, or heteroaryl; wherein each C$_{1-9}$ alkyl, C$_{2-9}$ alkenyl, C$_{2-9}$ alkynyl, C$_{3-10}$ cycloalkyl, heterocyclyl, aryl, or heteroaryl of R$^{20}$ and R$^{21}$ is independently optionally substituted with one to five Z$^{1a}$; or an R$^{20}$ and R$^{21}$ are taken together with the atoms to which they are attached to form heterocyclyl independently optionally substituted by one to five Z$^{1a}$; and each $Z^{1a}$ is independently halo, hydroxy, cyano, nitro, oxo, —SH, —NH$_2$, —NH—C$_{1-9}$ alkyl, —N(C$_{1-9}$ alkyl)$_2$, —S—C$_{1-9}$ alkyl, C$_{1-9}$ alkoxy, C$_{1-9}$ alkyl, C$_{2-9}$ alkenyl, C$_{2-9}$ alkynyl, C$_{3-10}$ cycloalkyl, heterocyclyl, aryl, or heteroaryl; wherein each —NH—C$_{1-9}$ alkyl, —N(C$_{1-9}$ alkyl)$_2$, —S—C$_{1-9}$ alkyl, C$_{1-9}$ alkoxy, C$_{1-9}$ alkyl, C$_{2-9}$ alkenyl, C$_{2-9}$ alkynyl, C$_{3-10}$ cycloalkyl, heterocyclyl, aryl, or heteroaryl of Z$^{1a}$ is independently optionally substituted with one to five substituents independently selected from C$_{1-9}$ alkyl, oxo, halo, hydroxy, and cyano.

Also provided herein are pharmaceutical compositions comprising a compound of Formula I, or a pharmaceutically acceptable salt, stereoisomer, mixture of stereoisomers, tautomer, isotopically enriched analog, or solvate thereof, and a pharmaceutically acceptable excipient.

Also provided herein are methods for treating or preventing an LPA-associated disease in a subject in need thereof, the method comprising administering to subject a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition thereof. In some embodiments, the LPA-associated disease is an LPA$_1$-associated disease, such as, but not limited to, fibrosis, transplant rejection, cancer, osteoporosis, or an inflammatory disorder.

In some embodiments, the LPA-associated disease is fibrosis, transplant rejection, cancer, osteoporosis, or inflammatory disorders. In certain of these embodiments, the fibrosis is pulmonary, liver, renal, cardiac, dermal, ocular, or pancreatic fibrosis. In certain embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

In some embodiments, the LPA-associated disease is idiopathic pulmonary fibrosis (IPF), non-alcoholic steatohepatitis (NASH), non-alcoholic fatty liver disease (NAFLD), chronic kidney disease, diabetic kidney disease, systemic sclerosis, COVID-19, chronic obstructive pulmonary disease (COPD), neuroinflammation, or multiple sclerosis.

Also provided herein are methods for treating or preventing fibrosis in a subject in need thereof, the method comprising administering to subject a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutically acceptable salt, stereoisomer, mixture of stereoisomers, tautomer, isotopically enriched analog, or solvate thereof, or a pharmaceutical composition thereof.

In some embodiments, the fibrosis is idiopathic pulmonary fibrosis (IPF), nonalcoholic steatohepatitis (NASH), chronic kidney disease, diabetic kidney disease, and systemic sclerosis. For example, the fibrosis can be IPF.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH (CH$_3$)$_2$), and tert-butyl (i.e., —C(CH$_3$)$_3$), and "propyl" includes n-propyl (i.e., —(CH$_2$)$_2$CH$_3$), and isopropyl (i.e., —CH(CH$_3$)$_2$).

"Alkenyl" refers to an alkyl group containing at least one (e.g., 1-3, or 1) carbon-carbon double bond and having from 2 to 20 carbon atoms (i.e., $C_{2-20}$ alkenyl), 2 to 12 carbon atoms (i.e., $C_{2-12}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include, e.g., ethenyl, propenyl, butadienyl (including 1,2-butadienyl, and 1,3-butadienyl).

"Alkynyl" refers to an alkyl group containing at least one (e.g., 1-3, or 1) carbon-carbon triple bond and having from 2 to 20 carbon atoms (i.e., $C_{2-20}$ alkynyl), 2 to 12 carbon atoms (i.e., $C_{2-12}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy, and 1,2-dimethylbutoxy.

"Haloalkyl" refers to an unbranched or branched alkyl group as defined above, wherein one or more (e.g., 1 to 6 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Haloalkoxy" refers to an alkoxy group as defined above, wherein one or more (e.g., 1 to 6 or 1 to 3) hydrogen atoms are replaced by a halogen.

"Hydroxyalkyl" refers to an alkyl group as defined above, wherein one or more (e.g., 1 to 6 or 1 to 3) hydrogen atoms are replaced by a hydroxy group.

"Alkylthio" refers to the group "alkyl-S—".

"Acyl" refers to a group —C(O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein, or R$^y$ and R$^z$ are taken together to form a cycloalkyl or heterocyclyl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Amidino" refers to —C(NR$^y$)(NR$^z{}_2$), wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl, and anthryl. Aryl, however, does not encompass or overlap in any way with heteroaryl defined below. If one or more aryl groups are fused with a heteroaryl, the resulting ring system is heteroaryl regardless of point of attachment. If one or more aryl groups are fused with a heterocyclyl, the resulting ring system is heterocyclyl regardless of point of attachment. If one or more aryl groups are fused with a cycloalkyl, the resulting ring system is cycloalkyl regardless of point of attachment.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Carboxyl ester" or "ester" refer to both —OC(O)R$^x$ and —C(O)OR$^x$, wherein R$^x$ is alkyl, alkenyl, alkynyl, cycloalkyl, heterocyclyl, aryl, heteroalkyl, or heteroaryl; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_{3-20}$ cycloalkyl), 3 to 14 ring carbon atoms (i.e., $C_{3-12}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl, and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl, and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Imino" refers to a group —C(NR$^y$)R$^z$, wherein R$^y$ and R$^z$ are each independently hydrogen, alkyl, alkenyl, alkynyl, cycloalkyl, heterocyclyl, aryl, heteroalkyl, or heteroaryl; each of which may be optionally substituted, as defined herein.

"Halogen" or "halo" refers to atoms occupying group VIIA of the periodic table, such as fluoro, chloro, bromo, or iodo.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroalkylene" refers to a divalent heteroalkyl group. "Heteroalkylene" groups must have at least one carbon and at least one heteroatomic group within the chain. The term "heteroalkylene" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R is hydrogen, alkyl, alkenyl, alkynyl, cycloalkyl, heterocyclyl, aryl, heteroalkyl or heteroaryl; each of which may be optionally substituted, as defined herein. Examples of heteroalkylene groups include, e.g., —CH$_2$OCH$_2$—, —CH(CH$_3$)OCH$_2$—, —CH$_2$CH$_2$OCH$_2$—, —OCH$_2$—, —CH(CH$_3$)O—, —CH$_2$CH$_2$O—, —CH$_2$CH$_2$OCH$_2$CH$_2$OCH$_2$—, —CH$_2$CH$_2$OCH$_2$CH$_2$O—, —CH$_2$SCH$_2$—, —CH(CH$_3$)SCH$_2$—, —CH$_2$CH$_2$SCH$_2$—, —CH$_2$CH$_2$SCH$_2$CH$_2$SCH$_2$—, —SCH$_2$—, —CH(CH$_3$)S—, —CH$_2$CH$_2$S—, —CH$_2$CH$_2$SCH$_2$CH$_2$S—, —CH$_2$S(O)$_2$CH$_2$—, —CH(CH$_3$)S(O)$_2$CH$_2$—, —CH$_2$CH$_2$S(O)$_2$CH$_2$—, —CH$_2$CH$_2$S(O)$_2$CH$_2$CH$_2$OCH$_2$—, —CH$_2$NR$^y$CH$_2$—, —CH(CH$_3$)NR$^y$CH$_2$—, —CH$_2$CH$_2$NR$^y$CH$_2$—, —CH$_2$CH$_2$NR$^y$CH$_2$CH$_2$NR$^y$CH$_2$—, etc., where R$^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkylene includes 1 to 10 carbon atoms, 1 to 8 carbon atoms, or 1 to 4 carbon atoms; and 1 to 3 heteroatoms, 1 to 2 heteroatoms, or 1 heteroatom. As used herein, the term "heteroalkylene" does not include groups such as amides or other functional groups having an oxo present on one or more carbon atoms.

"Heteroaryl" refers to an aromatic group having a single ring or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothienyl (dibenzothiophenyl), furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiophenyl (thienyl), thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thienyl (benzo[b]thiophenyl), indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or partially unsaturated cyclic alkyl group, with one or more ring heteroatoms independently selected from nitrogen, oxygen, and sulfur. The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro, and may comprise one or more (e.g., 1 to 3) oxo (=O) or N-oxide (—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to a cycloalkyl, an aryl, or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur, or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, tetrahydrothiophenyl (benzo[b]thienyl), thiomorpholinyl, thiamorpholinyl, 1-oxo-thiomorpholinyl, and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as oxabicyclo[2.2.2]octanyl, 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Sulfonyl" refers to the group —S(O)$_2$R$^y$, where R$^y$ is hydrogen, alkyl, alkenyl, alkynyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl, and toluenesulfonyl.

"Alkylsulfonyl" refers to the group —S(O)$_2$R, where R is alkyl.

"Alkylsulfinyl" refers to the group —S(O)R, where R is alkyl.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

As used herein, the term "compound," is meant to include all stereoisomers, geometric isomers, tautomers, and isotopes of the structures depicted. Compounds herein identified by name or structure as one particular tautomeric form are intended to include other tautomeric forms unless otherwise specified.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^{3}H$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life, reduced dosage requirements, and/or an improvement in therapeutic index. An $^{18}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, aluminum, ammonium, calcium, and magnesium salts. Salts derived from organic bases include, but are not limited to, salts of $NH_3$, or primary, secondary, tertiary amines, such as salts derived from a N-containing heterocycle, a N-containing heteroaryl, or derived from an amine of formula $N(R^N)_3$ (e.g., $HN^+(R^N)_3$ or $(alkyl)N^+(R^N)_3$) where each $R^N$ is independently hydrogen, alkyl, alkenyl, alkynyl, haloalkyl, cycloalkyl, heterocyclyl, aryl, or heteroaryl, wherein each is optionally substituted, such as by one or more (e.g., 1-5 or 1-3) substituents (e.g., halo, cyano, hydroxy, amino, alkyl, alkenyl, alkynyl, haloalkyl, alkoxy, or haloalkoxy). Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

The term "LPA-associated disease" as used herein is meant to include, without limitation, those diseases, disorders, or conditions in which activation of at least one LPA receptor by LPA contributes to the symptomology or progression of the disease, disorder or condition. These diseases, disorders, or conditions may arise from one or more of a genetic, iatrogenic, immunological, infectious, metabolic, oncological, toxic, surgical, and/or traumatic etiology. Accordingly, inhibiting of one or more lysophosphatidic acid (LPA) receptors (e.g., $LPA_1$, $LPA_2$, $LPA_3$, $LPA_4$, $LPA_5$, or $LPA_6$ receptor) signaling can alter the pathology and/or symptoms and/or progression of the disease, disorder, or condition. In some embodiments, the LPA-associated disease is an LPA1-associated disease, wherein modulating LPA1 receptor signaling can alter the pathology and/or symptoms and/or progression of the disease, disorder, or condition.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

The term "pharmaceutically acceptable" as used herein indicates that the compound, or salt or composition thereof is compatible chemically and/or toxicologically with the other ingredients comprising a formulation and/or the subject being treated therewith.

The term "administration" or "administering" refers to a method of giving a dosage of a compound or pharmaceutical composition to a vertebrate or invertebrate, including a mammal, a bird, a fish, or an amphibian. The method of administration can vary depending on various factors, e.g., the components of the pharmaceutical composition, the site of the disease, and the severity of the disease.

The terms "effective amount" or "effective dosage" or "pharmaceutically effective amount" or "therapeutically effective amount," as used herein, refer to a sufficient amount of a chemical entity (e.g., a compound of Formula I, or a pharmaceutically acceptable salt, stereoisomer, mixture of stereoisomers, tautomer, isotopically enriched analog, or solvate thereof) being administered which will relieve to some extent one or more of the symptoms of the disease or condition being treated, and can include curing the disease. "Curing" means that the symptoms of active disease are eliminated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study. In some embodiments, a "therapeutically effective amount" of a compound as provided herein refers to an amount of the compound that is effective as a monotherapy or combination therapy.

The term "excipient" or "pharmaceutically acceptable excipient" means a pharmaceutically-acceptable material, composition, or vehicle, such as a liquid or solid filler, diluent, carrier, solvent, or encapsulating material. In some embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009.

The term "pharmaceutical composition" refers to a mixture of a compound of Formula I, or a pharmaceutically acceptable salt, stereoisomer, mixture of stereoisomers, tautomer, isotopically enriched analog, or solvate thereof as provided herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to, rectal, oral, intravenous, aerosol, parenteral, ophthalmic, pulmonary, and topical administration.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "preventing," as used herein, is the prevention of the onset, recurrence or spread, in whole or in part, of the disease or condition as described herein, or a symptom thereof.

The terms "subject," "patient," or "individual," as used herein, are used interchangeably and refers to any animal, including mammals such as mice, rats, other rodents, rabbits, dogs, cats, swine, cattle, sheep, horses, primates, and humans. In some embodiments, the term refers to a subject, particularly a mammalian subject, for whom diagnosis, prognosis, or therapy is desired or needed. In some embodiments, the subject is a human. In some embodiments, the subject has experienced and/or exhibited at least one symptom of the disease, disorder, or condition to be treated and/or prevented.

The terms "treatment regimen" and "dosing regimen" are used interchangeably to refer to the dose and timing of administration of each therapeutic agent in a combination.

The term "pharmaceutical combination," as used herein, refers to a pharmaceutical treatment resulting from the mixing or combining of more than one active ingredient and includes both fixed and non-fixed combinations of the active ingredients.

The term "combination therapy" as used herein refers to a dosing regimen of two different therapeutically active agents (i.e., the components or combination partners of the combination), wherein the therapeutically active agents are administered together or separately in a manner prescribed by a medical care taker or according to a regulatory agency as defined herein.

The term "modulate," "modulating," or "modulation," as used herein, refers to a regulation or an adjustment (e.g., increase or decrease) and can include, for example agonism, partial agonism or antagonism.

Compounds

In one aspect, provided herein is a compound of Formula I:

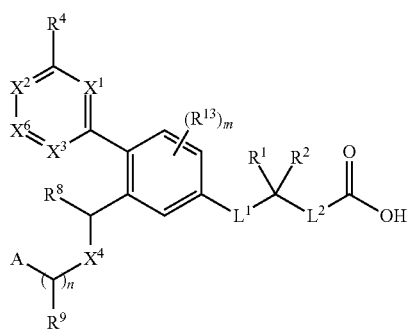

or a pharmaceutically acceptable salt, stereoisomer, mixture of stereoisomers, tautomer, isotopically enriched analog, or solvate thereof, wherein:

A is $C_{1-6}$ alkyl, $C_{3-10}$ cycloalkyl, heterocyclyl, aryl, or heteroaryl; wherein each $C_{1-6}$ alkyl, $C_{3-10}$ cycloalkyl, heterocyclyl, aryl, or heteroaryl of A is independently optionally substituted with one to five $Z^1$;

$L^1$ is a bond, —O—, —S—, —S(O)—, —S(O)$_2$—, —NR$^{10}$—, $C_{1-3}$ alkylene, $C_{2-3}$ alkenylene, $C_{2-3}$ alkynylene, or $C_{1-3}$ heteroalkylene; wherein the $C_{1-3}$ alkylene, $C_{2-3}$ alkenylene, $C_{2-3}$ alkynylene, or $C_{1-3}$ heteroalkylene of $L^1$ is independently optionally substituted with one to five substituents independently selected from $C_{1-9}$ alkyl, halo, hydroxy, and cyano;

$L^2$ is a bond, $C_{1-3}$ alkylene, $C_{2-3}$ alkenylene, $C_{2-3}$ alkynylene, or $C_{1-3}$ heteroalkylene; wherein the $C_{1-3}$ alkylene, $C_{2-3}$ alkenylene, $C_{2-3}$ alkynylene, or $C_{1-3}$ heteroalkylene of $L^2$ is independently optionally substituted with one to five substituents independently selected from $C_{1-9}$ alkyl, halo, hydroxy, and cyano;

$X^1$ is N or $CR^3$;

$X^2$ is N or $CR^5$;

$X^3$ is N or $CR^7$;

$X^4$ is O or $CHR^{11}$; provided that when A is $C_{1-6}$ alkyl, then $X^4$ is O;

$X^6$ is N or $CR^6$;

n is 0, 1, or 2;

m is 0, 1, 2, or 3;

$R^1$ and $R^2$ are each independently hydrogen, $C_{1-9}$ alkyl, $C_{2-9}$ alkenyl, $C_{2-9}$ alkynyl, $C_{3-10}$ cycloalkyl, or heterocyclyl; wherein each $C_{1-9}$ alkyl, $C_{2-9}$ alkenyl, $C_{2-9}$ alkynyl, $C_{3-10}$ cycloalkyl, or heterocyclyl of $R^1$ and $R^2$ are independently optionally substituted with one to five $Z^1$;

or $R^1$ and $R^2$ are taken together with the atom to which they are attached to form a $C_{3-10}$ cycloalkyl or heterocyclyl; wherein the $C_{3-10}$ cycloalkyl or heterocyclyl is optionally substituted by one to five $Z^1$;

$R^3$ is hydrogen, halo, cyano, nitro, —OH, —SH, —NH$_2$, —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl; wherein the —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl of $R^3$ is independently optionally substituted with one to five substituents independently selected from halo, hydroxy, and cyano;

$R^4$ is halo, cyano, nitro, —OR$^{14}$, —N(R$^{14}$)$_2$, —SR$^{14}$, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^4$ is independently optionally substituted with one to five substituents independently selected from halo, hydroxy, $C_{1-5}$ alkoxy, and cyano;

or $R^3$ and $R^4$ are taken together with the atoms to which they are attached to form a cycloalkyl, aryl, heterocyclyl, or heteroaryl; wherein the cycloalkyl, aryl, heterocyclyl, or heteroaryl is optionally substituted with one to five substituents independently selected from halo, hydroxy, and cyano;

$R^5$ is hydrogen, halo, cyano, nitro, —OR$^{15}$, —N(R$^{15}$)$_2$, —SR$^{15}$, —C(O)R$^{15}$, —C(O)OR$^{15}$, $C_{1-5}$ alkyl, $C_{2-5}$ alkenyl, $C_{2-5}$ alkynyl, $C_{3-5}$ cycloalkyl, 3-5 membered heterocyclyl or 5 membered heteroaryl; wherein the $C_{1-5}$ alkyl, $C_{2-5}$ alkenyl, $C_{2-5}$ alkynyl, $C_{3-5}$ cycloalkyl, 3-5 membered heterocyclyl or 5 membered heteroaryl of $R^5$ is independently optionally substituted with one to five $Z^1$;

$R^6$ is hydrogen, halo, cyano, nitro, —OR$^{16}$, —N(R$^{16}$)$_2$, —SR$^{16}$, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^6$ is independently optionally substituted with one to five substituents independently selected from halo, hydroxy, and cyano;

$R^7$ is hydrogen, halo, cyano, nitro, —OH, —SH, —NH$_2$, —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl; wherein the —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl of $R^7$ is independently optionally substituted with one to five substituents independently selected from halo, hydroxy, and cyano;

or $R^6$ and $R^7$ are taken together with the atoms to which they are attached to form a cycloalkyl, aryl, heterocyclyl, or heteroaryl; wherein the cycloalkyl, aryl, heterocyclyl, or heteroaryl is optionally substituted with one to five substituents independently selected from halo, hydroxy, and cyano;

$R^8$ is hydrogen, $C_{1-9}$ alkyl, oxo, halo, hydroxy, or cyano;

$R^9$ is hydrogen, $C_{1-9}$ alkyl, oxo, halo, hydroxy, or cyano;

$R^{10}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{10}$ is independently optionally substituted with one to five substituents independently selected from halo, hydroxy, and cyano;

$R^{11}$ is hydrogen, $C_{1-9}$ alkyl, oxo, halo, hydroxy, or cyano;

each $R^{13}$ is independently hydrogen, halo, cyano, nitro, —OH, —SH, —NH$_2$, —NH—$C_{1-9}$ alkyl, —N($C_{1-9}$ alkyl)$_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-6}$ cycloalkyl, or 3 to 6-membered heterocyclyl; wherein each —NH—$C_{1-9}$ alkyl, —N($C_{1-9}$ alkyl)$_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-6}$ cycloalkyl, or 3 to 6-membered heterocyclyl of $R^{13}$ is independently optionally substituted with one to five substituents independently selected from halo, hydroxy, and cyano;

$R^{14}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{14}$ is independently optionally substituted with one to five substituents independently selected from halo, hydroxy, and cyano;

$R^{15}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{15}$ is independently optionally substituted with one to five substituents independently selected from halo, hydroxy, and cyano; $R^{16}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{16}$ is independently optionally substituted with one to five substituents independently selected from halo, hydroxy, and cyano;

each $Z^1$ is independently halo, cyano, nitro, oxo, $C_{1-9}$ alkyl, $C_{2-9}$ alkenyl, $C_{2-9}$ alkynyl, $C_{3-10}$ cycloalkyl, heterocyclyl, aryl, heteroaryl, -L-H, -L-$C_{1-9}$ alkyl, -L-$C_{2-9}$ alkenyl, -L-$C_{2-9}$ alkynyl, -L-$C_{3-10}$ cycloalkyl, -L-heterocyclyl, -L-aryl, or -L-heteroaryl; wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $Z^1$ is independently optionally substituted with one to five $Z^{1a}$;

each L is independently —O—, —S—, —NR$^{20}$—, —C(O)—, —C(O)O—, —OC(O)—, —OC(O)O—, —C(O)NR$^{20}$—, —NR$^{20}$C(O)—, —OC(O)NR$^{20}$—, —NR$^{20}$C(O)O—, —NR$^{20}$C(O)NR$^{21}$—, —S(O)—, —S(O)$_2$—, —S(O)NR$^{20}$—, —S(O)$_2$NR$^{20}$—, —NR$^{20}$S(O)—, —NR$^{20}$S(O)$_2$—, —NR$^{20}$S(O)NR$^{21}$—, or —NR$^{20}$S(O)$_2$NR$^{21}$—;

each $R^{20}$ and $R^{21}$ is independently hydrogen, $C_{1-9}$ alkyl, $C_{2-9}$ alkenyl, $C_{2-9}$ alkynyl, $C_{3-10}$ cycloalkyl, heterocyclyl, aryl, or heteroaryl; wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $R^{20}$ and $R^{21}$ is independently optionally substituted with one to five $Z^{1a}$; or an $R^{20}$ and $R^{21}$ are taken together with the atoms to which they are attached to form heterocyclyl independently optionally substituted by one to five $Z^{1a}$; and each $Z^{1a}$ is independently halo, hydroxy, cyano, nitro, oxo, —SH, —NH$_2$, —NH—$C_{1-9}$ alkyl, —N($C_{1-9}$ alkyl)$_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, or heteroaryl; wherein each —NH—$C_{1-9}$ alkyl, —N($C_{1-9}$ alkyl)$_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, or heteroaryl of $Z^1$ is independently optionally substituted with one to five substituents independently selected from $C_{1-9}$ alkyl, oxo, halo, hydroxy, and cyano.

In some embodiments, provided herein is a compound of Formula II:

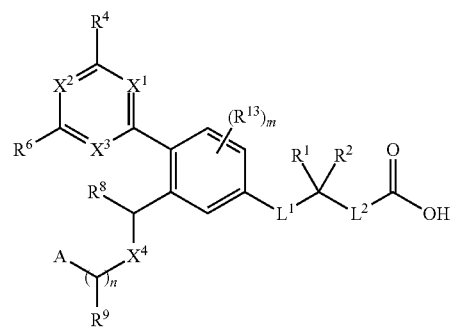

II or a pharmaceutically acceptable salt, stereoisomer, mixture of stereoisomers, tautomer, isotopically enriched analog, or solvate thereof, wherein each of A, $R^1$, $R^2$, $R^4$, $R^6$, $R^8$, $R^9$, $R^{13}$, $X^1$, $X^2$, $X^3$, $X^4$, n, m, $L^1$, and $L^2$ are independently as defined herein.

In some embodiments, provided herein is a compound of Formula II:

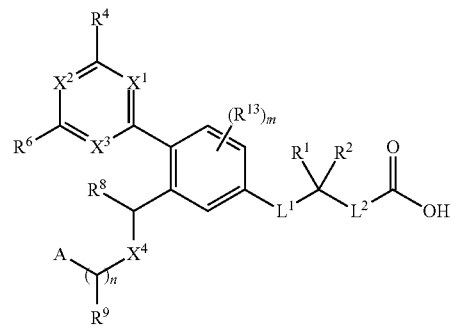

II or a pharmaceutically acceptable salt, stereoisomer, mixture of stereoisomers, tautomer, isotopically enriched analog, or solvate thereof, wherein:

A is $C_{1-6}$ alkyl, $C_{3-10}$ cycloalkyl, heterocyclyl, aryl, or heteroaryl; wherein each $C_{1-6}$ alkyl, $C_{3-10}$ cycloalkyl, heterocyclyl, aryl, or heteroaryl of A is independently optionally substituted with one to five $Z^1$;

$L^1$ is a bond, —O—, —S—, —S(O)—, —S(O)$_2$—, —NR$^{10}$—, $C_{1-3}$ alkylene, $C_{2-3}$ alkenylene, $C_{2-3}$ alkynylene, or $C_{1-3}$ heteroalkylene; wherein the $C_{1-3}$ alkylene, $C_{2-3}$ alkenylene, $C_{2-3}$ alkynylene, or $C_{1-3}$ heteroalkylene of $L^1$ is independently optionally substituted with one to five substituents independently selected from $C_{1-9}$ alkyl, halo, hydroxy, and cyano;

$L^2$ is a bond, $C_{1-3}$ alkylene, $C_{2-3}$ alkenylene, $C_{2-3}$ alkynylene, or $C_{1-3}$ heteroalkylene; wherein the $C_{1-3}$ alkylene, $C_{2-3}$ alkenylene, $C_{2-3}$ alkynylene, or $C_{1-3}$ heteroalkylene of $L^2$ is independently optionally substituted with one to five substituents independently selected from $C_{1-9}$ alkyl, halo, hydroxy, and cyano;

$X^1$ is N or $CR^3$;
$X^2$ is N or $CR^5$;
$X^3$ is N or $CR^7$;
$X^4$ is O or $CHR^{11}$; provided that when A is $C_{1-6}$ alkyl, then $X^4$ is O;
n is 0, 1, or 2;
m is 0, 1, 2, or 3;

$R^1$ and $R^2$ are each independently hydrogen, $C_{1-9}$ alkyl, $C_{2-9}$ alkenyl, $C_{2-9}$ alkynyl, $C_{3-10}$ cycloalkyl, or heterocyclyl; wherein each $C_{1-9}$ alkyl, $C_{2-9}$ alkenyl, $C_{2-9}$ alkynyl, $C_{3-10}$ cycloalkyl, or heterocyclyl of $R^1$ and $R^2$ are independently optionally substituted with one to five $Z^1$;

or $R^1$ and $R^2$ are taken together with the atom to which they are attached to form a $C_{3-10}$ cycloalkyl or heterocyclyl; wherein the $C_{3-10}$ cycloalkyl or heterocyclyl is optionally substituted by one to five $Z^1$;

$R^3$ is hydrogen, halo, cyano, nitro, —OH, —SH, —NH$_2$, —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl; wherein the —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl of $R^3$ is independently optionally substituted with one to five substituents independently selected from halo, hydroxy, and cyano;

$R^4$ is halo, cyano, nitro, —OR$^{14}$, —N(R$^{14}$)$_2$, —SR$^{14}$, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^4$ is independently optionally substituted with one to five substituents independently selected from halo, hydroxy, $C_{1-5}$ alkoxy, and cyano;

or $R^3$ and $R^4$ are taken together with the atoms to which they are attached to form a cycloalkyl, aryl, heterocyclyl, or heteroaryl; wherein the cycloalkyl, aryl, heterocyclyl, or heteroaryl is optionally substituted with one to five substituents independently selected from halo, hydroxy, and cyano;

$R^5$ is hydrogen, halo, cyano, nitro, —OR$^{15}$, —N(R$^5$)$_2$, —SR$^{15}$, —C(O)R$^5$, —C(O)OR$^5$, $C_{1-5}$ alkyl, $C_{2-5}$ alkenyl, $C_{2-5}$ alkynyl, $C_{3-5}$ cycloalkyl, 3-5 membered heterocyclyl or 5 membered heteroaryl; wherein the $C_{1-5}$ alkyl, $C_{2-5}$ alkenyl, $C_{2-5}$ alkynyl, $C_{3-5}$ cycloalkyl, 3-5 membered heterocyclyl or 5 membered heteroaryl of $R^5$ is independently optionally substituted with one to five $Z^1$;

$R^6$ is hydrogen, halo, cyano, nitro, —OR$^{16}$, —N(R$^{16}$)$_2$, —SR$^{16}$, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^6$ is independently optionally substituted with one to five substituents independently selected from halo, hydroxy, and cyano;

$R^7$ is hydrogen, halo, cyano, nitro, —OH, —SH, —NH$_2$, —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl; wherein the —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl of R is independently optionally substituted with one to five substituents independently selected from halo, hydroxy, and cyano;

or $R^6$ and $R^7$ are taken together with the atoms to which they are attached to form a cycloalkyl, aryl, heterocyclyl, or heteroaryl; wherein the cycloalkyl, aryl, heterocyclyl, or heteroaryl is optionally substituted with one to five substituents independently selected from halo, hydroxy, and cyano;

$R^8$ is hydrogen, $C_{1-9}$ alkyl, oxo, halo, hydroxy, or cyano;
$R^9$ is hydrogen, $C_{1-9}$ alkyl, oxo, halo, hydroxy, or cyano;
$R^{10}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{10}$ is independently optionally substituted with one to five substituents independently selected from halo, hydroxy, and cyano;

$R^{11}$ is hydrogen, $C_{1-9}$ alkyl, oxo, halo, hydroxy, or cyano;
each $R^{13}$ is independently hydrogen, halo, cyano, nitro, —OH, —SH, —NH$_2$, —NH—$C_{1-9}$ alkyl, —N($C_{1-9}$ alkyl)$_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-6}$cycloalkyl, or 3 to 6-membered heterocyclyl; wherein each —NH—$C_{1-9}$ alkyl, —N($C_{1-9}$ alkyl)$_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-6}$ cycloalkyl, or 3 to 6-membered heterocyclyl of $R^{13}$ is independently optionally substituted with one to five substituents independently selected from halo, hydroxy, and cyano;

$R^{14}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{14}$ is independently optionally substituted with one to five substituents independently selected from halo, hydroxy, and cyano;

$R^{15}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{15}$ is independently optionally substituted with one to five substituents independently selected from halo, hydroxy, and cyano;

$R^{16}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{16}$ is independently optionally substituted with one to five substituents independently selected from halo, hydroxy, and cyano;

each $Z^1$ is independently halo, cyano, nitro, oxo, $C_{1-9}$ alkyl, $C_{2-9}$ alkenyl, $C_{2-9}$ alkynyl, $C_{3-10}$ cycloalkyl, heterocyclyl, aryl, heteroaryl, -L-H, -L-$C_{1-9}$ alkyl, -L-$C_{2-9}$ alkenyl, -L-$C_{2-9}$ alkynyl, -L-$C_{3-10}$ cycloalkyl, -L-heterocyclyl, -L-aryl, or -L-heteroaryl; wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $Z^1$ is independently optionally substituted with one to five $Z^{1a}$;

each L is independently —O—, —S—, —NR$^{20}$—, —C(O)—, —C(O)O—, —OC(O)—, —OC(O)O—, —C(O)NR$^{20}$—, —NR$^{20}$C(O)—, —OC(O)NR$^{20}$—, —NR$^{20}$C(O)O—, —NR$^{20}$C(O)NR$^{21}$—, —S(O)—, —S(O)$_2$—, —S(O)NR$^{20}$—, —S(O)$_2$NR$^{20}$—, —NR$^{20}$S(O)—, —NR$^{20}$S(O)$_2$—, —NR$^{20}$S(O)NR$^{21}$—, or —NR$^{20}$S(O)$_2$NR$^{21}$—;

each R$^{20}$ and R$^{21}$ is independently hydrogen, C$_{1-9}$ alkyl, C$_{2-9}$ alkenyl, C$_{2-9}$ alkynyl, C$_{3-10}$ cycloalkyl, heterocyclyl, aryl, or heteroaryl; wherein each C$_{1-9}$ alkyl, C$_{2-9}$ alkenyl, C$_{2-9}$ alkynyl, C$_{3-10}$ cycloalkyl, heterocyclyl, aryl, or heteroaryl of R$^{20}$ and R$^{21}$ is independently optionally substituted with one to five Z$^{1a}$; or an R$^{20}$ and R$^{21}$ are taken together with the atoms to which they are attached to form heterocyclyl independently optionally substituted by one to five Z$^{1a}$; and each Z$^{1a}$ is independently halo, hydroxy, cyano, nitro, oxo, —SH, —NH$_2$, —NH—C$_{1-9}$ alkyl, —N(C$_{1-9}$ alkyl)$_2$, —S—C$_{1-9}$ alkyl, C$_{1-9}$ alkoxy, C$_{1-9}$ alkyl, C$_{2-9}$ alkenyl, C$_{2-9}$ alkynyl, C$_{3-10}$ cycloalkyl, heterocyclyl, aryl, or heteroaryl; wherein each —NH—C$_{1-9}$ alkyl, —N(C$_{1-9}$ alkyl)$_2$, —S—C$_{1-9}$ alkyl, C$_{1-9}$ alkoxy, C$_{1-9}$ alkyl, C$_{2-9}$ alkenyl, C$_{2-9}$ alkynyl, C$_{3-10}$ cycloalkyl, heterocyclyl, aryl, or heteroaryl of Z$^{1a}$ is independently optionally substituted with one to five substituents independently selected from C$_{1-9}$ alkyl, oxo, halo, hydroxy, and cyano.

In some embodiments, provided herein is a compound of Formula IXA:

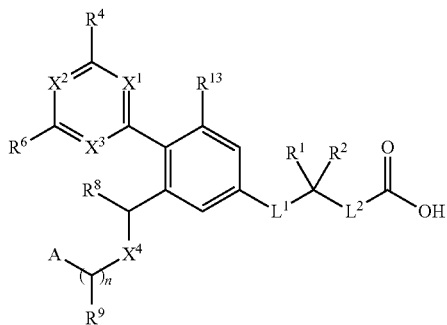

or a pharmaceutically acceptable salt, stereoisomer, mixture of stereoisomers, tautomer, isotopically enriched analog, or solvate thereof, wherein each of A, R$^1$, R$^2$, R$^4$, R$^6$, R$^8$, R$^9$, R$^{13}$, X$^1$, X$^2$, X$^3$, X$^4$, n, L$^1$, and L$^2$ are independently as defined herein.

In some embodiments, provided herein is a compound of Formula IXB:

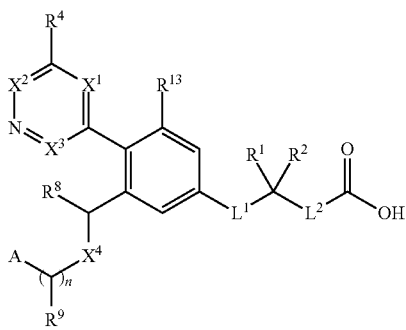

or a pharmaceutically acceptable salt, stereoisomer, mixture of stereoisomers, tautomer, isotopically enriched analog, or solvate thereof, wherein each of A, R$^1$, R$^2$, R$^4$, R$^8$, R$^9$, R$^{13}$, X$^1$, X$^2$, X$^3$, X$^4$, n, L$^1$, and L$^2$ are independently as defined herein.

In some embodiments, A is C$_{1-6}$ alkyl. In some embodiments, A is C$_{3-4}$ alkyl. In some embodiments, A is n-propyl, n-butyl, isopropyl, or isobutyl.

In one aspect, provided herein is a compound of Formula IIA:

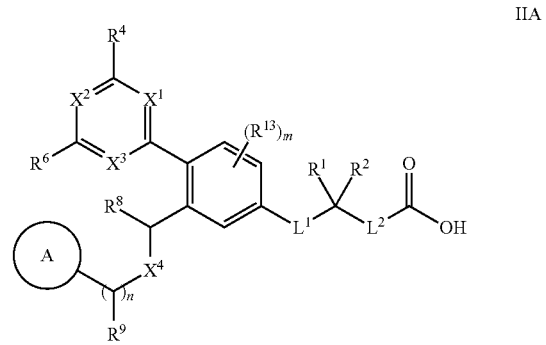

or a pharmaceutically acceptable salt, stereoisomer, mixture of stereoisomers, tautomer, isotopically enriched analog, or solvate thereof, wherein each of R$^1$, R$^2$, R$^4$, R$^6$, R$^8$, R$^9$, R$^{13}$, X$^1$, X$^2$, X$^3$, X$^4$, n, m, L$^1$, and L$^2$ are independently as defined herein, and ring A is C$_{3-10}$ cycloalkyl, heterocyclyl, aryl, or heteroaryl; wherein each C$_{3-10}$ cycloalkyl, heterocyclyl, aryl, or heteroaryl of ring A is independently optionally substituted with one to five Z$^1$.

In one aspect, provided herein is a compound of Formula IIA:

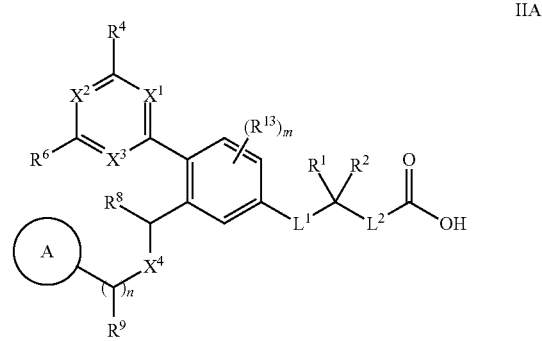

or a pharmaceutically acceptable salt, stereoisomer, mixture of stereoisomers, tautomer, isotopically enriched analog, or solvate thereof, wherein:

ring A is C$_{3-10}$ cycloalkyl, heterocyclyl, aryl, or heteroaryl; wherein each C$_{3-10}$ cycloalkyl, heterocyclyl, aryl, or heteroaryl of ring A is independently optionally substituted with one to five Z$^1$;

L$^1$ is a bond, —O—, —S—, —S(O)—, —S(O)$_2$—, —NR$^{10}$—, C$_{1-3}$ alkylene, C$_{2-3}$ alkenylene, C$_{2-3}$ alkynylene, or C$_{1-3}$ heteroalkylene; wherein the C$_{1-3}$ alkylene, C$_{2-3}$ alkenylene, C$_{2-3}$ alkynylene, or C$_{1-3}$ heteroalkylene of L$^1$ is independently optionally substituted with one to five substituents independently selected from $C_{1-9}$ alkyl, halo, hydroxy, and cyano;

$L^2$ is a bond, $C_{1-3}$ alkylene, $C_{2-3}$ alkenylene, $C_{2-3}$ alkynylene, or $C_{1-3}$ heteroalkylene; wherein the $C_{1-3}$ alkylene, $C_{2-3}$ alkenylene, $C_{2-3}$ alkynylene, or $C_{1-3}$ heteroalkylene of $L^2$ is independently optionally substituted with one to five substituents independently selected from $C_{1-9}$ alkyl, halo, hydroxy, and cyano;

$X^1$ is N or $CR^3$;

$X^2$ is N or CR;

$X^3$ is N or $CR^7$;

$X^4$ is O or $CHR^{11}$;

n is 0, 1, or 2;

m is 0, 1, 2, or 3;

$R^1$ and $R^2$ are each independently hydrogen, $C_{1-9}$ alkyl, $C_{2-9}$ alkenyl, $C_{2-9}$ alkynyl, $C_{3-10}$ cycloalkyl, or heterocyclyl; wherein each $C_{1-9}$ alkyl, $C_{2-9}$ alkenyl, $C_{2-9}$ alkynyl, $C_{3-10}$ cycloalkyl, or heterocyclyl of $R^1$ and $R^2$ are independently optionally substituted with one to five $Z^1$;

or $R^1$ and $R^2$ are taken together with the atom to which they are attached to form a $C_{3-10}$ cycloalkyl or heterocyclyl; wherein the $C_{3-10}$ cycloalkyl or heterocyclyl is optionally substituted by one to five $Z^1$;

$R^3$ is hydrogen, halo, cyano, nitro, —OH, —SH, —NH$_2$, —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl; wherein the —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl of $R^3$ is independently optionally substituted with one to five substituents independently selected from halo, hydroxy, and cyano;

$R^4$ is halo, cyano, nitro, —OR$^{14}$, —N(R$^{14}$)$_2$, —SR$^{14}$, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of R is independently optionally substituted with one to five substituents independently selected from halo, hydroxy, and cyano;

or $R^3$ and $R^4$ are taken together with the atoms to which they are attached to form a cycloalkyl, aryl, heterocyclyl, or heteroaryl; wherein the cycloalkyl, aryl, heterocyclyl, or heteroaryl is optionally substituted with one to five substituents independently selected from halo, hydroxy, and cyano;

$R^5$ is hydrogen, halo, cyano, nitro, —OR$^{15}$, —N(R$^{15}$)$_2$, —SR$^{15}$, —C(O)R$^{15}$, —C(O)OR$^{15}$, $C_{1-5}$ alkyl, $C_{2-5}$ alkenyl, $C_{2-5}$ alkynyl, $C_{3-5}$ cycloalkyl, 3-5 membered heterocyclyl or 5 membered heteroaryl; wherein the $C_{1-5}$ alkyl, $C_{2-5}$ alkenyl, $C_{2-5}$ alkynyl, $C_{3-5}$ cycloalkyl, 3-5 membered heterocyclyl or 5 membered heteroaryl of $R^5$ is independently optionally substituted with one to five $Z^1$;

$R^6$ is hydrogen, halo, cyano, nitro, —OR$^{16}$, —N(R$^{16}$)$_2$, —SR$^{16}$, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^6$ is independently optionally substituted with one to five substituents independently selected from halo, hydroxy, and cyano;

$R^7$ is hydrogen, halo, cyano, nitro, —OH, —SH, —NH$_2$, —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl; wherein the —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl of $R^7$ is independently optionally substituted with one to five substituents independently selected from halo, hydroxy, and cyano;

or $R^6$ and $R^7$ are taken together with the atoms to which they are attached to form a cycloalkyl, aryl, heterocyclyl, or heteroaryl; wherein the cycloalkyl, aryl, heterocyclyl, or heteroaryl is optionally substituted with one to five substituents independently selected from halo, hydroxy, and cyano;

$R^8$ is hydrogen, $C_{1-9}$ alkyl, oxo, halo, hydroxy, or cyano;

$R^9$ is hydrogen, $C_{1-9}$ alkyl, oxo, halo, hydroxy, or cyano;

$R^{10}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{10}$ is independently optionally substituted with one to five substituents independently selected from halo, hydroxy, and cyano;

$R^{11}$ is hydrogen, $C_{1-9}$ alkyl, oxo, halo, hydroxy, or cyano;

each $R^{13}$ is independently hydrogen, halo, cyano, nitro, —OH, —SH, —NH$_2$, —NH—$C_{1-9}$ alkyl, —N($C_{1-9}$ alkyl)$_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-6}$ cycloalkyl, or 3 to 6-membered heterocyclyl; wherein each —NH—$C_{1-9}$ alkyl, —N($C_{1-9}$ alkyl)$_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-6}$ cycloalkyl, or 3 to 6-membered heterocyclyl of $R^{13}$ is independently optionally substituted with one to five substituents independently selected from halo, hydroxy, and cyano;

$R^{14}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{14}$ is independently optionally substituted with one to five substituents independently selected from halo, hydroxy, and cyano;

$R^{15}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{15}$ is independently optionally substituted with one to five substituents independently selected from halo, hydroxy, and cyano;

$R^{16}$ is hydrogen, $C_{1-5}$ alkyl, $C_{2-5}$ alkenyl, $C_{2-5}$ alkynyl, $C_{3-5}$ cycloalkyl, or 3-5 membered heterocyclyl; wherein the $C_{1-5}$ alkyl, $C_{2-5}$ alkenyl, $C_{2-5}$ alkynyl, $C_{3-5}$ cycloalkyl, or 3-5 membered heterocyclyl of $R^{16}$ is independently optionally substituted with one to five substituents independently selected from halo, hydroxy, and cyano;

each $Z^1$ is independently halo, cyano, nitro, oxo, $C_{1-9}$ alkyl, $C_{2-9}$ alkenyl, $C_{2-9}$ alkynyl, $C_{3-10}$ cycloalkyl, heterocyclyl, aryl, heteroaryl, -L-H, -L-$C_{1-9}$ alkyl, -L-$C_{2-9}$ alkenyl, -L-$C_{2-9}$ alkynyl, -L-$C_{3-10}$ cycloalkyl, -L-heterocyclyl, -L-aryl, or -L-heteroaryl; wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $Z^1$ is independently optionally substituted with one to five $Z^{1a}$;

each L is independently —O—, —S—, —NR$^{20}$—, —C(O)—, —C(O)O—, —OC(O)—, —OC(O)O—, —C(O)NR$^{20}$—, —NR$^{20}$C(O)—, —OC(O)NR$^{20}$—, —NR$^{20}$C(O)O—, —NR$^{20}$C(O)NR$^{21}$—, —S(O)—, —S(O)$_2$—, —S(O)NR$^{20}$—, —S(O)$_2$NR$^{20}$—, —NR$^{20}$S(O)—, —NR$^{20}$S(O)$_2$—, —NR$^{20}$S(O)NR$^{21}$—, or —NR$^{20}$S(O)$_2$NR$^{21}$—;

each $R^{20}$ and $R^{21}$ is independently hydrogen, $C_{1-9}$ alkyl, $C_{2-9}$ alkenyl, $C_{2-9}$ alkynyl, $C_{3-10}$ cycloalkyl, heterocyclyl, aryl, or heteroaryl; wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $R^{20}$ and $R^{21}$ is independently optionally substituted with one to five $Z^{1a}$; or an $R^{20}$ and $R^{21}$ are taken together with the atoms to which they are attached to form heterocyclyl independently optionally substituted by one to five $Z^{1a}$; and each $Z^{1a}$ is independently halo, hydroxy, cyano, nitro, oxo, —SH, —NH$_2$, —NH—C$_{1-9}$ alkyl, —N(C$_{1-9}$ alkyl)$_2$, —S—C$_{1-9}$ alkyl, C$_{1-9}$ alkoxy, C$_{1-9}$ alkyl, C$_{2-9}$ alkenyl, C$_{2-9}$ alkynyl, C$_{3-10}$ cycloalkyl, heterocyclyl, aryl, or heteroaryl; wherein each —NH—C$_{1-9}$ alkyl, —N(C$_{1-9}$ alkyl)$_2$, —S—C$_{1-9}$ alkyl, C$_{1-9}$ alkoxy, C$_{1-9}$ alkyl, C$_{2-9}$ alkenyl, C$_{2-9}$ alkynyl, C$_{3-10}$ cycloalkyl, heterocyclyl, aryl, or heteroaryl of $Z^{1a}$ is independently optionally substituted with one to five substituents independently selected from C$_{1-9}$ alkyl, oxo, halo, hydroxy, and cyano.

In one aspect, provided herein is a compound of Formula IIB:

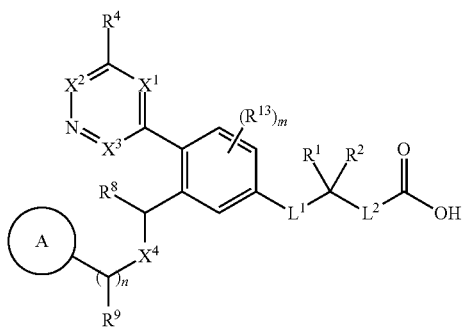

IIB or a pharmaceutically acceptable salt, stereoisomer, mixture of stereoisomers, tautomer, isotopically enriched analog, or solvate thereof, wherein each of $R^1$, $R^2$, $R^4$, $R^6$, $R^8$, $R^9$, $R^{13}$, $X^1$, $X^2$, $X^3$, $X^4$, n, m, $L^1$, and $L^2$ are independently as defined herein, and ring A is C$_{3-10}$ cycloalkyl, heterocyclyl, aryl, or heteroaryl; wherein each C$_{3-10}$ cycloalkyl, heterocyclyl, aryl, or heteroaryl of ring A is independently optionally substituted with one to five $Z^1$.

In one aspect, provided herein is a compound of Formula IIC:

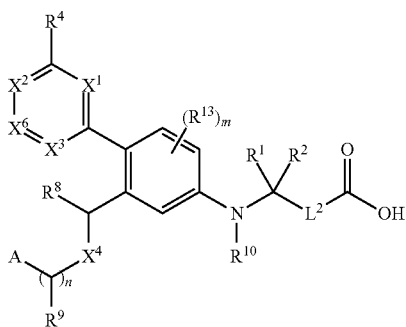

IIC or a pharmaceutically acceptable salt, stereoisomer, mixture of stereoisomers, tautomer, isotopically enriched analog, or solvate thereof, wherein each of $R^1$, $R^2$, $R^4$, $R^8$, $R^9$, $R^{10}$, $R^{13}$, $X^1$, $X^2$, $X^3$, $X^4$, $X^6$, A, n, m, and $L^2$ are independently as defined herein.

In one aspect, provided herein is a compound of Formula IID:

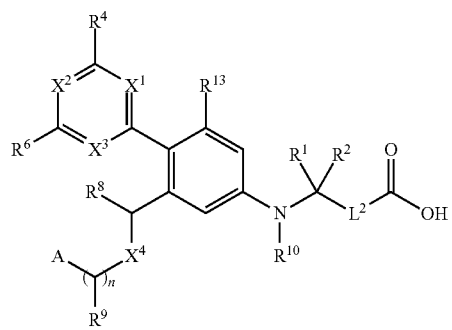

IID or a pharmaceutically acceptable salt, stereoisomer, mixture of stereoisomers, tautomer, isotopically enriched analog, or solvate thereof, wherein each of $R^1$, $R^2$, $R^4$, $R^6$, $R^8$, $R^9$, $R^{10}$, $R^{13}$, $X^1$, $X^2$, $X^3$, $X^4$, A, n, and $L^2$ are independently as defined herein.

In one aspect, provided herein is a compound of Formula IIE:

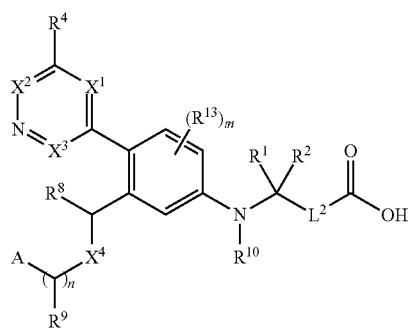

IIE or a pharmaceutically acceptable salt, stereoisomer, mixture of stereoisomers, tautomer, isotopically enriched analog, or solvate thereof, wherein each of $R^1$, $R^2$, $R^4$, $R^8$, $R^9$, $R^{10}$, $R^{13}$, $X^1$, $X^2$, $X^3$, $X^4$, A, n, m, and $L^2$ are independently as defined herein.

In one aspect, provided herein is a compound of Formula IIF:

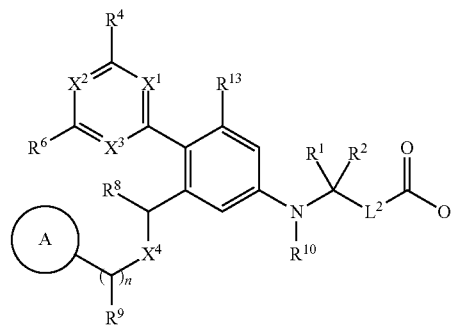

IIF or a pharmaceutically acceptable salt, stereoisomer, mixture of stereoisomers, tautomer, isotopically enriched analog, or solvate thereof, wherein each of $R^1$, $R^2$, $R^4$, $R^6$, $R^8$, $R^9$, $R^{10}$, $R^{13}$, $X^1$, $X^2$, $X^3$, $X^4$, ring A, n, and $L^2$ are independently as defined herein.

In some embodiments, the compound of Formula I or II is represented by Formula IA:

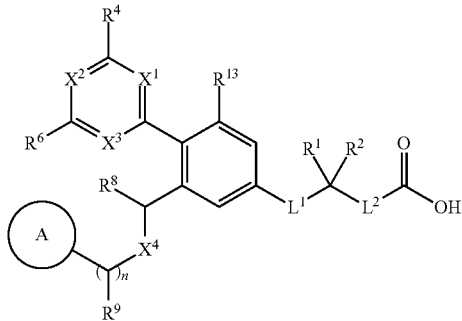

IA or a pharmaceutically acceptable salt, stereoisomer, mixture of stereoisomers, tautomer, isotopically enriched analog, or solvate thereof, wherein each of $R^1$, $R^2$, $R^4$, $R^6$, $R^8$, $R^9$, $R^{13}$, $X^1$, $X^2$, $X^3$, $X^4$, ring A, n, $L^1$, and $L^2$ are independently as defined herein.

In some embodiments, $X^1$ is N. In some embodiments, $X^1$ is $CR^3$.

In some embodiments, $X^2$ is N. In some embodiments, $X^2$ is $CR^5$.

In some embodiments, $X^3$ is N. In some embodiments, $X^3$ is $CR^7$.

In some embodiments, $X^1$ is N, $X^2$ is N, and $X^3$ is N. In some embodiments, $X^1$ is N, $X^2$ is N, and $X^3$ is CR. In some embodiments, $X^1$ is N, $X^2$ is $CR^5$, and $X^3$ is N. In some embodiments, $X^1$ is $CR^3$, $X^2$ is N, and $X^3$ is N. In some embodiments, $X^1$ is $CR^3$, $X^2$ is N, and $X^3$ is $CR^7$. In some embodiments, $X^1$ is $CR^3$, $X^2$ is $CR^5$, and $X^3$ is N. In some embodiments, $X^1$ is $CR^3$, $X^2$ is $CR^5$, and $X^3$ is $CR^7$. In some embodiments, $X^1$ is N, $X^2$ is $CR^5$, and $X^3$ is $CR^7$.

In some embodiments, $R^3$ is hydrogen, halo, cyano, nitro, —OH, —SH, —$NH_2$, —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl; wherein the —NH—$C_{1-5}$ alkyl, —N($C_{1-5}$ alkyl)$_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl of $R^3$ is independently optionally substituted with one to five substituents independently selected from halo, hydroxy, and cyano.

In some embodiments, $R^3$ is hydrogen, halo, or $C_{1-5}$ alkyl, wherein the $C_{1-5}$ alkyl is optionally substituted with one to five halo. In some embodiments, $R^3$ is hydrogen, halo, $C_{1-5}$ alkyl, or $C_{1-5}$ haloalkyl. In some embodiments, $R^3$ is hydrogen, fluoro, chloro, methyl, ethyl, or difluoromethyl. In some embodiments, $R^3$ is hydrogen. In some embodiments, $R^3$ is halo. In some embodiments, $R^3$ is $C_{1-5}$ alkyl. In some embodiments, $R^3$ is $C_{1-5}$ haloalkyl.

In some embodiments, $R^4$ is —$OR^{14}$, —$N(R^{14})_2$, or $C_{1-5}$ alkyl, wherein the $C_{1-5}$ alkyl is optionally substituted with hydroxy or $C_{1-5}$ alkoxy. In some embodiments, $R^4$ is —$OR^{14}$ or $C_{1-5}$ alkyl, wherein the $C_{1-5}$ alkyl is optionally substituted with hydroxy or $C_{1-5}$ alkoxy.

In some embodiments, $R^4$ is —$OR^{14}$ or —$N(R^{14})_2$. In some embodiments, $R^4$ is —O—$C_{1-5}$ alkyl, —O—$C_{3-5}$ cycloalkyl, or —NH—$C_{1-5}$ alkyl. In some embodiments, $R^4$ is methoxy, ethoxy, iso-butoxy, cyclopropoxy, or ethylamino.

In some embodiments, $R^4$ is —$OR^{14}$. In some embodiments, $R^4$ is —O—$C_{1-5}$ alkyl. In some embodiments, $R^4$ is hydroxy, methoxy, ethoxy, n-propoxy, iso-propoxy, cyclopropoxy, cyclobutoxy, methyl, ethyl, n-propyl, iso-propyl, 2-hydroxyethyl, or methoxymethyl. In some embodiments, $R^4$ is —$OR^{14}$, and $R^{14}$ is $C_{1-5}$ alkyl or $C_{3-5}$ cycloalkyl. In some embodiments, $R^4$ is hydroxy, methoxy, ethoxy, n-propoxy, cyclopropoxy, cyclobutoxy, methyl, ethyl, n-propyl, 2-hydroxyethyl, or methoxymethyl. In some embodiments, $R^4$ is hydroxy, methoxy, ethoxy, or cyclopropyloxy. In some embodiments, $R^4$ is hydroxy, methoxy, or ethoxy. In some embodiments, $R^4$ is methoxy or ethoxy. In some embodiments, $R^4$ is methoxy. In some embodiments, $R^4$ is ethoxy. In some embodiments, $R^4$ is cyclopropyloxy.

In some embodiments, $R^3$ and $R^4$ are taken together with the atoms to which they are attached to form a cycloalkyl, aryl, heterocyclyl, or heteroaryl; wherein the cycloalkyl, aryl, heterocyclyl, or heteroaryl is optionally substituted with one to five substituents independently selected from halo, hydroxy, and cyano.

In some embodiments, $R^3$ and $R^4$ are taken together with the atoms to which they are attached to form a cycloalkyl optionally substituted with one to five substituents independently selected from halo, hydroxy, and cyano. In some embodiments, $R^3$ and $R^4$ are taken together with the atoms to which they are attached to form a $C_6$ cycloalkyl optionally substituted with one to five substituents independently selected from halo, hydroxy, and cyano. In some embodiments, $R^3$ and $R^4$ are taken together with the atoms to which they are attached to form a $C_s$ cycloalkyl optionally substituted with one to five substituents independently selected from halo, hydroxy, and cyano. In some embodiments, the cycloalkyl is unsubstituted.

In some embodiments, $R^3$ and $R^4$ are taken together with the atoms to which they are attached to form an aryl optionally substituted with one to five substituents independently selected from halo, hydroxy, and cyano. In some embodiments, $R^3$ and $R^4$ are taken together with the atoms to which they are attached to form a $C_6$ aryl optionally substituted with one to five substituents independently selected from halo, hydroxy, and cyano. In some embodiments, the aryl is unsubstituted.

In some embodiments, $R^3$ and $R^4$ are taken together with the atoms to which they are attached to form a heterocyclyl optionally substituted with one to five substituents independently selected from halo, hydroxy, and cyano. In some embodiments, $R^3$ and $R^4$ are taken together with the atoms to which they are attached to form a 5 or 6 membered heterocyclyl optionally substituted with one to five substituents independently selected from halo, hydroxy, and cyano. In some embodiments, $R^3$ and $R^4$ are taken together with the atoms to which they are attached to form a 5 membered heterocyclyl optionally substituted with one to five substituents independently selected from halo, hydroxy, and cyano. In some embodiments, $R^3$ and $R^4$ are taken together with the atoms to which they are attached to form a 5 membered oxygen containing heterocyclyl optionally substituted with one to five substituents independently selected from halo, hydroxy, and cyano. In some embodiments, the heterocyclyl is unsubstituted.

In some embodiments, $R^3$ and $R^4$ are taken together with the atoms to which they are attached to form a heteroaryl optionally substituted with one to five substituents independently selected from halo, hydroxy, and cyano. In some embodiments, $R^3$ and $R^4$ are taken together with the atoms to which they are attached to form a 5 or 6 membered heteroaryl optionally substituted with one to five substituents independently selected from halo, hydroxy, and cyano. In some embodiments, $R^3$ and $R^4$ are taken together with the atoms to which they are attached to form a 6 membered heteroaryl optionally substituted with one to five substituents independently selected from halo, hydroxy, and cyano. In some embodiments, the heteroaryl is unsubstituted.

In some embodiments, $R^6$ is hydrogen, cyano, —$OR^{16}$, or $C_{1-5}$ alkyl. In some embodiments, $R^6$ is hydrogen, cyano, —O—$C_{1-5}$ alkyl, or $C_{1-5}$ alkyl. In some embodiments, $R^6$ is —$OR^{16}$. In some embodiments, $R^6$ is —O—$C_{1-5}$ alkyl. In some embodiments, $R^6$ is hydroxy, cyano, methoxy, or ethoxy. In some embodiments, $R^6$ is methoxy.

In some embodiments, $R^4$ is —$OR^{14}$ or —$N(R^{14})_2$ and $R^6$ is hydrogen, cyano, —$OR^{16}$, or $C_{1-5}$ alkyl. In some embodiments, $R^4$ is —O—$C_{1-5}$ alkyl, —O— $C_{3-5}$ cycloalkyl, or —NH—$C_{1-5}$ alkyl and $R^6$ is hydrogen, cyano, —O—$C_{1-5}$ alkyl, or $C_{1-5}$ alkyl. In some embodiments, $R^4$ is methoxy, ethoxy, iso-butyloxy, cyclopropoxy, or ethylamino and $R^6$ is hydroxy, cyano, methoxy, or ethoxy.

In some embodiments, $R^4$ is —O—$C_{1-5}$ alkyl and $R^6$ is hydrogen, cyano, —$OR^{16}$, or $C_{1-5}$ alkyl. In some embodiments, $R^4$ is —O—$C_{1-5}$ alkyl and $R^6$ is hydrogen, cyano, —O—$C_{1-5}$ alkyl, or $C_{1-5}$ alkyl. In some embodiments, $R^4$ is —O—$C_{1-5}$ alkyl and $R^6$ is —$OR^{16}$. In some embodiments, $R^4$ is —O—$C_{1-5}$ alkyl and $R^6$ is —O—$C_{1-5}$ alkyl. In some embodiments, $R^4$ is —O—$C_{1-5}$ alkyl and $R^6$ is hydroxy, cyano, methoxy, or ethoxy. In some embodiments, $R^4$ is —O—$C_{1-5}$ alkyl and $R^6$ is methoxy. In some embodiments, $R^4$ is methoxy and $R^6$ is hydrogen. In some embodiments, $R^4$ is methoxy and $R^6$ is methoxy.

In some embodiments, $R^5$ is hydrogen, halo, cyano, —C(O)—$C_{1-5}$ alkyl, or $C_{1-5}$ alkyl optionally substituted with one to three substituents independently selected from halo, hydroxy, and $C_{1-5}$ alkoxy. In some embodiments, $R^5$ is hydrogen, cyano, —C(O)—$C_{1-5}$ alkyl, or $C_{1-5}$ alkyl optionally substituted with one to three substituents independently selected from halo and hydroxy. In some embodiments, $R^5$ is hydrogen. In some embodiments, $R^5$ is cyano. In some embodiments, $R^5$ is halo. In some embodiments, $R^5$ is fluoro. In some embodiments, $R^5$ is —C(O)—$C_{1-5}$ alkyl. In some embodiments, $R^5$ is $C_{1-5}$ alkyl optionally substituted with one to three substituents independently selected from halo and hydroxy. In some embodiments, $R^5$ is $C_{1-5}$ haloalkyl.

In some embodiments, $R^4$ is —O—$C_{1-5}$ alkyl, $R^5$ is hydrogen, cyano, —C(O)—$C_{1-5}$ alkyl, or $C_{1-5}$ alkyl optionally substituted with one to three substituents independently selected from halo and hydroxy, and $R^6$ is hydrogen, cyano, —$OR^{16}$, or $C_{1-5}$ alkyl.

In some embodiments, $R^1$ is hydrogen, halo, cyano, nitro, —OH, —SH, —$NH_2$, —NH—$C_{1-5}$ alkyl, —$N(C_{1-5}$ alkyl$)_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl; wherein the —NH—$C_{1-5}$ alkyl, —$N(C_{1-5}$ alkyl$)_2$, —S—$C_{1-5}$ alkyl, $C_{1-5}$ alkoxy, $C_{1-5}$ alkyl, $C_{2-5}$ alkenyl, $C_{2-5}$ alkynyl, $C_{3-5}$ cycloalkyl, or 3-5 membered heterocyclyl of $R^1$ is independently optionally substituted with one to five substituents independently selected from halo, hydroxy, and cyano.

In some embodiments, $R^7$ is hydrogen, halo, or $C_{1-5}$ alkyl, or $C_{1-5}$ haloalkyl. In some embodiments, $R^7$ is hydrogen, fluoro, chloro, methyl, ethyl, or difluoromethyl. In some embodiments, $R^7$ is hydrogen or $C_{1-5}$ alkyl. In some embodiments, $R^7$ is hydrogen, methyl, or ethyl. In some embodiments, $R^7$ is hydrogen. In some embodiments, $R^7$ is halo. In some embodiments, $R^7$ is $C_{1-5}$ alkyl. In some embodiments, $R^1$ is $C_{1-5}$ haloalkyl.

In some embodiments, $R^3$ is hydrogen and $R^7$ is hydrogen, halo, or $C_{1-5}$ alkyl, or $C_{1-5}$ haloalkyl. In some embodiments, $R^3$ is halo and $R^7$ is hydrogen, halo, or $C_{1-5}$ alkyl, or $C_{1-5}$ haloalkyl. In some embodiments, $R^3$ is $C_{1-5}$ alkyl and $R^7$ is hydrogen, halo, or $C_{1-5}$ alkyl, or $C_{1-5}$ haloalkyl. In some embodiments, $R^3$ is $C_{1-5}$ haloalkyl and $R^7$ is hydrogen, halo, or $C_{1-5}$ alkyl, or $C_{1-5}$ haloalkyl.

In some embodiments, $R^3$ is hydrogen and $R^7$ is hydrogen. In some embodiments, $R^7$ is hydrogen and $R^3$ is hydrogen, halo, or $C_{1-5}$ alkyl, or $C_{1-5}$ haloalkyl. In some embodiments, $R^7$ is halo and $R^3$ is hydrogen, halo, or $C_{1-5}$ alkyl, or $C_{1-5}$ haloalkyl. In some embodiments, $R^7$ is $C_{1-5}$ alkyl and $R^3$ is hydrogen, halo, or $C_{1-5}$ alkyl, or $C_{1-5}$ haloalkyl. In some embodiments, $R^7$ is $C_{1-5}$ haloalkyl and $R^3$ is hydrogen, halo, or $C_{1-5}$ alkyl, or $C_{1-5}$ haloalkyl.

In some embodiments, A or ring A is $C_{3-10}$ cycloalkyl or heterocyclyl, wherein each is independently optionally substituted with one to five $Z^1$. In some embodiments, A or ring A is $C_{3-10}$ cycloalkyl or heterocyclyl.

In some embodiments, A or ring A is $C_{3-10}$ cycloalkyl optionally substituted with one to five $Z^1$. In some embodiments, A or ring A is $C_{3-10}$ cycloalkyl optionally substituted with one to five substituents independently selected from halo, hydroxy, cyano, nitro, oxo, —SH, —$NH_2$, —NH—$C_{1-9}$ alkyl, —NHC(O)—$C_{1-9}$ alkyl, —$N(C_{1-9}$ alkyl$)_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, and heteroaryl; wherein each —NH—$C_{1-9}$ alkyl, —$N(C_{1-9}$ alkyl$)_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, or heteroaryl is independently optionally substituted with one to five substituents independently selected from $C_{1-9}$ alkyl, oxo, halo, hydroxy, and cyano. In some embodiments, A or ring A is $C_{3-10}$ cycloalkyl optionally substituted with one to five substituents independently selected from $C_{1-9}$ alkyl, oxo, halo, hydroxy, and cyano.

In some embodiments, A or ring A is heterocyclyl optionally substituted with one to five $Z^1$. In some embodiments, A or ring A is heterocyclyl optionally substituted with one to five substituents independently selected from halo, hydroxy, cyano, nitro, oxo, —SH, —$NH_2$, —NH—$C_{1-9}$ alkyl, —NHC(O)—$C_{1-9}$ alkyl, —$N(C_{1-9}$ alkyl$)_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, and heteroaryl; wherein each —NH—$C_{1-9}$ alkyl, —$N(C_{1-9}$ alkyl$)_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, or heteroaryl is independently optionally substituted with one to five substituents independently selected from $C_{1-9}$ alkyl, oxo, halo, hydroxy, and cyano. In some embodiments, A or ring A is heterocyclyl optionally substituted with one to five substituents independently selected from $C_{1-9}$ alkyl, oxo, halo, hydroxy, and cyano.

In some embodiments, A or ring A is aryl optionally substituted with one to five $Z^1$. In some embodiments, A or ring A is aryl optionally substituted with one to five substituents independently selected from halo, hydroxy, cyano, nitro, oxo, —SH, —$NH_2$, —NH—$C_{1-9}$ alkyl, —NHC(O)—$C_{1-9}$ alkyl, —$N(C_{1-9}$ alkyl$)_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, and heteroaryl; wherein each —NH—$C_{1-9}$ alkyl, —$N(C_{1-9}$ alkyl$)_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, or heteroaryl is independently optionally substituted with one to five substituents independently selected from $C_{1-9}$ alkyl, oxo, halo, hydroxy, and cyano. In some embodiments, A or ring A is aryl optionally substituted with one to five substituents independently selected from $C_{1-9}$ alkyl, oxo, halo, hydroxy, and cyano.

In some embodiments, A or ring A is heteroaryl optionally substituted with one to five $Z^1$. In some embodiments, A or ring A is heteroaryl optionally substituted with one to five substituents independently selected from halo, hydroxy, cyano, nitro, oxo, —SH, —$NH_2$, —NH—$C_{1-9}$ alkyl, —NHC(O)—$C_{1-9}$ alkyl, —$N(C_{1-9}$ alkyl$)_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, and heteroaryl; wherein each —NH—$C_{1-9}$ alkyl, —$N(C_{1-9}$ alkyl$)_2$, —S—$C_{1-9}$ alkyl, $C_{1-9}$ alkoxy, $C_{1-9}$ alkyl, $C_{2-9}$ alkenyl, $C_{2-9}$ alkynyl, $C_{3-10}$ cycloalkyl, heterocyclyl, aryl, or heteroaryl is independently optionally substituted with one to five substituents independently selected from $C_{1-9}$ alkyl, oxo, halo, hydroxy, and cyano. In some embodiments, A or ring A is heteroaryl optionally substituted with one to five substituents independently selected from $C_{1-9}$ alkyl, oxo, halo, hydroxy, and cyano.

In any embodiment described herein, for groups having two or more substituents, those substituents can be the same or different. For example, in —N($C_{1-5}$ alkyl)$_2$ or —N($C_{1-9}$ alkyl)$_2$, the alkyl groups can be the same or different, and where further substituted, those substituents can also be the same or different (e.g., —N(CH$_3$)$_2$, —N(CH$_3$)CH$_2$CH$_3$, —N(CH$_3$)CH$_2$CF$_3$, —N(CHF$_2$)CH$_2$CH$_2$CN, and the like).

In some embodiments, $X^4$ is O. In some embodiments, $X^4$ is CHR$^{11}$. In some embodiments, $X^4$ is CH$_2$.

In some embodiments, $R^8$ is hydrogen.
In some embodiments, $R^9$ is hydrogen.
In some embodiments, n is 0. In some embodiments, n is 1. In some embodiments, n is 2. In some embodiments, n is 0 or 1. In some embodiments, n is 1 or 2.

In some embodiments, $R^{13}$ is hydrogen, halo, $C_{1-9}$ alkyl, $C_{1-9}$ haloalkyl, or $C_{1-9}$ alkyl-CN.

In some embodiments, $R^{13}$ is hydrogen, halo, or $C_{1-9}$ alkyl. In some embodiments, $R^{13}$ is hydrogen.

In some embodiments, m is 0. In some embodiments, m is 1. In some embodiments, m is 1, and $R^{13}$ is hydrogen, halo, or $C_{1-9}$ alkyl.

In some embodiments, $L^1$ is a bond, —O—, —NR$^{10}$—, $C_{1-3}$ alkylene, or $C_{1-3}$ heteroalkylene. In some embodiments, $L^1$ is —O—, —NR$^{10}$—, or $C_{1-3}$ alkylene, and $R^{10}$ is hydrogen or $C_{1-9}$ alkyl. In some embodiments, $L^1$ is a bond, —O—, —NH—, —NCH$_3$—, $C_{1-3}$ alkylene, or $C_{1-3}$ heteroalkylene. In some embodiments, $L^1$ is a bond. In some embodiments, $L^1$ is —O—. In some embodiments, $L^1$ is —NR$^{10}$—. In some embodiments, $L^1$ is —O— or —NR$^{10}$—. In some embodiments, $L^1$ is —NH— or —NCH$_3$—. In some embodiments, $L^1$ is —NH—. In some embodiments, $L^1$ is —O— or —NH—. In some embodiments, $L^1$ is $C_{1-3}$ alkylene. In some embodiments, $L^1$ is $C_{1-3}$ heteroalkylene. In some embodiments, $L^1$ is —O—CH$_2$—.

In some embodiments, $L^2$ is a bond.
In some embodiments, $L^1$ is a bond, —O—, —NR$^{10}$—, $C_{1-3}$ alkylene, or $C_{1-3}$ heteroalkylene, and $L^2$ is a bond. In some embodiments, $L^1$ is a bond, —O—, or —NR$^{10}$—, and $L^2$ is a bond. In some embodiments, $L^1$ is —O— or —NR$^{10}$—, and $L^2$ is a bond.

In some embodiments, provided is a compound of Formula IB:

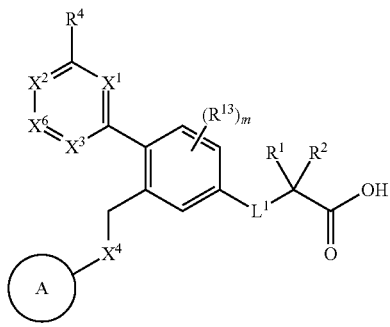

IB or a pharmaceutically acceptable salt, stereoisomer, mixture of stereoisomers, tautomer, isotopically enriched analog, or solvate thereof, wherein each of m, $R^1$, $R^2$, $R^4$, $R^{13}$, $X^1$, $X^2$, $X^3$, $X^4$, $X^6$, ring A, and $L^1$ are independently as defined herein.

In some embodiments, provided is a compound of Formula IC:

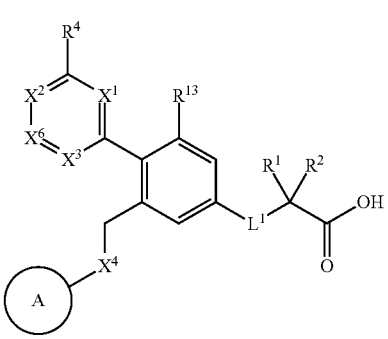

IC or a pharmaceutically acceptable salt, stereoisomer, mixture of stereoisomers, tautomer, isotopically enriched analog, or solvate thereof, wherein each of $R^1$, $R^2$, $R^4$, $R^{13}$, $X^1$, $X^2$, $X^3$, $X^4$, $X^6$, ring A, and $L^1$ are independently as defined herein.

In some embodiments, provided is a compound of Formula ID:

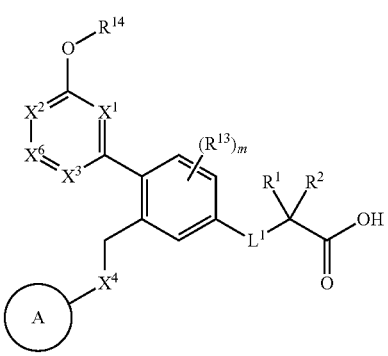

ID or a pharmaceutically acceptable salt, stereoisomer, mixture of stereoisomers, tautomer, isotopically enriched analog, or solvate thereof, wherein each of m, $R^1$, $R^2$, $R^6$, $R^{13}$, $R^{14}$, $X^1$, $X^2$, $X^3$, $X^4$, ring A, and $L^1$ are independently as defined herein.

In some embodiments, provided is a compound of Formula IE:

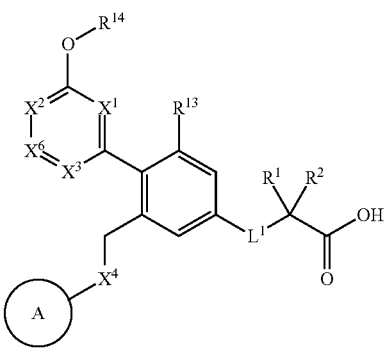

IE or a pharmaceutically acceptable salt, stereoisomer, mixture of stereoisomers, tautomer, isotopically enriched analog, or solvate thereof, wherein each of $R^1$, $R^2$, $R^6$, $R^{13}$, $R^{14}$, $X^1$, $X^2$, $X^3$, $X^4$, ring A, and $L^1$ are independently as defined herein.

In some embodiments, provided is a compound of Formula IF:

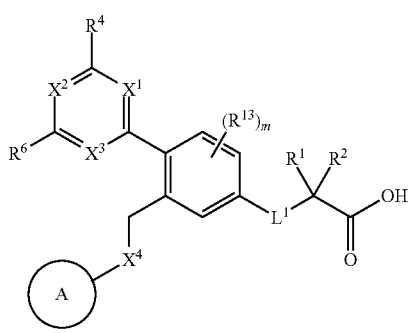

IF or a pharmaceutically acceptable salt, stereoisomer, mixture of stereoisomers, tautomer, isotopically enriched analog, or solvate thereof, wherein each of m, $R^1$, $R^2$, $R^4$, $R^6$, $R^{13}$, $X^1$, $X^2$, $X^3$, $X^4$, ring A, and $L^1$ are independently as defined herein.

In some embodiments, provided is a compound of Formula IG:

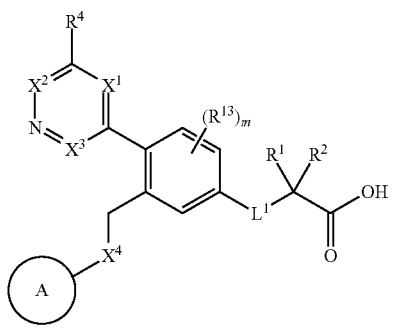

IG or a pharmaceutically acceptable salt, stereoisomer, mixture of stereoisomers, tautomer, isotopically enriched analog, or solvate thereof, wherein each of m, $R^1$, $R^2$, $R^4$, $R^6$, $R^{13}$, $X^1$, $X^2$, $X^3$, $X^4$, ring A, and $L^1$ are independently as defined herein.

In some embodiments, provided is a compound of Formula IH:

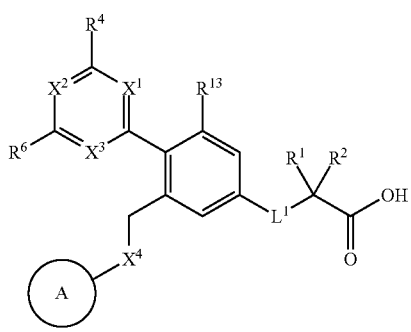

IH or a pharmaceutically acceptable salt, stereoisomer, mixture of stereoisomers, tautomer, isotopically enriched analog, or solvate thereof, wherein each of $R^1$, $R^2$, $R^4$, $R^6$, $R^{13}$, $X^1$, $X^2$, $X^3$, $X^4$, ring A, and $L^1$ are independently as defined herein.

In some embodiments, provided is a compound of Formula IJ:

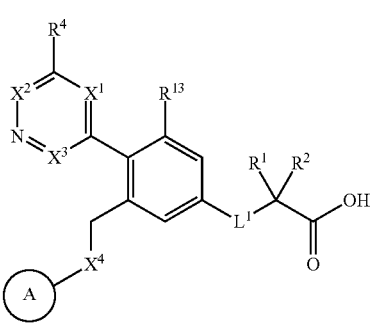

IJ or a pharmaceutically acceptable salt, stereoisomer, mixture of stereoisomers, tautomer, isotopically enriched analog, or solvate thereof, wherein each of $R^1$, $R^2$, $R^4$, $R^6$, $R^{13}$, $X^1$, $X^2$, $X^3$, $X^4$, ring A, and $L^1$ are independently as defined herein.

In some embodiments, provided is a compound of Formula IK:

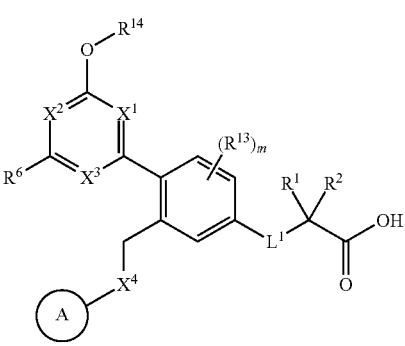

IK or a pharmaceutically acceptable salt, stereoisomer, mixture of stereoisomers, tautomer, isotopically enriched analog, or solvate thereof, wherein each of m, $R^1$, $R^2$, $R^6$, $R^{13}$, $R^{14}$, $X^1$, $X^2$, $X^3$, $X^4$, ring A, and $L^1$ are independently as defined herein.

In some embodiments, provided is a compound of Formula IL:

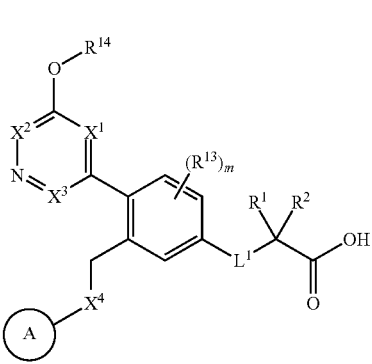

IL or a pharmaceutically acceptable salt, stereoisomer, mixture of stereoisomers, tautomer, isotopically enriched analog, or solvate thereof, wherein each of m, $R^1$, $R^2$, $R^6$, $R^{13}$, $R^{14}$, $X^1$, $X^2$, $X^3$, $X^4$, ring A, and $L^1$ are independently as defined herein.

In some embodiments, provided is a compound of Formula IM:

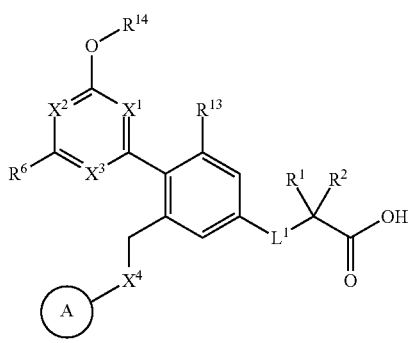

IM or a pharmaceutically acceptable salt, stereoisomer, mixture of stereoisomers, tautomer, isotopically enriched analog, or solvate thereof, wherein each of $R^1$, $R^2$, $R^6$, $R^{13}$, $R^{14}$, $X^1$, $X^2$, $X^3$, $X^4$, ring A, and $L^1$ are independently as defined herein.

In some embodiments, provided is a compound of Formula IN:

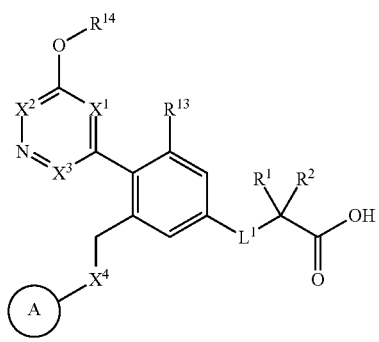

IN or a pharmaceutically acceptable salt, stereoisomer, mixture of stereoisomers, tautomer, isotopically enriched analog, or solvate thereof, wherein each of $R^1$, $R^2$, $R^6$, $R^{13}$, $R^{14}$, $X^1$, $X^2$, $X^3$, $X^4$, ring A, and $L^1$ are independently as defined herein.

In some embodiments, $R^{14}$ is $C_{1-5}$ alkyl or $C_{3-5}$ cycloalkyl. In some embodiments, $R^{14}$ is methyl, ethyl, or cyclopropyl.

In some embodiments, $R^{14}$ is $C_{3-5}$ cycloalkyl. In some embodiments, $R^{14}$ is cyclopropyl. In some embodiments, $R^{14}$ is cyclobutyl.

In some embodiments, $R^{14}$ is $C_{1-5}$ alkyl. In some embodiments, $R^{14}$ is methyl or ethyl. In some embodiments, $R^{14}$ is methyl. In some embodiments, $R^{14}$ is ethyl.

In some embodiments, $R^1$ and $R^2$ are each independently $C_{1-9}$ alkyl. In some embodiments, $R^1$ and $R^2$ are each methyl. In some embodiments, $R^1$ and $R^2$ are each hydrogen.

In some embodiments, $R^1$ and $R^2$ are taken together with the atom to which they are attached to form a $C_{3-10}$ cycloalkyl optionally substituted by one to five $Z^1$. In some embodiments, $R^1$ and $R^2$ are taken together with the atom to which they are attached to form a $C_{3-6}$ cycloalkyl optionally substituted by one to five $Z^1$. In some embodiments, $R^1$ and $R^2$ are taken together with the atom to which they are attached to form a $C_{3-4}$ cycloalkyl optionally substituted by one to five $Z^1$. In some embodiments, the cycloalkyl is unsubstituted. In some embodiments, the cycloalkyl is substituted by one to five halo, hydroxy, $C_{1-9}$ alkyl, $C_{1-9}$ alkoxy, —$CH_2$—O—$C_{1-9}$ alkyl, or —NHC(O)O—$C_{1-9}$ alkyl.

In some embodiments, $R^1$ and $R^2$ are taken together with the atom to which they are attached to form a heterocyclyl optionally substituted by one to five $Z^1$. In some embodiments, $R^1$ and $R^2$ are taken together with the atom to which they are attached to form a 4 to 6 membered heterocyclyl optionally substituted by one to five $Z^1$. In some embodiments, the heterocyclyl is unsubstituted. In some embodiments, the heterocyclyl is substituted by one to five $C_{1-9}$ alkyl, —C(O)—$C_{1-9}$ alkyl, —C(O)O—$C_{1-9}$ alkyl, or —C(O)—$CH_2$—O—$C_{1-9}$ alkyl.

In some embodiments, $R^1$ and $R^2$ are taken together with the atom to which they are attached to form a $C_{3-6}$ cycloalkyl or a 4 to 6 membered heterocyclyl, wherein each is optionally substituted by one to five halo, hydroxy, $C_{1-9}$ alkyl, $C_{1-9}$ alkoxy, —$CH_2$—O—$C_{1-9}$ alkyl, —NHC(O)O—$C_{1-9}$ alkyl, —C(O)—$C_{1-9}$ alkyl, —C(O)O—$C_{1-9}$ alkyl, or —C(O)—$CH_2$—O—$C_{1-9}$ alkyl.

In some embodiments, $R^{13}$ is hydrogen, halo, or $C_{1-9}$ alkyl.

In some embodiments, m is 0. In some embodiments, m is 1.

In some embodiments, provided is a compound of Formula III:

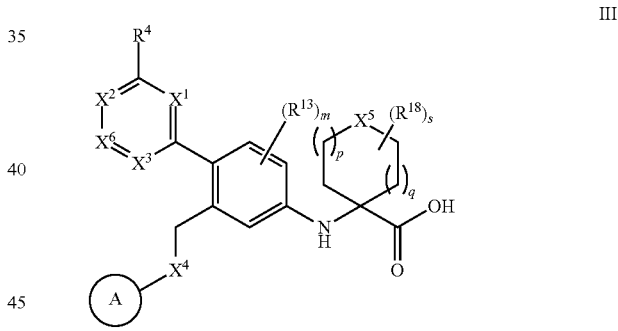

III or a pharmaceutically acceptable salt, stereoisomer, mixture of stereoisomers, tautomer, isotopically enriched analog, or solvate thereof, wherein each of m, $R^4$, $X^6$, $R^{13}$, $X^1$, $X^2$, $X^3$, $X^4$, and ring A are independently as defined herein.

In some embodiments, provided is a compound of Formula III, or a pharmaceutically acceptable salt, stereoisomer, mixture of stereoisomers, tautomer, isotopically enriched analog, or solvate thereof, wherein each of m, $R^4$, $X^6$, $R^{13}$, $X^1$, $X^2$, $X^3$, $X^4$, and ring A are independently as defined herein, p is 0, 1, or 2;
q is 0, 1, or 2;
s is 0, 1, 2, or 3;
$X^5$ is absent, O, $NR^{17}$, or $C(R^{18})_2$;
$R^{17}$ is hydrogen, $C_{1-9}$ alkyl, $C_{2-9}$ alkenyl, $C_{2-9}$ alkynyl, $C_{3-10}$ cycloalkyl, heterocyclyl, aryl, heteroaryl, —C(O)$R^{20}$, —C(O)O$R^{20}$, —C(O)N$R^{20}$, —S(O)$R^{20}$, —S(O)$_2$$R^{20}$, —S(O)N$R^{20}R^{21}$, or —S(O)$_2$N$R^{20}R^{21}$; wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $R^{17}$ is independently optionally substituted with one to five $Z^{1a}$; and each $R^{18}$ is independently hydrogen or $Z^1$.

In some embodiments, m is 1, $X^4$ is —O—, and $R^4$ is —$OR^{14}$. In some embodiments, m is 0, $X^4$ is —O—, and $R^4$ is —$OR^{14}$. In some embodiments, p is 1, q is 1, m is 0 or 1, $X^4$ is —O—, and $R^4$ is —$OR^{14}$.

In some embodiments, provided is a compound of Formula IIIA:

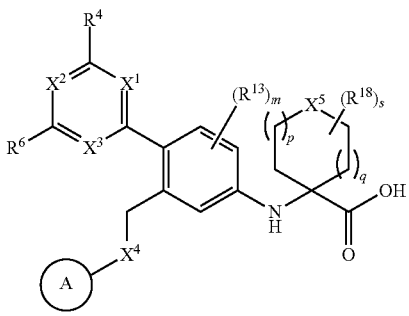

IIIA or a pharmaceutically acceptable salt, stereoisomer, mixture of stereoisomers, tautomer, isotopically enriched analog, or solvate thereof, wherein each of m, $R^4$, $R^6$, $R^{13}$, $R^{17}$, $R^{18}$, $X^1$, $X^2$, $X^3$, $X^4$, X, p, q, s, and ring A are independently as defined herein.

In some embodiments, provided is a compound of Formula IIIA:

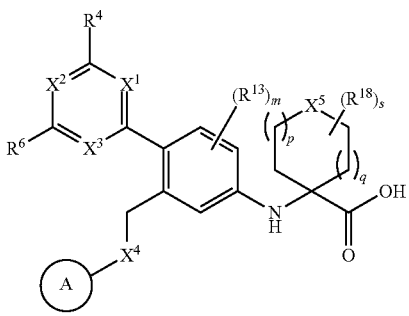

IIIA or a pharmaceutically acceptable salt, stereoisomer, mixture of stereoisomers, tautomer, isotopically enriched analog, or solvate thereof, wherein each of m, $R^4$, $R^6$, $R^{13}$, $X^1$, $X^2$, $X^3$, $X^4$, and ring A are independently as defined herein:

p is 0, 1, or 2;
q is 0, 1, or 2;
s is 0, 1, 2, or 3;
$X^5$ is absent, O, $NR^{17}$, or $C(R^{18})_2$;
$R^{17}$ is hydrogen, $C_{1-9}$ alkyl, $C_{2-9}$ alkenyl, $C_{2-9}$ alkynyl, $C_{3-10}$ cycloalkyl, heterocyclyl, aryl, heteroaryl, —C(O)$R^{20}$, —C(O)$OR^{20}$, —C(O)$NR^{20}$, —S(O)$R^{20}$, —S(O)$_2$ $R^{20}$, —S(O)$NR^{20}R^{21}$, or —S(O)$_2NR^{20}R^{21}$. wherein each $C_{19}$ alkyl, $C_{2-9}$ alkenyl, $C_{2-9}$ alkynyl, $C_{3-10}$ cycloalkyl, heterocyclyl, aryl, or heteroaryl of $R^{17}$ is independently optionally substituted with one to five $Z^{1a}$; and each $R^{18}$ is independently hydrogen or $Z^1$.

In some embodiments, provided is a compound of Formula IIIB:

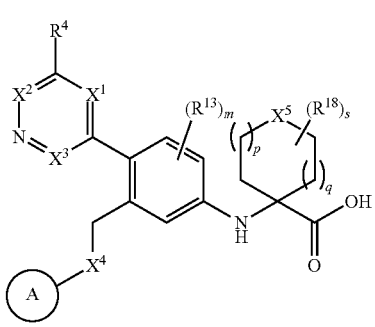

IIIB or a pharmaceutically acceptable salt, stereoisomer, mixture of stereoisomers, tautomer, isotopically enriched analog, or solvate thereof, wherein each of m, $R^4$, $R^{13}$, $R^{17}$, $R^{18}$, $X^1$, $X^2$, $X^3$, $X^4$, $X^5$, p, q, s, and ring A are independently as defined herein.

In some embodiments, provided is a compound of Formula IIIC:

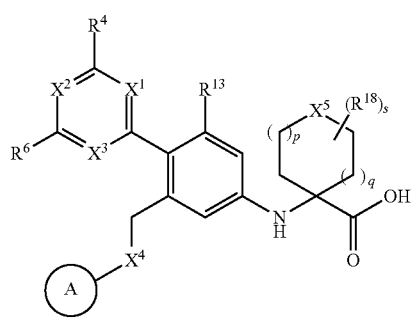

IIIC or a pharmaceutically acceptable salt, stereoisomer, mixture of stereoisomers, tautomer, isotopically enriched analog, or solvate thereof, wherein each of $R^4$, $R^6$, $R^{13}$, $X^1$, $X^2$, $X^3$, $X^4$, and ring A are independently as defined herein:

p is 0, 1, or 2;
q is 0, 1, or 2;
s is 0, 1, 2, or 3;
$X^5$ is absent, O, $NR^{17}$, or $C(R^{18})_2$;
$R^{17}$ is hydrogen, $C_{1-9}$ alkyl, $C_{2-9}$ alkenyl, $C_{2-9}$ alkynyl, $C_{3-10}$ cycloalkyl, heterocyclyl, aryl, heteroaryl, —C(O)$R^{20}$, —C(O)$OR^{20}$, —C(O)$NR^{20}$, —S(O)$R^{20}$, —S(O)$_2$ $R^{20}$, —S(O)$NR^{20}R^{21}$, or —S(O)$_2NR^{20}R^{21}$. wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $R^{17}$ is independently optionally substituted with one to five $Z^{1a}$; and each $R^{18}$ is independently hydrogen or $Z^1$.

In some embodiments, provided is a compound of Formula IIID:

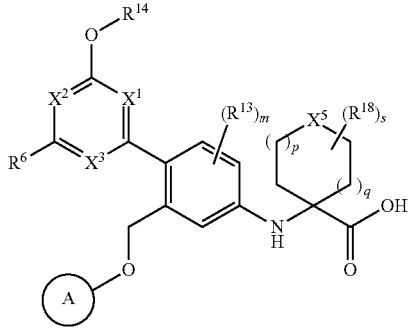

IIID or a pharmaceutically acceptable salt, stereoisomer, mixture of stereoisomers, tautomer, isotopically enriched analog, or solvate thereof, wherein each of m, $R^6$, $R^{13}$, $R^{14}$, $X^1$, $X^2$, $X^3$, and ring A are independently as defined herein:

p is 0, 1, or 2;
q is 0, 1, or 2;
s is 0, 1, 2, or 3;
$X^5$ is absent, O, $NR^{17}$, or $C(R^{18})_2$;
$R^{17}$ is hydrogen, $C_{1-9}$ alkyl, $C_{2-9}$ alkenyl, $C_{2-9}$ alkynyl, $C_{3-10}$ cycloalkyl, heterocyclyl, aryl, heteroaryl, —C(O)$R^{20}$, —C(O)O$R^{20}$, —C(O)N$R^{20}$, —S(O)$R^{20}$, —S(O)$_2$$R^{20}$, —S(O)N$R^{20}R^{21}$, or —S(O)$_2$N$R^{20}R^{21}$. wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $R^{17}$ is independently optionally substituted with one to five $Z^{1a}$; and
each $R^{18}$ is independently hydrogen or $Z^1$.

In some embodiments, provided is a compound of Formula IIIE:

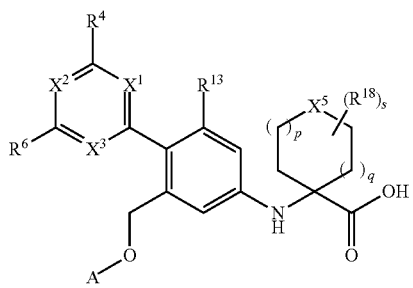

IIIE or a pharmaceutically acceptable salt, stereoisomer, mixture of stereoisomers, tautomer, isotopically enriched analog, or solvate thereof, wherein each of $R^6$, $R^{13}$, $R^{14}$, $X^1$, $X^2$, $X^3$, and A are independently as defined herein:

p is 0, 1, or 2;
q is 0, 1, or 2;
s is 0, 1, 2, or 3;
$X^5$ is absent, O, $NR^{17}$, or $C(R^{18})_2$;
$R^{17}$ is hydrogen, $C_{1-9}$ alkyl, $C_{2-9}$ alkenyl, $C_{2-9}$ alkynyl, $C_{3-10}$ cycloalkyl, heterocyclyl, aryl, heteroaryl, —C(O)$R^{20}$, —C(O)O$R^{20}$, —C(O)N$R^{20}$, —S(O)$R^{20}$, —S(O)$_2$$R^{20}$, —S(O)N$R^{20}R^{21}$, or —S(O)$_2$N$R^{20}R^{21}$. wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $R^{17}$ is independently optionally substituted with one to five $Z^{1a}$; and
each $R^{18}$ is independently hydrogen or $Z^1$.

In some embodiments, provided is a compound of Formula IIIF:

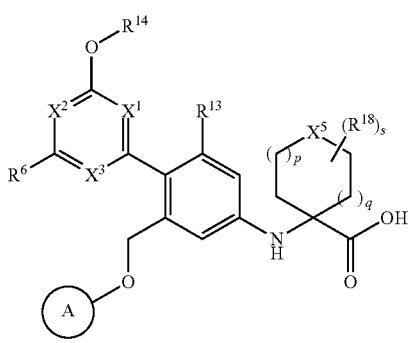

IIIF or a pharmaceutically acceptable salt, stereoisomer, mixture of stereoisomers, tautomer, isotopically enriched analog, or solvate thereof, wherein each of R, $R^{13}$, $R^{14}$, $X^1$, $X^2$, $X^3$, and ring A are independently as defined herein:

p is 0, 1, or 2;
q is 0, 1, or 2;
s is 0, 1, 2, or 3;
$X^5$ is absent, O, $NR^{17}$, or $C(R^{18})_2$;
$R^{17}$ is hydrogen, $C_{1-9}$ alkyl, $C_{2-9}$ alkenyl, $C_{2-9}$ alkynyl, $C_{3-10}$ cycloalkyl, heterocyclyl, aryl, heteroaryl, —C(O)$R^{20}$, —C(O)O$R^{20}$, —C(O)N$R^{20}$, —S(O)$R^{20}$, —S(O)$_2$$R^{20}$, —S(O)N$R^{20}R^{21}$, or —S(O)$_2$N$R^{20}R^{21}$. wherein each $C_{1-9}$ alkyl, $C_{2-9}$ alkenyl, $C_{2-9}$ alkynyl, $C_{3-10}$ cycloalkyl, heterocyclyl, aryl, or heteroaryl of $R^{17}$ is independently optionally substituted with one to five $Z^{1a}$; and
each $R^{18}$ is independently hydrogen or $Z^1$.

In some embodiments, $R^{14}$ is $C_{1-5}$ alkyl. In some embodiments, $R^{14}$ is methyl or ethyl. In some embodiments, $R^{14}$ is methyl. In some embodiments, $R^{14}$ is ethyl.

In some embodiments, $X^5$ is absent. In some embodiments, $X^5$ is O. In some embodiments, $X^5$ is $NR^4$. In some embodiments, $X^5$ is $C(R^{18})_2$.

In some embodiments, each $R^{18}$ is independently hydrogen or $Z^1$. In some embodiments, each $R^{18}$ is hydrogen. In some embodiments, $X^5$ is $CH_2$. In some embodiments, each $R^{18}$ is independently $Z^1$.

In some embodiments, each $R^{18}$ is independently halo. In some embodiments, each $R^{18}$ is fluoro.

In some embodiments, $R^{17}$ is hydrogen, $C_{1-9}$ alkyl, —C(O)$R^{20}$, or —C(O)O$R^{20}$.

In some embodiments, p is 0. In some embodiments, p is 1. In some embodiments, p is 2.

In some embodiments, q is 0. In some embodiments, q is 1. In some embodiments, q is 2.

In some embodiments, s is 0. In some embodiments, s is 1. In some embodiments, s is 2. In some embodiments, s is 3.

In some embodiments, provided is a compound of Formula IIIG:

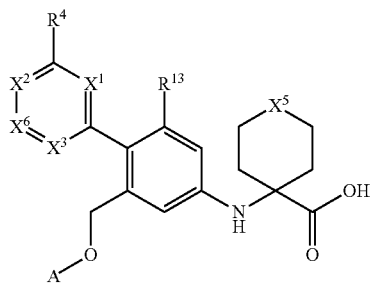

IIIG or a pharmaceutically acceptable salt, stereoisomer, mixture of stereoisomers, tautomer, isotopically enriched analog, or solvate thereof, wherein each of $R^4$, $R^{13}$, $X^1$, $X^2$, $X^3$, $X^5$, $X^6$, and A are independently as defined herein.

In some embodiments, $X^6$ is $CR^6$, In some embodiments, $X^6$ is N, In some embodiments, $X^5$ is O. In some embodiments, A is Ring A.

In some embodiments, provided is a compound of Formula IIIH:

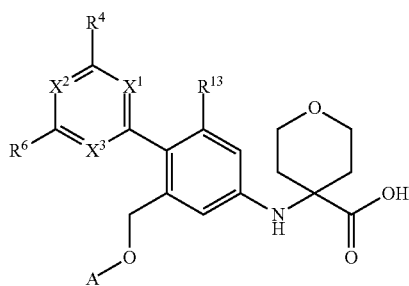

IIIH or a pharmaceutically acceptable salt, stereoisomer, mixture of stereoisomers, tautomer, isotopically enriched analog, or solvate thereof, wherein each of $R^4$, $R^6$, $R^{13}$, $X^1$, $X^2$, $X^3$, and A are independently as defined herein.

In some embodiments, $R^{13}$ is hydrogen. In some embodiments, A is $C_{1-6}$ alkyl. In some embodiments, A is $C_{3-4}$ alkyl. In some embodiments, A is $C_{3-10}$ cycloalkyl or heterocyclyl. In some embodiments, $R^4$ is —O—$R^{14}$.

In some embodiments, provided is a compound of Formula IIIJ:

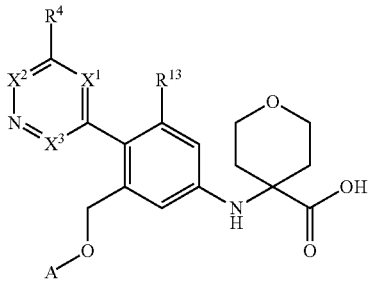

IIIJ or a pharmaceutically acceptable salt, stereoisomer, mixture of stereoisomers, tautomer, isotopically enriched analog, or solvate thereof, wherein each of $R^4$, $R^{13}$, $X^1$, $X^2$, $X^3$, and A are independently as defined herein.

In some embodiments, $R^{13}$ is hydrogen. In some embodiments, A is $C_{1-6}$ alkyl. In some embodiments, A is $C_{3-4}$ alkyl. In some embodiments, A is $C_{3-10}$ cycloalkyl or heterocyclyl. In some embodiments, $R^4$ is —O—$R^{14}$.

In some embodiments, provided is a compound of Formula IIIK:

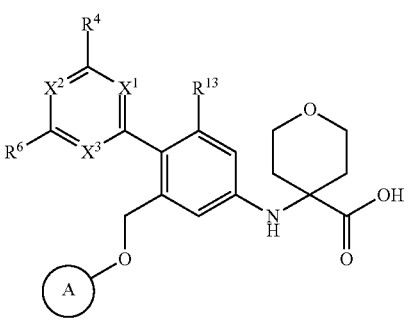

IIIK or a pharmaceutically acceptable salt, stereoisomer, mixture of stereoisomers, tautomer, isotopically enriched analog, or solvate thereof, wherein each of $R^4$, $R^6$, $R^{13}$, $X^1$, $X^2$, $X^3$, and ring A are independently as defined herein.

In some embodiments, $R^{13}$ is hydrogen. In some embodiments, ring A is $C_{3-10}$ cycloalkyl or heterocyclyl. In some embodiments, $R^4$ is —O—$R^{14}$.

In some embodiments, provided is compound selected from Table 1, or a pharmaceutically acceptable salt, stereoisomer, mixture of stereoisomers, tautomer, isotopically enriched analog, or solvate thereof:

TABLE 1

| Compound | Structure |
|---|---|
| 101 | ![structure of compound 101 with OMe, Me, MeO substituents on a biphenyl linked via NH to a propanoic acid, with an indanyloxy-methyl group] |

TABLE 1-continued
| Compound | Structure |
|---|---|
| 102 | 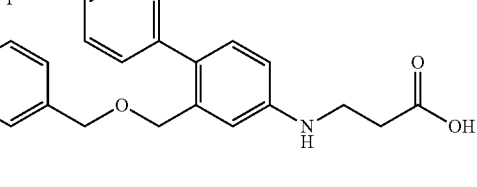 |
| 103 | 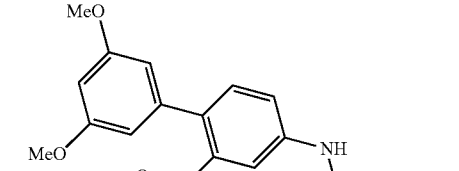 |
| 104 | 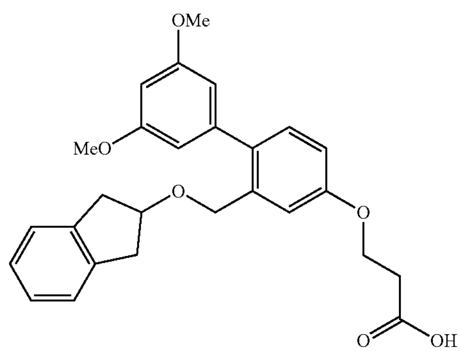 [SMILES: COc1cc(OC)cc(-c2ccc(OCCC(=O)O)cc2COC2Cc3ccccc3C2)c1] |
| 105 | 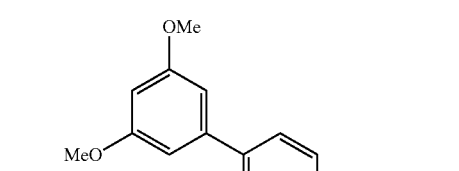 |
| 106 | 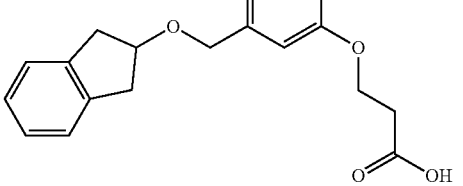 |

TABLE 1-continued

| Compound | Structure |
|---|---|
| 107 | *(chemical structure)* |
| 108 | *(chemical structure)* |
| 109 | *(chemical structure)* |
| 110 | *(chemical structure)* |

TABLE 1-continued

| Compound | Structure |
|---|---|
| 111 | 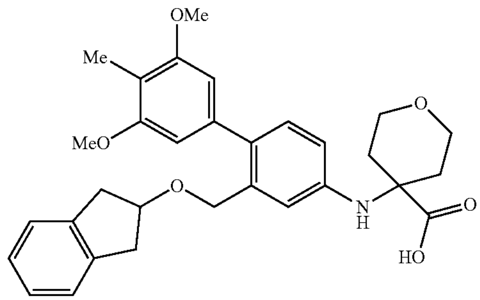 [SMILES: COc1cc(-c2ccc(NC3(C(=O)O)CCOCC3)cc2COC2Cc3ccccc3C2)cc(OC)c1C] |
| 112 | 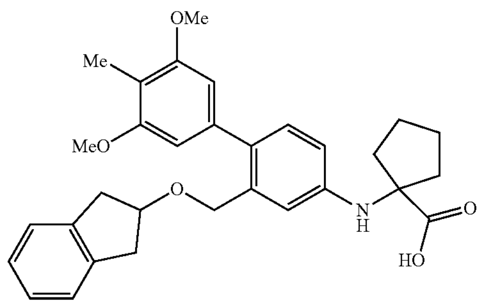 [SMILES: COc1cc(-c2ccc(NC3(C(=O)O)CCCC3)cc2COC2Cc3ccccc3C2)cc(OC)c1C] |
| 113 | 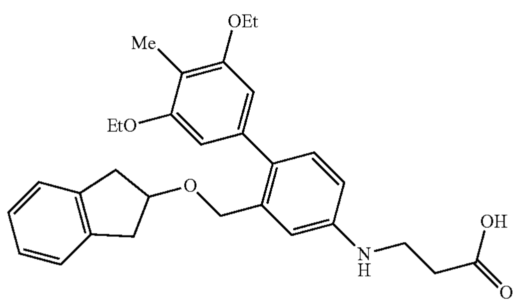 [SMILES: CCOc1cc(-c2ccc(NCCC(=O)O)cc2COC2Cc3ccccc3C2)cc(OCC)c1C] |
| 114 | 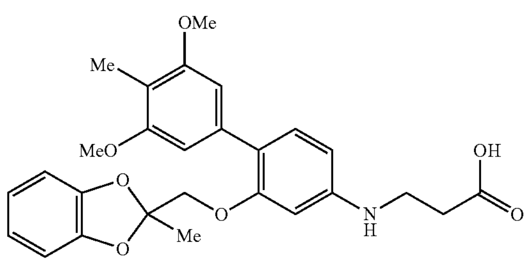 [SMILES: COc1cc(-c2ccc(NCCC(=O)O)cc2OCC2(C)Oc3ccccc3O2)cc(OC)c1C] |
| 115 | 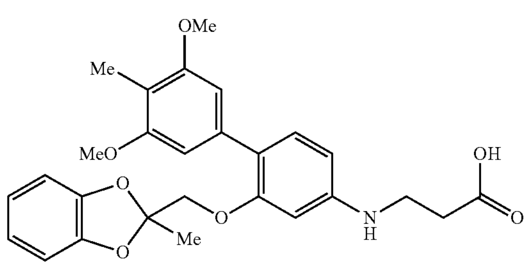 [SMILES: COc1cc(-c2ccc(NCCC(=O)O)cc2OCC2(C)Oc3ccccc3O2)cc(OC)c1C] |

TABLE 1-continued
| Compound | Structure |
|---|---|
| 116 | 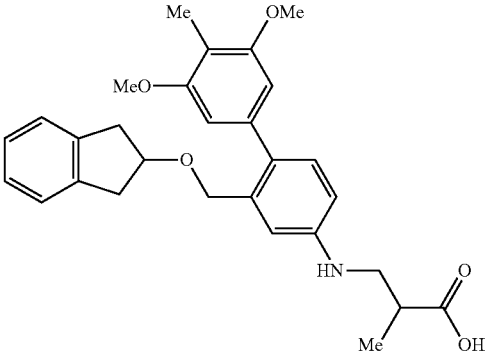 [SMILES: COc1cc(-c2ccc(NCC(C)C(=O)O)cc2COC2Cc3ccccc3C2)cc(OC)c1C] |
| 117 | 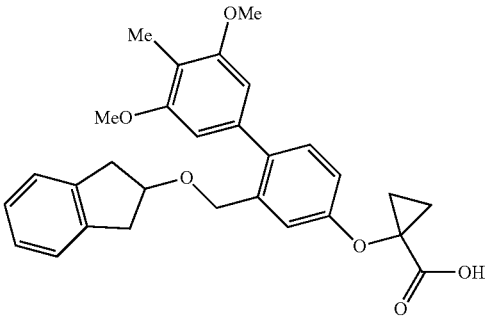 [SMILES: COc1cc(-c2ccc(OC3(C(=O)O)CC3)cc2COC2Cc3ccccc3C2)cc(OC)c1C] |
| 118 | 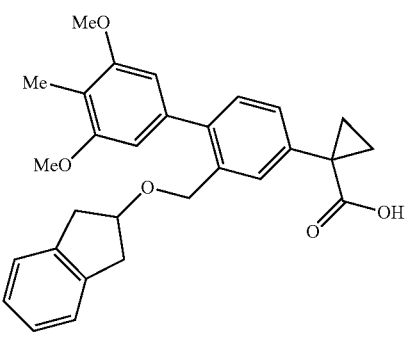 [SMILES: COc1cc(-c2ccc(C3(C(=O)O)CC3)cc2COC2Cc3ccccc3C2)cc(OC)c1C] |
| 119 | 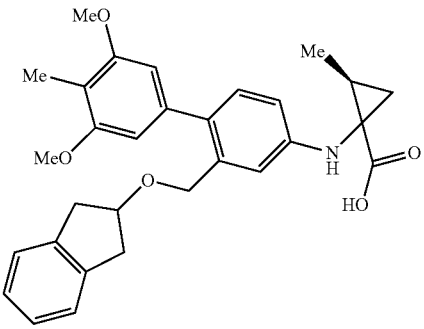 |

TABLE 1-continued

| Compound | Structure |
|---|---|
| 120 | 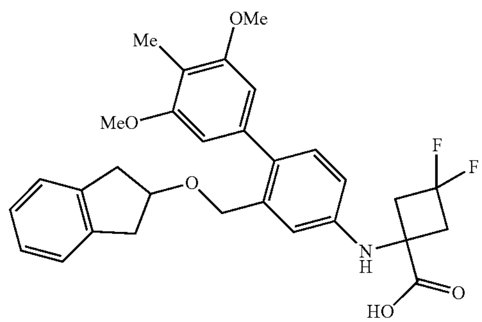 [SMILES: COc1cc(-c2ccc(NC3(C(=O)O)CC(F)(F)C3)cc2COC2Cc3ccccc3C2)cc(OC)c1C] |
| 121 | 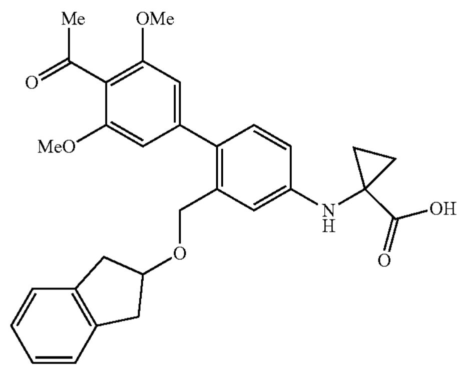 [SMILES: COc1cc(-c2ccc(NC3(C(=O)O)CC3)cc2COC2Cc3ccccc3C2)cc(OC)c1C(C)=O] |
| 122 | 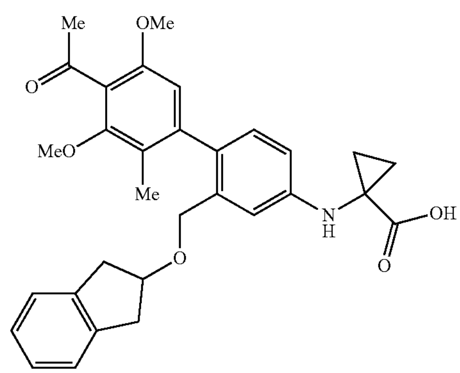 [SMILES: COc1cc(-c2ccc(NC3(C(=O)O)CC3)cc2COC2Cc3ccccc3C2)c(C)c(OC)c1C(C)=O] |
| 123 | 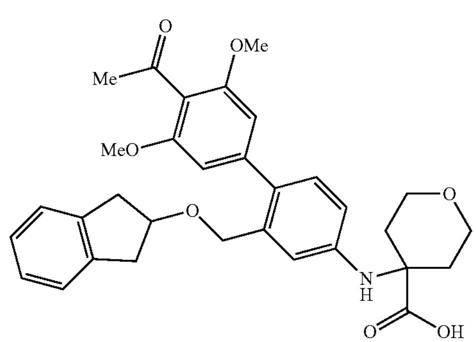 [SMILES: COc1cc(-c2ccc(NC3(C(=O)O)CCOCC3)cc2COC2Cc3ccccc3C2)cc(OC)c1C(C)=O] |

TABLE 1-continued

| Compound | Structure |
| --- | --- |
| 124 | (structure) |
| 125 | (structure) Enantiomer 1 |
| 126 | (structure) Enantiomer 2 |
| 127 | (structure) |

TABLE 1-continued

| Compound | Structure |
|---|---|
| 128 | (structure) |
| 129 | (structure) |
| 130 | (structure) Enantiomer 1 |
| 131 | (structure) Enantiomer 2 |

TABLE 1-continued

| Compound | Structure |
|---|---|
| 132 | 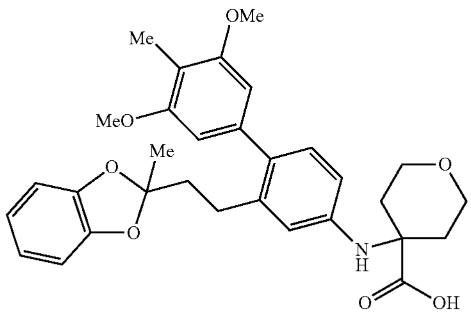 [SMILES: COc1cc(-c2ccc(NC3(C(=O)O)CCOCC3)cc2CCC2(C)Oc3ccccc3O2)cc(OC)c1C] |
| 133 | 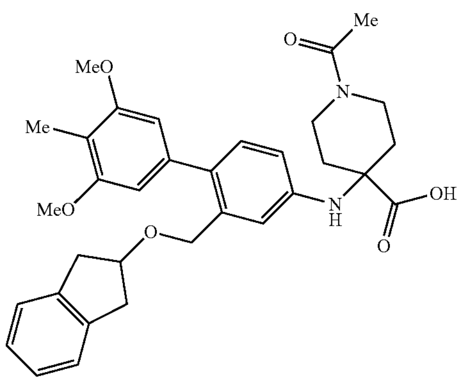 [SMILES: COc1cc(-c2ccc(NC3(C(=O)O)CCN(C(C)=O)CC3)cc2COC2Cc3ccccc3C2)cc(OC)c1C] |
| 134 | 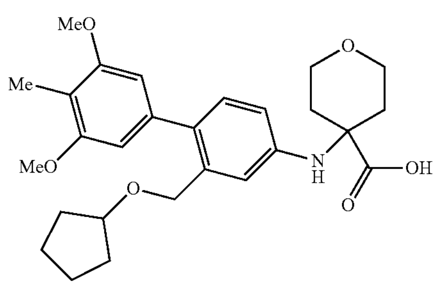 [SMILES: COc1cc(-c2ccc(NC3(C(=O)O)CCOCC3)cc2COC2CCCC2)cc(OC)c1C] |
| 135 | 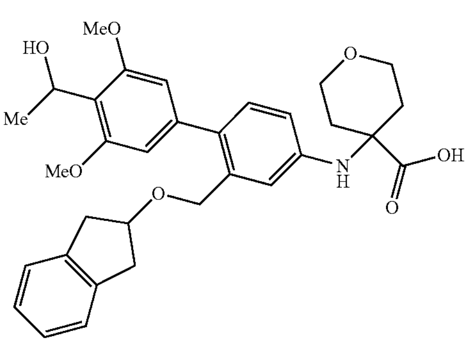 [SMILES: COc1cc(-c2ccc(NC3(C(=O)O)CCOCC3)cc2COC2Cc3ccccc3C2)cc(OC)c1C(C)O] |

TABLE 1-continued

| Compound | Structure |
|---|---|
| 136 | 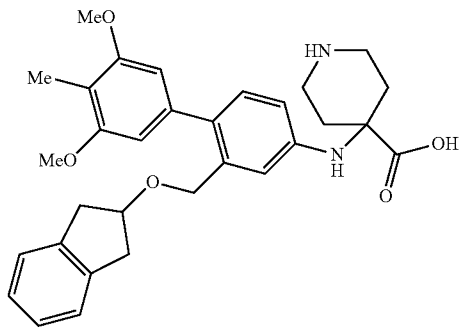 [SMILES: COc1cc(-c2ccc(NC3(C(=O)O)CCNCC3)cc2COC2Cc3ccccc3C2)cc(OC)c1C] |
| 137 | 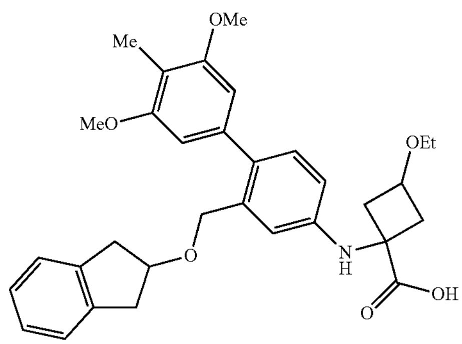 [SMILES: CCOC1CC(Nc2ccc(-c3cc(OC)c(C)c(OC)c3)c(COC3Cc4ccccc4C3)c2)(C(=O)O)C1] |
| 138 | 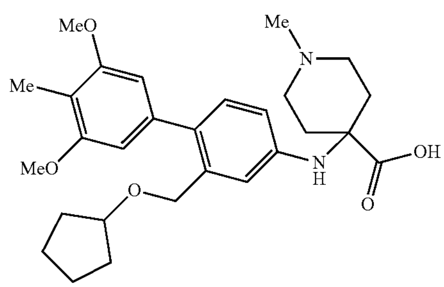 [SMILES: COc1cc(-c2ccc(NC3(C(=O)O)CCN(C)CC3)cc2COC2CCCC2)cc(OC)c1C] |
| 139 | 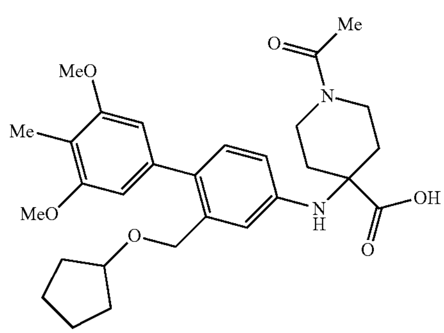 [SMILES: COc1cc(-c2ccc(NC3(C(=O)O)CCN(C(C)=O)CC3)cc2COC2CCCC2)cc(OC)c1C] |
| 140 | 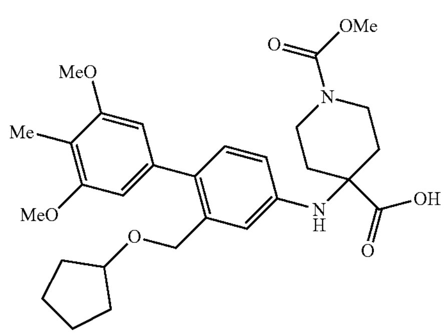 [SMILES: COC(=O)N1CCC(Nc2ccc(-c3cc(OC)c(C)c(OC)c3)c(COC3CCCC3)c2)(C(=O)O)CC1] |

TABLE 1-continued
| Compound | Structure |
|---|---|
| 141 | 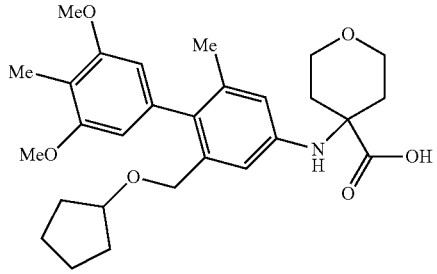 [SMILES: COc1cc(-c2c(C)cc(NC3(C(=O)O)CCOCC3)cc2COC2CCCC2)cc(OC)c1C] |
| 142 | 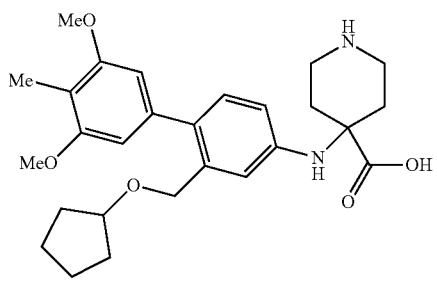 |
| 143 | 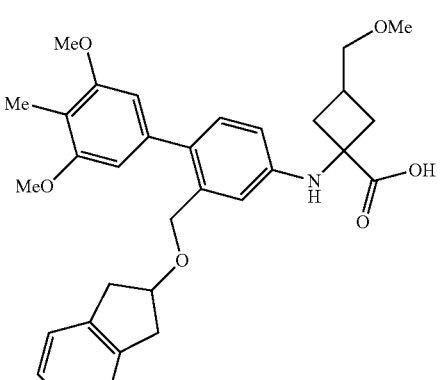 |
| 144 | 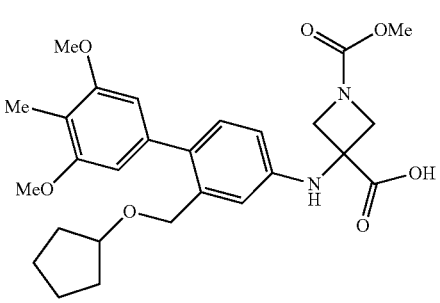 [SMILES: COC(=O)N1CC(Nc2ccc(-c3cc(OC)c(C)c(OC)c3)c(COC3CCCC3)c2)(C(=O)O)C1] |
| 145 | 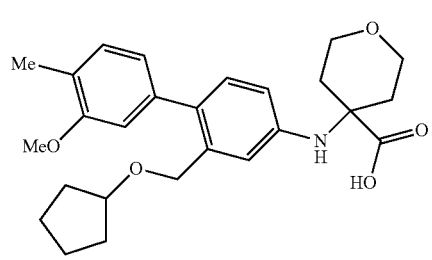 [SMILES: COc1cc(-c2ccc(NC3(C(=O)O)CCOCC3)cc2COC2CCCC2)ccc1C] |

TABLE 1-continued
| Compound | Structure |
|---|---|
| 146 | 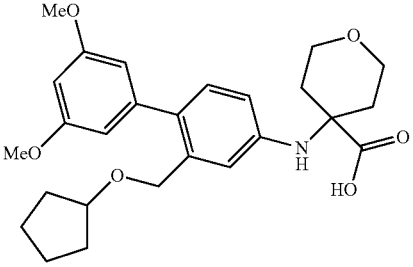 [SMILES: COc1cc(OC)cc(-c2ccc(NC3(C(=O)O)CCOCC3)cc2COC2CCCC2)c1] |
| 147 | 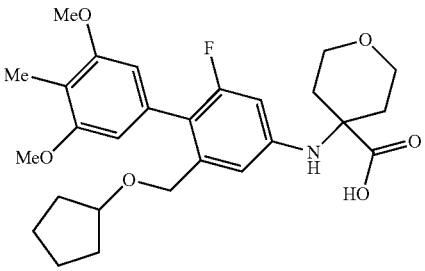 [SMILES: COc1cc(-c2c(F)cc(NC3(C(=O)O)CCOCC3)cc2COC2CCCC2)cc(OC)c1C] |
| 148 | 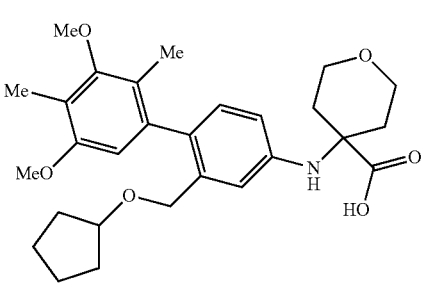 [SMILES: COc1cc(-c2ccc(NC3(C(=O)O)CCOCC3)cc2COC2CCCC2)c(C)c(OC)c1C] |
| 149 | 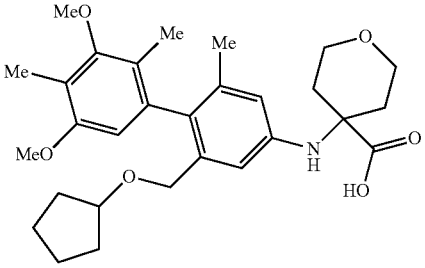 [SMILES: COc1cc(-c2c(C)cc(NC3(C(=O)O)CCOCC3)cc2COC2CCCC2)c(C)c(OC)c1C] |
| 151 | 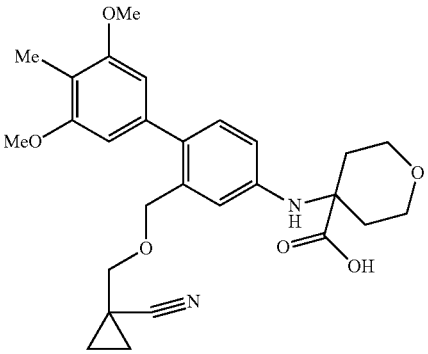 [SMILES: COc1cc(-c2ccc(NC3(C(=O)O)CCOCC3)cc2COCC2(C#N)CC2)cc(OC)c1C] |

TABLE 1-continued

| Compound | Structure |
|---|---|
| 152 | (structure) |
| 153 | (structure) |
| 154 | (structure) |
| 155 | (structure) |
| 156 | (structure) |

TABLE 1-continued

| Compound | Structure |
|---|---|
| 157 | (structure: 3,5-dimethoxyphenyl-biphenyl with cyclopentylmethoxymethyl substituent, NH linked to 4-(methoxycarbonyl)piperidine-4-carboxylic acid) |
| 158 | (structure: 3,5-dimethoxyphenyl-biphenyl with 2,3-dihydrobenzofuran-3-yloxymethyl substituent, NH linked to 4-(tetrahydropyran-4-yl)-4-carboxylic acid) Enantiomer 1 |
| 159 | (structure: same as 158) Enantiomer 2 |
| 160 | (structure: 3-methoxy-5-methylphenyl-2′,6-dimethylbiphenyl with cyclopentylmethoxymethyl substituent, NH linked to 4-(tetrahydropyran-4-yl)-4-carboxylic acid) |

TABLE 1-continued

| Compound | Structure |
|---|---|
| 161 | 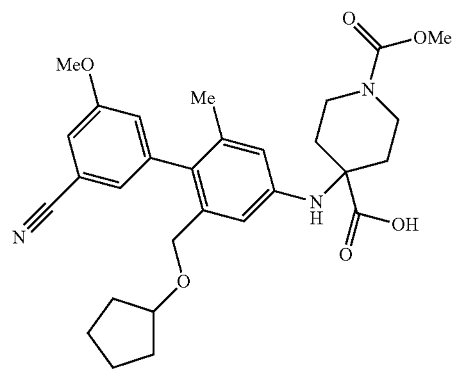 [SMILES: COC(=O)N1CCC(Nc2cc(C)c(-c3cc(C#N)cc(OC)c3)c(COC3CCCC3)c2)(C(=O)O)CC1] |
| 163 | 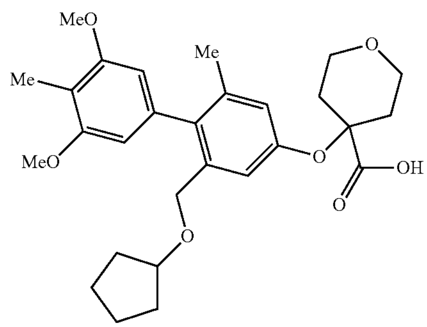 [SMILES: COc1cc(-c2c(C)cc(OC3(C(=O)O)CCOCC3)cc2COC2CCCC2)cc(OC)c1C] |
| 164 | 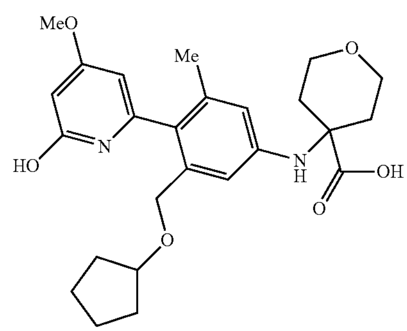 [SMILES: COc1cc(O)nc(-c2c(C)cc(NC3(C(=O)O)CCOCC3)cc2COC2CCCC2)c1] |
| 165 | 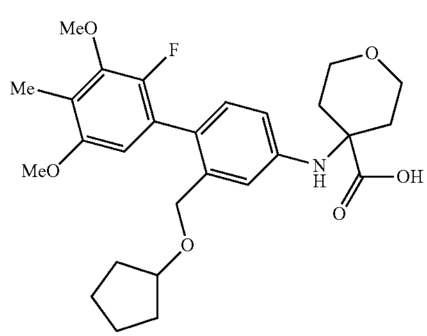 [SMILES: COc1cc(-c2ccc(NC3(C(=O)O)CCOCC3)cc2COC2CCCC2)c(F)c(OC)c1C] |

TABLE 1-continued

| Compound | Structure |
|---|---|
| 166 | 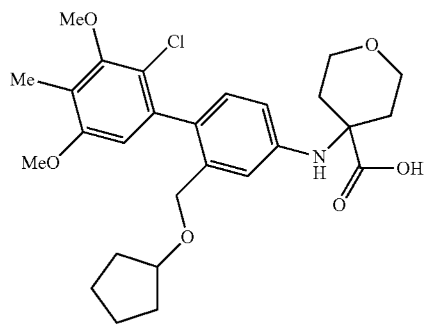 [SMILES: COc1cc(-c2ccc(NC3(C(=O)O)CCOCC3)cc2COC2CCCC2)c(Cl)c(OC)c1C] |
| 168 | 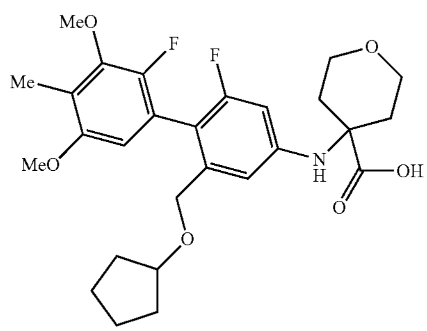 [SMILES: COc1cc(-c2c(F)cc(NC3(C(=O)O)CCOCC3)cc2COC2CCCC2)c(F)c(OC)c1C] |
| 169 | 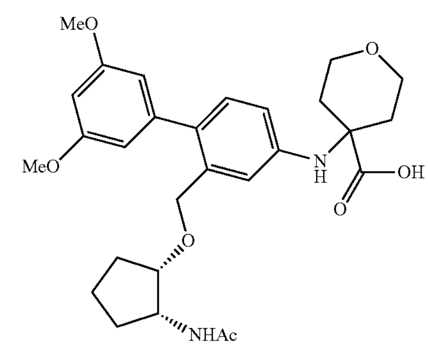 [SMILES: COc1cc(OC)cc(-c2ccc(NC3(C(=O)O)CCOCC3)cc2CO[C@H]2CCC[C@H]2NC(C)=O)c1] |
| 170 | 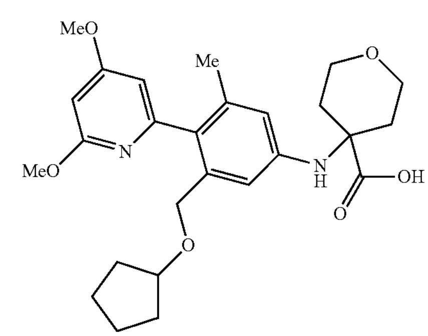 [SMILES: COc1cc(OC)nc(-c2c(C)cc(NC3(C(=O)O)CCOCC3)cc2COC2CCCC2)c1] |

TABLE 1-continued

| Compound | Structure |
|---|---|
| 171 | 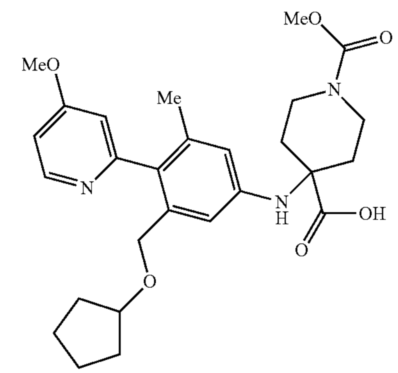 [SMILES: COC(=O)N1CCC(Nc2cc(C)c(-c3cc(OC)ccn3)c(COC3CCCC3)c2)(C(=O)O)CC1] |
| 172 | 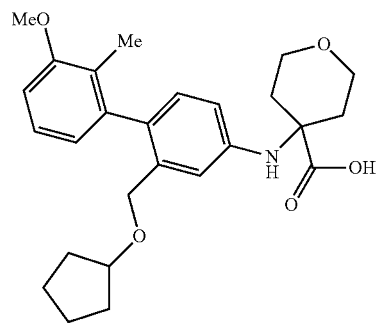 [SMILES: COc1cccc(-c2ccc(NC3(C(=O)O)CCOCC3)cc2COC2CCCC2)c1C] |
| 173 | 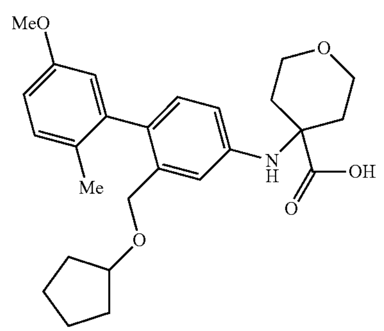 [SMILES: COc1ccc(C)c(-c2ccc(NC3(C(=O)O)CCOCC3)cc2COC2CCCC2)c1] |
| 174 | 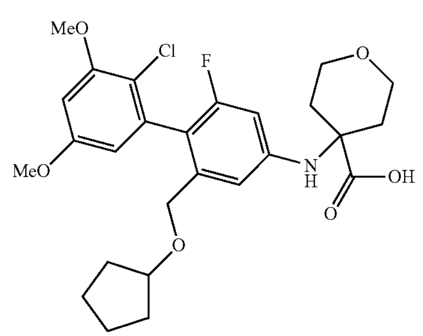 [SMILES: COc1cc(OC)c(Cl)c(-c2c(F)cc(NC3(C(=O)O)CCOCC3)cc2COC2CCCC2)c1] |

TABLE 1-continued
| Compound | Structure |
|---|---|
| 175 | 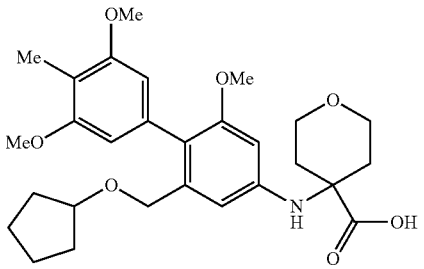 [SMILES: COc1cc(-c2c(COC3CCCC3)cc(NC3(C(=O)O)CCOCC3)cc2OC)cc(OC)c1C] |
| 176 | 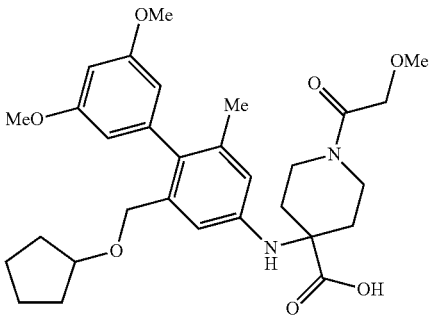 [SMILES: COCC(=O)N1CCC(Nc2cc(C)c(-c3cc(OC)cc(OC)c3)c(COC3CCCC3)c2)(C(=O)O)CC1] |
| 178 | 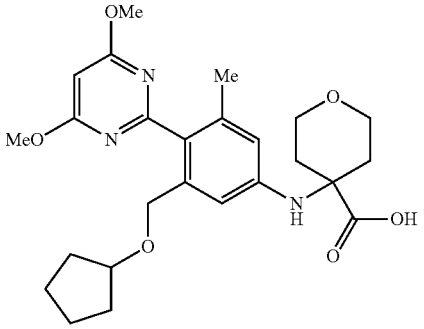 [SMILES: COc1cc(OC)nc(-c2c(C)cc(NC3(C(=O)O)CCOCC3)cc2COC2CCCC2)n1] |
| 179 | 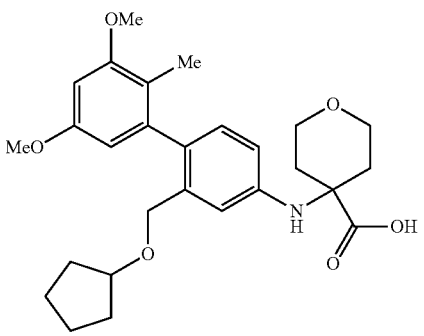 [SMILES: COc1cc(OC)c(C)c(-c2ccc(NC3(C(=O)O)CCOCC3)cc2COC2CCCC2)c1] |
| 180 | 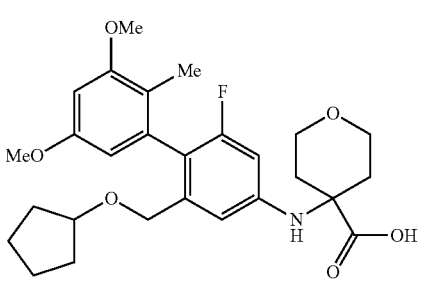 [SMILES: COc1cc(OC)c(C)c(-c2c(F)cc(NC3(C(=O)O)CCOCC3)cc2COC2CCCC2)c1] |

TABLE 1-continued

| Compound | Structure |
|---|---|
| 181 | (structure) |
| 182 | (structure) |
| 184 | (structure) |
| 185 | (structure) Enantiomer 1 |
| 186 | (structure) Enantiomer 2 |

TABLE 1-continued

| Compound | Structure |
|---|---|
| 188 | 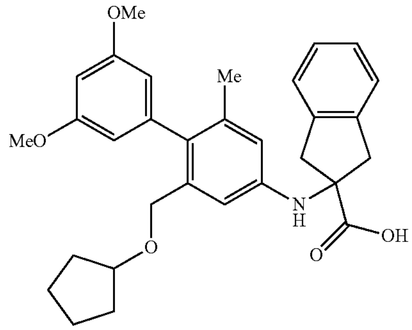 [SMILES: COc1cc(OC)cc(-c2c(C)cc(NC3(C(=O)O)Cc4ccccc4C3)cc2COC2CCCC2)c1] |
| 189 | 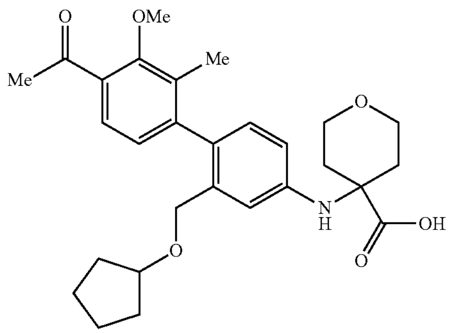 [SMILES: COc1c(C(C)=O)ccc(-c2ccc(NC3(C(=O)O)CCOCC3)cc2COC2CCCC2)c1C] |
| 190 | 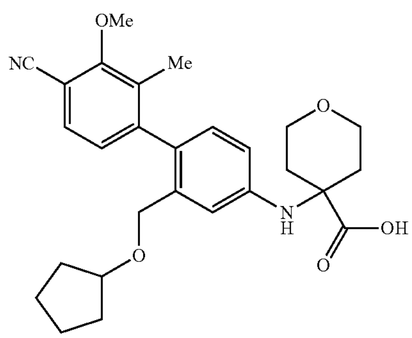 [SMILES: COc1c(C#N)ccc(-c2ccc(NC3(C(=O)O)CCOCC3)cc2COC2CCCC2)c1C] |
| 191 | 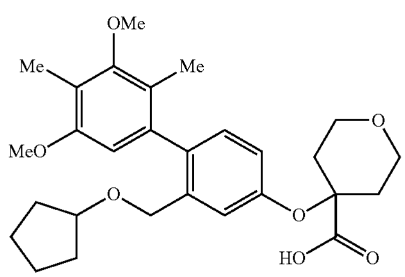 [SMILES: COc1cc(-c2ccc(OC3(C(=O)O)CCOCC3)cc2COC2CCCC2)c(C)c(OC)c1C] |
| 192 | 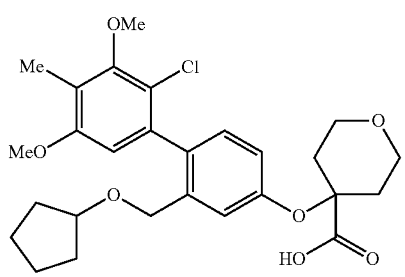 [SMILES: COc1cc(-c2ccc(OC3(C(=O)O)CCOCC3)cc2COC2CCCC2)c(Cl)c(OC)c1C] |

TABLE 1-continued
| Compound | Structure |
|---|---|
| 193 | 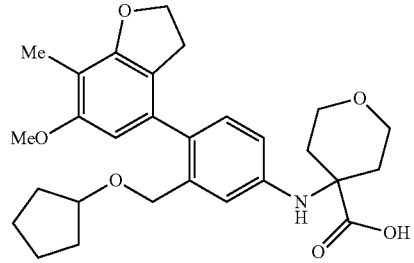 [SMILES: COc1cc(-c2ccc(NC3(C(=O)O)CCOCC3)cc2COC2CCCC2)c2c(c1C)OCC2] |
| 194 | 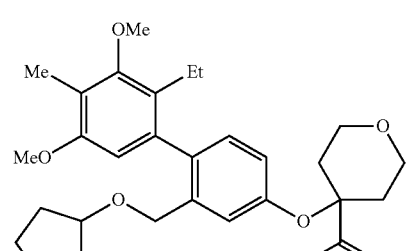 |
| 195 | 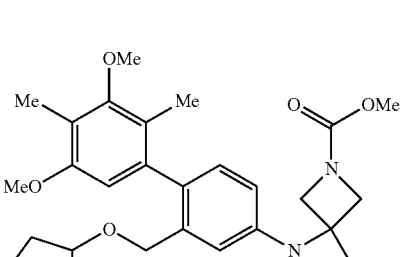 |
| 196 | 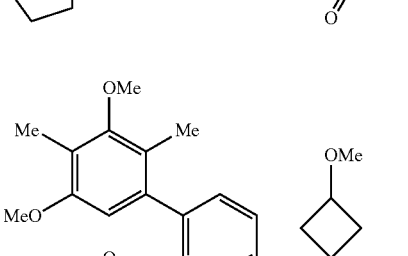<br>Enantiomer 1 |
| 197 | 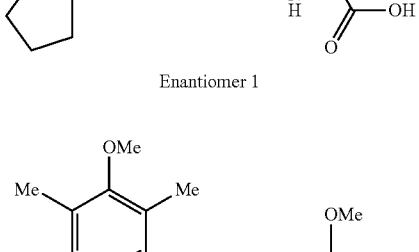<br>Enantiomer 2 |

TABLE 1-continued
| Compound | Structure |
|---|---|
| 198 | 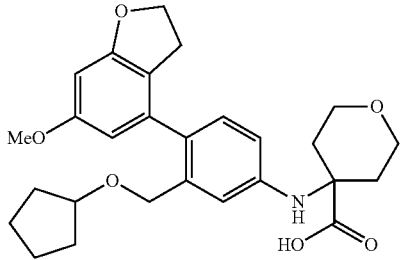 [SMILES: COc1cc2c(c(-c3ccc(NC4(C(=O)O)CCOCC4)cc3COC3CCCC3)c1)CCO2] |
| 199 | 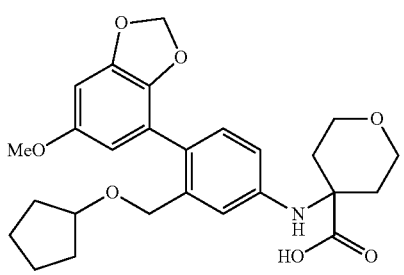 [SMILES: COc1cc2c(c(-c3ccc(NC4(C(=O)O)CCOCC4)cc3COC3CCCC3)c1)OCO2] |
| 200 | 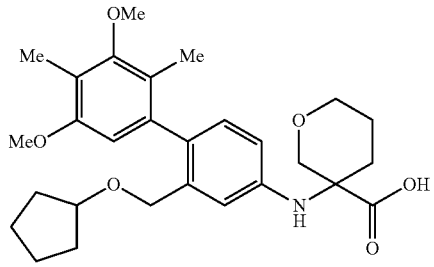
Enantiomer 1 |
| 201 | 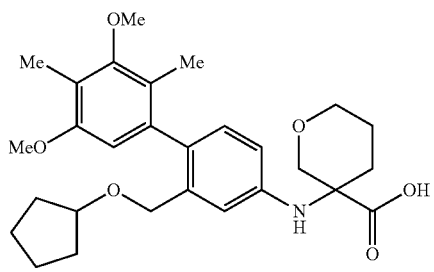
Enantiomer 2 |
| 202 | 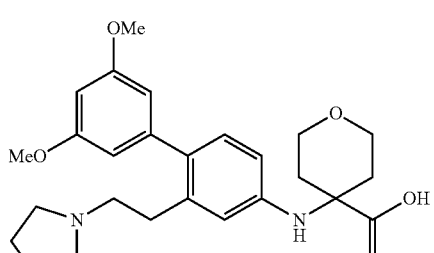 |

TABLE 1-continued

| Compound | Structure |
|---|---|
| 203 | 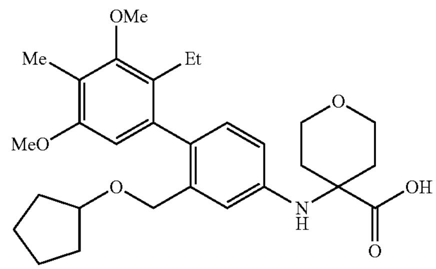 [SMILES: CCc1c(-c2ccc(NC3(C(=O)O)CCOCC3)cc2COC2CCCC2)cc(OC)c(C)c1OC] |
| 204 | Trans (mixture of enantiomers) |
| 205 | 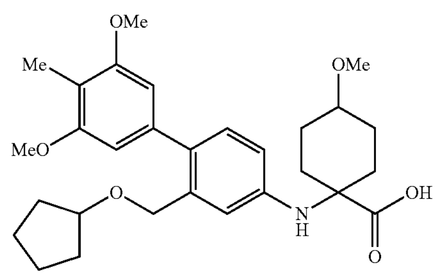 [SMILES: COc1cc(-c2ccc(NC3(C(=O)O)CCC(OC)CC3)cc2COC2CCCC2)cc(OC)c1C] |
| 206 | 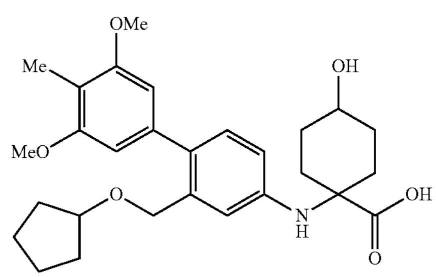 [SMILES: COc1cc(-c2ccc(NC3(C(=O)O)CCC(O)CC3)cc2COC2CCCC2)cc(OC)c1C] |
| 207 | 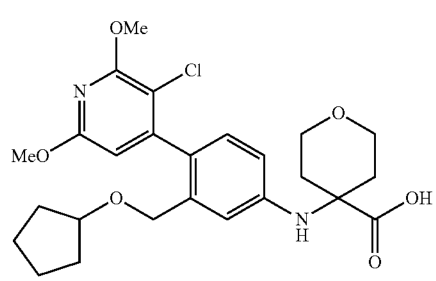 [SMILES: COc1cc(-c2ccc(NC3(C(=O)O)CCOCC3)cc2COC2CCCC2)c(Cl)c(OC)n1] |

TABLE 1-continued

| Compound | Structure |
|---|---|
| 208 | 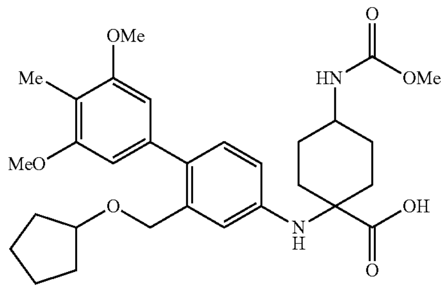 [SMILES: COC(=O)NC1CCC(Nc2ccc(-c3cc(OC)c(C)c(OC)c3)c(COC3CCCC3)c2)(C(=O)O)CC1] |
| 209 | 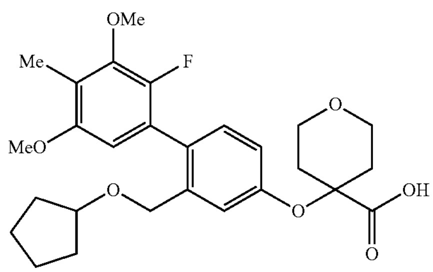 [SMILES: COc1cc(-c2ccc(OC3(C(=O)O)CCOCC3)cc2COC2CCCC2)c(F)c(OC)c1C] |
| 210 | Enantiomer 1 |
| 211 | Enantiomer 2 |
| 212 | 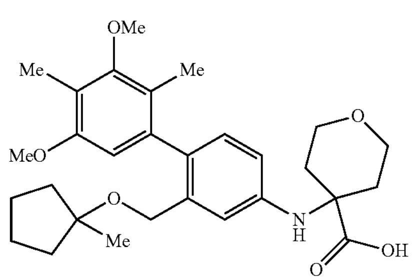 [SMILES: COc1cc(-c2ccc(NC3(C(=O)O)CCOCC3)cc2COC2(C)CCCC2)c(C)c(OC)c1C] |

TABLE 1-continued
| Compound | Structure |
|---|---|
| 213 | 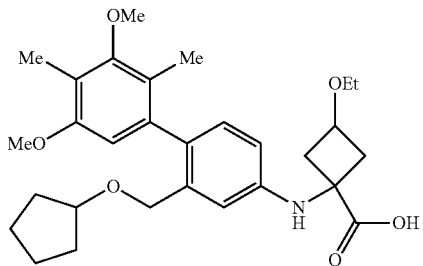
Enantiomer 1 |
| 214 | 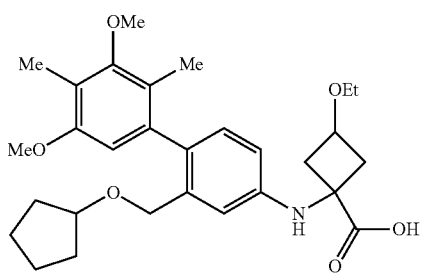
Enantiomer 2 |
| 215 | 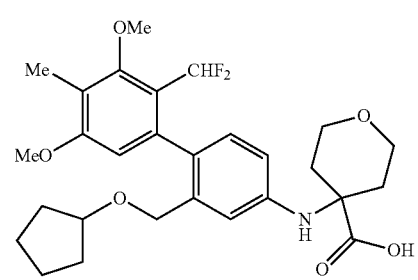 [SMILES: COc1cc(-c2ccc(NC3(C(=O)O)CCOCC3)cc2COC2CCCC2)c(C(F)F)c(OC)c1C] |
| 216 | 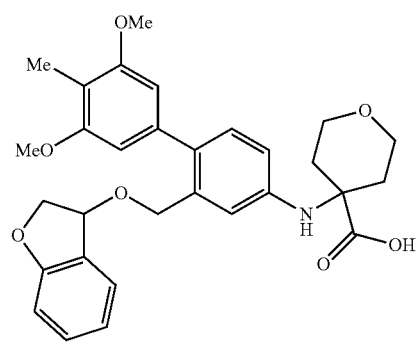
Enantiomer 1 |

TABLE 1-continued

| Compound | Structure |
|---|---|
| 217 | (structure shown) Enantiomer 2 |
| 218 | (structure shown) |
| 219 | (structure shown) |
| 220 | (structure shown) |

TABLE 1-continued

| Compound | Structure |
|---|---|
| 222 | (structure) |
| 223 | (structure) Enantiomer 1 |
| 224 | (structure) Enantiomer 2 |
| 225 | (structure) |

TABLE 1-continued
| Compound | Structure |
|---|---|
| 226 | 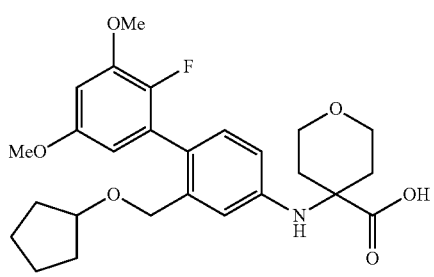 [SMILES: COc1cc(OC)c(F)c(-c2ccc(NC3(C(=O)O)CCOCC3)cc2COC2CCCC2)c1] |
| 227 | 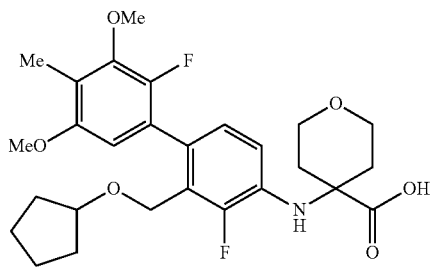 [SMILES: COc1cc(-c2ccc(NC3(C(=O)O)CCOCC3)c(F)c2COC2CCCC2)c(F)c(OC)c1C] |
| 228 | 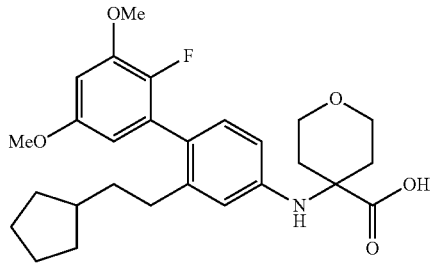 [SMILES: COc1cc(OC)c(F)c(-c2ccc(NC3(C(=O)O)CCOCC3)cc2CCC2CCCC2)c1] |
| 229 | 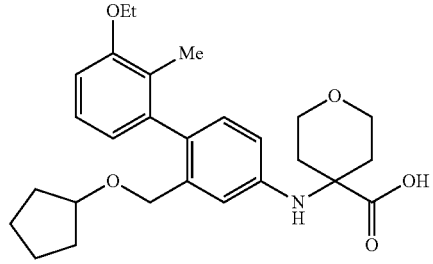 [SMILES: CCOc1cccc(-c2ccc(NC3(C(=O)O)CCOCC3)cc2COC2CCCC2)c1C] |
| 230 | 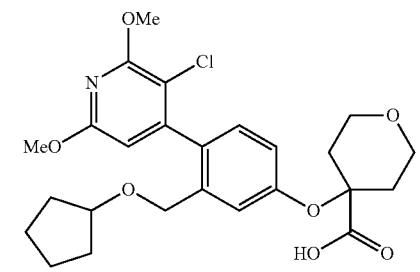 [SMILES: COc1cc(-c2ccc(OC3(C(=O)O)CCOCC3)cc2COC2CCCC2)c(Cl)c(OC)n1] |

TABLE 1-continued

| Compound | Structure |
|---|---|
| 232 | 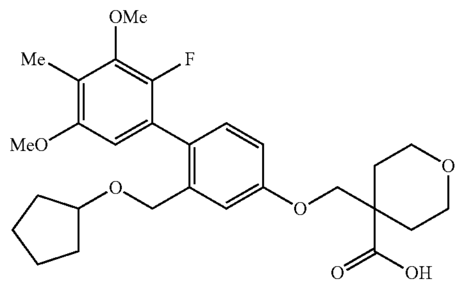 [SMILES: COc1cc(-c2ccc(OCC3(C(=O)O)CCOCC3)cc2COC2CCCC2)c(F)c(OC)c1C] |
| 233 | 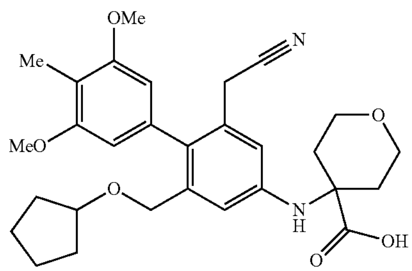 [SMILES: COc1cc(-c2c(CC#N)cc(NC3(C(=O)O)CCOCC3)cc2COC2CCCC2)cc(OC)c1C] |
| 234 | 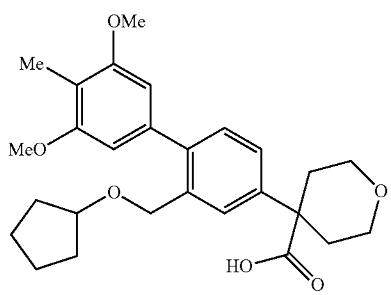 [SMILES: COc1cc(-c2ccc(C3(C(=O)O)CCOCC3)cc2COC2CCCC2)cc(OC)c1C] |
| 235 | 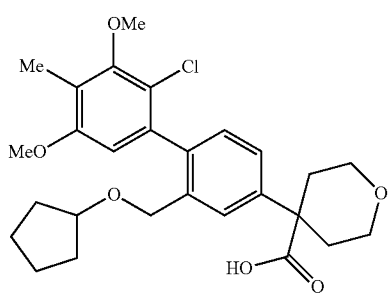 [SMILES: COc1cc(-c2ccc(C3(C(=O)O)CCOCC3)cc2COC2CCCC2)c(Cl)c(OC)c1C] |
| 236 | 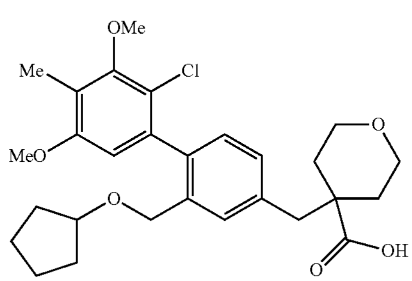 |

TABLE 1-continued
| Compound | Structure |
|---|---|
| 237 | 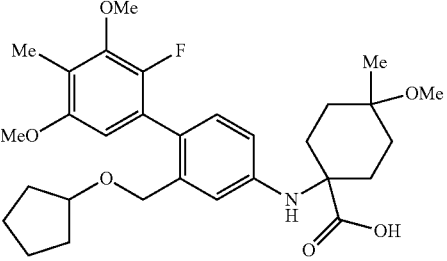<br>Enantiomer 1 |
| 238 | 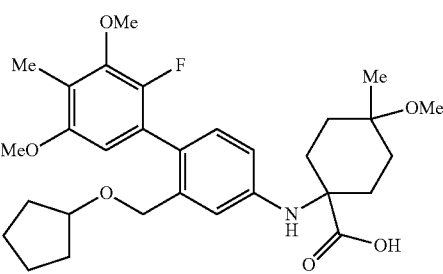<br>Enantiomer 2 |
| 239 | 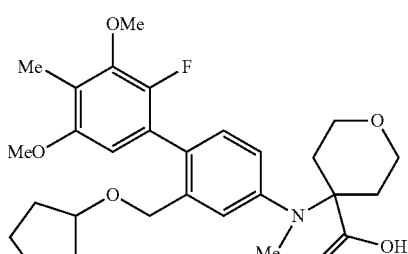 |
| 240 | 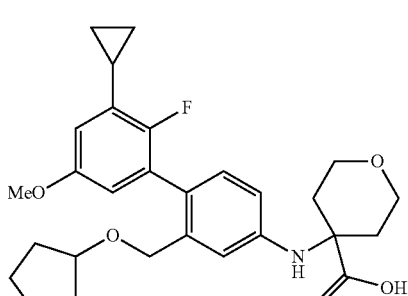 |
| 241 | 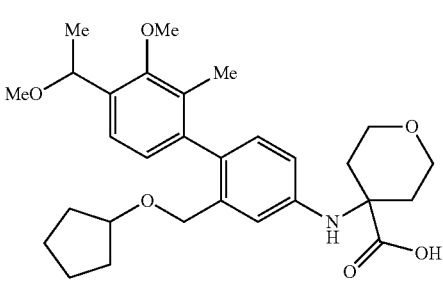<br>Enantiomer 1 |

TABLE 1-continued
| Compound | Structure |
|---|---|
| 242 | 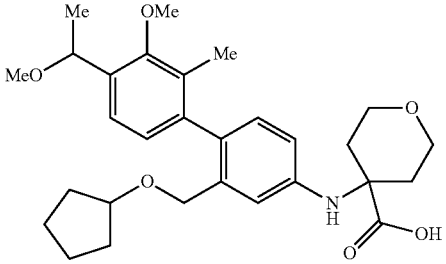  Enantiomer 2 |
| 243 | 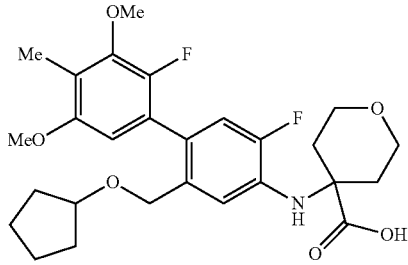 [SMILES: COc1cc(-c2cc(F)c(NC3(C(=O)O)CCOCC3)cc2COC2CCCC2)c(F)c(OC)c1C] |
| 244 | 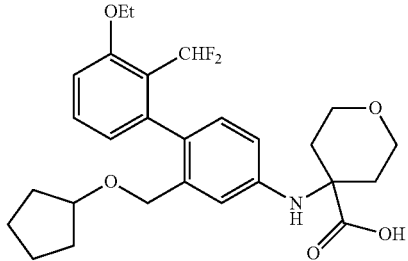 [SMILES: CCOc1cccc(-c2ccc(NC3(C(=O)O)CCOCC3)cc2COC2CCCC2)c1C(F)F] |
| 245 | 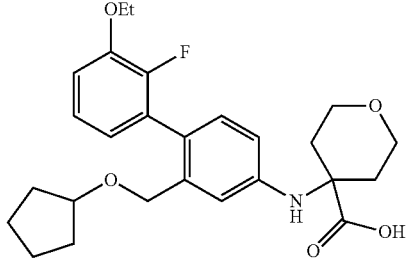 [SMILES: CCOc1cccc(-c2ccc(NC3(C(=O)O)CCOCC3)cc2COC2CCCC2)c1F] |
| 246 | 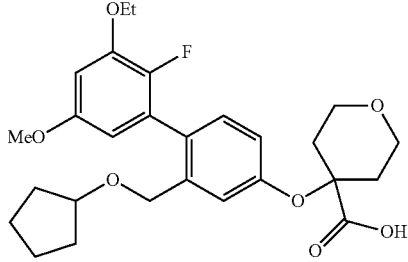 [SMILES: CCOc1cc(OC)cc(-c2ccc(OC3(C(=O)O)CCOCC3)cc2COC2CCCC2)c1F] |

TABLE 1-continued

| Compound | Structure |
|---|---|
| 247 | 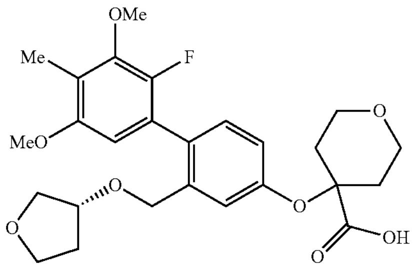 [SMILES: COc1cc(-c2ccc(OC3(C(=O)O)CCOCC3)cc2CO[C@@H]2CCOC2)c(F)c(OC)c1C] |
| 248 | 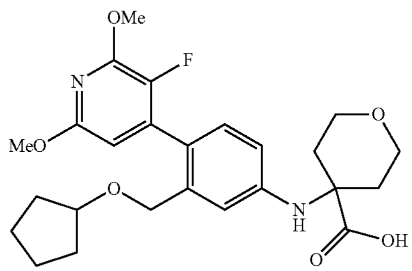 [SMILES: COc1cc(-c2ccc(NC3(C(=O)O)CCOCC3)cc2COC2CCCC2)c(F)c(OC)n1] |
| 249 | 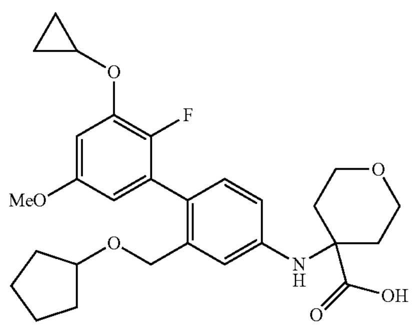 [SMILES: COc1cc(OC2CC2)c(F)c(-c2ccc(NC3(C(=O)O)CCOCC3)cc2COC2CCCC2)c1] |
| 250 | 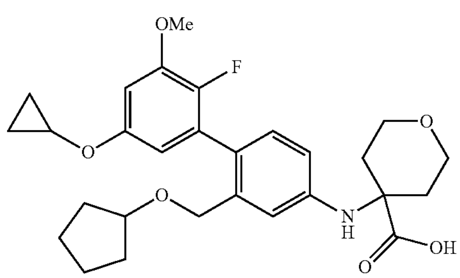 [SMILES: COc1cc(OC2CC2)cc(-c2ccc(NC3(C(=O)O)CCOCC3)cc2COC2CCCC2)c1F] |
| 251 | 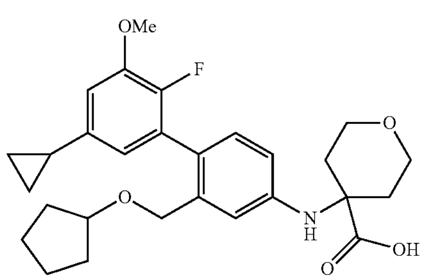 [SMILES: COc1cc(C2CC2)cc(-c2ccc(NC3(C(=O)O)CCOCC3)cc2COC2CCCC2)c1F] |

TABLE 1-continued
| Compound | Structure |
|---|---|
| 252 | 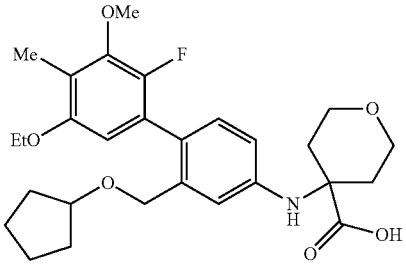 [SMILES: CCOc1cc(-c2ccc(NC3(C(=O)O)CCOCC3)cc2COC2CCCC2)c(F)c(OC)c1C] |
| 253 | 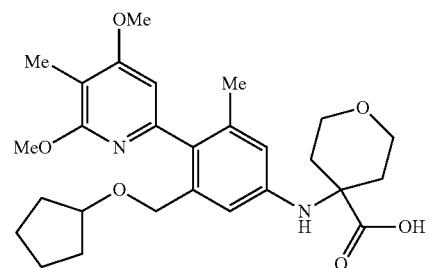 [SMILES: COc1cc(-c2c(C)cc(NC3(C(=O)O)CCOCC3)cc2COC2CCCC2)nc(OC)c1C] |
| 254 | 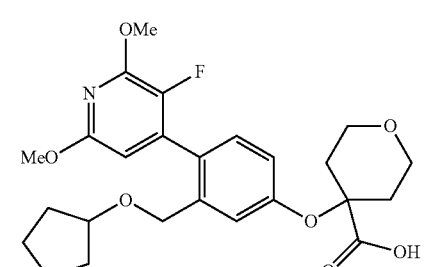 |
| 255 | 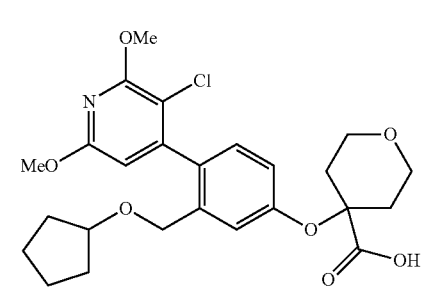 [SMILES: COc1cc(-c2ccc(OC3(C(=O)O)CCOCC3)cc2COC2CCCC2)c(Cl)c(OC)n1] |
| 256 | 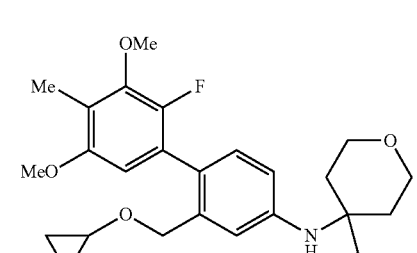 |

TABLE 1-continued

| Compound | Structure |
|---|---|
| 257 | 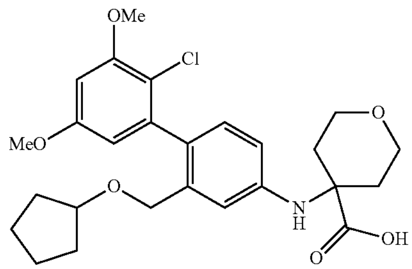 [SMILES: COc1cc(OC)c(Cl)c(-c2ccc(NC3(C(=O)O)CCOCC3)cc2COC2CCCC2)c1] |
| 259 | Enantiomer 1 |
| 260 | Enantiomer 2 |
| 261 | 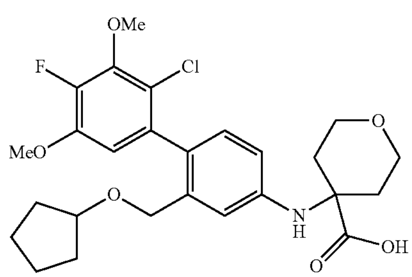 [SMILES: COc1cc(-c2ccc(NC3(C(=O)O)CCOCC3)cc2COC2CCCC2)c(Cl)c(OC)c1F] |
| 262 | 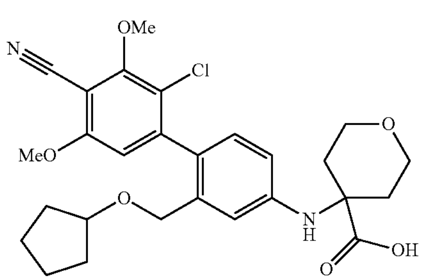 [SMILES: COc1cc(-c2ccc(NC3(C(=O)O)CCOCC3)cc2COC2CCCC2)c(Cl)c(OC)c1C#N] |

TABLE 1-continued

| Compound | Structure |
|---|---|
| 263 | 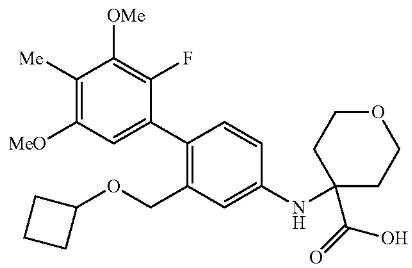 [SMILES: COc1cc(-c2ccc(NC3(C(=O)O)CCOCC3)cc2COC2CCC2)c(F)c(OC)c1C] |
| 264 | 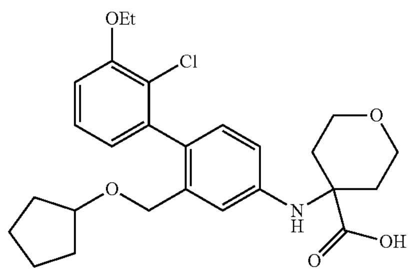 [SMILES: CCOc1cccc(-c2ccc(NC3(C(=O)O)CCOCC3)cc2COC2CCCC2)c1Cl] |
| 265 | 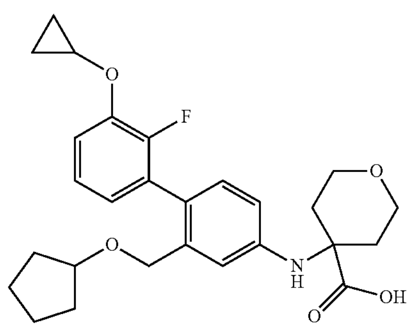 [SMILES: O=C(O)C1(Nc2ccc(-c3cccc(OC4CC4)c3F)c(COC3CCCC3)c2)CCOCC1] |
| 266 | 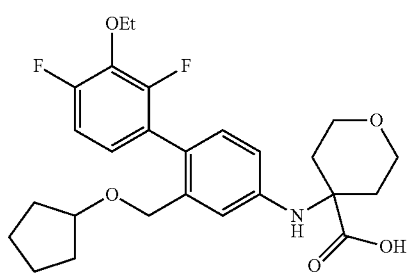 [SMILES: CCOc1c(F)ccc(-c2ccc(NC3(C(=O)O)CCOCC3)cc2COC2CCCC2)c1F] |
| 267 | 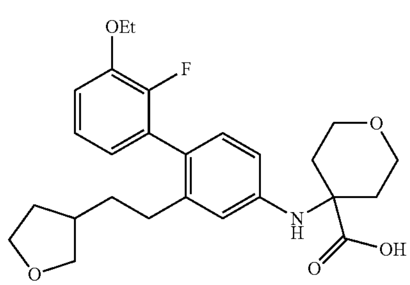 [SMILES: CCOc1cccc(-c2ccc(NC3(C(=O)O)CCOCC3)cc2CCC2CCOC2)c1F] |

TABLE 1-continued
| Compound | Structure |
|---|---|
| 268 | 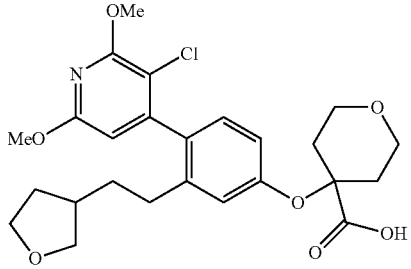<br>Enantiomer 1 |
| 269 | 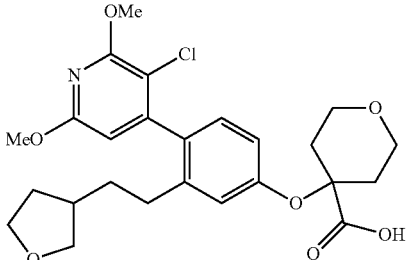<br>Enantiomer 2 |
| 270 | 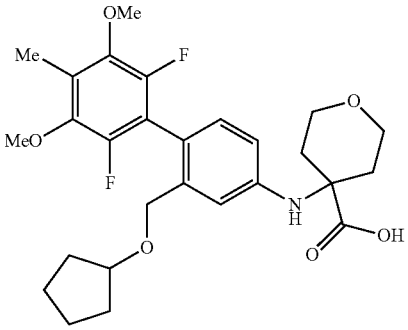 [SMILES: COc1c(C)c(OC)c(F)c(-c2ccc(NC3(C(=O)O)CCOCC3)cc2COC2CCCC2)c1F] |
| 271 | 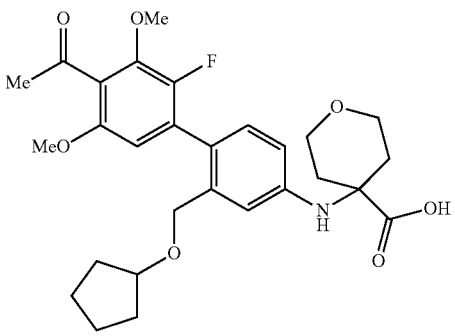 [SMILES: COc1cc(-c2ccc(NC3(C(=O)O)CCOCC3)cc2COC2CCCC2)c(F)c(OC)c1C(C)=O] |

TABLE 1-continued

| Compound | Structure |
|---|---|
| 272 | 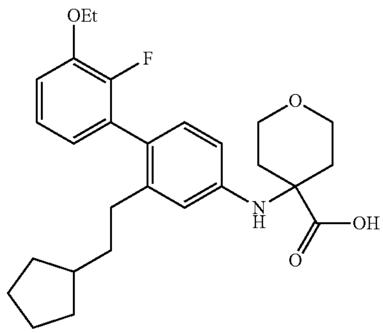 [SMILES: CCOc1cccc(-c2ccc(NC3(C(=O)O)CCOCC3)cc2CCC2CCCC2)c1F] |
| 273 | 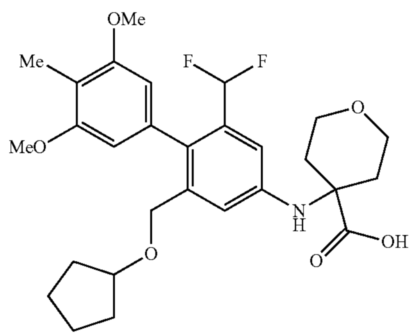 [SMILES: COc1cc(-c2c(COC3CCCC3)cc(NC3(C(=O)O)CCOCC3)cc2C(F)F)cc(OC)c1C] |
| 274 | 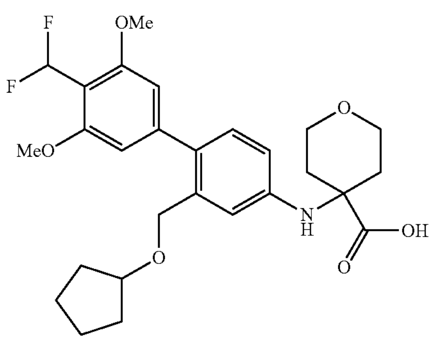 [SMILES: COc1cc(-c2ccc(NC3(C(=O)O)CCOCC3)cc2COC2CCCC2)cc(OC)c1C(F)F] |
| 275 | 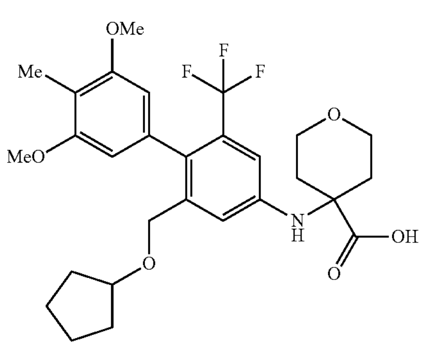 [SMILES: COc1cc(-c2c(COC3CCCC3)cc(NC3(C(=O)O)CCOCC3)cc2C(F)(F)F)cc(OC)c1C] |

TABLE 1-continued
| Compound | Structure |
|---|---|
| 276 | 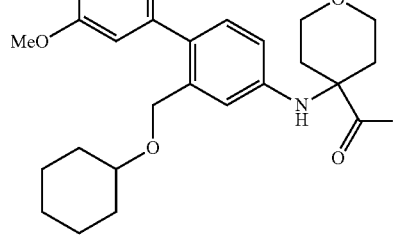 |
| 277 | 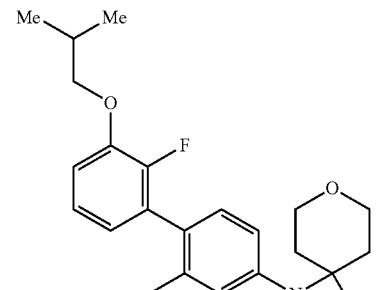 |
| 278 | 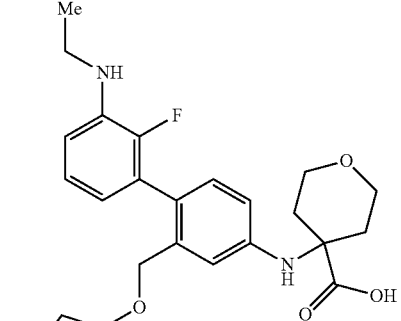 |
| 279 | 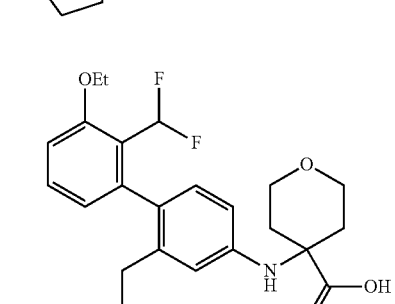 |

TABLE 1-continued
| Compound | Structure |
|---|---|
| 280 | 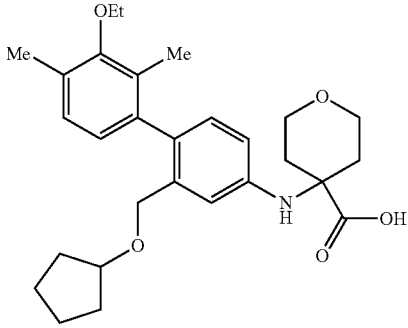 |
| 281 | 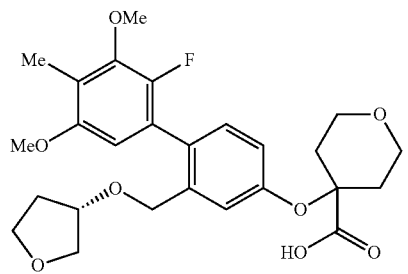 [SMILES: COc1cc(-c2ccc(OC3(C(=O)O)CCOCC3)cc2CO[C@H]2CCOC2)c(F)c(OC)c1C] |
| 282 | 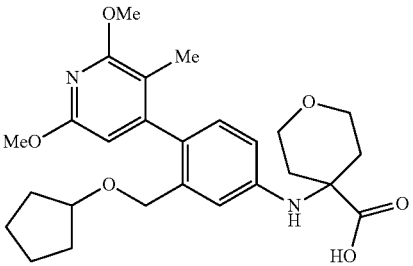 |
| 283 | 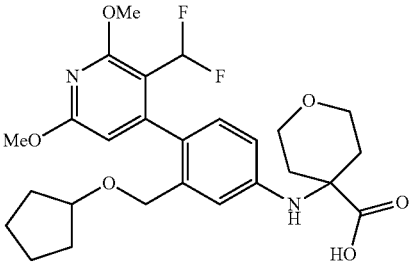 [SMILES: COc1cc(-c2ccc(NC3(C(=O)O)CCOCC3)cc2COC2CCCC2)c(C(F)F)c(OC)n1] |
| 284 | 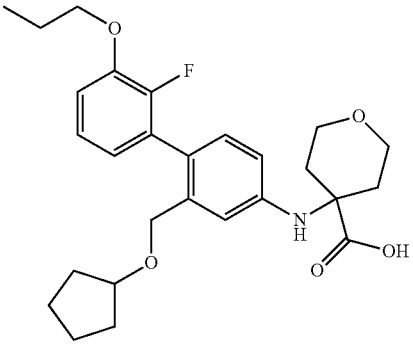 [SMILES: CCCOc1cccc(-c2ccc(NC3(C(=O)O)CCOCC3)cc2COC2CCCC2)c1F] |

TABLE 1-continued
| Compound | Structure |
|---|---|
| 285 | 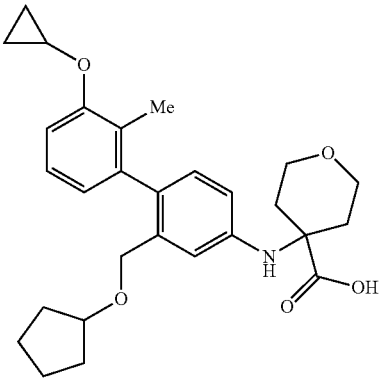 [SMILES: Cc1c(OC2CC2)cccc1-c1ccc(NC2(C(=O)O)CCOCC2)cc1COC1CCCC1] |
| 286 | 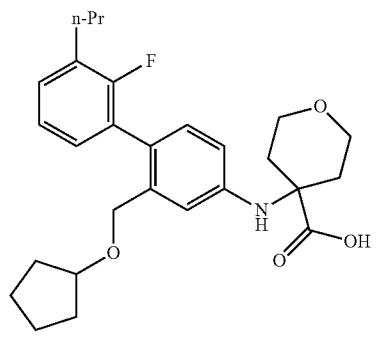 |
| 287 | 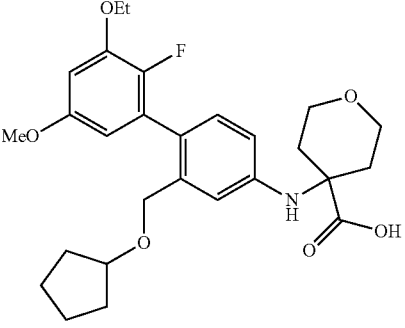 [SMILES: CCOc1cc(OC)cc(-c2ccc(NC3(C(=O)O)CCOCC3)cc2COC2CCCC2)c1F] |
| 288 | 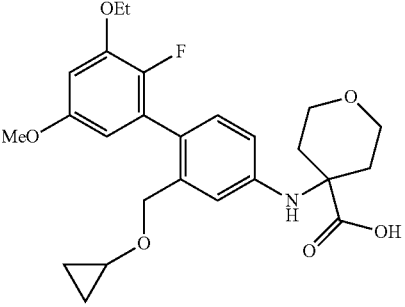 [SMILES: CCOc1cc(OC)cc(-c2ccc(NC3(C(=O)O)CCOCC3)cc2COC2CC2)c1F] |

TABLE 1-continued

| Compound | Structure |
|---|---|
| 289 | 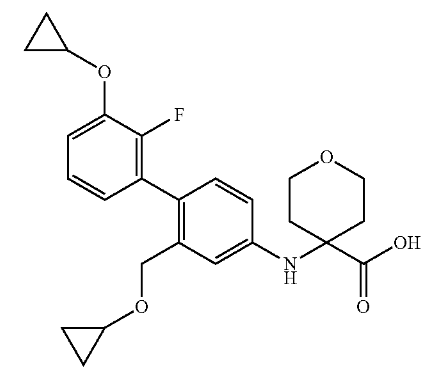 [SMILES: O=C(O)C1(Nc2ccc(-c3cccc(OC4CC4)c3F)c(COC3CC3)c2)CCOCC1] |
| 290 | 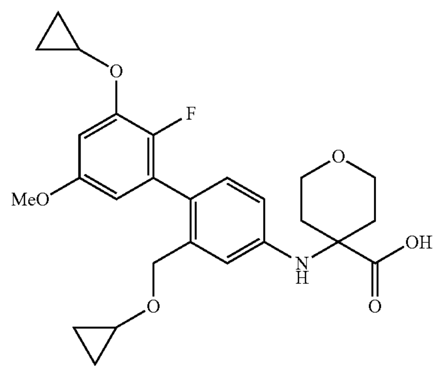 [SMILES: COc1cc(OC2CC2)c(F)c(-c2ccc(NC3(C(=O)O)CCOCC3)cc2COC2CC2)c1] |
| 291 | 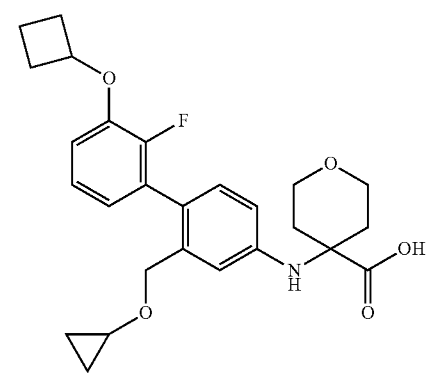 [SMILES: O=C(O)C1(Nc2ccc(-c3cccc(OC4CCC4)c3F)c(COC3CC3)c2)CCOCC1] |
| 292 | 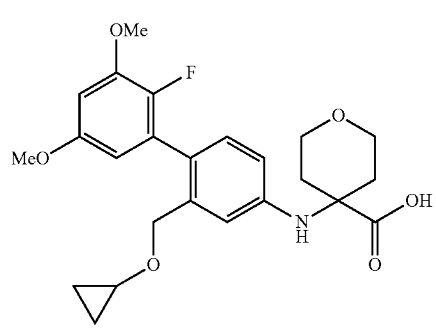 |

TABLE 1-continued
| Compound | Structure |
|---|---|
| 293 | 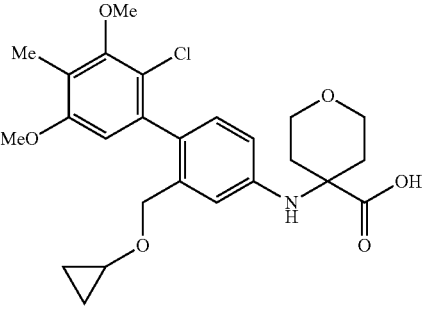 |
| 294 | 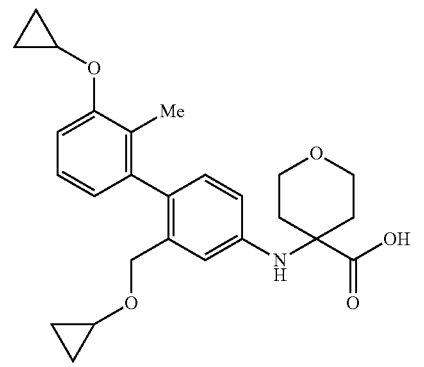 [SMILES: Cc1c(OC2CC2)cccc1-c1ccc(NC2(C(=O)O)CCOCC2)cc1COC1CC1] |
| 295 | 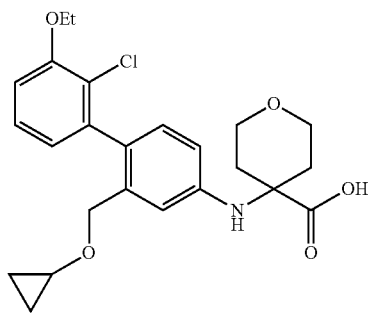 [SMILES: CCOc1cccc(-c2ccc(NC3(C(=O)O)CCOCC3)cc2COC2CC2)c1Cl] |
| 296 | 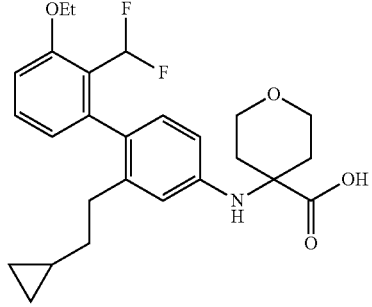 [SMILES: CCOc1cccc(-c2ccc(NC3(C(=O)O)CCOCC3)cc2CCC2CC2)c1C(F)F] |

TABLE 1-continued
| Compound | Structure |
|---|---|
| 297 | 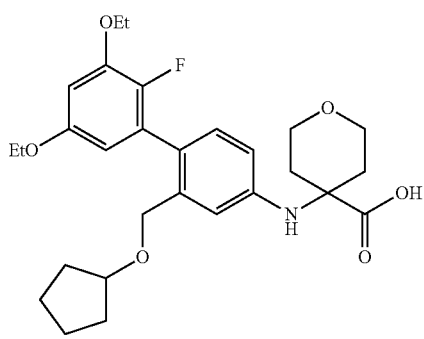 [SMILES: CCOc1cc(OCC)c(F)c(-c2ccc(NC3(C(=O)O)CCOCC3)cc2COC2CCCC2)c1] |
| 298 | 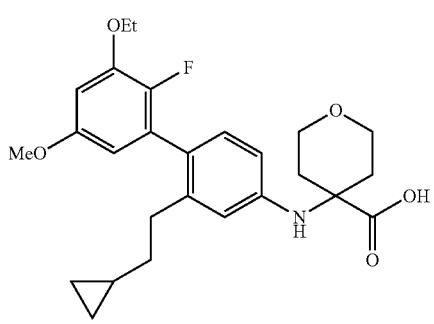 [SMILES: CCOc1cc(OC)cc(-c2ccc(NC3(C(=O)O)CCOCC3)cc2CCC2CC2)c1F] |
| 299 | 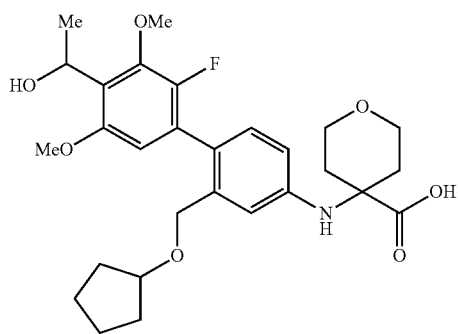<br>Enantiomer 1 |
| 300 | 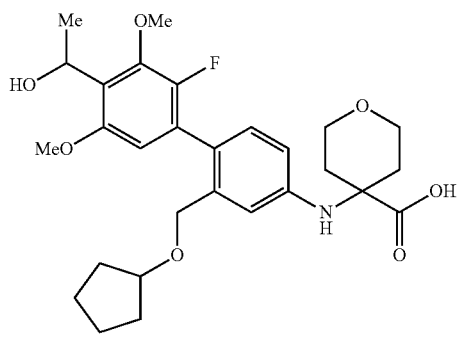<br>Enantiomer 2 |

TABLE 1-continued
| Compound | Structure |
|---|---|
| 301 | 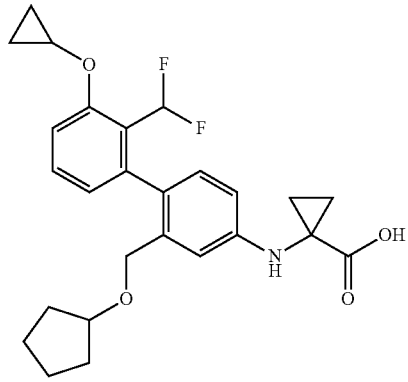 [SMILES: O=C(O)C1(Nc2ccc(-c3cccc(OC4CC4)c3C(F)F)c(COC3CCCC3)c2)CC1] |
| 302 | 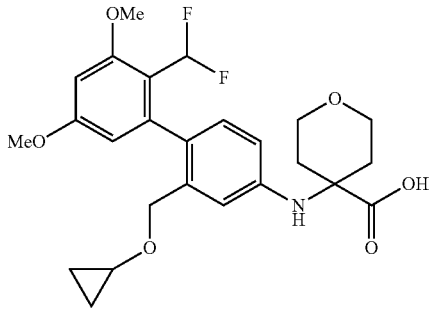 |
| 303 | 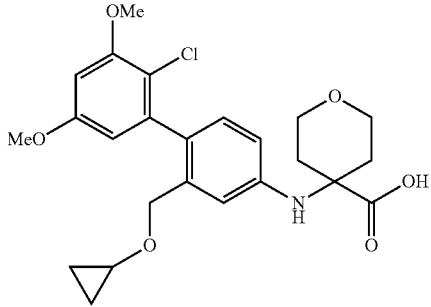 [SMILES: COc1cc(OC)c(Cl)c(-c2ccc(NC3(C(=O)O)CCOCC3)cc2COC2CC2)c1] |
| 304 | 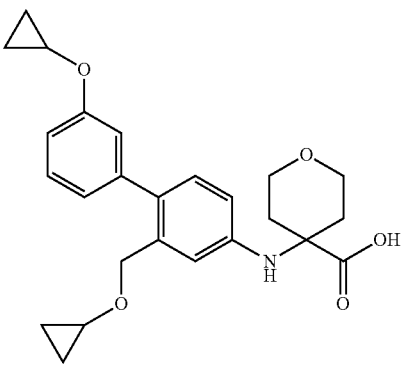 [SMILES: O=C(O)C1(Nc2ccc(-c3cccc(OC4CC4)c3)c(COC3CC3)c2)CCOCC1] |

TABLE 1-continued
| Compound | Structure |
|---|---|
| 305 | 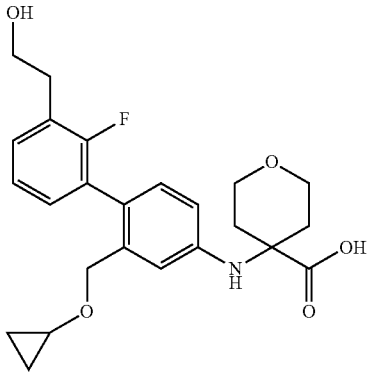 [SMILES: O=C(O)C1(Nc2ccc(-c3cccc(CCO)c3F)c(COC3CC3)c2)CCOCC1] |
| 306 | 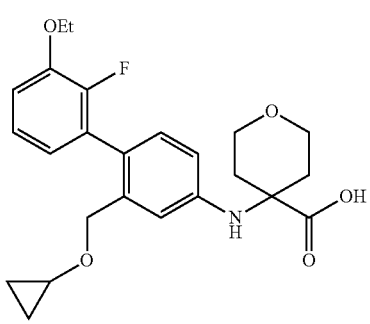 |
| 307 | 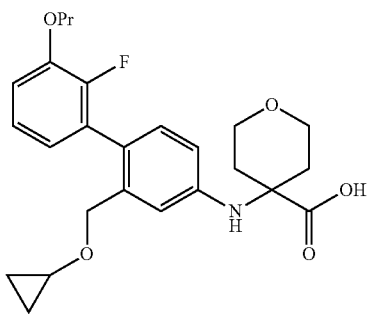 |
| 308 | 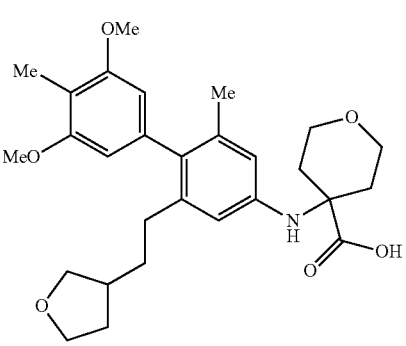
Enantiomer 1 |

TABLE 1-continued
| Compound | Structure |
|---|---|
| 309 | 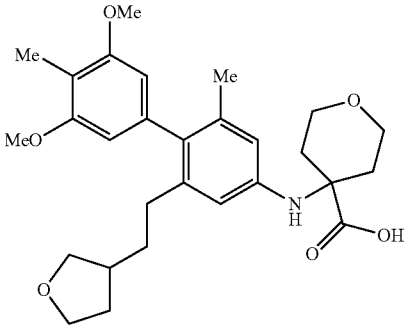<br>Enantiomer 2 |
| 310 | 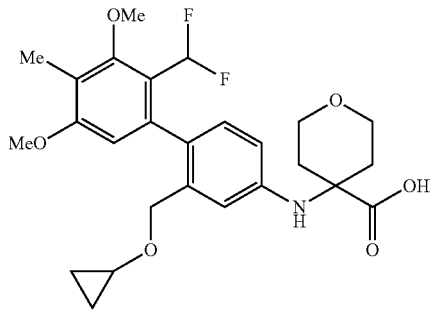 [SMILES: COc1cc(-c2ccc(NC3(C(=O)O)CCOCC3)cc2COC2CC2)c(C(F)F)c(OC)c1C] |
| 311 | 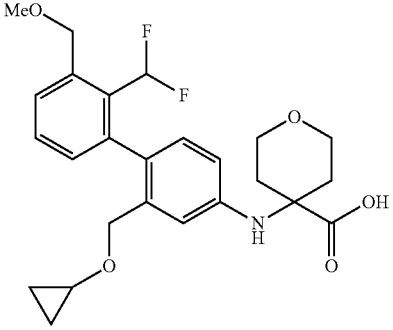 |
| 312 | 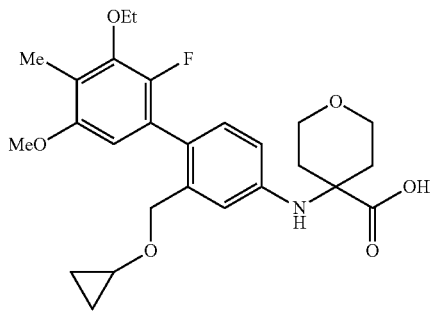 [SMILES: CCOc1c(C)c(OC)cc(-c2ccc(NC3(C(=O)O)CCOCC3)cc2COC2CC2)c1F] |

TABLE 1-continued

| Compound | Structure |
|---|---|
| 313 | 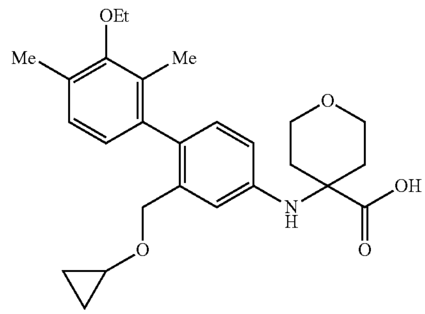 [SMILES: CCOc1c(C)ccc(-c2ccc(NC3(C(=O)O)CCOCC3)cc2COC2CC2)c1C] |
| 314 | 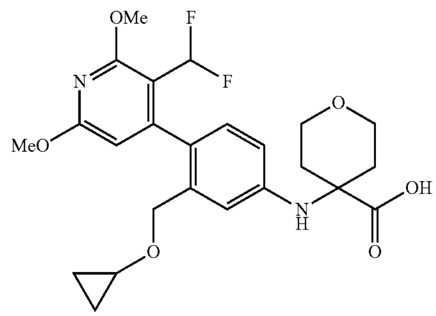 |
| 315 | 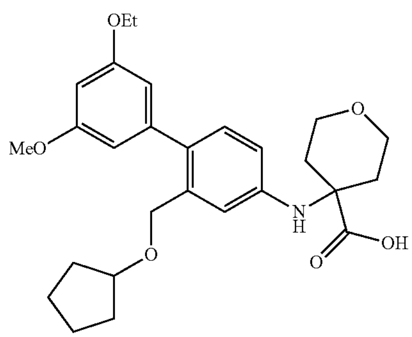 |
| 316 | 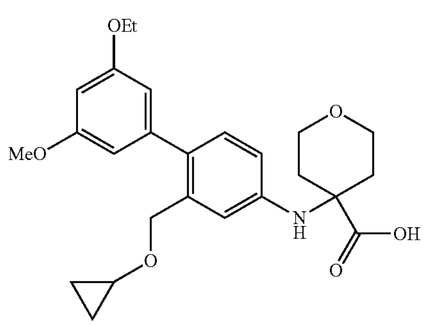 [SMILES: CCOc1cc(OC)cc(-c2ccc(NC3(C(=O)O)CCOCC3)cc2COC2CC2)c1] |

TABLE 1-continued
| Compound | Structure |
|---|---|
| 317 | 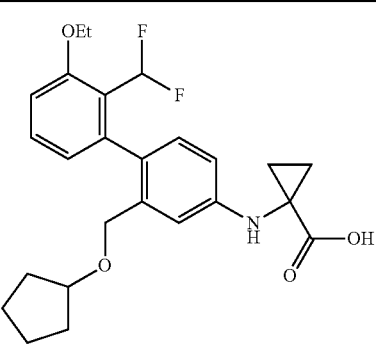 |
| 318 | 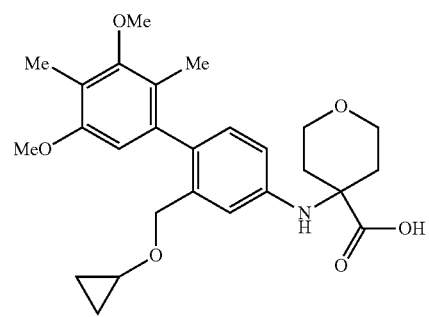 [SMILES: COc1cc(-c2ccc(NC3(C(=O)O)CCOCC3)cc2COC2CC2)c(C)c(OC)c1C] |
| 319 | 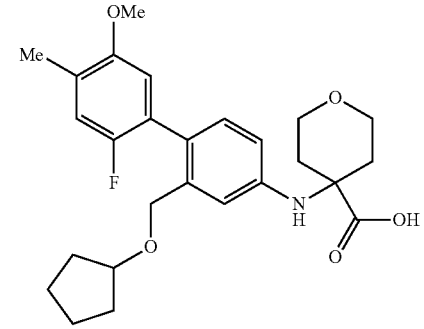 [SMILES: COc1cc(-c2ccc(NC3(C(=O)O)CCOCC3)cc2COC2CCCC2)c(F)cc1C] |
| 320 | 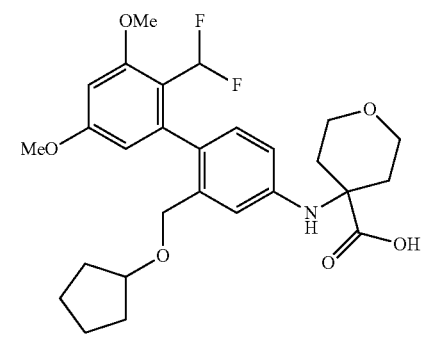 [SMILES: COc1cc(OC)c(C(F)F)c(-c2ccc(NC3(C(=O)O)CCOCC3)cc2COC2CCCC2)c1] |

TABLE 1-continued
| Compound | Structure |
|---|---|
| 322 | 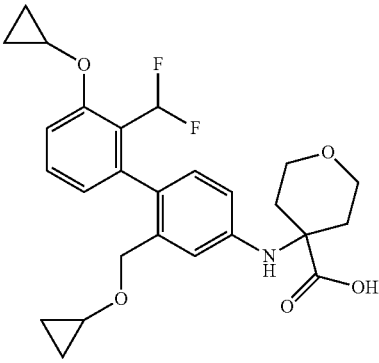 [SMILES: O=C(O)C1(Nc2ccc(-c3cccc(OC4CC4)c3C(F)F)c(COC3CC3)c2)CCOCC1] |
| 323 | 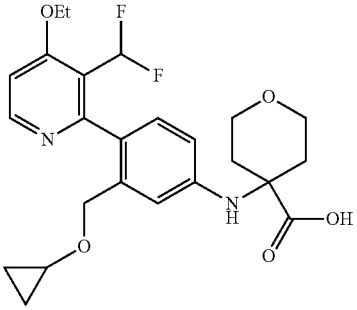 |
| 324 | 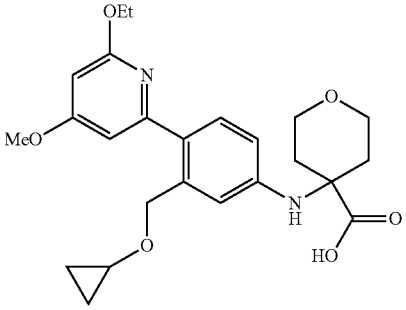 [SMILES: CCOc1cc(OC)cc(-c2ccc(NC3(C(=O)O)CCOCC3)cc2COC2CC2)n1] |
| 325 | 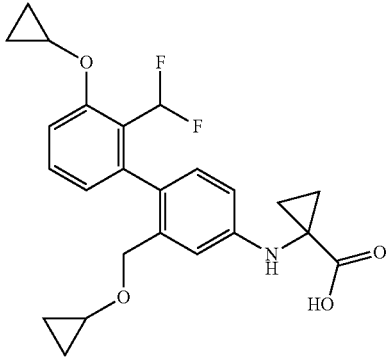 [SMILES: O=C(O)C1(Nc2ccc(-c3cccc(OC4CC4)c3C(F)F)c(COC3CC3)c2)CC1] |

TABLE 1-continued
| Compound | Structure |
|---|---|
| 326 | 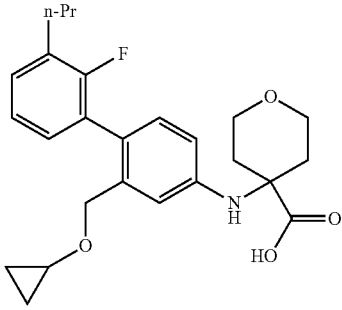 |
| 327 | 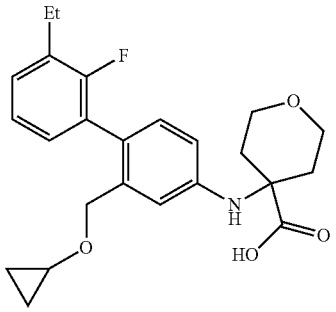 [SMILES: CCc1cccc(-c2ccc(NC3(C(=O)O)CCOCC3)cc2COC2CC2)c1F] |
| 328 | 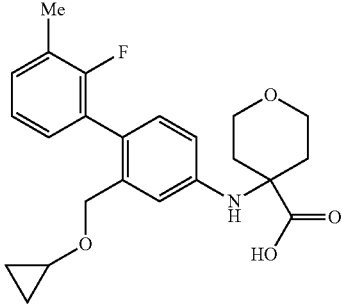 [SMILES: Cc1cccc(-c2ccc(NC3(C(=O)O)CCOCC3)cc2COC2CC2)c1F] |
| 329 | 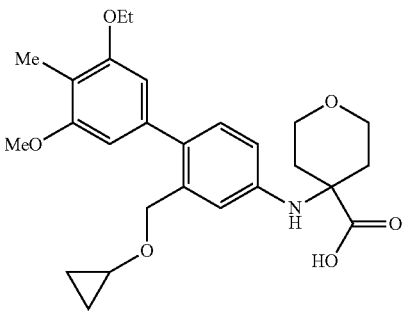 [SMILES: CCOc1cc(-c2ccc(NC3(C(=O)O)CCOCC3)cc2COC2CC2)cc(OC)c1C] |

TABLE 1-continued
| Compound | Structure |
|---|---|
| 330 | 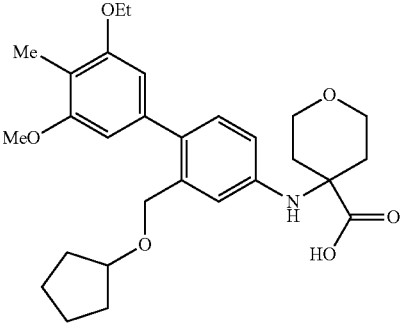 [SMILES: CCOc1cc(-c2ccc(NC3(C(=O)O)CCOCC3)cc2COC2CCCC2)cc(OC)c1C] |
| 331 | 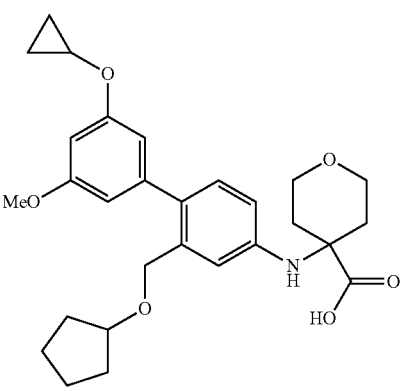 [SMILES: COc1cc(OC2CC2)cc(-c2ccc(NC3(C(=O)O)CCOCC3)cc2COC2CCCC2)c1] |
| 332 | 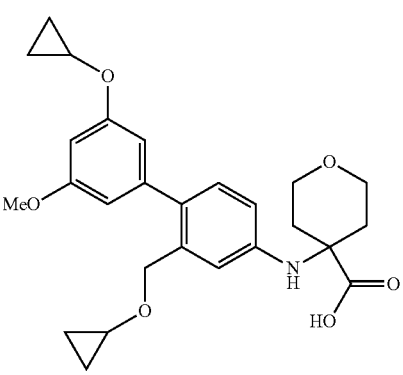 [SMILES: COc1cc(OC2CC2)cc(-c2ccc(NC3(C(=O)O)CCOCC3)cc2COC2CC2)c1] |
| 333 | 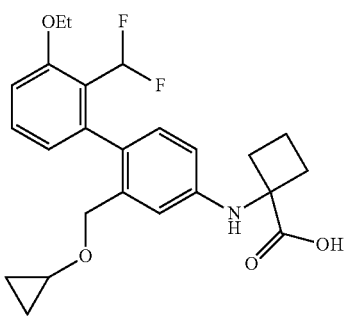 [SMILES: CCOc1cccc(-c2ccc(NC3(C(=O)O)CCC3)cc2COC2CC2)c1C(F)F] |

TABLE 1-continued

| Compound | Structure |
|---|---|
| 334 | (chemical structure) |
| 335 | (chemical structure) |
| 336 | (chemical structure) |
| 337 | (chemical structure) |
| 338 | (chemical structure) |

145                                                                 146
TABLE 1-continued
| Compound | Structure |
|---|---|
| 339 | 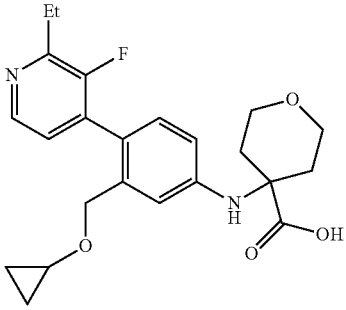 [SMILES: CCc1nccc(-c2ccc(NC3(C(=O)O)CCOCC3)cc2COC2CC2)c1F] |
| 340 | 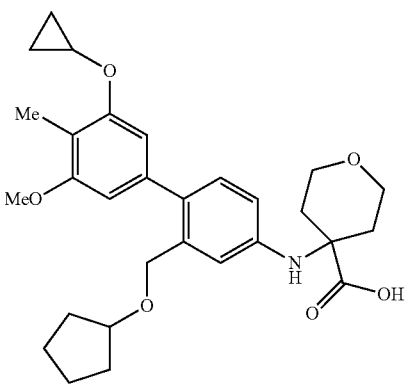 [SMILES: COc1cc(-c2ccc(NC3(C(=O)O)CCOCC3)cc2COC2CCCC2)cc(OC2CC2)c1C] |
| 341 | 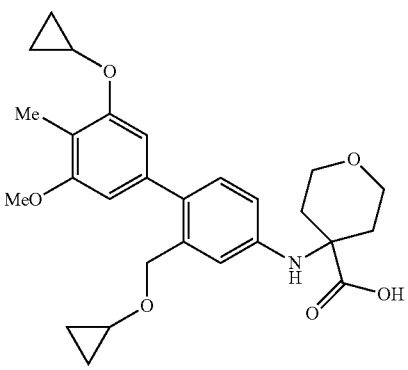 [SMILES: COc1cc(-c2ccc(NC3(C(=O)O)CCOCC3)cc2COC2CC2)cc(OC2CC2)c1C] |
| 342 | 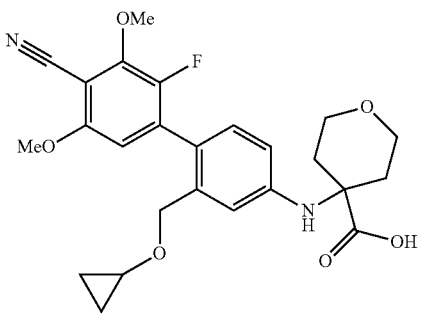 [SMILES: COc1cc(-c2ccc(NC3(C(=O)O)CCOCC3)cc2COC2CC2)c(F)c(OC)c1C#N] |

TABLE 1-continued
| Compound | Structure |
|---|---|
| 343 | 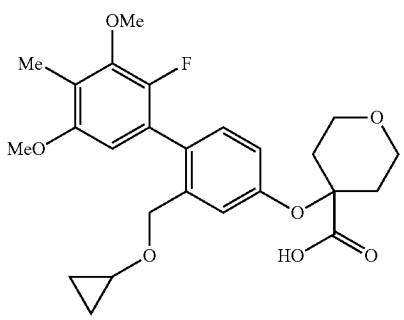 |
| 344 | 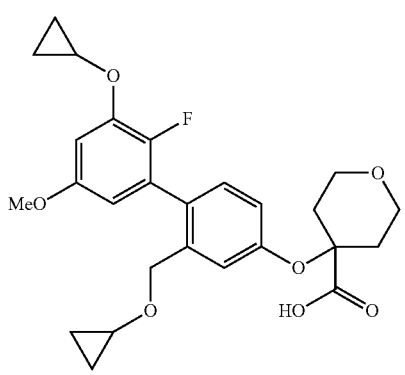 |
| 345 | 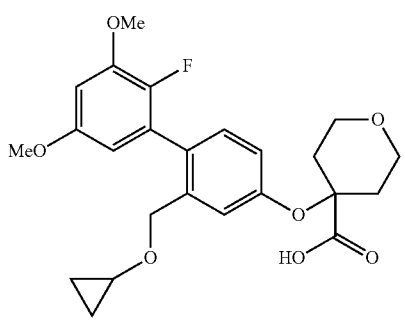 |
| 346 | 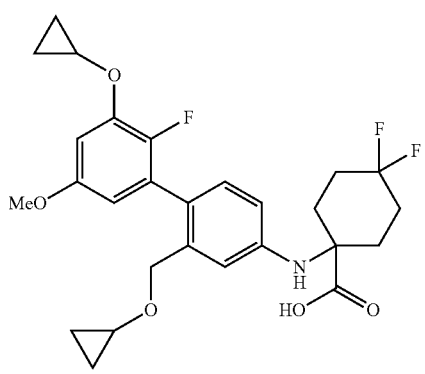 [SMILES: COc1cc(OC2CC2)c(F)c(-c2ccc(NC3(C(=O)O)CCC(F)(F)CC3)cc2COC2CC2)c1] |

TABLE 1-continued

| Compound | Structure |
|---|---|
| 347 | (chemical structure) |
| 348 | (chemical structure) |
| 349 | (chemical structure) |
| 350 | (chemical structure) |
| 351 | (chemical structure) |

TABLE 1-continued

| Compound | Structure |
|---|---|
| 352 | 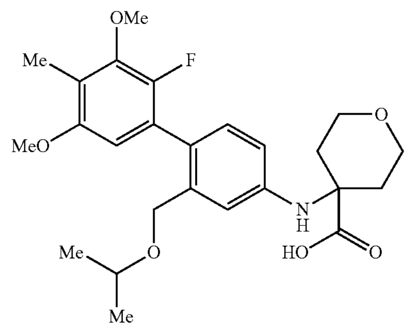 [SMILES: COc1cc(-c2ccc(NC3(C(=O)O)CCOCC3)cc2COC(C)C)c(F)c(OC)c1C] |
| 353 | 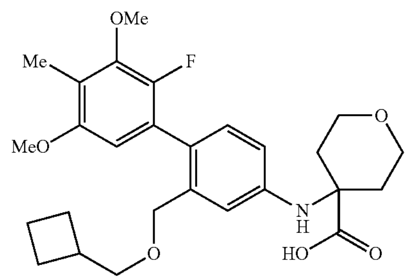 [SMILES: COc1cc(-c2ccc(NC3(C(=O)O)CCOCC3)cc2COCC2CCC2)c(F)c(OC)c1C] |
| 354 | 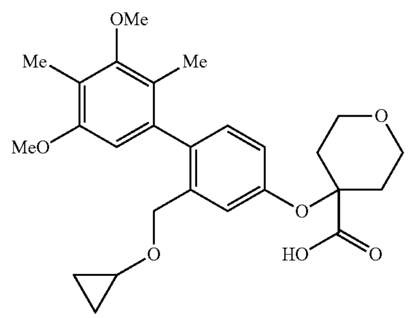 [SMILES: COc1cc(-c2ccc(OC3(C(=O)O)CCOCC3)cc2COC2CC2)c(C)c(OC)c1C] |
| 355 | 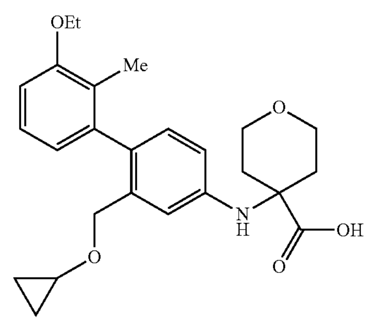 [SMILES: CCOc1cccc(-c2ccc(NC3(C(=O)O)CCOCC3)cc2COC2CC2)c1C] |
| 356 | 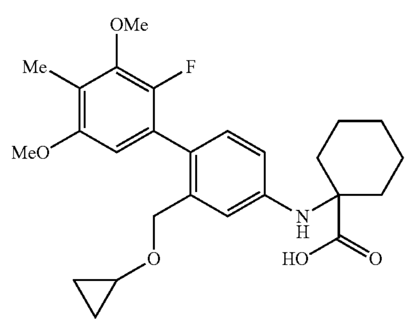 [SMILES: COc1cc(-c2ccc(NC3(C(=O)O)CCCCC3)cc2COC2CC2)c(F)c(OC)c1C] |

TABLE 1-continued

| Compound | Structure |
|---|---|
| 357 | 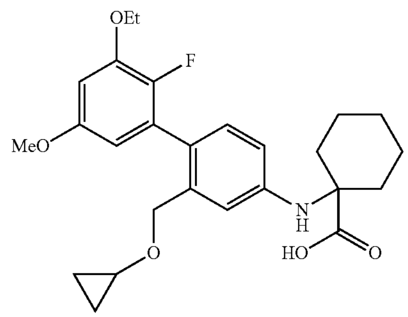 [SMILES: CCOc1cc(OC)cc(-c2ccc(NC3(C(=O)O)CCCCC3)cc2COC2CC2)c1F] |
| 358 | 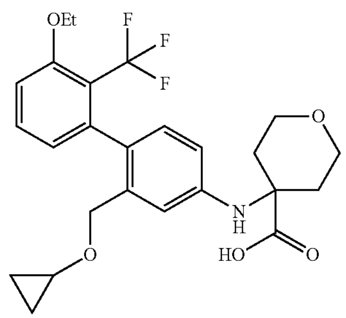 [SMILES: CCOc1cccc(-c2ccc(NC3(C(=O)O)CCOCC3)cc2COC2CC2)c1C(F)(F)F] |
| 359 | 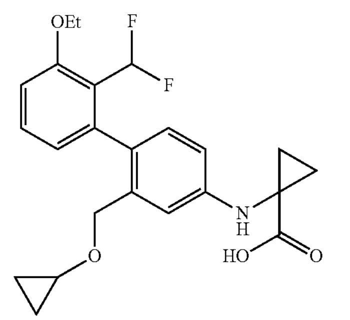 [SMILES: CCOc1cccc(-c2ccc(NC3(C(=O)O)CC3)cc2COC2CC2)c1C(F)F] |
| 360 | 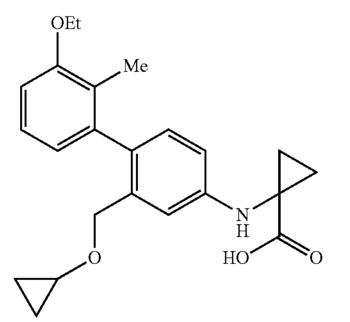 [SMILES: CCOc1cccc(-c2ccc(NC3(C(=O)O)CC3)cc2COC2CC2)c1C] |
| 361 | 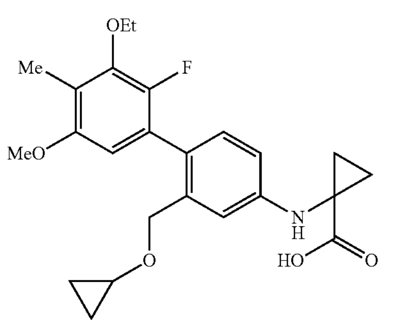 [SMILES: CCOc1c(C)c(OC)cc(-c2ccc(NC3(C(=O)O)CC3)cc2COC2CC2)c1F] |

TABLE 1-continued

| Compound | Structure |
|---|---|
| 362 | 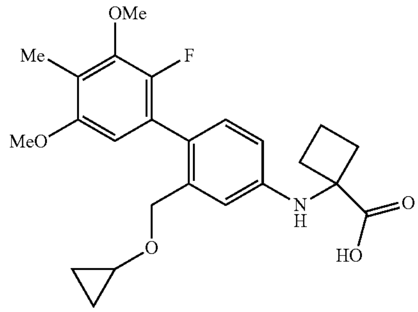 [SMILES: COc1cc(-c2ccc(NC3(C(=O)O)CCC3)cc2COC2CC2)c(F)c(OC)c1C] |
| 363 | 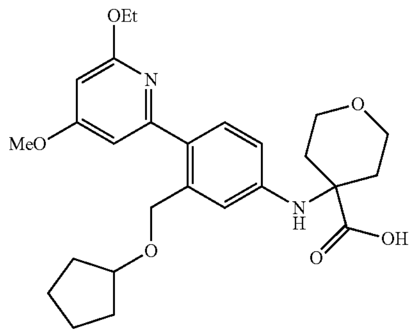 [SMILES: CCOc1cc(OC)cc(-c2ccc(NC3(C(=O)O)CCOCC3)cc2COC2CCCC2)n1] |
| 364 | 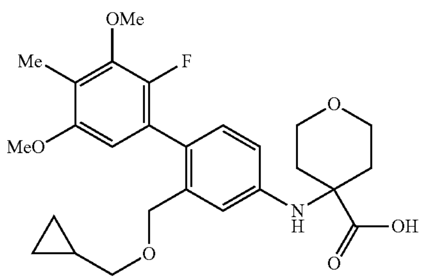 [SMILES: COc1cc(-c2ccc(NC3(C(=O)O)CCOCC3)cc2COCC2CC2)c(F)c(OC)c1C] |
| 365 | 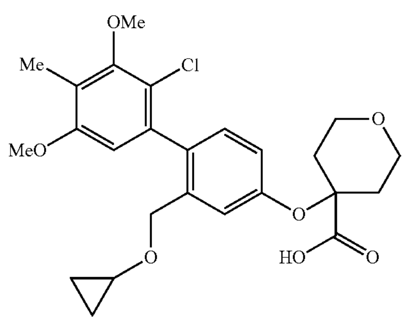 [SMILES: COc1cc(-c2ccc(OC3(C(=O)O)CCOCC3)cc2COC2CC2)c(Cl)c(OC)c1C] |
| 366 | 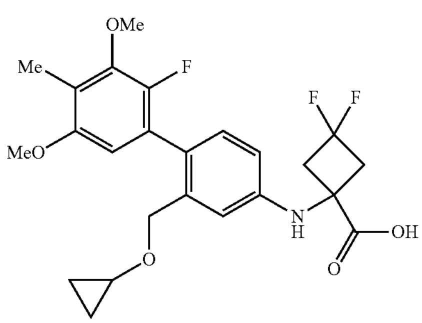 [SMILES: COc1cc(-c2ccc(NC3(C(=O)O)CC(F)(F)C3)cc2COC2CC2)c(F)c(OC)c1C] |

TABLE 1-continued

| Compound | Structure |
|---|---|
| 367 | 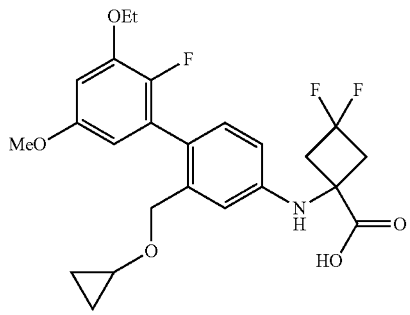 [SMILES: CCOc1cc(OC)cc(-c2ccc(NC3(C(=O)O)CC(F)(F)C3)cc2COC2CC2)c1F] |
| 368 | 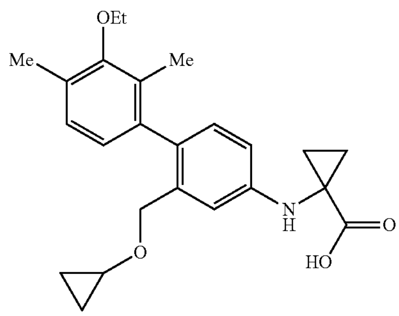 [SMILES: CCOc1c(C)ccc(-c2ccc(NC3(C(=O)O)CC3)cc2COC2CC2)c1C] |
| 369 | 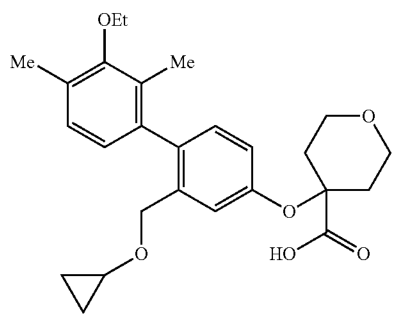 [SMILES: CCOc1c(C)ccc(-c2ccc(OC3(C(=O)O)CCOCC3)cc2COC2CC2)c1C] |
| 370 | 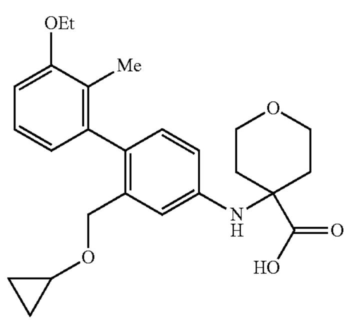 [SMILES: CCOc1cccc(-c2ccc(NC3(C(=O)O)CCOCC3)cc2COC2CC2)c1C] |
| 371 | 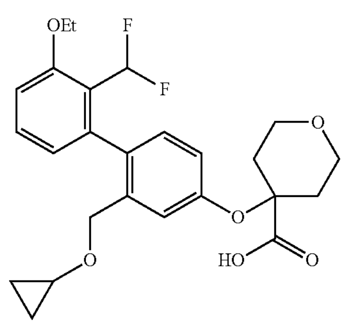 [SMILES: CCOc1cccc(-c2ccc(OC3(C(=O)O)CCOCC3)cc2COC2CC2)c1C(F)F] |

TABLE 1-continued
| Compound | Structure |
|---|---|
| 372 | 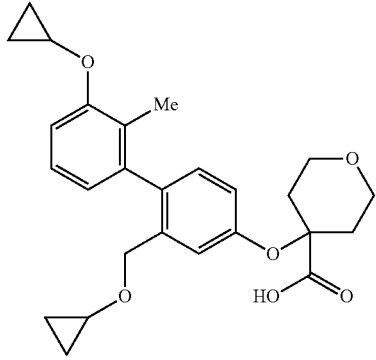 [SMILES: Cc1c(OC2CC2)cccc1-c1ccc(OC2(C(=O)O)CCOCC2)cc1COC1CC1] |
| 373 | 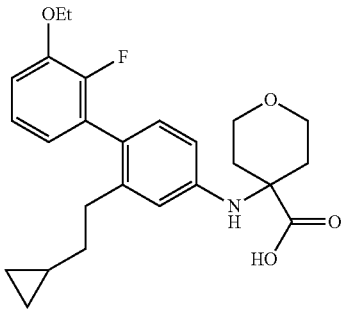 [SMILES: CCOc1cccc(-c2ccc(NC3(C(=O)O)CCOCC3)cc2CCC2CC2)c1F] |
| 374 | 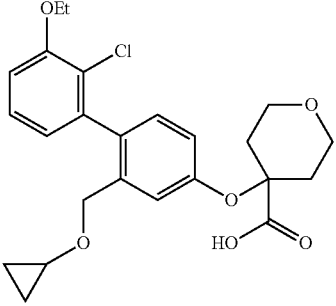 [SMILES: CCOc1cccc(-c2ccc(OC3(C(=O)O)CCOCC3)cc2COC2CC2)c1Cl] |
| 375 | 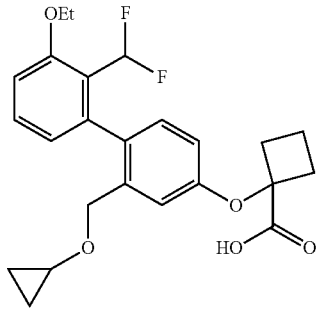 [SMILES: CCOc1cccc(-c2ccc(OC3(C(=O)O)CCC3)cc2COC2CC2)c1C(F)F] |

161 162
TABLE 1-continued
| Compound | Structure |
|---|---|
| 376 | 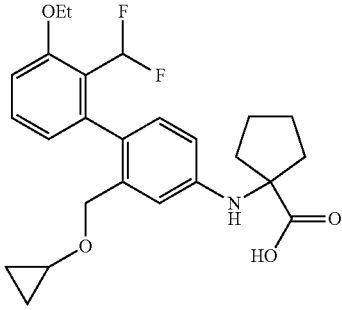 [SMILES: CCOc1cccc(-c2ccc(NC3(C(=O)O)CCCC3)cc2COC2CC2)c1C(F)F] |
| 377 | 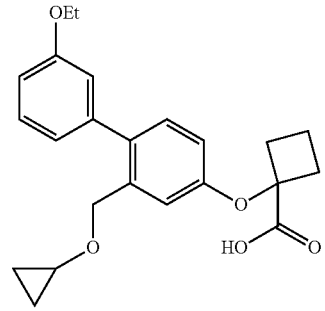 [SMILES: CCOc1cccc(-c2ccc(OC3(C(=O)O)CCC3)cc2COC2CC2)c1] |
| 378 | 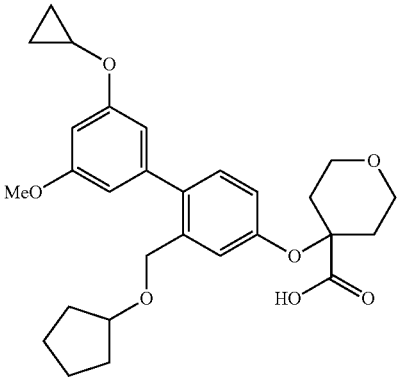 |
| 379 | 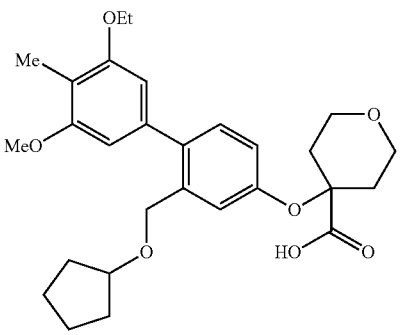 [SMILES: CCOc1cc(-c2ccc(OC3(C(=O)O)CCOCC3)cc2COC2CCCC2)cc(OC)c1C] |

TABLE 1-continued
| Compound | Structure |
|---|---|
| 380 | 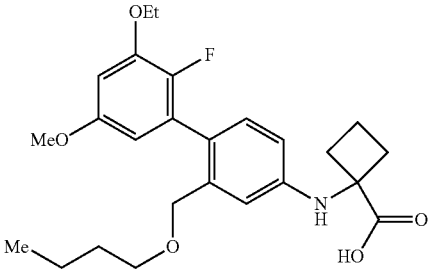 [SMILES: CCCCOCc1cc(NC2(C(=O)O)CCC2)ccc1-c1cc(OC)cc(OCC)c1F] |
| 381 | 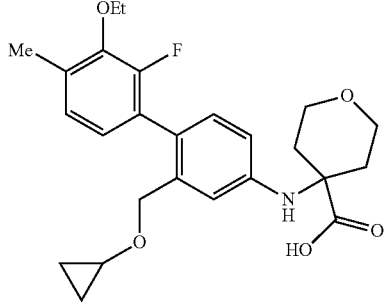 [SMILES: CCOc1c(C)ccc(-c2ccc(NC3(C(=O)O)CCOCC3)cc2COC2CC2)c1F] |
| 382 | 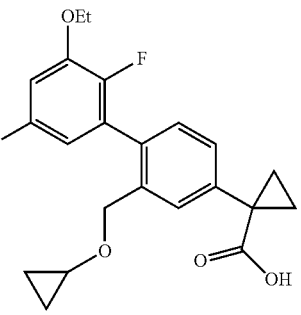 |
| 383 | 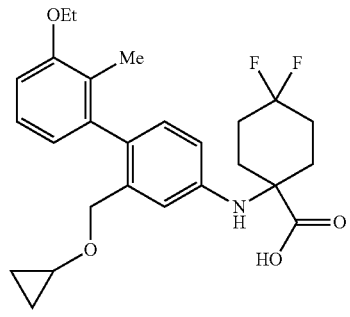 |
| 384 | 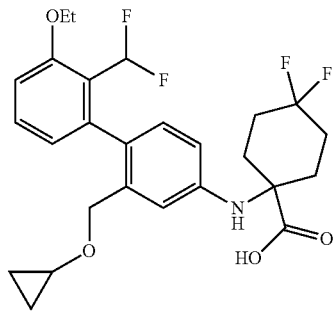 [SMILES: CCOc1cccc(-c2ccc(NC3(C(=O)O)CCC(F)(F)CC3)cc2COC2CC2)c1C(F)F] |

TABLE 1-continued
| Compound | Structure |
|---|---|
| 385 | 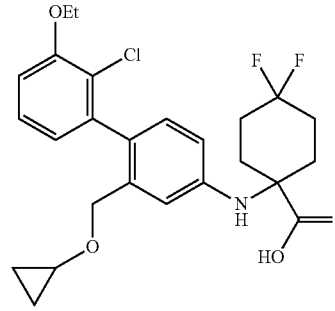 |
| 386 | 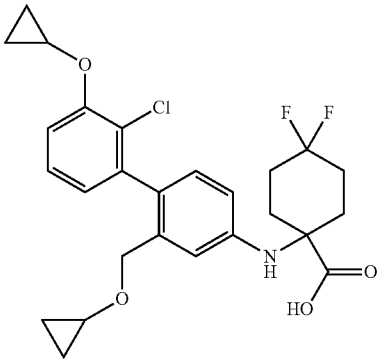 [SMILES: O=C(O)C1(Nc2ccc(-c3cccc(OC4CC4)c3Cl)c(COC3CC3)c2)CCC(F)(F)CC1] |
| 387 | 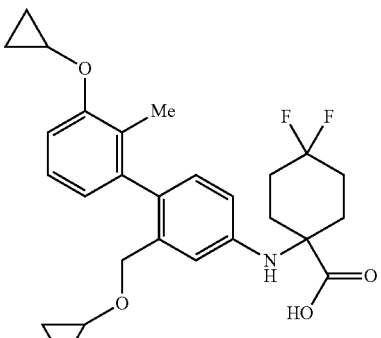 |
| 388 | 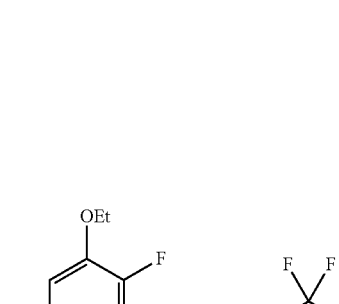 |

TABLE 1-continued
| Compound | Structure |
|---|---|
| 389 | 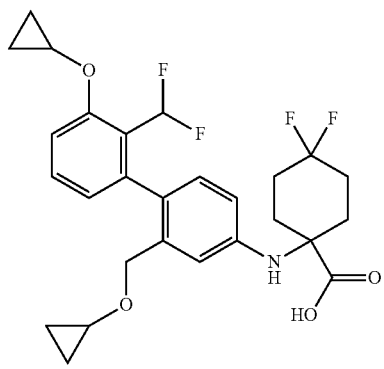 [SMILES: O=C(O)C1(Nc2ccc(-c3cccc(OC4CC4)c3C(F)F)c(COC3CC3)c2)CCC(F)(F)CC1] |
| 390 | 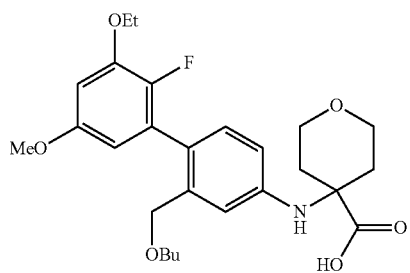 |
| 391 | 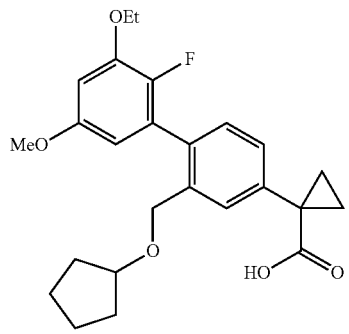 [SMILES: CCOc1cc(OC)cc(-c2ccc(C3(C(=O)O)CC3)cc2COC2CCCC2)c1F] |
| 392 | 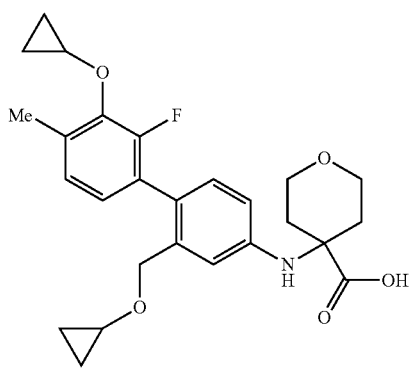 [SMILES: Cc1ccc(-c2ccc(NC3(C(=O)O)CCOCC3)cc2COC2CC2)c(F)c1OC1CC1] |

TABLE 1-continued

| Compound | Structure |
|---|---|
| 393 | 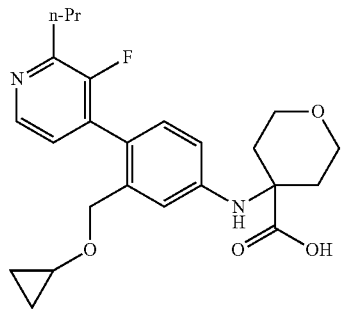 |
| 394 | 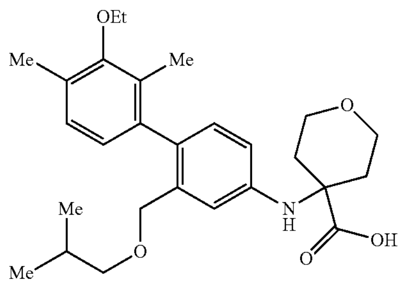 [SMILES: CCOc1c(C)ccc(-c2ccc(NC3(C(=O)O)CCOCC3)cc2COCC(C)C)c1C] |
| 395 | 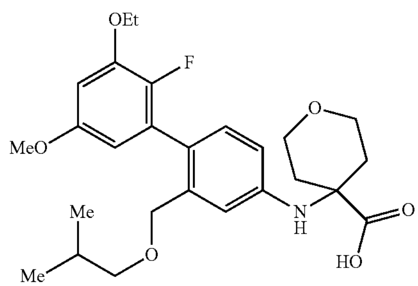 [SMILES: CCOc1cc(OC)cc(-c2ccc(NC3(C(=O)O)CCOCC3)cc2COCC(C)C)c1F] |
| 396 | 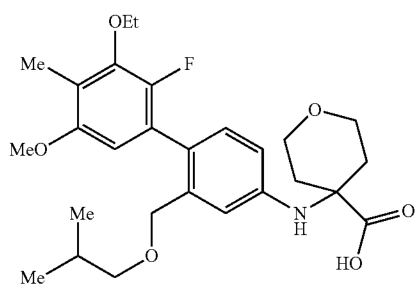 [SMILES: CCOc1c(C)c(OC)cc(-c2ccc(NC3(C(=O)O)CCOCC3)cc2COCC(C)C)c1F] |
| 397 | 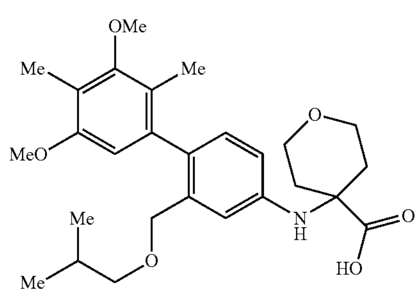 [SMILES: COc1cc(-c2ccc(NC3(C(=O)O)CCOCC3)cc2COCC(C)C)c(C)c(OC)c1C] |

TABLE 1-continued

| Compound | Structure |
|---|---|
| 398 | 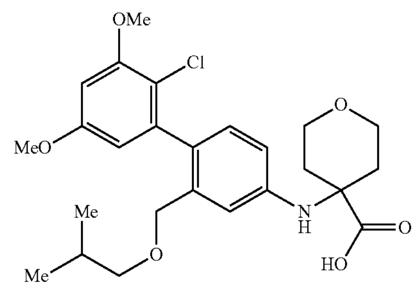 [SMILES: COc1cc(OC)c(Cl)c(-c2ccc(NC3(C(=O)O)CCOCC3)cc2COCC(C)C)c1] |
| 399 | 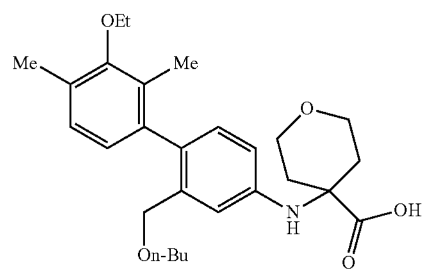 |
| 400 | 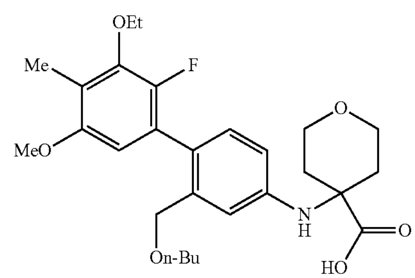 |
| 401 | 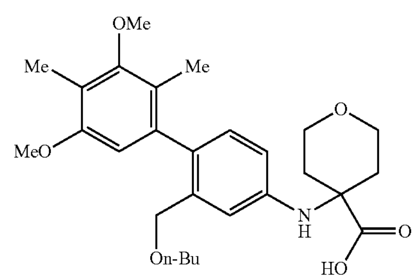 |
| 402 | 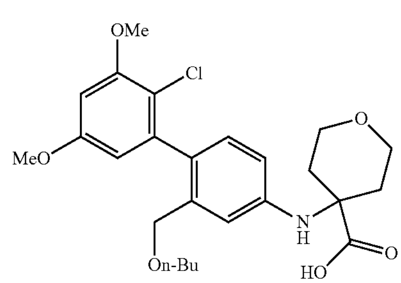 |

TABLE 1-continued

| Compound | Structure |
|---|---|
| 403 | 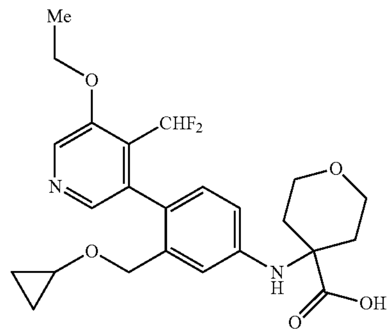 [SMILES: CCOc1cncc(-c2ccc(NC3(C(=O)O)CCOCC3)cc2COC2CC2)c1C(F)F] |
| 404 | 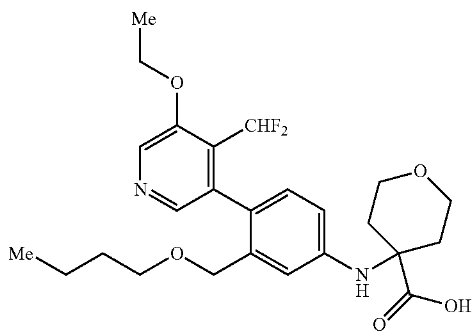 [SMILES: CCCCOCc1cc(NC2(C(=O)O)CCOCC2)ccc1-c1cncc(OCC)c1C(F)F] |
| 405 | 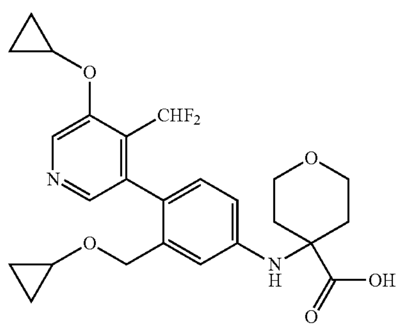 [SMILES: O=C(O)C1(Nc2ccc(-c3cncc(OC4CC4)c3C(F)F)c(COC3CC3)c2)CCOCC1] |
| 406 | 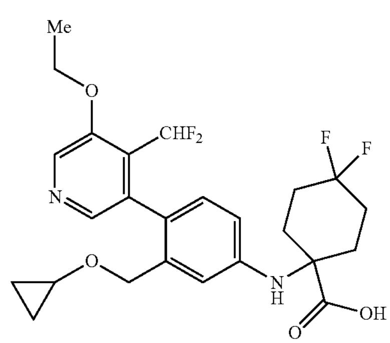 [SMILES: CCOc1cncc(-c2ccc(NC3(C(=O)O)CCC(F)(F)CC3)cc2COC2CC2)c1C(F)F] |

TABLE 1-continued
| Compound | Structure |
|---|---|
| 407 | 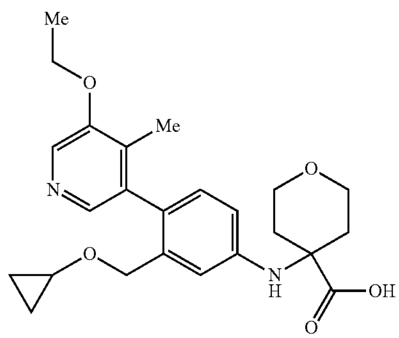 [SMILES: CCOc1cncc(-c2ccc(NC3(C(=O)O)CCOCC3)cc2COC2CC2)c1C] |
| 408 | 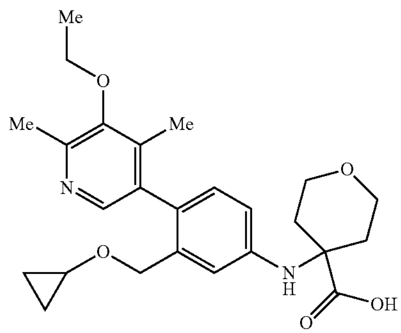 [SMILES: CCOc1c(C)ncc(-c2ccc(NC3(C(=O)O)CCOCC3)cc2COC2CC2)c1C] |
| 409 | 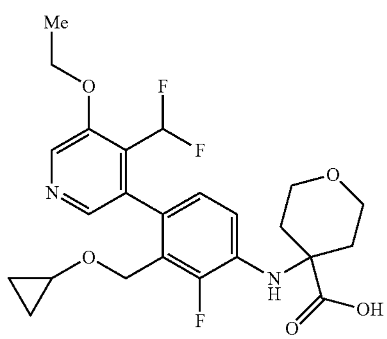 [SMILES: CCOc1cncc(-c2ccc(NC3(C(=O)O)CCOCC3)c(F)c2COC2CC2)c1C(F)F] |
| 410 | 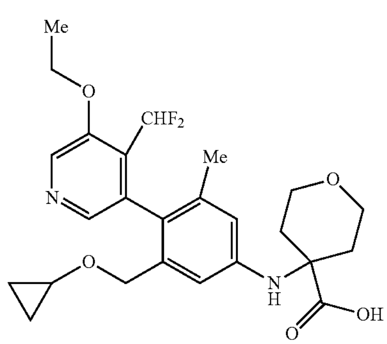 [SMILES: CCOc1cncc(-c2c(C)cc(NC3(C(=O)O)CCOCC3)cc2COC2CC2)c1C(F)F] |

TABLE 1-continued

| Compound | Structure |
|---|---|
| 411 | 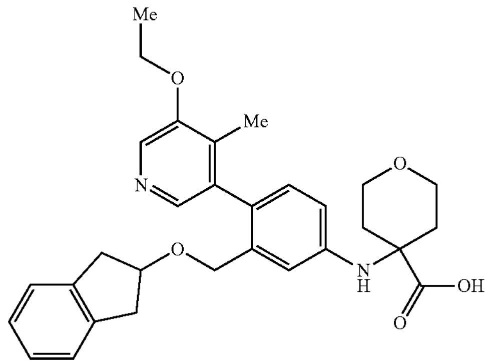 [SMILES: CCOc1cncc(-c2ccc(NC3(C(=O)O)CCOCC3)cc2COC2Cc3ccccc3C2)c1C] |
| 412 | 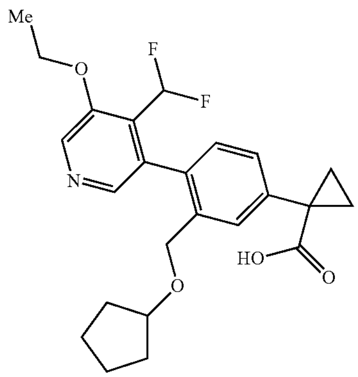 [SMILES: CCOc1cncc(-c2ccc(C3(C(=O)O)CC3)cc2COC2CCCC2)c1C(F)F] |
| 413 | 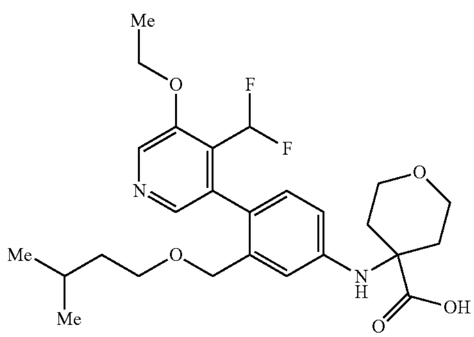 [SMILES: CCOc1cncc(-c2ccc(NC3(C(=O)O)CCOCC3)cc2COCCC(C)C)c1C(F)F] |
| 414 | 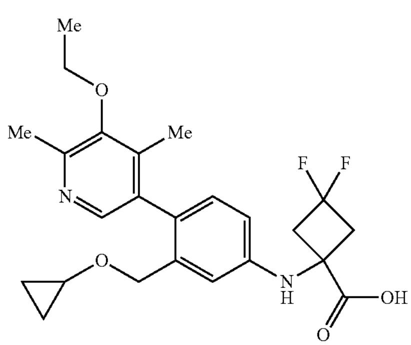 [SMILES: CCOc1c(C)ncc(-c2ccc(NC3(C(=O)O)CC(F)(F)C3)cc2COC2CC2)c1C] |

TABLE 1-continued

| Compound | Structure |
|---|---|
| 415 | 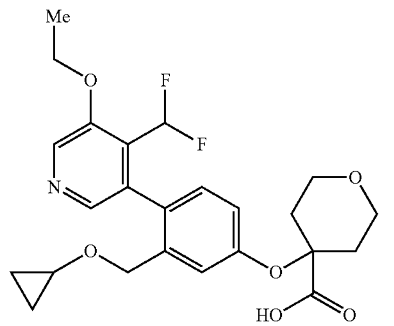 [SMILES: CCOc1cncc(-c2ccc(OC3(C(=O)O)CCOCC3)cc2COC2CC2)c1C(F)F] |
| 416 | 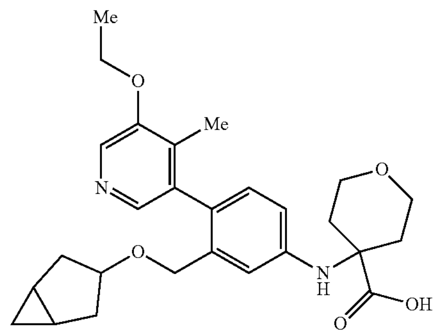 [SMILES: CCOc1cncc(-c2ccc(NC3(C(=O)O)CCOCC3)cc2COC2CC3CC3C2)c1C] |
| 417 | 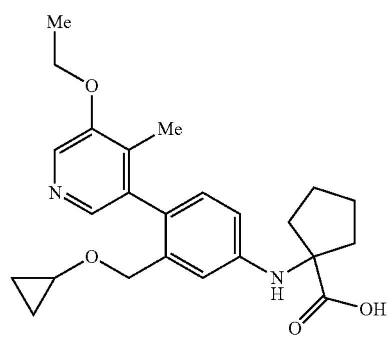 [SMILES: CCOc1cncc(-c2ccc(NC3(C(=O)O)CCCC3)cc2COC2CC2)c1C] |

The compounds of Formula I provided herein encompass stereochemical forms of the compounds, for example, optical isomers, such as enantiomers, diastereomers, as well as mixtures thereof, e.g., mixtures of enantiomers and/or diastereomers, including racemic mixtures, as well as equal or non-equal mixtures of individual enantiomers and/or diastereomers. All stereochemical forms are contemplated in this disclosure. Unless otherwise indicated, when a disclosed compound is named or depicted by a structure without specifying the stereochemistry and has one or more chiral centers, it is understood to represent all possible stereoisomers of the compound. Representative stereochemical forms are provided throughout the specification, including but not limited to those delineated in Table 2. In some embodiments, provided is compound selected from Table 2, or a pharmaceutically acceptable salt, stereoisomer, mixture of stereoisomers, tautomer, isotopically enriched analog, or solvate thereof:

TABLE 2

| Structure |
|---|
| |

| 181 | 182 |
|---|---|
| TABLE 2-continued | TABLE 2-continued |
| Structure | Structure |
| 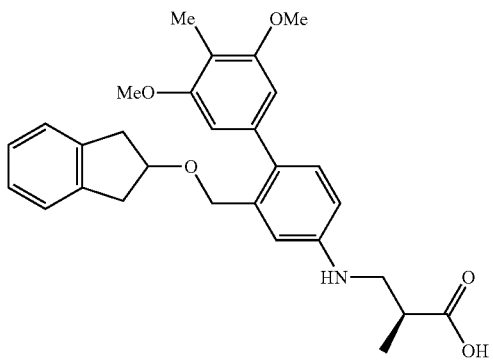 [SMILES: COc1cc(-c2ccc(NC[C@H](C)C(=O)O)cc2COC2Cc3ccccc3C2)cc(OC)c1C] | 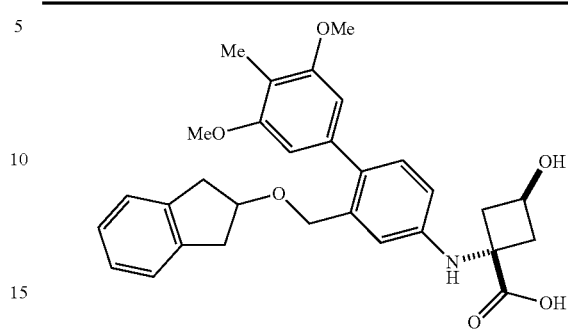 |
| 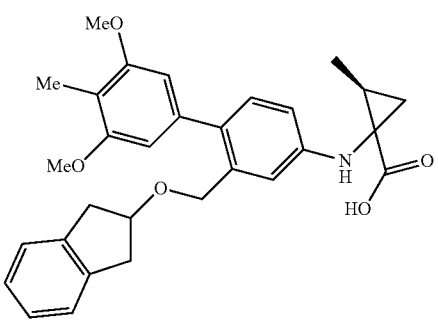 [SMILES: COc1cc(-c2ccc(NC3(C(=O)O)C[C@@H]3C)cc2COC2Cc3ccccc3C2)cc(OC)c1C] | 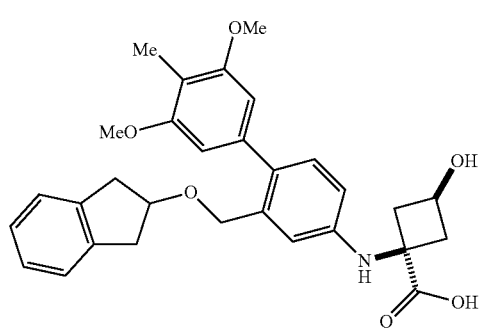 |
| 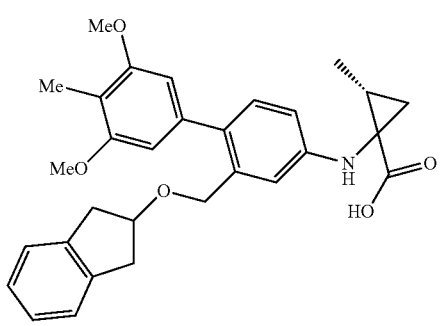 [SMILES: COc1cc(-c2ccc(NC3(C(=O)O)C[C@H]3C)cc2COC2Cc3ccccc3C2)cc(OC)c1C] | 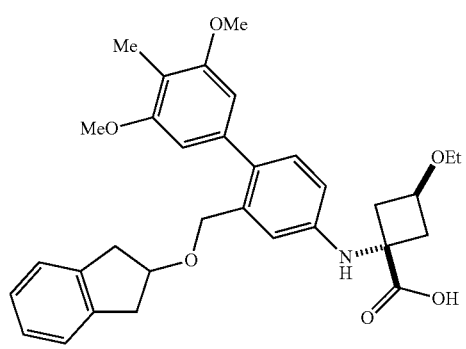 |
| 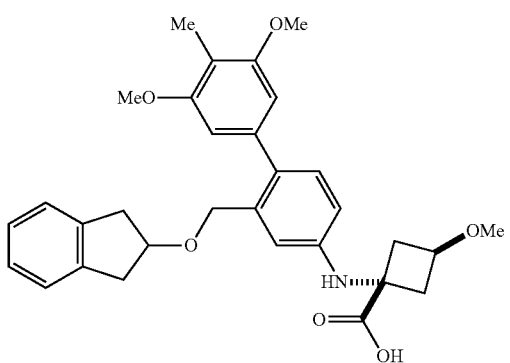 | 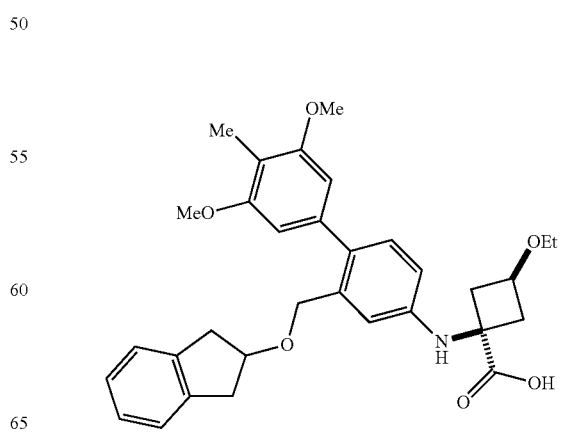 |

TABLE 2-continued
Structure
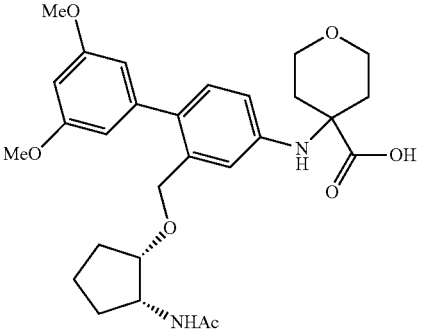 [SMILES: COc1cc(OC)cc(-c2ccc(NC3(C(=O)O)CCOCC3)cc2CO[C@H]2CCC[C@H]2NC(C)=O)c1]
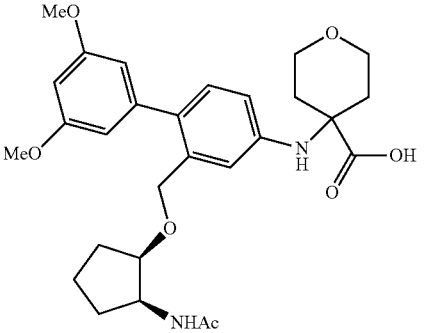 [SMILES: COc1cc(OC)cc(-c2ccc(NC3(C(=O)O)CCOCC3)cc2CO[C@@H]2CCC[C@@H]2NC(C)=O)c1]
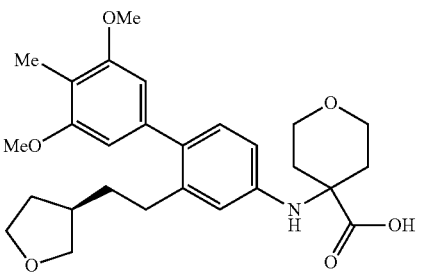 [SMILES: COc1cc(-c2ccc(NC3(C(=O)O)CCOCC3)cc2CC[C@@H]2CCOC2)cc(OC)c1C]
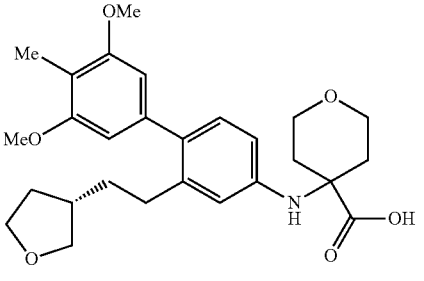 [SMILES: COc1cc(-c2ccc(NC3(C(=O)O)CCOCC3)cc2CC[C@H]2CCOC2)cc(OC)c1C]
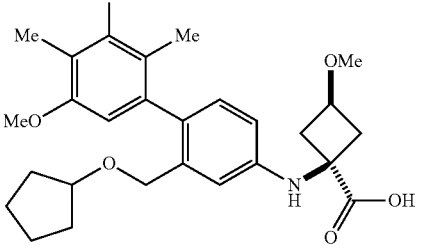
TABLE 2-continued
Structure
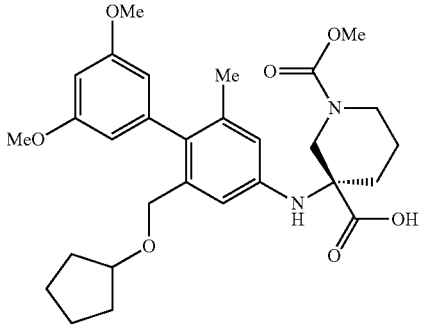 [SMILES: COC(=O)N1CCC[C@@](Nc2cc(C)c(-c3cc(OC)cc(OC)c3)c(COC3CCCC3)c2)(C(=O)O)C1]
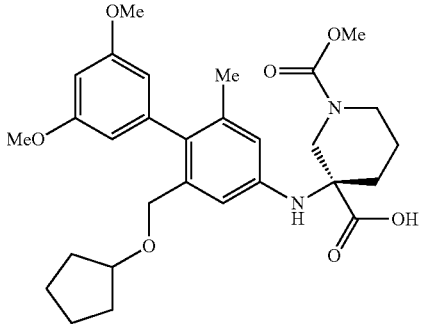 [SMILES: COC(=O)N1CCC[C@](Nc2cc(C)c(-c3cc(OC)cc(OC)c3)c(COC3CCCC3)c2)(C(=O)O)C1]
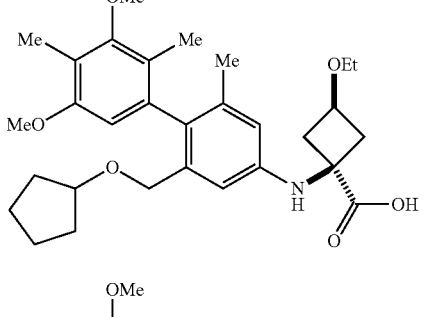
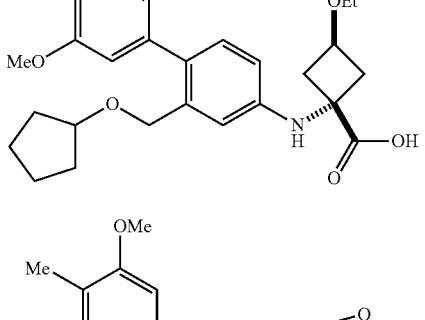
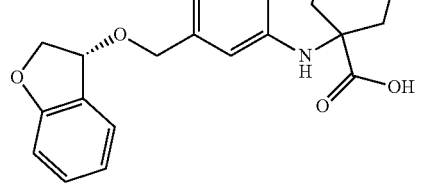

TABLE 2-continued

| Structure |
|---|

TABLE 2-continued

| Structure |
|---|

TABLE 2-continued

| Structure |
|---|

TABLE 2-continued

| Structure |
|---|

TABLE 2-continued

Structure

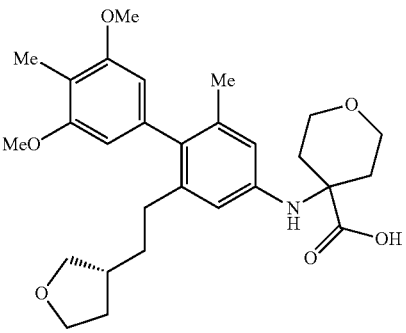 [SMILES: COc1cc(-c2c(C)cc(NC3(C(=O)O)CCOCC3)cc2CC[C@@H]2CCOC2)cc(OC)c1C]

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include trifluoroacetic acid salts.

It will further be appreciated that the compounds of Formula I or their salts may be isolated in the form of solvates, and accordingly that any such solvate is included within the scope of the present disclosure. For example, compounds of Formula I and salts thereof can exist in unsolvated as well as solvated forms with pharmaceutically acceptable solvents such as water, ethanol, and the like.

Treatment Methods and Uses

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The compounds as provided herein, or pharmaceutically acceptable salts or solvates thereof, or pharmaceutical compositions of such compounds, are useful as inhibitors of one or more LPA receptors. As described further herein, a compound antagonizing to an LPA receptor can be useful for prevention and/or treatment of diseases such as various kinds of disease including, for example, fibrosis (e.g., renal fibrosis, pulmonary fibrosis, hepatic fibrosis, arterial fibrosis, systemic sclerosis), urinary system disease, carcinoma-associated disease, proliferative disease, inflammation/immune system disease, disease by secretory dysfunction, brain-related disease, and chronic disease.

In some embodiments, this disclosure provides methods for treating a subject (e.g., a human) having a disease, disorder, or condition in which inhibition of one or more LPA receptors (i.e., an LPA-associated disease) is beneficial for the treatment of the underlying pathology and/or symptoms and/or progression of the disease, disorder, or condition. In some embodiments, the methods provided herein can include or further include treating one or more conditions associated, co-morbid or sequela with any one or more of the conditions provided herein.

Provided herein is a method for treating a LPA-associated disease, the method comprising administering to a subject in need thereof an effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as disclosed herein.

In some embodiments, an LPA-associated disease includes, but is not limited to treating fibrosis of an organ (e.g., liver, kidney, lung, heart, and skin), liver disease (acute hepatitis, chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (e.g., cancer, including solid tumors, solid tumor metastasis, vascular fibroma, myeloma, multiple myeloma, Kaposi's sarcoma, leukemia, and chronic lymphocytic leukemia (CLL), and invasive metastasis of cancer cells, inflammatory disease (e.g., psoriasis, nephropathy, and pneumonia), gastrointestinal tract disease (e.g., irritable bowel syndrome (TBS), inflammatory bowel disease (IBD), and abnormal pancreatic secretion), renal disease, urinary tract-associated disease (e.g., benign prostatic hyperplasia or symptoms associated with neuropathic bladder disease, spinal cord tumor, hernia of intervertebral disk, spinal canal stenosis, symptoms derived from diabetes, lower urinary tract disease (e.g., obstruction of lower urinary tract), inflammatory disease of the lower urinary tract, dysuna, and frequent urination), pancreas disease, abnormal angiogenesis-associated disease (e.g., arterial obstruction), scleroderma, brain-associated disease (e.g., cerebral infarction and cerebral hemorrhage), neuropathic pain, peripheral neuropathy, ocular disease (e.g., age-related macular degeneration (AMD), diabetic retinopathy, proliferative vitreoretinopathy (PVR), cicatricial pemphigoid, and glaucoma filtration surgery scarring).

In some embodiments, provided herein are methods of treating or preventing fibrosis, the method comprising administering to a subject in need thereof a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as disclosed herein. For example, the methods can include treating renal fibrosis, pulmonary fibrosis, hepatic fibrosis, arterial fibrosis or systemic sclerosis. In some embodiments, provided herein are methods of treating pulmonary fibrosis (e.g., Idiopathic Pulmonary Fibrosis (IPF)), the method comprising administering to a subject in need thereof a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to treat or prevent fibrosis in a subject. For example, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, can be used to treat fibrosis of an organ or tissue in a subject. In some embodiments, provided herein is a method for preventing a fibrosis condition in a subject, the method comprising administering to the subject at risk of developing one or more fibrosis conditions a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein. For example, the subject may have been exposed to one or more environmental conditions that are known to increase the risk of fibrosis of an organ or tissue. In some embodiments, the subject has been exposed to one or more environmental conditions that are known to increase the risk of lung, liver or kidney fibrosis. In some embodiments, the subject has a genetic predisposition of developing fibrosis of an organ or tissue. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is administered to a subject to prevent or minimize scarring following injury. For example, the injury can include surgery.

Exemplary diseases, disorders, or conditions that involve fibrosis include, but are not limited to: lung diseases associated with fibrosis, for example, idiopathic pulmonary fibrosis, iatrogenic drug induced, occupational/environmental induced fibrosis (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, inherited diseases (e.g., Hermansky-Pudlak Syndrome, Tuberous sclerosis, neurofibromatosis, metabolic storage disorders, and familial interstitial lung disease), pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, bleomycin induced pulmonary fibrosis, chronic asthma, silicosis, asbestos induced pulmonary or pleural fibrosis, acute lung injury, acute respiratory distress syndrome (ARDS), and acute respiratory distress (including bacterial pneumonia induced, trauma induced, viral pneumonia induced, ventilator induced, non-pulmonary sepsis induced, and aspiration induced). Chronic nephropathies associated with injury/fibrosis, kidney fibrosis (renal fibrosis), glomerulonephritis secondary to systemic inflammatory diseases such as lupus and scleroderma, tubulointerstitium fibrosis, glomerular nephritis, glomerular sclerosis, focal segmental, diabetes, glomerular nephritis, focal segmental glomerular sclerosis, IgA nephropathy, hypertension, allograft and Alport Syndrome; dermatological disorders, gut fibrosis, for example, scleroderma, and radiation induced gut fibrosis; liver fibrosis, for example, cirrhosis, alcohol induced liver fibrosis, nonalcoholic steatohepatitis (NASH), non-alcoholic fatty liver disease (NAFLD), toxic/drug induced liver fibrosis (e.g., hemochromatosis), biliary duct injury, primary biliary cirrhosis, infection or viral induced liver fibrosis (e.g., chronic HCV infection), inflammatory/immune disorders, and autoimmune hepatitis; head and neck fibrosis, for example, corneal scarring, e.g., LASIK (laser-assisted in situ keratomileusis), corneal transplant, and trabeculectomy; hypertrophic scarring, Duputren disease, cutaneous fibrosis, cutaneous sceroderma, keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, chronic lymphocytic leukemia, tumor metastasis, transplant organ rejection (e.g., Bronchiolitis obliterans), endometriosis, neonatal respiratory distress syndrome, and neuropathic pain, fibromyalgia, mixed connective tissue disease, and Peyronie's disease.

Provided herein is a method of improving lung function in a subject comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, to the subject in need thereof. In some embodiments, the subject has been diagnosed as having lung fibrosis. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to treat idiopathic pulmonary fibrosis in a subject. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to treat usual interstitial pneumonia in a subject.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is used to treat diffuse parenchymal interstitial lung diseases in subject such as iatrogenic drug induced, occupational/environmental induced fibrosis (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, inherited diseases (e.g., Hermansky-Pudlak Syndrome, Tuberous sclerosis, neurofibromatosis, metabolic storage disorders, and familial interstitial lung disease).

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat post-transplant fibrosis associated with chronic rejection in a subject such as Bronchiolitis obliterans following a lung transplant.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat cutaneous fibrosis in a subject such as cutaneous scleroderma, Dupuytren disease, and keloids.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat hepatic fibrosis with or without cirrhosis in a subject. For example, toxic/drug induced (hemochromatosis), alcoholic liver disease, viral hepatitis (hepatitis B virus, hepatitis C virus, HCV), nonalcoholic liver disease (NAFLD, NASH), and metabolic and auto-immune disease.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat renal fibrosis in a subject (e.g., tubulointerstitium fibrosis and glomerular sclerosis).

Further examples of diseases, disorders, or conditions as provided herein include atherosclerosis, thrombosis, heart disease, vasculitis, formation of scar tissue, restenosis, phlebitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is administered to a subject with fibrosis of an organ or tissue or with a predisposition of developing fibrosis of an organ or tissue with one or more other agents that are used to treat fibrosis. In some embodiments, the one or more agents include corticosteroids, immunosuppressants, B-cell antagonists, and uteroglobin.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to treat a dermatological disorder in a subject. Such dermatological disorders include, but are not limited to, proliferative or inflammatory disorders of the skin such as, atopic dermatitis, bullous disorders, collagenoses, psoriasis, scleroderma, psoriatic lesions, dermatitis, contact dermatitis, eczema, urticaria, rosacea, wound healing, scarring, hypertrophic scarring, keloids, Kawasaki Disease, rosacea, Sjogren-Larsso Syndrome, or urticaria. In some embodiments, a compound disclosed herein (e.g., a compound of Formula I, or a pharmaceutically acceptable salt, stereoisomer, mixture of stereoisomers, tautomer, isotopically enriched analog, or solvate thereof) is used to treat systemic sclerosis.

In some embodiments, a compound disclosed herein (e.g., a compound of Formula I, or a pharmaceutically acceptable salt, stereoisomer, mixture of stereoisomers, tautomer, isotopically enriched analog, or solvate thereof) is useful to treat or prevent inflammation in a subject. For example, a compound disclosed herein (e.g., a compound of Formula I, or a pharmaceutically acceptable salt, stereoisomer, mixture of stereoisomers, tautomer, isotopically enriched analog, or solvate thereof) can be used in the treatment or prevention of inflammatory/immune disorders in a subject.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used in the treatment of pain in a subject. In some embodiments, the pain is acute pain or chronic pain. In some embodiments, the pain is neuropathic pain.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used in the treatment of fibromyalgia. Fibromyalgia is believed to stem from the formation of fibrous scar tissue in contractile (voluntary) muscles. Fibrosis binds the tissue and inhibits blood flow, resulting in pain.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used in the treatment of cancer. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used in the treatment of malignant and benign proliferative disease. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to prevent or reduce proliferation of tumor cells, invasion and metastasis of carcinomas, pleural mesothelioma (Yamada, Cancer Sci., 2008, 99(8), 1603-1610) or peritoneal mesothelioma, cancer pain, bone metastases (Boucharaba et al, J Clin. Invest., 2004, 114(12), 1714-1725; Boucharaba et al, Proc. Natl. Acad. Sci., 2006, 103(25) 9643-9648). Provided herein is a method of treating cancer in a subject, the method comprising administering to the subject a therapeutically effective amount a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein. In some embodiments, the methods provided herein further include administration of a second therapeutic agent, wherein the second therapeutic agent is an anti-cancer agent.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

Further non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, Ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, provided herein is a method of treating an allergic disorder in a subject, the method comprising administration of a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof) as provided herein. In some embodiments, a compound disclosed herein (e.g., a compound of Formula I, or a pharmaceutically acceptable salt, stereoisomer, mixture of stereoisomers, tautomer, isotopically enriched analog, or solvate thereof), is useful for the treatment of respiratory diseases, disorders, or conditions in a subject. For example, a compound disclosed herein (e.g., a compound of Formula I, or a pharmaceutically acceptable salt, stereoisomer, mixture of stereoisomers, tautomer, isotopically enriched analog, or solvate thereof) can treat asthma (e.g., chronic asthma) in a subject.

The term "respiratory disease," as used herein, refers to diseases affecting the organs that are involved in breathing, such as the nose, throat, larynx, eustachian tubes, trachea, bronchi, lungs, related muscles (e.g., diaphragm and intercostals), and nerves. Non-limiting examples of respiratory diseases include asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

Further provided herein are methods for treating or preventing chronic obstructive pulmonary disease in a subject comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof) as provided herein. Examples of chronic obstructive pulmonary disease include, but are not limited to, chronic bronchitis or emphysema, pulmonary hypertension, interstitial lung fibrosis and/or airway inflammation, and cystic fibrosis.

In some embodiments, a compound disclosed herein (e.g., a compound of Formula I, or a pharmaceutically acceptable salt, stereoisomer, mixture of stereoisomers, tautomer, isotopically enriched analog, or solvate thereof) is useful in the treatment or prevention of a nervous system disorder in a subject. The term "nervous system disorder," as used herein, refers to conditions that alter the structure or function of the brain, spinal cord or peripheral nervous system, including but not limited to Alzheimer's Disease, cerebral edema, cerebral ischemia, stroke, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica.

In some embodiments, provided herein is a method for treating or preventing a CNS disorder in a subject. Non-limiting examples of CNS disorders include multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

Also provided herein are methods of treating or preventing cardiovascular disease in a subject. The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. For example, provided herein are methods for treating or preventing vasoconstriction, atherosclerosis and its sequelae myocardial ischemia, myocardial infarction, aortic aneurysm, vasculitis and stroke comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof).

In some embodiments, provided herein are methods for reducing cardiac reperfusion injury following myocardial ischemia and/or endotoxic shock comprising administering to a subject in need thereof a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof).

Further provided herein are methods for reducing the constriction of blood vessels in a subject comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof). For example, methods for lowering or preventing an increase in blood pressure of a subject comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof) are provided herein.

The ability of test compounds to act as inhibitors of an LGA receptor can be demonstrated by assays known in the art. The activity of the compounds and compositions provided herein as LGA receptor inhibitors can be assayed in vitro, in vivo, or in a cell line.

For example, Chinese hamster ovary cells overexpressing human LPA1 can be plated overnight (15,000 cells/well) in microplates in DMEM/F12 medium. Following overnight culture, cells are loaded with calcium indicator dye for 30 minutes at 37° C. The cells are then equilibrated to room temperature for 30 minutes before the assay. Test compounds solubilized in DMSO are transferred to a multiwell non-binding surface plate and diluted with assay buffer (e.g., IX HBSS with calcium/magnesium, 20 mM HEPES, and 0.1% fatty acid free BSA) to a final concentration of 0.5% DMSO. Diluted compounds are added to the cells at final concentrations ranging from 0.08 nM to 5 mM and are then incubated for 20 min at room temperature at which time LPA is added at final concentrations of 10 nM to stimulate the cells. The compound $IC_{50}$ value is defined as the concentration of test compound which inhibited 50% of the calcium flux induced by LPA alone. $IC_{50}$ values can be determined by fitting data to a 4-parameter logistic equation.

In another example, a compound disclosed herein (e.g., a compound of Formula I, or a pharmaceutically acceptable salt, stereoisomer, mixture of stereoisomers, tautomer, isotopically enriched analog, or solvate thereof) as provided herein is dosed orally p.o. 2 hours to CD-1 female mice prior to an LPA challenge. The mice are then dosed via tail vein (IV) with 0.15 mL of LPA in 0.1% BSA/PBS (2 pg/pL). Exactly 2 minutes following the LPA challenge, the mice are euthanized by decapitation and the trunk blood is collected. These samples are collectively centrifuged and individual 75 pL samples are frozen at −20° C. until performance of a histamine assay. The plasma histamine analysis can be run by standard EIA (Enzyme Immunoassay) methods. Plasma samples are thawed and diluted 1:30 in 0.1% BSA in PBS. An EIA protocol for histamine analysis as previously described can be used in this assay.

LPA has a role as a biological effector molecule, and has a diverse range of physiological actions that include effects on blood pressure, platelet activation, and smooth muscle contraction, and a variety of cellular effects, which include cell growth, cell rounding, neurite retraction, and actin stress fiber formation and cell migration. These effects are predominantly receptor mediated.

Activation of the LPA receptors ($LPA_1$, $LPA_2$, $LPA_3$, $LPA_4$, $LPA_5$, $LPA_6$) with LPA mediates a range of downstream signaling cascades. Non-limiting examples include, mitogen-activated protein kinase (MAPK) activation, adenylyl cyclase (AC) inhibition/activation, phospholipase C (PLC) activation/$Ca^{2+}$ mobilization, arachidonic acid release, Akt/PKB activation, and the activation of small GTPases, Rho, ROCK, Rae, and Ras. Additional pathways that are affected by LPA receptor activation include, for example, cyclic adenosine monophosphate (cAMP), cell division cycle 42/GTP-binding protein (Cdc42), proto-oncogene serine/threonine-protein kinase Raf (c-RAF), proto-oncogene tyrosine-protein kinase Src (c-src), extracellular signal-regulated kinase (ERK), focal adhesion kinase (FAK), guanine nucleotide exchange factor (GEF), glycogen synthase kinase 3b (GSK3b), c-jun amino-terminal kinase (JNK), MEK, myosin light chain II (MLC II), nuclear factor kB (NF-kB), N-methyl-D-aspartate (NMDA) receptor activation, phosphatidylinositol 3-kinase (PBK), protein kinase A (PKA), protein kinase C (PKC), ms-related C3 botulinum toxin substrate 1 (RAC1). Nearly all mammalian cells, tissues and organs co-express several LPA-receptor subtypes, which indicates that LPA receptors signal in a cooperative manner. LPA1, LPA2, and LPA3 share high amino acid sequence similarity.

$LPA_1$ (previously called VZG-1/EDG-2/mrecl.3) couples with three types of G proteins, $G_{i/o}$, $G_q$, and $G_{12/13}$. Through activation of these G proteins, LPA induces a range of cellular responses through $LPA_1$ including, for example, cell proliferation, serum-response element (SRE) activation, mitogen-activated protein kinase (MAPK) activation, adenylyl cyclase (AC) inhibition, phospholipase C (PLC) activation, $Ca^{2+}$ mobilization, Akt activation, and Rho activation.

Expression of $LPA_1$ is observed in the testis, brain, heart, lung, small intestine, stomach, spleen, thymus, and skeletal muscle of in mice. Similarly, $LPA_1$ is expressed in human tissues such as the brain, heart, lung, placenta, colon, small intestine, prostate, testis, ovary, pancreas, spleen, kidney, skeletal muscle, and thymus.

$LPA_2$ (EDG-4) also couples with three types of G proteins, $G_{i/o}$, $G_q$, and $G_{12/13}$, to mediate LPA-induced cellular signaling. Expression of $LPA_2$ is observed in the testis, kidney, lung, thymus, spleen, and stomach of adult mice and in the human testis, pancreas, prostate, thymus, spleen, and peripheral blood leukocytes. Expression of $LPA_2$ is upregulated in various cancer cell lines, and several human $LPA_2$ transcriptional variants with mutations in the 3-untranslated region have been observed.

$LPA_3$ can mediate pleiotropic LPA-induced signaling that includes PLC activation, $Ca^{2+}$ mobilization, AC inhibition/activation, and MAPK activation. Overexpression of $LPA_3$ in neuroblastoma cells leads to neurite elongation. Expression of $LPA_3$ is observed in adult mouse testis, kidney, lung, small intestine, heart, thymus, and brain. In humans, it is found in the heart, pancreas, prostate, testis, lung, ovary, and brain (frontal cortex, hippocampus, and amygdala).

$LPA_4$ ($p2y_9$/GPR23) is of divergent sequence compared to $LPA_1$, $LPA_2$, and $LPA_3$ with closer similarity to the platelet-activating factor (PAF) receptor. $LPA_4$ mediates LPA induced $Ca^{2+}$ mobilization and cAMP accumulation, and functional coupling to the G protein Gs for AC activation, as well as coupling to other G proteins. The $LPA_4$ gene is expressed in the ovary, pancreas, thymus, kidney and skeletal muscle.

$LPA_5$(GPR92) is a member of the purinocluster of GPCRs and is structurally most closely related to $LPA_4$. $LPA_5$ is expressed in human heart, placenta, spleen, brain, lung and gut. LPAs also shows very high expression in the CD8+ lymphocyte compartment of the gastrointestinal tract.

$LPA_6$ (p2y5) is a member of the purinocluster of GPCRs and is structurally most closely related to $LPA_4$. $LPA_6$ is an LPA receptor coupled to the G12/13-Rho signaling pathways and is expressed in the inner root sheaths of human hair follicles.

Improvements in any of the foregoing response criteria are specifically provided by the methods of the present disclosure.

Combination Therapies

The compounds as provided herein, or pharmaceutically acceptable salts or solvates thereof, or pharmaceutical compositions of such compounds, are useful as inhibitors of one or more LPA receptors. As described further herein, a compound antagonizing to an LPA receptor can be useful for prevention and/or treatment of diseases such as various kinds of disease including, for example, fibrosis (e.g., renal fibrosis, pulmonary fibrosis, hepatic fibrosis, arterial fibrosis, systemic sclerosis), urinary system disease, carcinoma-associated disease, proliferative disease, inflammation/immune system disease, disease by secretory dysfunction, brain-related disease, and chronic disease.

In some embodiments, this disclosure provides methods for treating a subject (e.g., a human) having a disease, disorder, or condition in which inhibition of one or more LPA receptors (i.e., an LPA-associated disease) is beneficial for the treatment of the underlying pathology and/or symptoms and/or progression of the disease, disorder, or condition. In some embodiments, the methods provided herein can include or further include treating one or more conditions associated, co-morbid or sequela with any one or more of the conditions provided herein.

Provided herein is a method for treating a LPA-associated disease, the method comprising administering to a subject in need thereof an effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as disclosed herein.

In some embodiments, an LPA-associated disease includes, but is not limited to treating fibrosis of an organ (e.g., liver, kidney, lung, heart, and skin), liver disease (acute hepatitis, chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (e.g., cancer, including solid tumors, solid tumor metastasis, vascular fibroma, myeloma, multiple myeloma, Kaposi's sarcoma, leukemia, and chronic lymphocytic leukemia (CLL), and invasive metastasis of cancer cells, inflammatory disease (e.g., psoriasis, nephropathy, and pneumonia), gastrointestinal tract disease (e.g., irritable bowel syndrome (TBS), inflammatory bowel disease (IBD), and abnormal pancreatic secretion), renal disease, urinary tract-associated disease (e.g., benign prostatic hyperplasia or symptoms associated with neuropathic bladder disease, spinal cord tumor, hernia of intervertebral disk, spinal canal stenosis, symptoms derived from diabetes, lower urinary tract disease (e.g., obstruction of lower urinary tract), inflammatory disease of the lower urinary tract, dysuna, and frequent urination), pancreas disease, abnormal angiogenesis-associated disease (e.g., arterial obstruction), scleroderma, brain-associated disease (e.g., cerebral infarction and cerebral hemorrhage), neuropathic pain, peripheral neuropathy, ocular disease (e.g., age-related macular degeneration (AMD), diabetic retinopathy, proliferative vitreoretinopathy (PVR), cicatricial pemphigoid, and glaucoma filtration surgery scarring).

In some embodiments, provided herein are methods of treating or preventing fibrosis, the method comprising administering to a subject in need thereof a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as disclosed herein. For example, the methods can include treating renal fibrosis, pulmonary fibrosis, hepatic fibrosis, arterial fibrosis or systemic sclerosis. In some embodiments, provided herein are methods of treating pulmonary fibrosis (e.g., Idiopathic Pulmonary Fibrosis (IPF)), the method comprising administering to a subject in need thereof a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to treat or prevent fibrosis in a subject. For example, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, can be used to treat fibrosis of an organ or tissue in a subject. In some embodiments, provided herein is a method for preventing a fibrosis condition in a subject, the method comprising administering to the subject at risk of developing one or more fibrosis conditions a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein. For example, the subject may have been exposed to one or more environmental conditions that are known to increase the risk of fibrosis of an organ or tissue. In some embodiments, the subject has been exposed to one or more environmental conditions that are known to increase the risk of lung, liver or kidney fibrosis. In some embodiments, the subject has a genetic predisposition of developing fibrosis of an organ or tissue. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is administered to a subject to prevent or minimize scarring following injury. For example, the injury can include surgery.

Exemplary diseases, disorders, or conditions that involve fibrosis include, but are not limited to: lung diseases associated with fibrosis, for example, idiopathic pulmonary fibrosis, iatrogenic drug induced, occupational/environmental induced fibrosis (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, inherited diseases (e.g., Hermansky-Pudlak Syndrome, Tuberous sclerosis, neurofibromatosis, metabolic storage disorders, and familial interstitial lung disease), pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, bleomycin induced pulmonary fibrosis, chronic asthma, silicosis, asbestos induced pulmonary or pleural fibrosis, acute lung injury, acute respiratory distress syndrome (ARDS), and acute respiratory distress (including bacterial pneumonia induced, trauma induced, viral pneumonia induced, ventilator induced, non-pulmonary sepsis induced, and aspiration induced). Chronic nephropathies associated with injury/fibrosis, kidney fibrosis (renal fibrosis), glomerulonephritis secondary to systemic inflammatory diseases such as lupus and scleroderma, tubulointerstitium fibrosis, glomerular nephritis, glomerular sclerosis, focal segmental, diabetes, glomerular nephritis, focal segmental glomerular sclerosis, IgA nephropathy, hypertension, allograft and Alport Syndrome; dermatological disorders, gut fibrosis, for example, scleroderma, and radiation induced gut fibrosis; liver fibrosis, for example, cirrhosis, alcohol induced liver fibrosis, nonalcoholic steatohepatitis (NASH), non-alcoholic fatty liver disease (NAFLD), toxic/drug induced liver fibrosis (e.g., hemochromatosis), biliary duct injury, primary biliary cirrhosis, infection or viral induced liver fibrosis (e.g., chronic HCV infection), inflammatory/immune disorders, and autoimmune hepatitis; head and neck fibrosis, for example, corneal scarring, e.g., LASIK (laser-assisted in situ keratomileusis), corneal transplant, and trabeculectomy; hypertrophic scarring, Duputren disease, cutaneous fibrosis, cutaneous sceroderma, keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, chronic lymphocytic leukemia, tumor metastasis, transplant organ rejection (e.g., Bronchiolitis obliterans), endometriosis, neonatal respiratory distress syndrome, and neuropathic pain, fibromyalgia, mixed connective tissue disease, and Peyronie's disease.

Provided herein is a method of improving lung function in a subject comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, to the subject in need thereof. In some embodiments, the subject has been diagnosed as having lung fibrosis. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to treat idiopathic pulmonary fibrosis in a subject. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to treat usual interstitial pneumonia in a subject.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is used to treat diffuse parenchymal interstitial lung diseases in subject such as iatrogenic drug induced, occupational/environmental induced fibrosis (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, inherited diseases (e.g., Hermansky-Pudlak Syndrome, Tuberous sclerosis, neurofibromatosis, metabolic storage disorders, and familial interstitial lung disease).

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat post-transplant fibrosis associated with chronic rejection in a subject such as Bronchiolitis obliterans following a lung transplant.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat cutaneous fibrosis in a subject such as cutaneous scleroderma, Dupuytren disease, and keloids.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat hepatic fibrosis with or without cirrhosis in a subject. For example, toxic/drug induced (hemochromatosis), alcoholic liver disease, viral hepatitis (hepatitis B virus, hepatitis C virus, HCV), nonalcoholic liver disease (NAFLD, NASH), and metabolic and auto-immune disease.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat renal fibrosis in a subject (e.g., tubulointerstitium fibrosis and glomerular sclerosis).

Further examples of diseases, disorders, or conditions as provided herein include atherosclerosis, thrombosis, heart disease, vasculitis, formation of scar tissue, restenosis, phlebitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat one or more symptoms of COVID-19.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat chronic obstructive pulmonary disease (COPD).

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat neuroinflammation.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein is useful to treat multiple sclerosis.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is administered to a subject with fibrosis of an organ or tissue or with a predisposition of developing fibrosis of an organ or tissue with one or more other agents that are used to treat fibrosis. In some embodiments, the one or more agents include corticosteroids, immunosuppressants, B-cell antagonists, and uteroglobin.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to treat a dermatological disorder in a subject. Such dermatological disorders include, but are not limited to, proliferative or inflammatory disorders of the skin such as, atopic dermatitis, bullous disorders, collagenoses, psoriasis, scleroderma, psoriatic lesions, dermatitis, contact dermatitis, eczema, urticaria, rosacea, wound healing, scarring, hypertrophic scarring, keloids, Kawasaki Disease, rosacea, Sjogren-Larsso Syndrome, or urticaria. In some embodiments, a compound disclosed herein (e.g., a compound of Formula I, or a pharmaceutically acceptable salt, stereoisomer, mixture of stereoisomers, tautomer, isotopically enriched analog, or solvate thereof) is used to treat systemic sclerosis.

In some embodiments, a compound disclosed herein (e.g., a compound of Formula I, or a pharmaceutically acceptable salt, stereoisomer, mixture of stereoisomers, tautomer, isotopically enriched analog, or solvate thereof) is useful to treat or prevent inflammation in a subject. For example, a compound disclosed herein (e.g., a compound of Formula I, or a pharmaceutically acceptable salt, stereoisomer, mixture of stereoisomers, tautomer, isotopically enriched analog, or solvate thereof) can be used in the treatment or prevention of inflammatory/immune disorders in a subject.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used in the treatment of pain in a subject. In some embodiments, the pain is acute pain or chronic pain. In some embodiments, the pain is neuropathic pain.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used in the treatment of fibromyalgia. Fibromyalgia is believed to stem from the formation of fibrous scar tissue in contractile (voluntary) muscles. Fibrosis binds the tissue and inhibits blood flow, resulting in pain.

In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used in the treatment of cancer. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used in the treatment of malignant and benign proliferative disease. In some embodiments, a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein, is used to prevent or reduce proliferation of tumor cells, invasion and metastasis of carcinomas, pleural mesothelioma (Yamada, Cancer Sci., 2008, 99(8), 1603-1610) or peritoneal mesothelioma, cancer pain, bone metastases (Boucharaba et al, J Clin. Invest., 2004, 114(12), 1714-1725; Boucharaba et al, Proc. Natl. Acad. Sci., 2006, 103(25) 9643-9648). Provided herein is a method of treating cancer in a subject, the method comprising administering to the subject a therapeutically effective amount a compound disclosed herein (e.g., a compound of Formula I, or a pharmaceutically acceptable salt, stereoisomer, mixture of stereoisomers, tautomer, isotopically enriched analog, or solvate thereof), or a pharmaceutical composition as provided herein. In some embodiments, the methods provided herein further include administration of a second therapeutic agent, wherein the second therapeutic agent is an anti-cancer agent.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

Further non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, Ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, provided herein is a method of treating an allergic disorder in a subject, the method comprising administration of a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof) as provided herein. In some embodiments, a compound disclosed herein (e.g., a compound of Formula I, or a pharmaceutically acceptable salt, stereoisomer, mixture of stereoisomers, tautomer, isotopically enriched analog, or solvate thereof), is useful for the treatment of respiratory diseases, disorders or conditions in a subject. For example, a compound disclosed herein (e.g., a compound of Formula I, or a pharmaceutically acceptable salt, stereoisomer, mixture of stereoisomers, tautomer, isotopically enriched analog, or solvate thereof) can treat asthma (e.g., chronic asthma) in a subject.

The term "respiratory disease," as used herein, refers to diseases affecting the organs that are involved in breathing, such as the nose, throat, larynx, eustachian tubes, trachea, bronchi, lungs, related muscles (e.g., diaphragm and intercostals), and nerves. Non-limiting examples of respiratory diseases include asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

Further provided herein are methods for treating or preventing chronic obstructive pulmonary disease in a subject comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof) as provided herein. Examples of chronic obstructive pulmonary disease include, but are not limited to, chronic bronchitis or emphysema, pulmonary hypertension, interstitial lung fibrosis and/or airway inflammation, and cystic fibrosis.

In some embodiments, a compound disclosed herein (e.g., a compound of Formula I, or a pharmaceutically acceptable salt, stereoisomer, mixture of stereoisomers, tautomer, isotopically enriched analog, or solvate thereof) is useful in the treatment or prevention of a nervous system disorder in a subject. The term "nervous system disorder," as used herein, refers to conditions that alter the structure or function of the brain, spinal cord or peripheral nervous system, including but not limited to Alzheimer's Disease, cerebral edema, cerebral ischemia, stroke, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica.

In some embodiments, provided herein is a method for treating or preventing a CNS disorder in a subject. Non-limiting examples of CNS disorders include multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

Also provided herein are methods of treating or preventing cardiovascular disease in a subject. The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. For example, provided herein are methods for treating or preventing vasoconstriction, atherosclerosis and its sequelae myocardial ischemia, myocardial infarction, aortic aneurysm, vasculitis and stroke comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof).

In some embodiments, provided herein are methods for reducing cardiac reperfusion injury following myocardial ischemia and/or endotoxic shock comprising administering to a subject in need thereof a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof).

Further provided herein are methods for reducing the constriction of blood vessels in a subject comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof). For example, methods for lowering or preventing an increase in blood pressure of a subject comprising administering a therapeutically effective amount of a compound disclosed herein (e.g., a compound of Formula I, or a pharmaceutically acceptable salt, stereoisomer, mixture of stereoisomers, tautomer, isotopically enriched analog, or solvate thereof) are provided herein.

Pharmaceutical Compositions and Modes of Administration

Compounds provided herein are usually administered in the form of pharmaceutical compositions.

When employed as pharmaceuticals, a compound disclosed herein (e.g., a compound of Formula I, or a pharmaceutically acceptable salt, stereoisomer, mixture of stereoisomers, tautomer, isotopically enriched analog, or solvate thereof), including pharmaceutically acceptable salts or solvates thereof, can be administered in the form of a pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound disclosed herein, or a pharmaceutically acceptable salt, stereoisomer, mixture of stereoisomers, tautomer, isotopically enriched analog, or solvate thereof, (e.g., a compound of Formula I, or a pharmaceutically acceptable salt, stereoisomer, mixture of stereoisomers, tautomer, isotopically enriched analog, or solvate thereof), in combination with one or more pharmaceutically acceptable excipients (carriers). For example, a pharmaceutical composition prepared using a compound disclosed herein, or a pharmaceutically acceptable salt, stereoisomer, mixture of stereoisomers, tautomer, isotopically enriched analog, or solvate thereof, (e.g., a compound of Formula I, or a pharmaceutically acceptable salt, stereoisomer, mixture of stereoisomers, tautomer, isotopically enriched analog, or solvate thereof). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound disclosed herein, or a pharmaceutically acceptable salt, stereoisomer, mixture of stereoisomers, tautomer, isotopically enriched analog, or solvate thereof, (e.g., a compound of Formula I, or a pharmaceutically acceptable salt, stereoisomer, mixture of stereoisomers, tautomer, isotopically enriched analog, or solvate thereof) with a pharmaceutically acceptable excipient. Pharmaceutical compositions containing a compound disclosed herein, or a pharmaceutically acceptable salt, stereoisomer, mixture of stereoisomers, tautomer, isotopically enriched analog, or solvate thereof, (e.g., a compound of Formula I, or a pharmaceutically acceptable salt, stereoisomer, mixture of stereoisomers, tautomer, isotopically enriched analog, or solvate thereof) as the active ingredient can be prepared by intimately mixing a compound disclosed herein, or a pharmaceutically acceptable salt, stereoisomer, mixture of stereoisomers, tautomer, isotopically enriched analog, or solvate thereof, (e.g., a compound of Formula I, or a pharmaceutically acceptable salt, stereoisomer, mixture of stereoisomers, tautomer, isotopically enriched analog, or solvate thereof) with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in The Handbook of Pharmaceutical Excipients, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds as provided herein. Dosage forms or compositions containing a chemical entity as provided herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22nd Edition (Pharmaceutical Press, London, U K. 2012).

In some embodiments, a compound disclosed herein, or a pharmaceutically acceptable salt, stereoisomer, mixture of stereoisomers, tautomer, isotopically enriched analog, or solvate thereof, (e.g., a compound of Formula I, or a pharmaceutically acceptable salt, stereoisomer, mixture of stereoisomers, tautomer, isotopically enriched analog, or solvate thereof), or pharmaceutical compositions as provided herein can be administered to a subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal (e.g., intranasal), nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In some embodiments, a preferred route of administration is parenteral (e.g., intratumoral).

In some embodiments, a compound disclosed herein (e.g., a compound of Formula I, or a pharmaceutically acceptable salt, stereoisomer, mixture of stereoisomers, tautomer, isotopically enriched analog, or solvate thereof) as provided herein or pharmaceutical compositions thereof can be formulated for parenteral administration, e.g., formulated for injection via the intraarterial, intrasternal, intracranial, intravenous, intramuscular, sub-cutaneous, or intraperitoneal routes. For example, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure. In some embodiments, devices are used for parenteral administration. For example, such devices may include needle injectors, microneedle injectors, needle-free injectors, and infusion techniques.

In some embodiments, the pharmaceutical forms suitable for injection include sterile aqueous solutions or dispersions; formulations including sesame oil, peanut oil, or aqueous propylene glycol; and sterile powders for the extemporaneous preparation of sterile injectable solutions or dispersions. In some embodiments, the form must be sterile and must be fluid to the extent that it may be easily injected. In some embodiments, the form should be stable under the conditions of manufacture and storage and must be preserved against the contaminating action of microorganisms, such as bacteria and fungi.

In some embodiments, the carrier also can be a solvent or dispersion medium containing, for example, water, ethanol, polyol (for example, glycerol, propylene glycol, and liquid polyethylene glycol, and the like), suitable mixtures thereof, and vegetable oils. In some embodiments, the proper fluidity can be maintained, for example, by the use of a coating, such as lecithin, by the maintenance of the required particle size in the case of dispersion, and by the use of surfactants. In some embodiments, the prevention of the action of microorganisms can be brought about by various antibacterial and antifungal agents, for example, parabens, chlorobutanol, phenol, sorbic acid, thimerosal, and the like. In some embodiments, isotonic agents, for example, sugars or sodium chloride are included. In some embodiments, prolonged absorption of the injectable compositions can be brought about by the use in the compositions of agents delaying absorption, for example, aluminum monostearate and gelatin.

In some embodiments, sterile injectable solutions are prepared by incorporating a compound disclosed herein (e.g., a compound of Formula I, or a pharmaceutically acceptable salt, stereoisomer, mixture of stereoisomers, tautomer, isotopically enriched analog, or solvate thereof) in the required amount in the appropriate solvent with various of the other ingredients enumerated above, as required, followed by filtered sterilization. In some embodiments, dispersions are prepared by incorporating the various sterilized active ingredients into a sterile vehicle which contains the basic dispersion medium and the required other ingredients from those enumerated above. In some embodiments, sterile powders are used for the preparation of sterile injectable solutions. In some embodiments, the methods of preparation are vacuum-drying and freeze-drying techniques, which yield a powder of the active ingredient, plus any additional desired ingredient from a previously sterile-filtered solution thereof.

In some embodiments, pharmacologically acceptable excipients usable in a rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol, Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In some embodiments, suppositories can be prepared by mixing a compound disclosed herein (e.g., a compound of Formula I, or a pharmaceutically acceptable salt, stereoisomer, mixture of stereoisomers, tautomer, isotopically enriched analog, or solvate thereof) or pharmaceutical compositions as provided herein with suitable non-irritating excipients or carriers such as cocoa butter, polyethylene glycol or a suppository wax which are solid at ambient temperature but liquid at body temperature and therefore melt in the rectum and release the active compound. In some embodiments, compositions for rectal administration are in the form of an enema.

In some embodiments, a compound disclosed herein (e.g., a compound of Formula I, or a pharmaceutically acceptable salt, stereoisomer, mixture of stereoisomers, tautomer, isotopically enriched analog, or solvate thereof) as provided herein or a pharmaceutical composition thereof is formulated for local delivery to the digestive or GI tract by way of oral administration (e.g., solid or liquid dosage forms.).

In some embodiments, solid dosage forms for oral administration include capsules, tablets, pills, powders, and granules. In some embodiments, a compound disclosed herein, or a pharmaceutically acceptable salt, stereoisomer, mixture of stereoisomers, tautomer, isotopically enriched analog, or solvate thereof, (e.g., a compound of Formula I, or a pharmaceutically acceptable salt, stereoisomer, mixture of stereoisomers, tautomer, isotopically enriched analog, or solvate thereof) is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For example, in the case of capsules, tablets and pills, the dosage form may also comprise buffering agents. In some embodiments, solid compositions of a similar type may also be employed as fillers in soft and hard-filled gelatin capsules using such excipients as lactose or milk sugar as well as high molecular weight polyethylene glycols and the like.

In some embodiments, the pharmaceutical compositions will take the form of a unit dosage form such as a pill or tablet and thus the composition may contain, along with a compound disclosed herein (e.g., a compound of Formula I, or a pharmaceutically acceptable salt, stereoisomer, mixture of stereoisomers, tautomer, isotopically enriched analog, or solvate thereof) as provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In some embodiments, another solid dosage form, a powder, marume, solution or suspension (e.g., in propylene carbonate, vegetable oils, PEG's, poloxamer 124 or triglycerides) is encapsulated in a capsule (gelatin or cellulose base capsule). In some embodiments, unit dosage forms in which one or more compounds and pharmaceutical compositions as provided herein or additional active agents are physically separated are also contemplated; e.g., capsules with granules (or tablets in a capsule) of each drug; two-layer tablets; two-compartment gel caps, etc. In some embodiments, enteric coated or delayed release oral dosage forms are also contemplated.

In some embodiments, other physiologically acceptable compounds may include wetting agents, emulsifying agents, dispersing agents or preservatives that are particularly useful for preventing the growth or action of microorganisms. For example, various preservatives are well known and include, for example, phenol and ascorbic acid.

In some embodiments, the excipients are sterile and generally free of undesirable matter. For example, these compositions can be sterilized by conventional, well-known sterilization techniques. In some embodiments, for various oral dosage form excipients such as tablets and capsules, sterility is not required. For example, the United States Pharmacopeia/National Formulary (USP/NF) standard can be sufficient.

In some embodiments, a compound disclosed herein (e.g., a compound of Formula I, or a pharmaceutically acceptable salt, stereoisomer, mixture of stereoisomers, tautomer, isotopically enriched analog, or solvate thereof) as provided herein or a pharmaceutical composition thereof is formulated for ocular administration. In some embodiments, ocular compositions can include, without limitation, one or more of viscogens (e.g., carboxymethylcellulose, glycerin, polyvinylpyrrolidone, polyethylene glycol); stabilizers (e.g., pluronic (triblock copolymers), cyclodextrins); preservatives (e.g., benzalkonium chloride, EDTA, SofZia (boric acid, propylene glycol, sorbitol, and zinc chloride; Alcon Laboratories, Inc.), Purite (stabilized oxychloro complex; Allergan, Inc.)).

In some embodiments, a compound disclosed herein (e.g., a compound of Formula I, or a pharmaceutically acceptable salt, stereoisomer, mixture of stereoisomers, tautomer, isotopically enriched analog, or solvate thereof) as provided herein or a pharmaceutical composition thereof is formulated for topical administration to the skin or mucosa (e.g., dermally or transdermally). In some embodiments, topical compositions can include ointments and creams. In some embodiments, ointments are semisolid preparations that are typically based on petrolatum or other petroleum derivatives. In some embodiments, creams containing the selected active agent are typically viscous liquid or semisolid emulsions, often either oil-in-water or water-in-oil. For example, cream bases are typically water-washable, and contain an oil phase, an emulsifier, and an aqueous phase. For example, the oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. In some embodiments, the emulsifier in a cream formulation is generally a nonionic, anionic, cationic or amphoteric surfactant. In some embodiments, as with other carriers or vehicles, an ointment base should be inert, stable, nonirritating, and non-sensitizing.

In any of the foregoing embodiments, pharmaceutical compositions as provided herein can include one or more one or more of lipids, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

In some embodiments, the dosage for a compound disclosed herein (e.g., a compound of Formula I, or a pharmaceutically acceptable salt, stereoisomer, mixture of stereoisomers, tautomer, isotopically enriched analog, or solvate thereof), is determined based on a multiple factors including, but not limited to, type, age, weight, sex, medical condition of the subject, severity of the medical condition of the subject, route of administration, and activity of the compound or pharmaceutically acceptable salt or solvate thereof. In some embodiments, proper dosage for a particular situation can be determined by one skilled in the medical arts. In some embodiments, the total daily dosage may be divided and administered in portions throughout the day or by means providing continuous delivery.

In some embodiments, a compound disclosed herein (e.g., a compound of Formula I, or a pharmaceutically acceptable salt, stereoisomer, mixture of stereoisomers, tautomer, isotopically enriched analog, or solvate thereof), is administered at a dose from about 0.01 to about 1000 mg. For example, from about 0.1 to about 30 mg, about 10 to about 80 mg, about 0.5 to about 15 mg, about 50 mg to about 200 mg, about 100 mg to about 300 mg, about 200 to about 400 mg, about 300 mg to about 500 mg, about 400 mg to about 600 mg, about 500 mg to about 800 mg, about 600 mg to about 900 mg, or about 700 mg to about 1000 mg. In some embodiments, the dose is a therapeutically effective amount.

In some embodiments, a compound disclosed herein (e.g., a compound of Formula I, or a pharmaceutically acceptable salt, stereoisomer, mixture of stereoisomers, tautomer, isotopically enriched analog, or solvate thereof) as provided herein is administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg). In some embodiments, a compound disclosed herein (e.g., a compound of Formula I, or a pharmaceutically acceptable salt, stereoisomer, mixture of stereoisomers, tautomer, isotopically enriched analog, or solvate thereof) as provided herein is administered as a dosage of about 100 mg/Kg.

In some embodiments, the foregoing dosages of a compound disclosed herein (e.g., a compound of Formula I, or a pharmaceutically acceptable salt, stereoisomer, mixture of stereoisomers, tautomer, isotopically enriched analog, or solvate thereof), can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound disclosed herein (e.g., a compound of Formula I, or a pharmaceutically acceptable salt, stereoisomer, mixture of stereoisomers, tautomer, isotopically enriched analog, or solvate thereof) as provided herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a compound disclosed herein (e.g., a compound of Formula I, or a pharmaceutically acceptable salt, stereoisomer, mixture of stereoisomers, tautomer, isotopically enriched analog, or solvate thereof) is administered to a subject for a period of time followed by a separate period of time where administration of a compound disclosed herein, or a pharmaceutically acceptable salt, stereoisomer, mixture of stereoisomers, tautomer, isotopically enriched analog, or solvate thereof, (e.g., a compound of Formula I, or a pharmaceutically acceptable salt, stereoisomer, mixture of stereoisomers, tautomer, isotopically enriched analog, or solvate thereof) is stopped. In some embodiments, a compound disclosed herein (e.g., a compound of Formula I, or a pharmaceutically acceptable salt, stereoisomer, mixture of stereoisomers, tautomer, isotopically enriched analog, or solvate thereof) is administered for a first period and a second period following the first period, with administration stopped during the second period, followed by a third period where administration of a compound disclosed herein, or a pharmaceutically acceptable salt, stereoisomer, mixture of stereoisomers, tautomer, isotopically enriched analog, or solvate thereof, (e.g., a compound of Formula I, or a pharmaceutically acceptable salt, stereoisomer, mixture of stereoisomers, tautomer, isotopically enriched analog, or solvate thereof) is started and then a fourth period following the third period where administration is stopped. For example, the period of administration of a compound disclosed herein (e.g., a compound of Formula I, or a pharmaceutically acceptable salt, stereoisomer, mixture of stereoisomers, tautomer, isotopically enriched analog, or solvate thereof) followed by a period where administration is stopped is repeated for a determined or undetermined period of time. In some embodiments, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In some embodiments, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In some embodiments, a compound disclosed herein (e.g., a compound of Formula I, or a pharmaceutically acceptable salt, stereoisomer, mixture of stereoisomers, tautomer, isotopically enriched analog, or solvate thereof), is orally administered to the subject one or more times per day (e.g., one time per day, two times per day, three times per day, four times per day per day or a single daily dose).

In some embodiments, a compound disclosed herein (e.g., a compound of Formula I, or a pharmaceutically acceptable salt, stereoisomer, mixture of stereoisomers, tautomer, isotopically enriched analog, or solvate thereof), is administered by parenteral administration to the subject one or more times per day (e.g., 1 to 4 times one time per day, two times per day, three times per day, four times per day or a single daily dose).

In some embodiments, a compound disclosed herein (e.g., a compound of Formula I, or a pharmaceutically acceptable salt, stereoisomer, mixture of stereoisomers, tautomer, isotopically enriched analog, or solvate thereof), is administered by parenteral administration to the subject weekly.

Synthesis of the Compounds

The compounds of this disclosure can be prepared from readily available starting materials using, for example, the following general methods, and procedures. It will be appreciated that where certain process conditions (i.e., reaction temperatures, times, mole ratios of reactants, solvents, pressures, etc.) are given, other process conditions can also be used unless otherwise stated. Optimum reaction conditions may vary with the reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting certain functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance CA USA), EMKA-Chemie Gmbh & Co. KG (Eching Germany), or Millipore Sigma (Burlington MA USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplements (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

Scheme I illustrates a general method which can be employed for the synthesis of compounds described herein, where each wherein each of $R^1$, $R^2$, $R^4$, R, $R^9$, $R^{13}$, $X^1$, $X^2$, $X^3$, $X^4$, $X^6$, A, m, n, $L^1$ and L2 are independently as defined herein, LG and LG' are a suitable leaving group, such as halo (e.g., Cl, Br, or I), where LG and LG' are not the same, PG is a suitable carboxyl protecting group, such as alkyl or benzyl, and B is a suitable coupling functional group such as, but not limited to, a boronic acid or a derivative thereof, such as a boronic ester (e.g., —B($R^{50}$)$_2$, where each $R^{50}$ is independently an alkyl or substituted alkyl, or the two $R^{50}$ join to form a cyclic boronic ester, which may be optionally substituted (e.g., pinacol boronic ester).

Scheme I

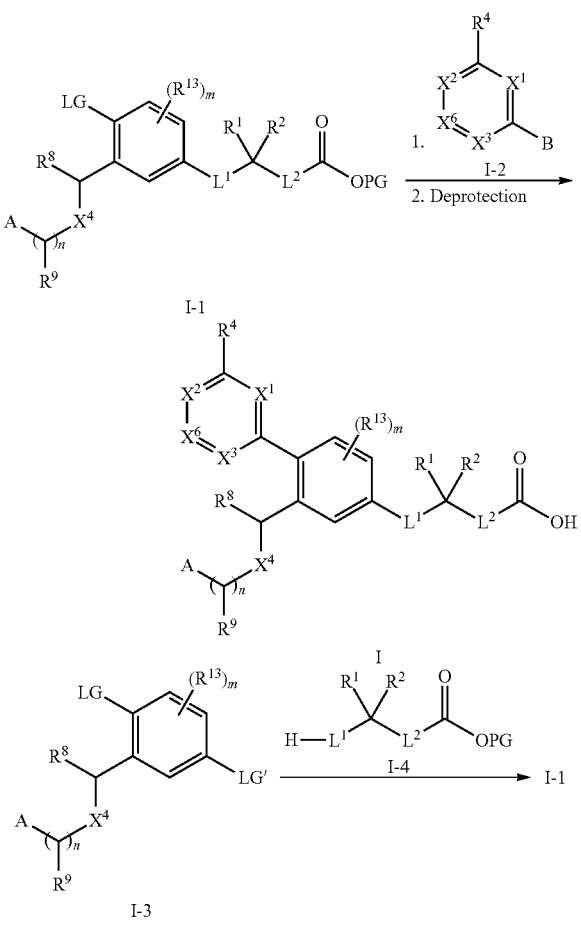

The compounds of Formula I are prepared by first coupling compound I-1, followed by deprotection to afford the free acid of Formula I, wherein B is a suitable coupling functional group such as, but not limited to, a boronic acid or a derivative thereof, such as a boronic ester (cyclic or acyclic), zinc or magnesium halide, an organotin compound, such as tributylstannane or trimethylstannane, fluorosulfonyl esters, tin, sodium, and the like. Such reactions are commonly utilized for aromatic functionalization, and are typically conducted in the presence of suitable catalyst such as, but not limited to, a palladium catalyst including [1,1'-bis(diphenylphosphino)ferrocene]palladium(II) dichloride, $Pd(OAc)_2$, $Pd(PPh_3)_4$, $PdCl_2(PPh_3)_2$ or tris(dibenzylideneacetone)dipalladium(O), and the like, or a copper catalyst such as CuCl or CuI, and if required suitable mediator, co-catalyst and/or base known to one skilled in the art using suitable solvents/solvent mixtures. Upon reaction completion, compounds of Formula I can be recovered by conventional techniques such as neutralization, extraction, precipitation, chromatography, filtration and the like. In certain embodiments, when control of stereochemistry is desired, proper control of reaction conditions and selection of substituents for the reagents can at least partially dictate or preserve the formation of the various stereoisomers. Compounds I-1 and I-2 may be commercially obtained or synthesized de novo. For example, as shown above in Scheme I, Compound I-1 may be prepared by coupling compound I-3 with compound I-4 under standard nucleophilic aromatic substitution conditions.

Scheme II illustrates a general method which can be employed for the synthesis of compounds described herein, where each wherein each of $R^1$, $R_2$, $R^4$, $R^6$, $R^8$, $R^9$, $R^{13}$, $X^1$, $X^2$, $X^3$, $X^4$, A, m, n, $L^1$ and L2 are independently as defined herein, LG and LG' are a suitable leaving group, such as halo (e.g., Cl, Br, or I), where LG and LG' are not the same, PG is a suitable carboxyl protecting group, such as alkyl or benzyl, and B is a suitable coupling functional group such as, but not limited to, a boronic acid or a derivative thereof, such as a boronic ester (e.g., —$B(R^{50})_2$, where each $R^{50}$ is independently an alkyl or substituted alkyl, or the two $R^{50}$ join to form a cyclic boronic ester, which may be optionally substituted (e.g., pinacol boronic ester).

Scheme II

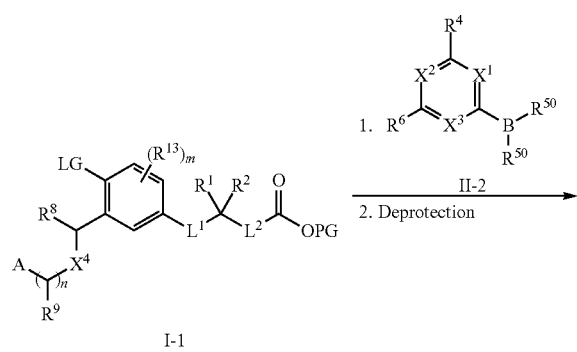

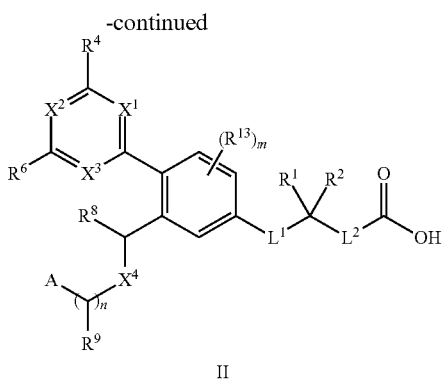

II

The compounds of Formula II are prepared by first coupling compound II-1, followed by deprotection to afford the free acid of Formula II, wherein B is a suitable functional group such as, but not limited to, a boronic acid or a derivative thereof, such as a boronic ester (cyclic or acyclic), zinc or magnesium halide, an organotin compound, such as tributylstannane or trimethylstannane, fluorosulfonyl esters, tin, sodium, hydrogen, and the like. Such reactions are commonly utilized for aromatic functionalization, and are typically conducted in the presence of suitable catalyst such as, but not limited to, a palladium catalyst including [1,1'-bis(diphenylphosphino)ferrocene]palladium(II) dichloride, $Pd(OAc)_2$, $Pd(PPh_3)_4$, $PdCl_2(PPh_3)_2$ or tris(dibenzylideneacetone)dipalladium(O), and the like, or a copper catalyst such as CuCl or CuI, and if required suitable mediator, co-catalyst and/or base known to one skilled in the art using suitable solvents/solvent mixtures. Upon reaction completion, compounds of Formula II can be recovered by conventional techniques such as neutralization, extraction, precipitation, chromatography, filtration and the like. In certain embodiments, when control of stereochemistry is desired, proper control of reaction conditions and selection of substituents for the reagents can at least partially dictate or preserve the formation of the various stereoisomers. Compounds I-1 and II-2 may be commercially obtained or synthesized de novo.

Scheme III illustrates a general method which can be employed for the synthesis of compounds described herein, where each wherein each of $R^1$, $R^2$, $R^4$, $R^6$, $R^8$, $R^9$, $R^{13}$, $X^1$, $X^2$, $X^3$, $X^4$, ring A, m, n, L and $L^2$ are independently as defined herein, LG and LG' are a suitable leaving group, such as halo (e.g., Cl, Br, or I), where LG and LG' are not the same, PG is a suitable carboxyl protecting group, such as alkyl or benzyl, and B is a suitable coupling functional group such as, but not limited to, a boronic acid or a derivative thereof, such as a boronic ester (e.g., —$B(R^{50})_2$, where each $R^{50}$ is independently an alkyl or substituted alkyl, or the two $R^{50}$ join to form a cyclic boronic ester, which may be optionally substituted (e.g., pinacol boronic ester).

Scheme III

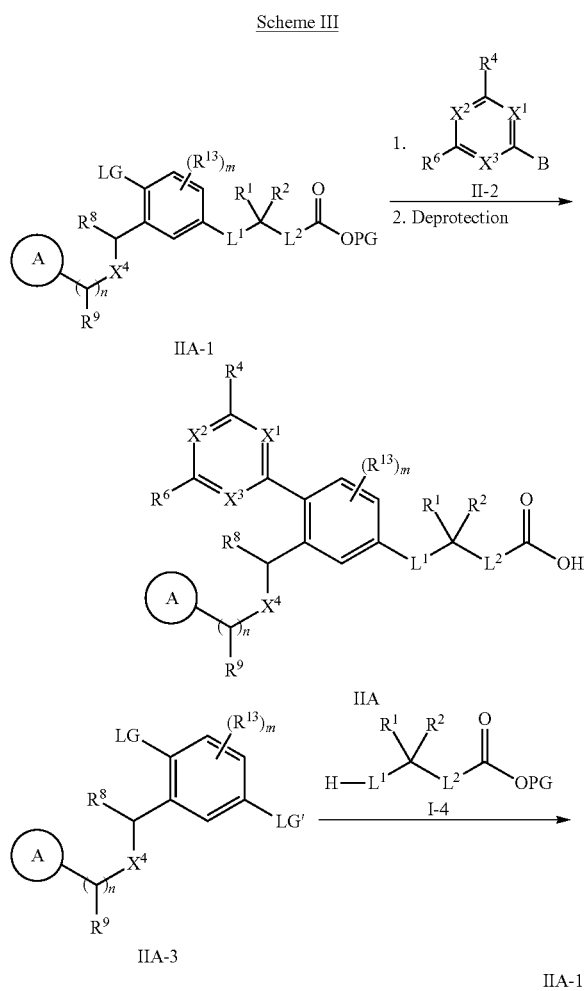

The compounds of Formula IIA are prepared by first coupling compound IIA-1, followed by deprotection to afford the free acid of Formula IIA, wherein B is a suitable functional group such as, but not limited to, a boronic acid or a derivative thereof, such as a boronic ester (cyclic or acyclic), zinc or magnesium halide, an organotin compound, such as tributylstannane or trimethylstannane, fluorosulfonyl esters, tin, sodium, hydrogen, and the like. Such reactions are commonly utilized for aromatic functionalization, and are typically conducted in the presence of suitable catalyst such as, but not limited to, a palladium catalyst including [1,1'-bis(diphenylphosphino)ferrocene]palladium (II) dichloride, Pd(OAc)$_2$, Pd(PPh$_3$)$_4$, PdCl$_2$(PPh$_3$)$_2$ or tris(dibenzylideneacetone)dipalladium(O), and the like, or a copper catalyst such as CuCl or CuI, and if required suitable mediator, co-catalyst and/or base known to one skilled in the art using suitable solvents/solvent mixtures. Upon reaction completion, compounds of Formula IIA can be recovered by conventional techniques such as neutralization, extraction, precipitation, chromatography, filtration and the like. In certain embodiments, when control of stereochemistry is desired, proper control of reaction conditions and selection of substituents for the reagents can at least partially dictate or preserve the formation of the various stereoisomers. Compounds IIA-1 and II-2 may be commercially obtained or synthesized de novo. For example, as shown above in Scheme III, Compound IIA-1 may be prepared by coupling compound IIA-3 with compound I-4 under standard nucleophilic aromatic substitution conditions.

It will be appreciated that the various substituents of each intermediate (e.g., compound I-1, II-1, I-2, I-3, II-3, and 1-4) can be modified or added either before (as shown in Scheme I, Scheme II, or Scheme II) or after the addition of the I-2 or II-2 moiety. For example, A or the ring A may be appended before or after the steps shown in the Schemes above. The A or ring A moiety may be coupled to an $X^4$ precursor under substitution reaction conditions.

For any compound shown in Scheme I, Scheme II, or Scheme II, it should be understood that various derivatives can be provided by functional group interconversion at any step. In some embodiments, the various substituents of Formula I-1, II-1, IIA-1, I-2, II-2, I-3, II-3, IIA-3, or I-4, (e.g., A, ring A, $R^1$, $R^2$, $R^4$, $R^6$, $R^8$, $R^9$, $R^{13}$, $X^1$, $X^2$, $X^3$, $X^4$, $X^6$, m, n, $L^1$ and $L^2$) are as defined herein. However, derivatization of compounds I, II, IIA, I-1, II-1, IIA-1, I-2, II-2, I-3, II-3, IAI-3, or I-4, prior to reacting in any step, and/or further derivatization of the resulting reaction product, provides various compounds of Formula I, Formula II, or Formula IIA. Appropriate starting materials and reagents can be purchased or prepared by methods known to one of skill in the art. Upon each reaction completion, each of the intermediate or final compounds can be recovered, and optionally purified, by conventional techniques such as neutralization, extraction, precipitation, chromatography, filtration, and the like. Other modifications to arrive at compounds of this disclosure are within the skill of the art.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

| Abbreviations (as used herein): | |
|---|---|
| AcOH | acetic acid |
| AgOTf | silver trifluoromethanesulfonate |
| AIBN | azobisisobutyronitrile |
| aq. | aqueous |
| Catacxium A-Pd-G2 | Chloro[(di(1-adamantyl)-N-butylphosphine)-2-(2-aminobiphenyl)]palladium(II) (CAS: 1375477-29-4) |
| CCl$_4$ | carbon tetrachloride |
| CH$_3$CN | acetonitrile |
| Cs$_2$CO$_3$ | cesium carbonate |
| DCM or CH$_2$Cl$_2$ | dichloromethane |
| CuI | copper(I) iodide |
| DAST | diethylaminosulfur trifluoride |
| DIBALH | diisobutylaluminium hydride |
| DBU | 1,8-diazabicyclo[5.4.0]undec-7-ene |
| DCE | 1,2-dichloroethane |
| DIAD | diisopropyl azodicarboxylate |
| DMAc or DMA | N,N-Dimethylacetamide |
| DMAP | 4-(dimethylamino)pyridine |
| DMF | N,N-dimethyl-formamide |
| DPPA | diphenylphosphorazindate |
| EtOAc | ethyl acetate |
| EtOH | ethanol |
| Et$_3$N | triethylamine |
| h | hour |
| HCl | hydrochloric acid |
| H$_2$O | water |
| HPLC | High Performance Liquid Chromatography |
| prep. HPLC | Preparative High Performance Liquid Chromatography |
| [Ir(COD)(OMe)]$_2$ | (1,5-cyclooctadiene)(methoxy)iridium(1) dimer |
| K$_2$CO$_3$ | potassium carbonate |
| KOAc | potassium Acetate |
| LiCl | lithium chloride |
| LiOH | lithium hydroxide |
| MeI | iodomethane |
| MeOH | methanol |
| Na$_2$CO$_3$ | sodium carbonate |
| Na$_2$SO$_4$ | sodium sulfate |
| NaH | sodium hydride |
| NaI | sodium iodide |
| NaNO$_2$ | sodium nitrite |
| NaOH | sodium hydroxide |
| NBS | bromosuccinimide |
| NH$_4$Cl | ammonium chloride |
| NFSI | N-fluorobenzenesulfonimide |
| NMP | 1-methyl-pyrrolidin-2-one |
| Pd$_2$(dba)$_3$ | tris(dibenzylideneacetone)dipalladium |
| Pd(dppf)Cl$_2$ | [1,1'-bis(diphenylphosphino)-ferrocene]palladium(II) chloride |
| Pd(dppf)Cl$_2$•CH$_2$Cl$_2$ | [1,1'-bis(diphenylphosphino)-ferrocene]palladium(II) chloride-dichloromethane complex |
| Pd(OAc)$_2$ | palladium (II) Acetate |
| PE | Petrol ether |
| PPh$_3$ | triphenylphosphine |
| Prep. HPLC | Preparative High-Performance Liquid Chromatography |
| PTSA | p-toluenesulfonic acid |
| sat. | saturated |
| SFC | Supercritical Fluid Chromatography |
| S-Phos | 2-Dicyclohexylphosphino-2',6'-diMethoxy-1,1'-biphenyl |
| t-BuOH | tert-butanol |
| t-BuOK | potassium tert-butoxide |
| t-BuONa | sodium tert-butoxide |
| TFA | trifluoroacetic acid |
| THF | tetrahydrofuran |
| TLC | Thin Layer Chromatography |
| Xphos | dicyclohexyl(2',4',6'-triisopropyl-[1,1'-biphenyl]-2-yl)phosphane |

General information: All evaporations or concentrations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (100-200 mesh). Solvent systems were reported as mixtures by volume. NMR spectra were recorded on a Bruker 400 or Varian (400 MHz) spectrometer. $^1$H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on SHIMADZU LC20-MS2020 or Agilent 1260 series 6125B mass spectrometer or Agilent 1200 series, 6110 or 6120 mass spectrometer with electrospray ionization and excepted as otherwise indicated.

Example A1

3-((2-(((2,3-dihydro-1H-inden-2-yl)oxy)methyl)-3', 5'-dimethoxy-4'-methyl-[1,1'-biphenyl]-4-yl)oxy) propanoic acid (Compound 105)

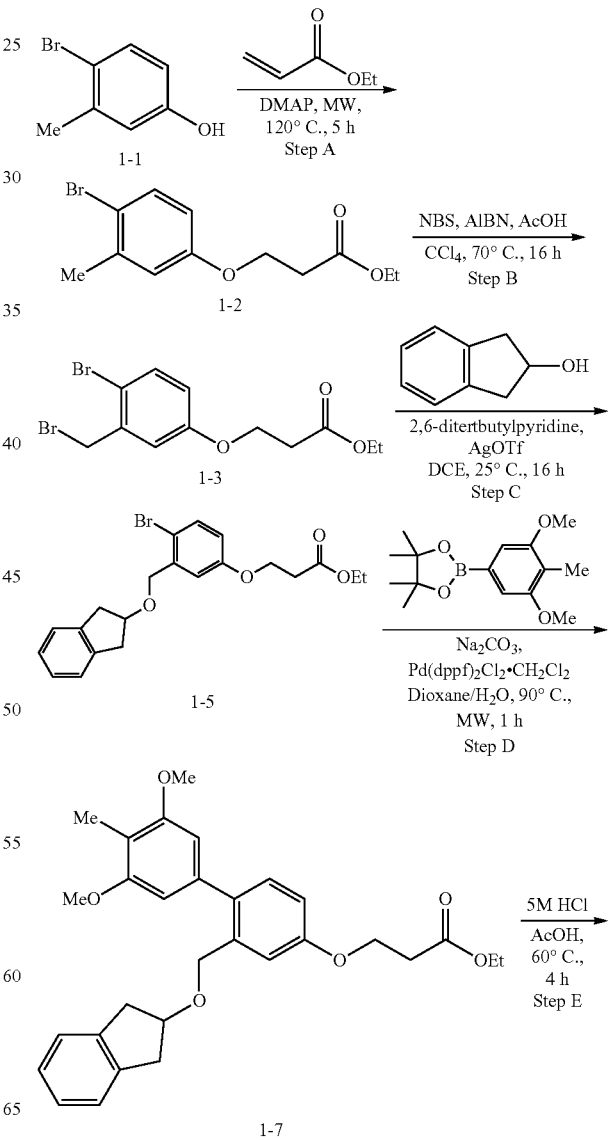

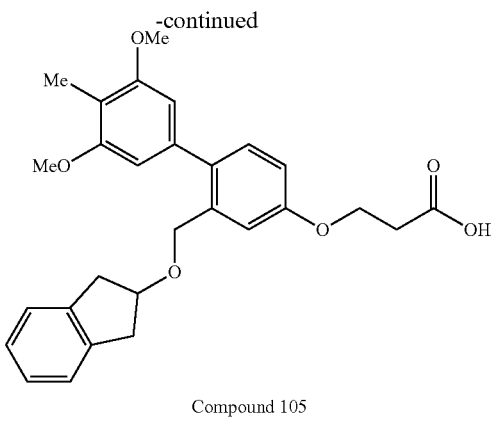

Compound 105

Step A: ethyl 3-(4-bromo-3-methylphenoxy)propanoate

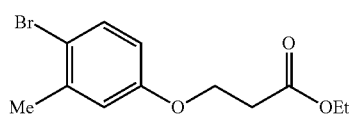 [SMILES: CCOC(=O)CCOc1ccc(Br)c(C)c1]

To a mixture of 4-bromo-3-methylphenol (3.20 g, 17.10 mmol) in ethyl acrylate (14 mL) was added DMAP (522 mg, 4.28 mmol) at room temperature. The mixture was stirred at 120° C. for 5 h under microwave irradiation. Then the reaction mixture was concentrated under reduced pressure. The residue was purified with silica gel column (PE/EtOAc=20:1) to afford ethyl 3-(4-bromo-3-methylphenoxy)propanoate (1.20 g, 24% yield). $^1$H NMR (400 MHz, CDCl$_3$) δ 7.39 (d, J=8.8 Hz, 1H), 6.80 (d, J=2.8 Hz, 1H), 6.62 (dd, J=8.8 Hz, 3.2 Hz, 1H), 4.25-4.13 (m, 4H), 2.77 (t, J=6.4 Hz, 2H), 2.35 (s, 3H), 1.27 (t, J=7.2 Hz, 3H).

Step B: ethyl 3-(4-bromo-3-(bromomethyl)phenoxy)propanoate

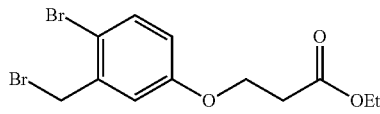 [SMILES: CCOC(=O)CCOc1ccc(Br)c(CBr)c1]

To a mixture of ethyl 3-(4-bromo-3-methylphenoxy)propanoate (300 mg, 1.04 mmol) in CCl$_4$ (8 mL) were added NBS (222 mg, 1.25 mmol), AIBN (7 mg, 0.042 mmol), and AcOH (0.15 mL). The reaction mixture was heated to 70° C. and stirred for 16 h. The reaction mixture was concentrated. The residue was diluted with water (10 mL), extracted with EtOAc (10 mL×3). The organic layer was dried over anhydrous Na$_2$SO$_4$, filtered and concentrated. The residue was purified with prep. TLC (PE/EtOAc=7/1) to afford ethyl 3-(4-bromo-3-(bromomethyl)phenoxy)propanoate (200 mg, 52% yield). $^1$H NMR (400 MHz, CDCl$_3$) δ 7.44 (d, J=8.8 Hz, 1H), 7.01 (d, J=3.2 Hz, 1H), 6.74 (dd, J=8.8 Hz, 2.8 Hz, 1H), 4.54 (s, 2H), 4.28-4.13 (m, 4H), 2.78 (t, J=6.4 Hz, 2H), 1.28 (t, J=7.2 Hz, 3H).

Step C: ethyl 3-(4-bromo-3-(((2,3-dihydro-1H-inden-2-yl)oxy)methyl)phenoxy)propanoate

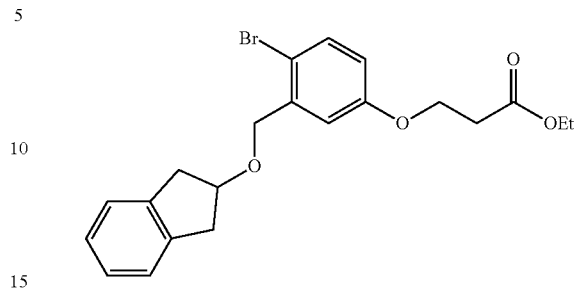

To a mixture of ethyl 3-(4-bromo-3-(bromomethyl)phenoxy)propanoate (220 mg, 0.60 mmol) and 2,3-dihydro-1H-inden-2-ol (139 mg, 1.05 mmol) in DCE (8 mL) were added 2,6-di-tert-butylpyridine (197 mg, 1.80 mmol) and AgOTf (269 mg, 1.05 mmol) at room temperature. The mixture was stirred at 25° C. for 16 h. The reaction mixture was filtered and concentrated. The residue was purified with silica gel column (PE/EtOAc=10:1) to afford ethyl 3-(4-bromo-3-(((2,3-dihydro-1H-inden-2-yl)oxy)methyl)phenoxy)propanoate (100 mg, 40% yield). $^1$H NMR (400 MHz, CDCl$_3$) δ 7.39 (d, J=8.4 Hz, 1H), 7.25-7.20 (m, 2H), 7.19-7.14 (m, 2H), 7.04 (d, J=3.2 Hz, 1H), 6.70 (dd, J=8.8 Hz, 2.8 Hz, 1H), 4.59 (s, 2H), 4.54-4.47 (m, 1H), 4.28-4.12 (m, 4H), 3.23 (dd, J=16.4 Hz, 6.4 Hz, 2H), 3.10 (dd, J=16.0 Hz, 4.8 Hz, 2H), 2.76 (t, J=6.4 Hz, 2H), 1.27 (t, J=6.8 Hz, 3H).

Step D: ethyl 3-((2-(((2,3-dihydro-1H-inden-2-yl)oxy)methyl)-3',5'-dimethoxy-4'-methyl-[1,1'-biphenyl]-4-yl)oxy)propanoate

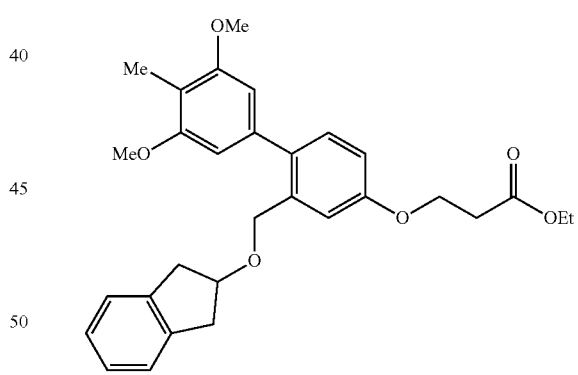

To a mixture of ethyl 3-(4-bromo-3-(((2,3-dihydro-1H-inden-2-yl)oxy)methyl)phenoxy)propanoate (20.0 mg, 0.048 mmol) in 1,4-dioxane/H$_2$O (1 mL/0.2 mL) were added 2-(3,5-dimethoxyphenyl)-4,4,5,5-tetramethyl-1,3,2-dioxaborolane (20.0 mg, 0.072 mmol), Na$_2$CO$_3$ (15.2 mg, 0.144 mmol) and Pd(dppf)Cl$_2$·CH$_2$Cl$_2$ (2.00 mg, 0.0024 mmol) at room temperature. The reaction mixture was stirred at 90° C. for 1 h under microwave irradiation. After cooling, the reaction mixture was filtered, and the filter cake was washed with EtOAc (10 mL). The filtrate was dried over Na$_2$SO$_4$ and concentrated. The residue was purified with prep. TLC (PE/EtOAc=5/1) to afford ethyl 3-((2-(((2,3-dihydro-1H-inden-2-yl)oxy)methyl)-3',5'-dimethoxy-4'-methyl-[1,1'-biphenyl]-yl)oxy)propanoate (13.0 mg, 56% yield). $^1$H NMR (400 MHz, CDCl$_3$) δ 7.21 (d, J=8.4 Hz, 1H), 7.17-7.12 (m, 4H), 7.09 (d, J=2.4 Hz, 1H), 6.88 (dd, J=8.4 Hz, 2.4 Hz, 1H), 6.51 (s, 2H), 4.44 (s, 2H), 4.42-4.35 (m, 1H), 4.28 (t, J=6.4 Hz, 2H), 4.20 (q, J=7.2 Hz, 2H), 3.77 (s, 6H), 3.12 (dd, J=16.0 Hz, 6.4 Hz, 2H), 2.97 (dd, J=16.0 Hz, 4.4 Hz, 2H), 2.80 (t, J=6.4 Hz, 2H), 2.14 (s, 3H), 1.29 (d, J=7.2 Hz, 3H).

Step E: 3-((2-(((2,3-dihydro-1H-inden-2-yl)oxy)methyl)-3',5'-dimethoxy-4'-methyl-[1,1'-biphenyl]-4-yl)oxy)propanoic acid (Compound 105)

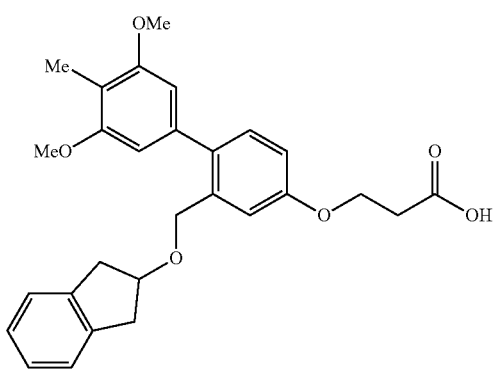 [SMILES: COc1cc(-c2ccc(OCCC(=O)O)cc2COC2Cc3ccccc3C2)cc(OC)c1C]

The mixture of ethyl 3-((2-(((2,3-dihydro-1H-inden-2-yl)oxy)methyl)-3',5'-dimethoxy-4'-methyl-[1,1'-biphenyl]-yl)oxy)propanoate (50.0 mg, 0.102 mmol) in AcOH (2 mL) and 5M aq. HCl solution (2 mL) was stirred at 60° C. for 4 h. The reaction mixture was concentrated. The residue was purified with prep. TLC (PE/EtOAc=1/2) and further by prep. HPLC (0.1% formic acid in H$_2$O and MeOH) to afford 3-((2-(((2,3-dihydro-1H-inden-2-yl)oxy)methyl)-3',5'-dimethoxy-4'-methyl-[1,1'-biphenyl]-4-yl)oxy)propanoic acid (12.0 mg, 32% yield). LC-MS: m/z 485.3 (M+Na)+. $^1$H NMR (400 MHz, CDCl$_3$) δ 7.21 (d, J=8.4 Hz, 1H), 7.19-7.11 (m, 4H), 7.09 (d, J=2.4 Hz, 1H), 6.88 (dd, J=8.4 Hz, 2.8 Hz, 1H), 6.50 (s, 2H), 4.45 (s, 2H), 4.41-4.36 (m, 1H), 4.29 (t, J=6.4 Hz, 2H), 3.77 (s, 6H), 3.12 (dd, J=16.0 Hz, 6.4 Hz, 2H), 2.97 (dd, J=16.4 Hz, 4.4 Hz, 2H), 2.87 (t, J=6.0 Hz, 2H), 2.14 (s, 3H).

Example A2

3-((2-(((2,3-dihydro-1H-inden-2-yl)oxy)methyl)-3',5'-dimethoxy-4'-methyl-[1,1'-biphenyl]-4-yl)amino)propanoic acid (Compound 101)

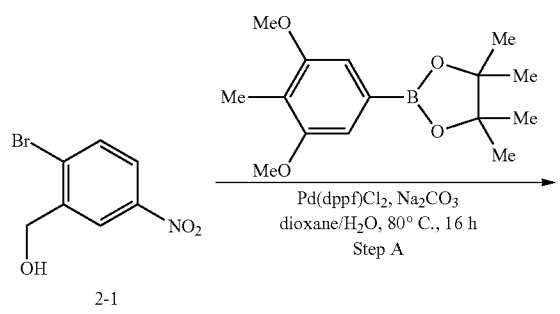

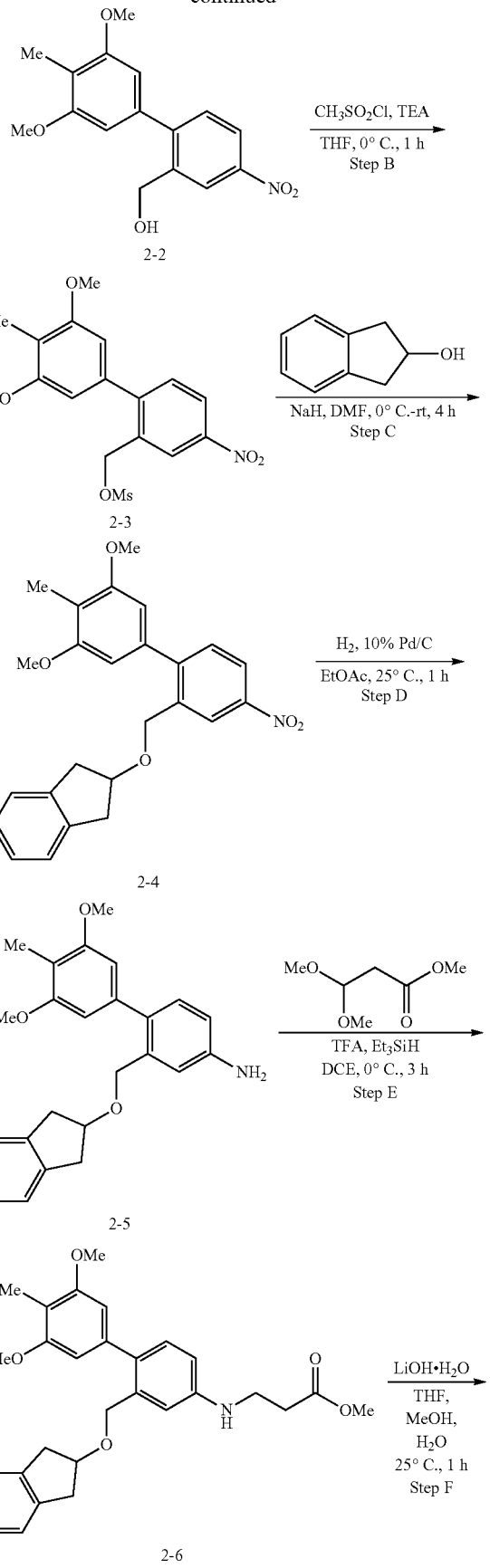

231

-continued

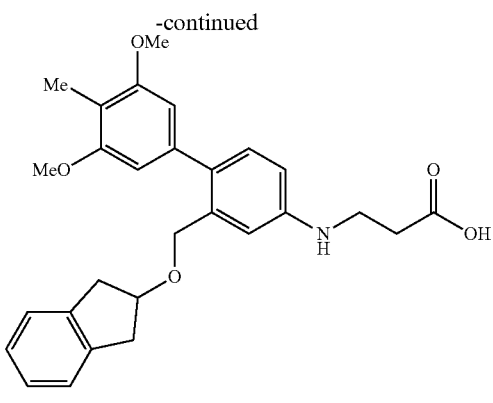

Compound 101

Step A: (3',5'-dimethoxy-4'-methyl-4-nitro-[1,1'-biphenyl]-2-yl)methanol

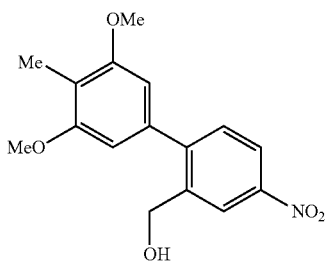 [SMILES: COc1cc(-c2ccc([N+](=O)[O-])cc2CO)cc(OC)c1C]

To a solution of (2-bromo-5-nitro-phenyl)methanol (2 g, 8.62 mmol) and 2-(3,5-dimethoxy-4-methyl-phenyl)-4,4,5,5-tetramethyl-1,3,2-dioxaborolane (2.40 g, 8.62 mmol) in dioxane (30 mL) and H$_2$O (10 mL) was added Na$_2$CO$_3$ (2.74 g, 25.86 mmol) and Pd(dppf)Cl$_2$ (631 mg, 861.95 μmol). The mixture was stirred under nitrogen at 85° C. for 16 h. After cooling, the mixture was diluted with H$_2$O (15 mL), extracted with EtOAc (20 mL×3). The combined organic layer was washed with brine (50 mL), dried over anhydrous Na$_2$SO$_4$, filtered and concentrated. The residue was purified by silica gel column (PE/EtOAc=10/1) to afford (3',5'-dimethoxy-4'-methyl-4-nitro-[1,1'-biphenyl]-2-yl)methanol (2.2 g, 84% yield). H NMR (400 MHz, CD$_3$OD) δ 8.50 (d, J=2.4 Hz, 1H), 8.20 (dd, J=8.4 Hz, 2.4 Hz, 1H), 7.53 (d, J=8.4 Hz, 1H), 6.62 (s, 2H), 4.64 (s, 2H), 3.85 (s, 6H), 2.11 (s, 3H).

Step B: (3',5'-dimethoxy-4'-methyl-4-nitro-[1,1'-biphenyl]-2-yl)methylmethanesulfonate

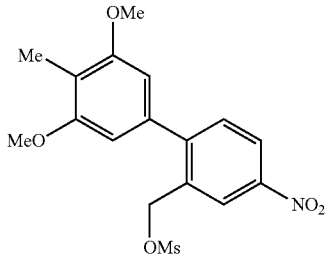 [SMILES: COc1cc(-c2ccc([N+](=O)[O-])cc2COS(C)(=O)=O)cc(OC)c1C]

To a solution of [2-(3,5-dimethoxy-4-methyl-phenyl)-5-nitro-phenyl]methanol (2.2 g, 7.25 mmol) in THF (25 mL) was added TEA (1.47 g, 14.51 mmol) and MsCl (1.25 g, 10.88 mmol) at 0° C. The reaction mixture was stirred at 0° C. for 1 h. Then the mixture was diluted with H$_2$O (10 mL), extracted with EtOAc (20 mL×3). The combined organic layer was washed with brine (50 mL), dried over anhydrous Na$_2$SO$_4$, filtered and concentrated. The residue was purified by silica gel column (PE/EtOAc=10/1) to afford (3',5'-dimethoxy-4'-methyl-4-nitro-[1,1'-biphenyl]-2-yl) methylmethanesulfonate (2.50 g, 90% yield). $^1$H NMR (400 MHz, DMSO-d6) δ 8.49 (d, J=2.4 Hz, 1H), 8.32 (dd, J=8.4 Hz, 2.4 Hz, 1H), 7.70 (d, J=8.4 Hz, 1H), 6.67 (s, 2H), 5.32 (s, 2H), 3.83 (s, 6H), 3.24 (s, 3H), 2.06 (s, 3H).

Step C: 2-((3',5'-dimethoxy-4'-methyl-4-nitro-[1,1'-biphenyl]-2-yl)methoxy)-2,3-dihydro-1H-indene

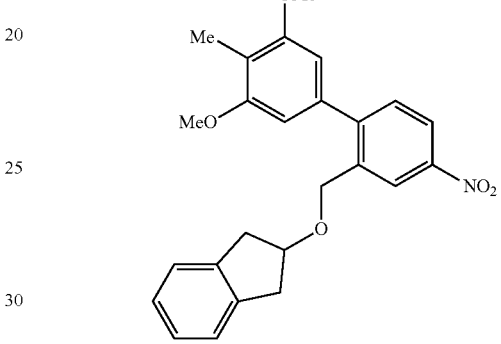

To a solution of indan-2-ol (1.42 g, 10.62 mmol) in THF (20 mL) was added NaH (424.71 mg, 10.62 mmol, 60% wt in mineral oil) at 0° C. After being stirred for 30 min, to the above solution was added (3',5'-dimethoxy-4'-methyl-4-nitro-[1,1'-biphenyl]-2-yl)methymethanesulfonate (2.7 g, 7.08 mmol) in THF (10 mL). The mixture was stirred at 25° C. for 12 h. The mixture was diluted with H$_2$O (30 mL), extracted with EtOAc (30 mL×3). The combined organic layer was washed with brine (50 mL), dried over anhydrous Na$_2$SO$_4$, filtered and concentrated. The residue was purified by silica gel column (PE/EtOAc=10/1) to afford 2-((3',5'-dimethoxy-4'-methyl-4-nitro-[1,1'-biphenyl]-2-yl) methoxy)-2,3-dihydro-1H-indene (220 mg, 7% yield). LC-MS: m/z 442.1 (M+Na)+.

Step D: 4-(3,5-dimethoxy-4-methyl-phenyl)-3-(indan-2-yloxymethyl)aniline

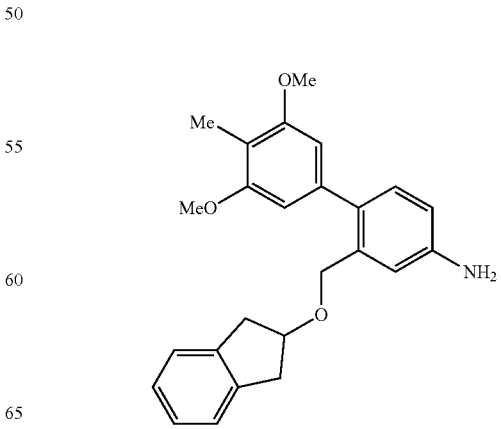

To a solution of 2-((3',5'-dimethoxy-4'-methyl-4-nitro-[1,1'-biphenyl]-2-yl)methoxy)-2,3-dihydro-1H-indene (200 mg, 47.68 µmol) in EtOAc (5 mL) was added 10% Pd/C (100 mg) under nitrogen. The suspension was degassed under vacuum and purged with H₂ for three times. The mixture was stirred under H₂ (15 psi) at 25° C. for 1 h. The mixture was filtered and the filtrate was concentrated to afford 4-(3,5-dimethoxy-4-methyl-phenyl)-3-(indan-2-yloxymethyl)aniline (170 mg, 91% yield), which used for next step without purification. LC-MS: m/z 390.1 (M+H)⁺.

Step E: methyl 3-((2-(((2,3-dihydro-1H-inden-2-yl)oxy)methyl)-3',5'-dimethoxy-4'-methyl-[1,1'-biphenyl]-4-yl)amino)propanoate

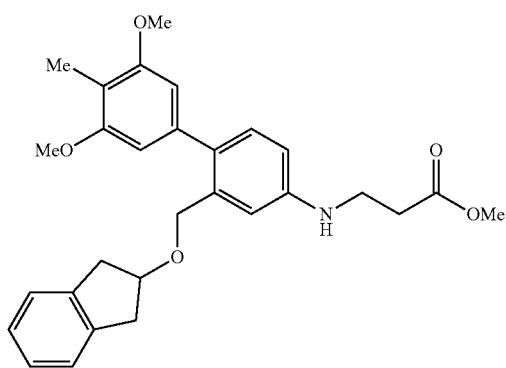 [SMILES: COC(=O)CCNc1ccc(-c2cc(OC)c(C)c(OC)c2)c(COC2Cc3ccccc3C2)c1]

To a solution of 4-(3,5-dimethoxy-4-methyl-phenyl)-3-(indan-2-yloxymethyl)aniline (170 mg, 436.47 µmol) and methyl 3,3-dimethoxypropanoate (64.67 mg, 436.47 µmol) in DCE (5 mL) was added TFA (3.23 g, 28.37 mmol) and Et₃SiH (167 mg, 1.44 mmol) at 0° C. The reaction mixture was stirred at 0° C. for 3 h. The mixture was diluted with H₂O (10 mL), extracted with EtOAc (20 mL×3). The combined organic layer was washed with brine (50 mL), dried over anhydrous Na₂SO₄, filtered and concentrated. The residue was purified by silica gel column (PE/EtOAc=5/1) to afford methyl 3-((2-(((2,3-dihydro-1H-inden-2-yl)oxy)methyl)-3',5'-dimethoxy-4'-methyl-[1,1'-biphenyl]-4-yl)amino)propanoate (70 mg, 33% yield). LC-MS: m/z 476.2 (M+H)⁺.

Step F: 3-((2-(((2,3-dihydro-1H-inden-2-yl)oxy)methyl)-3',5'-dimethoxy-4'-methyl-[1,1'-biphenyl]-4-yl)amino)propanoic acid (Compound 101)

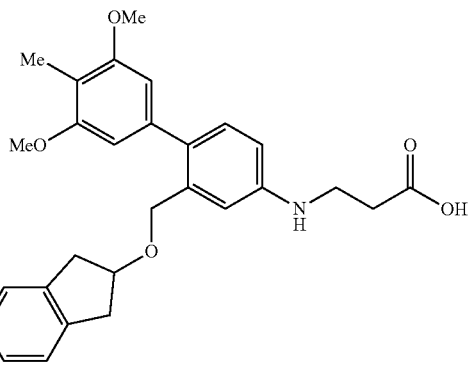

To a solution of methyl 3-[4-(3,5-dimethoxy-4-methyl-phenyl)-3-(indan-2-yloxymethyl)anilino]propanoate (50 mg, 105.14 µmol) in MeOH (1 mL), THF (1 mL) and H₂O (1 mL) was added LiOH·H₂O (22 mg, 525.68 µmol). The mixture was stirred at 25° C. for 1 h. The reaction mixture was acidified by 1N HCl to pH=4, extracted with EtOAc (20 mL×3). The combined organic layer was washed with brine (50 mL), dried over anhydrous Na₂SO₄, filtered and concentrated. The residue was purified by prep. HPLC (Column: Phenomenex Gemini-NX 80*30 mm*3 um; mobile phase: [water (10 mM NH₄HCO₃)—CH₃CN]; B %: 12%-82%, 9 min) to afford 3-((2-(((2,3-dihydro-1H-inden-2-yl)oxy)methyl)-3',5'-dimethoxy-4'-methyl-[1,1'-biphenyl]-4-yl)amino)propanoic acid (43 mg, 87% yield). LC-MS: m/z 462.0 (M+H). ¹H NMR (400 MHz, CD₃OD) δ 7.18-7.06 (m, 5H), 6.81 (d, J=2.4 Hz, 1H), 6.67 (dd, J=8.0 Hz, 2.4 Hz, 1H), 6.54 (s, 2H), 4.43 (s, 2H), 4.41-4.36 (m, 1H), 3.73 (s, 6H), 3.43 (t, J=6.8 Hz, 2H), 3.09 (dd, J=16.0 Hz, 8.0 Hz, 2H), 2.89 (dd, J=16.0 Hz, 4.0 Hz, 2H), 2.59 (t, J=6.8 Hz, 2H), 2.09 (s, 3H).

Example A3

4-({2-[(2,3-dihydro-1H-inden-2-yloxy)methyl]-3',5'-dimethoxy-4'-methyl-[1,1'-biphenyl]-4-yl}amino)oxane-4-carboxylic acid (Compound 111)

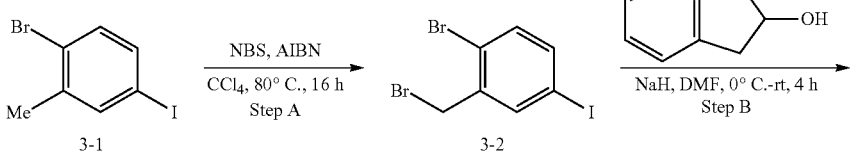

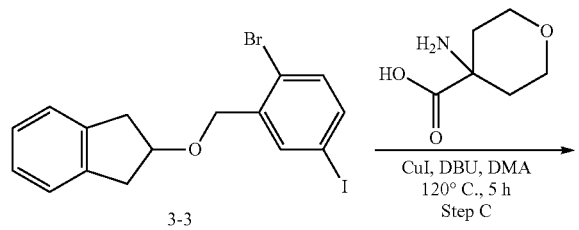

-continued

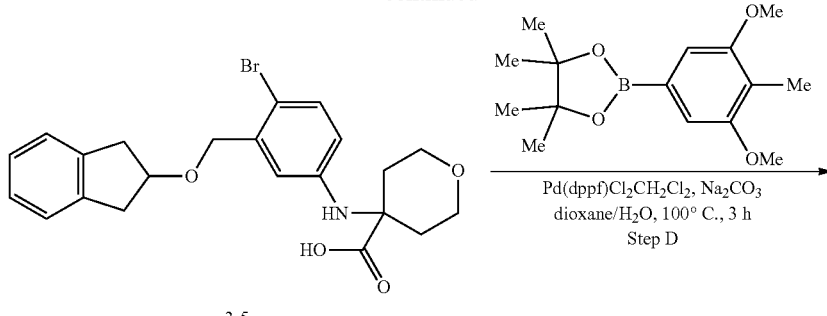

3-5

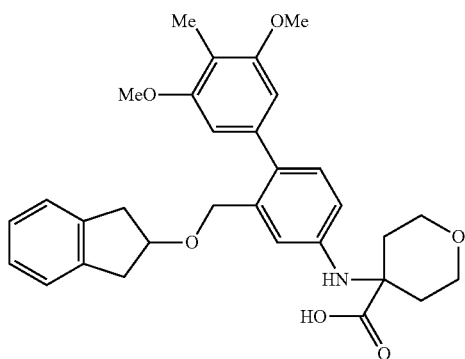

Compound 111

Step A: 1-bromo-2-(bromomethyl)-4-iodobenzene

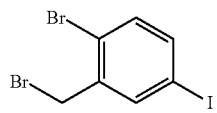

The mixture of bromo-4-iodo-2-methylbenzene (20.0 g, 67.36 mmol), AIBN (5.53 g, 33.68 mmol) and NBS (11.99 g, 67.36 mmol) in CCl$_4$ (300 mL) was heated to 80° C. and stirred for 16 h. After cooling to room temperature, the reaction mixture was concentrated under vacuum. The residue was purified by silica gel column (100% PE) to afford 1-bromo-2-(bromomethyl)-4-iodobenzene (8.0 g, 31.6% yield). Alternatively, 1-bromo-2-(bromomethyl)-4-iodobenzene is provided from (2-bromo-5-iodophenyl)methanol using PPh$_3$ and CBr$_4$ at 25° C.

Step B: 2-[(2-bromo-5-iodophenyl)methoxy]-2,3-dihydro-1H-indene

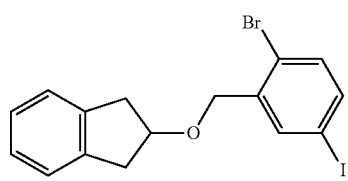 [SMILES: Brc1ccc(I)cc1COC1Cc2ccccc2C1]

To the solution of 2,3-dihydro-1H-inden-2-ol (0.86 g, 6.39 mmol) in DMF (40 mL), was added NaH (319 mg, 7.98 mmol, 60% wt in mineral oil) under nitrogen atmosphere. The reaction mixture was stirred at 0° C. for 1 h. Then a solution of 1-bromo-2-(bromomethyl)-4-iodobenzene (2.00 g, 5.32 mmol) in DMF (10 mL) was added into the above solution. The reaction mixture was stirred at room temperature for 3 h. Then the reaction mixture was quenched with sat. aq. NH$_4$Cl (100 mL), extracted with EtOAc (100 mL×3). The combined organic layer was washed with brine, dried over anhydrous Na$_2$SO$_4$, filtered and concentrated. The residue was purified by silica gel column (0~10% EtOAc in PE) to afford 2-[(2-bromo-5-iodophenyl)methoxy]-2,3-dihydro-1H-indene (450 mg, 19.7% yield).

Step C: 4-({4-bromo-3-[(2,3-dihydro-1H-inden-2-yloxy)methyl]phenyl}amino)oxane-4-carboxylic acid

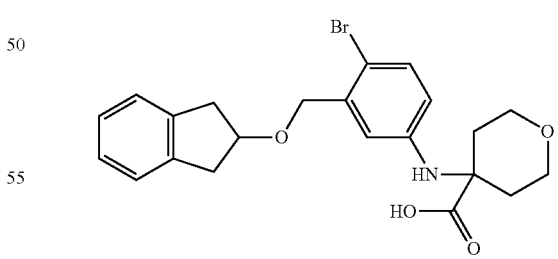

To a solution of 2-[(2-bromo-5-iodophenyl)methoxy]-2,3-dihydro-1H-indene (450 mg, 1.05 mmol) in DMAc (10 mL) was added CuI (40 mg, 0.21 mmol), 4-aminotetrahydro-2H-pyran-4-carboxylic acid (304 mg, 2.10 mmol) and DBU (93.13 mg, 0.61 mmol). The resulting mixture was stirred at 120° C. for 5 h under nitrogen atmosphere. The reaction mixture was cooled to room temperature, poured into water (20 mL). The pH value was adjusted to 7 by acetic acid. The resulting mixture was extracted with CH$_2$Cl$_2$ (20 mL×2). The combined organic layer was dried over anhydrous Na$_2$SO$_4$, filtered and concentrated. The residue was purified by silica gel column (0-10% MeOH in CH$_2$C2) to afford 4-({4-bromo-3-[(2,3-dihydro-1H-inden-2-yloxy)methyl]phenyl}amino)oxane-4-carboxylic acid (35 mg, 44.9% yield). LC-MS: m/z 447.9 (M+H)$^+$.

Step D: 4-({2-[(2,3-dihydro-1H-inden-2-yloxy)methyl]-3',5'-dimethoxy-4'-methyl-[1,1'-biphenyl]-4-yl}amino)oxane-4-carboxylic acid (Compound 111)

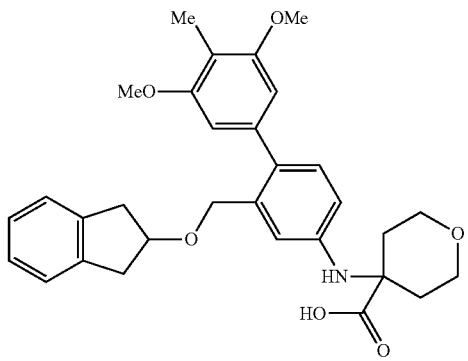 [SMILES: COc1cc(-c2ccc(NC3(C(=O)O)CCOCC3)cc2COC2Cc3ccccc3C2)cc(OC)c1C]

The mixture of 4-({4-bromo-3-[(2,3-dihydro-1H-inden-2-yloxy)methyl]phenyl}amino)oxane-4-carboxylic acid (190 mg, 0.43 mmol), 2-(3,5-dimethoxy-4-methylphenyl)-4,4,5,5-tetramethyl-1,3,2-dioxaborolane (118 mg, 0.43 mmol), Na$_2$CO$_3$ (135 mg, 1.28 mmol) and Pd(dppf)Cl$_2$·CH$_2$Cl$_2$ (69.35 mg, 0.09 mmol) in 1,4-dioxane (4 mL)/water (1 mL), was stirred at 100° C. for 3 h under nitrogen atmosphere. The reaction mixture was cooled to room temperature and filtered. The filtrate was concentrated. The residue was purified by prep. HPLC (Column: Xselect CSH C18 OBD Column 30*150 mm*5 m; Mobile Phase A: Water (0.05% FA), Mobile Phase B: CH$_3$CN; Flow rate: 60 mL/min; Gradient: 30% B to 81% B in 10 min) to afford 4-({2-[(2,3-dihydro-1H-inden-2-yloxy)methyl]-3',5'-dimethoxy-4'-methyl-[1,1'-biphenyl]-4-yl}-amino)oxane-4-carboxylic acid (102.8 mg, 45.9% yield). LC-MS: m/z 518.4 (M+H)$^+$. $^1$H NMR (400 MHz, DMSO-d6) δ 7.20-7.18 (m, 2H), 7.16-7.08 (m, 2H), 7.02 (d, J=8.4 Hz, 1H), 6.77 (d, J=2.6 Hz, 1H), 6.51 (s, 2H), 6.50-6.37 (m, 1H) 4.36-4.33 (m, 3H), 3.72 (s, 6H), 3.71-3.59 (m, 4H), 3.10 (dd, J=16.4 Hz, 6.3 Hz, 2H), 2.87 (dd, J=16.4 Hz, 3.7 Hz, 2H), 2.08-1.97 (m, 2H), 1.91-1.89 (m, 2H).

Example A4

1-((2-(((2,3-dihydro-1H-inden-2-yl)oxy)methyl)-3',5'-dimethoxy-4'-methyl-[1,1'-biphenyl]-4-yl)amino)cyclopropane-1-carboxylic acid (Compound 109)

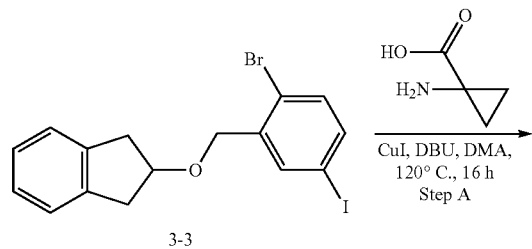

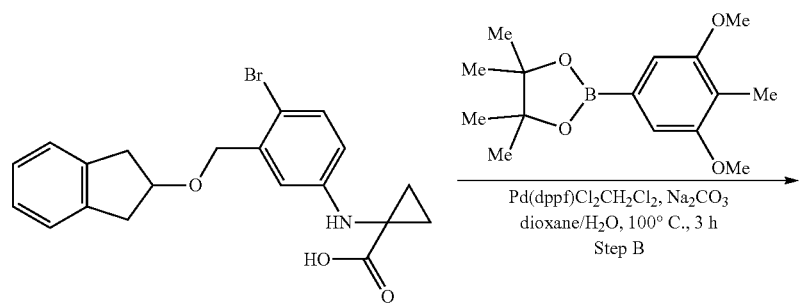

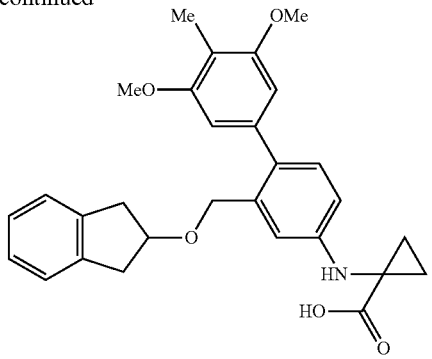

Compound 109

1-((2-(((2,3-dihydro-1H-inden-2-yl)oxy)methyl)-3',5'-dimethoxy-4'-methyl-[1,1'-biphenyl]-4-yl)amino)cyclopropane-1-carboxylic acid (Compound 109) was synthesized according to the procedures described for the preparation of Example A3 (step C and D) by using 1-aminocyclopropane-1-carboxylic acid in step C. LC-MS: m/z 496.2 (M+Na)+. $^1$H NMR (400 MHz, CDCl$_3$) δ 12.29 (brs, 1H), 7.21-7.16 (m, 2H), 7.15-7.09 (m, 2H), 7.04 (d, J=8.0 Hz, 1H), 6.74 (d, J=2.4 Hz, 1H), 6.58-6.56 (m, 2H), 6.54 (s, 2H), 4.38-4.30 (m, 3H), 3.73 (s, 6H), 3.08 (dd, J=16.4 Hz, 6.0 Hz, 2H), 2.85 (dd, J=16.4 Hz, 3.6 Hz, 2H), 2.01 (s, 3H), 1.47-1.39 (m, 2H), 1.03-0.96 (m, 2H).

Example A5

1-({2-[(2,3-dihydro-1H-inden-2-yloxy)methyl]-3',5'-dimethoxy-4'-methyl-[1,1'-biphenyl]-4-yl}oxy)cyclopropane-1-carboxylic acid (Compound 117)

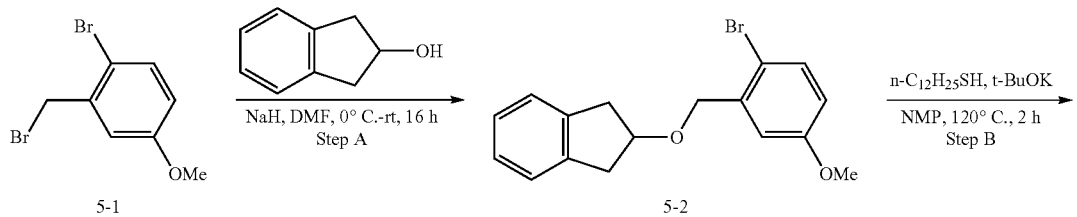

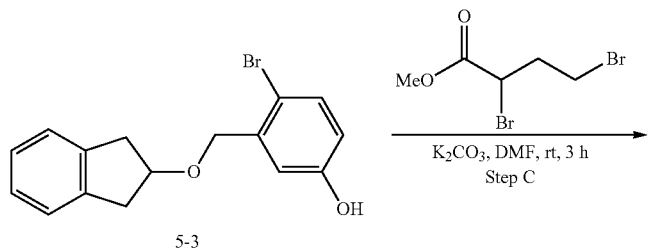

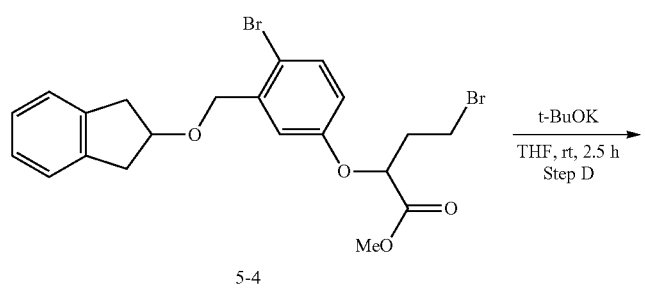

-continued

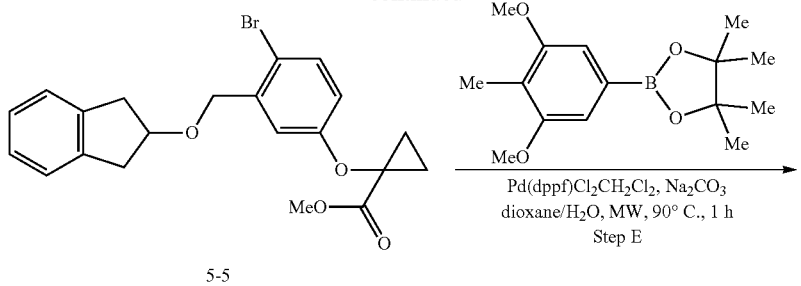

5-5

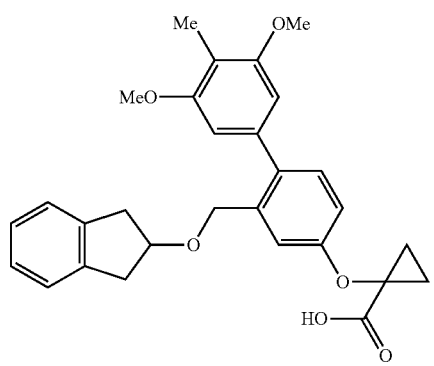

Compound 117

Step A: 2-[(2-bromo-5-methoxyphenyl)methoxy]-2,3-dihydro-1H-indene

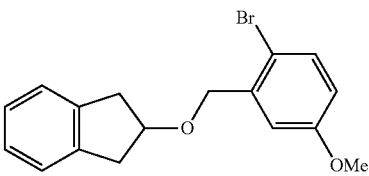 [SMILES: COc1ccc(Br)c(COC2Cc3ccccc3C2)c1]

At 0° C., to the solution of 2,3-dihydro-1H-inden-2-ol (3.59 g, 26.79 mmol) in DMF (50 mL) was added NaH (1.07 g, 26.79 mmol, 60% wt in mineral oil). The reaction mixture was stirred at 0° C. for 0.5 h. Then 1-bromo-2-(bromomethyl)-4-methoxybenzene (5.00 g, 17.86 mmol) was added to the above solution. The reaction mixture was stirred at room temperature for 16 h. The reaction mixture was quenched with water (50 mL), extracted with EtOAc (50 mL×3). The combined organic phase was washed with brine, dried over anhydrous Na₂SO₄, filtered and concentrated. The residue was purified by silica gel column (0% to 10% EtOAc in PE) to afford 2-[(2-bromo-5-methoxyphenyl)methoxy]-2,3-dihydro-1H-indene (4.10 g, 68.9% yield).

Step B: 4-bromo-3-[(2,3-dihydro-1H-inden-2-yloxy)methyl]phenol

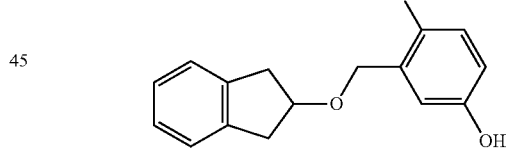

The mixture of dodecane-1-thiol (5.52 g, 32.41 mmol) and t-BuOK (3.64 g, 32.41 mmol) in NMP (100 mL) was stirred at room temperature for 10 min under nitrogen atmosphere. Then to the above mixture, was added 2-[(2-bromo-5-methoxyphenyl)methoxy]-2,3-dihydro-1H-indene (9.00 g, 27.01 mmol). The resulting mixture was stirred at 120° C. for 2 h under nitrogen atmosphere. After cooling, the reaction mixture was diluted with water (200 mL), neutralized to pH=7 with sat. aq. NH₄Cl. The resulting mixture was extracted with EtOAc (100 mL×3). The combined organic layer was washed with brine (100 mL×3), dried over anhydrous Na₂SO₄, filtered and concentrated. The residue was purified by reverse flash column (30%-80% CH₃CN in water) to afford 4-bromo-3-[(2,3-dihydro-1H-inden-2-yloxy)methyl]phenol (4.0 g, 11.6% yield). LC-MS: m/z 318.9 (M−H)⁻.

Step C: methyl 4-bromo-2-{4-bromo-3-[(2,3-dihydro-1H-inden-2-yloxy)methyl]phenoxy}-butanoate

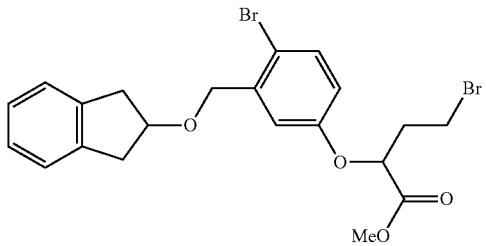 [SMILES: COC(=O)C(CCBr)Oc1ccc(Br)c(COC2Cc3ccccc3C2)c1]

The mixture of 4-bromo-3-[(2,3-dihydro-1H-inden-2-yloxy)methyl]phenol (500 mg, 1.57 mmol), methyl 2,4-dibromobutanoate (489 mg, 1.88 mmol) and K$_2$CO$_3$ (432.98 mg, 3.13 mmol) in DMF (10 mL) was stirred at room temperature for 3 h. The reaction mixture was diluted with water (20 mL), extracted with EtOAc (30 mL×3). The combined organic layer was washed with brine, dried over anhydrous Na$_2$SO$_4$, filtered and concentrated to afford crude methyl 4-bromo-2-{4-bromo-3-[(2,3-dihydro-1H-inden-2-yloxy)methyl]phenoxy}butanoate (720 mg, 92.3% yield). LC-MS: m/z 520.8 (M+Na)+.

Step D: methyl 1-({4-bromo-3-[(2,3-dihydro-1H-inden-2-yloxy)methyl]phenyl}oxy)cyclopropane-1-carboxylate

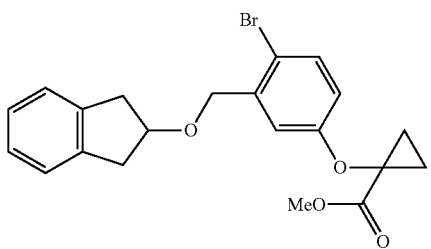 [SMILES: COC(=O)C1(Oc2ccc(Br)c(COC3Cc4ccccc4C3)c2)CC1]

The mixture of methyl 4-bromo-2-{4-bromo-3-[(2,3-dihydro-1H-inden-2-yloxy)methyl]phenoxy}butanoate (710 mg, 1.43 mmol) and tert-butoxy potassium (320 mg, 2.85 mmol) in THF (10 mL) was stirred at room temperature for 2.5 h. The reaction mixture was quenched with water (20 mL), extracted with EtOAc (30 mL×3). The combined organic layer was washed with brine, dried over anhydrous Na$_2$SO$_4$. After filtration, the filtrate was concentrated to afford crude methyl 1-({4-bromo-3-[(2,3-dihydro-1H-inden-2-yloxy)methyl]phenyl}oxy)cyclopropane-1-carboxylate (520 mg, 90.5% yield). LC-MS: m/z 440.9 (M+Na)+.

Step E: 1-({2-[(2,3-dihydro-1H-inden-2-yloxy)methyl]-3',5'-dimethoxy-4'-methyl-[1,1'-biphenyl]-4-yl}oxy)cyclopropane-1-carboxylic acid (Compound 117)

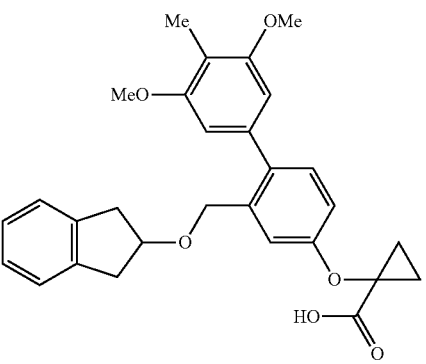 [SMILES: COc1cc(-c2ccc(OC3(C(=O)O)CC3)cc2COC2Cc3ccccc3C2)cc(OC)c1C]

To the mixture of 1-{4-bromo-3-[(2,3-dihydro-1H-inden-2-yloxy)methyl]phenoxy}cyclopropane-1-carboxylic acid (470 mg, 1.17 mmol), 2-(3,5-dimethoxyphenyl)-4,4,5,5-tetramethyl-1,3,2-dioxaborolane (400 mg, 1.44 mmol) and Na$_2$CO$_3$ (370.58 mg, 3.50 mmol) in 1,4-dioxane (8 mL) and water (2 mL), was added Pd(dppf)Cl$_2$·CH$_2$Cl$_2$ (190 mg, 0.23 mmol). The reaction mixture was heated to 90° C. and stirred at 90° C. for 1 h under nitrogen under microware irradiation. After cooling, the reaction mixture was poured into water (100 mL), extracted with EtOAc (30 mL×3). The combined organic layer was washed with brine, dried over anhydrous Na$_2$SO$_4$. After filtration, the filtrate was concentrated under vacuum. The residue was purified by prep. HPLC (Column: CHIRAL ART Cellulose-SB, 4.6*100 mm, 3 m; Mobile Phase A: Hex(0.1% FA):EtOH=90:10; Flow rate: 1 mL/min; Gradient: 0% B to 0% B; Injection Volume: 5 mL) to afford 1-({2-[(2,3-dihydro-1H-inden-2-yloxy)methyl]-3',5'-dimethoxy-4'-methyl-[1,1'-biphenyl]-4-yl}oxy)cyclopropane-1-carboxylic acid (8.3 mg, 1.5% yield). LC-MS: m/z 497.2 (M+Na)+. $^1$H NMR (400 MHz, DMSO-d6) δ 7.21-7.07 (m, 5H), 6.97 (d, J=2.6 Hz, 1H), 6.86 (dd, J=8.4 Hz, 2.7 Hz, 1H), 6.56 (s, 2H), 4.38 (s, 2H), 4.37-4.36 (m, 1H), 3.73 (s, 6H), 3.10-3.00 (m, 2H), 2.90-2.80 (m, 2H), 2.02 (s, 3H), 1.42-1.30 (m, 2H), 1.00-0.90 (m, 2H).

Example A6

1-{2-[(2,3-dihydro-1H-inden-2-yloxy)methyl]-3',5'-dimethoxy-4'-methyl-[1,1'-biphenyl]-4-yl}cyclopropane-1-carboxylic acid (Compound 118)

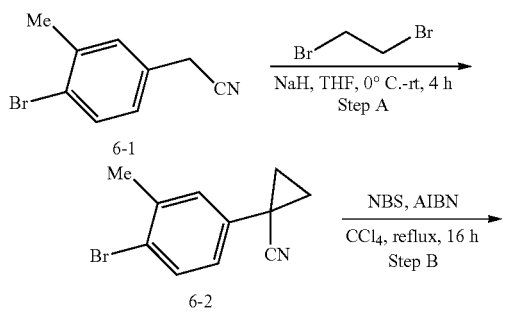

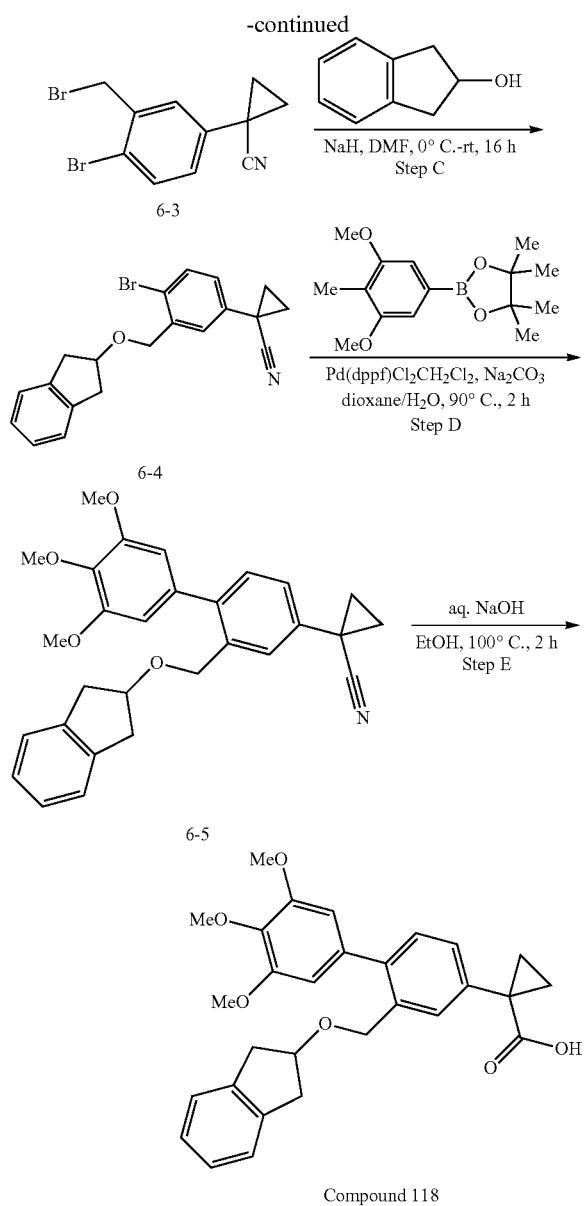

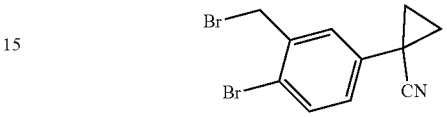

6-4

6-5

Compound 118

Step A: 1-(4-bromo-3-methylphenyl)cyclopropane-1-carbonitrile

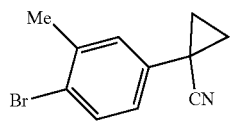 [SMILES: Cc1cc(C2(C#N)CC2)ccc1Br]

To a solution of 2-(4-bromo-3-methylphenyl)acetonitrile (6.00 g, 28.56 mmol) in THF (120 mL), was added sodium hydride (1.14 g, 28.56 mmol, 60% wt in mineral oil) at 0° C. After being stirred for 15 min, dibromoethane (5.37 g, 28.56 mmol) was added to the above reaction mixture. The resulting reaction mixture was allowed to warm to room temperature and stirred for 4 h. The reaction mixture was quenched by ice water (200 mL), extracted with EtOAc (100 mL×3). The combined organic layer was washed with brine (200 mL×2), dried over anhydrous $Na_2SO_4$, filtered and concentrated. The residue was purified by silica gel column (10% to 20% EtOAc in PE) to afford 1-(4-bromo-3-methylphenyl)cyclopropane-1-carbonitrile (800 mg, 11.9% yield).

Step B: 1-[4-bromo-3-(bromomethyl)phenyl]cyclopropane-1-carbonitrile

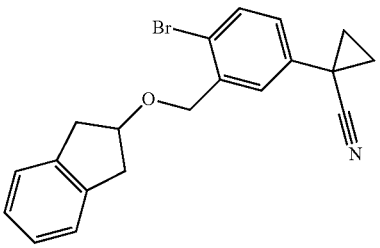 [SMILES: N#CC1(c2ccc(Br)c(COC3Cc4ccccc4C3)c2)CC1]

To the mixture of 1-(4-bromo-3-methylphenyl)cyclopropane-1-carbonitrile (800 mg, 3.39 mmol) and NBS (1.21 g, 6.78 mmol) in $CCl_4$ (16 mL), was added AIBN (278 mg, 1.70 mmol) at room temperature under nitrogen atmosphere. The resulting mixture was stirred at reflux for 16 h. After cooling, the reaction mixture was diluted with water (100 mL), extracted with $CH_2Cl_2$ (20 mL×3). The combined organic layer was washed with water (50 mL×2), dried over anhydrous $Na_2SO_4$, filtered and concentrated. The residue was purified by silica gel column (10%-20% EtOAc in PE) to afford 1-[4-bromo-3-(bromomethyl)phenyl]cyclopropane-1-carbonitrile (550 mg, 51.5% yield).

Step C: 1-{4-bromo-3-[(2,3-dihydro-1H-inden-2-yloxy)methyl]phenyl}cyclopropane-1-carbonitrile To a solution of 1-[4-bromo-3-(bromomethyl)phenyl]cyclopropane-1-carbonitrile (500 mg, 1.59 mmol) in DMF (10 mL) was added sodium hydride (190 mg, 4.76 mmol, 60% wt in mineral oil) at 0° C. The reaction mixture was stirred for 15 min at 0° C. To the above reaction mixture, was added 2,3-dihydro-1H-inden-2-ol (639 mg, 4.76 mmol). The resulting reaction mixture was allowed to warm to room temperature and stirred for 16 h. The reaction mixture was quenched by ice water (20 mL), extracted with EtOAc (10 mL×3). The combined organic layer was washed with brine (30 mL×2), dried over anhydrous $Na_2SO_4$, filtered and concentrated. The residue was purified by silica gel column (10%-20% EtOAc in PE) to afford 1-{4-bromo-3-[(2,3-dihydro-1H-inden-2-yloxy)methyl]phenyl}cyclopropane-1-carbonitrile (370 mg, 63.3% yield).

247

Step D: 1-{2-[(2,3-dihydro-1H-inden-2-yloxy)methyl]-3',5'-dimethoxy-4'-methyl-[1,1'-biphenyl]-4-yl}cyclopropane-1-carbonitrile

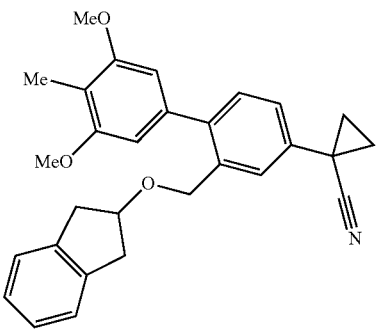 [SMILES: COc1cc(-c2ccc(C3(C#N)CC3)cc2COC2Cc3ccccc3C2)cc(OC)c1C]

To a stirred solution of 1-{4-bromo-3-[(2,3-dihydro-1H-inden-2-yloxy)methyl]phenyl}cyclopropane-1-carbonitrile (220 mg, 0.60 mmol), 2-(3,5-dimethoxy-4-methylphenyl)-4,4,5,5-tetramethyl-1,3,2-dioxaborolane (199 mg, 0.716 mmol) and Na$_2$CO$_3$ (190 mg, 1.79 mmol) in 1,4-dioxane (4 mL) and water (0.8 mL), was added Pd(dppf)Cl$_2$·CH$_2$Cl$_2$ (49 mg, 0.06 mmol) at room temperature under nitrogen atmosphere. The resulting mixture was stirred at 90° C. for 2 h. After cooling, the reaction mixture was concentrated under reduced pressure. The residue was purified by silica gel column (10%-30% EtOAc in PE) to afford 1-{2-[(2,3-dihydro-1H-inden-2-yloxy)methyl]-3',5'-dimethoxy-4'-methyl-[1,1'-biphenyl]-4-yl}cyclopropane-1-carbonitrile (220 mg, 83.8% yield). LC-MS: m/z 440.0 (M+H)$^+$.

248

Step E: 1-{2-[(2,3-dihydro-1H-inden-2-yloxy)methyl]-3',5'-dimethoxy-4'-methyl-[1,1'-biphenyl]-4-yl}cyclopropane-1-carboxylic acid (Compound 118)

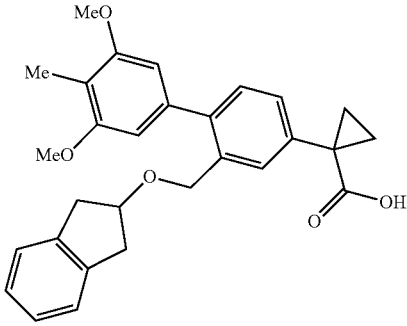 [SMILES: COc1cc(-c2ccc(C3(C(=O)O)CC3)cc2COC2Cc3ccccc3C2)cc(OC)c1C]

To a stirred solution of 1-{2-[(2,3-dihydro-1H-inden-2-yloxy)methyl]-3',5'-dimethoxy-4'-methyl-[1,1'-biphenyl]-4-yl}cyclopropane-1-carbonitrile (100 mg, 0.29 mmol) in EtOH (5 mL) was added a solution of NaOH (500 mg, 12.5 mmol) in water (1 mL). The reaction mixture was stirred at 100° C. for 2 h under nitrogen atmosphere. After cooling, the reaction mixture was acidified to pH=5 with 2 M HCl. The resulting mixture was extracted with EtOAc (10 mL×3). The combined organic layer was washed with brine (30 mL×3), dried over anhydrous Na$_2$SO$_4$, filtered and concentrated. The residue was purified by prep. HPLC (Column: Xselect CSH C18 OBD Column 30*150 mm 5 m, n; Mobile Phase A: Water (0.05% HCl), Mobile Phase B: CH$_3$CN; Flow rate: 60 mL/min; Gradient: 50% B to 90% B in 10 min) to afford 1-{2-[(2,3-dihydro-1H-inden-2-yloxy)methyl]-3',5'-dimethoxy-4'-methyl-[1,1'-biphenyl]-4-yl}cyclopropane-1-carboxylic acid (40.6 mg, 38.9% yield). LC-MS: m/z 457.0 (M−H)$^−$. $^1$H NMR (400 MHz, DMSO-d6) δ 12.33 (s, 1H), 7.41 (d, J=1.9 Hz, 1H), 7.30 (dd, J=7.8 Hz, 1.9 Hz, 1H), 7.23 (d, J=7.9 Hz, 1H), 7.20-7.16 (m, 2H), 7.14-7.09 (m, 2H), 6.61 (s, 2H), 4.43-4.31 (m, 3H), 3.73 (s, 6H), 3.08 (dd, J=16.4 Hz, 6.3 Hz, 2H), 2.86 (dd, J=16.4 Hz, 3.7 Hz, 2H), 2.03 (s, 3H), 1.46-1.44 (m, 2H), 1.14-1.12 (m, 2H).

Example A7

(2S)-1-((2-(((2,3-dihydro-1H-inden-2-yl)oxy)methyl)-3',5'-dimethoxy-4'-methyl-[1,1'-biphenyl]-4-yl)amino)-2-methylcyclopropane-1-carboxylic acid (Compound 119)

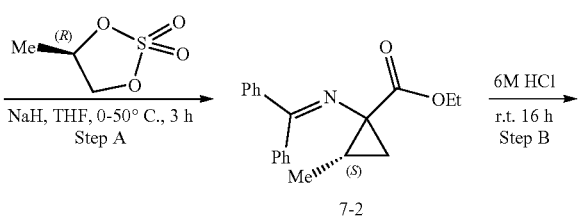

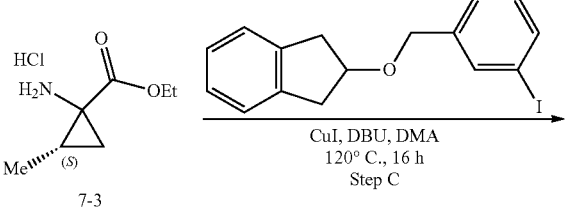

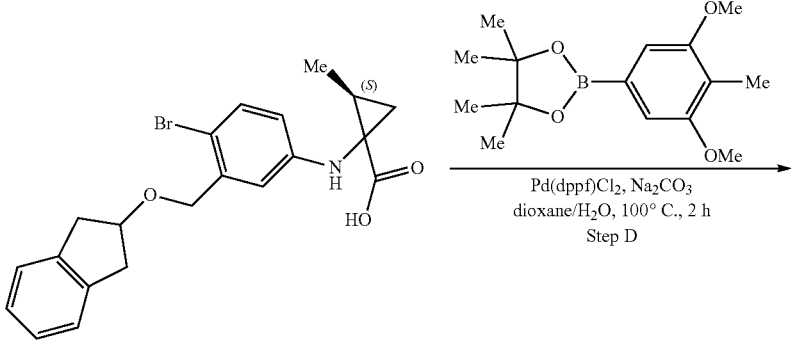

7-4

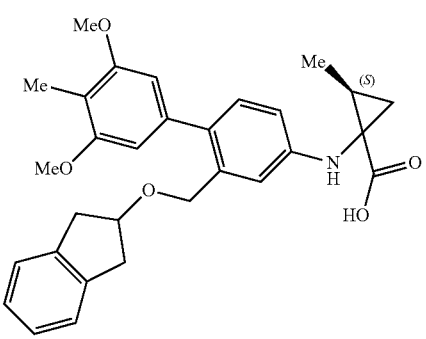

Compound 119

Step A: ethyl (2S)-1-((diphenylmethylene)amino)-2-methylcyclopropane-1-carboxylate

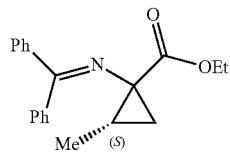

To a solution of ethyl 2-[(diphenylmethylidene)amino]acetate (5 g, 18.70 mmol) in THF (50 mL) was added NaH (1.35 g, 56.11 mmol, 60% wt in mineral oil) at 0° C. After being stirred for 15 min, (R)-(−)-4-methyl-2,2-dioxo-1,3,2-dioxathiolane (2.28 g, 14.30 mmol) was added into the above solution. The resulting reaction mixture was heated to 50° C. and stirred for 3 h. The resulting mixture was concentrated under reduced pressure. The residue was diluted with hexane (50 mL), filtered, the filter cake was washed with hexane (10 mL×3). The combined filtrate was concentrated under reduced pressure to afford ethyl (2S)-1-[(diphenylmethylidene)amino]-2-methylcyclopropane-1-carboxylate (3.4 g, crude). LC-MS: m/z 308.0 (M+H)+.

Step B: ethyl (2S)-1-amino-2-methylcyclopropane-1-carboxylate hydrochloride

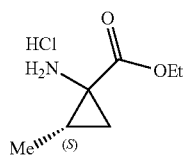

To the stirred solution of ethyl (2S)-1-[(diphenylmethylidene)amino]-2-methylcyclopropane-1-carboxylate (3.4 g, 11.06 mmol) in ether (35 mL) was added 6 M aq. HCl (3.87 mL, 13.27 mmol) at room temperature under nitrogen atmosphere. The resulting mixture was stirred at room temperature for 16 h. The resulting mixture was extracted with EtOAc (20 mL×2). The combined water layer was concentrated under reduced pressure to afford ethyl (2S)-1-amino-2-methylcyclopropane-1-carboxylate hydrochloride (1.2 g, 60.4% yield).

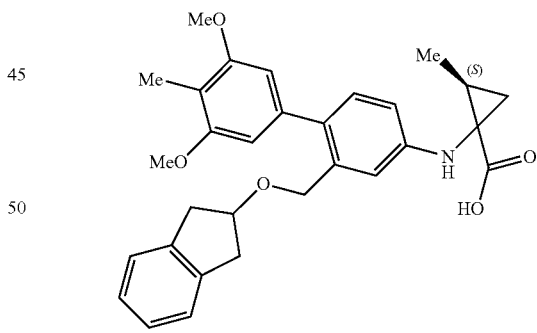

(2S)-1-((2-(((2,3-dihydro-1H-inden-2-yl)oxy)methyl)-3',5'-dimethoxy-4'-methyl-[1,1'-biphenyl]-4-yl)amino)-2-methylcyclopropane-1-carboxylic acid (Compound 119) was synthesized according to the procedures described for the preparation of Example A3 (step C and D) by using ethyl (2S)-1-amino-2-methylcyclopropane-1-carboxylate hydrochloride in step C. LC-MS: m/z 488.2 (M+H)+. $^1$H NMR (400 MHz, DMSO-d6) δ 7.22-7.15 (m, 2H), 7.16-7.09 (m, 2H), 7.05-7.00 (m, 1H), 6.76 (s, 1H), 6.62-6.51 (m, 3H), 6.39 (s, 1H), 4.36-4.35 (m, 3H), 3.73 (s, 6H), 3.12-3.04 (m, 2H), 2.89-2.82 (m, 2H), 2.01 (s, 3H), 1.94-1.45 (m, 2H), 1.15-1.10 (m, 3H), 0.62-0.60 (m, 1H).

Example A8

1-({4'-acetyl-2-[(2,3-dihydro-1H-inden-2-yloxy)methyl]-3',5'-dimethoxy-[1,1'-biphenyl]-4-yl}amino)cyclopropane-1-carboxylic acid (Compound 121)

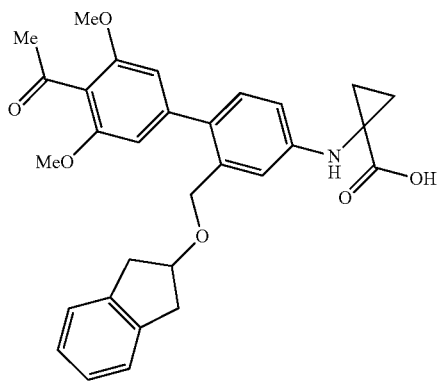 [SMILES: COc1cc(-c2ccc(NC3(C(=O)O)CC3)cc2COC2Cc3ccccc3C2)cc(OC)c1C(C)=O]

Step A: 1-[2,6-dimethoxy-4-(4,4,5,5-tetramethyl-1,3,2-dioxaborolan-2-yl)phenyl]ethanone

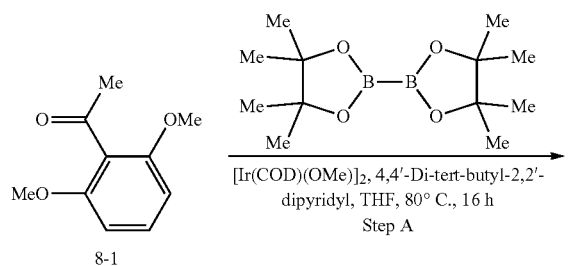

To a stirred mixture of 2',6'-dimethoxyacetophenone (1.00 g, 5.55 mmol), bis(pinacolato)diboron (1.69 g, 6.66 mmol) and 4,4'-Di-tert-butyl-2,2'-dipyridyl (dtbpy) (0.30 g, 1.11 mmol) in THF (10 mL), was added [Ir(COD)(OMe)]$_2$ (0.18 g, 0.28 mmol) at room temperature under nitrogen atmosphere. The reaction mixture was stirred at 80° C. for 16 h under nitrogen atmosphere. After cooling, the reaction mixture was diluted with water (30 mL), extracted with EtOAc (20 mL×3). The combined organic layer was washed with brine (20 mL), dried over anhydrous Na$_2$SO$_4$, filtered and concentrated. The residue was purified by silica gel column (3% to 7% MeOH in CH$_2$Cl$_2$) to afford 1-[2,6-dimethoxy-4-(4,4,5,5-tetramethyl-1,3,2-dioxaborolan-2-yl)phenyl]ethanone (600 mg, 35.3%). LC-MS: m/z 306.9 (M+H)$^+$.

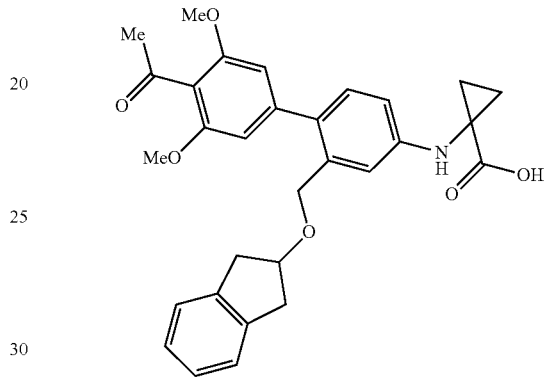

1-({4'-acetyl-2-[(2,3-dihydro-1H-inden-2-yloxy)methyl]-3',5'-dimethoxy-[1,1'-biphenyl]-4-yl}amino)cyclopropane-1-carboxylic acid (Compound 121) was synthesized according to the procedures described for the preparation of Example A3 (step C and D) by using 1-aminocyclopropane-1-carboxylic acid in step C and 1-[2,6-dimethoxy-4-(4,4,5,5-tetramethyl-1,3,2-dioxaborolan-2-yl)phenyl]ethanone in step D. LC-MS: m/z 502.2 (M+H)$^+$. $^1$H NMR (400 MHz, DMSO-d6) δ 7.20-7.18 (m, 2H), 7.13-7.10 (m, 2H), 7.06 (d, J=8.3 Hz, 1H), 6.74 (d, J=2.0 Hz, 1H), 6.63-6.61 (m, 3H), 6.54 (s, 1H), 4.36-4.35 (m, 3H), 3.71 (s, 6H), 3.09 (dd, J=16.4 Hz, 6.3 Hz, 2H), 2.85 (dd, J=16.3 Hz, 3.7 Hz, 2H), 2.38 (s, 3H), 1.39-1.37 (m, 2H), 0.94-0.90 (m, 2H).

Example A9

4-({3',5'-dimethoxy-4'-methyl-2-[2-(2-methyl-1,3-benzodioxol-2-yl)ethyl]-[1,1'-biphenyl]-4-yl}amino)oxane-4-carboxylic acid (Compound 132)

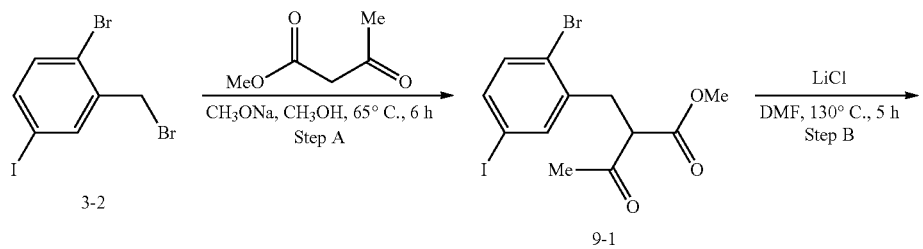

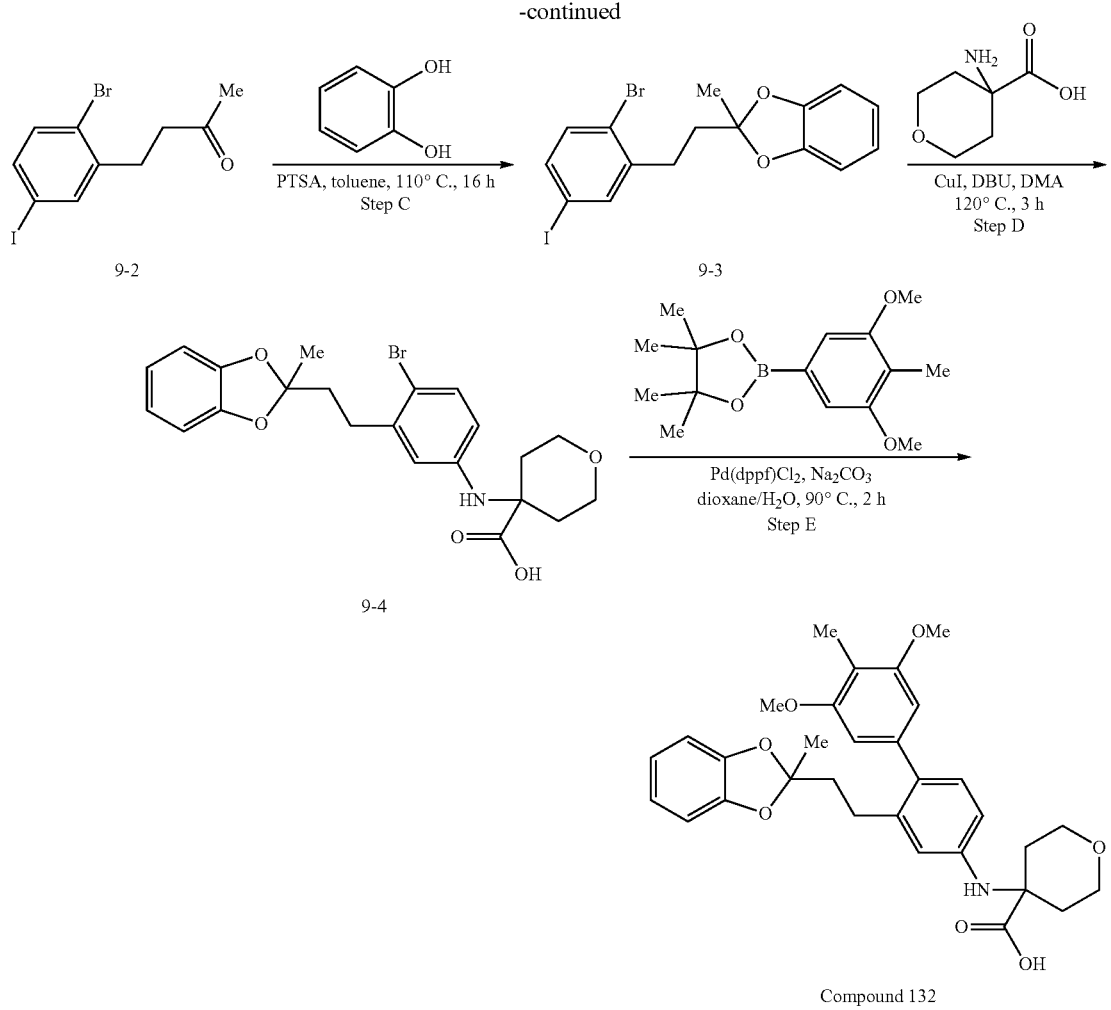

Step A: methyl 2-[(2-bromo-5-iodophenyl)methyl]-3-oxobutanoate

Step B: 4-(2-bromo-5-iodophenyl)butan-2-one

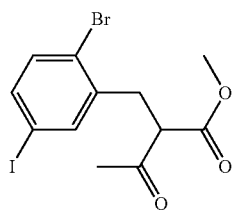 [SMILES: COC(=O)C(Cc1cc(I)ccc1Br)C(C)=O]

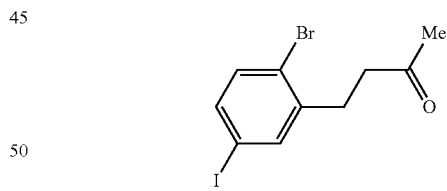

To the solution of methyl 3-oxobutanoate (927 mg, 7.99 mmol) in MeOH (20 mL) was added NaOMe (540 mg, 9.99 mmol). After being stirred for 10 min, to the mixture was added 1-bromo-2-(bromomethyl)-4-iodobenzene (2.5 g, 6.66 mmol). The resulting mixture was stirred for 6 h at 65° C. After cooling, the mixture was poured into water (50 mL), extracted with EtOAc (100 mL×3). The combined organic layer was washed with brine (50 mL), dried over anhydrous $Na_2SO_4$, filtered and concentrated. The residue was purified by silica gel column (PE/EtOAc=10/1) to afford methyl 2-(2-bromo-5-iodobenzyl)-3-oxobutanoate (1.7 g, 52.3% yield, 80% purity).

To the solution of methyl 2-[(2-bromo-5-iodophenyl)methyl]-3-oxobutanoate (700 mg, 1.70 mmol) in DMF (10 mL) were added lithium chloride (361 mg, 8.52 mmol) under nitrogen. The resulting mixture was stirred at 130° C. for 5 h. After cooling, the mixture was poured into water (50 mL), extracted with $CH_2Cl_2$ (50 mL×3). The combined organic layer was washed with brine (50 mL), dried over anhydrous $Na_2SO_4$, filtered and concentrated. The residue was purified by silica gel column (PE/EtOAc=10/1) to afford 4-(2-bromo-5-iodophenyl)butan-2-one (488 mg, 81.3% yield).

Step C: 2-[2-(2-bromo-5-iodophenyl)ethyl]-2-methyl-1,3-benzodioxole

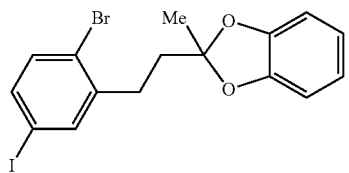 [SMILES: CC1(CCc2cc(I)ccc2Br)Oc2ccccc2O1]

The mixture of 4-(2-bromo-5-iodophenyl)butan-2-one (550 mg, 1.56 mmol), catechol (858 mg, 7.79 mmol), PTSA (54 mg, 0.31 mmol) in toluene (10 ml) was stirred at 110° C. for 16 h. After cooling, the mixture was poured into water (50 mL), extracted with $CH_2Cl_2$ (50 mL×3). The combined organic layer was washed with brine (50 mL) and dried over anhydrous $Na_2SO_4$, filtered and concentrated. The residue was purified by silica gel column (PE/EA=10:1) to afford 2-[2-(2-bromo-5-iodophenyl)ethyl]-2-methyl-1,3-benzodioxole (110 mg, 15.9% yield).

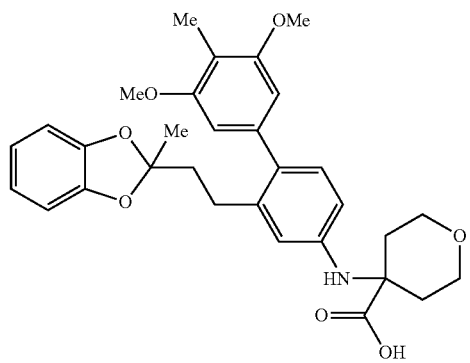 [SMILES: COc1cc(-c2ccc(NC3(C(=O)O)CCOCC3)cc2CCC2(C)Oc3ccccc3O2)cc(OC)c1C]

4-({3',5'-dimethoxy-4'-methyl-2-[2-(2-methyl-1,3-benzodioxol-2-yl)ethyl]-[1,1'-biphenyl]-4-yl}amino)oxane-4-carboxylic acid (Compound 132) was synthesized according to the procedures described for the preparation of Example A3 (step C and D) by using 2-[2-(2-bromo-5-iodophenyl)ethyl]-2-methyl-1,3-benzodioxole in step C. LC-MS: m/z 534.1 $(M+H)^+$. $^1H$ NMR (400 MHz, DMSO-d6) δ 6.90 (d, J=8.3 Hz, 1H), 6.74-6.71 (s, 4H), 6.56 (s, 1H), 6.46-6.42 (m, 3H), 3.71 (s, 6H), 3.63-3.62 (m, 3H), 2.66-2.58 (m, 2H), 2.29-2.14 (m, 2H), 2.09-2.00 (m, 4H), 1.86-1.84 (m, 2H), 1.50 (s, 3H).

Example A10

4-({2-[(cyclopentyloxy)methyl]-3',5'-dimethoxy-4'-methyl-[1,1'-biphenyl]-4-yl} amino)-oxane-4-carboxylic acid (Compound 134)

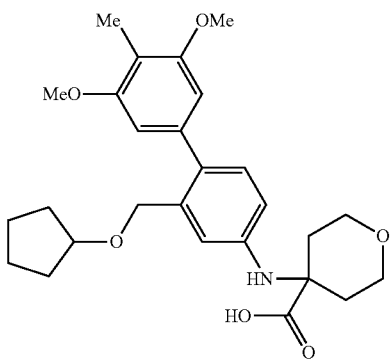 [SMILES: COc1cc(-c2ccc(NC3(C(=O)O)CCOCC3)cc2COC2CCCC2)cc(OC)c1C]

4-({2-[(cyclopentyloxy)methyl]-3',5'-dimethoxy-4'-methyl-[1,1'-biphenyl]-4-yl}amino)-oxane-4-carboxylic acid (Compound 134) was synthesized according to the procedures described for the preparation of Example A3 (step B to Step D) by using cyclopentanol in step B. LC-MS: m/z 470.2 $(M+H)^+$. $^1H$ NMR (400 MHz, DMSO-d6) δ 6.98 (d, J=8.3 Hz, 1H), 6.75 (d, J=2.4 Hz, 1H), 6.54-6.52 (m, 3H), 4.19 (s, 2H), 3.91-3.90 (m, 1H), 3.76 (s, 6H), 3.65-3.57 (m, 4H), 2.04-2.00 (m, 5H), 1.99-1.87 (m, 2H), 1.69-1.53 (m, 6H), 1.46-1.44 (m, 2H).

Example A11

4-((2-((cyclopentyloxy)methyl)-3',5'-dimethoxy-4'-methyl-[1,1'-biphenyl]-4-yl) amino)-1-(methoxycarbonyl)piperidine-4-carboxylic acid (Compound 140)

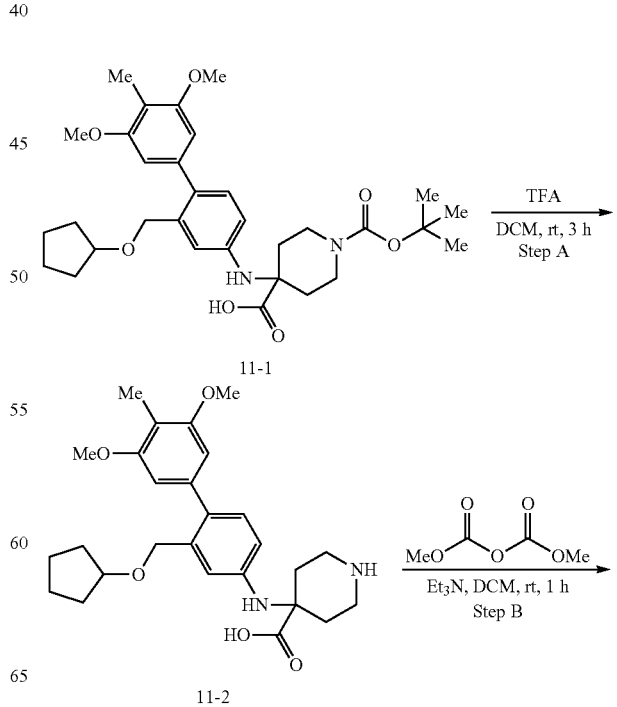

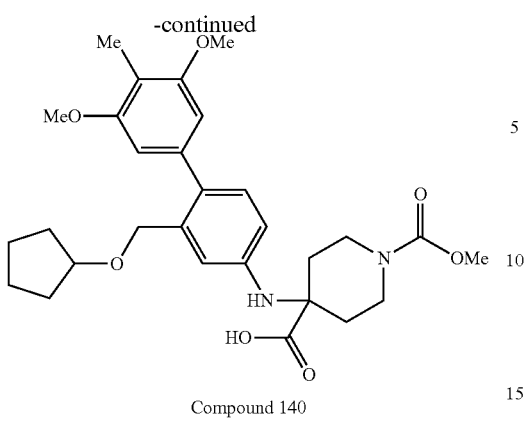

Compound 140

1-(tert-butoxycarbonyl)-4-((2-((cyclopentyloxy)methyl)-3',5'-dimethoxy-4'-methyl-[1,1'-biphenyl]-4-yl)amino)piperidine-4-carboxylic acid (11-1) was synthesized according to the procedures described for the preparation of Example A3 (step B to step D) by using cyclopentanol in step B and 4-amino-1-(tert-butoxycarbonyl)piperidine-4-carboxylic acid in step C. LC-MS: m/z 587.1 (M+H$_2$O+H).

Step A: 4-((2-((cyclopentyloxy)methyl)-3',5'-dimethoxy-4'-methyl-[1,1'-biphenyl]-4-yl)amino)piperidine-4-carboxylic acid

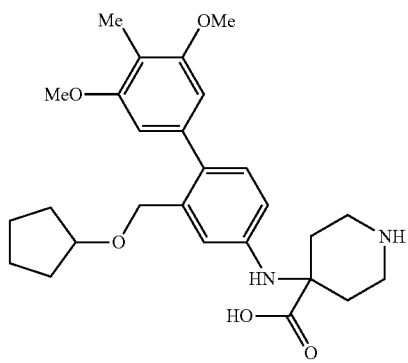 [SMILES: COc1cc(-c2ccc(NC3(C(=O)O)CCNCC3)cc2COC2CCCC2)cc(OC)c1C]

The mixture of 1-(tert-butoxycarbonyl)-4-((2-((cyclopentyloxy)methyl)-3',5'-dimethoxy-4'-methyl-[1,1'-biphenyl]-4-yl)amino)piperidine-4-carboxylic acid (120 mg, 0.211 mmol) in TFA (2 mL) and CH$_2$Cl$_2$ (4 mL) was stirred at room temperature for 3 h. The reaction mixture was concentrated under vacuum, the residue was purified by prep. HPLC (Column: XBridge Prep OBD C18 Column, 30*150 mm, 5 m; Mobile Phase A: Water (10 mmol/L NHIHCO$_3$), Mobile Phase B: CH$_3$CN; Flow rate: 60 mL/min; Gradient: 5% B to 60% B in 10 min) to afford 4-((2-((cyclopentyloxy)methyl)-3',5'-dimethoxy-4'-methyl-[1,1'-biphenyl]-4-yl)amino)piperidine-4-carboxylic acid (77 mg, 77.9% yield). LC-MS: m/z 469.1 (M+H)$^+$.

Step B: 4-((2-((cyclopentyloxy)methyl)-3'-hydroxy-5'-methoxy-4'-methyl-[1,1'-biphenyl]-4-yl) amino)-1-(methoxycarbonyl)piperidine-4-carboxylic acid (Compound 140)

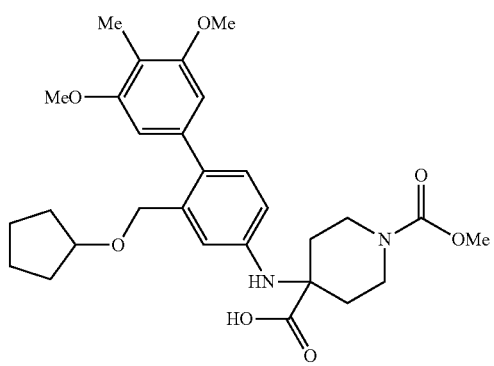 [SMILES: COC(=O)N1CCC(Nc2ccc(-c3cc(OC)c(C)c(OC)c3)c(COC3CCCC3)c2)(C(=O)O)CC1]

At 0° C., to the solution of 4-((2-((cyclopentyloxy)methyl)-3',5'-dimethoxy-4'-methyl-[1,1'-biphenyl]-4-yl)amino)piperidine-4-carboxylic acid (60 mg, 0.13 mmol) and Et$_3$N (38.87 mg, 0.39 mmol) in CH$_2$Cl$_2$ (3 mL) was added a solution of dimethyl dicarbonate (7.73 mg, 0.06 mmol) in CH$_2$Cl$_2$ (1 mL) dropwise. After addition, the reaction mixture was stirred at 0° C. for 1 h. The resulting mixture was concentrated under reduced pressure. The crude was purified by prep. HPLC (Column: XBridge Prep OBD C18 Column, 30*150 mm, 5 m; Mobile Phase A: Water (10 mM NH$_4$HCO$_3$), Mobile Phase B: CH$_3$CN; Flow rate: 60 mL/min; Gradient: 5% B to 60% B in 8 min) to afford 4-((2-((cyclopentyloxy)methyl)-3'-hydroxy-5'-methoxy-4'-methyl-[1,1'-biphenyl]-4-yl) amino)-1-(methoxycarbonyl) piperidine-4-carboxylic (16.8 mg, 24.9% yield). LC-MS: m/z 527.2 (M+H)$^+$. $^1$H NMR (400 MHz, DMSO-d6) δ 6.96 (d, J=8.4 Hz, 1H), 6.79-6.70 (m, 1H), 6.57-6.44 (m, 3H), 4.19 (s, 2H), 3.96-3.86 (m, 1H), 3.76 (s, 6H), 3.68-3.50 (m, 5H), 3.30-3.20 (m, 2H), 2.00 (s, 3H), 1.97-1.84 (m, 4H), 1.68-1.53 (m, 6H), 1.49-1.38 (m, 2H).

Example A12

4-((2-((cyclopentyloxy)methyl)-3',5'-dimethoxy-4',6-dimethyl-[1,1'-biphenyl]-4-yl)amino) tetrahydro-2H-pyran-4-carboxylic acid (Compound 141)

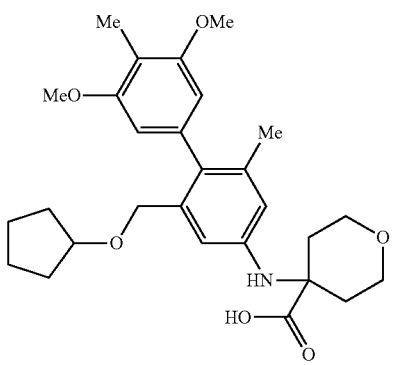 [SMILES: COc1cc(-c2c(C)cc(NC3(C(=O)O)CCOCC3)cc2COC2CCCC2)cc(OC)c1C]

4-((2-((cyclopentyloxy)methyl)-3',5'-dimethoxy-4',6-dimethyl-[1,1'-biphenyl]-4-yl)amino) tetrahydro-2H-pyran-4-carboxylic acid (Compound 141) was synthesized according to the procedures described for the preparation of Example A3 (step A to step D) by using 2-bromo-5-iodo-1,3-dimethylbenzene in step A and cyclopentanol in step B. LC-MS: m/z 484.1 (M+H)+. $^1$H NMR (400 MHz, DMSO-d6) δ 6.57 (d, J=2.4 Hz, 1H), 6.40 (d, J=2.4 Hz, 1H), 6.33 (s, 2H), 3.96 (s, 2H), 3.76-3.74 (m, 1H), 3.69 (s, 6H), 3.68-3.54 (m, 4H), 2.09-1.93 (m, 5H), 1.88-1.80 (m, 5H), 1.66-1.47 (m, 4H), 1.47-1.33 (m, 4H).

Example A13

4-((2-((cyclopentyloxy)methyl)-6-fluoro-3',5'-dimethoxy-4'-methyl-[1,1'-biphenyl]-4-yl)amino)tetrahydro-2H-pyran-4-carboxylic acid (Compound 147)

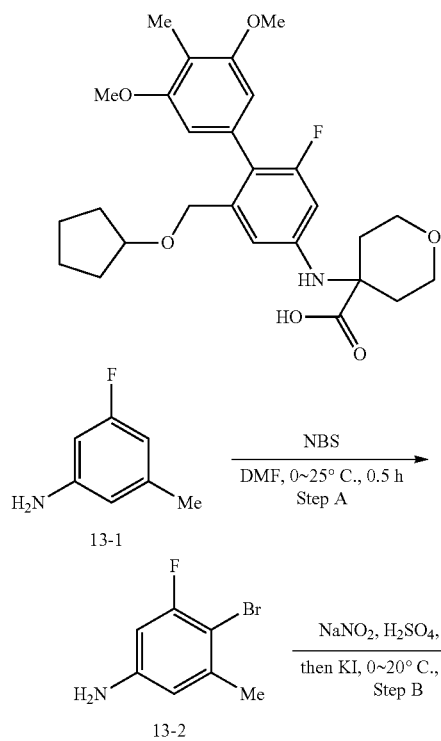

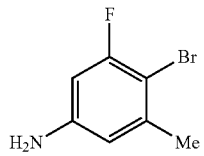

Step A: 4-bromo-3-fluoro-5-methylaniline

To the mixture of 3-fluoro-5-methyl-aniline (5 g, 40.0 mmol) in DMF (40 mL) was added NBS (7.25 g, 40.8 mmol) at 0° C. The mixture was stirred at 25° C. for 0.5 h. The reaction was quenched with H$_2$O (20 mL). The mixture was extracted with EtOAc (30 mL×3). The combined organic layer was washed with H$_2$O (20 mL×3), dried over anhydrous Na$_2$SO$_4$, filtered and concentrated. The residue was purified by flash silica gel column (ISCO®; 120 g SepaFlash® Silica Flash Column, Eluent of 0-20% EtOAc/PE gradient at 85 mL/min) to give 4-bromo-3-fluoro-5-methyl-aniline (8.0 g, 98.1% yield). $^1$H NMR (400 MHz, CDCl$_3$): δ 6.36 (s, 1H), 6.32-6.28 (m, 1H), 2.31 (s, 3H).

Step B: 2-bromo-1-fluoro-5-iodo-3-methylbenzene

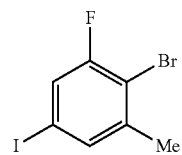

To a solution of 4-bromo-3-fluoro-5-methyl-aniline (21.7 g, 106 mmol) in MeCN (500 mL) was added a solution of H$_2$SO$_4$ (14.0 mL, 263 mmol) in H$_2$O (30 mL) at 0° C. After being stirred for 5 minutes, a solution of NaNO$_2$ (14.7 g, 213 mmol) in water (30 mL) was added dropwise, and the reaction mixture was stirred for an additional 15 minutes at 0° C. Then a solution of KI (70.6 g, 425 mmol) in water (60 mL) was added. After addition, the ice-bath was removed and warmed up to 25° C., the resulting reaction mixture was stirred for an additional 20 minutes. The mixture was quenched with sat. aq. Na$_2$S$_2$O$_3$ aqueous, diluted with water (300 mL), extracted with EtOAc (160 mL×2). The combined organic layer was dried over anhydrous Na$_2$SO$_4$, filtered and concentrated. The residue was purified by flash silica gel column (ISCO®; 220 g SepaFlash® Silica Flash Column, Eluent of 0% EtOAc/PE gradient at 100 mL/min) to give 2-bromo-1-fluoro-5-iodo-3-methyl-benzene (31.6 g, 94.2% yield). $^1$H NMR (400 MHz, CDCl$_3$) δ 7.38 (s, 1H), 7.30-7.26 (m, 1H), 2.38 (s, 3H).

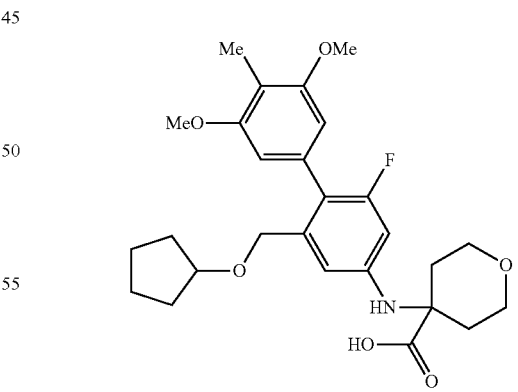

4-((2-((cyclopentyloxy)methyl)-6-fluoro-3',5'-dimethoxy-4'-methyl-[1,1'-biphenyl]-4-yl)amino)tetrahydro-2H-pyran-4-carboxylic acid (Compound 147) was synthesized according to the procedures described for the preparation of Example A3 (step A and D) by using 2-bromo-1-fluoro-5-iodo-3-methylbenzene in step A and cyclopentanol in step B. LC-MS: m/z 488.4 (M+H)+. $^1$H NMR (400 MHz, CD$_3$OD)

δ 6.65 (s, 1H), 6.46 (s, 2H), 6.39 (d, J=12.0 Hz, 1H), 4.18 (s, 2H), 3.87-3.74 (m, 11H), 2.28-2.20 (m, 2H), 2.09 (s, 3H), 2.06-2.01 (m, 2H), 1.66-1.50 (m, 8H).

Example A14

4-((2-((cyclopentyloxy)methyl)-3',5'-dimethoxy-2', 4'-dimethyl-[1,1'-biphenyl]-4-yl)amino)tetrahydro-2H-pyran-4-carboxylic acid (Compound 148)

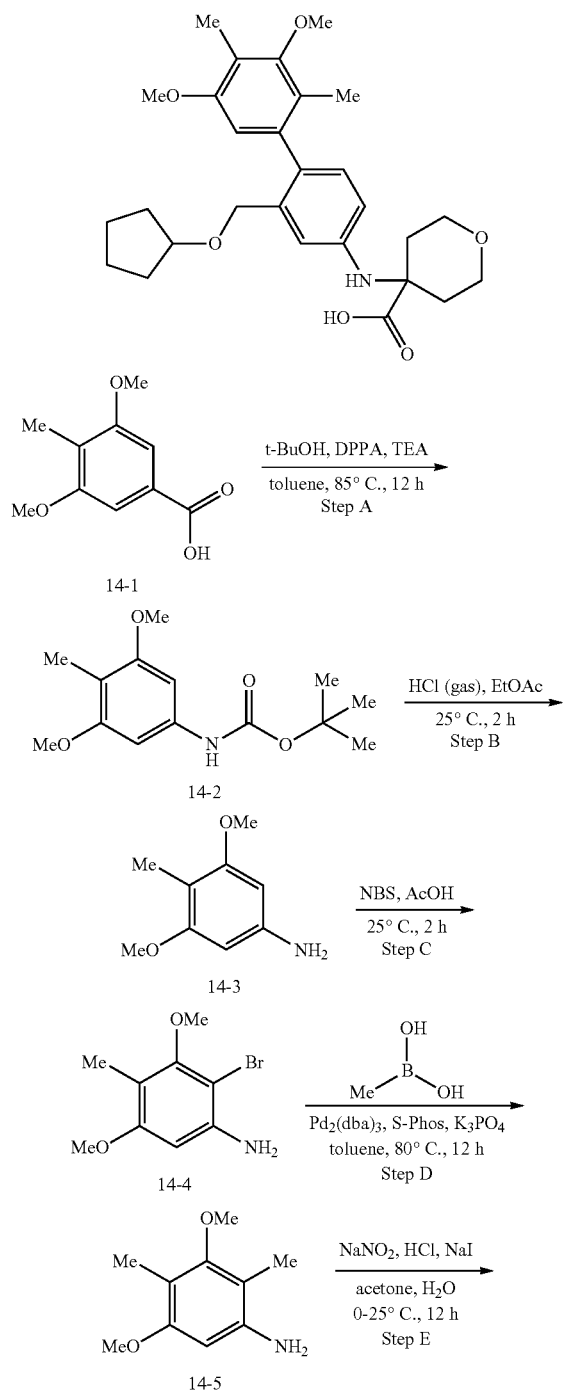

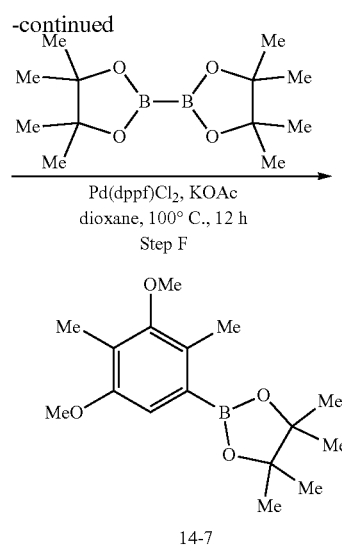

Step A: tert-butyl (3,5-dimethoxy-4-methylphenyl)carbamate

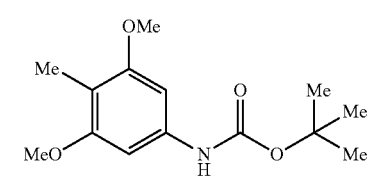 [SMILES: COc1cc(NC(=O)OC(C)(C)C)cc(OC)c1C]

To a solution of 3,5-dimethoxy-4-methylbenzoic acid (25 g, 127.42 mmol) in toluene (70 mL) and t-BuOH (70 mL) was added TEA (39 mL, 280.20 mmol) and DPPA (38.10 g, 138.44 mmol). After being degassed and purged with nitrogen for 3 times, the resulting mixture was stirred at 85° C. for 12 h under nitrogen atmosphere. The reaction mixture was diluted with H$_2$O (200 mL) and extracted with EtOAc (200 mL×3). The combined organic layer was dried over anhydrous Na$_2$SO$_4$, filtered and concentrated. The residue was purified by silica gel column (PE/EtOAc=9/2) to give tert-butyl (3,5-dimethoxy-4-methylphenyl)carbamate (28.86 g, 79.9% yield). LC-MS: m/z 268.1 (M+H)$^+$.

Step B: 3,5-dimethoxy-4-methylaniline

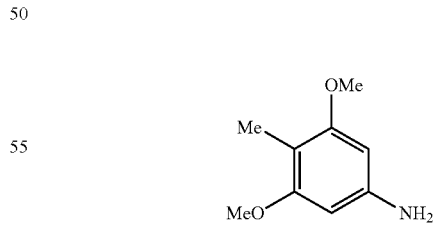

The mixture of tert-butyl (3,5-dimethoxy-4-methylphenyl)carbamate (28.86 g, 107.96 mmol) in 4 M HCl (gas)/EtOAc (258 mL) was stirred at 25° C. for 2 h. Then pH value was adjusted to 8-9 with sat. aq. NaHCO$_3$, the mixture was extracted with EtOAc (200 mL×3). The combined organic layer was dried over anhydrous Na$_2$SO$_4$, filtered and concentrated to give 3,5-dimethoxy-4-methylaniline (18.03 g, 99.9% yield).

Step C: 2-bromo-3,5-dimethoxy-4-methylaniline

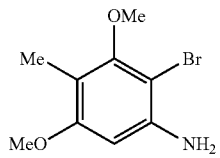

To a solution of 3,5-dimethoxy-4-methylaniline (5 g, 29.90 mmol) in AcOH (20 mL) was added NBS (5.32 g, 29.90 mmol) and the mixture was stirred at 25° C. for 2 h. Then the pH value was adjusted to 8-9 with sat. aq. NaHCO$_3$, the mixture was extracted with EtOAc (50 mL×3). The combined organic layer was dried over anhydrous Na$_2$SO$_4$, filtered and concentrated. The residue was purified by silica gel column (PE/EtOAc=9/1) to give 2-bromo-3,5-dimethoxy-4-methylaniline (4.59 g, 56.3% yield). LC-MS: m/z 246.1 (M+H)$^+$.

Step D: 3,5-dimethoxy-2,4-dimethylaniline

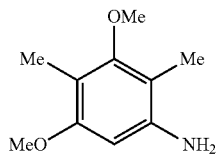 [SMILES: COc1cc(N)c(C)c(OC)c1C]

To a solution of 2-bromo-3,5-dimethoxy-4-methylaniline (4.59 g, 18.65 mmol) in toluene (30 mL) was added methylboronic acid (2.79 g, 46.63 mmol), K$_3$PO$_4$ (15.84 g, 74.60 mmol), S-Phos (1.53 g, 3.73 mmol) and Pd$_2$(dba)$_3$ (1.71 g, 1.87 mmol) under nitrogen. After being degassed and purged with nitrogen for 3 times. Then the mixture was stirred at 80° C. for 12 h under nitrogen atmosphere. After cooling and filtered, the filtrate was concentrated. The residue was purified by silica gel column (PE/EtOAc=9/1) to give 3,5-dimethoxy-2,4-dimethylaniline (2.45 g, 72.5% yield). LC-MS: m/z 182.2 (M+H)$^+$.

Step E: 1-iodo-3,5-dimethoxy-2,4-dimethylbenzene

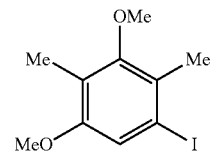 [SMILES: COc1cc(I)c(C)c(OC)c1C]

To a solution of 3,5-dimethoxy-2,4-dimethylaniline (2.25 g, 12.42 mmol) in 37% HCl (12 mL, 124.15 mmol) and acetone (15 mL) was added a solution of NaNO$_2$ (2.14 g, 31.04 mmol) in H$_2$O (5 mL) at 0° C. and the mixture was stirred at 0° C. for 0.5 h. A solution of NaI (7.44 g, 49.66 mmol) in H$_2$O (5 mL) was added and the mixture was stirred at 25° C. for 16 h. The reaction was quenched with H$_2$O (30 mL), extracted with EtOAc (30 mL×3). The combined organic layer was concentrated and purified by silica gel column (100% PE) to give the red crude product. The crude was dissolved in EtOAc (40 mL) and the mixture was washed with sat. aq. Na$_2$S$_2$O$_3$ solution (30 mL×3). The organic layer was dried over anhydrous Na$_2$SO$_4$, filtered and concentrated to give 1-iodo-3,5-dimethoxy-2,4-dimethylbenzene (2.64 g, 71.6% yield). LC-MS: m/z 292.9 (M+H)$^+$.

Step F: 2-(3,5-dimethoxy-2,4-dimethylphenyl)-4,4,5,5-tetramethyl-1,3,2-dioxaborolane

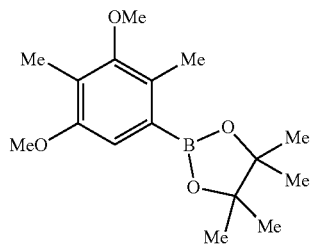 [SMILES: COc1cc(B2OC(C)(C)C(C)(C)O2)c(C)c(OC)c1C]

To a solution of 1-iodo-3,5-dimethoxy-2,4-dimethylbenzene (1 g, 3.42 mmol) in 1,4-dioxane (20 mL) was added 4,4,4',4',5,5,5',5'-octamethyl-2,2'-bi(1,3,2-dioxaborolane) (1.74 g, 6.85 mmol), KOAc (1.01 g, 10.27 mmol) and Pd(dppf)Cl$_2$ (250.49 mg, 342.33 µmol). After being degassed and purged with nitrogen for 3 times, the reaction mixture was stirred at 100° C. for 12 h under nitrogen. After cooling, the reaction mixture was filtered, the filtrate was concentrated. The residue was purified by silica gel column (PE/EtOAc=32/1) to give 2-(3,5-dimethoxy-2,4-dimethylphenyl)-4,4,5,5-tetramethyl-1,3,2-dioxaborolane (404 mg, 40.4% yield). $^1$H NMR (400 MHz, CDCl$_3$) δ 6.96 (s, 1H), 3.77 (s, 3H), 3.60 (s, 3H), 2.35 (s, 3H), 2.10 (s, 3H), 1.27 (s, 12H).

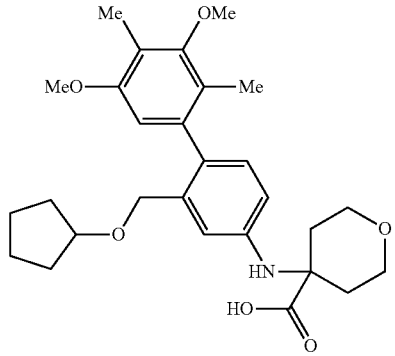 [SMILES: COc1cc(-c2ccc(NC3(C(=O)O)CCOCC3)cc2COC2CCCC2)c(C)c(OC)c1C]

4-((2-((cyclopentyloxy)methyl)-3',5'-dimethoxy-2',4'-dimethyl-[1,1'-biphenyl]-4-yl)amino)tetrahydro-2H-pyran-4-carboxylic acid (Compound 148) was synthesized according to the procedures described for the preparation of Example A3 (step A and D) by using cyclopentanol in step B and 2-(3,5-dimethoxy-2,4-dimethylphenyl)-4,4,5,5-tetramethyl-1,3,2-dioxaborolane in step D. LC-MS: m/z 484.2 (M+H)$^+$. $^1$H NMR (400 MHz, CD$_3$OD) δ 6.87-6.80 (m, 2H), 6.68 (dd, J=8.4 Hz, 2.4 Hz, 1H), 6.47 (s, 1H), 4.14-4.02 (m, 2H), 3.88-3.77 (m, 5H), 3.76 (s, 3H), 3.71 (s, 3H), 2.30-2.20 (m, 2H), 2.16 (s, 3H), 2.05-1.95 (m, 2H), 1.90 (s, 3H), 1.63-1.39 (m, 8H).

Example A15
(S)-4-((3',5'-dimethoxy-4'-methyl-2-(2-(tetrahydro-furan-3-yl)ethyl)-[1,1'-biphenyl]-4-yl)amino)tetrahydro-2H-pyran-4-carboxylic acid and (R)-4-((3',5'-dimethoxy-4'-methyl-2-(2-(tetrahydrofuran-3-yl)ethyl)-[1,1'-biphenyl]-4-yl)amino)tetrahydro-2H-pyran-4-carboxylic acid (Compounds 185 and 186)
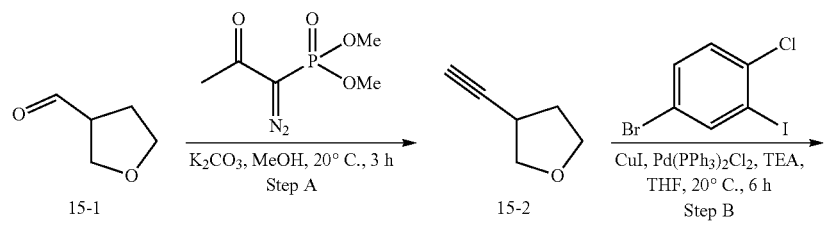
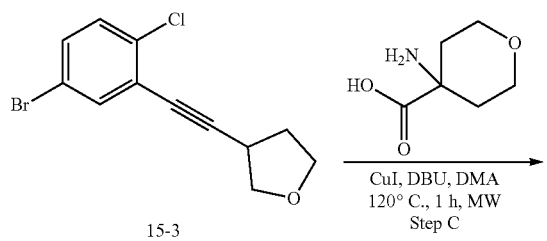
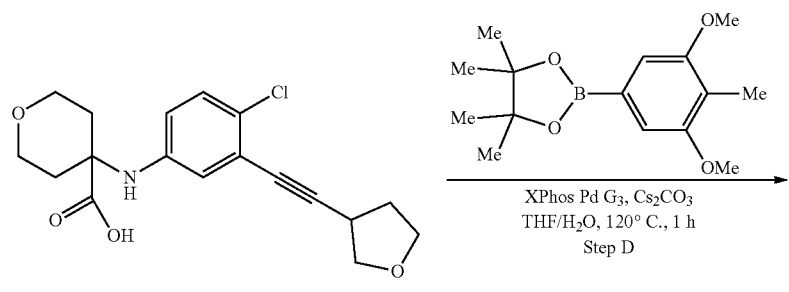
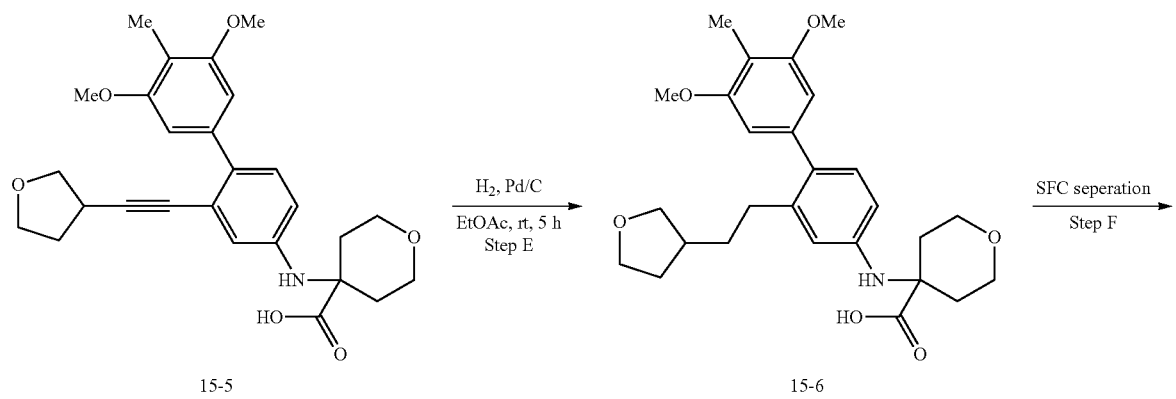

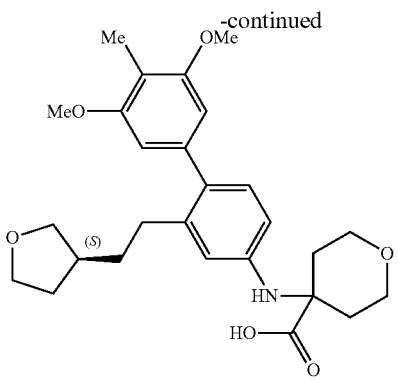
+
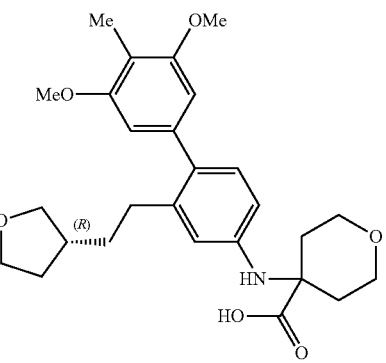

Step A: 3-ethynyltetrahydrofuran

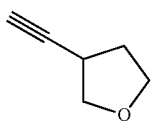

To a mixture of tetrahydrofuran-3-carbaldehyde (5.0 g, 49.9 mmol), $K_2CO_3$ (10.0 g, 72.4 mmol) in MeOH (60 mL) was added dimethyl (1-diazo-2-oxopropyl)phosphonate (10.6 g, 54.9 mmol). The reaction mixture was stirred at 20° C. for 3 h. The suspension was filtered through a pad of Celite® and the pad washed with petroleum ether (30 mL), the filtrate was concentrated in vacuo (the bath temperature below 15° C.) to give the 3-ethynyltetrahydrofuran (10 g, crude), which was used in the next step without further purification. $^1$H NMR (400 MHz, CDCl$_3$) δ 4.02 (t, J=7.8 Hz, 1H), 3.97-3.80 (m, 2H), 3.67 (dd, J=8.0 Hz, 7.2 Hz, 1H), 3.07-2.93 (m, 1H), 2.30-2.16 (m, 1H), 2.12 (d, J=2.2 Hz, 1H), 2.05-1.97 (m, 1H).

Step B: 3-((5-bromo-2-chlorophenyl)ethynyl)tetrahydrofuran

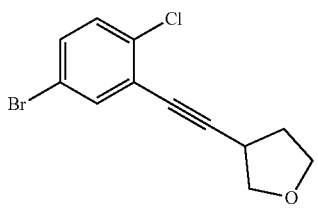 [SMILES: Clc1ccc(Br)cc1C#CC1CCOC1]

A mixture of CuI (50.0 mg, 263 µmol), Pd(PPh$_3$)$_2$Cl$_2$ (92.2 mg, 131 µmol) and TEA (3.99 g, 39.4 mmol) in THF (100 mL) was degassed and purged with nitrogen for 3 times, and then 4-bromo-1-chloro-2-iodobenzene (5.00 g, 15.8 mmol), 3-ethynyltetrahydrofuran (10.0 g, 104 mmol) was added. The resulting mixture was stirred at 20° C. for 6 h under nitrogen atmosphere. The reaction mixture was diluted with sat. aq. NH$_4$Cl (40 mL), extracted with ethyl acetate (40 mL×2). The combined organic layer was washed with brined (50 mL), dried over anhydrous Na$_2$SO$_4$, filtered and concentrated under reduced pressure. The crude was purified by flash silica gel chromatography (ISCO®; 80 g SepaFlash® Silica Flash Column, Eluent of 0-15% EtOAc/PE gradient at 60 mL/min) to afford 3-((5-bromo-2-chlorophenyl)ethynyl)tetrahydrofuran (1.5 g, 40.0% yield). $^1$H NMR (400 MHz, CDCl$_3$) δ 7.57 (d, J=2.2 Hz, 1H), 7.34 (dd, J=8.6 Hz, 2.2 Hz, 1H), 7.26-7.22 (m, 1H), 4.10 (t, J=7.8 Hz, 1H), 4.02-3.86 (m, 2H), 3.78-3.76 (m, 1H), 3.31-3.20 (m, 1H), 2.37-2.25 (m, 1H), 2.18-2.05 (m, 1H).

Step C: 4-((4-chloro-3-((tetrahydrofuran-3-yl)ethynyl)phenyl)amino)tetrahydro-2H-pyran-4-carboxylic acid

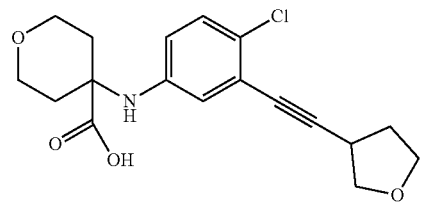 [SMILES: O=C(O)C1(Nc2ccc(Cl)c(C#CC3CCOC3)c2)CCOCC1]

The mixture of 3-((5-bromo-2-chlorophenyl)ethynyl)tetrahydrofuran (1 g, 3.50 mmol), 4-aminotetrahydro-2H-pyran-4-carboxylic acid (1.02 g, 7.00 mmol), CuI (133 mg, 700.37 µmol) and DBU (1.33 g, 8.75 mmol, 1.32 mL) in DMA (10 mL) was heated at 120° C. for 60 min under microwave. The reaction mixture was concentrated under reduced pressure to remove the solvent. The residue was diluted with brine (50 mL), extracted with EtOAc (50 mL×2), dried over anhydrous Na$_2$SO$_4$, filtered and concentrated under reduced pressure. The residue was purified by flash silica gel chromatography (Silica Flash Column, Eluent of 0~50% EtOAc/PE gradient) to give 4-((4-chloro-3-((tetrahydrofuran-3-yl)ethynyl)phenyl)amino)tetrahydro-2H-pyran-4-carboxylic acid (450 mg, 1.29 mmol). LC-MS: m/z 349.8 (M+H)$^+$.

Step D: 4-((3',5'-dimethoxy-4'-methyl-2-((tetrahydrofuran-3-yl)ethynyl)-[1,1'-biphenyl]-4-yl)amino)tetrahydro-2H-pyran-4-carboxylic acid

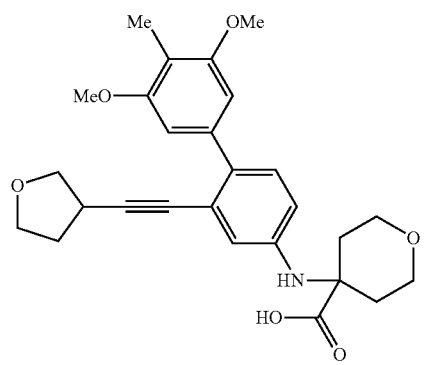 [SMILES: COc1cc(-c2ccc(NC3(C(=O)O)CCOCC3)cc2C#CC2CCOC2)cc(OC)c1C]

To a solution of 4-((4-chloro-3-((tetrahydrofuran-3-yl)ethynyl)phenyl)amino)tetrahydro-2H-pyran-4-carboxylic acid (400 mg, 1.14 mmol) and 2-(3,5-dimethoxy-4-methylphenyl)-4,4,5,5-tetramethyl-1,3,2-dioxaborolane (636 mg, 2.29 mmol) in THF (4 mL) and H₂O (4 mL) was added XPhos Pd G3 (96.8 mg, 114 μmol) and Cs₂CO₃ (745 mg, 2.29 mmol). The mixture was stirred at 120° C. for 1 h. The reaction mixture was concentrated under reduced pressure to remove the solvent. The residue was diluted with brine (50 mL), acidified with 1N HCl to pH=5, extracted with EtOAc (50 mL×2), dried over anhydrous Na₂SO₄, filtered and concentrated under reduced pressure. The residue was purified by flash silica gel chromatography (Silica Flash Column, Eluent of 0~50% EtOAc/PE gradient) to give 4-((3',5'-dimethoxy-4'-methyl-2-((tetrahydrofuran-3-yl)ethynyl)-[1,1'-biphenyl]-4-yl)amino)tetrahydro-2H-pyran-4-carboxylic acid (470 mg, 1.01 mmol). LC-MS: m/z 465.9 (M+H)⁺.

Step E: 4-((3',5'-dimethoxy-4'-methyl-2-(2-(tetrahydrofuran-3-yl)ethyl)-[1,1'-biphenyl]-4-yl)amino) tetrahydro-2H-pyran-4-carboxylic acid

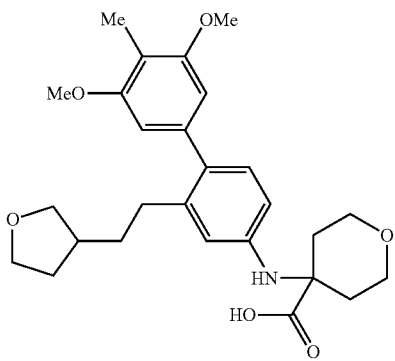 [SMILES: COc1cc(-c2ccc(NC3(C(=O)O)CCOCC3)cc2CCC2CCOC2)cc(OC)c1C]

To a solution of 4-((3',5'-dimethoxy-4'-methyl-2-((tetrahydrofuran-3-yl)ethynyl)-[1,1'-biphenyl]-4-yl)amino)tetrahydro-2H-pyran-4-carboxylic acid (470 mg, 1.01 mmol) in EtOAc (0.5 mL) was added 10% Pd/C (100 mg). The reaction mixture was stirred under H₂ atmosphere (15 psi) at 25° C. for 5 h. The mixture was diluted with EtOAc (20 mL) filtered and evaporated. The residue was purified by flash silica gel chromatography (Silica Flash Column, Eluent of 0~40% EtOAc/PE gradient) to give 4-((3',5'-dimethoxy-4'-methyl-2-(2-(tetrahydrofuran-3-yl)ethyl)-[1,1'-biphenyl]-4-yl)amino)tetrahydro-2H-pyran-4-carboxylic acid (90 mg, 19.0% yield, 80% purity). LC-MS: m/z 470.3 (M+H)⁺.

Step F: (S)-4-((3',5'-dimethoxy-4'-methyl-2-(2-(tetrahydrofuran-3-yl)ethyl)-[1,1'-biphenyl]-4-yl)amino) tetrahydro-2H-pyran-4-carboxylic acid and (R)-4-((3',5'-dimethoxy-4'-methyl-2-(2-(tetrahydrofuran-3-yl)ethyl)-[1,1'-biphenyl]-4-yl)amino)tetrahydro-2H-pyran-4-carboxylic acid (Compound 185 and 186)

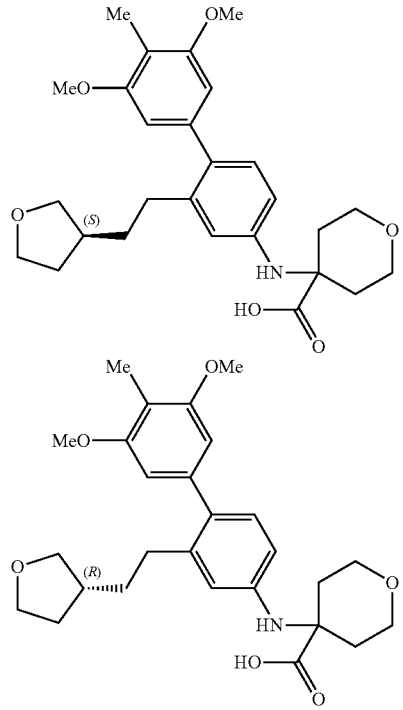

Sample of 4-((3',5'-dimethoxy-4'-methyl-2-(2-(tetrahydrofuran-3-yl)ethyl)-[1,1'-biphenyl]-4-yl)amino)tetrahydro-2H-pyran-4-carboxylic acid was subjected to SFC separation (column: DAICEL CHIRALPAK AD (250 mm*30 mm, 1 μm); mobile phase: A for CO₂, B for [0.1% NH₃H₂O in EtOH]; B %: 20%-20%). After removal of the solvent, the samples were lyophilized to provide the title compounds. The absolute stereochemistry of each product was not identified.

Enantiomer 1 4-((3',5'-dimethoxy-4'-methyl-2-(2-(tetrahydrofuran-3-yl)ethyl)-[1,1'-biphenyl]-4-yl)amino)tetrahydro-2H-pyran-4-carboxylic acid (Compound 185) SFC analysis condition: Column: ChiralPak AD-3 150×4.6 mm I.D., 3 um; Mobile phase: A: CO₂ B: ethanol (0.05% diethylamine); Isocratic: 15% B, Flow rate: 2.5 mL/min; Column temp.: 40° C., Retention time: 3.908 min. ¹H NMR (400 MHz, DMSO-d6) δ 6.84 (d, J=8.2 Hz, 1H), 6.55 (s, 1H), 6.48-6.41 (m, 3H), 3.73 (s, 6H), 3.64-3.61 (m, 6H), 3.52-3.51 (m, 2H), 3.09-3.04 (m, 1H), 2.42-2.40 (m, 1H), 2.05-1.97 (m, 7H), 1.88-1.76 (m, 3H), 1.49-1.44 (m, 2H). LC-MS: m/z 470.3 (M+H)⁺.

Enantiomer 2 4-((3',5'-dimethoxy-4'-methyl-2-(2-(tetrahydrofuran-3-yl)ethyl)-[1,1'-biphenyl]-4-yl)amino)tetrahydro-2H-pyran-4-carboxylic acid (Compound 186) SFC analysis condition: Column: ChiralPak AD-3 150×4.6 mm I.D., 3 um; Mobile phase: A: CO₂ B: ethanol (0.05% diethylamine); Gradient: from 5% to 40% of B in 4.5 min, then 5% of B for 1.5 min, Flow rate: 2.5 mL/min; Column temp.: 40° C., Retention time: 3.827 min. ¹H NMR (400 MHz, DMSO-d6) δ 6.86 (d, J=8.4 Hz, 1H), 6.54 (s, 1H), 6.45-6.40 (m, 3H), 3.73 (s, 6H), 3.65-3.60 (m, 6H), 3.53-3.49 (m, 2H), 3.09-3.04 (m, 1H), 2.44-2.37 (m, 1H), 2.06-1.94 (m, 7H), 1.89-1.77 (m, 3H), 1.50-1.44 (m, 2H). LC-MS: m/z 470.3 (M+H)⁺.

Example A16

4-((2'-chloro-2-((cyclopentyloxy)methyl)-3',5'-dimethoxy-4'-methyl-[1,1'-biphenyl]-4-yl)oxy)tetrahydro-2H-pyran-4-carboxylic acid (Compound 192)

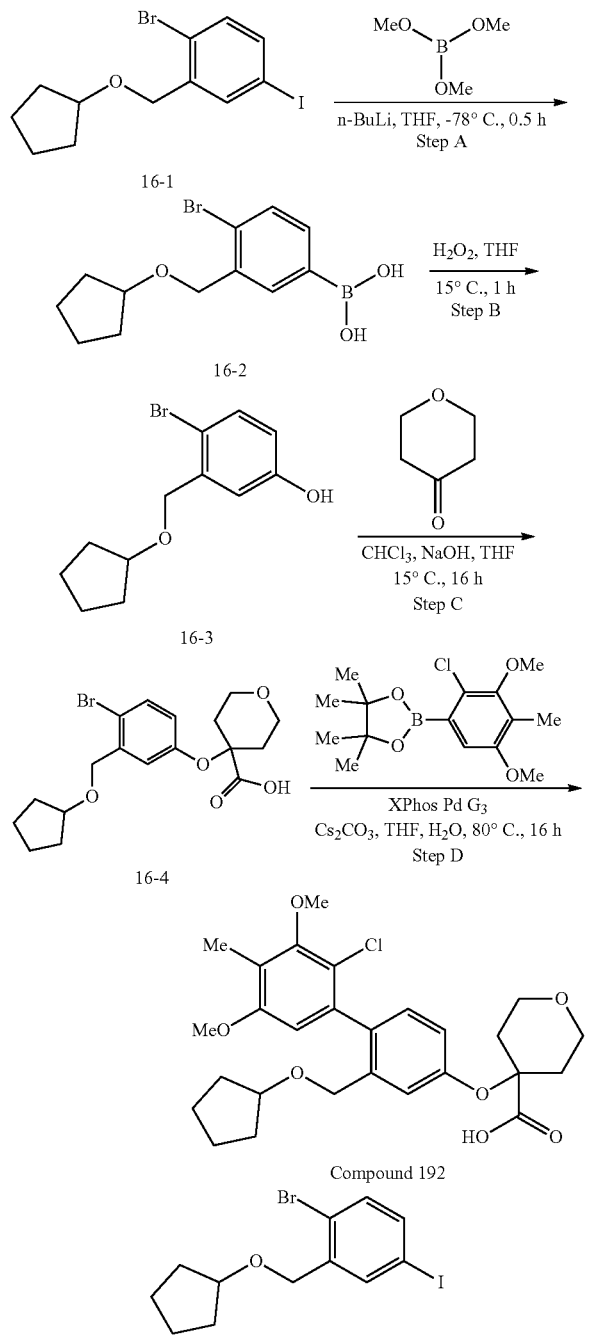

1-bromo-2-(cyclopentoxymethyl)-4-iodo-benzene (16-1) was synthesized according to the procedures described for the preparation of Example A3 (step A to step B) by using cyclopentanol in step B. ¹H NMR (400 MHz, CDCl₃) δ 7.80 (d, J=2.0 Hz, 1H), 7.44 (dd, J=8.4 Hz, 2.2 Hz, 1H), 7.23 (d, J=8.4 Hz, 1H), 4.45 (s, 2H), 4.10-4.02 (m, 1H), 1.85-1.52 (m, 8H).

Step A: (4-bromo-3-((cyclopentyloxy)methyl)phenyl)boronic acid

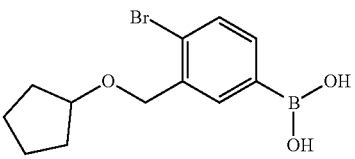 [SMILES: OB(O)c1ccc(Br)c(COC2CCCC2)c1]

At −78° C., n-BuLi (2.5 M, 1.3 mL) was added into the mixture of 1-bromo-2-(cyclopentoxymethyl)-4-iodo-benzene (1.2 g, 3.2 mmol) in THF (10 mL) under nitrogen atmosphere. After being stirred for 0.5 h, trimethyl borate (356 μL, 3.2 mmol) was added dropwise. The resulting mixture was stirred at −78° C. for 0.5 h and 15° C. for 0.5 h. Then it was quenched with 2N HCl (15 mL), extracted with ethyl acetate (30 mL×3). The organic layer was dried over anhydrous Na₂SO₄, filtered and concentrated under vacuum to give the crude [4-bromo-3-(cyclopentoxymethyl) phenyl]boronic acid (1 g, crude) as a brown solid, which used in the next step without purification.

Step B: 4-bromo-3-((cyclopentyloxy)methyl)phenol

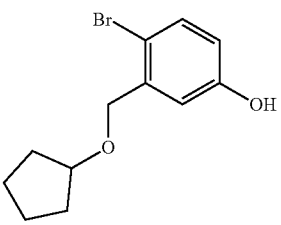 [SMILES: Oc1ccc(Br)c(COC2CCCC2)c1]

To the mixture of [4-bromo-3-(cyclopentoxymethyl)phenyl]boronic acid (1 g, 3.3 mmol) in THF (10 mL) was added 30% H₂O₂ (10 mL, 104.1 mmol). The resulting mixture was stirred at 15° C. for 1 h. The reaction mixture was quenched with sat. aq. Na₂SO₃ (50 mL) carefully, extracted with ethyl acetate (50 mL×2). The organic layer was dried over anhydrous Na₂SO₄, filtered and concentrated under reduced pressure to give a residue. The residue was purified by flash silica gel chromatography (ISCO®; 20 g SepaFlash® Silica Flash Column, Eluent of 0~20% EtOAc/PE gradient at 40 mL/min) to give 4-bromo-3-(cyclopentoxymethyl)phenol (360 mg, 39.7% yield). LC-MS: m/z 269.1 (M−H)⁻.

Step C: 4-(4-bromo-3-((cyclopentyloxy)methyl) phenoxy)tetrahydro-2H-pyran-4-carboxylic acid

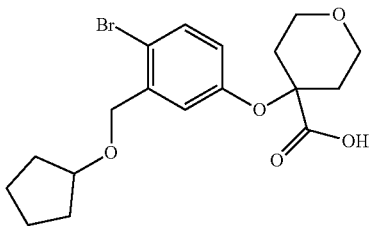 [SMILES: O=C(O)C1(Oc2ccc(Br)c(COC3CCCC3)c2)CCOCC1]

At 0° C., to the mixture of 4-bromo-3-(cyclopentoxymethyl)phenol (360 mg, 1.3 mmol) in THF (6 mL) were added NaOH (266 mg, 6.6 mmol) and tetrahydropyran-4-one (399 mg, 4.0 mmol, 366 μL). Subsequently, CHCl$_3$ (536 μL, 6.6 mmol) was added dropwise. The resulting mixture was stirred at 15° C. for 16 h. The reaction mixture was acidified with 1N HCl (~3 mL), extracted with ethyl acetate (15 mL×3). The organic layer was dried over anhydrous Na$_2$SO$_4$, filtered and concentrated under vacuum. The residue was purified by flash silica gel chromatography (ISCO®; 12 g SepaFlash® Silica Flash Column, Eluent of 0~30% EtOAc/PE gradient at 40 mL/min) to give 4-[4-bromo-3-(cyclopentoxymethyl)phenoxy]tetrahydropyran-4-carboxylic acid (280 mg, 52.8% yield). $^1$H NMR (400 MHz, CDCl$_3$) δ 7.37 (d, J=8.8 Hz, 1H), 7.08 (d, J=2.8 Hz, 1H), 6.68 (dd, J=8.8, 3.2 Hz, 1H), 4.44 (s, 2H), 4.04-3.98 (m, 1H), 3.82-3.76 (m, 4H), 2.26-2.13 (m, 4H), 1.77-1.53 (m, 8H).

Step D: 4-((2'-chloro-2-((cyclopentyloxy)methyl)-3', 5'-dimethoxy-4'-methyl-[1,1'-biphenyl]-4-yl)oxy) tetrahydro-2H-pyran-4-carboxylic acid (Compound 192)

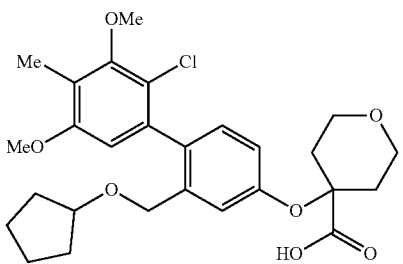 [SMILES: COc1cc(-c2ccc(OC3(C(=O)O)CCOCC3)cc2COC2CCCC2)c(Cl)c(OC)c1C]

To the mixture of 4-[4-bromo-3-(cyclopentoxymethyl)phenoxy]tetrahydropyran-4-carboxylic acid (220 mg, 551 μmol) and 2-(2-chloro-3,5-dimethoxy-4-methyl-phenyl)-4, 4,5,5-tetramethyl-1,3,2-dioxaborolane (189 mg, 606 μmol) in THF (3 mL) and H$_2$O (3 mL) was added XPhos Pd G3 (46.6 mg, 55.1 μmol) and Cs$_2$CO$_3$ (359 mg, 1.1 mmol). The resulting mixture was stirred at 80° C. under nitrogen for 16 h. After cooling, the reaction mixture was acidified by 1N HCl to pH=4. The mixture was extracted with ethyl acetate (10 mL×3). The organic layer was dried over anhydrous Na$_2$SO$_4$, filtered and concentrated under vacuum. The residue was purified by flash silica gel chromatography (ISCO®; 12 g SepaFlash® Silica Flash Column, Eluent of 0~40% EtOAc/PE gradient at 40 mL/min) and further purified by prep. HPLC (column: Welch Xtimate C18 150*25 mm*5 um; mobile phase: [water (0.05% NH$_3$·H$_2$O+ 10 mM NH$_4$HCO$_3$)—CH$_3$CN]; B %: 35%-65%, 7 min) to give 4-[4-(2-chloro-3,5-dimethoxy-4-methyl-phenyl)-3-(cyclopentoxymethyl)phenoxy]tetrahydropyran-4-carboxylic acid (70.3 mg, 25.3% yield). LC-MS: m/z 522.2 (M+NH$_3$+H)$^+$. $^1$H NMR (400 MHz, CD$_3$OD) δ 7.10 (d, J=2.8 Hz, 1H), 7.05 (d, J=8.4 Hz, 1H), 6.93 (dd, J=8.4 Hz, 2.8 Hz, 1H), 6.62 (s, 1H), 4.92 (s, 14H), 4.20 (dd, J=28.4 Hz, 12 Hz, 1H), 3.87-3.77 (m, 11H), 2.33-2.09 (m, 7H), 1.70-1.39 (m, 8H).

Example A17

4-((3-((cyclopentyloxy)methyl)-4-(6-methoxy-7-methyl-2,3-dihydrobenzofuran-4-yl)phenyl)amino) tetrahydro-2H-pyran-4-carboxylic acid (Compound 193)

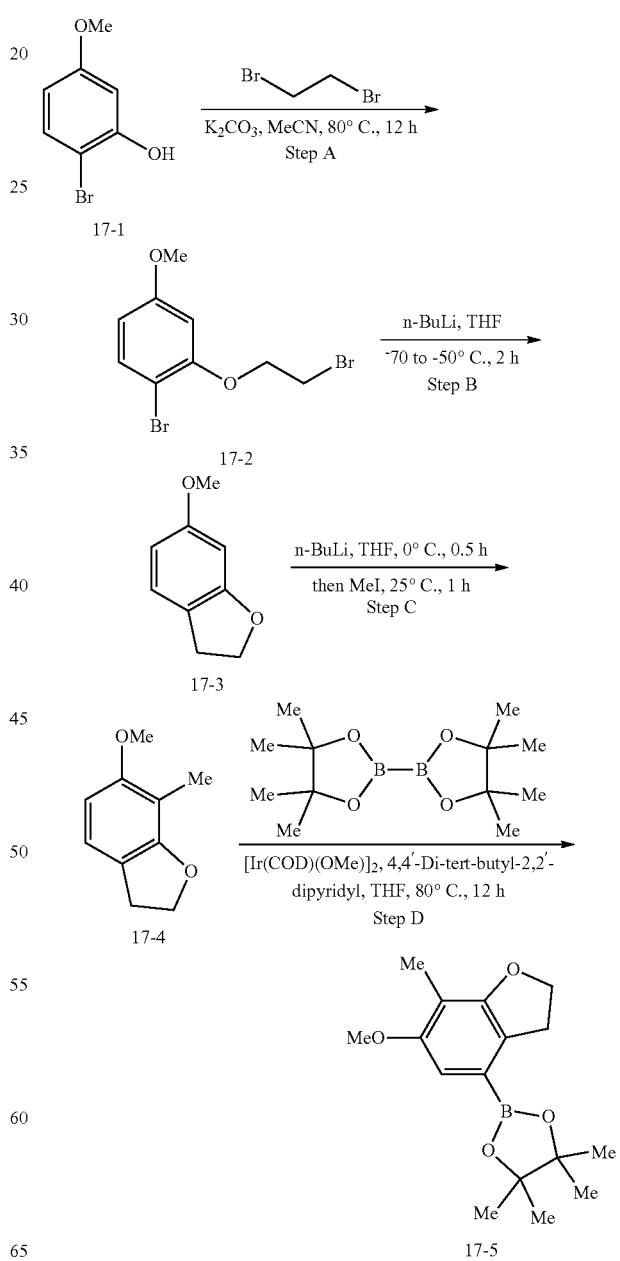

Step A: 1-bromo-2-(2-bromoethoxy)-4-methoxy-benzene

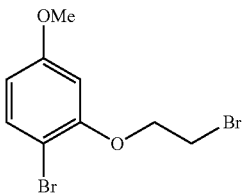 [SMILES: COc1ccc(Br)c(OCCBr)c1]

To a solution of 2-bromo-5-methoxy-phenol (7.3 g, 36 mmol) and 1,2-dibromoethane (34 g, 180 mmol) in MeCN (150 mL) was added K$_2$CO$_3$ (7.45 g, 54 mmol). The mixture was stirred at 80° C. for 12 h. After cooling, the mixture was diluted with water (100 mL), extracted with ethyl acetate (120 mL×3). The combined organic layer was dried over anhydrous Na$_2$SO$_4$, filtered and evaporated to give a residue. The residue was purified by flash silica gel chromatography (ISCO®; 120 g SepaFlash® Silica Flash Column, Eluent of 0~2% EtOAc/PE gradient at 100 mL/min) to give 1-bromo-2-(2-bromoethoxy)-4-methoxy-benzene (7.2 g, 64.6% yield). $^1$H NMR (400 MHz, CDCl$_3$) δ 7.42 (d, J=8.6 Hz, 1H), 6.52-6.40 (m, 2H), 4.30 (t, J=6.4 Hz, 2H), 3.79 (s, 3H), 3.67 (t, J=6.4 Hz, 2H).

Step B: 6-methoxy-2,3-dihydrobenzofuran

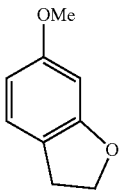

To a solution of 1-bromo-2-(2-bromoethoxy)-4-methoxy-benzene (7.2 g, 23.2 mmol) in THF (60 mL) was added n-BuLi (2.5 M, 10.22 mL) dropwise at −70° C. The reaction mixture was stirred at −70° C. for 1 h and then −50° C. for 2 h. The mixture was quenched with sat. aq. NH$_4$Cl (60 mL), extracted with ethyl acetate (50 mL×3). The combined organic layer was dried over anhydrous Na$_2$SO$_4$, filtered and evaporated to give a residue. The residue was purified by flash silica gel chromatography (ISCO®; 120 g SepaFlash® Silica Flash Column, Eluent of 0~3% EtOAc/PE gradient at 100 mL/min) to give 6-methoxy-2,3-dihydrobenzofuran (1.08 g, 31.0% yield). $^1$H NMR (400 MHz, CDCl$_3$) δ 7.03-6.91 (m, 1H), 6.32-6.31 (m, 2H), 4.48 (t, J=8.6 Hz, 2H), 3.67 (s, 3H), 3.04 (t, J=8.6 Hz, 2H).

Step C: 6-methoxy-7-methyl-2,3-dihydrobenzofuran

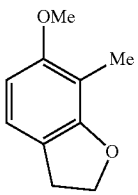 [SMILES: COc1ccc2c(c1C)OCC2]

To a solution of 6-methoxy-2,3-dihydrobenzofuran (1.08 g, 7.19 mmol) in THF (20 mL) was added n-BuLi (2.5 M, 3.16 mL) dropwise at 80° C. After being stirred for 0.5 h, MeI (1.22 g, 8.63 mmol) was added dropwise. The resulting mixture was stirred at 25° C. for 1 h. Then the mixture was diluted with water (20 mL), extracted with ethyl acetate (30 mL×3). The combined organic layer was dried over anhydrous Na$_2$SO$_4$, filtered and evaporated to give a residue. The residue was purified by flash silica gel chromatography (ISCO®; 20 g SepaFlash® Silica Flash Column, Eluent of 0~2% EtOAc/PE gradient at 80 mL/min) to give 6-methoxy-7-methyl-2,3-dihydrobenzofuran (192 mg, 16.3% yield). $^1$H NMR (400 MHz, CDCl$_3$) δ 6.87 (d, J=8.0 Hz, 1H), 6.28 (d, J=8.4 Hz, 2H), 4.49 (t, J=8.6 Hz, 2H), 3.72 (s, 3H), 3.08 (t, J=8.6 Hz, 2H), 2.01 (s, 3H).

Step D: 2-(6-methoxy-7-methyl-2,3-dihydrobenzofuran-4-yl)-4,4,5,5-tetramethyl-1,3,2-dioxaborolane

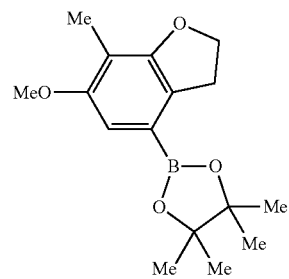 [SMILES: COc1cc(B2OC(C)(C)C(C)(C)O2)c2c(c1C)OCC2]

To a solution of 6-methoxy-7-methyl-2,3-dihydrobenzofuran (192 mg, 1.17 mmol) and 4,4,5,5-tetramethyl-2-(4,4,5,5-tetramethyl-1,3,2-dioxaborolan-2-yl)-1,3,2-dioxaborolane (267 mg, 1.05 mmol) in THF (5 mL) was added [Ir(COD)(OMe)]$_2$ (3.88 mg, 5.85 µmol) and 4,4'-Di-tert-butyl-2,2'-dipyridyl (dtbpy) (3.14 mg, 11.7 µmol). The reaction mixture was stirred at 80° C. for 12 h. The mixture was evaporated to give a residue. The residue was purified by flash silica gel chromatography (ISCO®; 12 g SepaFlash® Silica Flash Column, Eluent of 0~3% EtOAc/PE gradient at 80 mL/min) to give 2-(6-methoxy-7-methyl-2,3-dihydrobenzofuran-4-yl)-4,4,5,5-tetramethyl-1,3,2-dioxaborolane (129 mg, 38.0% yield). $^1$H NMR (400 MHz, CDCl$_3$) δ 6.69 (s, 1H), 4.48 (t, J=8.8 Hz, 2H), 3.77 (s, 3H), 3.25 (t, J=8.8 Hz, 2H), 2.03 (s, 3H), 1.25 (s, 12H).

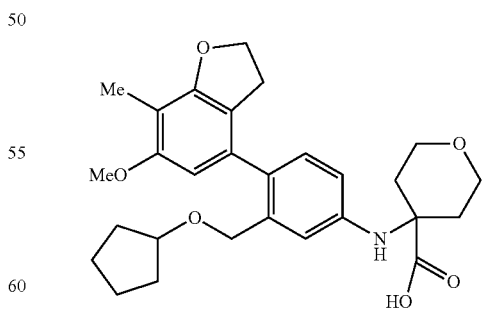

4-((3-((cyclopentyloxy)methyl)-4-(6-methoxy-7-methyl-2,3-dihydrobenzofuran-4-yl)phenyl)amino)tetrahydro-2H-pyran-4-carboxylic acid (Compound 193) was synthesized according to the procedures described for the preparation of Example A3 (step A and D) by using cyclopentanol in step B and 2-(6-methoxy-7-methyl-2,3-dihydrobenzofuran-4-yl)-4,4,5,5-tetramethyl-1,3,2-dioxaborolane in step D. LC-MS: m/z 482.3 (M+H)+. 1H NMR (400 MHz, CD3OD) δ 6.94 (d, J=8.2 Hz, 1H), 6.78 (s, 1H), 6.67 (d, J=8.2 Hz, 1H), 6.23 (s, 1H), 4.47 (t, J=8.4 Hz, 2H), 4.20 (s, 2H), 3.89-3.75 (m, 5H), 3.74 (s, 3H), 2.89 (t, J=8.0 Hz, 2H), 2.27-2.16 (m, 2H), 2.03-1.90 (m, 5H), 1.65-1.47 (m, 8H).

Example A18

4-((2-((bicyclo[3.1.0]hexan-3-yloxy)methyl)-3',5'-dimethoxy-4'-methyl-[1,1'-biphenyl]-4-yl)amino)tetrahydro-2H-pyran-4-carboxylic acid (Compound 182)

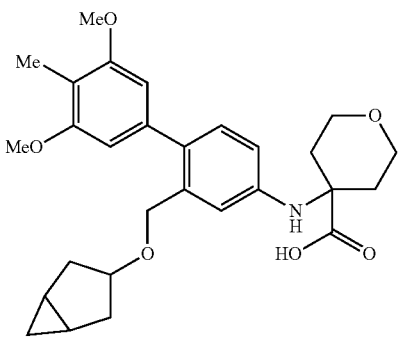 [SMILES: COc1cc(-c2ccc(NC3(C(=O)O)CCOCC3)cc2COC2CC3CC3C2)cc(OC)c1C]

4-((2-((bicyclo[3.1.0]hexan-3-yloxy)methyl)-3',5'-dimethoxy-4'-methyl-[1,1'-biphenyl]-4-yl)amino)tetrahydro-2H-pyran-4-carboxylic acid (Compound 182) was synthesized according to the procedures described for the preparation of Example A3 (step B to Step D) by using bicyclo[3.1.0]hexan-3-ol in step B. LC-MS: m/z 482.1 (M+H)+. 1H NMR (400 MHz, DMSO-d6) δ 7.02 (d, J=8.0 Hz, 1H), 6.80 (d, J=2.4 Hz, 1H), 6.68 (dd, J=8.4 Hz, 2.0 Hz, 1H), 6.51 (s, 1H), 4.20 (s, 2H), 3.99-3.95 (m, 1H), 3.82-3.76 (m, 10H), 2.28-2.21 (m, 2H), 2.07 (s, 3H), 2.00-1.94 (m, 2H), 1.85-1.82 (m, 2H), 1.23-1.21 (m, 2H), 0.49-0.46 (m, 1H), 0.38-0.37 (m, 1H).

Example A19

4-((4-(3-chloro-2,6-dimethoxypyridin-4-yl)-3-((cyclopentyloxy)methyl)phenyl)amino) tetrahydro-2H-pyran-4-carboxylic acid (Compound 207)

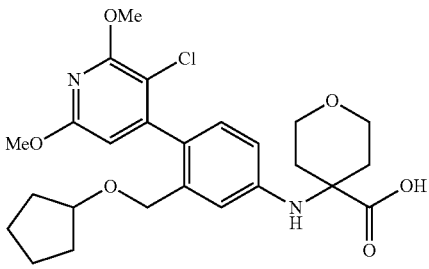

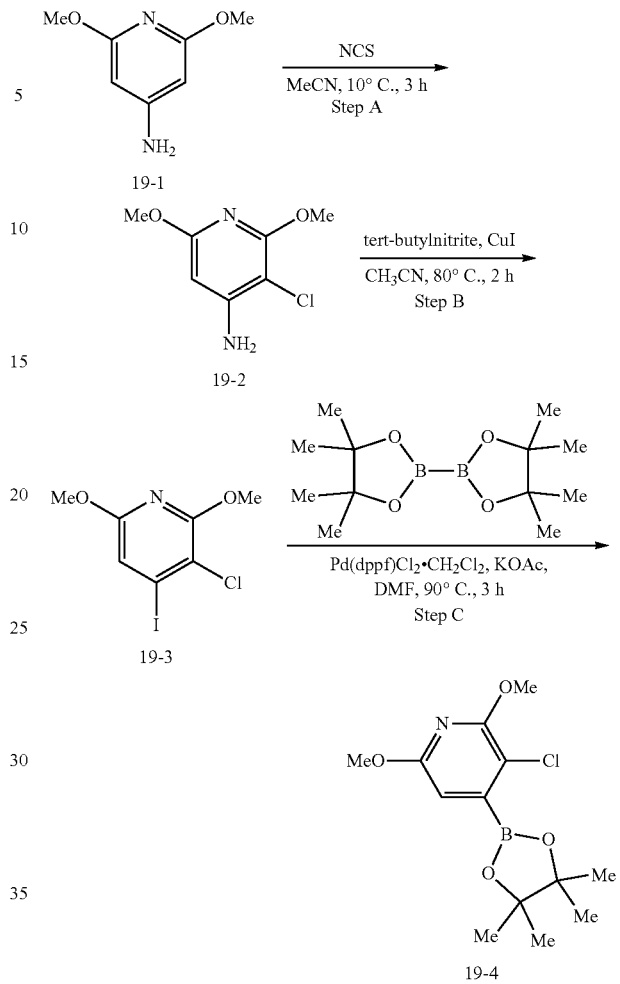

Step A: 3-chloro-2,6-dimethoxypyridin-4-amine

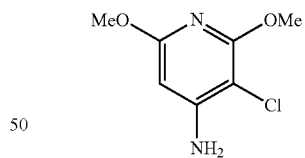

To the mixture of 2,6-dimethoxypyridin-4-amine (1 g, 6.5 mmol) in MeCN (8 mL) was added NCS (866 mg, 6.5 mmol). The reaction mixture was stirred at 10° C. for 3 h. The reaction mixture was quenched with H2O (10 mL), extracted with ethyl acetate (30 mL×3). The organic layer was dried over anhydrous Na2SO4 and concentrated under vacuum. The residue was purified by flash silica gel chromatography (ISCO®; 40 g SepaFlash® Silica Flash Column, Eluent of 0~18% EtOAc/PE gradient at 40 mL/min) to give 3-chloro-2,6-dimethoxy-pyridin-4-amine (1.22 g, 99% yield). 1H NMR (400 MHz, CDCl3) δ 5.72 (s, 1H), 4.48 (brs, 2H), 3.96 (s, 3H), 3.84 (s, 3H).

Step B: 3-chloro-4-iodo-2,6-dimethoxypyridine

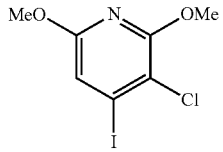 [SMILES: COc1cc(I)c(Cl)c(OC)n1]

To the suspension of CuI (2.49 g, 13.1 mmol) in CH₃CN (10 mL) was added tert-butylnitrite (3.37 g, 32.7 mmol, 3.9 mL) at 80° C. under nitrogen. After being stirred for 0.5 h, a solution 3-chloro-2,6-dimethoxy-pyridin-4-amine (1.23 g, 6.5 mmol) in CH₃CN (10 mL) was added dropwise. The resulting mixture was stirred at 80° C. for 2 h. After cooling, the reaction was quenched with H₂O (20 mL), extracted with ethyl acetate (50 mL×3). The organic layer was dried over Na₂SO₄ and concentrated under vacuum. The residue was purified by flash silica gel chromatography (ISCO®; 40 g SepaFlash® Silica Flash Column, Eluent of 0~7% EtOAc/PE gradient at 100 mL/min) to give 3-chloro-4-iodo-2,6-dimethoxy-pyridine (1.23 g, 62.8% yield). $^1$H NMR (400 MHz, CDCl₃) δ 6.84 (s, 1H), 3.98 (s, 3H), 3.90 (s, 3H).

Step C: 3-chloro-2,6-dimethoxy-4-(4,4,5,5-tetramethyl-1,3,2-dioxaborolan-2-yl)pyridine

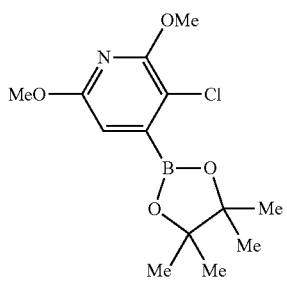 [SMILES: COc1cc(B2OC(C)(C)C(C)(C)O2)c(Cl)c(OC)n1]

To the mixture of 3-chloro-4-iodo-2,6-dimethoxy-pyridine (1.23 g, 4.1 mmol) and 4,4,5,5-tetramethyl-2-(4,4,5,5-tetramethyl-1,3,2-dioxaborolan-2-yl)-1,3,2-dioxaborolane (1.25 g, 4.9 mmol) in DMF (8 mL) was added Pd(dppf)Cl₂·CH₂Cl₂ (335 mg, 411 μmol) and KOAc (1.21 g, 12.3 mmol). The reaction mixture was stirred at 90° C. for 3 h. After cooling, the reaction solution was poured into water (10 mL), extracted with ethyl acetate (25 mL×3). The organic layer was washed with brine (30 mL), dried over anhydrous Na₂SO₄, filtered and concentrated. The residue was purified by flash silica gel chromatography (ISCO®; 20 g SepaFlash® Silica Flash Column, Eluent of 0~10% EtOAc/PE gradient at 40 mL/min) to give 3-chloro-2,6-dimethoxy-4-(4,4,5,5-tetramethyl-1,3,2-dioxaborolan-2-yl)pyridine (300 mg, 24.4% yield). $^1$H NMR (400 MHz, CDCl₃) δ 6.52 (s, 1H), 3.99 (s, 3H), 3.89 (s, 3H), 1.34 (s, 12H).

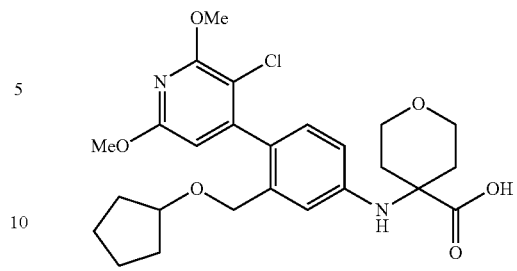

4-((4-(3-chloro-2,6-dimethoxypyridin-4-yl)-3-((cyclopentyloxy)methyl)phenyl)amino) tetrahydro-2H-pyran-4-carboxylic acid (Compound 207) was synthesized according to the procedures described for the preparation of Example A3 (step A and D) by using cyclopentanol in step B and 3-chloro-2,6-dimethoxy-4-(4,4,5,5-tetramethyl-1,3,2-dioxaborolan-2-yl)pyridine in step D. LC-MS: m/z 491.2 (M+H)⁺. $^1$H NMR (400 MHz, CD₃OD) δ 6.87 (d, J=8.4 Hz, 1H), 6.81 (d, J=2.0 Hz, 1H), 6.64 (dd, J=8.4, 2.4 Hz, 1H), 6.25 (s, 1H), 4.17 (dd, J=32.0 Hz, 11.6 Hz, 1H), 4.03 (s, 3H), 3.94 (s, 3H), 3.86-3.75 (m, 5H), 2.27-2.21 (m, 2H), 2.05-2.02 (m, 2H), 1.60-1.47 (m, 8H).

Example A20

4-((2-((cyclopentyloxy)methyl)-2'-fluoro-3',5'-dimethoxy-4'-methyl-[1,1'-biphenyl]-4-yl)oxy)tetrahydro-2H-pyran-4-carboxylic acid (Compound 209)

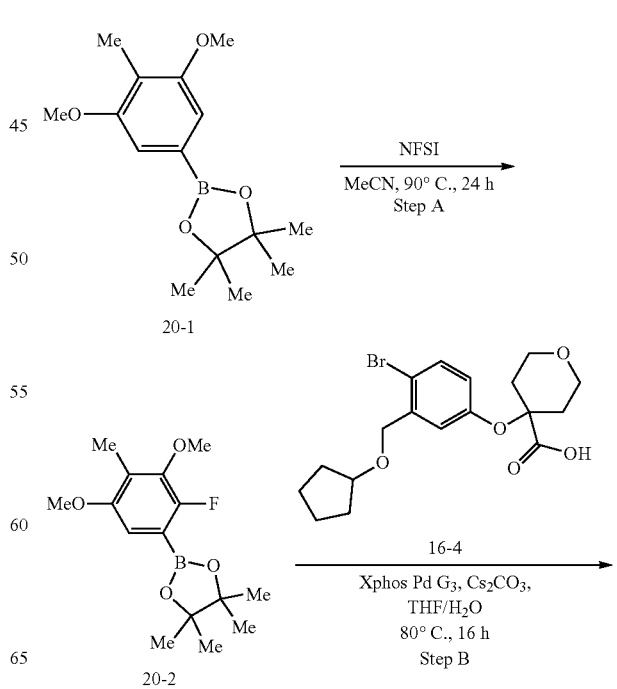

281

-continued

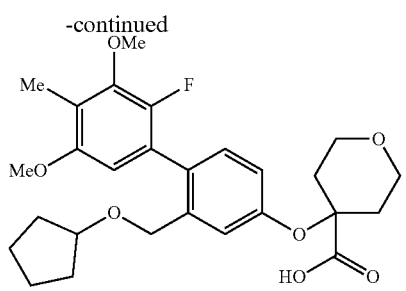

Step A: 2-(2-fluoro-3,5-dimethoxy-4-methylphenyl)-4,4,5,5-tetramethyl-1,3,2-dioxaborolane

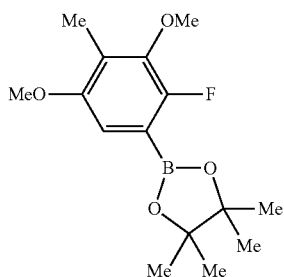 [SMILES: COc1cc(B2OC(C)(C)C(C)(C)O2)c(F)c(OC)c1C]

To a solution of 2-(3,5-dimethoxy-4-methyl-phenyl)-4,4,5,5-tetramethyl-1,3,2-dioxaborolane (12.2 g, 43.9 mmol) in THF (100 mL) was added NFSI (20.8 g, 65.8 mmol). The resulting mixture was stirred at 90° C. for 12 h. Then additional NFSI (20.8 g, 65.8 mmol) was added and stirred at 90° C. for another 12 h. After cooling, the solvent was removed under reduced pressure to give a residue. The residue was purified by flash silica gel chromatography (ISCO®; 120 g SepaFlash® Silica Flash Column, Eluent of 0-4% EtOAc/PE gradient at 100 mL/min) to give 2-(2-fluoro-3,5-dimethoxy-4-methyl-phenyl)-4,4,5,5-tetramethyl-1,3,2-dioxaborolane (4.7 g, 36.2% yield). $^1$H NMR (400 MHz, CDCl$_3$) δ 6.84 (s, 1H), 3.88 (s, 3H), 3.84 (s, 3H), 2.16 (s, 3H), 1.37 (s, 12H).

Step B: 4-((2-((cyclopentyloxy)methyl)-2'-fluoro-3', 5'-dimethoxy-4'-methyl-[1,1'-biphenyl]-4-yl)oxy) tetrahydro-2H-pyran-4-carboxylic acid (Compound 209)

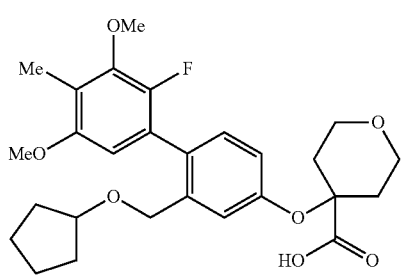

To the mixture of 4-[4-bromo-3-(cyclopentoxymethyl) phenoxy]tetrahydropyran-4-carboxylic acid (70 mg, 175 µmol) and 2-(2-fluoro-3,5-dimethoxy-4-methyl-phenyl)-4, 4,5,5-tetramethyl-1,3,2-dioxaborolane (130 mg, 438 µmol)

282 in THF (2 mL) and H$_2$O (2 mL) were added XPhos Pd G3 (14.8 mg, 17.5 µmol) and Cs$_2$CO$_3$ (114 mg, 351 µmol). The reaction mixture was stirred at 80° C. under nitrogen for 16 h. After cooling, the reaction mixture was acidified by 1N HCl to pH=3. The mixture was extracted with ethyl acetate (10 mL×3). The organic layer was dried over anhydrous Na$_2$SO$_4$ and concentrated under vacuum. The residue was purified by flash silica gel chromatography (ISCO®; 4 g SepaFlash® Silica Flash Column, Eluent of 0~36% EtOAc/PE gradient at 40 mL/min) and further purified by prep. HPLC (column: Welch Xtimate C18 150*25 mm*5 µm; mobile phase: [water (0.05% NH$_3$·H$_2$O+10 mM NH$_4$HCO$_3$)—CH$_3$CN]; B %: 35%-65%, 7 min) to give 4-[3-(cyclopentoxymethyl)-4-(2-fluoro-3,5-dimethoxy-4-methyl-phenyl)phenoxy]tetrahydropyran-4-carboxylic acid (21.3 mg, 24.9% yield). LC-MS: m/z 506.3 (M+H)$^+$. $^1$H NMR (400 MHz, CD$_3$OD) δ 7.15-7.09 (m, 2H), 6.96 (dd, J=8.4, 2.6 Hz, 1H), 6.51 (d, J=8.0 Hz, 1H), 4.28 (s, 2H), 3.89-3.79 (m, 11H), 2.26-2.20 (m, 2H), 2.18-2.10 (m, 5H), 1.67-1.47 (m, 8H).

Example A21

(2R, 6S)-4-((3',5'-dimethoxy-4'-methyl-2-(2-(tetrahydrofuran-3-yl)ethyl)-[1,1'-biphenyl]-4-yl)amino) tetrahydro-2H-pyran-4-carboxylic acid (Compound 225)

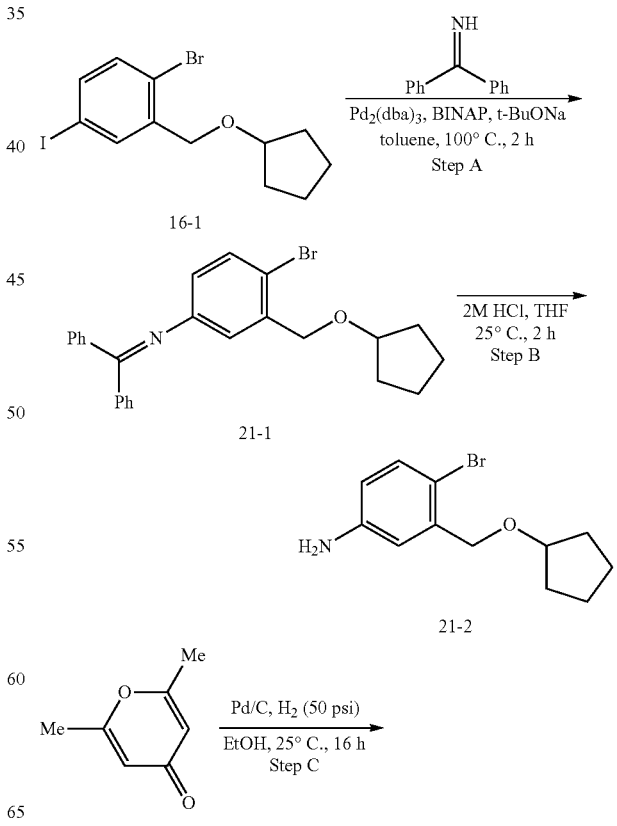

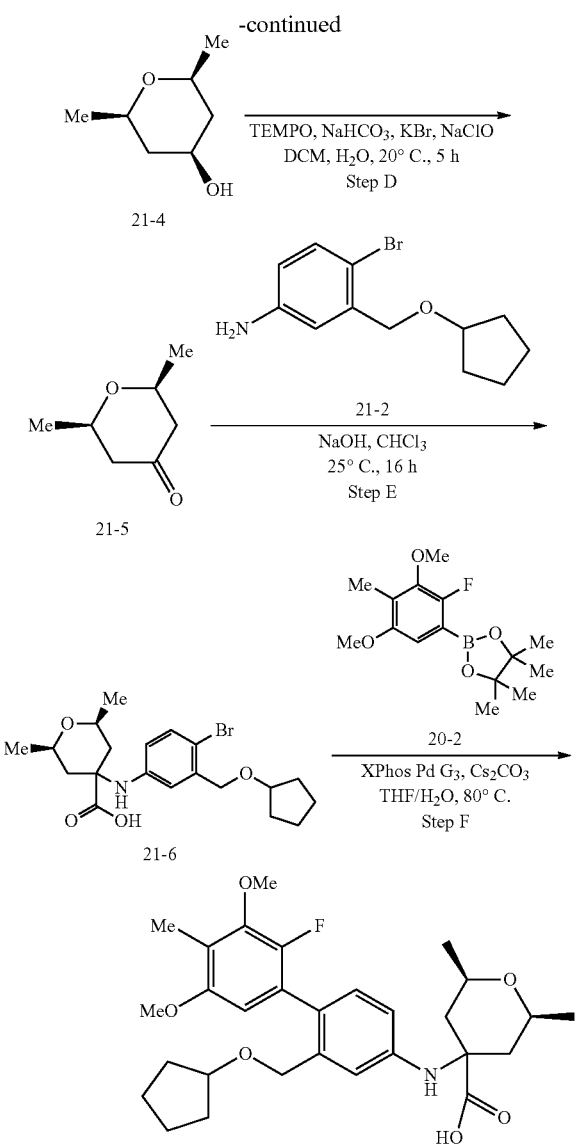

Step A: N-[4-bromo-3-(cyclopentoxymethyl)phenyl]-1,1-diphenyl-methanimine

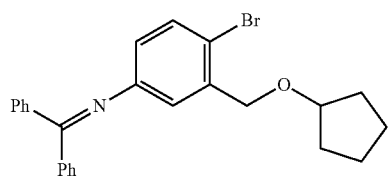 [SMILES: Brc1ccc(N=C(c2ccccc2)c2ccccc2)cc1COC1CCCC1]

To a solution of 1-bromo-2-(cyclopentoxymethyl)-4-iodo-benzene (600 mg, 1.57 mmol) and diphenylmethanimine (285 mg, 1.57 mmol) in toluene (10 mL) was added Pd$_2$(dba)$_3$ (72.1 mg, 78.7 μmol), t-BuONa (303 mg, 3.15 mmol) and [1-(2-diphenylphosphanyl-1-naphthyl)-2-naphthyl]-diphenyl-phosphane (BINAP) (98.1 mg, 157 μmol). The mixture was stirred at 100° C. for 2 h. After cooling, the mixture was diluted with water (40 mL), extracted with ethyl acetate (25 mL×3). The combined organic layer was dried over anhydrous Na$_2$SO$_4$, filtered and evaporated to give a residue. The residue was purified by flash silica gel chromatography (ISCO®; 12 g SepaFlash® Silica Flash Column, Eluent of 0~2% EtOAc/PE gradient at 40 mL/min) to give N-[4-bromo-3-(cyclopentoxymethyl)phenyl]-1,1-diphenyl-methanimine (653 mg, 95.5% yield). LC-MS: m/z 434.2 (M+H)$^+$.

Step B: 4-bromo-3-((cyclopentyloxy)methyl)aniline

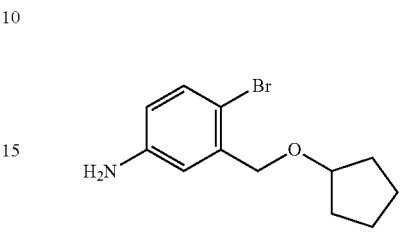

To a solution of N-[4-bromo-3-(cyclopentoxymethyl)phenyl]-1,1-diphenyl-methanimine (653 mg, 1.50 mmol) in THF (10 mL) was added 2 M HCl (752 μL). The reaction mixture was stirred at 25° C. for 2 h. The mixture was diluted with water (40 mL), basified by sat. aq. NaHCO$_3$ (20 mL), extracted with ethyl acetate (25 mL×3). The combined organic layer was dried over anhydrous Na$_2$SO$_4$, filtered and evaporated to give a residue. The residue was purified by flash silica gel chromatography (ISCO®; 4 g SepaFlash® Silica Flash Column, Eluent of 0~50% EtOAc/PE gradient at 40 mL/min) to give 4-bromo-3-(cyclopentoxymethyl)aniline (323 mg, 79.5% yield). $^1$H NMR (400 MHz, CDCl$_3$) δ 7.19 (d, J=8.4 Hz, 1H), 6.76 (d, J=3.2 Hz, 1H), 6.39 (dd, J=8.4, 3.2 Hz, 1H), 4.32 (s, 2H), 4.06-3.89 (m, 1H), 3.61 (s, 2H), 1.80-1.36 (m, 8H).

Step C: (2R,4S,6S)-2,6-dimethyltetrahydro-2H-pyran-4-ol

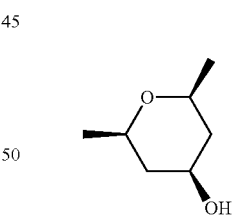

To a solution of 2,6-dimethyl-4H-pyran-4-one (10.0 g, 80.6 mmol) in EtOH (150 mL) was added 10% Pd/C (4 g) under N$_2$ atmosphere. The suspension was degassed and purged with H$_2$ for 3 times. The mixture was stirred under H$_2$ (45 Psi) at 25° C. for 16 h. The suspension was filtered through a pad of Celite® and the pad was washed with ethanol (50 mL). The filtrate was concentrated to dryness under reduced pressure to give crude (2R,4S,6S)-2,6-dimethyltetrahydro-2H-pyran-4-ol (10 g), which used in the next step without further purification.

Step D: (2R,6S)-2,6-dimethyldihydro-2H-pyran-4(3H)-one

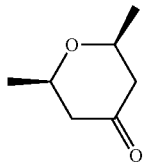

To a solution of (2R,4S,6S)-2,6-dimethyltetrahydro-2H-pyran-4-ol (10.0 g, 76.8 mmol, crude) in DCM (120 mL) was added a solution of NaHCO$_3$ (645 mg, 7.68 mmol) and KBr (914 mg, 7.68 mmol) in H$_2$O (40 mL). Then TEMPO (121 mg, 768 μmol) was added. The mixture was treated at 0° C. under vigorous stirring with aq. NaClO (78.6 g, 84.5 mmol, 5%~7%) over 1 h. Then the whole system was allowed to stir at 20° C. for 5 h. The reaction mixture was poured into H$_2$O (100 mL), extracted with dichloromethane (100 mL×3). The combined organic layer was washed with brine (100 mL), dried over anhydrous Na$_2$SO$_4$, filtered and concentrated to dryness under reduced pressure to give crude (2,6-dimethyldihydro-2H-pyran-4(3H)-one (7 g, crude), which used in the next step without further purification. $^1$H NMR (400 MHz, CDCl$_3$) δ 3.77-3.72 (m, 2H), 2.39-2.32 (m, 2H), 2.27-2.17 (m, 2H), 1.34 (d, J=6.2 Hz, 6H)

Step E (2R,6S)-4-((4-bromo-3-((cyclopentyloxy)methyl)phenyl)amino)-2,6-dimethyltetrahydro-2H-pyran-4-carboxylic acid

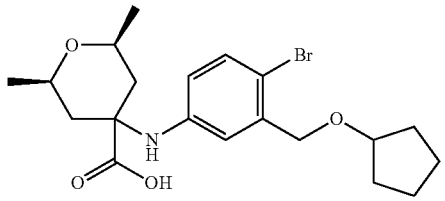 [SMILES: C[C@@H]1CC(Nc2ccc(Br)c(COC3CCCC3)c2)(C(=O)O)C[C@H](C)O1]

To a solution of 4-bromo-3-((cyclopentyloxy)methyl)aniline (500 mg, 1.85 mmol) and (2R,6S)-2,6-dimethyltetrahydro-4H-pyran-4-one (474 mg, 3.70 mmol, crude) in THF (4 mL) was added NaOH (370 mg, 9.25 mmol) and CHCl$_3$ (1.10 g, 9.25 mmol) at 0° C. The reaction mixture was stirred at 25° C. for 16 h. Then the mixture was poured into sat. aq. NH$_4$Cl (150 mL) at 0° C., extracted with ethyl acetate (20 mL×3). The combined organic layer was washed with brine (20 mL×3), dried over anhydrous Na$_2$SO$_4$, filtered and concentrated. The residue was purified by flash silica gel chromatography (ISCO®; 12 g SepaFlash® Silica Flash Column, Eluent of 0~10% EtOAc/PE gradient at 10 mL/min) to give (2R,6S)-4-((4-bromo-3-((cyclopentyloxy)methyl)phenyl)amino)-2,6-dimethyltetrahydro-2H-pyran-4-carboxylic acid (320 mg, crude). LC-MS: m/z 426.2 (M+H)$^+$.

Step F (2R,6S)-4-((2-((cyclopentyloxy)methyl)-2'-fluoro-3',5'-dimethoxy-4'-methyl-[1,1'-biphenyl]-4-yl)amino)-2,6-dimethyltetrahydro-2H-pyran-4-carboxylic acid (Compound 225)

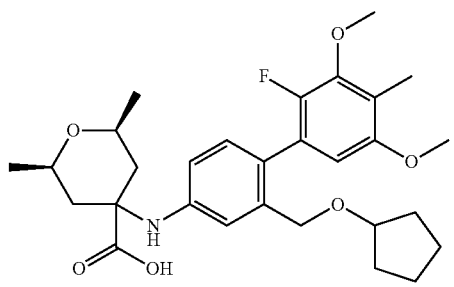

The mixture of (2R,6S)-4-((4-bromo-3-((cyclopentyloxy)methyl)phenyl)amino)-2,6-dimethyltetrahydro-2H-pyran-4-carboxylic acid (320 mg, 751 μmol, crude), 2-(2-fluoro-3,5-dimethoxy-4-methylphenyl)-4,4,5,5-tetramethyl-1,3,2-dioxaborolane (667 mg, 1.13 mmol, 50% purity), XPhos Pd G3 (63.5 mg, 75.1 μmol), Cs$_2$CO$_3$ (489 mg, 1.50 mmol) in THF (5 mL) and H$_2$O (1 mL) was degassed and purged with N$_2$ for 3 times. The resulting mixture was stirred at 110° C. for 16 h under N$_2$ atmosphere. After cooling, the reaction mixture was filtered and the filtrate was evaporated to give a residue. The crude product was purified by prep. HPLC (Column: Boston Prime C18 150*30 mm*5 μm Eluent: 30% to 60% water (0.05% NH$_3$·H$_2$O+10 mM NH$_4$HCO$_3$)—CH$_3$CN) to give the product (2R,6S)-4-((2-((cyclopentyloxy)methyl)-2'-fluoro-3',5'-dimethoxy-4'-methyl-[1,1'-biphenyl]-4-yl)amino)-2,6-dimethyltetrahydro-2H-pyran-4-carboxylic acid (52.4 mg, 13.5% yield. LC-MS: m/z 516.4 (M+H)$^+$. $^1$H NMR (400 MHz, DMSO-d6) δ 6.88 (d, J=8.0 Hz, 1H), 6.80 (s, 1H), 6.62 (d, J=8.0 Hz, 1H), 6.51 (d, J=5.2 Hz, 1H), 4.11 (s, 2H), 3.84-3.60 (m, 9H), 2.43-2.34 (m, 2H), 2.08 (s, 3H), 1.60-1.36 (m, 8H), 1.23-1.13 (m, 2H), 1.09 (d, J=5.6 Hz, 6H).

Example A22

1-((2-(((2,3-dihydro-1H-inden-2-yl)oxy)methyl)-3',5'-dimethoxy-4'-methyl-[1,1'-biphenyl]-4-yl)amino)cyclobutane-1-carboxylic acid (Compound 110)

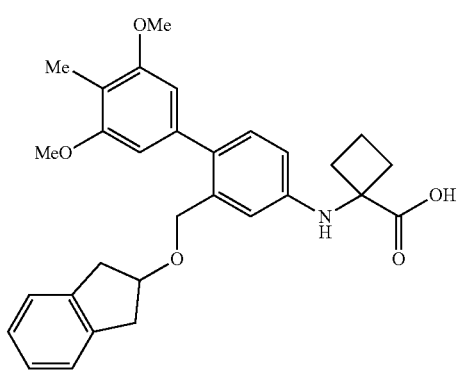

287

-continued

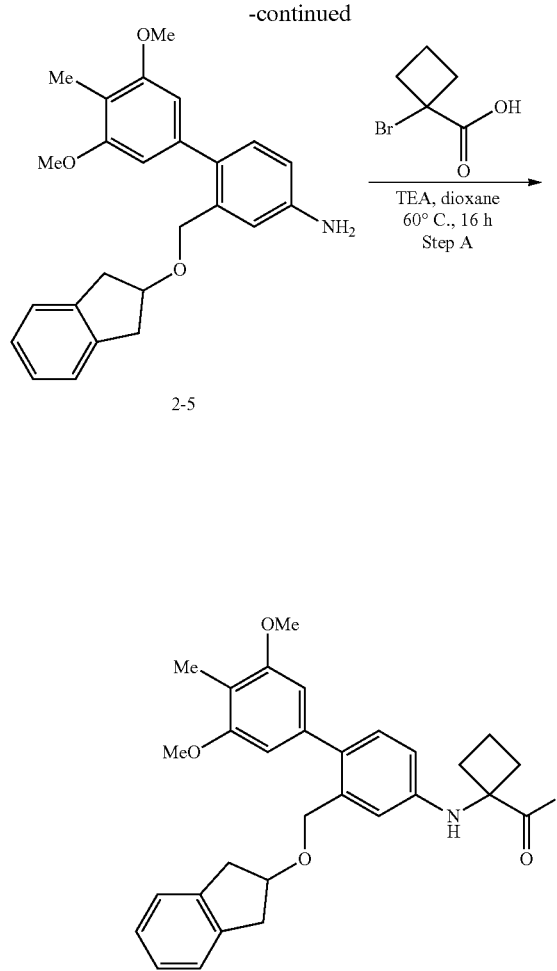

2-5

Compound 110

To a mixture of 2-(((2,3-dihydro-1H-inden-2-yl)oxy)methyl)-3',5'-dimethoxy-4'-methyl-[1,1'-biphenyl]-4-amine (70 mg, 0.18 mmol) in dioxane (2 mL) was added TEA (0.15 mL, 1.08 mmol). Then the mixture was heated to 60° C., and 1-bromocyclobutane-1-carboxylic acid (49 mg, 0.27 mmol) in dioxane (1 mL) was added. The resulting mixture was stirred at 60° C. overnight under $N_2$ protection. After cooling, the reaction mixture was concentrated. The crude was purified by prep. HPLC (0.1% $NH_4HCO_3$ in water and acetonitrile) to afford 1-((2-(((2,3-dihydro-1H-inden-2-yl)oxy)methyl)-3',5'-dimethoxy-4'-methyl-[1,1'-biphenyl]-4-yl)amino)cyclobutane-1-carboxylic acid (29 mg, 34% yield). LC-MS: m/z 488.2 (M+H)+. $^1$H NMR (400 MHz, DMSO-d6) δ 7.21-7.17 (m, 2H), 7.13-7.11 (m, 2H), 6.99 (d, J=8.4 Hz, 1H), 6.59 (d, J=2.4 Hz, 1H), 6.53 (s, 2H), 6.31 (dd, J=8.4, 2.4 Hz, 1H), 4.38-4.33 (m, 1H), 4.32 (s, 2H), 3.72 (s, 6H), 3.08 (dd, J=16.0, 6.4 Hz, 2H), 2.85 (d, J=16.0, 3.6 Hz, 2H), 2.61-2.53 (m, 2H), 2.17-2.07 (m, 2H), 2.00 (s, 3H), 1.97-1.87 (m, 2H).

288

Example A23

4-((3-(((cyclopentyloxy)methyl)-4-(2,6-dimethoxy-pyridin-4-yl)phenyl)amino) tetrahydro-2H-pyran-4-carboxylic acid (Compound 152)

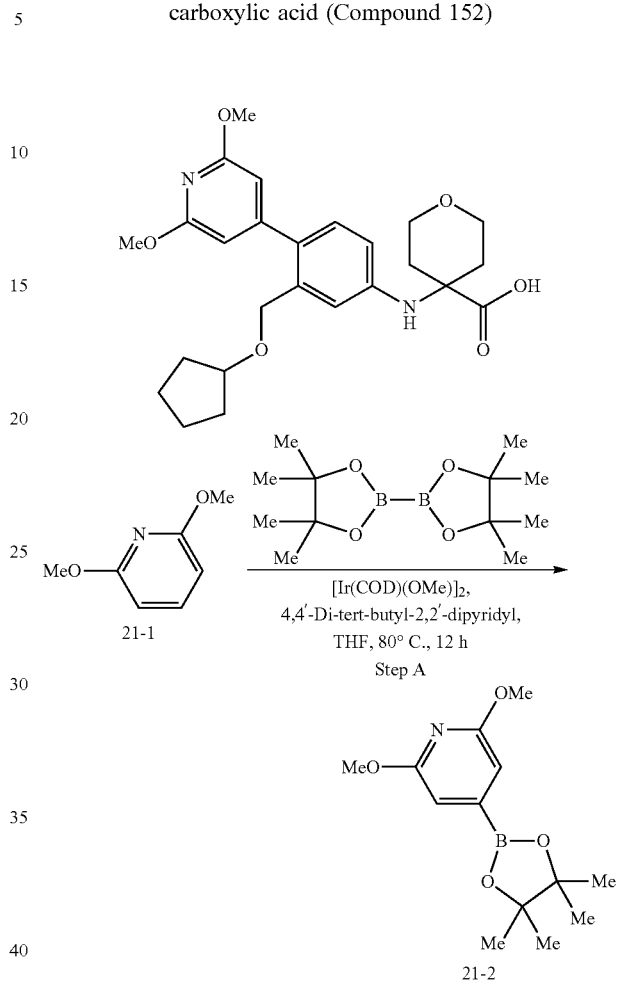

Step A 2,6-dimethoxy-4-(4,4,5,5-tetramethyl-1,3,2-dioxaborolan-2-yl)pyridine

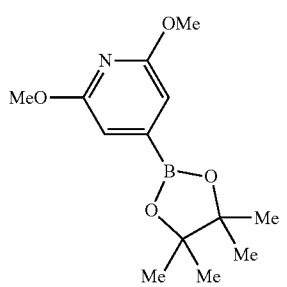 [SMILES: COc1cc(B2OC(C)(C)C(C)(C)O2)cc(OC)n1]

To a solution of 2,6-dimethoxypyridine (1.0 g, 7.19 mmol) and bis(pinacolato)diboron (912 mg, 3.59 mmol) in THF (15 mL) were added 4,4'-Di-tert-butyl-2,2'-dipyridyl (dtbpy) (96.4 mg, 0.36 mmol) and [Ir(COD)OMe]$_2$ (119.1 mg, 0.18 mmol). The resulting mixture was stirred at 80° C. for 12 h under nitrogen atmosphere. Then it was concentrated. The residue was purified by silica gel column chromatography (0~10% EtOAc in PE) to afford 2,6-dimethoxy-4-(4,4,5,5-tetramethyl-1,3,2-dioxaborolan-2-yl)pyridine (640 mg, 33.6% yield) as a white solid. LC-MS: m/z 266.2 (M+H)+.

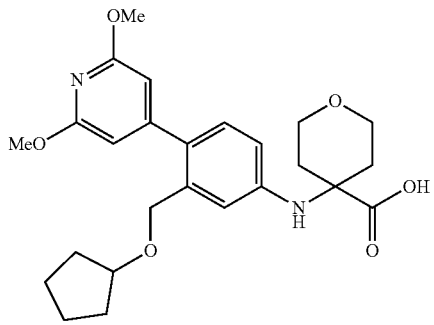 [SMILES: COc1cc(-c2ccc(NC3(C(=O)O)CCOCC3)cc2COC2CCCC2)cc(OC)n1]

4-((3-((cyclopentyloxy)methyl)-4-(2,6-dimethoxypyridin-4-yl)phenyl)amino) tetrahydro-2H-pyran-4-carboxylic acid (Compound 152) was synthesized according to the procedures described for the preparation of Example A3 (step B to D) by using cyclopentanol in step B, 4-aminotetrahydro-2H-pyran-4-carboxylic acid in step C and 2,6-dimethoxy-4-(4,4,5,5-tetramethyl-1,3,2-dioxaborolan-2-yl)pyridine in step D. LC-MS: m/z 457.1 (M+H)+. 1H NMR (400 MHz, DMSO-d6) δ 6.98 (d, J=8.4 Hz, 1H), 6.75 (d, J=2.5 Hz, 1H), 6.57-6.48 (m, 1H), 6.32 (s, 2H), 4.18 (s, 2H), 3.92-3.87 (m, 1H), 3.85 (s, 6H), 3.66-3.58 (m, 4H), 2.08-1.94 (m, 2H), 1.84 (d, J=13.4 Hz, 2H), 1.66-1.54 (m, 6H), 1.50-1.37 (m, 2H).

Example A24

4-((2-((cyclopentyloxy)methyl)-3'-ethoxy-2'-fluoro-[1,1'-biphenyl]-4-yl)amino)tetrahydro-2H-pyran-4-carboxylic acid (Compound 245)

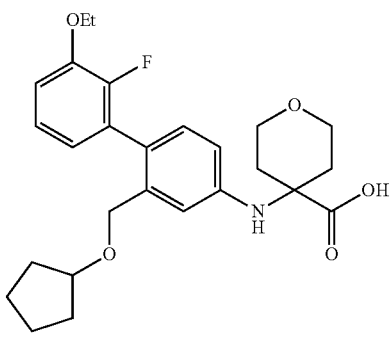

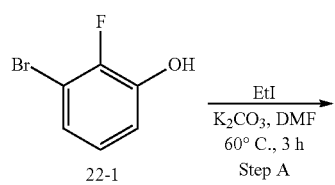

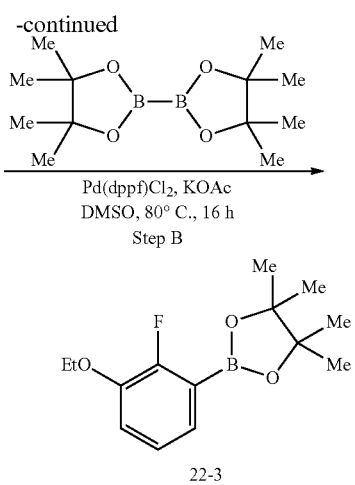

Step A 1-bromo-3-ethoxy-2-fluorobenzene

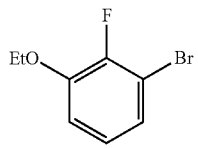

To a solution of 3-bromo-2-fluorophenol (5.0 g, 26.2 mmol) in DMF (50 mL) was added K2CO3 (9.05 g, 65.5 mmol) and iodoethane (3.14 mL, 39.3 mmol). The resulting mixture was stirred at 60° C. for 3 h. After cooling, the mixture was diluted with brine (100 mL), extracted with EtOAc (200 mL×2). The combined organic phase was dried over Na2SO4, filtered and concentrated. The residue was purified by flash silica gel chromatography (ISCO®; 40 g SepaFlash® Silica Flash Column, Eluent of 0~15% EtOAc/PE gradient @ 100 mL/min) to give 1-bromo-3-ethoxy-2-fluorobenzene (5.01 g, 87% yield).

Step B 2-(3-ethoxy-2-fluorophenyl)-4,4,5,5-tetramethyl-1,3,2-dioxaborolane

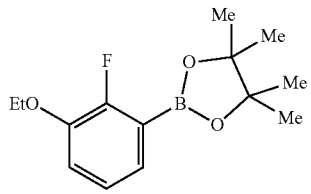 [SMILES: CCOc1cccc(B2OC(C)(C)C(C)(C)O2)c1F]

To a solution of 1-bromo-3-ethoxy-2-fluorobenzene (1.8 g, 8.22 mmol) and 4,4,5,5-tetramethyl-2-(4,4,5,5-tetramethyl-1,3,2-dioxaborolan-2-yl)-1,3,2-dioxaborolane (4.17 g, 16.4 mmol) in DMSO (15 mL) was added KOAc (2.42 g, 24.7 mmol) and Pd(dppf)Cl2 (601 mg, 822 mol). The reaction mixture was stirred at 100° C. for 2 h. After cooling, the mixture was diluted with brine (100 mL), extracted with EtOAc (100 mL×2). The combined organic phase was dried over Na2SO4, filtered and concentrated. The residue was purified by flash silica gel chromatography (Silica Flash Column, Eluent of 0~3% EtOAc/PE gradient) to give 2-(3-ethoxy-2-fluorophenyl)-4,4,5,5-tetramethyl-1,3,2-dioxaborolane (1.05 g, 48% yield). ¹H NMR (CDCl₃, 400 MHz) δ 7.19 (s, 1H), 7.03-6.92 (m, 2H), 4.05-4.00 (m, 2H), 1.34 (t, J=7.0 Hz, 3H), 1.29 (s, 12H).

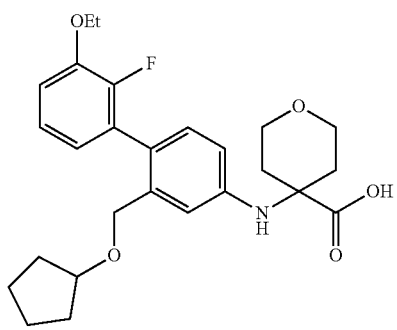 [SMILES: CCOc1cccc(-c2ccc(NC3(C(=O)O)CCOCC3)cc2COC2CCCC2)c1F]

4-((2-((cyclopentyloxy)methyl)-3'-ethoxy-2'-fluoro-[1,1'-biphenyl]-4-yl)amino)tetrahydro-2H-pyran-4-carboxylic acid (Compound 245) was synthesized according to the procedures described for the preparation of Example A3 (step B and D) by using cyclopentanol in step B, 4-aminotetrahydro-2H-pyran-4-carboxylic acid in step C and 2-(3-ethoxy-2-fluorophenyl)-4,4,5,5-tetramethyl-1,3,2-dioxaborolane in step D. LC-MS: m/z 458.5 (M+H)⁺. ¹H NMR (400 MHz, CDCl₃) δ 7.08-7.00 (m, 2H), 6.98-6.91 (m, 1H), 6.83 (s, 1H), 6.78 (t, J=7.0 Hz, 1H), 6.61 (d, J=8.2 Hz, 1H), 4.23 (s, 2H), 4.15 (q, J=7.0 Hz, 2H), 3.93-3.73 (m, 5H), 2.42-2.23 (m, 2H), 2.01-1.82 (m, 2H), 1.64-1.40 (m, 11H).

Example A25

4-((3-((cyclopentyloxy)methyl)-4-(4,6-dimethoxy-5-methylpyridin-2-yl)-5-methylphenyl)amino)tetrahydro-2H-pyran-4-carboxylic acid (Compound 253)

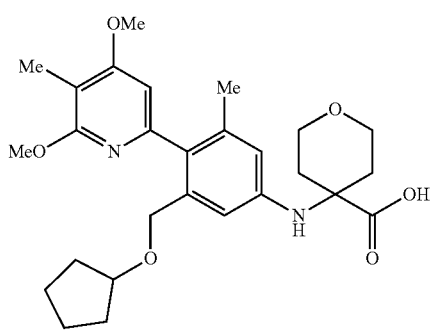 [SMILES: COc1cc(-c2c(C)cc(NC3(C(=O)O)CCOCC3)cc2COC2CCCC2)nc(OC)c1C]

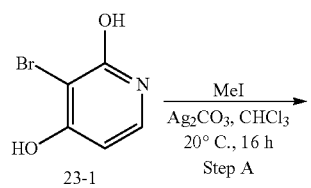

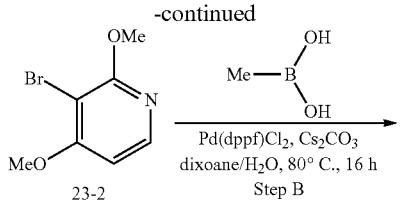

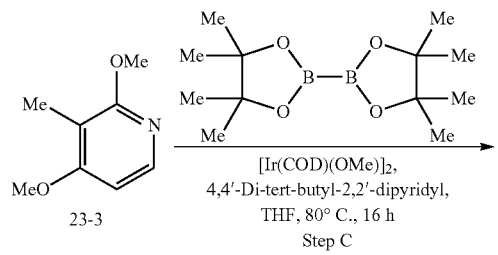

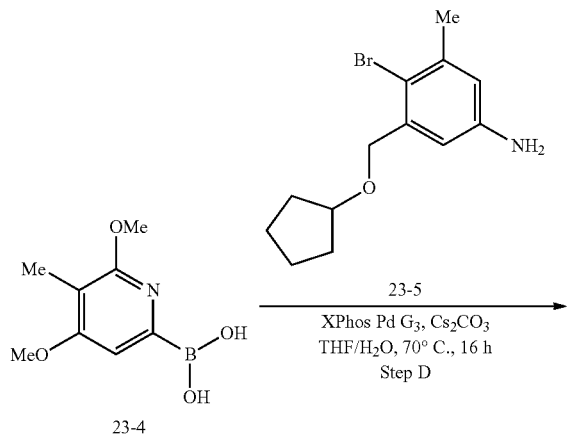

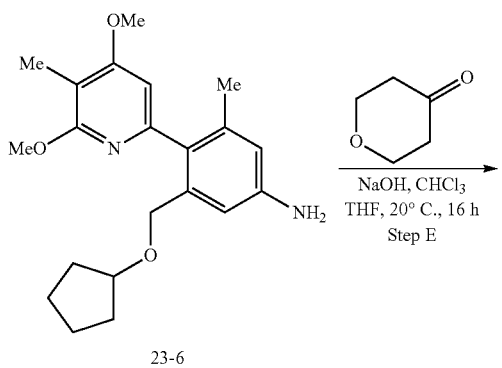

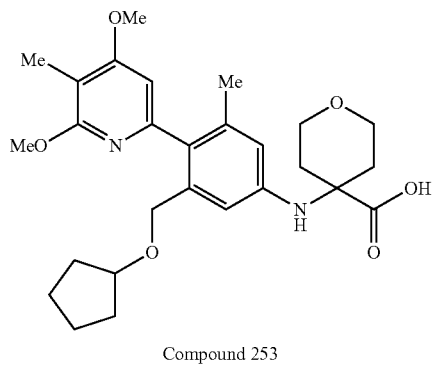

Compound 253

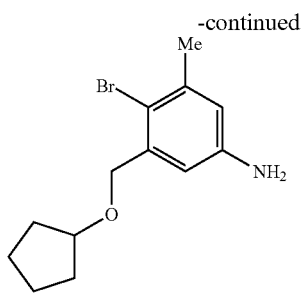

4-bromo-3-((cyclopentyloxy)methyl)-5-methylaniline (23-5) was synthesized according to the procedures described for the preparation of intermediate 21-2. LC-MS: m/z 284.1 (M+H)⁺.

Step A 3-bromo-2,4-dimethoxypyridine

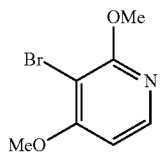

To a solution of 3-bromopyridine-2,4-diol (9.0 g, 47.4 mmol) in CHCl₃ (100 mL) was added iodomethane (14.7 mL, 237 mmol) and Ag₂CO₃ (52.3 g, 189 mmol). The mixture was stirred at 20° C. for 16 h. After filtration, the filtrate was concentrated. The residue was purified by flash silica gel chromatography (ISCO®; 80 g SepaFlash® Silica Flash Column, Eluent of 0~20% EtOAc/PE gradient @100 mL/min) to afford 3-bromo-2,4-dimethoxy-pyridine (7.2 g, 69.7% yield). LC-MS: m/z 219.9 (M+H)⁺.

Step B 2,4-dimethoxy-3-methylpyridine

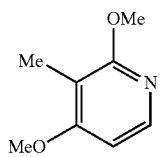

To a solution of 3-bromo-2,4-dimethoxy-pyridine (8.0 g, 36.7 mmol) and methylboronic acid (6.59 g, 110 mmol) in dioxane (100 mL) and H₂O (10 mL) was added Pd(dppf)Cl₂ (2.68 g, 3.30 mmol) and Cs₂CO₃ (23.9 g, 73.4 mmol). The mixture was stirred at 80° C. for 12 h under nitrogen. After cooling, the reaction was diluted with H₂O (200 mL) and extracted with EtOAc (200 mL×3). The combined organic layers were washed with brine (200 mL), dried over Na₂SO₄, filtered and concentrated. The residue was purified by silica gel column chromatography (10/1 to 3/1 EtOAc/PE) to afford 2,4-dimethoxy-3-methyl-pyridine (3.6 g, 64.1% yield). LC-MS: m/z 155.1 (M+H)⁺.

Step C
(4,6-dimethoxy-5-methylpyridin-2-yl)boronic acid

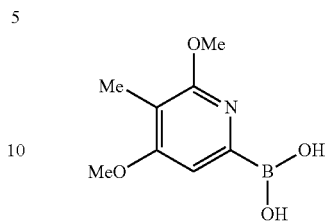

To a solution of 2,4-dimethoxy-3-methyl-pyridine (100 mg, 653 mol) and 4,4,4',4',5,5,5',5'-octamethyl-2,2'-bi(1,3,2-dioxaborolane) (166 mg, 653 μmol) in THF (1 mL) was added [Ir(COD)OMe]₂ (4.33 mg, 6.53 μmol) and 4-tert-butyl-2-(4-tert-butyl-2-pyridyl)pyridine (dtbpy) (3.50 mg, 13.1 μmol). The mixture was stirred at 80° C. for 16 h. The reaction mixture was diluted with H₂O (10 mL) and extracted with EtOAc (10 mL×3). The combined organic layers were washed with brine (10 mL), dried over Na₂SO₄, filtered and concentrated to afford (4,6-dimethoxy-5-methyl-2-pyridyl)boronic acid (120 mg, crude), which was used in the next step without further purification. LC-MS: m/z 198.7 (M+H)⁺.

Step D
(4,6-dimethoxy-5-methylpyridin-2-yl)boronic acid

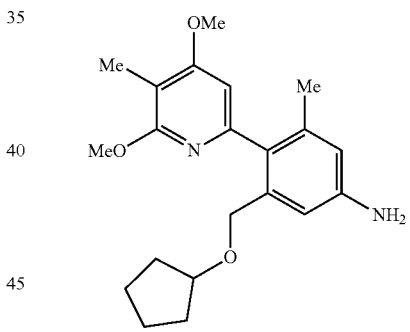

To a solution of (4,6-dimethoxy-5-methyl-2-pyridyl)boronic acid (120 mg, 609 μmol) and 4-bromo-3-((cyclopentyloxy)methyl)-5-methylaniline (86.6 mg, 305 μmol) in THF (1 mL) and H₂O (1 mL) was added XPhos Pd G3 (25.8 mg, 30.5 mol) and Cs₂CO₃ (198 mg, 609 μmol). The mixture was stirred at 70° C. for 16 h under nitrogen. After cooling, the reaction mixture was diluted with H₂O (10 mL) and extracted with EtOAc (10 mL×3). The combined organic layers were washed with brine (10 mL), dried over Na₂SO₄, filtered and concentrated. The residue was purified by flash silica gel chromatography (ISCO®; 4 g SepaFlash® Silica Flash Column, Eluent of 0~30% EtOAc/PE gradient @ 18 mL/min) to afford 3-((cyclopentyloxy)methyl)-4-(4,6-dimethoxy-5-methylpyridin-2-yl)-5-methylaniline (50 mg, 46.1% yield). LC-MS: m/z 379.0 (M+Na)+. ¹H NMR (400 MHz, CDCl₃) δ 6.71 (s, 1H), 6.51 (s, 1H), 6.47 (s, 1H), 4.18 (s, 2H), 3.90 (s, 3H), 3.89-3.81 (m, 4H), 3.66 (s, 2H), 2.06 (s, 3H), 1.91 (s, 3H), 1.63-1.45 (m, 8H).

Step E 4-((3-((cyclopentyloxy)methyl)-4-(4,6-dimethoxy-5-methylpyridin-2-yl)-5-methylphenyl)amino)tetrahydro-2H-pyran-4-carboxylic acid (Compound 253)

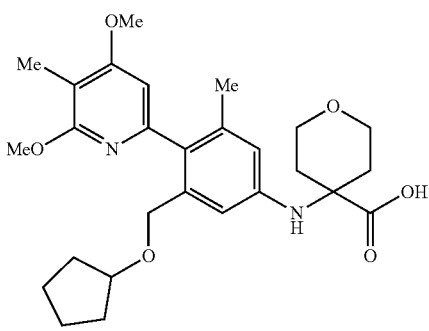 [SMILES: COc1cc(-c2c(C)cc(NC3(C(=O)O)CCOCC3)cc2COC2CCCC2)nc(OC)c1C]

To a solution of 3-(cyclopentoxymethyl)-4-(4,6-dimethoxy-5-methyl-2-pyridyl)-5-methyl-aniline (50 mg, 140 mol) and tetrahydropyran-4-one (21.1 mg, 210 μmol) in THF (1 mL) was added NaOH (28.1 mg, 701 mol) and chloroform (83.7 mg, 701 μmol). The mixture was stirred at 20° C. for 16 h. The reaction mixture was quenched by addition 1 N HCl to pH=7, extracted with EtOAc (10 mL×3). The combined organic layers were washed with brine (10 mL), dried over Na$_2$SO$_4$, filtered and concentrated. The residue was purified by prep. HPLC (Column: Welch Xtimate C18; Mobile Phase A: water (0.1% NH$_3$H$_2$O+NH$_4$HCO$_3$), Mobile Phase B: CH$_3$CN; Flow rate: 25 mL/min; Gradient: 25% B 5 min 25% B to 55% B in 20 min) to afford 4-((3-((cyclopentyloxy)methyl)-4-(4,6-dimethoxy-5-methylpyridin-2-yl)-5-methylphenyl)amino)tetrahydro-2H-pyran-4-carboxylic acid (8.44 mg, 12.0% yield). LC-MS: m/z 485.3 (M+H)$^+$. $^1$H NMR (400 MHz, CD$_3$OD) δ 6.65 (s, 1H), 6.56 (s, 1H), 6.54 (s, 1H), 4.15 (s, 2H), 3.86 (s, 3H), 3.84 (s, 3H), 3.82-3.73 (m, 5H), 2.25-2.17 (m, 2H), 2.05 (s, 3H), 2.03-1.99 (m, 5H), 1.60-1.45 (m, 8H).

Example A26

4-((2-(cyclopropoxymethyl)-2'-fluoro-3',5'-dimethoxy-4'-methyl-[1,1'-biphenyl]-4-yl)amino)tetrahydro-2H-pyran-4-carboxylic acid (Compound 256)

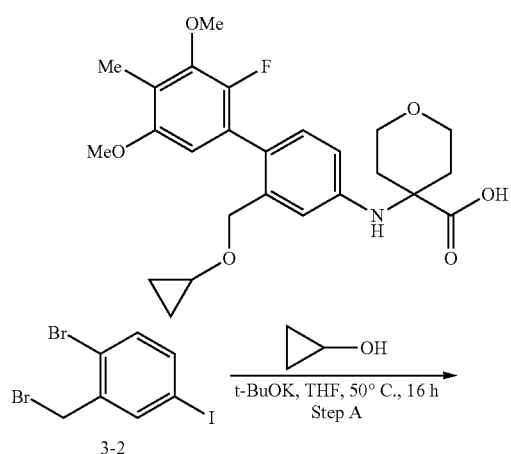

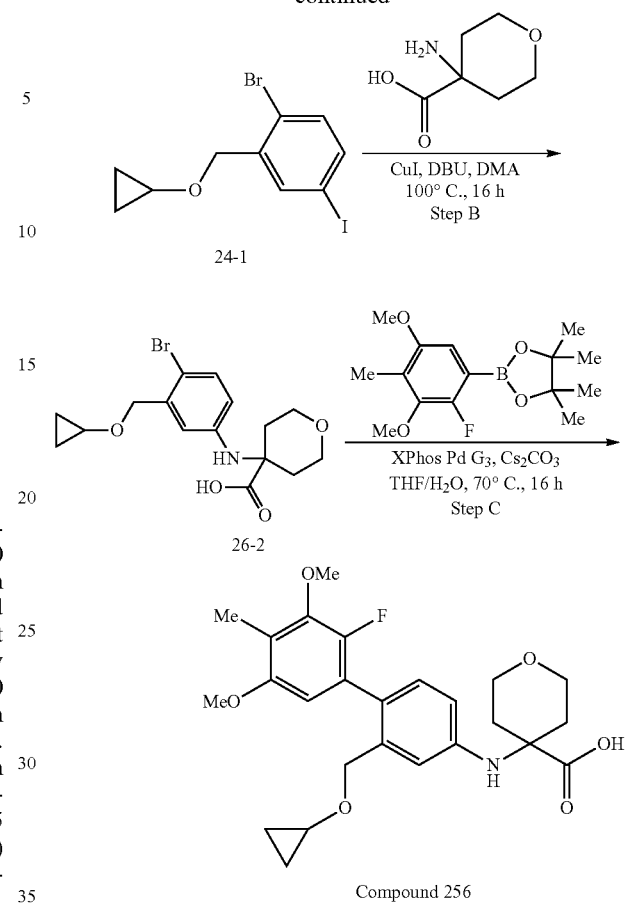

Compound 256

Step A
1-bromo-2-(cyclopropoxymethyl)-4-iodobenzene

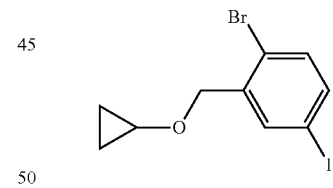

To a solution of 1-bromo-2-(bromomethyl)-4-iodobenzene (2.0 g, 5.32 mmol) in THF (20 mL) was added t-BuOK (717 mg, 6.38 mmol) and cyclopropanol (580 uL, 6.38 mmol). The reaction mixture was stirred at 50° C. for 16 h. after cooling, the reaction mixture was diluted with H$_2$O (50 mL) and extracted with EtOAc (50 mL×3). The combined organic layers were washed with brine (50 mL), dried over Na$_2$SO$_4$, filtered and concentrated. The residue was purified by flash silica gel chromatography (ISCO®; 40 g SepaFlash® Silica Flash Column, Eluent of 0~5% EtOAc/PE gradient @ 100 mL/min) to afford 1-bromo-2-(cyclopropoxymethyl)-4-iodo-benzene (1.4 g, 74.6% yield). $^1$H NMR (400 MHz, CDCl$_3$) δ 7.80 (d, J=1.2 Hz, 1H), 7.48 (dd, J=8.4, 0.6 Hz, 1H), 7.27 (d, J=8.4 Hz, 1H), 4.58 (s, 2H), 3.48-3.43 (m, 1H), 0.74-0.70 (m, 2H), 0.59-0.56 (m, 2H).

Step B 4-((4-bromo-3-(cyclopropoxymethyl)phenyl)amino)tetrahydro-2H-pyran-4-carboxylic acid

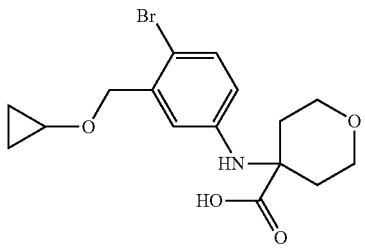 [SMILES: O=C(O)C1(Nc2ccc(Br)c(COC3CC3)c2)CCOCC1]

To a solution of 1-bromo-2-(cyclopropoxymethyl)-4-iodo-benzene (700 mg, 1.98 mmol) and 4-aminotetrahydro-2H-pyran-4-carboxylic acid (432 mg, 2.97 mmol) in DMA (15 mL) was added CuI (75.5 mg, 397 µmol) and DBU (604 mg, 3.97 mmol). The mixture was stirred at 100° C. for 16 h. The reaction mixture was diluted with $H_2O$ (50 mL) and extracted with EtOAc (50 mL×3). The combined organic layers were washed with brine (50 mL×3), dried over $Na_2SO_4$, filtered and concentrated. The residue was purified by flash silica gel chromatography (ISCO®; 20 g SepaFlash® Silica Flash Column, Eluent of 0~6% MeOH/DCM gradient @ 80 mL/min) to afford 4-((4-bromo-3-(cyclopropoxymethyl)phenyl)amino)tetrahydro-2H-carboxylic acid (330 mg, 45.0% yield). LC-MS: m/z 370.2 $(M+H)^+$. $^1H$ NMR (400 MHz, $CD_3OD$) δ 7.22 (d, J=8.8 Hz, 1H), 6.78 (d, J=3.0 Hz, 1H), 6.48 (dd, J=8.8, 3.0 Hz, 1H), 4.50 (s, 2H), 3.81-3.70 (m, 4H), 3.43-3.41 (m, 1H), 2.22-2.15 (m, 2H), 2.15-1.95 (m, 2H), 0.64-0.60 (m, 2H), 0.53-0.49 (m, 2H).

Step C 4-((2-(cyclopropoxymethyl)-2'-fluoro-3',5'-dimethoxy-4'-methyl-[1,1'-biphenyl]-4-yl)amino)tetrahydro-2H-pyran-4-carboxylic acid (Compound 256)

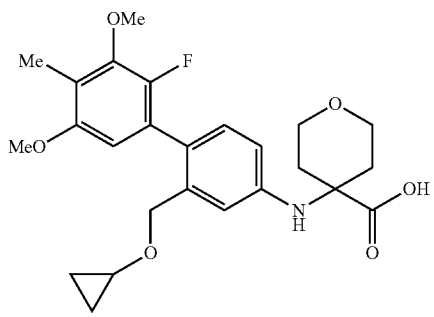 [SMILES: COc1cc(-c2ccc(NC3(C(=O)O)CCOCC3)cc2COC2CC2)c(F)c(OC)c1C]

To a solution of 4-[4-bromo-3-(cyclopropoxymethyl)anilino]tetrahydropyran-4-carboxylic acid (150 mg, 405 µmol) and 2-(2-fluoro-3,5-dimethoxy-4-methylphenyl)-4,4,5,5-tetramethyl-1,3,2-dioxaborolane (180 mg, 608 µmol) in THF (2 mL) and $H_2O$ (2 mL) was added XPhos Pd G3 (34.3 mg, 40.5 µmol) and $Cs_2CO_3$ (264 mg, 810 µmol). The mixture was stirred at 70° C. for 16 h under nitrogen. The reaction mixture was diluted with $H_2O$ (10 mL) and extracted with EtOAc (10 mL×3). The combined organic layers were washed with brine (10 mL×3), dried over $Na_2SO_4$, filtered and concentrated. The residue was purified by prep. HPLC (Column: Welch Xtimate C18; Mobile Phase A: water (0.1% $NH_3H_2O+NH_4HCO_3$), Mobile Phase B: CAN; Flow rate: 25 mL/min; Gradient: 35% B 5 min 35% B to 65% B in 20 min) to afford 4-((2-(cyclopropoxymethyl)-2'-fluoro-3',5'-dimethoxy-4'-methyl-[1,1'-biphenyl]-4-yl)amino)tetrahydro-2H-pyran-4-carboxylic acid (81.59 mg, 43.4% yield). Alternatively, $Pd(dppf)Cl_2$ and and $Na_2CO_3$ can be used in place of XPhos Pd G3 and $Cs_2CO_3$. LC-MS: m/z 460.3 $(M+H)^+$. $^1H$ NMR (400 MHz, $CD_3OD$) δ 6.96 (d, J=8.4 Hz, 1H), 6.82 (d, J=2.4 Hz, 1H), 6.66 (dd, J=8.4, 2.4 Hz, 1H), 6.48 (d, J=5.6 Hz, 1H), 4.30 (s, 2H), 3.84 (s, 3H), 3.82-3.73 (m, 7H), 3.31-3.23 (m, 1H), 2.26-2.22 (m, 2H), 2.20 (s, 3H), 2.14-1.97 (m, 2H), 0.37-0.36 (m, 4H).

Example A27

4-((2-((cyclopentyloxy)methyl)-3'-cyclopropoxy-2'-fluoro-[1,1'-biphenyl]-4-yl)amino)tetrahydro-2H-pyran-4-carboxylic acid (Compound 265)

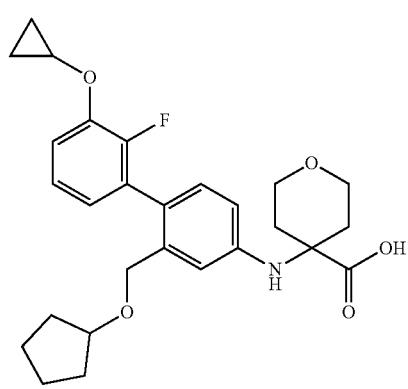 [SMILES: O=C(O)C1(Nc2ccc(-c3cccc(OC4CC4)c3F)c(COC3CCCC3)c2)CCOCC1]

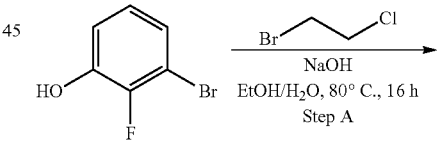

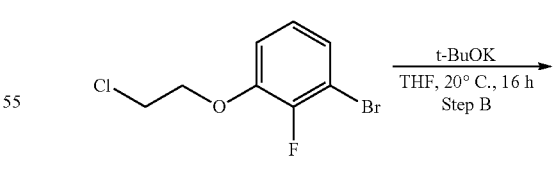

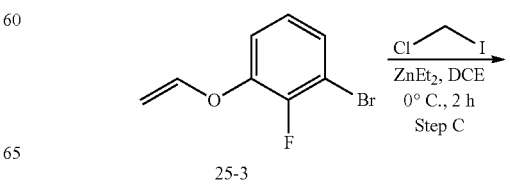

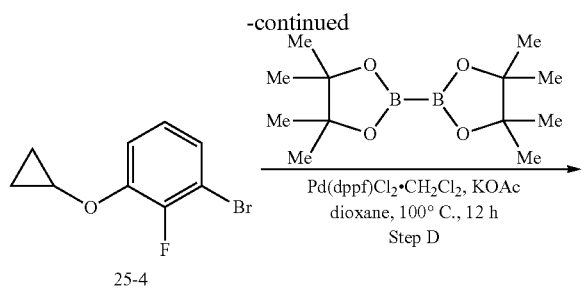

Step A 1-bromo-3-(2-chloroethoxy)-2-fluorobenzene

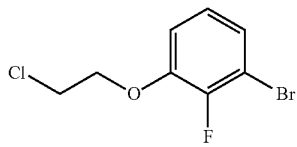 [SMILES: Fc1c(Br)cccc1OCCCl]

To a solution of 3-bromo-2-fluoro-phenol (5.0 g, 26.2 mmol) in EtOH (50 mL) was added NaOH (1.05 g, 26.2 mmol) in H$_2$O (10 mL). After being stirred for 0.5 h, to the mixture was added 1-bromo-2-chloro-ethane (4.34 mL, 52.4 mmol). The resulting reaction mixture was stirred at 80° C. for 16 h. After cooling, the reaction mixture was diluted with water (50 mL), extracted with ethyl acetate (50 mL×3). The combined organic layers were washed with brine (20 mL), dried over anhydrous Na$_2$SO$_4$, filtered, and concentrated. The residue was purified by flash silica gel chromatography (ISCO®; 120 g SepaFlash® Silica Flash Column, Eluent of 0-10% EtOAc/PE gradient @ 100 mL/min) to give 1-bromo-3-(2-chloroethoxy)-2-fluorobenzene (4.6 g, 69.3% yield). $^1$H NMR (400 MHz, CDCl$_3$) δ 7.17-7.05 (m, 1H), 6.89-6.87 (m, 2H), 4.23 (d, J=5.2 Hz, 2H), 3.76 (d, J=5.2 Hz, 2H).

Step B 1-bromo-2-fluoro-3-(vinyloxy)benzene

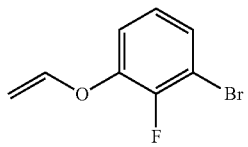

To a solution of 1-bromo-3-(2-chloroethoxy)-2-fluorobenzene (4.6 g, 18.2 mmol) in THF (40 mL) was added t-BuOK (4.07 g, 36.3 mmol). The mixture was stirred at 20° C. for 16 h. The reaction mixture was quenched by water (50 mL), extracted with ethyl acetate (50 mL×3). The combined organic layers were dried over Na$_2$SO$_4$, filtered and concentrated to give a residue. The residue was purified by flash silica gel chromatography (ISCO®; 80 g SepaFlash® Silica Flash Column, Eluent of 0-5% EtOAc/PE gradient @100 mL/min) to give 1-bromo-2-fluoro-3-vinyloxy-benzene (2.8 g, 71.1% yield). $^1$H NMR (400 MHz, CDCl$_3$) δ 7.21-7.19 (m, 1H), 6.96-6.90 (m, 2H), 6.54 (dd, J=14.0, 6.4 Hz, 1H), 4.68 (dd, J=13.6, 2.4 Hz, 1H), 4.43 (dd, J=6.4, 2.4 Hz, 1H).

Step C 1-bromo-3-cyclopropoxy-2-fluorobenzene

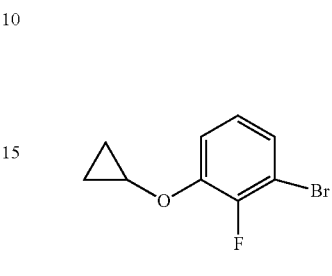

To a solution of 1-bromo-2-fluoro-3-vinyloxy-benzene (1.0 g, 4.61 mmol) and chloroiodomethane (1.34 mL, 18.4 mmol) in DCE (15 mL) was added 2 M ZnEt$_2$ (5.76 mL, 11.52 mmol). The reaction mixture was stirred at 0° C. for 2 h. Then it was quenched with sat. aq. NH$_4$Cl (10 mL), extracted with DCM (15 mL×3). The combined organic layers were washed with brine (50 mL), dried over anhydrous Na$_2$SO$_4$, filtered and concentrated. The residue was purified by flash silica gel chromatography (ISCO®; 12 g SepaFlash® Silica Flash Column, Eluent of 0-2% EtOAc/PE gradient @40 mL/min) to give 1-bromo-3-(cyclopropoxy)-2-fluoro-benzene (0.9 g, 84.5% yield). $^1$H NMR (400 MHz, CDCl$_3$) δ 7.18-7.13 (m, 1H), 7.08-7.03 (m, 1H), 6.92-6.85 (m, 1H), 3.78-3.72 (m, 1H), 0.80-0.72 (m, 4H)

Step D 2-(3-cyclopropoxy-2-fluorophenyl)-4,4,5,5-tetramethyl-1,3,2-dioxaborolane

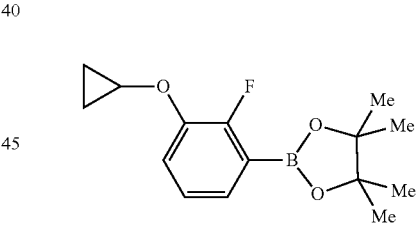

To a solution of 1-bromo-3-(cyclopropoxy)-2-fluoro-benzene (0.9 g, 3.90 mmol) and 4,4,5,5-tetramethyl-2-(4,4,5,5-tetramethyl-1,3,2-dioxaborolan-2-yl)-1,3,2-dioxaborolane (1.98 g, 7.79 mmol) in dioxane (20 mL) was added Pd(dppf)Cl$_2$·CH$_2$Cl$_2$ (318 mg, 390 μmol) and KOAc (1.15 g, 11.7 mmol). The mixture was stirred at 100° C. for 12 h. After cooling, the reaction mixture was quenched by water (20 mL), extracted with ethyl acetate (20 mL×3). The combined organic layers were dried over Na$_2$SO$_4$, filtered and concentrated. The residue was purified by flash silica gel chromatography (ISCO®; 20 g SepaFlash® Silica Flash Column, Eluent of 0~3% EtOAc/PE gradient @ 80 mL/min) to give 2-(3-cyclopropoxy-2-fluorophenyl)-4,4,5,5-tetramethyl-1,3,2-dioxaborolane (0.6 g, 55.4% yield). $^1$H NMR (400 MHz, CDCl$_3$) δ 7.30-7.26 (m, 1H), 7.20 (s, 1H), 6.99 (t, J=7.6 Hz, 1H), 3.78-3.73 (m, 1H), 1.29 (s, 12H), 0.75-0.68 (m, 4H).

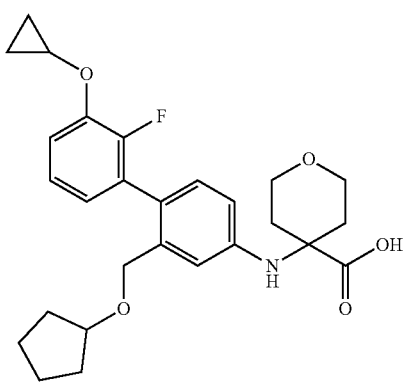 [SMILES: O=C(O)C1(Nc2ccc(-c3cccc(OC4CC4)c3F)c(COC3CCCC3)c2)CCOCC1]

4-((2-((cyclopentyloxy)methyl)-3'-cyclopropoxy-2'-fluoro-[1,1'-biphenyl]-4-yl)amino)tetrahydro-2H-pyran-4-carboxylic acid (Compound 265) was synthesized according to the procedures described for the preparation of Example A3 (step A and D) by using cyclopentanol in step B and 2-(3-cyclopropoxy-2-fluorophenyl)-4,4,5,5-tetramethyl-1,3,2-dioxaborolane in step D. LC-MS: m/z 470.3 (M+H)⁺. ¹H NMR (400 MHz, CD₃OD) δ 7.34 (s, 1H), 7.11 (s, 1H), 7.00-6.91 (m, 1H), 6.87-6.77 (m, 2H), 6.65 (s, 1H), 4.21 (s, 2H), 3.94-3.74 (m, 6H), 2.33-2.15 (m, 2H), 2.12-1.96 (m, 2H), 1.64-1.43 (m, 8H), 0.90-0.72 (m, 4H).

Example A28

4-((2-((cyclopentyloxy)methyl)-3'-(ethylamino)-2'-fluoro-[1,1'-biphenyl]-4-yl)amino)tetrahydro-2H-pyran-4-carboxylic acid (Compound 278)

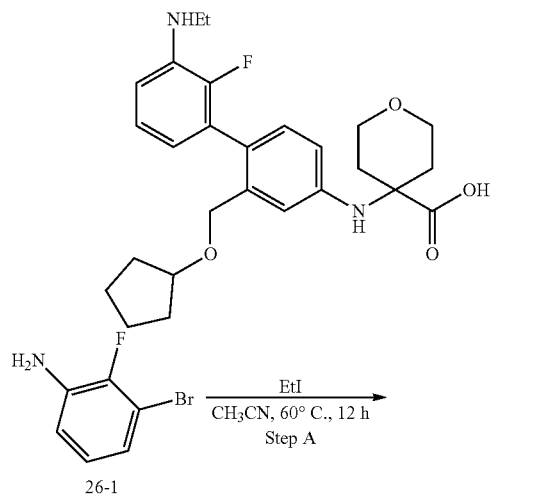

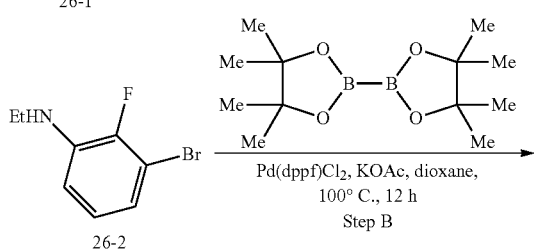

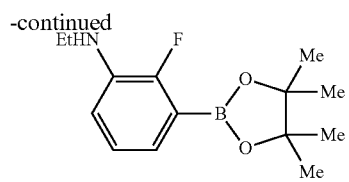

Step A 3-bromo-N-ethyl-2-fluoroaniline

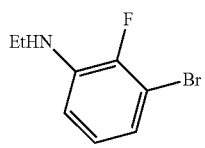

To a solution of 3-bromo-2-fluoroaniline (1.0 g, 5.26 mmol) in DMF (5 mL) was added iodoethane (337 uL, 4.21 mmol). The mixture was stirred at 60° C. for 12 h. The reaction mixture was quenched by water (20 mL), extracted with ethyl acetate (20 mL×3). The combined organic layers were washed with brine (10 mL×3), dried over Na₂SO₄, filtered and concentrated to give a residue. The residue was purified by flash silica gel chromatography (ISCO®; 20 g SepaFlash® Silica Flash Column, Eluent of 0-10% EtOAc/PE gradient @ 40 mL/min) to give 3-bromo-N-ethyl-2-fluoro-aniline (0.5 g, 43.6% yield). H NMR (400 MHz, CDCl₃) δ 6.89-6.83 (m, 1H), 6.81-6.78 (m, 1H), 6.63-6.59 (m, 1H), 3.89 (s, 1H), 3.25-3.16 (m, 2H), 1.29 (t, J=7.2 Hz, 3H).

Step B N-ethyl-2-fluoro-3-(4,4,5,5-tetramethyl-1,3,2-dioxaborolan-2-yl)aniline

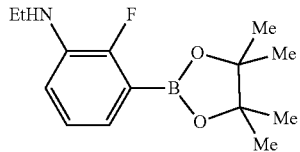

To a solution of 3-bromo-N-ethyl-2-fluoro-aniline (0.5 g, 2.29 mmol) and 4,4,5,5-tetramethyl-2-(4,4,5,5-tetramethyl-1,3,2-dioxaborolan-2-yl)-1,3,2-dioxaborolane (1.05 g, 4.13 mmol) in dioxane (10 mL) was added Pd(dppf)Cl₂ (168 mg, 229 mol) and KOAc (675 mg, 6.88 mmol). The mixture was stirred at 100° C. for 12 h. The reaction mixture was quenched by water (20 mL), extracted with ethyl acetate (20 mL×3). The combined organic layers were dried over Na₂SO₄, filtered and concentrated under reduced pressure to give a residue. The residue was purified by flash silica gel chromatography (ISCO®; 12 g SepaFlash® Silica Flash Column, Eluent of 0~5% EtOAc/PE gradient @ 40 mL/min) to give N-ethyl-2-fluoro-3-(4,4,5,5-tetramethyl-1,3,2-dioxaborolan-2-yl)aniline (0.52 g, 85.5% yield). ¹H NMR (400 MHz, CDCl₃) δ 7.04-6.96 (m, 2H), 6.83-6.76 (m, 1H), 3.82 (brs, 1H), 3.23-3.14 (m, 2H), 1.36 (s, 12H), 1.30 (t, J=7.2 Hz, 3H).

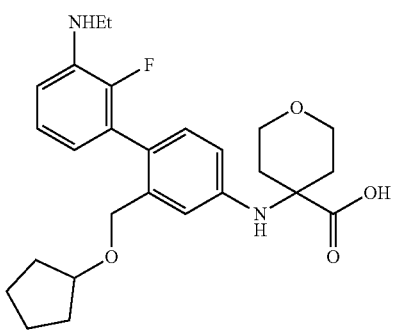

4-((2-((cyclopentyloxy)methyl)-3'-(ethylamino)-2'-fluoro-[1,1'-biphenyl]-4-yl)amino)tetrahydro-2H-pyran-4-carboxylic acid (Compound 278) was synthesized according to the procedures described for the preparation of Example A3 (step A and D) by using cyclopentanol in step B and N-ethyl-2-fluoro-3-(4,4,5,5-tetramethyl-1,3,2-dioxaborolan-2-yl)aniline in step D. LC-MS: m/z 457.3 (M+H)$^+$. $^1$H NMR (400 MHz, CD$_3$OD) δ 7.00-6.92 (m, 2H), 6.86 (d, J=2.4 Hz, 1H), 6.76-6.65 (m, 2H), 6.48 (t, J=6.4 Hz, 1H), 4.24 (s, 2H), 3.88-3.74 (m, 5H), 3.18-3.26 (q, J=7.2 Hz, 1H), 2.30-2.20 (m, 2H), 2.06-1.96 (m, 2H), 1.64-1.43 (m, 8H), 1.28 (t, J=7.2 Hz, 3H).

Example A29

4-((2-(cyclopropoxymethyl)-2'-(difluoromethyl)-3'-ethoxy-[1,1'-biphenyl]-4-yl)amino)tetrahydro-2H-pyran-4-carboxylic acid (Compound 279)

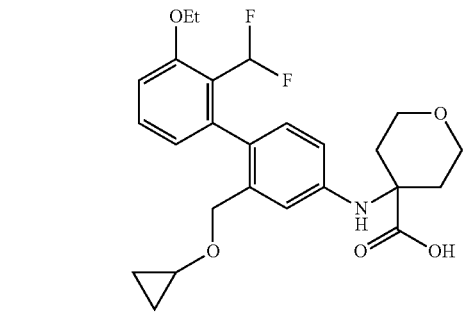

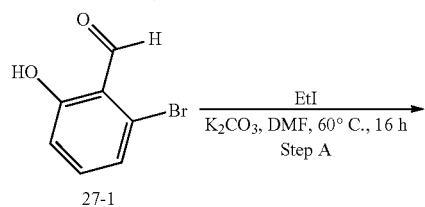

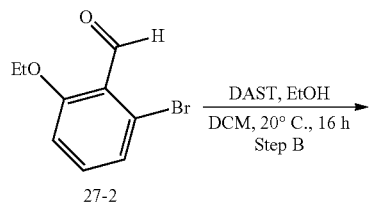

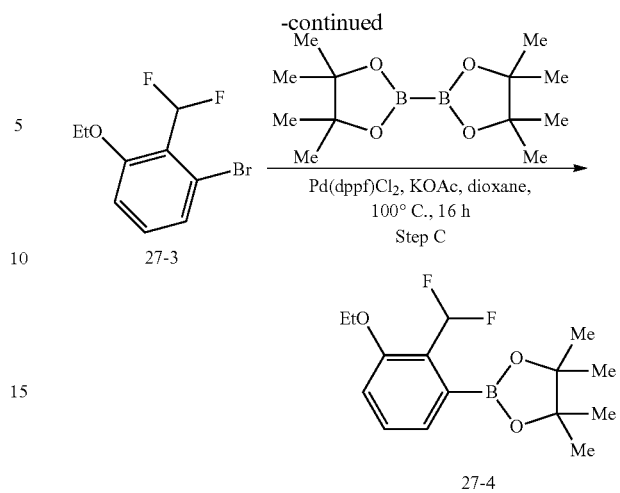

Step A 2-bromo-6-ethoxybenzaldehyde

To a solution of 2-bromo-6-hydroxybenzaldehyde (5.0 g, 24.9 mmol) in DMF (50 mL) was added iodoethane (2.98 mL, 37.3 mmol) and K$_2$CO$_3$ (6.88 g, 49.8 mmol). The reaction mixture was stirred at 60° C. for 16 h. After cooling, the mixture was diluted with H$_2$O (100 mL), extracted with EtOAc (30 mL×3). The combined organic phases were washed with brine (50 mL×2), dried over anhydrous Na$_2$SO$_4$, filtered and concentrated. The residue was purified by flash silica gel chromatography (ISCO®; 80 g SepaFlash® Silica Flash Column, Eluent of 0~10% EtOAc/PE gradient @ 50 mL/min) to afford 2-bromo-6-ethoxybenzaldehyde (5.0 g, 87.8% yield). LC-MS: m/z 228.9 (M+H)$^+$.

Step B
1-bromo-2-(difluoromethyl)-3-ethoxybenzene

To a solution of 2-bromo-6-ethoxybenzaldehyde (2.0 g, 8.73 mmol) in DCM (20 mL) was added DAST (1.73 mL, 13.1 mmol) and EtOH (402 mg, 8.73 mmol) at 0° C. The reaction mixture was stirred at 20° C. for 16 h. The mixture was diluted with H$_2$O (20 mL), extracted with DCM (10 mL×2). The combined organic phases were washed with brine (20 mL×2), dried over anhydrous Na$_2$SO$_4$, filtered and concentrated. The residue was purified by flash silica gel chromatography (ISCO®; 20 g SepaFlash® Silica Flash Column, Eluent of 0~7% EtOAc/PE gradient @ 50 mL/min) to give 1-bromo-2-(difluoromethyl)-3-ethoxybenzene (1.1 g, 4.38 mmol, 50.2% yield). $^1$H NMR (400 MHz, CDCl$_3$) δ 7.33-7.05 (m, 3H), 6.88 (d, J=7.2 Hz, 1H), 4.10 (q, J=6.8 Hz, 2H), 1.44 (t, J=7.0 Hz, 3H).

Step C 2-(2-(difluoromethyl)-3-ethoxyphenyl)-4,4,5,5-tetramethyl-1,3,2-dioxaborolane

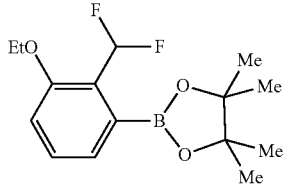 [SMILES: CCOc1cccc(B2OC(C)(C)C(C)(C)O2)c1C(F)F]

To a solution of 1-bromo-2-(difluoromethyl)-3-ethoxybenzene (1.0 g, 3.98 mmol) in DMSO (10 mL) was added 4,4,5,5-tetramethyl-2-(4,4,5,5-tetramethyl-1,3,2-dioxaborolan-2-yl)-1,3,2-dioxaborolane (1.52 g, 5.97 mmol), Pd(dppf)Cl$_2$ (145.72 mg, 199 μmol) and KOAc (1.17 g, 12.0 mmol). The reaction mixture was stirred at 100° C. for 16 h under nitrogen. After cooling, the mixture was diluted with water (100 mL), extracted with EtOAc (10 mL×3). The combined organic layers were washed with brine (10 mL×3), dried over Na$_2$SO$_4$ and concentrated. The residue was purified by flash silica gel chromatography (ISCO®; 12 g SepaFlash® Silica Flash Column, Eluent of 0~7% EtOAc/PE gradient @30 mL/min) to give 2-(2-(difluoromethyl)-3-ethoxyphenyl)-4,4,5,5-tetramethyl-1,3,2-dioxaborolane (900 mg, 75.8% yield). LC-MS: m/z 299.2 (M+H)$^+$.

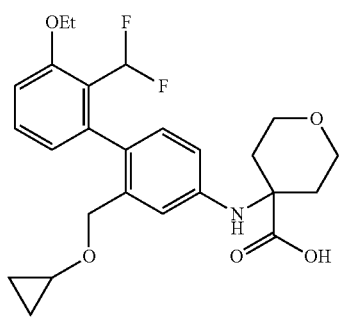 [SMILES: CCOc1cccc(-c2ccc(NC3(C(=O)O)CCOCC3)cc2COC2CC2)c1C(F)F]

4-((2-(cyclopropoxymethyl)-2'-(difluoromethyl)-3'-ethoxy-[1,1'-biphenyl]-4-yl)amino)tetrahydro-2H-pyran-4-carboxylic acid (Compound 279) was synthesized according to the procedures described for the preparation of Example A3 (step A and D) by using cyclopropanol in step B and 2-(2-(difluoromethyl)-3-ethoxyphenyl)-4,4,5,5-tetramethyl-1,3,2-dioxaborolane in step D. LC-MS: m/z 462.2 (M+H)$^+$. $^1$H NMR (400 MHz, CD$_3$OD) δ 7.37 (t, J=7.8 Hz, 1H), 7.06 (d, J=8.4 Hz, 1H), 6.84-6.79 (m, 2H), 6.76-6.61 (m, 2H), 6.41 (t, J=54.0 Hz, 1H), 4.22-4.11 (m, 4H), 3.85-3.74 (m, 4H), 3.24-3.04 (m, 1H), 2.28-2.17 (m, 2H), 2.01-1.92 (m, 2H), 1.43 (t, J=6.8 Hz, 3H), 0.31-0.21 (m, 4H).

Example A30

4-((2-((cyclopentyloxy)methyl)-3'-ethoxy-2'-methyl-[1,1'-biphenyl]-4-yl)amino)tetrahydro-2H-pyran-4-carboxylic acid (Compound 229)

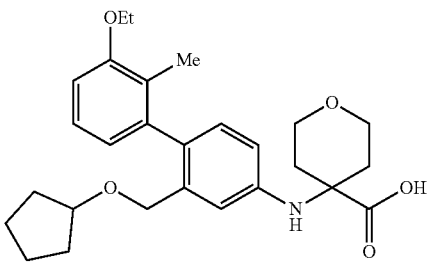

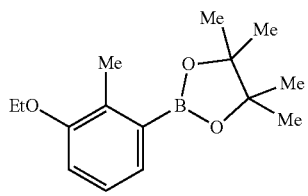

2-(3-ethoxy-2-methylphenyl)-4,4,5,5-tetramethyl-1,3,2-dioxaborolane was synthesized according to the procedures described for the preparation of 22-3 (step A and B in Example A24) by using 3-bromo-2-methylphenol in step A. LC-MS: m/z 263.2 (M+H)$^+$.

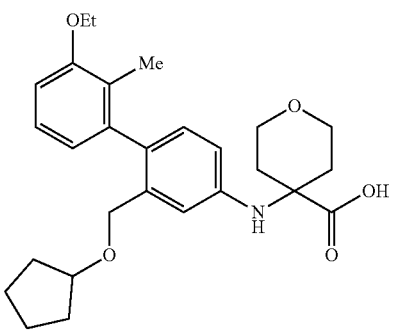 [SMILES: CCOc1cccc(-c2ccc(NC3(C(=O)O)CCOCC3)cc2COC2CCCC2)c1C]

4-((2-((cyclopentyloxy)methyl)-3'-ethoxy-2'-methyl-[1,1'-biphenyl]-4-yl)amino)tetrahydro-2H-pyran-4-carboxylic acid (Compound 229) was synthesized according to the procedures described for the preparation of Example A3 (step B and D) by using cyclopentanol in step B, 2-(3-ethoxy-2-methylphenyl)-4,4,5,5-tetramethyl-1,3,2-dioxaborolane in step D. LC-MS: m/z 454.1 (M+H)$^+$. $^1$H NMR (400 MHz, CD$_3$OD) δ 7.08 (t, J=7.6 Hz, 1H), 6.86-6.79 (m, 3H), 6.66-6.63 (m, 2H), 4.10-4.00 (m, 4H), 3.84-3.74 (m, 5H), 2.26-2.19 (m, 2H), 2.10-2.02 (m, 2H), 1.88 (s, 3H), 1.57-1.40 (m, 11H).

Example A31

4-((2-((cyclopentyloxy)methyl)-3'-cyclopropoxy-2'-fluoro-5'-methoxy-[1,1'-biphenyl]-4-yl)amino)tetrahydro-2H-pyran-4-carboxylic acid (Compound 249)

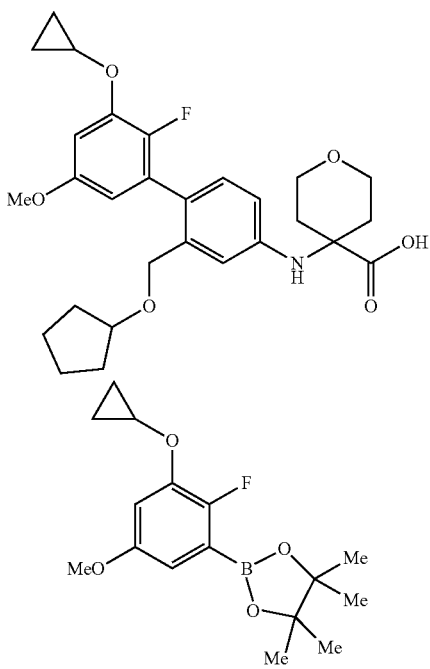

2-[3-(cyclopropyloxy)-2-fluoro-5-methoxyphenyl]-4,4,5,5-tetramethyl-1,3,2-dioxaborolane was synthesized according to the procedures described for the preparation of 25-5 (step A to D in Example A27) by using 2-fluoro-5-methoxyphenol in step A. LC-MS: m/z 309.2 (M+H)$^+$.

4-((2-((cyclopentyloxy)methyl)-3'-cyclopropoxy-2'-fluoro-5'-methoxy-[1,1'-biphenyl]-4-yl)amino)tetrahydro-2H-pyran-4-carboxylic acid (Compound 249) was synthesized according to the procedures described for the preparation of Example A3 (step A and D) by using cyclopentanol in step B and 2-[3-(cyclopropyloxy)-2-fluoro-5-methoxyphenyl]-4,4,5,5-tetramethyl-1,3,2-dioxaborolane in step D. LC-MS: m/z 500.1 (M+H)$^+$. $^1$H NMR (400 MHz, CD$_3$OD) δ 6.96 (d, J=8.8 Hz, 1H), 6.90 (dd, J=6.4, 2.8 Hz, 1H), 7.08 (d, J=2.4 Hz, 1H), 6.90 (dd, J=8.4, 2.4 Hz, 1H), 6.90 (dd, J=5.2, 3.6 Hz, 1H), 4.23 (s, 2H), 3.90-3.78 (m, 9H), 2.28-2.21 (m, 2H), 2.02-1.99 (m, 2H), 1.61-1.47 (m, 8H), 0.84-0.78 (m, 4H).

Example A32

4-((3'-cyclopropoxy-2-(cyclopropoxymethyl)-2'-methyl-[1,1'-biphenyl]-4-yl)amino)tetrahydro-2H-pyran-4-carboxylic acid (Compound 294)

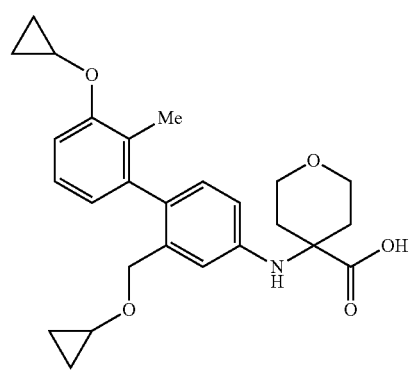 [SMILES: Cc1c(OC2CC2)cccc1-c1ccc(NC2(C(=O)O)CCOCC2)cc1COC1CC1]

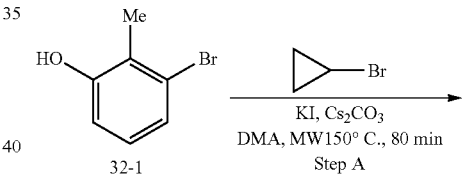

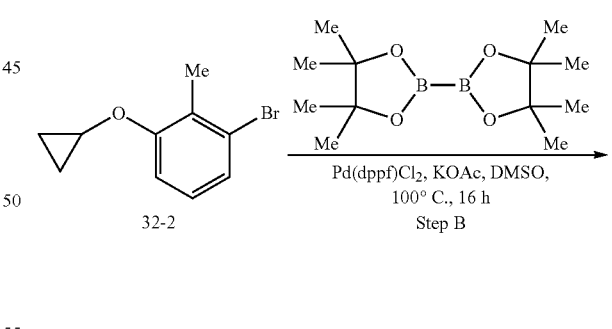

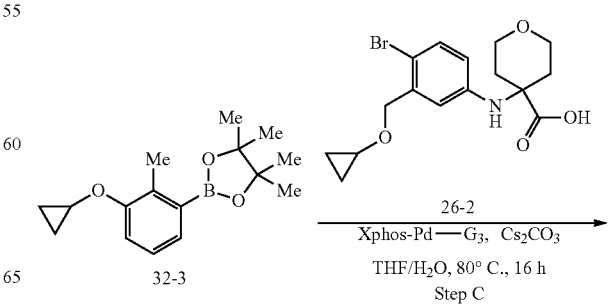

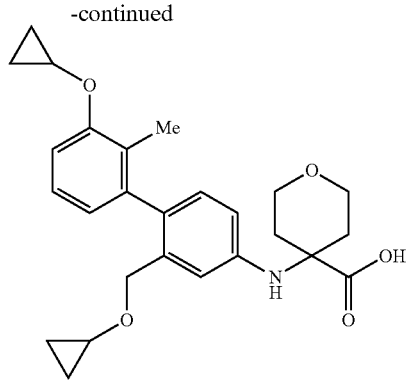

Compound 294

Step A 1-bromo-3-cyclopropoxy-2-methylbenzene

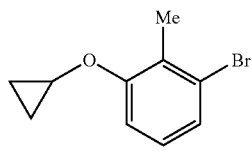 [SMILES: Cc1c(Br)cccc1OC1CC1]

The mixture of 3-bromo-2-methylphenol (2 g, 10.7 mmol), bromocyclopropane (5.17 g, 43 mmol), Cs$_2$CO$_3$ (6.97 g, 21.39 mmol) and KI (355 mg, 2.14 mmol) in DMA (20 mL) was heated at 150° C. for 80 min under Biotage microwave. After cooling, the mixture was diluted with brine (100 mL) and extracted with EtOAc (50 mL×2). The organic layers were washed with brine (20 mL×3), dried over anhydrous Na2SO4, filtered, and concentrated. The residue was purified by flash silica gel chromatography (ISCO®; 120 g SepaFlash® Silica Flash Column, Eluent of 100% PE gradient @ 100 mL/min) to give 1-bromo-3-cyclopropoxy-2-methylbenzene (1.5 g, 61.7% yield). $^1$H NMR (400 MHz, CDCl$_3$) δ 7.17-7.14 (m, 2H), 7.01 (t, J=8.0 Hz, 1H), 3.83-3.60 (m, 1H), 2.26 (s, 3H), 0.79-0.77 (m, 4H).

Step B 2-(3-cyclopropoxy-2-methylphenyl)-4,4,5,5-tetramethyl-1,3,2-dioxaborolane

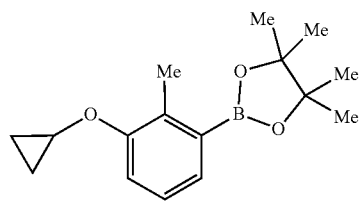 [SMILES: Cc1c(OC2CC2)cccc1B1OC(C)(C)C(C)(C)O1]

To a solution of 1-bromo-3-cyclopropoxy-2-methylbenzene (1.5 g, 6.61 mmol) and 4,4,5,5-tetramethyl-2-(4,4,5,5-tetramethyl-1,3,2-dioxaborolan-2-yl)-1,3,2-dioxaborolane (2.01 g, 7.93 mmol) in DMSO (10 mL) was added Pd(dppf) Cl$_2$ (483 mg, 661 umol) and KOAc (1.30 g, 13.2 mmol). The mixture was stirred at 100° C. for 16 h. After cooling, the reaction mixture was poured into H$_2$O (120 mL) and extracted with ethyl acetate (100 mL×2). The combined organic layers were washed with brine (60 mL×2), dried over anhydrous Na$_2$SO$_4$, filtered and concentrated. The residue was purified by flash silica gel chromatography (ISCO®; 120 g SepaFlash® Silica Flash Column, Eluent of 100% PE gradient @ 100 mL/min) to give 2-(3-cyclopropoxy-2-methylphenyl)-4,4,5,5-tetramethyl-1,3,2-dioxaborolane (1.24 g, 68% yield). $^1$H NMR (400 MHz, CDCl$_3$) δ 7.21 (d, J=8.0 Hz, 1H), 7.17 (d, J=7.2 Hz, 1H), 7.01 (t, J=8.0 Hz, 1H), 4.02-3.99 (m, 1H), 2.20 (s, 3H), 1.24 (s, 12H), 0.70-0.66 (m, 2H), 0.59-0.55 (m, 2H).

4-((3'-cyclopropoxy-2-(cyclopropoxymethyl)-2'-methyl-[1,1'-biphenyl]-4-yl)amino)tetrahydro-2H-pyran-4-carboxylic acid

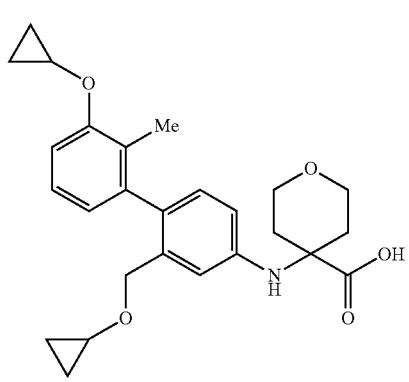 [SMILES: Cc1c(OC2CC2)cccc1-c1ccc(NC2(C(=O)O)CCOCC2)cc1COC1CC1]

To a solution of 4-[4-bromo-3-(cyclopropoxymethyl)anilino]tetrahydropyran-4-carboxylic acid (1.4 g, 3.78 mmol) and 2-(3-cyclopropoxy-2-methylphenyl)-4,4,5,5-tetramethyl-1,3,2-dioxaborolane (1.14 g, 4.16 mmol) in THF (8 mL) and H$_2$O (4 mL) was added XPhos Pd G3 (320 mg, 378 umol) and Cs$_2$CO$_3$ (2.46 g, 7.56 mmol). The mixture was stirred at 80° C. for 16 h. The mixture was adjusted with 1N HCl to pH=5, extracted with EtOAc (100 mL×2). The combined organic layers were dried over anhydrous Na$_2$SO$_4$, filtered and concentrated. The crude product was purified by prep. HPLC (column: Xtimate C18 150*40 mm*10 um; mobile phase: [water (NH$_3$·H$_2$O+NH$_4$HCO$_3$)—CH$_3$CN]; B %: 25%-55%, 8 min) to give 4-((3'-cyclopropoxy-2-(cyclopropoxymethyl)-2'-methyl-[1,1'-biphenyl]-4-yl)amino)tetrahydro-2H-pyran-4-carboxylic acid (586.7 mg, 35.46% yield). LC-MS: m/z 438.2 (M+H)$^+$. $^1$H NMR (400 MHz, CD$_3$OD) δ 7.20 (d, J=8.0 Hz, 1H), 7.09 (t, J=8.0 Hz, 1H), 6.79-6.76 (m, 2H), 6.65-6.62 (m, 2H), 4.16-4.10 (m, 2H), 3.83-3.75 (m, 5H), 3.16-3.12 (m, 1H), 2.24-2.18 (m, 2H), 1.98-1.95 (m, 2H), 1.78 (s, 3H), 0.79-0.71 (m, 2H), 0.69-0.67 (m, 2H), 0.28-0.23 (m, 4H).

311

Example A33

4-((2'-chloro-2-(cyclopropoxymethyl)-3'-ethoxy-[1,1'-biphenyl]-4-yl)amino)tetrahydro-2H-pyran-4-carboxylic acid (Compound 295)

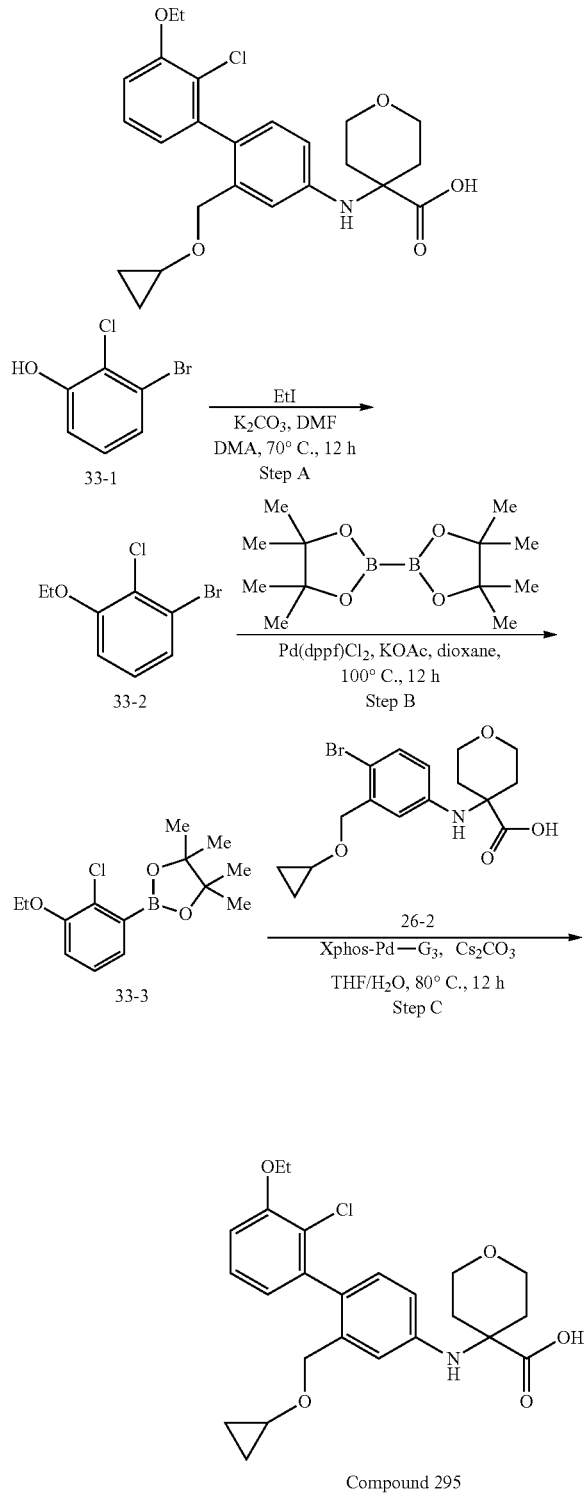

312

Step A 1-bromo-2-chloro-3-ethoxybenzene

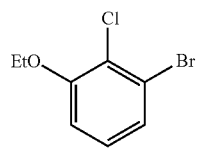

To a solution of 3-bromo-2-chlorophenol (10 g, 48.2 mmol) in DMF (30 mL) was added EtI (15.0 g, 96.4 mmol) and $K_2CO_3$ (13.3 g, 96.4 mmol). The mixture was stirred at 70° C. for 12 h. After cooling, the reaction mixture was diluted with water (100 mL) and then extracted with ethyl acetate (100 mL×3). The combined organic layers were washed with brine (100 mL×3), dried over anhydrous $Na_2SO_4$, filtered and concentrated. The residue was purified by flash silica gel chromatography (ISCO®; 80 g Sepa-Flash® Silica Flash Column, Eluent of 0~4% EtOAc/PE @ 100 mL/min) to give 1-bromo-2-chloro-3-ethoxybenzene (11 g, 96.9% yield). $^1$H NMR (400 MHz, $CDCl_3$) δ 7.22 (dd, J=8.2, 1.2 Hz, 1H), 7.07 (t, J=8.2 Hz, 1H), 6.89-6.84 (m, 1H), 4.10 (q, J=7.0 Hz, 2H), 1.48 (t, J=7.0 Hz, 3H).

Step B 2-(2-chloro-3-ethoxyphenyl)-4,4,5,5-tetramethyl-1,3,2-dioxaborolane

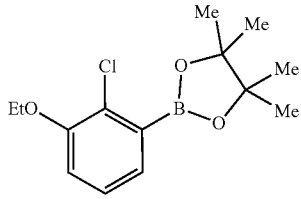 [SMILES: CCOc1cccc(B2OC(C)(C)C(C)(C)O2)c1Cl]

To a solution of 1-bromo-2-chloro-3-ethoxy-benzene (11 g, 46.7 mmol) and 4,4,5,5-tetramethyl-2-(4,4,5,5-tetramethyl-1,3,2-dioxaborolan-2-yl)-1,3,2-dioxaborolane (13.1 g, 51.4 mmol) in dioxane (100 mL) was added $Pd(dppf)Cl_2$ (3.42 g, 4.67 mmol) and KOAc (13.8 g, 140 mmol). The mixture was stirred at 100° C. for 12 h. The reaction mixture was quenched by addition water (100 mL), then extracted with ethyl acetate (100 mL×3). The combined organic layers were washed with brine (100 mL×3), dried over anhydrous $Na_2SO_4$, filtered and concentrated. The residue was purified by flash silica gel chromatography (ISCO®; 220 g Sepa-Flash® Silica Flash Column, Eluent of 0~12% EtOAc/PE gradient @ 100 mL/min) to give 2-(2-chloro-3-ethoxyphenyl)-4,4,5,5-tetramethyl-1,3,2-dioxaborolane (8.5 g, 64.4% yield). $^1$H NMR (400 MHz, $CDCl_3$) δ 7.25-7.14 (m, 2H), 6.98 (dd, J=8.0, 1.6 Hz, 1H), 4.13-4.06 (m, 2H), 1.45 (t, J=7.0 Hz, 3H), 1.37 (s, 12H).

4-((2'-chloro-2-(cyclopropoxymethyl)-3'-ethoxy-[1,1'-biphenyl]-4-yl)amino)tetrahydro-2H-pyran-4-carboxylic acid (Compound 295)

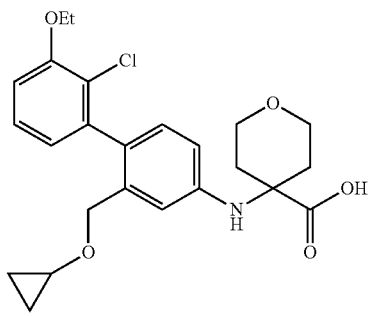 [SMILES: CCOc1cccc(-c2ccc(NC3(C(=O)O)CCOCC3)cc2COC2CC2)c1Cl]

To a solution of 4-[4-bromo-3-(cyclopropoxymethyl)anilino]tetrahydropyran-4-carboxylic acid (0.5 g, 1.35 mmol) and 2-(2-chloro-3-ethoxy-phenyl)-4,4,5,5-tetramethyl-1,3,2-dioxaborolane (420 mg, 1.49 mmol) in THF (15 mL) and H$_2$O (4 mL) was added XPhos Pd G3 (229 mg, 270 umol) and Cs$_2$CO$_3$ (1.32 g, 4.05 mmol). The mixture was stirred at 80° C. for 12 h. The reaction mixture was quenched by addition water (20 mL), acidified with 1N HCl to pH=5 and then extracted with ethyl acetate (20 mL×3). The combined organic layers were dried over anhydrous Na$_2$SO$_4$, filtered and concentrated. The crude product was purified by prep. HPLC (column: Boston Prime C18 150*30 mm*5 um; mobile phase: [water (NH$_3$·H$_2$O+NH$_4$HCO$_3$)—CH$_3$CN]; B %: 28%-58%, 7 min) to give 4-((2'-chloro-2-(cyclopropoxymethyl)-3'-ethoxy-[1,1'-biphenyl]-4-yl)amino)tetrahydro-2H-pyran-4-carboxylic acid (286 mg, 47% yield). LC-MS: m/z 446.2 (M+H)$^+$. $^1$H NMR (400 MHz, CD$_3$OD) δ 6.99 (t, J=8.0 Hz, 1H), 6.79 (d, J=8.0 Hz, 1H), 6.62-6.55 (m, 3H), 6.42 (dd, J=8.0, 2.4 Hz, 1H), 4.05-3.90 (m, 2H), 3.91-3.89 (m, 2H), 3.60-3.52 (m, 4H), 2.99-2.92 (m, 1H), 2.05-1.97 (m, 2H), 1.78-1.74 (m, 2H), 1.22 (t, J=7.0 Hz, 3H), 0.12-0.01 (m, 4H).

Example A34

4-((2-(cyclopropoxymethyl)-3'-ethoxy-2'-methyl-[1,1'-biphenyl]-4-yl)amino)tetrahydro-2H-pyran-4-carboxylic acid (Compound 355)

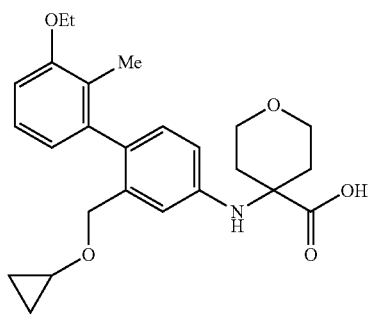

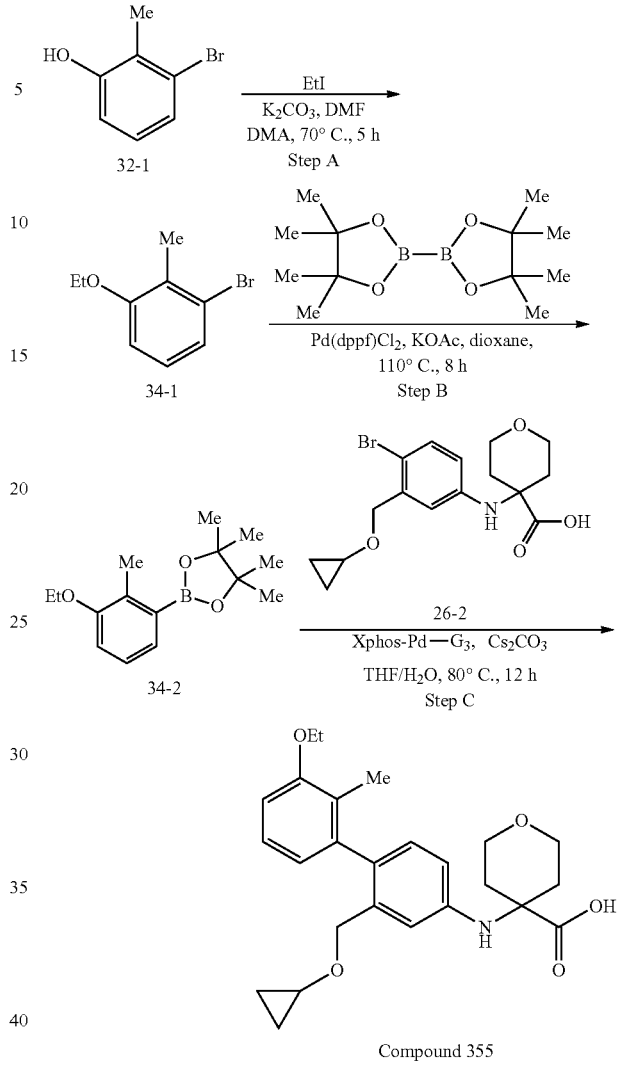

Step A 1-bromo-3-ethoxy-2-methylbenzene

To a solution of 3-bromo-2-methyl-phenol (3 g, 16.0 mmol) in DMF (30 mL) was added EtI (2.50 g, 16.0 mmol, 1.28 mL) and K$_2$CO$_3$ (5.54 g, 40.1 mmol). The mixture was stirred at 70° C. for 5 h. The mixture was diluted with water (120 mL), extracted with ethyl acetate (50 mL×2). The combined organic phase were washed with brine (60 mL), dried over anhydrous Na$_2$SO$_4$, filtered and concentrated. The residue was purified by flash silica gel chromatography (ISCO®; 80 g SepaFlash® Silica Flash Column, Eluent of 0~1% EtOAc/PE ether gradient at 100 mL/min) to give 1-bromo-3-ethoxy-2-methyl-benzene (2.9 g, 84.1% yield).

Step B 2-(3-ethoxy-2-methylphenyl)-4,4,5,5-tetramethyl-1,3,2-dioxaborolane

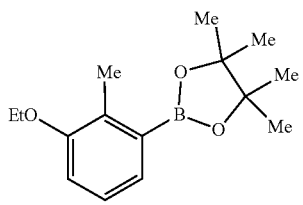 [SMILES: CCOc1cccc(B2OC(C)(C)C(C)(C)O2)c1C]

To a solution of 1-bromo-3-ethoxy-2-methyl-benzene (2.9 g, 13.5 mmol) and 4,4,5,5-tetramethyl-2-(4,4,5,5-tetramethyl-1,3,2-dioxaborolan-2-yl)-1,3,2-dioxaborolane (4.11 g, 16.2 mmol) in dioxane (50 mL) was added Pd(dppf)Cl$_2$ (987 mg, 1.35 mmol) and KOAc (2.65 g, 27.0 mmol). The mixture was stirred at 110° C. for 8 h. The reaction mixture was cooled to room temperature. The reaction mixture diluted with water (100 mL) and extracted with ethyl acetate (60 mL×2). The combined organic layers were dried over anhydrous Na$_2$SO$_4$, filtered and concentrated. The residue was purified by flash silica gel chromatography (ISCO®; 80 g SepaFlash® Silica Flash Column, Eluent of 0~2% EtOAc/PE gradient @ 100 mL/min) to give 2-(3-ethoxy-2-methyl-phenyl)-4,4,5,5-tetramethyl-1,3,2-dioxaborolane (2.8 g, 79.2% yield). LC-MS: m/z 262.9 (M+H)$^+$.

Step C 4-((2-(cyclopropoxymethyl)-3'-ethoxy-2'-methyl-[1,1'-biphenyl]-4-yl)amino)tetrahydro-2H-pyran-4-carboxylic acid (Compound 355)

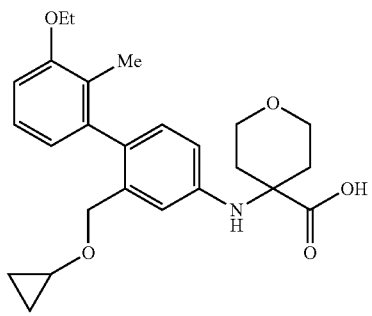

To a solution of 2-(3-ethoxy-2-methyl-phenyl)-4,4,5,5-tetramethyl-1,3,2-dioxaborolane (212 mg, 810 umol) and 4-((4-bromo-3-(cyclopropoxymethyl)phenyl)amino)tetrahydro-2H-pyran-4-carboxylic acid (150 mg, 405) in THF (3 mL) and H$_2$O (2 mL) was added XPhos Pd G3 (34.3 mg, 40.5 umol) and Cs$_2$CO$_3$ (264 mg, 810 umol). The mixture was stirred at 80° C. for 12 h. The reaction mixture was cooled to room temperature. The reaction mixture was diluted with water (30 mL), acidified with 1N HCl to pH=5, extracted with ethyl acetate (30 mL×2). The combined organic layers were washed with brine (20 mL×2), dried over anhydrous Na$_2$SO$_4$, filtered and concentrated. The residue was purified by flash silica gel chromatography (ISCO®; 4 g SepaFlash® Silica Flash Column, Eluent of 0~25% Ethyl acetate/Petroleum ether gradient at 100 mL/min) and further purified by purified by prep. HPLC (column: Welch Xtimate C18 150*30 mm*5 μm; mobile phase: [water (NH$_3$·H$_2$O+NH$_4$HCO$_3$)—CH$_3$CN]; B %: 25%-55%, 7 min) to give the product 4-((2-(cyclopropoxymethyl)-3'-ethoxy-2'-methyl-[1,1'-biphenyl]-4-yl)amino)tetrahydro-2H-pyran-4-carboxylic acid (16.15 mg, 9.3% yield). LC-MS: m/z 426.5 (M+H)$^+$. $^1$H NMR (400 MHz, CD$_3$OD) δ 7.08 (t, J=8.0 Hz, 1H), 6.86-6.77 (m, 3H), 6.68-6.62 (m, 2H), 4.19-4.05 (m, 4H), 3.82-3.75 (m, 4H), 3.18-3.13 (m, 1H), 2.26-2.19 (m, 2H), 1.99-1.94 (m, 2H), 1.86 (s, 3H), 1.42 (t, J=7.2 Hz, 3H), 0.29-0.26 (m, 4H).

Example A35

4-({3-[(2,3-dihydro-1H-inden-2-yloxy)methyl]-4-(5-ethoxy-4-methylpyridin-3-yl)phenyl}amino)oxane-4-carboxylic acid (Compound 411)

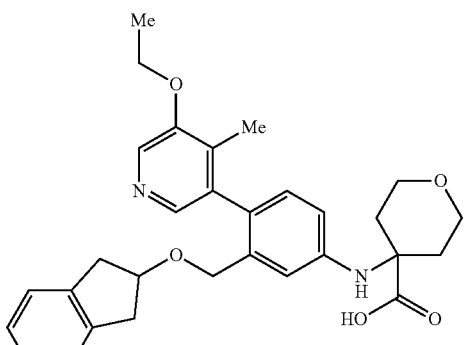

Compound 411

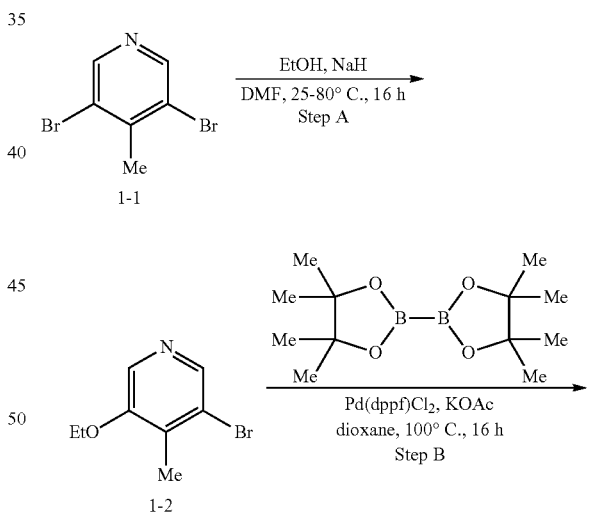

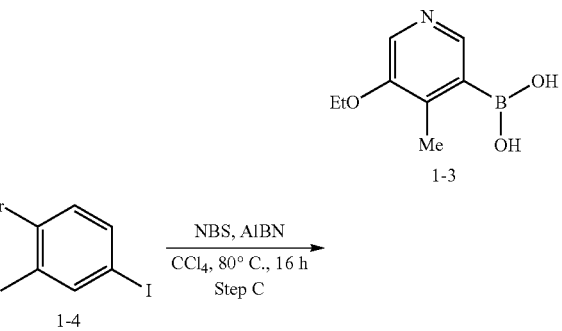

-continued

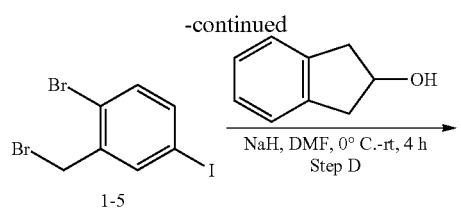

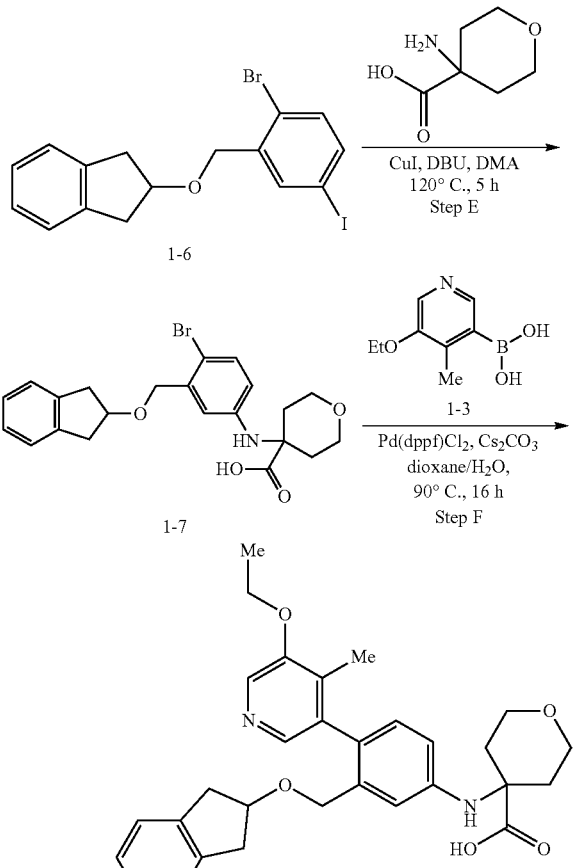

Compound 411

Step A: 3-bromo-5-ethoxy-4-methylpyridine

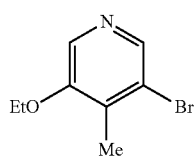

NaH (2.87 g, 71.7 mmol, 60% in mineral oil) was added to EtOH (25 mL) at 25° C. After being stirred for 0.5 h, then a solution of 3,5-dibromo-4-methylpyridine (10 g, 39.9 mmol) in DMF (100 mL) was added. The resulting mixture was heated to 80° C. and stirred for 16 h. After cooling, the reaction mixture was quenched by ice cold water (100 mL), extracted with ethyl acetate (100 mL×3). The combined organic layers were washed with water and brine, dried over anhydrous Na$_2$SO$_4$, filtered and concentrated. The residue was purified by flash silica gel chromatography (120 g SepaFlash® Silica Flash Column, Eluent of 0~30% EtOAc/ PE gradient @ 100 mL/min) to give 3-bromo-5-ethoxy-4-methylpyridine (6.1 g, 70.8% yield). LC-MS: m/z 217.4 (M+H)$^+$.

Step B: (5-ethoxy-4-methylpyridin-3-yl)boronic acid

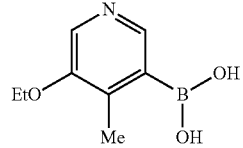 [SMILES: CCOc1cncc(B(O)O)c1C]

To the mixture of 3-bromo-5-ethoxy-4-methyl-pyridine (3.0 g, 13.9 mmol), 4,4,5,5-tetramethyl-2-(4,4,5,5-tetramethyl-1,3,2-dioxaborolan-2-yl)-1,3,2-dioxaborolane (4.58 g, 18.1 mmol) in dioxane (10 mL), was added KOAc (4.09 g, 41.7 mmol), Pd(dppf)Cl$_2$ (1.02 g, 1.39 mmol). After being degassed and purged with nitrogen three times. The reaction mixture was stirred at 100° C. for 16 h under nitrogen atmosphere. After cooling, the reaction was filtered and the filtrate was concentrated. The residue was purified by flash silica gel chromatography (80 g SepaFlash® Silica Flash Column, Eluent of 0~20% MeOH/DCM gradient @ 40 mL/min) to give a crude. This crude was further triturated with PE/EtOAc (V/V=10:1, 50 mL) to give (5-ethoxy-4-methyl-3-pyridyl)boronic acid (2.44 g, 97.1% yield). LC-MS: m/z 182.2 (M+H)$^+$.

Step C: 1-bromo-2-(bromomethyl)-4-iodobenzene

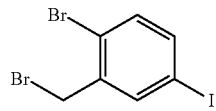

The mixture of bromo-4-iodo-2-methylbenzene (20.0 g, 67.36 mmol), AIBN (5.53 g, 33.68 mmol) and NBS (11.99 g, 67.36 mmol) in CCl$_4$ (300 mL) was heated to 80° C. and stirred for 16 h. After cooling to room temperature, the reaction mixture was concentrated. The residue was purified by silica gel column (100% PE) to afford 1-bromo-2-(bromomethyl)-4-iodobenzene (8.0 g, 31.6% yield).

Step D: 2-[(2-bromo-5-iodophenyl)methoxy]-2,3-dihydro-1H-indene

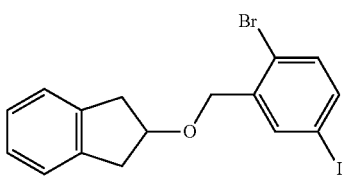 [SMILES: Brc1ccc(I)cc1COC1Cc2ccccc2C1]

To the solution of 2,3-dihydro-1H-inden-2-ol (0.86 g, 6.39 mmol) in DMF (40 mL), was added NaH (319 mg, 7.98 mmol, 60% in mineral oil) under nitrogen atmosphere. The reaction mixture was stirred at 0° C. for 1 h. Then a solution of 1-bromo-2-(bromomethyl)-4-iodobenzene (2.00 g, 5.32 mmol) in DMF (10 mL) was added into the above solution. The reaction mixture was stirred at room temperature for 3 h. Then the reaction mixture was quenched with sat. aq. NH₄Cl (100 mL), extracted with EtOAc (100 mL×3). The combined organic layer was washed with brine, dried over anhydrous Na₂SO₄, filtered and concentrated. The residue was purified by silica gel column (0~10% EtOAc in PE) to afford 2-[(2-bromo-5-iodophenyl)methoxy]-2,3-dihydro-1H-indene (450 mg, 19.7% yield).

Step E: 4-((4-bromo-3-(((2,3-dihydro-1H-inden-2-yl)oxy)methyl)phenyl)amino) tetrahydro-2H-pyran-4-carboxylic acid

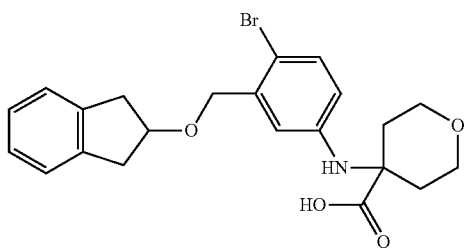 [SMILES: O=C(O)C1(Nc2ccc(Br)c(COC3Cc4ccccc4C3)c2)CCOCC1]

To a solution of 2-[(2-bromo-5-iodophenyl)methoxy]-2,3-dihydro-1H-indene (450 mg, 1.05 mmol) in DMAc (10 mL) was added CuI (40 mg, 0.21 mmol), 4-aminotetrahydro-2H-pyran-4-carboxylic acid (304 mg, 2.10 mmol) and DBU (93.13 mg, 0.61 mmol). The resulting mixture was stirred at 120° C. for 5 h under nitrogen atmosphere. The reaction mixture was cooled to room temperature, poured into water (20 mL). The pH value was adjusted to 7 by acetic acid. The resulting mixture was extracted with CH₂Cl₂ (20 mL×2). The combined organic layer was dried over anhydrous Na₂SO₄, filtered and concentrated. The residue was purified by silica gel column (0-10% MeOH in CH₂C2) to afford 4-({4-bromo-3-[(2,3-dihydro-1H-inden-2-yloxy)methyl]phenyl}amino)oxane-4-carboxylic acid (35 mg, 44.9% yield). LC-MS: m/z 447.9 (M+H)⁺.

Step F: 4-({3-[(2,3-dihydro-1H-inden-2-yloxy)methyl]-4-(5-ethoxy-4-methylpyridin-3-yl)phenyl}amino)oxane-4-carboxylic acid (Compound 411)

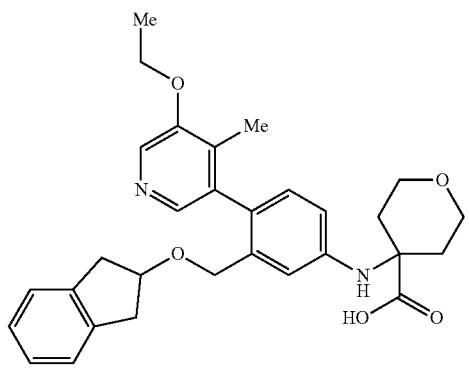 [SMILES: CCOc1cncc(-c2ccc(NC3(C(=O)O)CCOCC3)cc2COC2Cc3ccccc3C2)c1C]

To the mixture of 4-((4-bromo-3-(((2,3-dihydro-1H-inden-2-yl)oxy) methyl)phenyl)amino) tetrahydro-2H-pyran-4-carboxylic acid (225 mg, 0.504 mmol), (5-ethoxy-4-methyl-3-pyridyl)boronic acid (365 mg, 2.02 mmol) in H₂O (1 mL) and dioxane (4 mL), was added Cs₂CO₃ (329 mg, 1.01 mmol) and Pd(dppf)Cl₂ (73.8 mg, 101 μmol). After being degassed and purged with N₂ for 3 times. The reaction mixture was stirred at 90° C. for 16 h under N₂ atmosphere. After cooling, the mixture was diluted with water (10 mL), acidified with 1M aq. HCl to pH=5, extracted with ethyl acetate (10 mL×3). The combined organic layers were dried over anhydrous Na₂SO₄, filtered and concentrated. The residue was purified by flash silica gel chromatography (ISCO®; 4 g SepaFlash® Silica Flash Column, Eluent of 0~10% MeOH/DCM gradient @ 20 mL/min) and further purified by prep. HPLC (Phenomenex C18 80*40 mm*5 m; Mobile Phase A: Water (0.05% NH₃·H₂O+10 mM NH₄HCO₃), Mobile Phase B: CH₃CN; Flow rate: 40 mL/min; Gradient: 25% B to 55% B in 7 min) to give 4-({3-[(2,3-dihydro-1H-inden-2-yloxy)methyl]-4-(5-ethoxy-4-methylpyridin-3-yl)phenyl}amino)oxane-4-carboxylic acid (20.6 mg, 7.7% yield). LC-MS: m/z 503.6 (M+H)⁺. ¹H NMR (400 MHz, CD₃OD) δ 8.09 (s, 1H), 7.88 (s, 1H), 7.13-7.07 (m, 4H), 6.87-6.82 (m, 2H), 6.67 (dd, J=8.2, 2.0 Hz, 1H), 4.23-4.10 (m, 5H), 3.85-3.74 (m, 4H), 3.04-2.93 (m, 2H), 2.73 (dd, J=16.2, 4.0 Hz, 1H), 2.64 (dd, J=16.2, 4.0 Hz, 1H), 2.26-2.19 (m, 2H), 2.04-1.98 (m, 2H), 1.93 (s, 3H), 1.45 (t, J=7.2 Hz, 3H).

Example A36

4-({4-[4-(difluoromethyl)-5-ethoxypyridin-3-yl]-3-[(3-methylbutoxy)methyl] phenyl}amino) oxane-4-carboxylic acid (Compound 413)

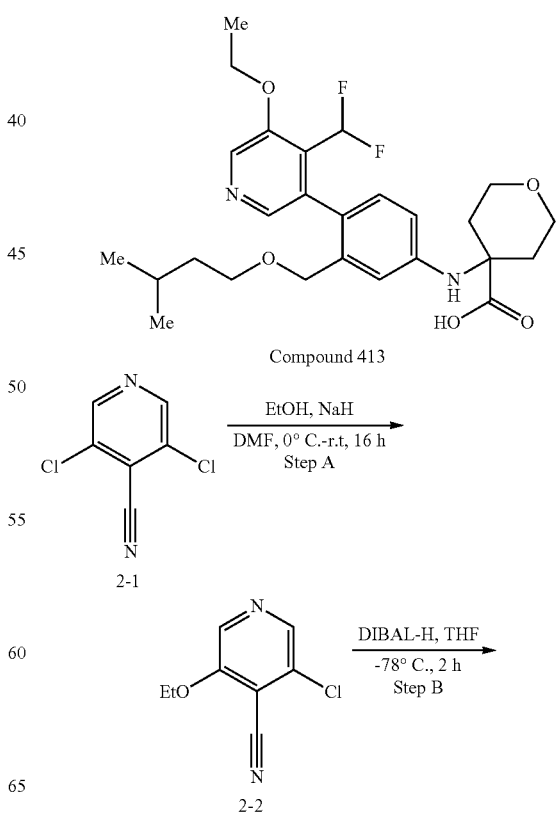

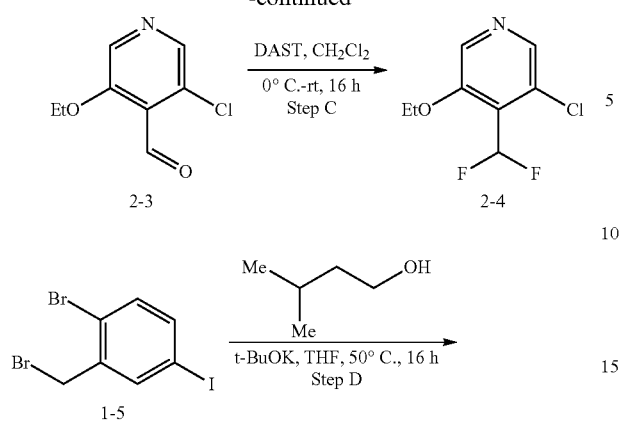

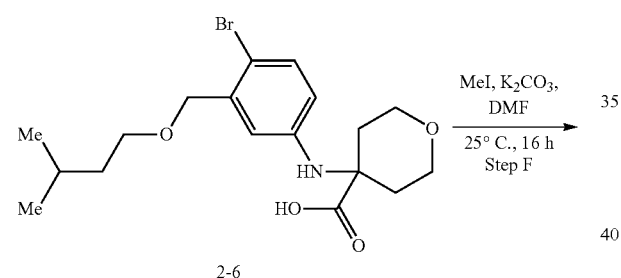

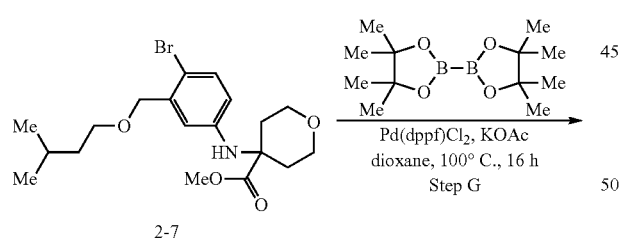

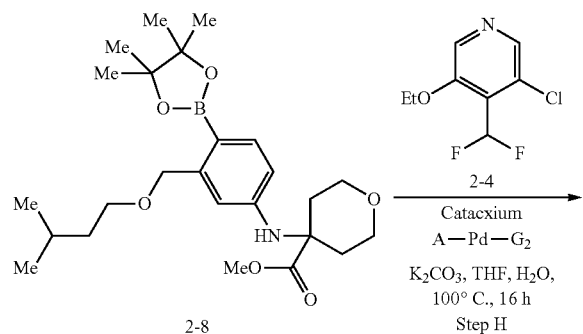

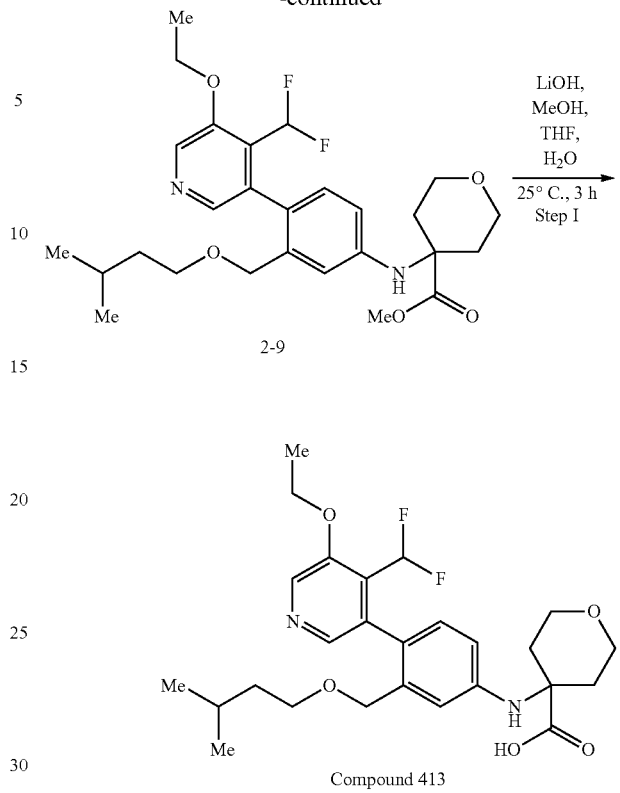

Compound 413

Step A: 3-chloro-5-ethoxyisonicotinonitrile

To a solution of EtOH (2.53 g, 55 mmol) in DMF (25 mL) was added NaH (2.20 g, 55 mmol, 60% in mineral oil) at 0° C. After being stirred for 0.5 h, 3,5-dichloroisonicotinonitrile (10.0 g, 57.8 mmol) was added. The resulting reaction mixture was stirred at 25° C. for 16 h. The reaction mixture was concentrated. The residue was diluted with brine (100 mL), extracted with EtOAc (100 mL×2). The combined organic layers were dried over anhydrous $Na_2SO_4$, filtered and concentrated. The residue was purified by flash silica gel chromatography (80 g SepaFlash® Silica Flash Column, Eluent of 0~40% EtOAc/PE gradient @ 50 mL/min) to give 3-chloro-5-ethoxyisonicotinonitrile (1.5 g, 14.2% yield). LC-MS: m/z 183.0 (M+H)$^+$. $^1$H NMR (400 MHz, CDCl$_3$) δ 8.37 (s, 1H), 8.34 (s, 1H), 4.31 (q, J=7.0 Hz, 2H), 1.54 (t, J=7.0 Hz, 3H).

Step B: 3-chloro-5-ethoxyisonicotinaldehyde

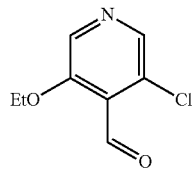 [SMILES: CCOc1cncc(Cl)c1C=O]

To a solution of 3-chloro-5-ethoxyisonicotinonitrile (1.0 g, 5.48 mmol) in DCM (30 mL) was added DIBAL-H (7.30 mL, 10.95 mmol, 1.5 M solution in toluene) at −78° C. The reaction mixture was stirred at −78° C. for 2 h. Then the reaction mixture quenched with saturated potassium sodium tartrate solution, extracted with DCM (100 mL×2). The combined organic layers were dried over anhydrous Na$_2$SO$_4$, filtered and concentrated. The residue was purified by flash silica gel chromatography (40 g SepaFlash®kSilica Flash Column, Eluent of 0~20% EtOAc/PE@ 50 mL/min) to give 3-chloro-5-ethoxyisonicotinaldehyde (380 mg, 37.4% yield). LC-MS: m/z 186.0 (M+H)$^+$.

Step C:
3-chloro-4-(difluoromethyl)-5-ethoxypyridine

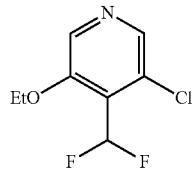 [SMILES: CCOc1cncc(Cl)c1C(F)F]

To the ice water cooled solution of 3-chloro-5-ethoxyisonicotinaldehyde (380 mg, 2.05 mmol) in DCM (5 mL) was added DAST (406 uL, 3.07 mmol). The reaction mixture was stirred at 25° C. for 16 h. The reaction mixture was diluted with sat·aq·NaHCO$_3$ (50 mL), extracted with DCM (50 mL×2). The combined organic layers were dried over anhydrous Na$_2$SO$_4$, filtered and concentrated. The residue was purified by flash silica gel chromatography (4 g SepaFlash® Silica Flash Column, Eluent of 10~40% EtOAc/PE gradient@ 50 mL/min) to give 3-chloro-4-(difluoromethyl)-5-ethoxypyridine (380 mg, 89.2% yield). LC-MS: m/z 208.1 (M+H)$^+$.

Step D:
1-bromo-4-iodo-2-((isopentyloxy)methyl)benzene

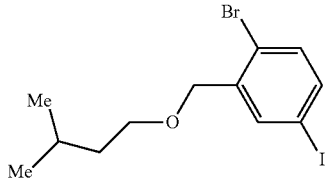 [SMILES: CC(C)CCOCc1cc(I)ccc1Br]

To a solution of 1-bromo-2-(bromomethyl)-4-iodo-benzene (2 g, 5.32 mmol) and 3-methylbutan-1-ol (469 mg, 5.32 mmol) in THF (6 mL) was added t-BuOK (896 mg, 7.98 mmol). The reaction mixture was heated to 50° C. and stirred for 16 h. After concentration, the residue was diluted with brine (30 mL), extracted with EtOAc (50 mL×2). The combined organic layers were dried over anhydrous Na$_2$SO$_4$, filtered and concentrated. The residue was purified by flash silica gel chromatography (40 g SepaFlash® Silica Flash Column, Eluent of 100% PE gradient@ 50 mL/min) to give 1-bromo-4-iodo-2-((isopentyloxy)methyl)benzene (1.7 g, 83.4% yield).

Step E: 4-((4-bromo-3-((isopentyloxy)methyl)phenyl)amino)tetrahydro-2H-pyran-4-carboxylic acid

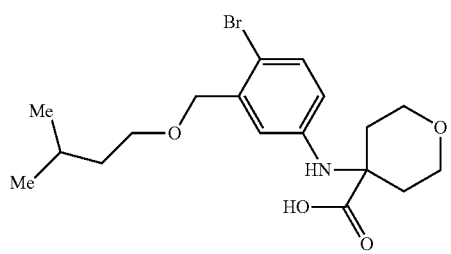 [SMILES: CC(C)CCOCc1cc(NC2(C(=O)O)CCOCC2)ccc1Br]

To a solution of 1-bromo-4-iodo-2-((isopentyloxy)methyl)benzene (1.7 g, 4.44 mmol) and 4-aminotetrahydro-2H-pyran-4-carboxylic.acid (1.29 g, 8.9 mmol) in DMA (15 mL) was added CuI (169 mg, 888 μmol) and DBU (2.03 g, 13.3 mmol). The reaction mixture was stirred at 90° C. for 16 h. After concentration, the residue was diluted with water (20 mL), acidified by 1M aq·HCl to pH=6, extracted with EtOAc (100 mL×2). The combined organic layers were washed with brine, dried over anhydrous Na$_2$SO$_4$, filtered and concentrated. The residue was purified by flash silica gel chromatography (40 g SepaFlash® Silica Flash Column, Eluent of 0~10% MeOH/DCM gradient) to give 4-((4-bromo-3-((isopentyloxy)methyl)phenyl)amino)tetrahydro-2H-pyran-4-carboxylic acid (1.0 g, 56.3% yield). LC-MS: m/z 400.2 (M+H)$^+$.

Step F: methyl 4-((4-bromo-3-((isopentyloxy)methyl)phenyl)amino)tetrahydro-2H-pyran-4-carboxylate

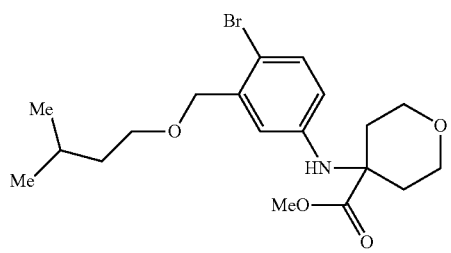 [SMILES: COC(=O)C1(Nc2ccc(Br)c(COCCC(C)C)c2)CCOCC1]

To a solution of 4-((4-bromo-3-((isopentyloxy)methyl)phenyl)amino)tetrahydro-2H-pyran-4-carboxylic acid (1.0 g, 2.50 mmol) and MeI (187 uL, 3.00 mmol) in DMF (10 mL) was added K$_2$CO$_3$ (863 mg, 6.25 mmol). The reaction mixture was stirred at 25° C. for 16 h. The reaction mixture was diluted with water (100 mL), extracted with EtOAc (50 mL×2). The combined organic layers were washed with brine, dried over anhydrous Na$_2$SO$_4$, filtered and concentrated. The residue was purified by flash silica gel chromatography (40 g SepaFlash® Silica Flash Column, Eluent of 10~40% EtOAc/PE gradient@ 50 mL/min) to give methyl 4-[4-bromo-3-(isopentyloxymethyl)anilino]tetrahydropyran-4-carboxylate (1.03 g, 99.6% yield). LC-MS: m/z 414.3 (M+H)+.

Step G: methyl 4-((3-((isopentyloxy)methyl)-4-(4,4,5,5-tetramethyl-1,3,2-dioxaborolan-2-yl)phenyl)amino)tetrahydro-2H-pyran-4-carboxylate

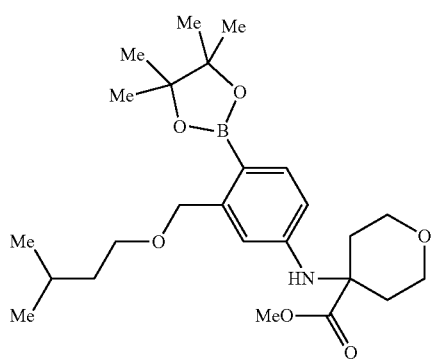 [SMILES: COC(=O)C1(Nc2ccc(B3OC(C)(C)C(C)(C)O3)c(COCCC(C)C)c2)CCOCC1]

To a solution of methyl 4-[4-bromo-3-(isopentyloxymethyl)anilino]tetrahydropyran-4-carboxylate (1.03 g, 2.49 mmol) and 4,4,5,5-tetramethyl-2-(4,4,5,5-tetramethyl-1,3,2-dioxaborolan-2-yl)-1,3,2-dioxaborolane (758 mg, 3 mmol) in dioxane (10 mL) was added KOAc (488 mg, 4.97 mmol) and Pd(dppf)Cl₂ (182 mg, 249 µmol). The reaction mixture was stirred at 100° C. for 16 h. After cooling and concentration, the residue was purified by flash silica gel chromatography (24 g SepaFlash® Silica Flash Column, Eluent of 0~20% EtOAc/PE gradient @ 50 mL/min) to give methyl 4-[3-(isopentyloxymethyl)-4-(4,4,5,5-tetramethyl-1,3,2-dioxaborolan-2-yl)anilino]tetrahydropyran-4-carboxylate (200 mg, 17.4% yield). LC-MS: m/z 462.3 (M+H)+.

Step H: methyl 4-((4-(4-(difluoromethyl)-5-ethoxypyridin-3-yl)-3-((isopentyloxy)methyl)phenyl)amino)tetrahydro-2H-pyran-4-carboxylate

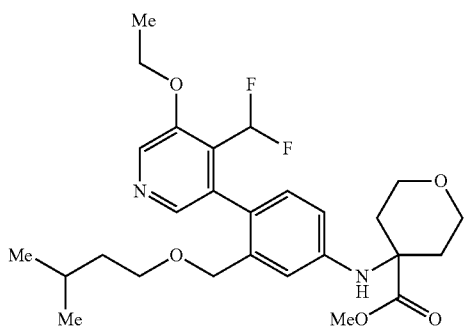 [SMILES: CCOc1cncc(-c2ccc(NC3(C(=O)OC)CCOCC3)cc2COCCC(C)C)c1C(F)F]

To the solution of methyl 4-[3-(isopentyloxymethyl)-4-(4,4,5,5-tetramethyl-1,3,2-dioxaborolan-2-yl)anilino]tetrahydropyran-4-carboxylate (111 mg, 241 µmol) and 3-chloro-4-(difluoromethyl)-5-ethoxypyridine (50 mg, 241 µmol) in THF (2 mL) and H₂O (0.2 mL) was added Catacxium A-Pd-G2 (16.1 mg, 24.1 µmol) and K₂CO₃ (66.6 mg, 482 µmol). The reaction mixture was stirred at 80° C. under nitrogen for 16 h. The reaction mixture was concentrated. The residue was diluted with brine (20 mL) and extracted with EtOAc (20 mL×2). The combined organic layers were dried over anhydrous Na₂SO₄, filtered and concentrated. The residue was purified by flash silica gel chromatography (4 g SepaFlash® Silica Flash Column, Eluent of 0~20% EtOAc/PE gradient @ 20 mL/min) to give methyl 4-((4-(4-(difluoromethyl)-5-ethoxypyridin-3-yl)-3-((isopentyloxy)methyl)phenyl)amino)tetrahydro-2H-pyran-4-carboxylate (60 mg, 48.9% yield). LC-MS: m/z 507.4 (M+H)+.

Step I: 4-({4-[4-(difluoromethyl)-5-ethoxypyridin-3-yl]-3-[(3-methylbutoxy)methyl]phenyl}amino)oxane-4-carboxylic acid (Compound 413)

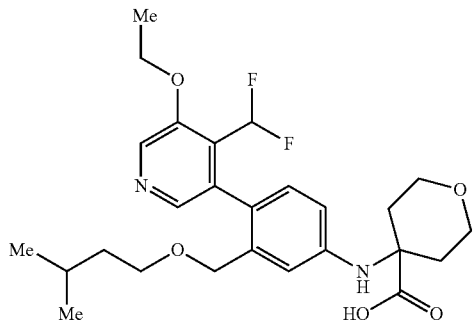 [SMILES: CCOc1cncc(-c2ccc(NC3(C(=O)O)CCOCC3)cc2COCCC(C)C)c1C(F)F]

To a solution of methyl 4-[4-[4-(difluoromethyl)-5-ethoxy-3-pyridyl]-3-(isopentyloxymethyl)anilino]tetrahydropyran-4-carboxylate (60 mg, 118 µmol) and in MeOH (4 mL), THF (1 mL) and H₂O (1 mL) was added LiOH·H₂O (24.9 mg, 592 µmol). The reaction mixture was stirred at 25° C. for 3 h. After concentration, the residue was diluted with water (20 mL), acidified with 1 M aq. HCl to pH=6, extracted with EtOAc (20 mL×2). The combined organic layers were dried over anhydrous Na₂SO₄, filtered and concentrated. The crude was purified by prep. HPLC (Column: Boston Prime C18 150*30 mm*5 um; Mobile Phase A: Water (0.05% NH₃·H₂O+10 mM NH₄HCO₃), Mobile Phase B: CH₃CN; Flow rate: 40 mL/min; Gradient: 30% B to 60% B in 7 min) to give 4-({4-[4-(difluoromethyl)-5-ethoxypyridin-3-yl]-3-[(3-methylbutoxy)methyl]phenyl}amino) oxane-4-carboxylic acid (8 mg, 13.3% yield). LC-MS: m/z 493.6 (M+H)+. ¹H NMR (400 MHz, CD₃OD) δ 8.41 (s, 1H), 8.05 (s, 1H), 6.91 (d, J=8.2 Hz, 1H), 6.83 (d, J=2.2 Hz, 1H), 6.72-6.42 (m, 2H), 4.31 (q, J=6.8 Hz, 2H), 4.14 (q, J=11.5 Hz, 2H), 3.91-3.74 (m, 4H), 3.29 (t, J=6.6 Hz, 2H), 2.35-2.17 (m, 2H), 2.11-1.96 (m, 2H), 1.64-1.54 (m, 1H), 1.49 (t, J=7.0 Hz, 3H), 1.34 (q, J=6.6 Hz, 2H), 0.84 (dd, J=6.6, 1.2 Hz, 6H).

Example A37

4-{[3-({bicyclo[3.1.0]hexan-3-yloxy}methyl)-4-(5-ethoxy-4-methylpyridin-3-yl)phenyl]amino} oxane-4-carboxylic acid (Compound 416)

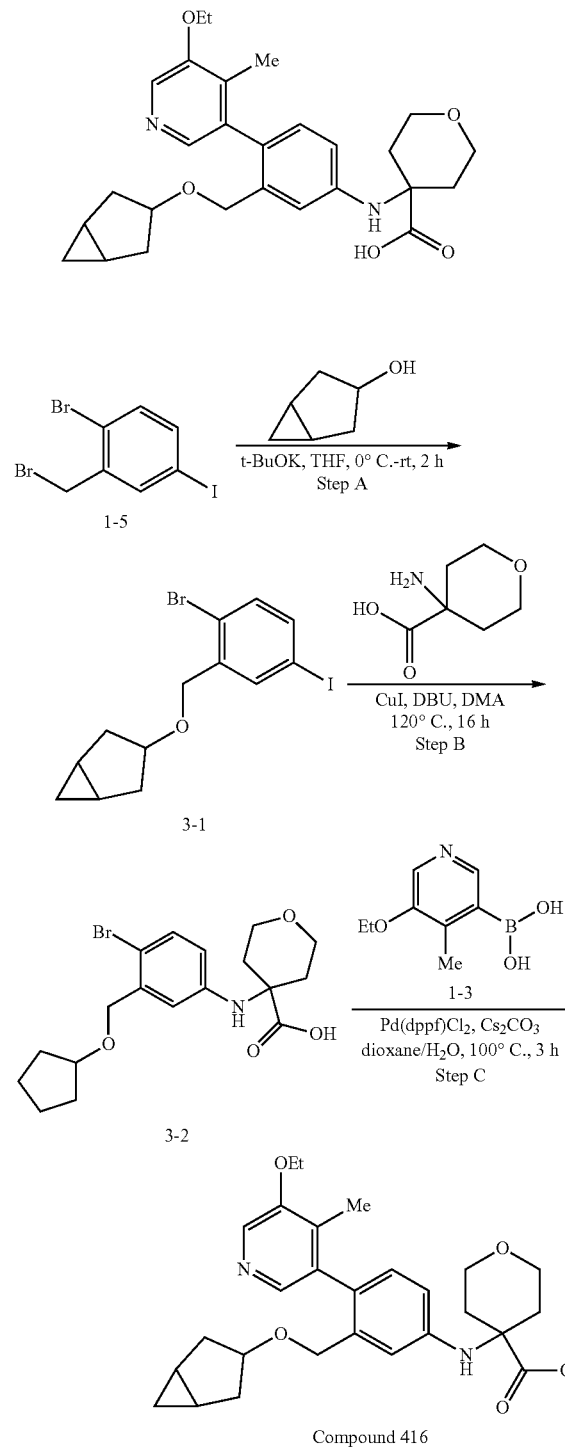

Step A: 3-((2-bromo-5-iodobenzyl)oxy)bicyclo[3.1.0]hexane

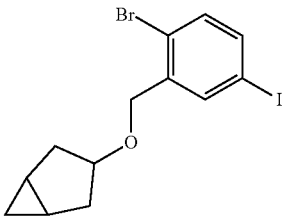 [SMILES: Brc1ccc(I)cc1COC1CC2CC2C1]

To a solution of bicyclo[3.1.0]hexan-3-ol (887.9 mg, 9.05 mmol) in THF (20 mL) was added t-BuOK (1.52 g, 13.57 mmol) at 0° C. After being stirred at 0° C. for 30 min under nitrogen, a solution of 1-bromo-2-(bromomethyl)-4-iodo-benzene (1.7 g, 4.52 mmol) in THF (8 mL) was added in dropwise. After addition, the resulting mixture was stirred at 25° C. for 2 h. Then the mixture was quenched with H₂O (20 mL), extracted with EtOAc (30 mL×3). The combined organic layers were washed with brine, dried over anhydrous Na₂SO₄, filtered and concentrated. The residue was purified by flash silica gel chromatography (40 g SepaFlash® Silica Flash Column, Eluent of 0~5% EtOAc/PE gradient @ 50 mL/min) to afford 3-[(2-bromo-5-iodo-phenyl)methoxy]bicyclo[3.1.0]hexane (1.19 g, 66.9% yield). $^1$H NMR (400 MHz, CD$_3$OD) δ 7.53 (d, J=2.4 Hz, 1H), 7.30 (dd, J=2.4, 8.4 Hz, 1H), 7.09 (d, J=8.4 Hz, 1H), 4.16 (s, 2H), 3.88 (t, J=6.4 Hz, 1H), 1.90-1.81 (m, 2H), 1.79-1.72 (m, 2H), 1.11-1.06 (m, 2H), 0.36-0.29 (m, 1H), 0.28-0.20 (m, 1H).

Step B: 4-((3-((bicyclo[3.1.0]hexan-3-yloxy)methyl)-4-bromophenyl)amino)tetrahydro-2H-pyran-4-carboxylic acid

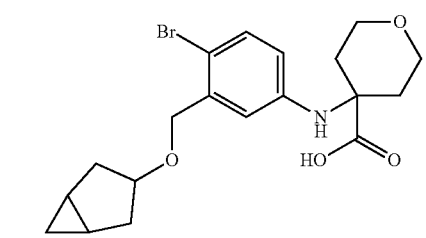 [SMILES: O=C(O)C1(Nc2ccc(Br)c(COC3CC4CC4C3)c2)CCOCC1]

To a solution of 3-[(2-bromo-5-iodo-phenyl)methoxy]bicyclo[3.1.0]hexane (500 mg, 1.27 mmol) and 4-aminotetrahydropyran-4-carboxylic acid (369.30 mg, 2.54 mmol) in DMA (8 mL), was added DBU (0.7 mL, 4.45 mmol) and CuI (48.45 mg, 254.42 μmol). The reaction mixture was stirred at 120° C. for 16 h. After cooling, the reaction mixture was poured into water (50 mL), neutralized with 1M aq. HCl to pH=7, extracted with EtOAc (40 mL×3). The combined organic layers were washed with brine, dried over anhydrous Na₂SO₄, filtered and concentrated. The residue was purified by flash silica gel chromatography (12 g SepaFlash® Silica Flash Column, Eluent of 0~50% EtOAc/PE gradient @ 50 mL/min) to afford 4-[3-(3-bicyclo[3.1.0]hexanyloxymethyl)-4-bromo-anilino]tetrahydropyran-4-carboxylic acid (400 mg, 74.7% yield). LC-MS: m/z 409.7 (M+H)⁺.

Step C: 4-{[3-({bicyclo[3.1.0]hexan-3-yloxy}methyl)-4-(5-ethoxy-4-methylpyridin-3-yl)phenyl]amino}oxane-4-carboxylic acid (Compound 416)

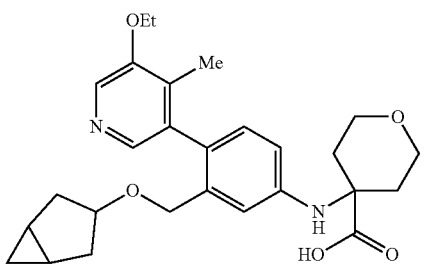 [SMILES: CCOc1cncc(-c2ccc(NC3(C(=O)O)CCOCC3)cc2COC2CC3CC3C2)c1C]

To a solution of 4-((3-((bicyclo[3.1.0]hexan-3-yloxy)methyl)-4-bromophenyl)amino)tetrahydro-2H-pyran-4-carboxylic acid (70 mg, 171 μmol) and (5-ethoxy-4-methylpyridin-3-yl)boronic acid (123 mg, 682 μmol) in dioxane (1 mL) and H$_2$O (0.25 mL) was added Pd(dppf)Cl$_2$ (24.9 mg, 34.1 μmol) and Cs$_2$CO$_3$ (111 mg, 341 μmol). The reaction mixture was stirred at 100° C. for 16 h under nitrogen. After cooling, the reaction mixture was diluted with water (5 mL), acidified by 2M aq. HCl to pH=6, extracted with EtOAc (5 mL×2). The combined organic phase was washed with brine, dried over anhydrous Na$_2$SO$_4$, filtered and concentrated. The residue was purified by prep. HPLC (Column: Phenomenex C18 80*40 mm*3 um; Mobile Phase A: Water (0.05% NH$_3$·H$_2$O+10 mM NH$_4$HCO$_3$), Mobile Phase B: CH$_3$CN; Flow rate: 40 mL/min; Gradient: 25% B to 55% B in 7 min) to give 4-{[3-({bicyclo[3.1.0]hexan-3-yloxy}methyl)-4-(5-ethoxy-4-methylpyridin-3-yl)phenyl]amino} oxane-4-carboxylic acid (9.32 mg, 11.2% yield). LC-MS: m/z 467.5 (M+H)$^+$. $^1$H NMR (400 MHz, CD$_3$OD) δ 8.10 (s, 1H), 7.85 (s, 1H), 6.87 (d, J=7.8 Hz, 1H), 6.78 (s, 1H), 6.65 (d, J=7.8 Hz, 1H), 4.22 (q, J=6.8 Hz, 2H), 4.05-3.90 (m, 2H), 3.85-3.70 (m, 5H), 2.28-2.19 (m, 2H), 2.06-2.02 (m, 2H), 1.98 (s, 3H), 1.90-1.78 (m, 2H), 1.62 (t, J=10.8 Hz, 2H), 1.47 (t, J=6.8 Hz, 3H), 1.23-1.13 (m, 2H), 0.38-0.27 (m, 2H).

The compounds in Table 1 were synthesized using a similar procedure described in the Examples above using the appropriate starting materials. Separation conditions for certain compounds is as follows.

Compounds 125 and 126 were separated as follows: Prep. HPLC purification (Column: YMC-Actus Triart C18, 30*150 mm, 5 m; Mobile Phase A: Water (10 mM NH$_4$HCO$_3$), Mobile Phase B: CH$_3$CN; Flow rate: 60 mL/min; Gradient: 20% B to 56% B in 8 min).

Compounds 130 and 131 were separated as follows: Prep. HPLC purification (Column: XBridge Prep OBD C18 Column, 30*150 mm, 5 m; Mobile Phase A: Water (10 mM NH$_4$HCO$_3$), Mobile Phase B: CH$_3$CN; Flow rate: 60 mL/min; Gradient: 5% B to 85% B in 8 min).

Compounds 158 and 159 were separated as follows: SFC separation (Column: DAICEL CHIRALPAK AD (250 mm*30 mm, 10 m); mobile phase: A for CO$_2$, B for [0.1% NH$_3$·H$_2$O in EtOH]; B %: 35%-35%).

Compounds 196 and 197 were separated as follows: Prep. HPLC purification (Column: Welch Xtimate C18 150*25 mm, 5 m; Mobile Phase A: Water (0.05% NH$_3$·H$_2$O+10 mM NH$_4$HCO$_3$), Mobile Phase B: CH$_3$CN; Flow rate: 40 mL/min; Gradient: 22% B to 55% B in 7 min).

Compounds 200 and 201 were separated as follows: SFC separation (Column: DAICEL CHIRALPAK IG (250 mm*30 mm, 10 m); mobile phase: A for CO$_2$, B for [0.1% NH$_3$·H$_2$O in MeOH]; B %: 30%-30%).

Compounds 210 and 211 were separated as follows: SFC separation (Column: DAICEL CHIRALPAK IG (250 mm*30 mm, 10 m); mobile phase: A for CO$_2$, B for [0.1% NH$_3$H$_2$O in EtOH]; B %: 35%-35%).

Compounds 213 and 214 were separated as follows: Prep. HPLC purification (Column: Welch Xtimate C18 150*30 mm, 5 m; Mobile Phase A: Water (0.05% NH$_3$·H$_2$O+10 mM NH$_4$HCO$_3$), Mobile Phase B: CH$_3$CN; Flow rate: 40 mL/min; Gradient: 22% B to 55% B in 7 min).

Compounds 216 and 217 were separated as follows: SFC separation (Column: DAICEL CHIRALPAK AD (250 mm*30 mm, 10 m); mobile phase: A for CO$_2$, B for [0.1% NH$_3$H$_2$O in MeOH]; B %: 30%-30%).

Compounds 223 and 224 were separated as follows: SFC separation (Column: DAICEL CHIRALPAK AD (250 mm*30 mm, 10 m); mobile phase: A for CO$_2$, B for [0.1% NH$_3$H$_2$O in MeOH]; B %: 20%-20%).

Compounds 237 and 238 were separated as follows: Prep. HPLC purification (Column: Boston Prime C18 150*30 mm, 5 m; Mobile Phase A: Water (0.05% NH$_3$·H$_2$O+10 mM NH$_4$HCO$_3$), Mobile Phase B: CH$_3$CN; Flow rate: 30 mL/min; Gradient: 30% B to 60% B in 7 min).

Compounds 241 and 242 were separated as follows: SFC separation (Column: DAICEL CHIRALPAK AD (250 mm*30 mm, 10 m); mobile phase: A for CO$_2$, B for [0.1% NH$_3$H$_2$O in MeOH]; B %: 35%-35%).

Compounds 259 and 260 were separated as follows: SFC separation (Column: DAICEL CHIRALPAK IG (250 mm*30 mm, 10 m); mobile phase: A for CO$_2$, B for [0.1% NH$_3$H$_2$O in i-PrOH]; B %: 20%-20%).

Compounds 268 and 269 were separated as follows: SFC separation (Column: DAICEL CHIRALPAK AD (250 mm*30 mm, 10 m); mobile phase: A for CO$_2$, B for [0.1% NH$_3$H$_2$O in EtOH]; B %: 20%-20%).

Compounds 299 and 300 were separated as follows: SFC separation (Column: DAICEL CHIRALPAK IG (250 mm*30 mm, 10 m); mobile phase: A for CO$_2$, B for [0.1% NH$_3$H$_2$O in i-PrOH]; B %: 30%-30%). Flow rate: 2.5 mL/min, Column temp.: 40° C.

Compounds 308 and 309 were separated as follows: SFC separation (Column: DAICEL CHIRALPAK OJ (250 mm*30 mm, 10 m); mobile phase: A for CO$_2$, B for [0.1% NH$_3$H$_2$O in i-PrOH]; B %: 20%-20%). Flow rate: 2.5 mL/min, Column temp.: 40° C.

| Compound | Structure | LC-MS: m/z |
|---|---|---|
| 101 | 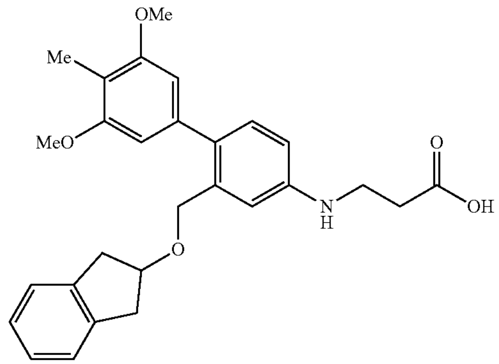 [SMILES: COc1cc(-c2ccc(NCCC(=O)O)cc2COC2Cc3ccccc3C2)cc(OC)c1C] | 462.0 (M + H)+ |
| 102 | 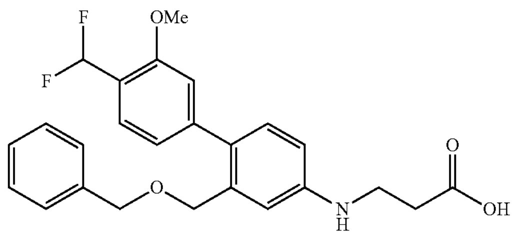 [SMILES: COc1cc(-c2ccc(NCCC(=O)O)cc2COCc2ccccc2)ccc1C(F)F] | 442.0 (M + H)+ |
| 103 | 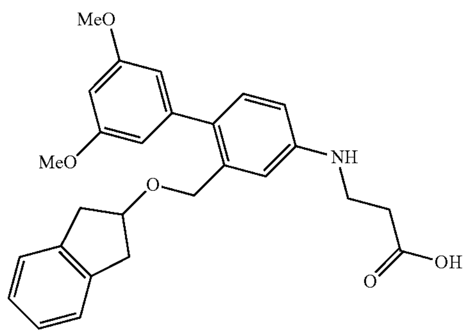 [SMILES: COc1cc(OC)cc(-c2ccc(NCCC(=O)O)cc2COC2Cc3ccccc3C2)c1] | 448.4 (M + H)+ |
| 104 | 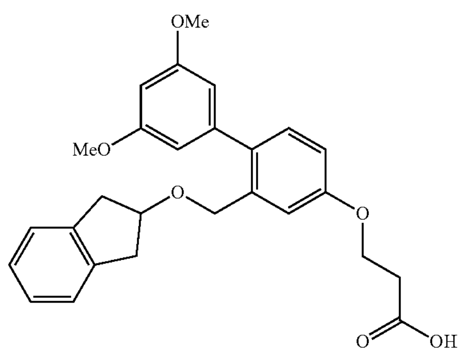 [SMILES: COc1cc(OC)cc(-c2ccc(OCCC(=O)O)cc2COC2Cc3ccccc3C2)c1] | 449.2 (M + H)+ |
| 105 | 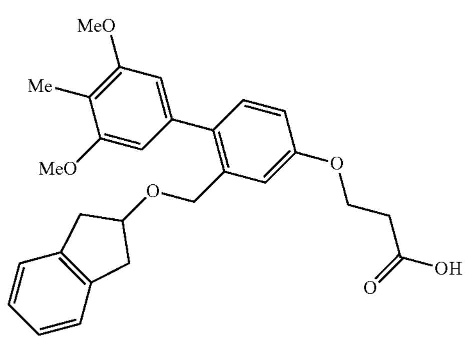 [SMILES: COc1cc(-c2ccc(OCCC(=O)O)cc2COC2Cc3ccccc3C2)cc(OC)c1C] | 485.3 (M + Na)+ |

-continued
| Compound | Structure | LC-MS: m/z |
|---|---|---|
| 106 | 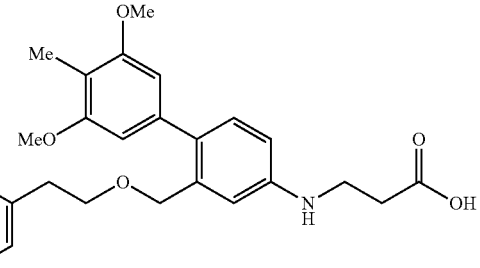 | 450.2 (M + H)+ |
| 107 | 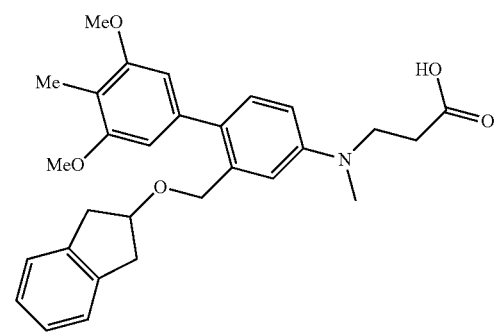 [SMILES: COc1cc(-c2ccc(N(C)CCC(=O)O)cc2COC2Cc3ccccc3C2)cc(OC)c1C] | 476.2 (M + H)+ |
| 108 | 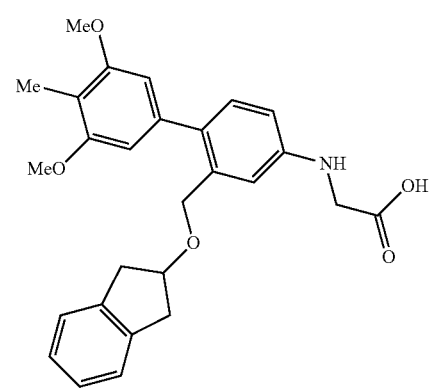 [SMILES: COc1cc(-c2ccc(NCC(=O)O)cc2COC2Cc3ccccc3C2)cc(OC)c1C] | 448.2 (M + H)+ |
| 109 | 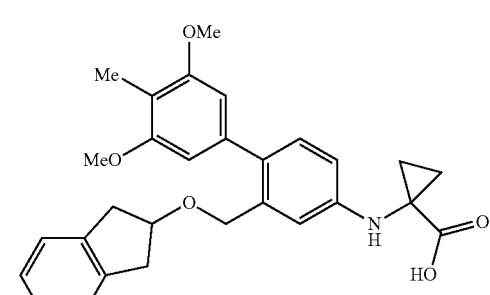 | 496.2 (M + Na)+ |

-continued

| Compound | Structure | LC-MS: m/z |
|---|---|---|
| 110 | 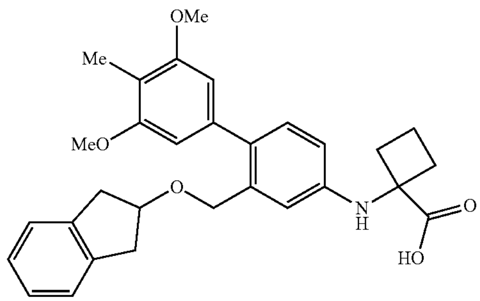 [SMILES: COc1cc(-c2ccc(NC3(C(=O)O)CCC3)cc2COC2Cc3ccccc3C2)cc(OC)c1C] | 488.2 (M + H)+ |
| 111 | 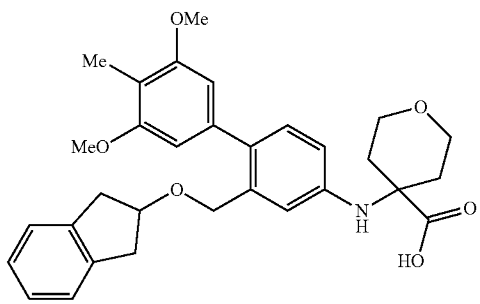 [SMILES: COc1cc(-c2ccc(NC3(C(=O)O)CCOCC3)cc2COC2Cc3ccccc3C2)cc(OC)c1C] | 518.4 (M + H)+ |
| 112 | 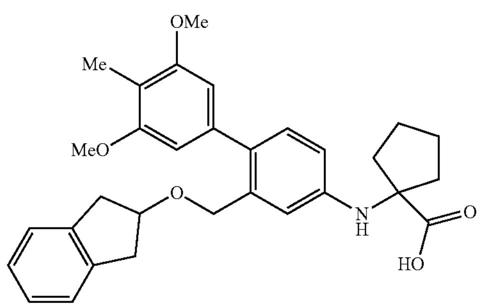 [SMILES: COc1cc(-c2ccc(NC3(C(=O)O)CCCC3)cc2COC2Cc3ccccc3C2)cc(OC)c1C] | 502.2 (M + H)+ |
| 113 | 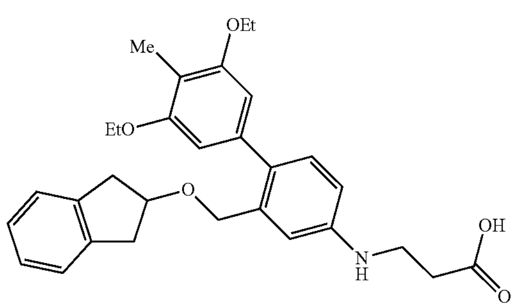 [SMILES: CCOc1cc(-c2ccc(NCCC(=O)O)cc2COC2Cc3ccccc3C2)cc(OCC)c1C] | 490.2 (M + H)+ |
| 114 | 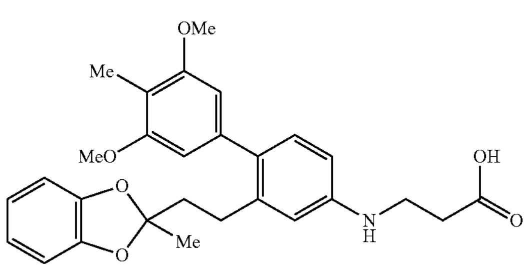 | 478.3 (M + H)+ |

-continued
| Compound | Structure | LC-MS: m/z |
|---|---|---|
| 115 | 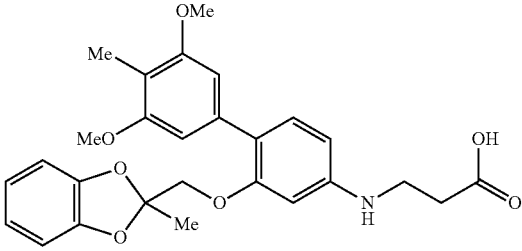 | 480.2 (M + H)+ |
| 116 | 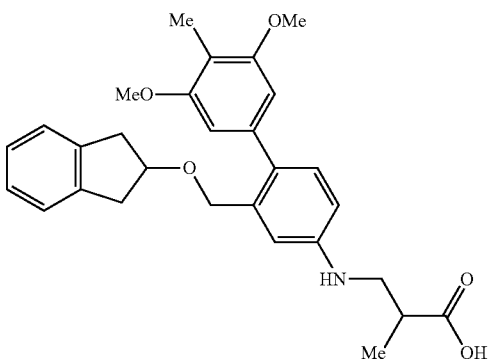 [SMILES: COc1cc(-c2ccc(NCC(C)C(=O)O)cc2COC2Cc3ccccc3C2)cc(OC)c1C] | 476.2 (M + H)+ |
| 117 | 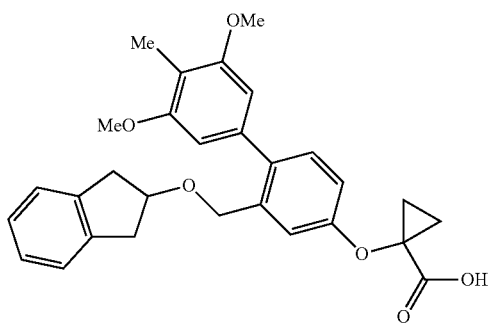 [SMILES: COc1cc(-c2ccc(OC3(C(=O)O)CC3)cc2COC2Cc3ccccc3C2)cc(OC)c1C] | 497.2 (M + Na)+ |
| 118 | 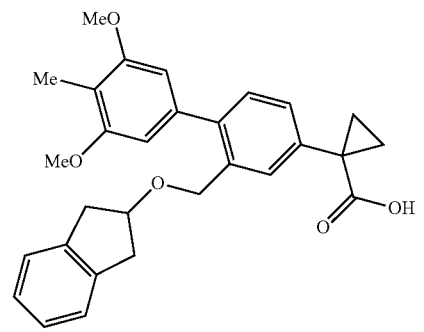 [SMILES: COc1cc(-c2ccc(C3(C(=O)O)CC3)cc2COC2Cc3ccccc3C2)cc(OC)c1C] | 457.0 (M − H)− |

-continued
| Compound | Structure | LC-MS: m/z |
|---|---|---|
| 119 | 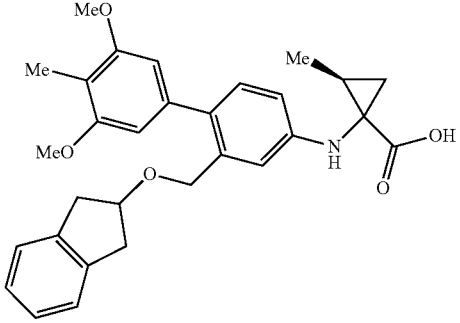 [SMILES: COc1cc(-c2ccc(NC3(C(=O)O)C[C@@H]3C)cc2COC2Cc3ccccc3C2)cc(OC)c1C] | 488.2 (M + H)+ |
| 120 | 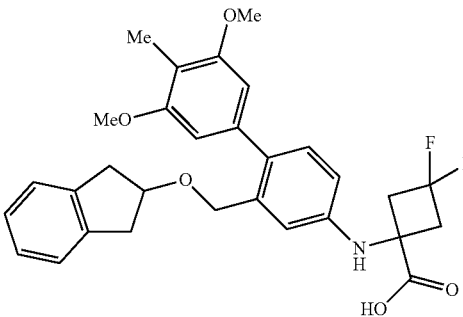 | 524.3 (M + H)+ |
| 121 | 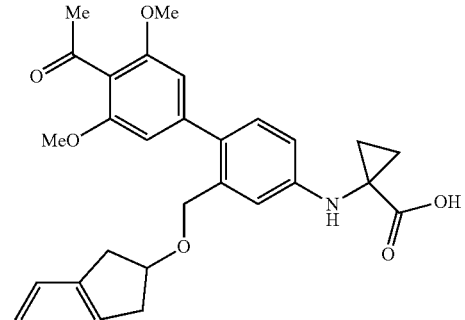 | 502.2 (M + H)+ |
| 122 | 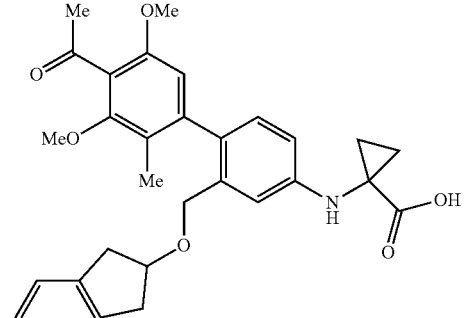 | 516.4 (M + H)+ |

-continued

| Compound | Structure | LC-MS: m/z |
|---|---|---|
| 123 | 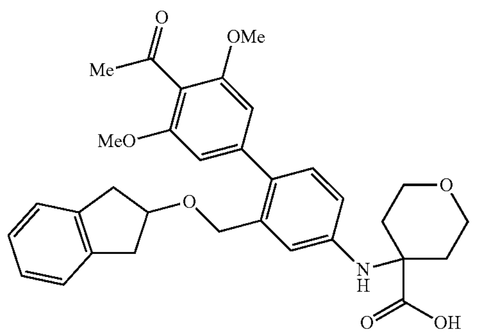 [SMILES: COc1cc(-c2ccc(NC3(C(=O)O)CCOCC3)cc2COC2Cc3ccccc3C2)cc(OC)c1C(C)=O] | 546.4 (M + H)+ |
| 124 | 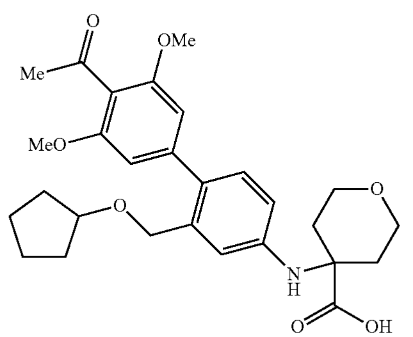 [SMILES: COc1cc(-c2ccc(NC3(C(=O)O)CCOCC3)cc2COC2CCCC2)cc(OC)c1C(C)=O] | 498.2 (M + H)+ |
| 125 | Enantiomer 1 | 518.3 (M + H)+ |
| 126 | Enantiomer 2 | 518.2 (M + H)+ |

-continued

| Compound | Structure | LC-MS: m/z |
|---|---|---|
| 127 | 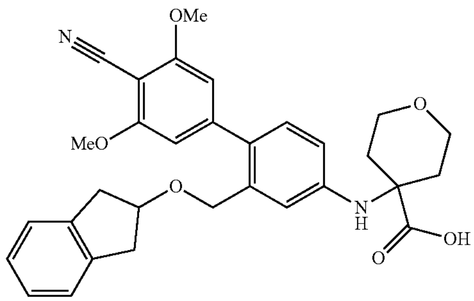 [SMILES: COc1cc(-c2ccc(NC3(C(=O)O)CCOCC3)cc2COC2Cc3ccccc3C2)cc(OC)c1C#N] | 529.2 (M + H)+ |
| 128 | 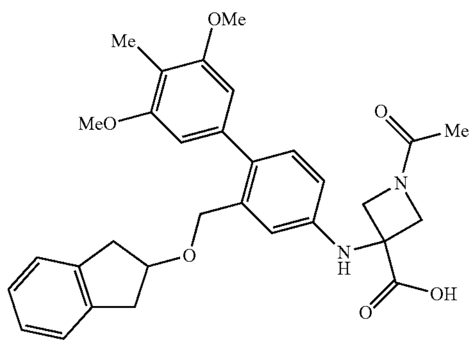 [SMILES: COc1cc(-c2ccc(NC3(C(=O)O)CN(C(C)=O)C3)cc2COC2Cc3ccccc3C2)cc(OC)c1C] | 531.2 (M + H)+ |
| 129 | 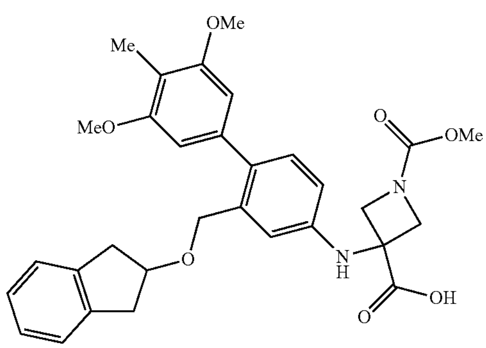 [SMILES: COC(=O)N1CC(Nc2ccc(-c3cc(OC)c(C)c(OC)c3)c(COC3Cc4ccccc4C3)c2)(C(=O)O)C1] | 547.3 (M + H)+ |
| 130 (Enantiomer 1) | | 504.1 (M + H)+ |

-continued
| Compound | Structure | LC-MS: m/z |
|---|---|---|
| 131 | 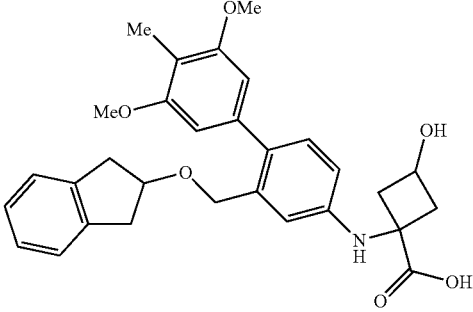 Enantiomer 2 | 504.1 (M + H)+ |
| 132 | 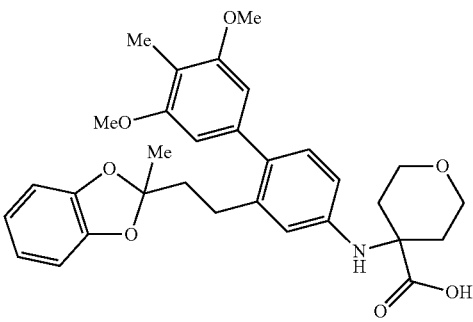 [SMILES: COc1cc(-c2ccc(NC3(C(=O)O)CCOCC3)cc2CCC2(C)Oc3ccccc3O2)cc(OC)c1C] | 534.1 (M + H)+ |
| 133 | 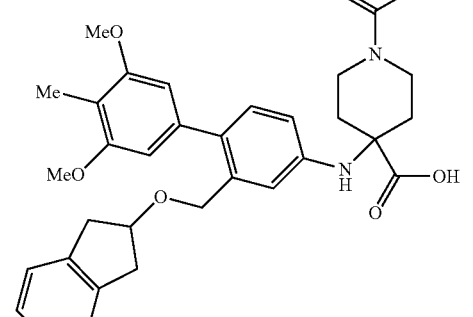 | 559.1 (M + H)+ |
| 134 | 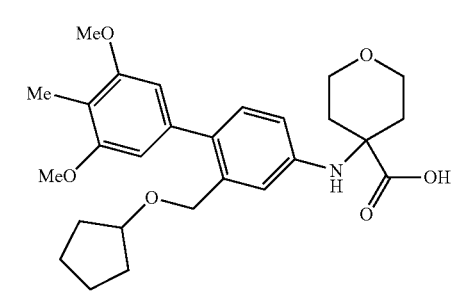 [SMILES: COc1cc(-c2ccc(NC3(C(=O)O)CCOCC3)cc2COC2CCCC2)cc(OC)c1C] | 470.2 (M + H)+ |

-continued
| Compound | Structure | LC-MS: m/z |
|---|---|---|
| 135 | 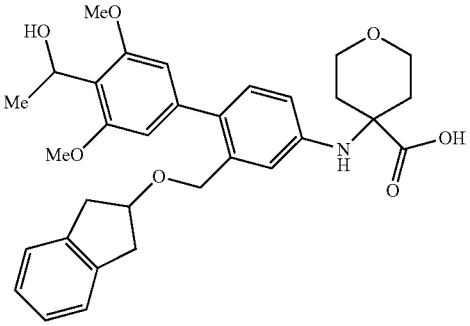 [SMILES: COc1cc(-c2ccc(NC3(C(=O)O)CCOCC3)cc2COC2Cc3ccccc3C2)cc(OC)c1C(C)O] | 548.3 (M + H)+ |
| 136 | 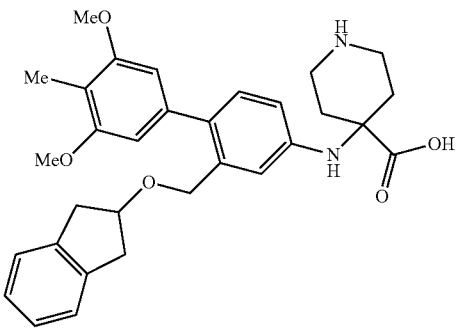 [SMILES: COc1cc(-c2ccc(NC3(C(=O)O)CCNCC3)cc2COC2Cc3ccccc3C2)cc(OC)c1C] | 517.3 (M + H)+ |
| 137 | 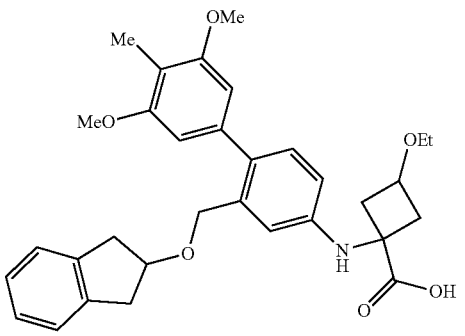 [SMILES: CCOC1CC(Nc2ccc(-c3cc(OC)c(C)c(OC)c3)c(COC3Cc4ccccc4C3)c2)(C(=O)O)C1] | 532.1 (M + H)+ |
| 138 | 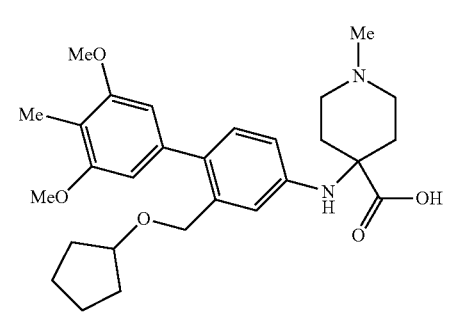 [SMILES: COc1cc(-c2ccc(NC3(C(=O)O)CCN(C)CC3)cc2COC2CCCC2)cc(OC)c1C] | 483.2 (M + H)+ |

-continued
| Compound | Structure | LC-MS: m/z |
|---|---|---|
| 139 | 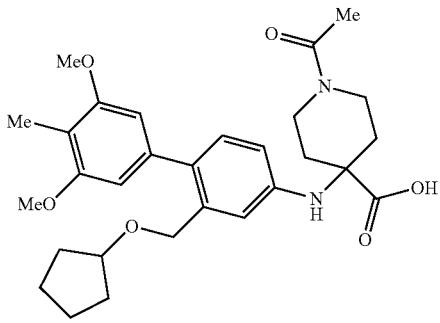 [SMILES: COc1cc(-c2ccc(NC3(C(=O)O)CCN(C(C)=O)CC3)cc2COC2CCCC2)cc(OC)c1C] | 511.3 (M + H)+ |
| 140 | 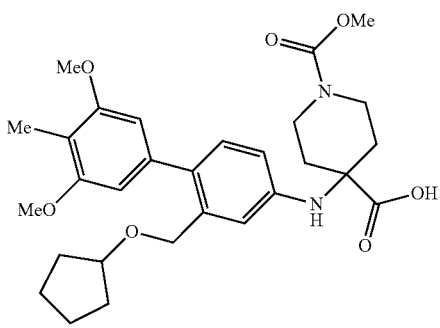 | 527.2 (M + H)+ |
| 141 | 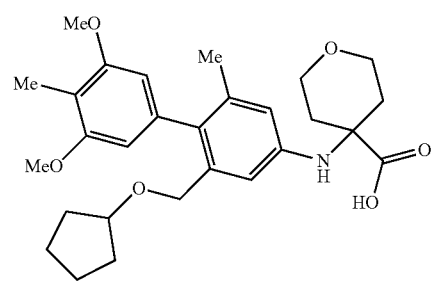 [SMILES: COc1cc(-c2c(C)cc(NC3(C(=O)O)CCOCC3)cc2COC2CCCC2)cc(OC)c1C] | 484.1 (M + H)+ |
| 142 | 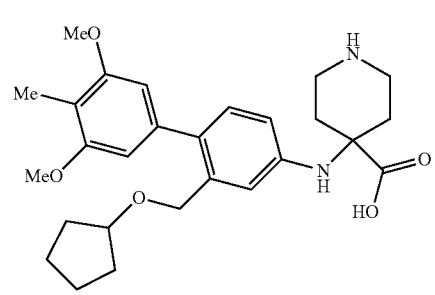 [SMILES: COc1cc(-c2ccc(NC3(C(=O)O)CCNCC3)cc2COC2CCCC2)cc(OC)c1C] | 469.1 (M + H)+ |

-continued

| Compound | Structure | LC-MS: m/z |
|---|---|---|
| 143 | 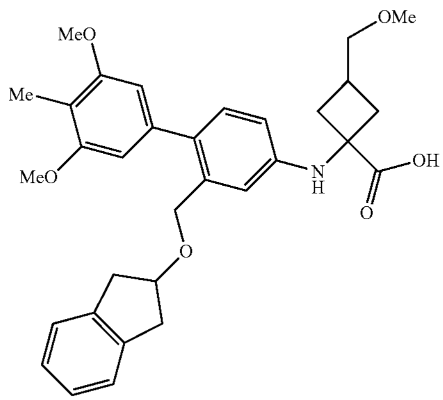 [SMILES: COCC1CC(Nc2ccc(-c3cc(OC)c(C)c(OC)c3)c(COC3Cc4ccccc4C3)c2)(C(=O)O)C1] | 532.4 (M + H)+ |
| 144 | 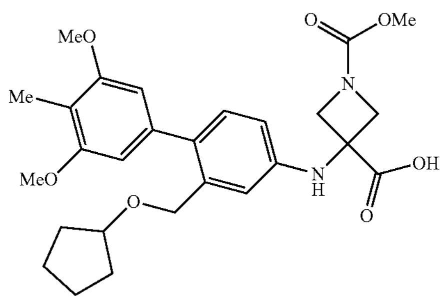 [SMILES: COC(=O)N1CC(Nc2ccc(-c3cc(OC)c(C)c(OC)c3)c(COC3CCCC3)c2)(C(=O)O)C1] | 499.1 (M + H)+ |
| 145 | 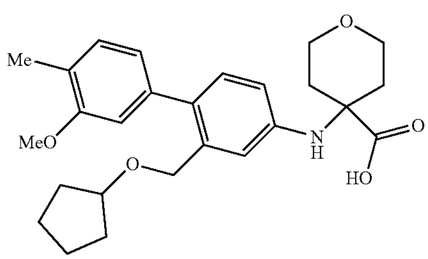 [SMILES: COc1cc(-c2ccc(NC3(C(=O)O)CCOCC3)cc2COC2CCCC2)ccc1C] | 440.1 (M + H)+ |
| 146 | 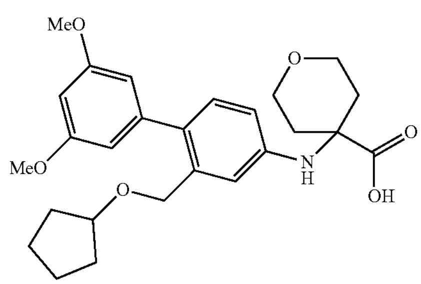 [SMILES: COc1cc(OC)cc(-c2ccc(NC3(C(=O)O)CCOCC3)cc2COC2CCCC2)c1] | 456.1 (M + H)+ |
| 147 | 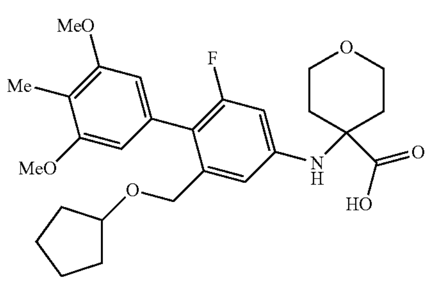 [SMILES: COc1cc(-c2c(F)cc(NC3(C(=O)O)CCOCC3)cc2COC2CCCC2)cc(OC)c1C] | 488.4 (M + H)+ |

-continued
| Compound | Structure | LC-MS: m/z |
|---|---|---|
| 148 | 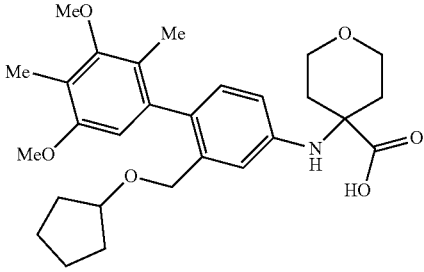 [SMILES: COc1cc(-c2ccc(NC3(C(=O)O)CCOCC3)cc2COC2CCCC2)c(C)c(OC)c1C] | 484.2 (M + H)+ |
| 149 | 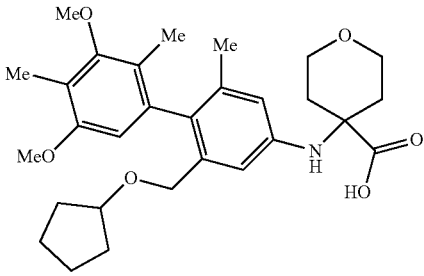 [SMILES: COc1cc(-c2c(C)cc(NC3(C(=O)O)CCOCC3)cc2COC2CCCC2)c(C)c(OC)c1C] | 498.2 (M + H)+ |
| 151 | 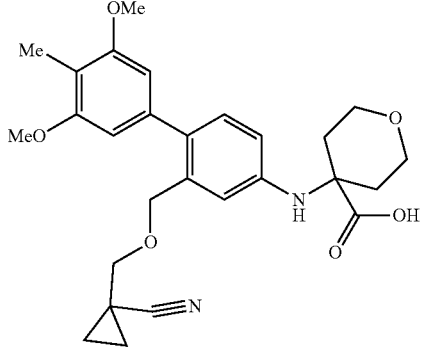 [SMILES: COc1cc(-c2ccc(NC3(C(=O)O)CCOCC3)cc2COCC2(C#N)CC2)cc(OC)c1C] | 481.1 (M + H)+ |
| 152 | 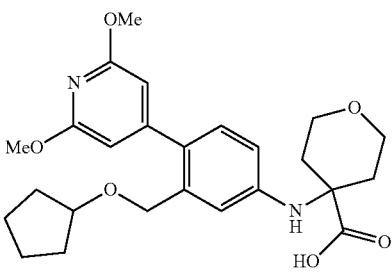 [SMILES: COc1cc(-c2ccc(NC3(C(=O)O)CCOCC3)cc2COC2CCCC2)cc(OC)n1] | 457.1 (M + H)+ |
| 153 | 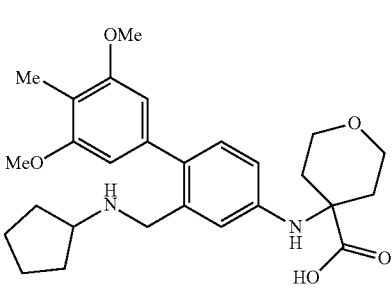 [SMILES: COc1cc(-c2ccc(NC3(C(=O)O)CCOCC3)cc2CNC2CCCC2)cc(OC)c1C] | 469.2 (M + H)+ |

-continued

| Compound | Structure | LC-MS: m/z |
|---|---|---|
| 154 | 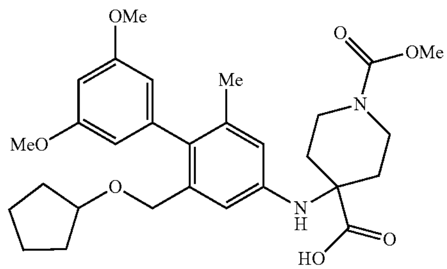 [SMILES: COC(=O)N1CCC(Nc2cc(C)c(-c3cc(OC)cc(OC)c3)c(COC3CCCC3)c2)(C(=O)O)CC1] | 549.4 (M + Na)+ |
| 155 | 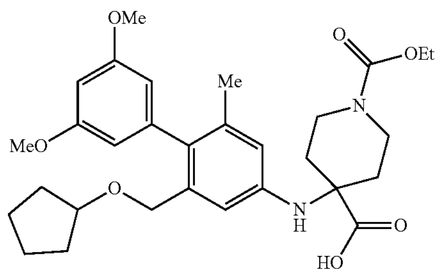 [SMILES: CCOC(=O)N1CCC(Nc2cc(C)c(-c3cc(OC)cc(OC)c3)c(COC3CCCC3)c2)(C(=O)O)CC1] | 541.4 (M + H)+ |
| 156 | 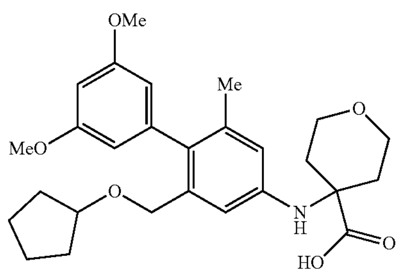 [SMILES: COc1cc(OC)cc(-c2c(C)cc(NC3(C(=O)O)CCOCC3)cc2COC2CCCC2)c1] | 470.1 (M + H)+ |
| 157 | 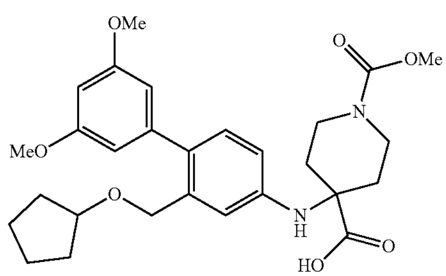 [SMILES: COC(=O)N1CCC(Nc2ccc(-c3cc(OC)cc(OC)c3)c(COC3CCCC3)c2)(C(=O)O)CC1] | 535.4 (M + Na)+ |
| 158 | Enantiomer 1 | 506.0 (M + H)+ |

-continued
| Compound | Structure | LC-MS: m/z |
|---|---|---|
| 159 | 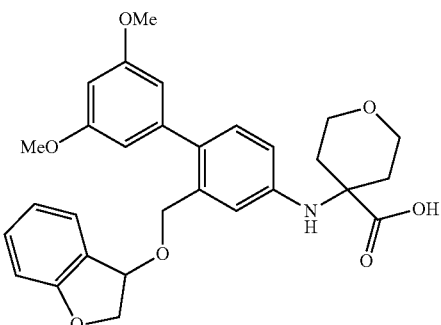<br>Enantiomer 2 | 506.0 (M + H)+ |
| 160 | 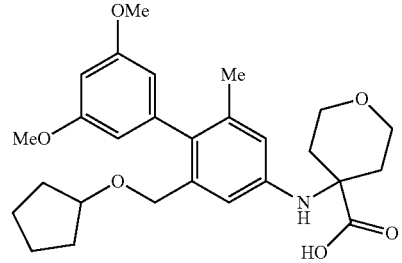 [SMILES: COc1cc(OC)cc(-c2c(C)cc(NC3(C(=O)O)CCOCC3)cc2COC2CCCC2)c1] | 454.2 (M + H)+ |
| 161 | 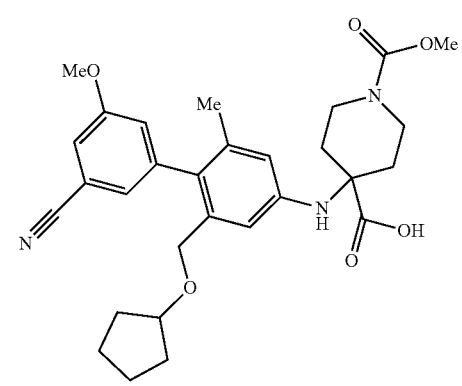 [SMILES: COC(=O)N1CCC(Nc2cc(C)c(-c3cc(C#N)cc(OC)c3)c(COC3CCCC3)c2)(C(=O)O)CC1] | 522.2 (M + H)+ |
| 163 | 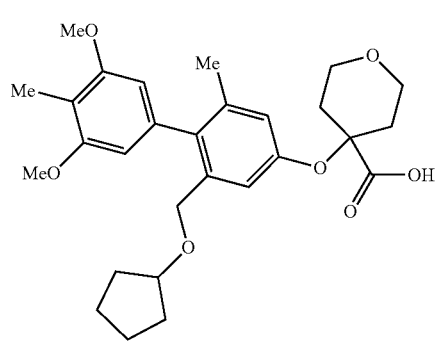 [SMILES: COc1cc(-c2c(C)cc(OC3(C(=O)O)CCOCC3)cc2COC2CCCC2)cc(OC)c1C] | 507.4 (M + Na)+ |

-continued

| Compound | Structure | LC-MS: m/z |
|---|---|---|
| 164 | 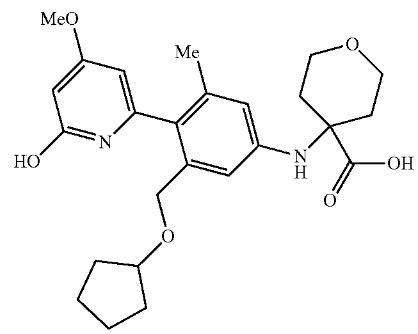 [SMILES: COc1cc(O)nc(-c2c(C)cc(NC3(C(=O)O)CCOCC3)cc2COC2CCCC2)c1] | 457.1 (M + H)+ |
| 165 | 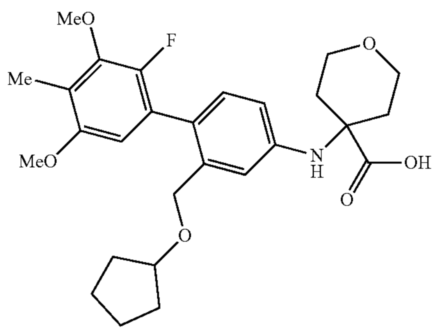 [SMILES: COc1cc(-c2ccc(NC3(C(=O)O)CCOCC3)cc2COC2CCCC2)c(F)c(OC)c1C] | 488.1 (M + H)+ |
| 166 | 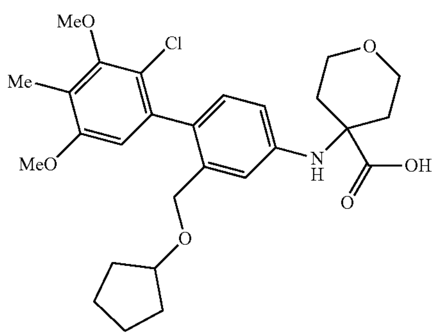 [SMILES: COc1cc(-c2ccc(NC3(C(=O)O)CCOCC3)cc2COC2CCCC2)c(Cl)c(OC)c1C] | 504.0 (M + H)+ |
| 168 | 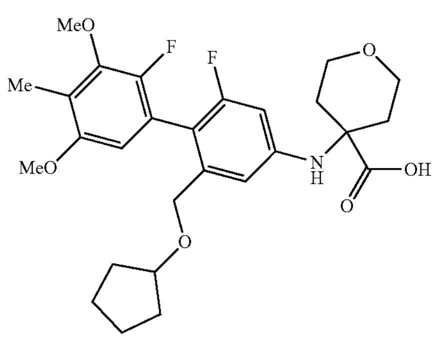 [SMILES: COc1cc(-c2c(F)cc(NC3(C(=O)O)CCOCC3)cc2COC2CCCC2)c(F)c(OC)c1C] | 506.4 (M + H)+ |

-continued

| Compound | Structure | LC-MS: m/z |
|---|---|---|
| 169 | 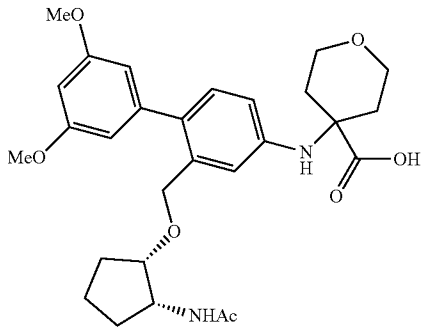 [SMILES: COc1cc(OC)cc(-c2ccc(NC3(C(=O)O)CCOCC3)cc2CO[C@H]2CCC[C@H]2NC(C)=O)c1] | 513.4 (M + H)+ |
| 170 | 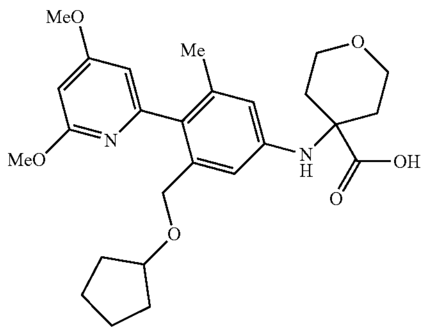 [SMILES: COc1cc(OC)nc(-c2c(C)cc(NC3(C(=O)O)CCOCC3)cc2COC2CCCC2)c1] | 471.2 (M + H)+ |
| 171 | 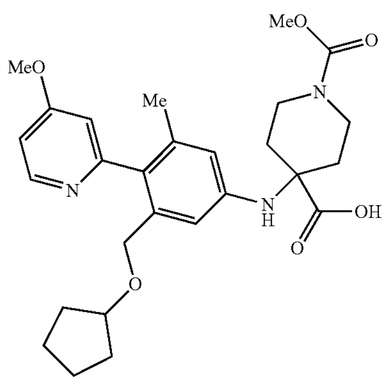 [SMILES: COC(=O)N1CCC(Nc2cc(C)c(-c3cc(OC)ccn3)c(COC3CCCC3)c2)(C(=O)O)CC1] | 498.4 (M + H)+ |
| 172 | 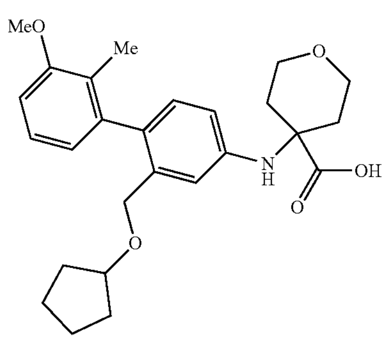 [SMILES: COc1cccc(-c2ccc(NC3(C(=O)O)CCOCC3)cc2COC2CCCC2)c1C] | 440.0 (M + H)+ |

-continued

| Compound | Structure | LC-MS: m/z |
|---|---|---|
| 173 | 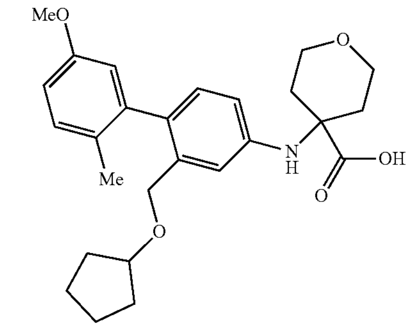 [SMILES: COc1ccc(C)c(-c2ccc(NC3(C(=O)O)CCOCC3)cc2COC2CCCC2)c1] | 440.0 (M + H)+ |
| 174 | 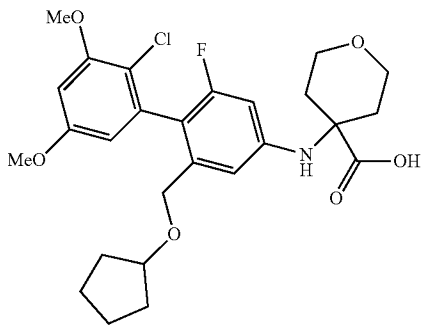 [SMILES: COc1cc(OC)c(Cl)c(-c2c(F)cc(NC3(C(=O)O)CCOCC3)cc2COC2CCCC2)c1] | 508.1 (M + H)+ |
| 175 | 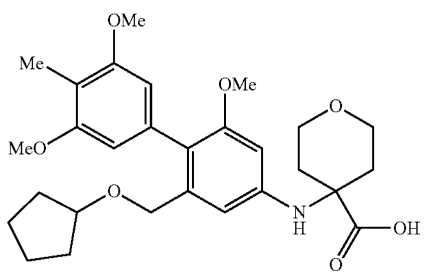 [SMILES: COc1cc(-c2c(COC3CCCC3)cc(NC3(C(=O)O)CCOCC3)cc2OC)cc(OC)c1C] | 500.4 (M + H)+ |
| 176 | 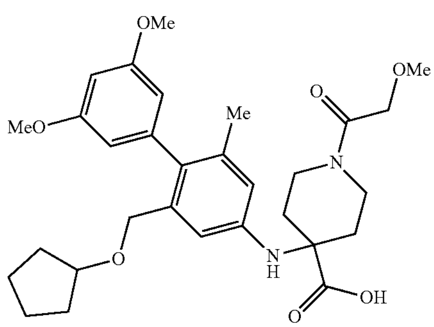 [SMILES: COCC(=O)N1CCC(Nc2cc(C)c(-c3cc(OC)cc(OC)c3)c(COC3CCCC3)c2)(C(=O)O)CC1] | 563.3 (M + Na)+ |
| 178 | 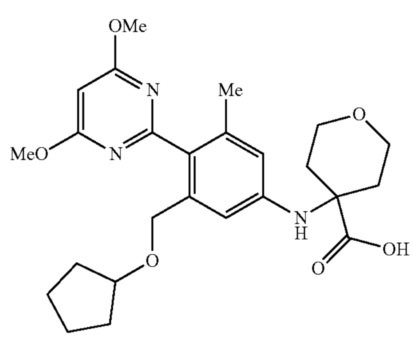 [SMILES: COc1cc(OC)nc(-c2c(C)cc(NC3(C(=O)O)CCOCC3)cc2COC2CCCC2)n1] | 472.0 (M + H)+ |

-continued

| Compound | Structure | LC-MS: m/z |
|---|---|---|
| 179 | 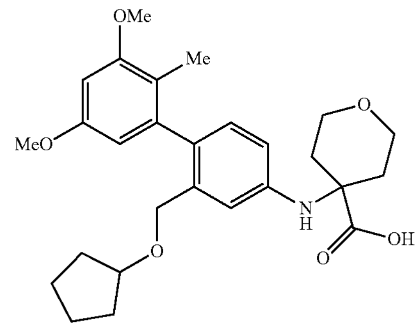 [SMILES: COc1cc(OC)c(C)c(-c2ccc(NC3(C(=O)O)CCOCC3)cc2COC2CCCC2)c1] | 470.0 (M + H)+ |
| 180 | 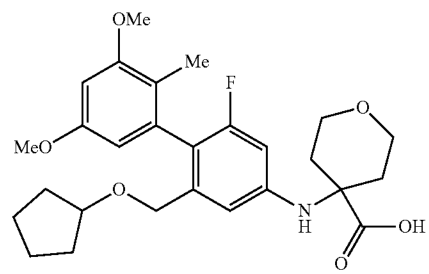 [SMILES: COc1cc(OC)c(C)c(-c2c(F)cc(NC3(C(=O)O)CCOCC3)cc2COC2CCCC2)c1] | 488.3 (M + H)+ |
| 181 | 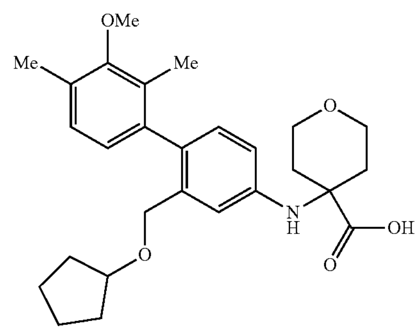 [SMILES: COc1c(C)ccc(-c2ccc(NC3(C(=O)O)CCOCC3)cc2COC2CCCC2)c1C] | 454.1 (M + H)+ |
| 182 | 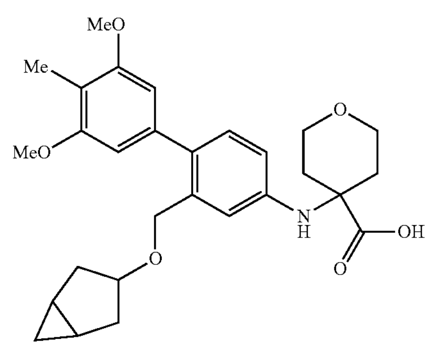 [SMILES: COc1cc(-c2ccc(NC3(C(=O)O)CCOCC3)cc2COC2CC3CC3C2)cc(OC)c1C] | 482.1 (M + H)+ |
| 184 | 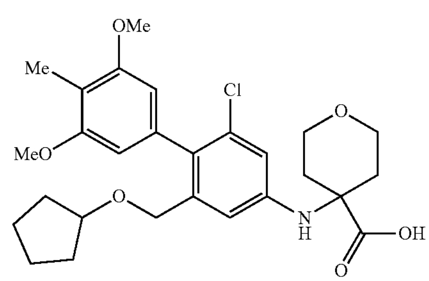 [SMILES: COc1cc(-c2c(Cl)cc(NC3(C(=O)O)CCOCC3)cc2COC2CCCC2)cc(OC)c1C] | 504.3 (M + H)+ |

-continued

| Compound | Structure | LC-MS: m/z |
|---|---|---|
| 185 | Enantiomer 1 | 470.3 (M + H)+ |
| 186 | Enantiomer 2 | 470.3 (M + H)+ |
| 188 | 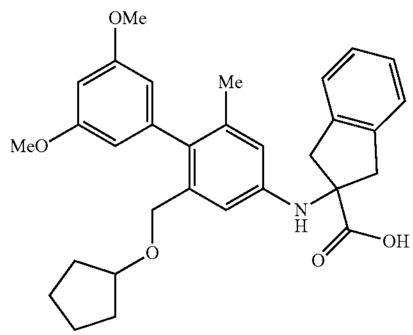 [SMILES: COc1cc(OC)cc(-c2c(C)cc(NC3(C(=O)O)Cc4ccccc4C3)cc2COC2CCCC2)c1] | 502.3 (M + H)+ |
| 189 | 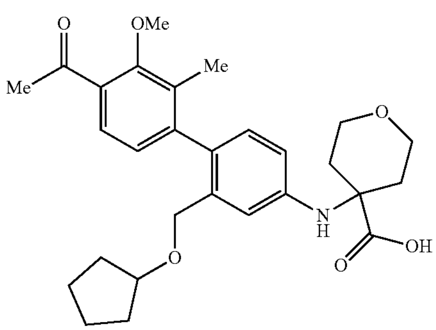 [SMILES: COc1c(C(C)=O)ccc(-c2ccc(NC3(C(=O)O)CCOCC3)cc2COC2CCCC2)c1C] | 482.1 (M + H)+ |
| 190 | 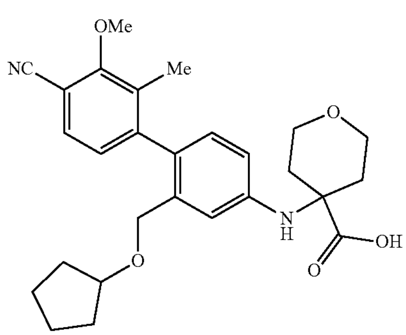 [SMILES: COc1c(C#N)ccc(-c2ccc(NC3(C(=O)O)CCOCC3)cc2COC2CCCC2)c1C] | 465.3 (M + H)+ |

-continued

| Compound | Structure | LC-MS: m/z |
|---|---|---|
| 191 | 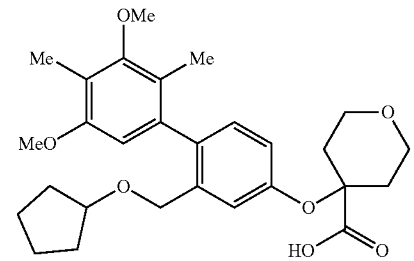 [SMILES: COc1cc(-c2ccc(OC3(C(=O)O)CCOCC3)cc2COC2CCCC2)c(C)c(OC)c1C] | 507.2 (M + Na)+ |
| 192 | 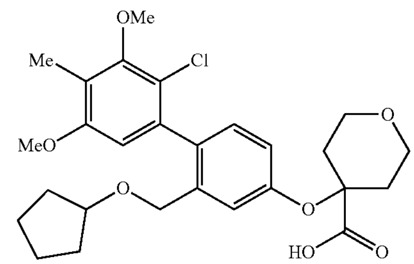 [SMILES: COc1cc(-c2ccc(OC3(C(=O)O)CCOCC3)cc2COC2CCCC2)c(Cl)c(OC)c1C] | 522.2 (M + NH4)+ |
| 193 | 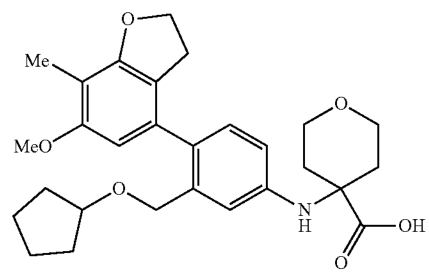 [SMILES: COc1cc(-c2ccc(NC3(C(=O)O)CCOCC3)cc2COC2CCCC2)c2c(c1C)OCC2] | 482.3 (M + H)+ |
| 194 | 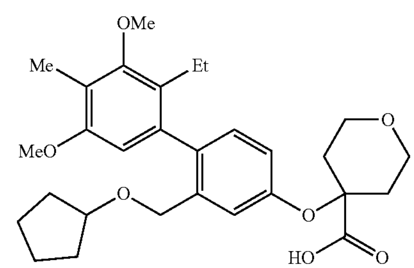 [SMILES: CCc1c(-c2ccc(OC3(C(=O)O)CCOCC3)cc2COC2CCCC2)cc(OC)c(C)c1OC] | 521.3 (M + Na)+ |
| 195 | 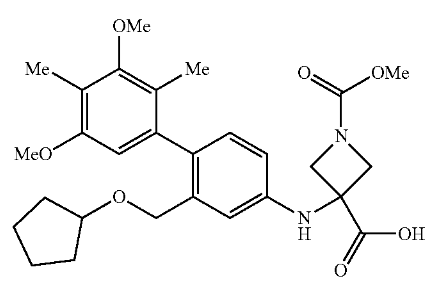 [SMILES: COC(=O)N1CC(Nc2ccc(-c3cc(OC)c(C)c(OC)c3C)c(COC3CCCC3)c2)(C(=O)O)C1] | 535.1 (M + Na)+ |

-continued
| Compound | Structure | LC-MS: m/z |
|---|---|---|
| 196 | 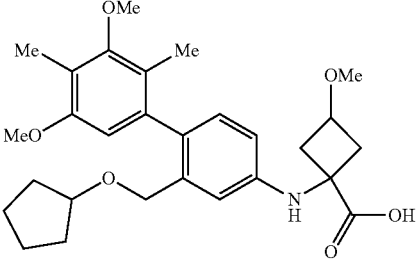<br>Enantiomer 1 | 484.3 (M + H)⁺ |
| 197 | 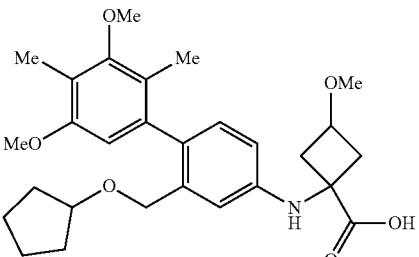<br>Enantiomer 2 | 484.3 (M + H)⁺ |
| 198 | 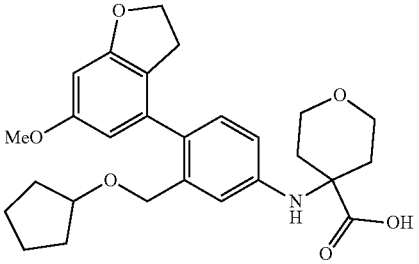 [SMILES: COc1cc2c(c(-c3ccc(NC4(C(=O)O)CCOCC4)cc3COC3CCCC3)c1)CCO2] | 468.3 (M + H)⁺ |
| 199 | 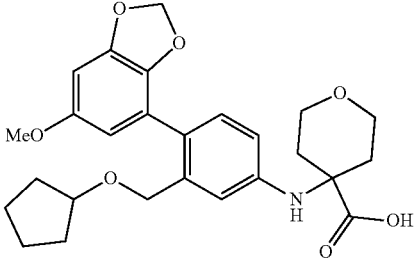 [SMILES: COc1cc2c(c(-c3ccc(NC4(C(=O)O)CCOCC4)cc3COC3CCCC3)c1)OCO2] | 470.3 (M + H)⁺ |
| 200 | 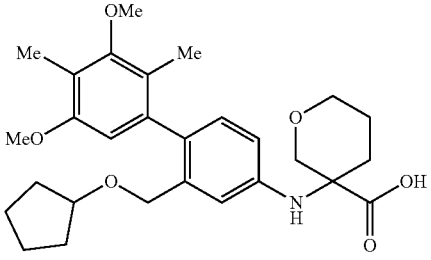<br>Enantiomer 1 | 484.3 (M + H)⁺ |

-continued
| Compound | Structure | LC-MS: m/z |
|---|---|---|
| 201 | 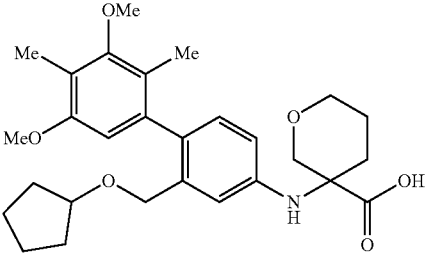<br>Enantiomer 2 | 484.3 (M + H)+ |
| 202 | 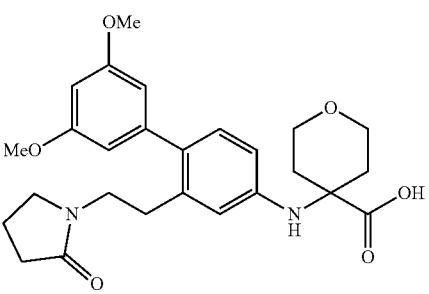 [SMILES: COc1cc(OC)cc(-c2ccc(NC3(C(=O)O)CCOCC3)cc2CCN2CCCC2=O)c1] | 469.0 (M + H)+ |
| 203 | 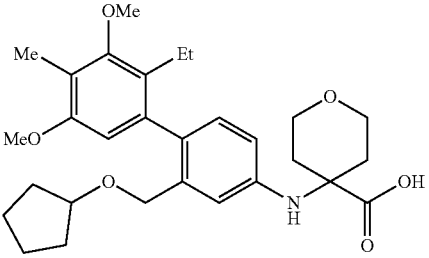 [SMILES: CCc1c(-c2ccc(NC3(C(=O)O)CCOCC3)cc2COC2CCCC2)cc(OC)c(C)c1OC] | 498.3 (M + H)+ |
| 204 | 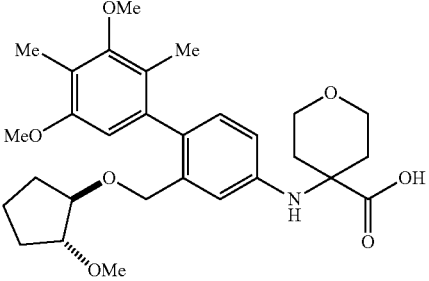<br>Trans (mixture of enantiomers) | 514.3 (M + H)+ |
| 205 | 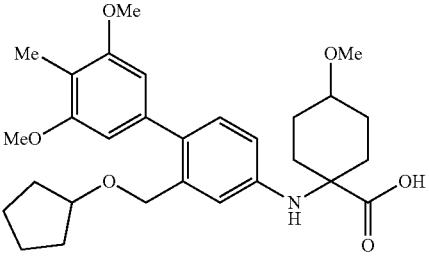 [SMILES: COc1cc(-c2ccc(NC3(C(=O)O)CCC(OC)CC3)cc2COC2CCCC2)cc(OC)c1C] | 498.1 (M + H)+ |

-continued
| Compound | Structure | LC-MS: m/z |
|---|---|---|
| 206 | 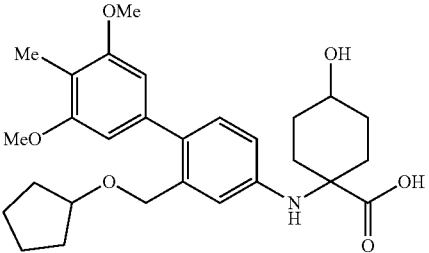 [SMILES: COc1cc(-c2ccc(NC3(C(=O)O)CCC(O)CC3)cc2COC2CCCC2)cc(OC)c1C] | 484.1 (M + H)+ |
| 207 | 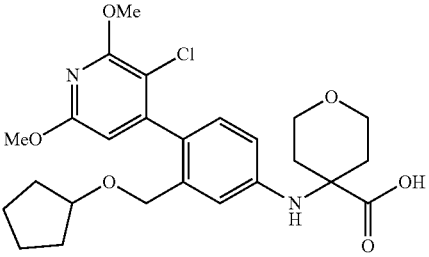 [SMILES: COc1cc(-c2ccc(NC3(C(=O)O)CCOCC3)cc2COC2CCCC2)c(Cl)c(OC)n1] | 491.2 M + H)+ |
| 208 | 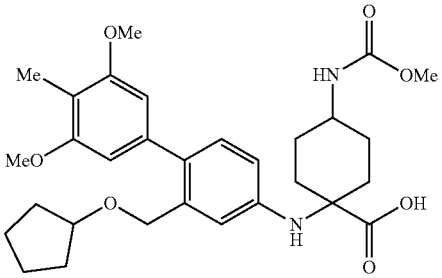 [SMILES: COC(=O)NC1CCC(Nc2ccc(-c3cc(OC)c(C)c(OC)c3)c(COC3CCCC3)c2)(C(=O)O)CC1] | 541.2 (M + H)+ |
| 209 | 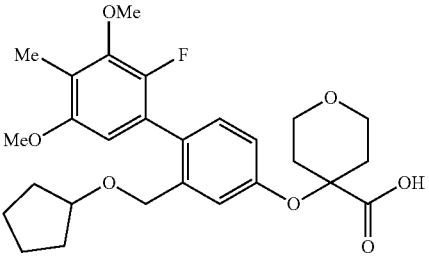 [SMILES: COc1cc(-c2ccc(OC3(C(=O)O)CCOCC3)cc2COC2CCCC2)c(F)c(OC)c1C] | 506.3 (M + NH$_4$)+ |
| 210 | 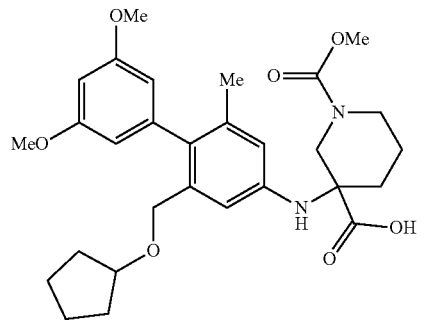<br>Enantiomer 1 | 527.2 (M + H)+ |

-continued

| Compound | Structure | LC-MS: m/z |
|---|---|---|
| 211 | Enantiomer 2 | 527.2 (M + H)+ |
| 212 | 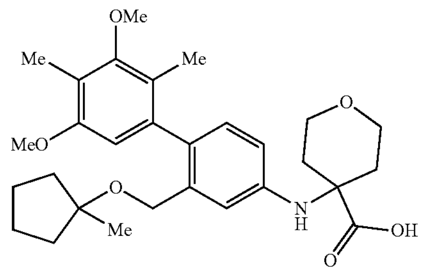 [SMILES: COc1cc(-c2ccc(NC3(C(=O)O)CCOCC3)cc2COC2(C)CCCC2)c(C)c(OC)c1C] | 498.4 (M + H)+ |
| 213 | Enantiomer 1 | 498.1 (M + H)+ |
| 214 | Enantiomer 2 | 498.2 (M + H)+ |
| 215 | 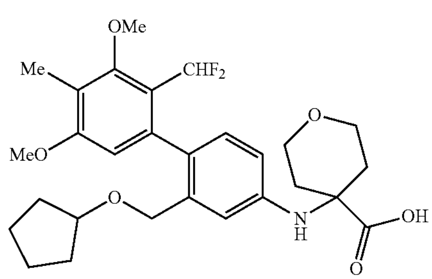 [SMILES: COc1cc(-c2ccc(NC3(C(=O)O)CCOCC3)cc2COC2CCCC2)c(C(F)F)c(OC)c1C] | 520.1 (M + H)+ |

-continued
| Compound | Structure | LC-MS: m/z |
| --- | --- | --- |
| 216 | 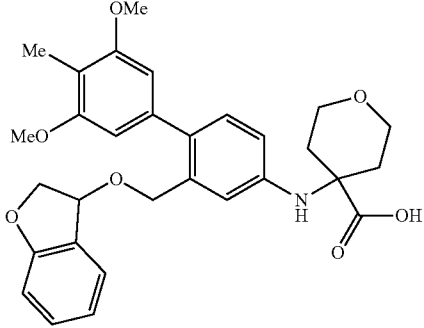<br>Enantiomer 1 | 520.4 (M + H)+ |
| 217 | 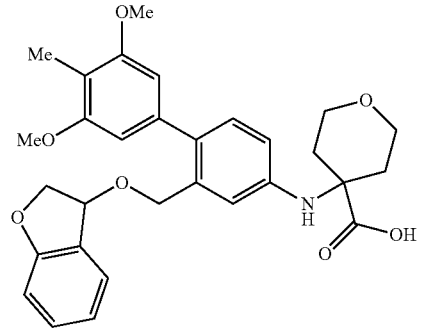<br>Enantiomer 2 | 520.4 (M + H)+ |
| 218 | 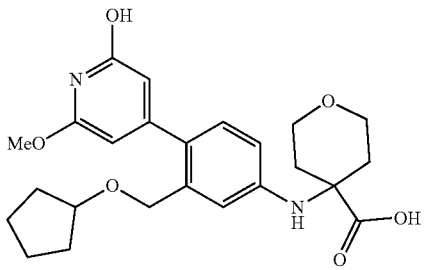 [SMILES: COc1cc(-c2ccc(NC3(C(=O)O)CCOCC3)cc2COC2CCCC2)cc(O)n1] | 443.0 (M + H)+ |
| 219 | 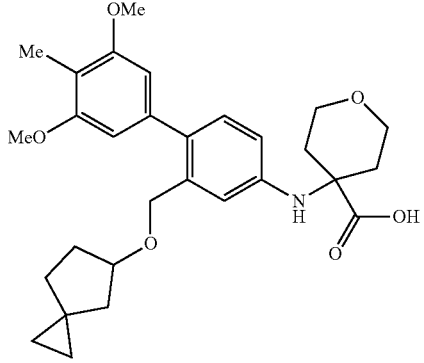 [SMILES: COc1cc(-c2ccc(NC3(C(=O)O)CCOCC3)cc2COC2CCC3(CC3)C2)cc(OC)c1C] | 496.1 (M + H)+ |

-continued
| Compound | Structure | LC-MS: m/z |
|---|---|---|
| 220 | 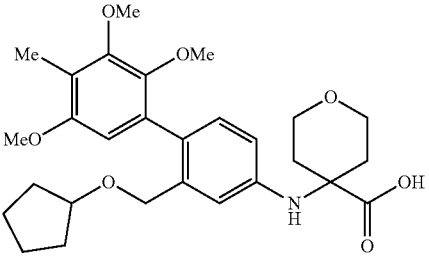 [SMILES: COc1cc(-c2ccc(NC3(C(=O)O)CCOCC3)cc2COC2CCCC2)c(OC)c(OC)c1C] | 500.4 (M + H)⁺ |
| 222 | 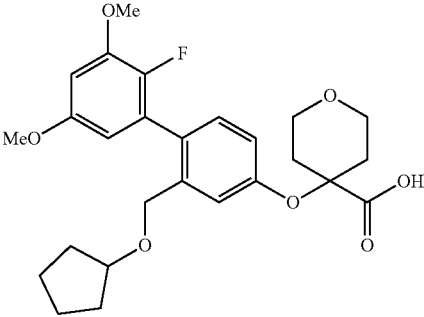 [SMILES: COc1cc(OC)c(F)c(-c2ccc(OC3(C(=O)O)CCOCC3)cc2COC2CCCC2)c1] | 492.2 (M + NH₄)⁺ |
| 223 | 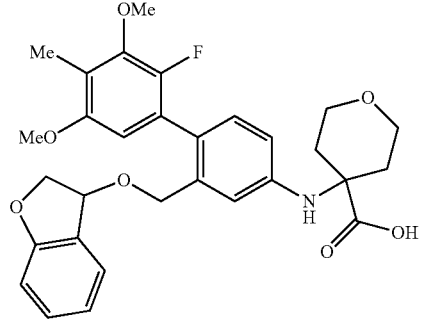<br>Enantiomer 1 | 538.3 (M + H)⁺ |
| 224 | 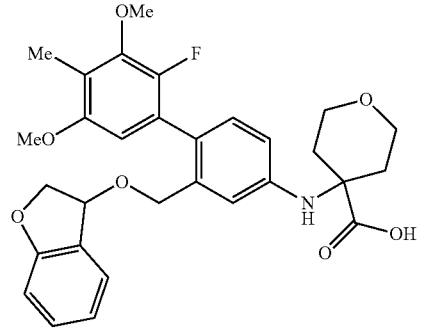<br>Enantiomer 2 | 538.3 (M + H)⁺ |

-continued

| Compound | Structure | LC-MS: m/z |
|---|---|---|
| 225 | 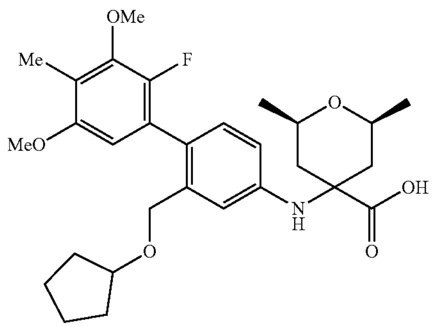 [SMILES: COc1cc(-c2ccc(NC3(C(=O)O)C[C@@H](C)O[C@@H](C)C3)cc2COC2CCCC2)c(F)c(OC)c1C] | 516.4 (M + H)+ |
| 226 | 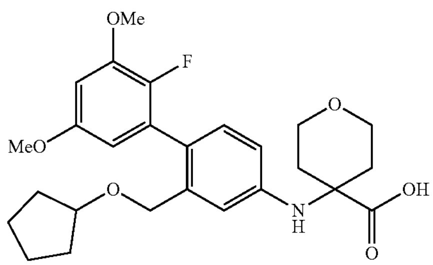 [SMILES: COc1cc(OC)c(F)c(-c2ccc(NC3(C(=O)O)CCOCC3)cc2COC2CCCC2)c1] | 474.0 (M + H)+ |
| 227 | 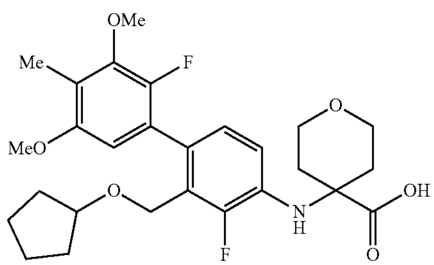 [SMILES: COc1cc(-c2ccc(NC3(C(=O)O)CCOCC3)c(F)c2COC2CCCC2)c(F)c(OC)c1C] | 528.1 (M + Na)+ |
| 228 | 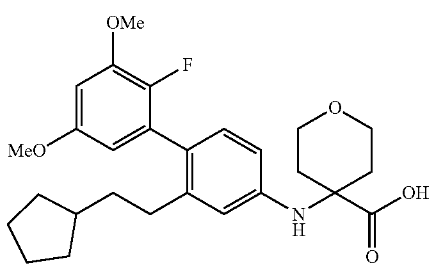 | 472.3 (M + H)+ |
| 229 | 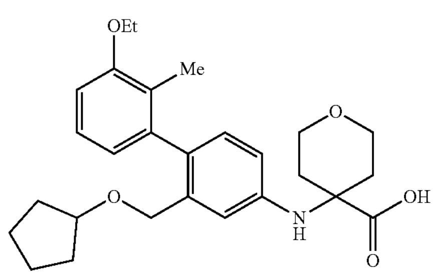 [SMILES: CCOc1cccc(-c2ccc(NC3(C(=O)O)CCOCC3)cc2COC2CCCC2)c1C] | 454.1 (M + H)+ |

| Compound | Structure | LC-MS: m/z |
|---|---|---|
| 230 | 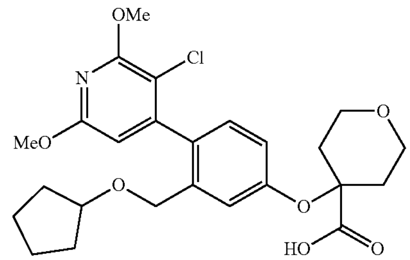 [SMILES: COc1cc(-c2ccc(OC3(C(=O)O)CCOCC3)cc2COC2CCCC2)c(Cl)c(OC)n1] | 492.0 (M + H)+ |
| 232 | 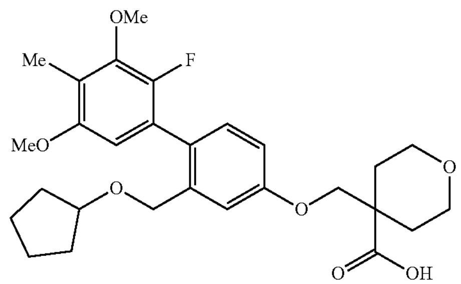 [SMILES: COc1cc(-c2ccc(OCC3(C(=O)O)CCOCC3)cc2COC2CCCC2)c(F)c(OC)c1C] | 520.3 (M + NH4)+ |
| 233 | 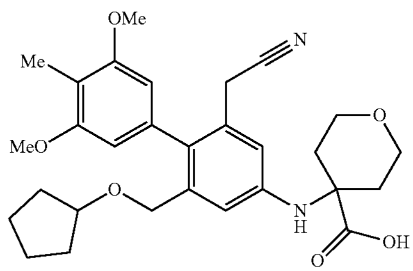 [SMILES: COc1cc(-c2c(CC#N)cc(NC3(C(=O)O)CCOCC3)cc2COC2CCCC2)cc(OC)c1C] | 509.1 (M + H)+ |
| 234 | 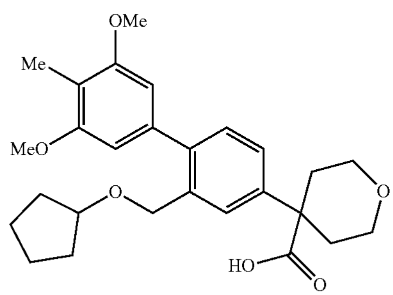 [SMILES: COc1cc(-c2ccc(C3(C(=O)O)CCOCC3)cc2COC2CCCC2)cc(OC)c1C] | 477.3 (M + Na)+ |
| 235 | 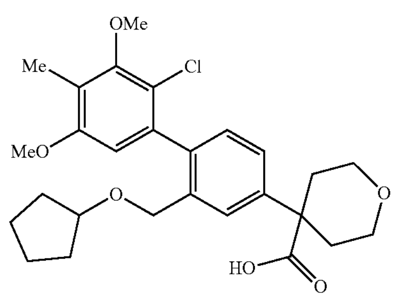 [SMILES: COc1cc(-c2ccc(C3(C(=O)O)CCOCC3)cc2COC2CCCC2)c(Cl)c(OC)c1C] | 506.2 (M + NH4)+ |

-continued

| Compound | Structure | LC-MS: m/z |
|---|---|---|
| 236 | 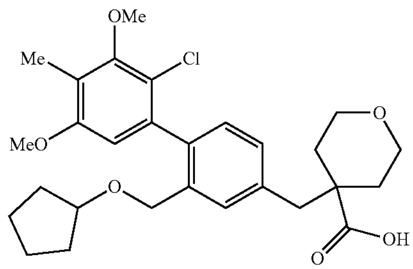 [SMILES: COc1cc(-c2ccc(CC3(C(=O)O)CCOCC3)cc2COC2CCCC2)c(Cl)c(OC)c1C] | 525.1 (M + Na)⁺ |
| 237 | Enantiomer 1 | 530.4 (M + H)⁺ |
| 238 | Enantiomer 2 | 530.4 (M + H)⁺ |
| 239 | 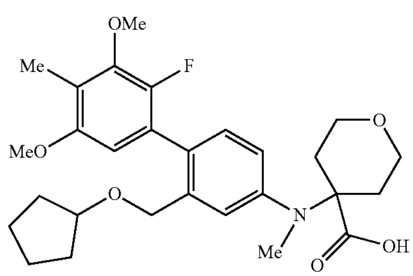 [SMILES: COc1cc(-c2ccc(N(C)C3(C(=O)O)CCOCC3)cc2COC2CCCC2)c(F)c(OC)c1C] | 502.3 (M + H)⁺ |
| 240 | 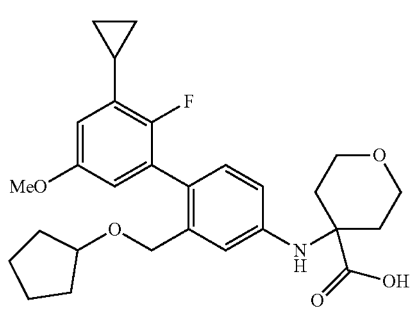 [SMILES: COc1cc(-c2ccc(NC3(C(=O)O)CCOCC3)cc2COC2CCCC2)c(F)c(C2CC2)c1] | 484.0 (M + H)⁺ |

-continued
| Compound | Structure | LC-MS: m/z |
|---|---|---|
| 241 | 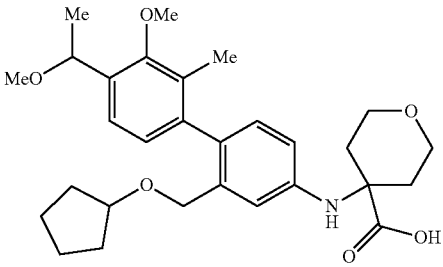<br>Enantiomer 1 | 498.2 (M + H)⁺ |
| 242 | 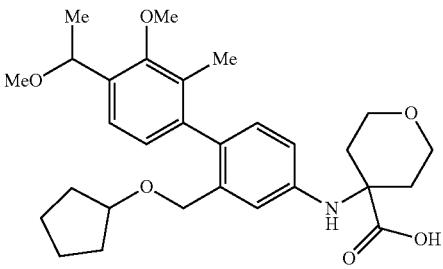<br>Enantiomer 2 | 498.1 (M + H)⁺ |
| 243 | 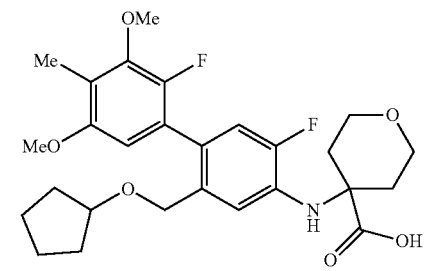 [SMILES: COc1cc(-c2cc(F)c(NC3(C(=O)O)CCOCC3)cc2COC2CCCC2)c(F)c(OC)c1C] | 506.0 (M + H)⁺ |
| 244 | 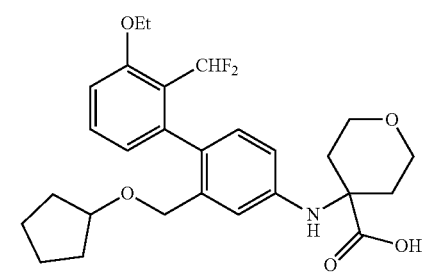 [SMILES: CCOc1cccc(-c2ccc(NC3(C(=O)O)CCOCC3)cc2COC2CCCC2)c1C(F)F] | 490.2 (M + NH$_4$)⁺ |
| 245 | 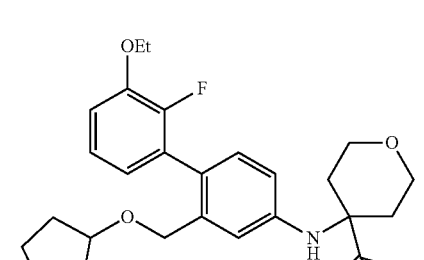 | 458.5 (M + NH$_4$)⁺ |

-continued
| Compound | Structure | LC-MS: m/z |
|---|---|---|
| 246 | 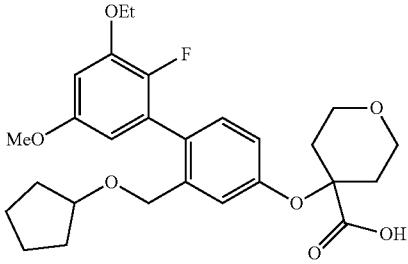 [SMILES: CCOc1cc(OC)cc(-c2ccc(OC3(C(=O)O)CCOCC3)cc2COC2CCCC2)c1F] | 511.1 (M + Na)+ |
| 247 | 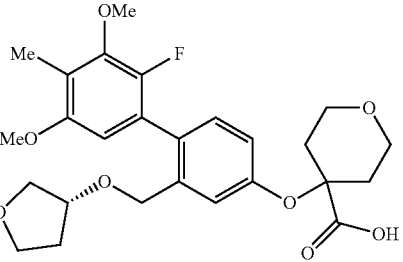 | 508.2 (M + NH4)+ |
| 248 | 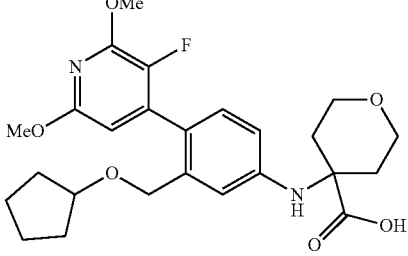 | 475.3 (M + H)+ |
| 249 | 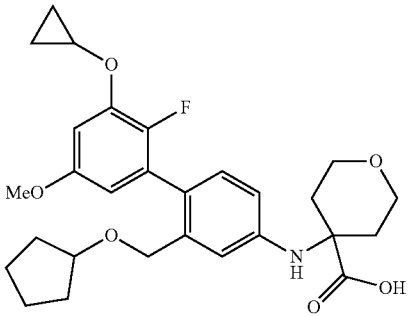 [SMILES: COc1cc(OC2CC2)c(F)c(-c2ccc(NC3(C(=O)O)CCOCC3)cc2COC2CCCC2)c1] | 500.1 (M + H)+ |
| 250 | 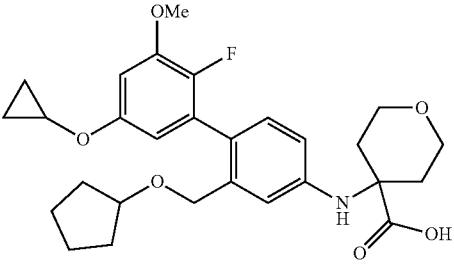 [SMILES: COc1cc(OC2CC2)cc(-c2ccc(NC3(C(=O)O)CCOCC3)cc2COC2CCCC2)c1F] | 500.1 (M + H)+ |

-continued

| Compound | Structure | LC-MS: m/z |
|---|---|---|
| 251 | 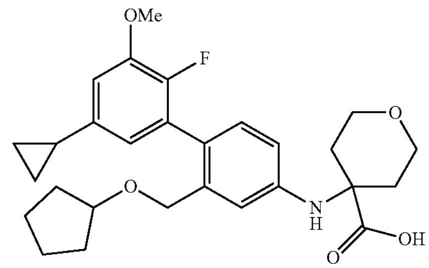 [SMILES: COc1cc(C2CC2)cc(-c2ccc(NC3(C(=O)O)CCOCC3)cc2COC2CCCC2)c1F] | 484.1 (M + H)+ |
| 252 | 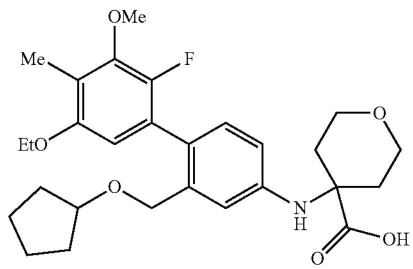 [SMILES: CCOc1cc(-c2ccc(NC3(C(=O)O)CCOCC3)cc2COC2CCCC2)c(F)c(OC)c1C] | 516.2 (M + H)+ |
| 253 | 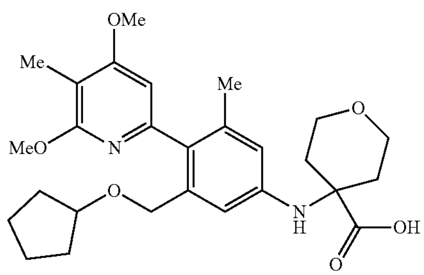 [SMILES: COc1cc(-c2c(C)cc(NC3(C(=O)O)CCOCC3)cc2COC2CCCC2)nc(OC)c1C] | 485.3 (M + H)+ |
| 254 | 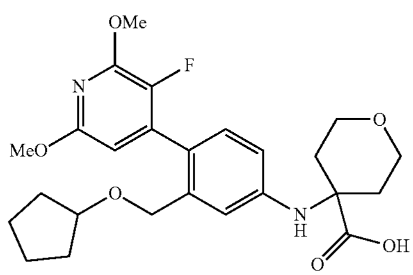 [SMILES: COc1cc(-c2ccc(NC3(C(=O)O)CCOCC3)cc2COC2CCCC2)c(F)c(OC)n1] | 476.1 (M + H)+ |
| 255 | 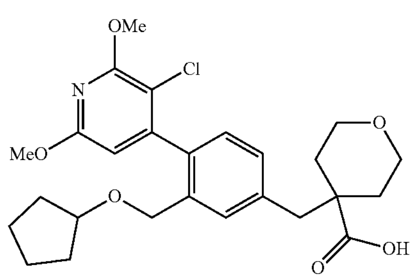 [SMILES: COc1cc(-c2ccc(CC3(C(=O)O)CCOCC3)cc2COC2CCCC2)c(Cl)c(OC)n1] | 490.0 (M + H)+ |

-continued

| Compound | Structure | LC-MS: m/z |
|---|---|---|
| 256 | 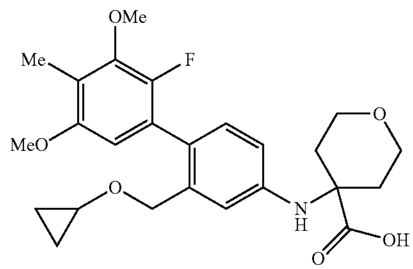 [SMILES: COc1cc(-c2ccc(NC3(C(=O)O)CCOCC3)cc2COC2CC2)c(F)c(OC)c1C] | 460.3 (M + H)+ |
| 257 | 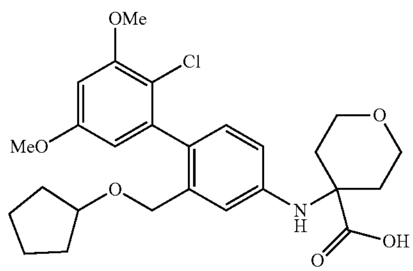 [SMILES: COc1cc(OC)c(Cl)c(-c2ccc(NC3(C(=O)O)CCOCC3)cc2COC2CCCC2)c1] | 490.1 (M + H)+ |
| 259 | Enantiomer 1 | 511.2 (M + Na)+ |
| 260 | Enantiomer 2 | 511.2 (M + Na)+ |
| 261 | 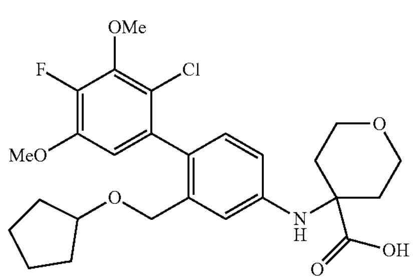 [SMILES: COc1cc(-c2ccc(NC3(C(=O)O)CCOCC3)cc2COC2CCCC2)c(Cl)c(OC)c1F] | 508.3 (M + H)+ |

-continued

| Compound | Structure | LC-MS: m/z |
|---|---|---|
| 262 | 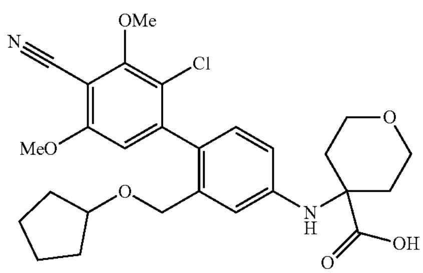 [SMILES: COc1cc(-c2ccc(NC3(C(=O)O)CCOCC3)cc2COC2CCCC2)c(Cl)c(OC)c1C#N] | 515.0 (M + H)⁺ |
| 263 | 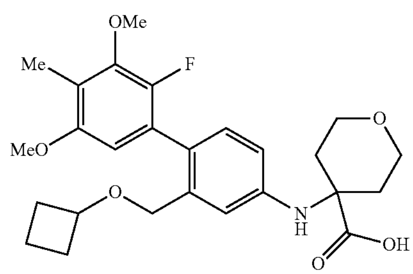 [SMILES: COc1cc(-c2ccc(NC3(C(=O)O)CCOCC3)cc2COC2CCC2)c(F)c(OC)c1C] | 474.0 (M + H)⁺ |
| 264 | 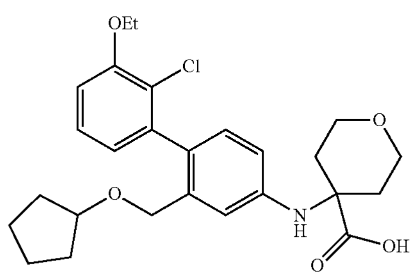 [SMILES: CCOc1cccc(-c2ccc(NC3(C(=O)O)CCOCC3)cc2COC2CCCC2)c1Cl] | 474.0 (M + H)⁺ |
| 265 | 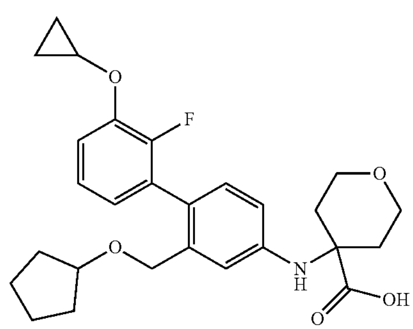 [SMILES: O=C(O)C1(Nc2ccc(-c3cccc(OC4CC4)c3F)c(COC3CCCC3)c2)CCOCC1] | 470.3 (M + H)⁺ |
| 266 | 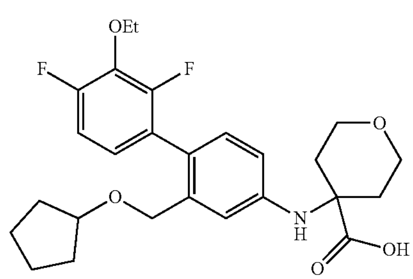 [SMILES: CCOc1c(F)ccc(-c2ccc(NC3(C(=O)O)CCOCC3)cc2COC2CCCC2)c1F] | 476.3 (M + H)⁺ |

-continued

| Compound | Structure | LC-MS: m/z |
|---|---|---|
| 267 | 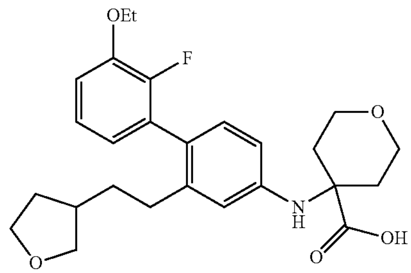 [SMILES: CCOc1cccc(-c2ccc(NC3(C(=O)O)CCOCC3)cc2CCC2CCOC2)c1F] | 458.0 (M + H)+ |
| 268 | Enantiomer 1 | 492.1 (M + H)+ |
| 269 | Enantiomer 2 | 492.1 (M + H)+ |
| 270 | 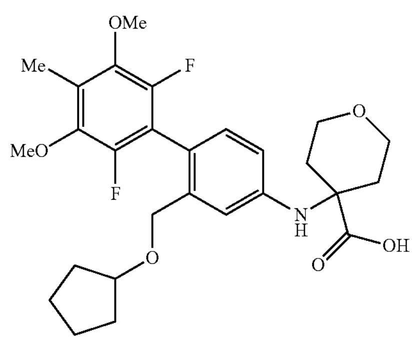 [SMILES: COc1c(C)c(OC)c(F)c(-c2ccc(NC3(C(=O)O)CCOCC3)cc2COC2CCCC2)c1F] | 506.2 (M + H)+ |
| 271 | 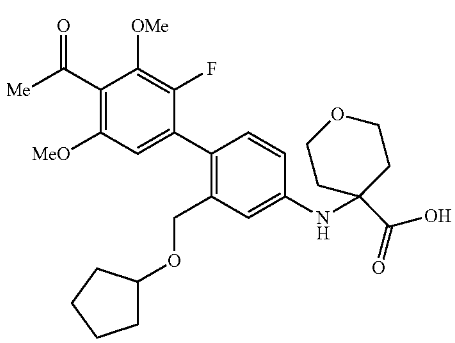 [SMILES: COc1cc(-c2ccc(NC3(C(=O)O)CCOCC3)cc2COC2CCCC2)c(F)c(OC)c1C(C)=O] | 516.2 (M + H)+ |

-continued

| Compound | Structure | LC-MS: m/z |
|---|---|---|
| 272 | 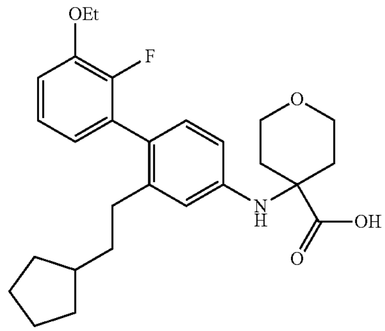 [SMILES: CCOc1cccc(-c2ccc(NC3(C(=O)O)CCOCC3)cc2CCC2CCCC2)c1F] | 456.3 (M + H)+ |
| 273 | 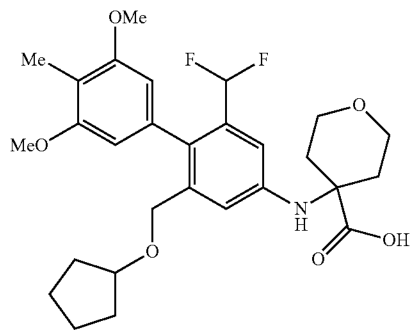 [SMILES: COc1cc(-c2c(COC3CCCC3)cc(NC3(C(=O)O)CCOCC3)cc2C(F)F)cc(OC)c1C] | 520.5 (M + H)+ |
| 274 | 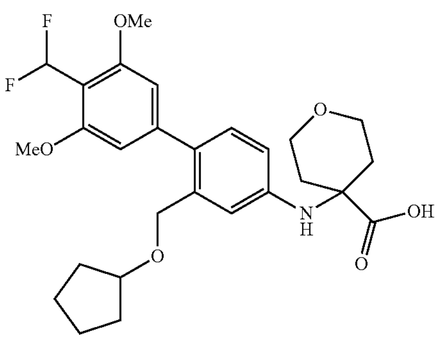 [SMILES: COc1cc(-c2ccc(NC3(C(=O)O)CCOCC3)cc2COC2CCCC2)cc(OC)c1C(F)F] | 506.1 (M + H)+ |
| 275 | 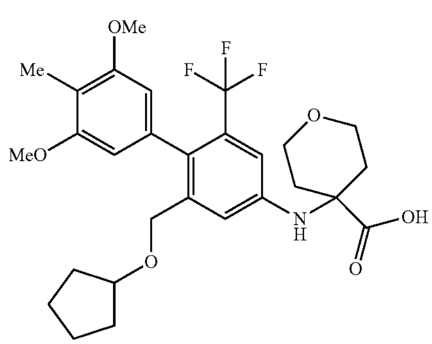 [SMILES: COc1cc(-c2c(COC3CCCC3)cc(NC3(C(=O)O)CCOCC3)cc2C(F)(F)F)cc(OC)c1C] | 538.1 (M + H)+ |

-continued
| Compound | Structure | LC-MS: m/z |
|---|---|---|
| 276 | 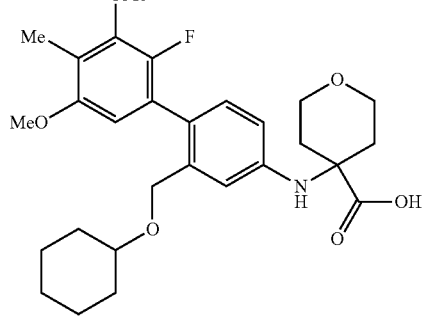 | 502.1 (M + H)+ |
| 277 | 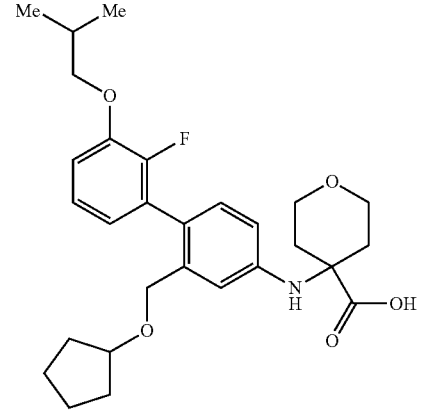 [SMILES: CC(C)COc1cccc(-c2ccc(NC3(C(=O)O)CCOCC3)cc2COC2CCCC2)c1F] | 486.1 (M + H)+ |
| 278 | 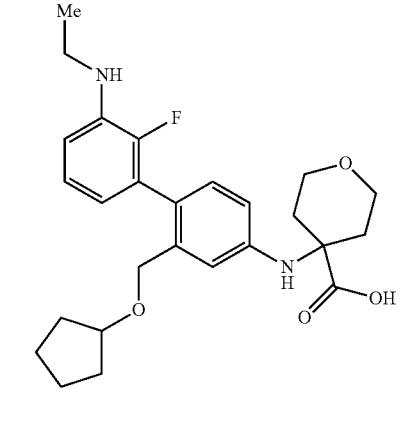 [SMILES: CCNc1cccc(-c2ccc(NC3(C(=O)O)CCOCC3)cc2COC2CCCC2)c1F] | 457.3 (M + H)+ |
| 279 | 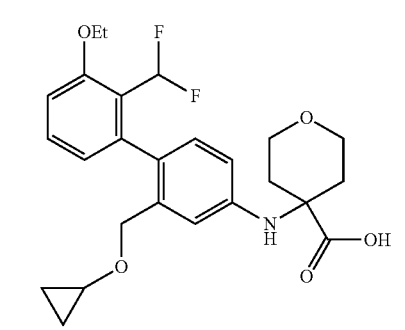 [SMILES: CCOc1cccc(-c2ccc(NC3(C(=O)O)CCOCC3)cc2COC2CC2)c1C(F)F] | 462.2 (M + H)+ |

-continued

| Compound | Structure | LC-MS: m/z |
|---|---|---|
| 280 | 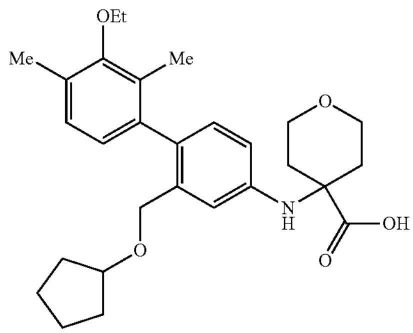 | 468.3 (M + H)+ |
| 281 | 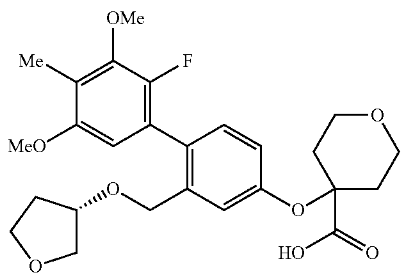 [SMILES: COc1cc(-c2ccc(OC3(C(=O)O)CCOCC3)cc2CO[C@H]2CCOC2)c(F)c(OC)c1C] | 508.1 (M + NH4)+ |
| 282 | 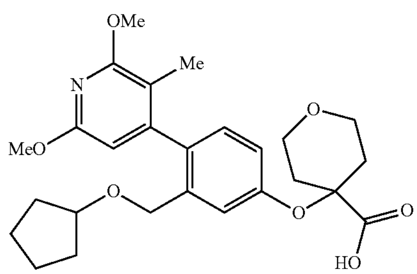 [SMILES: COc1cc(-c2ccc(OC3(C(=O)O)CCOCC3)cc2COC2CCCC2)c(C)c(OC)n1] | 471.3 (M + H)+ |
| 283 | 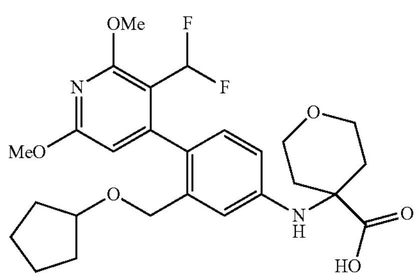 [SMILES: COc1cc(-c2ccc(NC3(C(=O)O)CCOCC3)cc2COC2CCCC2)c(C(F)F)c(OC)n1] | 507.3 (M + H)+ |
| 284 | 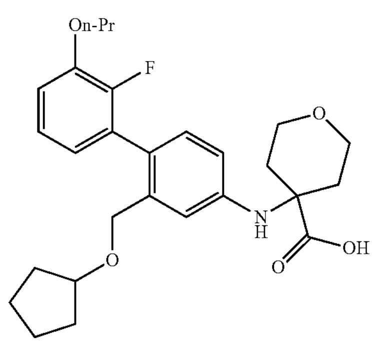 | 472.0 (M + H)+ |

-continued

| Compound | Structure | LC-MS: m/z |
|---|---|---|
| 285 | 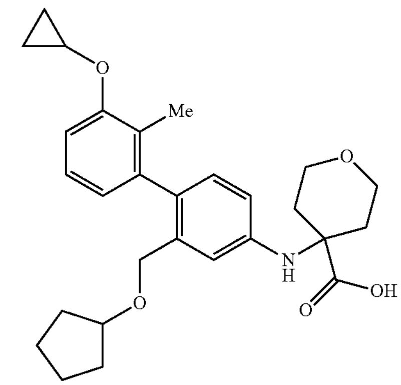 [SMILES: Cc1c(OC2CC2)cccc1-c1ccc(NC2(C(=O)O)CCOCC2)cc1COC1CCCC1] | 466.1 (M + H)+ |
| 286 | 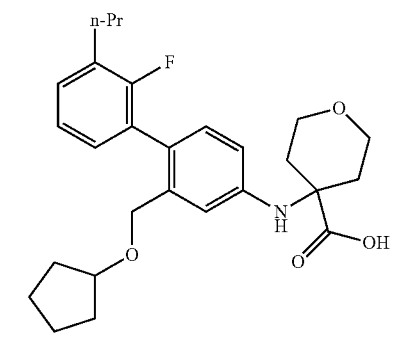 | 456.1 (M + H)+ |
| 287 | 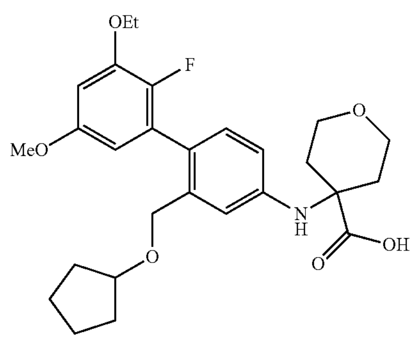 [SMILES: CCOc1cc(OC)cc(-c2ccc(NC3(C(=O)O)CCOCC3)cc2COC2CCCC2)c1F] | 486.5 (M − H)− |
| 288 | 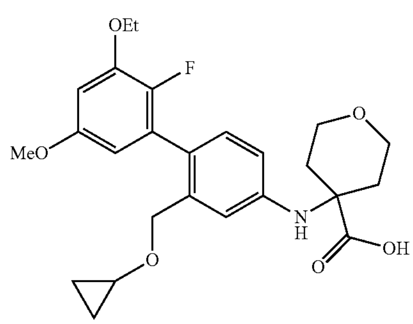 [SMILES: CCOc1cc(OC)cc(-c2ccc(NC3(C(=O)O)CCOCC3)cc2COC2CC2)c1F] | 458.4 (M − H)− |

-continued
| Compound | Structure | LC-MS: m/z |
|---|---|---|
| 289 | 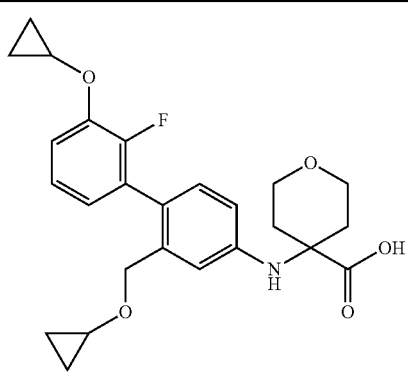 | 442.2 (M + H)+ |
| 290 | 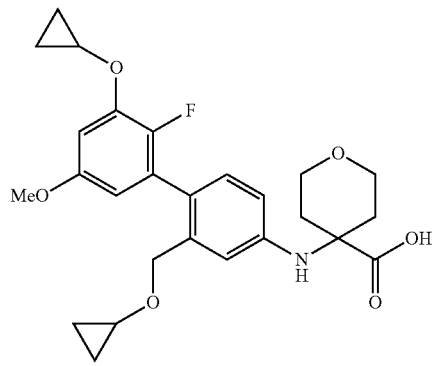 [SMILES: COc1cc(OC2CC2)c(F)c(-c2ccc(NC3(C(=O)O)CCOCC3)cc2COC2CC2)c1] | 472.0 (M + H)+ |
| 291 | 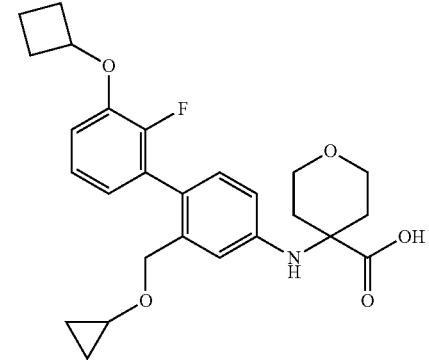 [SMILES: O=C(O)C1(Nc2ccc(-c3cccc(OC4CCC4)c3F)c(COC3CC3)c2)CCOCC1] | 456.2 (M + H)+ |
| 292 | 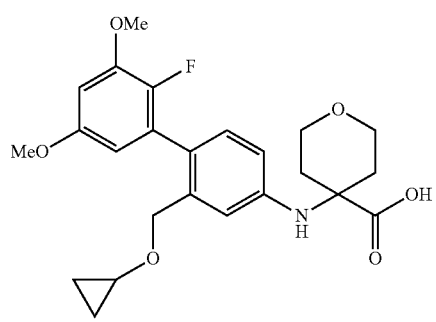 | 446.1 (M + H)+ |

| Compound | Structure | LC-MS: m/z |
|---|---|---|
| 293 | 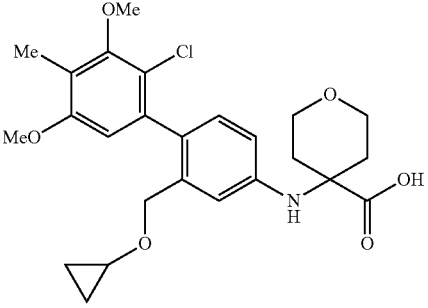 [SMILES: COc1cc(-c2ccc(NC3(C(=O)O)CCOCC3)cc2COC2CC2)c(Cl)c(OC)c1C] | 476.2 (M + H)+ |
| 294 | 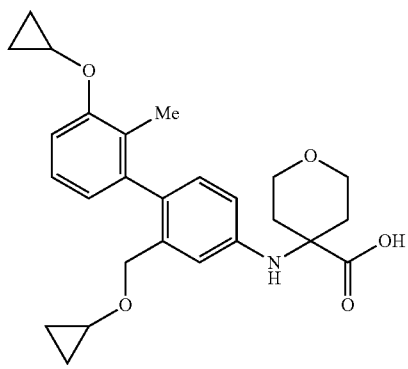 [SMILES: Cc1c(OC2CC2)cccc1-c1ccc(NC2(C(=O)O)CCOCC2)cc1COC1CC1] | 438.2 (M + H)+ |
| 295 | 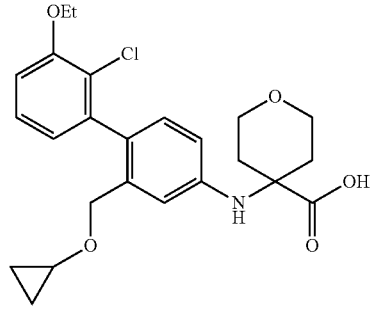 | 446.2 (M + H)+ |
| 296 | 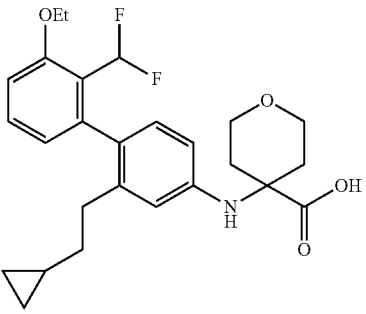 [SMILES: CCOc1cccc(-c2ccc(NC3(C(=O)O)CCOCC3)cc2CCC2CC2)c1C(F)F] | 460.1 (M + H)+ |

-continued
| Compound | Structure | LC-MS: m/z |
|---|---|---|
| 297 | 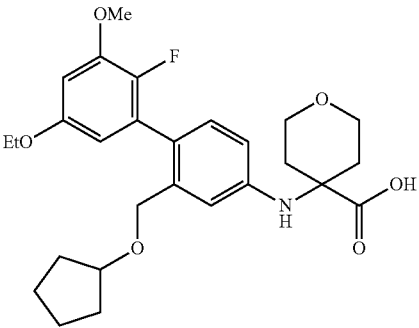 [SMILES: CCOc1cc(OC)c(F)c(-c2ccc(NC3(C(=O)O)CCOCC3)cc2COC2CCCC2)c1] | 488.1 (M + H)+ |
| 298 | 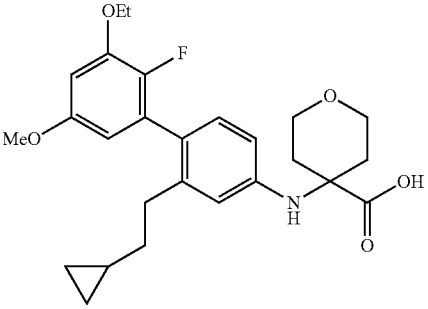 [SMILES: CCOc1cc(OC)cc(-c2ccc(NC3(C(=O)O)CCOCC3)cc2CCC2CC2)c1F] | 458.2 (M + H)+ |
| 299 | 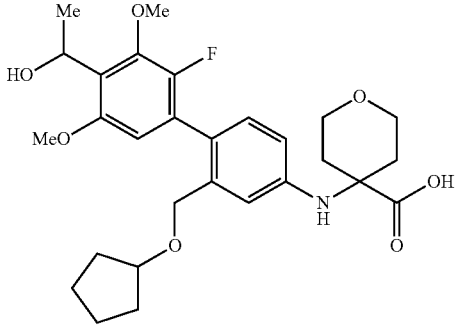<br>Enantiomer 1 | 518.1 (M + H)+ |
| 300 | 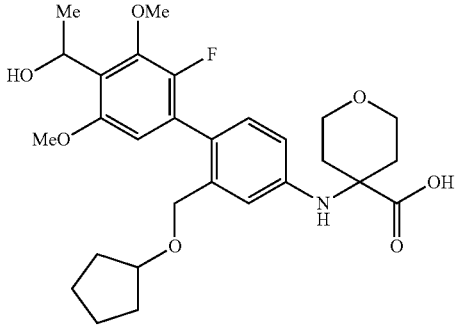<br>Enantiomer 2 | 518.2 (M + H)+ |

-continued

| Compound | Structure | LC-MS: m/z |
|---|---|---|
| 301 | 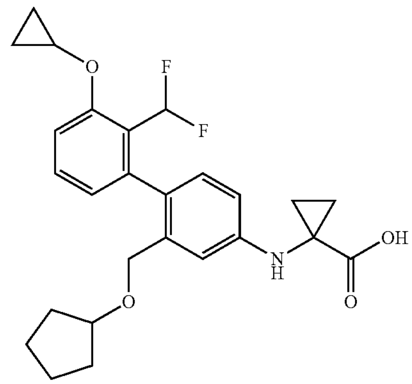 [SMILES: O=C(O)C1(Nc2ccc(-c3cccc(OC4CC4)c3C(F)F)c(COC3CCCC3)c2)CC1] | 480.1 (M + Na)+ |
| 302 | 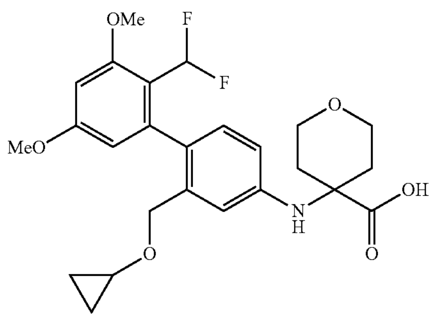 [SMILES: COc1cc(OC)c(C(F)F)c(-c2ccc(NC3(C(=O)O)CCOCC3)cc2COC2CC2)c1] | 478.2 (M + H)+ |
| 303 | 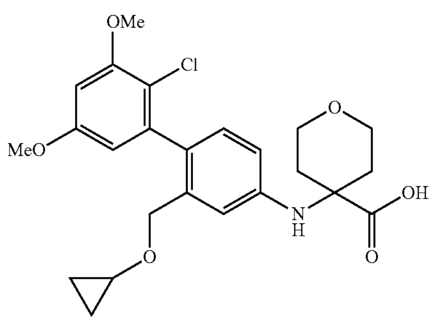 [SMILES: COc1cc(OC)c(Cl)c(-c2ccc(NC3(C(=O)O)CCOCC3)cc2COC2CC2)c1] | 462.2 (M + H)+ |
| 304 | 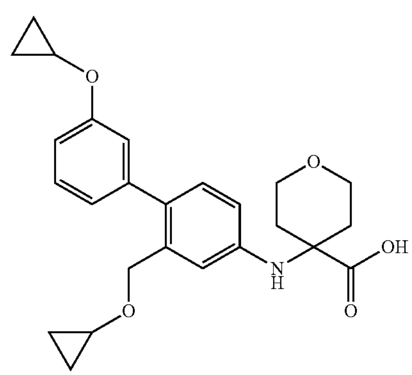 [SMILES: O=C(O)C1(Nc2ccc(-c3cccc(OC4CC4)c3)c(COC3CC3)c2)CCOCC1] | 424.2 (M + H)+ |

-continued

| Compound | Structure | LC-MS: m/z |
|---|---|---|
| 305 | 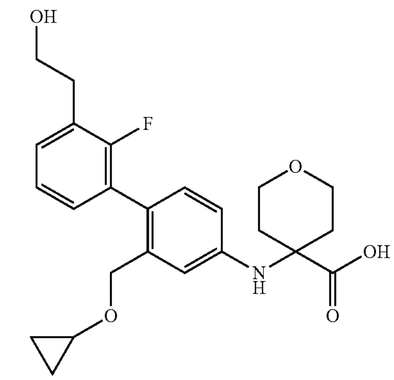 [SMILES: O=C(O)C1(Nc2ccc(-c3cccc(CCO)c3F)c(COC3CC3)c2)CCOCC1] | 430.1 (M + H)⁺ |
| 306 | 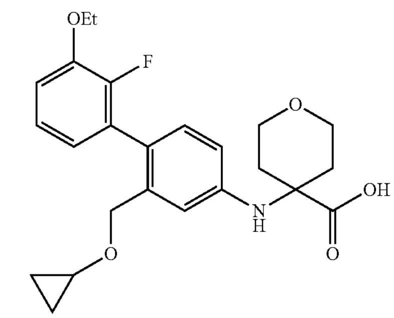 | 430.1 (M + H)⁺ |
| 307 | 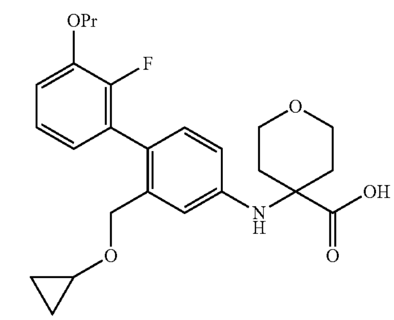 | 444.1 (M + H)⁺ |
| 308 | Enantiomer 1 | 484.1 (M + H)⁺ |

-continued
| Compound | Structure | LC-MS: m/z |
|---|---|---|
| 309 | 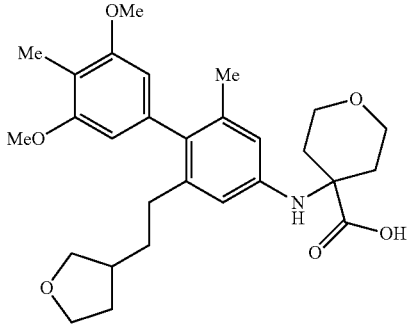 Enantiomer 2 | 484.1 (M + H)+ |
| 310 | 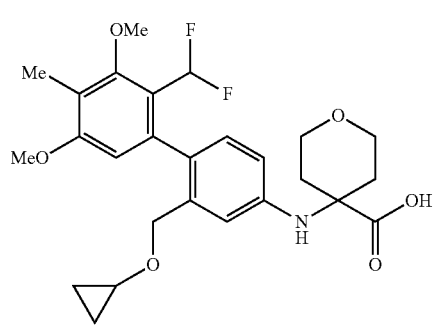 [SMILES: COc1cc(-c2ccc(NC3(C(=O)O)CCOCC3)cc2COC2CC2)c(C(F)F)c(OC)c1C] | 492.2 (M + H)+ |
| 311 | 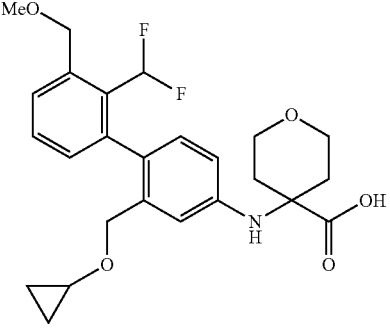 [SMILES: COCc1cccc(-c2ccc(NC3(C(=O)O)CCOCC3)cc2COC2CC2)c1C(F)F] | 462.5 (M + H)+ |
| 312 | 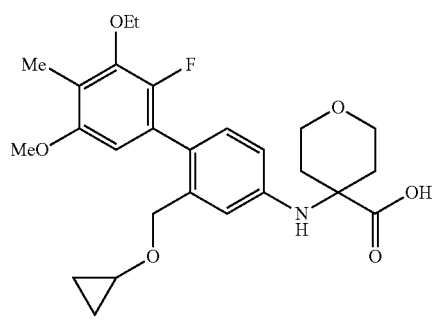 [SMILES: CCOc1c(C)c(OC)cc(-c2ccc(NC3(C(=O)O)CCOCC3)cc2COC2CC2)c1F] | 474.2 (M + H)+ |

-continued

| Compound | Structure | LC-MS: m/z |
|---|---|---|
| 313 | 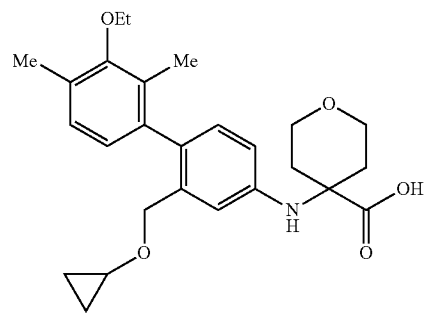 [SMILES: CCOc1c(C)ccc(-c2ccc(NC3(C(=O)O)CCOCC3)cc2COC2CC2)c1C] | 440.1 (M + H)+ |
| 314 | 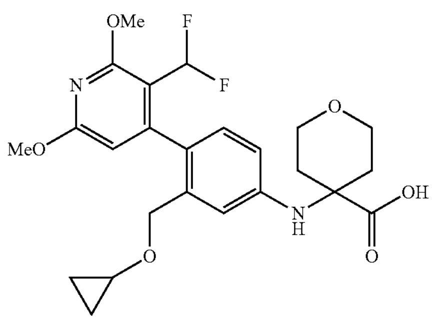 [SMILES: COc1cc(-c2ccc(NC3(C(=O)O)CCOCC3)cc2COC2CC2)c(C(F)F)c(OC)n1] | 479.1 (M + H)+ |
| 315 | 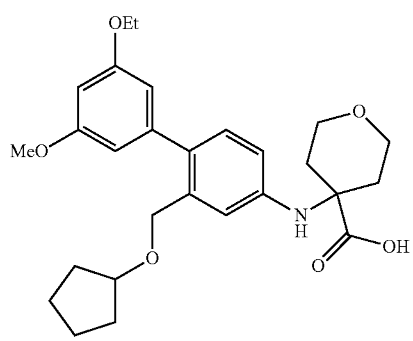 [SMILES: CCOc1cc(OC)cc(-c2ccc(NC3(C(=O)O)CCOCC3)cc2COC2CCCC2)c1] | 470.2 (M + H)+ |
| 316 | 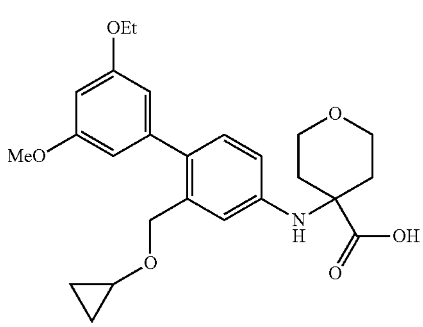 [SMILES: CCOc1cc(OC)cc(-c2ccc(NC3(C(=O)O)CCOCC3)cc2COC2CC2)c1] | 442.1 (M + H)+ |

-continued

| Compound | Structure | LC-MS: m/z |
|---|---|---|
| 317 | 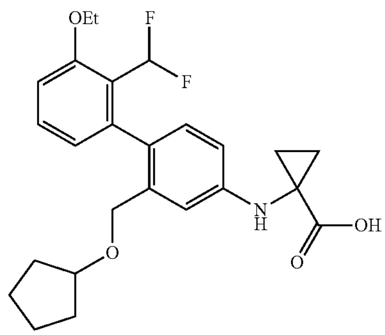 [SMILES: CCOc1cccc(-c2ccc(NC3(C(=O)O)CC3)cc2COC2CCCC2)c1C(F)F] | 446.0 (M + H)+ |
| 318 | 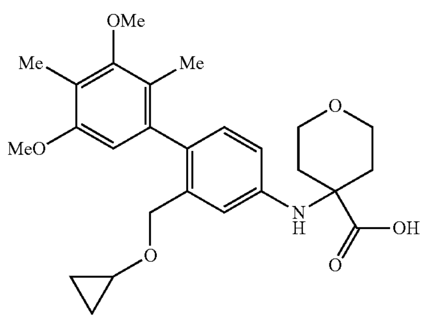 [SMILES: COc1cc(-c2ccc(NC3(C(=O)O)CCOCC3)cc2COC2CC2)c(C)c(OC)c1C] | 456.1 (M + H)+ |
| 319 | 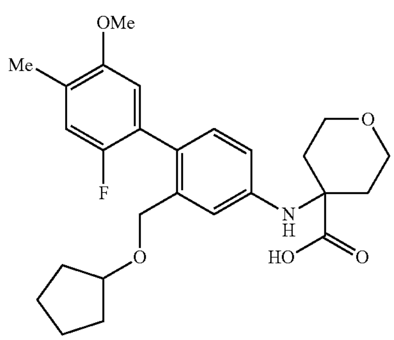 [SMILES: COc1cc(-c2ccc(NC3(C(=O)O)CCOCC3)cc2COC2CCCC2)c(F)cc1C] | 458.6 (M + H)+ |
| 320 | 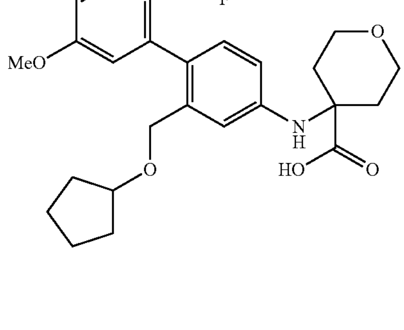 | 506.2 (M + H)+ |

-continued
| Compound | Structure | LC-MS: m/z |
|---|---|---|
| 322 | 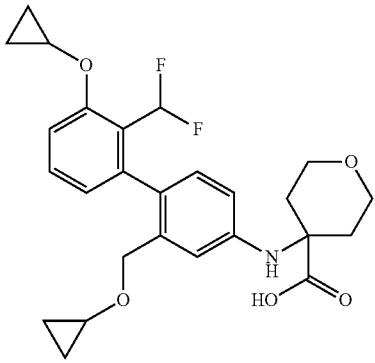 [SMILES: O=C(O)C1(Nc2ccc(-c3cccc(OC4CC4)c3C(F)F)c(COC3CC3)c2)CCOCC1] | 474.0 (M + H)⁺ |
| 323 | 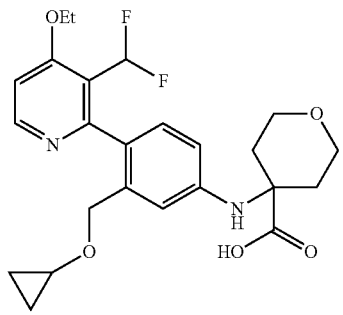 [SMILES: CCOc1ccnc(-c2ccc(NC3(C(=O)O)CCOCC3)cc2COC2CC2)c1C(F)F] | 463.5 (M + H)⁺ |
| 324 | 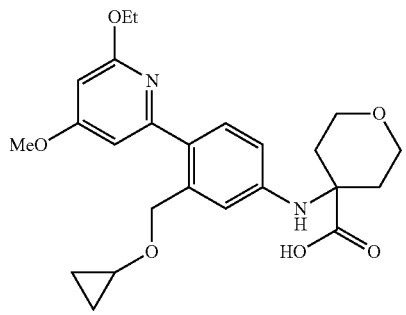 [SMILES: CCOc1cc(OC)cc(-c2ccc(NC3(C(=O)O)CCOCC3)cc2COC2CC2)n1] | 443.5 (M + H)⁺ |
| 325 | 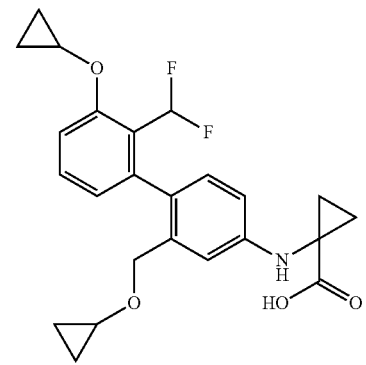 [SMILES: O=C(O)C1(Nc2ccc(-c3cccc(OC4CC4)c3C(F)F)c(COC3CC3)c2)CC1] | 430.2 (M + H)⁺ |

-continued

| Compound | Structure | LC-MS: m/z |
|---|---|---|
| 326 | 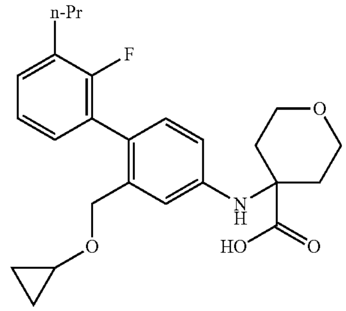 | 428.5 (M + H)+ |
| 327 | 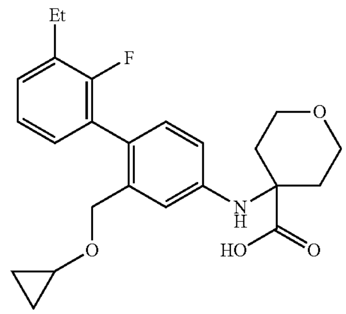 [SMILES: CCc1cccc(-c2ccc(NC3(C(=O)O)CCOCC3)cc2COC2CC2)c1F] | 414.5 (M + H)+ |
| 328 | 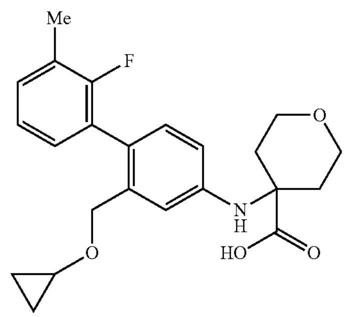 [SMILES: Cc1cccc(-c2ccc(NC3(C(=O)O)CCOCC3)cc2COC2CC2)c1F] | 400.5 (M + H)+ |
| 329 | 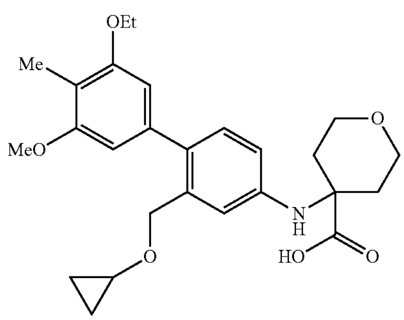 [SMILES: CCOc1cc(-c2ccc(NC3(C(=O)O)CCOCC3)cc2COC2CC2)cc(OC)c1C] | 456.6 (M + H)+ |
| 330 | 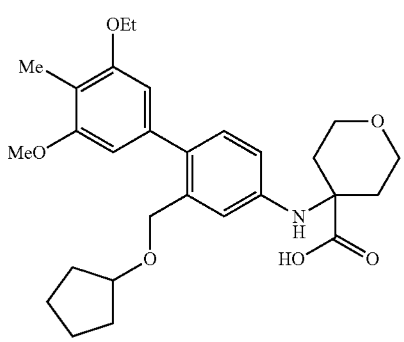 | 484.6 (M + H)+ |

-continued
| Compound | Structure | LC-MS: m/z |
|---|---|---|
| 331 | 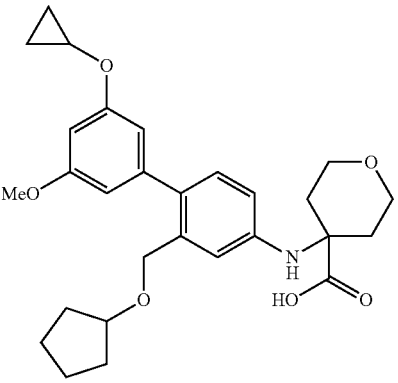 [SMILES: COc1cc(OC2CC2)cc(-c2ccc(NC3(C(=O)O)CCOCC3)cc2COC2CCCC2)c1] | 482.1 (M + H)+ |
| 332 | 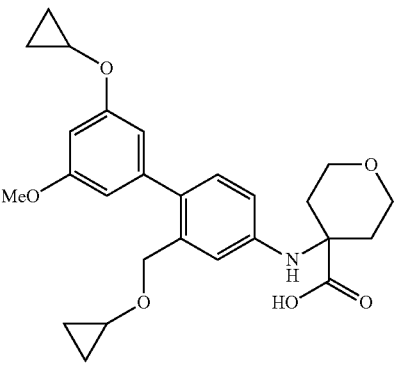 [SMILES: COc1cc(OC2CC2)cc(-c2ccc(NC3(C(=O)O)CCOCC3)cc2COC2CC2)c1] | 454.0 (M + H)+ |
| 333 | 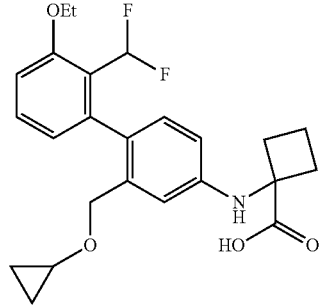 [SMILES: CCOc1cccc(-c2ccc(NC3(C(=O)O)CCC3)cc2COC2CC2)c1C(F)F] | 432.1 (M + H)+ |
| 334 | 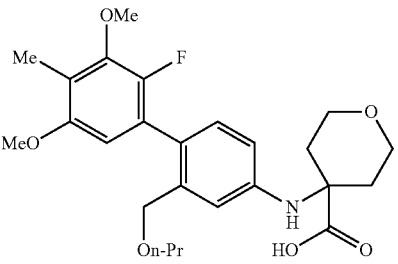 | 462.6 (M + H)+ |
| 335 | 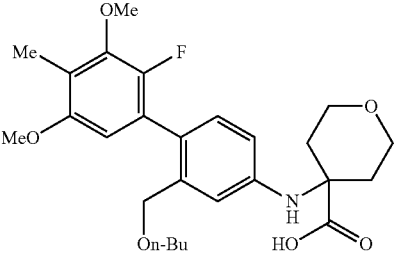 | 476.6 (M + H)+ |

-continued
| Compound | Structure | LC-MS: m/z |
|---|---|---|
| 336 | 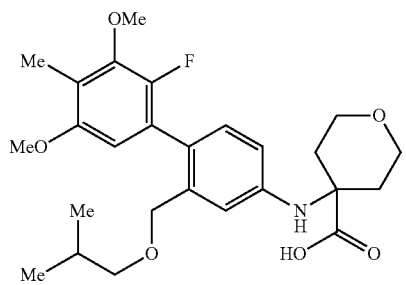 | 476.6 (M + H)+ |
| 337 | 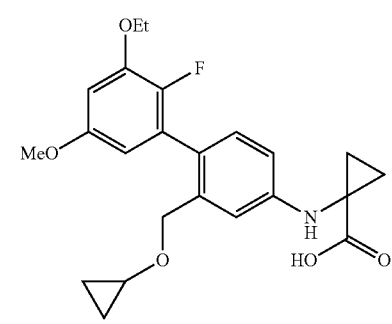 [SMILES: CCOc1cc(OC)cc(-c2ccc(NC3(C(=O)O)CC3)cc2COC2CC2)c1F] | 438.1 (M + Na)+ |
| 338 | 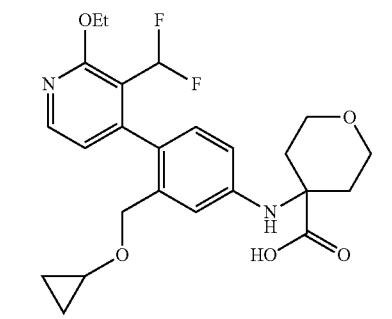 [SMILES: CCOc1nccc(-c2ccc(NC3(C(=O)O)CCOCC3)cc2COC2CC2)c1C(F)F] | 463.3 (M + H)+ |
| 339 | 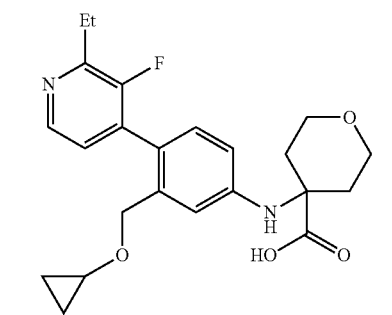 [SMILES: CCc1nccc(-c2ccc(NC3(C(=O)O)CCOCC3)cc2COC2CC2)c1F] | 415.2 (M + H)+ |

-continued

| Compound | Structure | LC-MS: m/z |
|---|---|---|
| 340 | 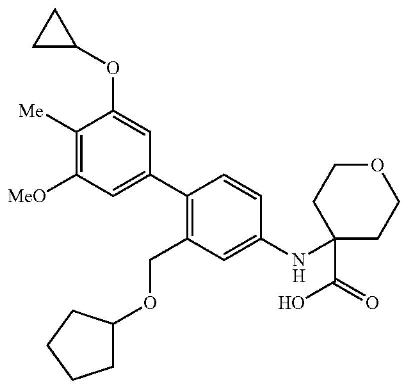 [SMILES: COc1cc(-c2ccc(NC3(C(=O)O)CCOCC3)cc2COC2CCCC2)cc(OC2CC2)c1C] | 496.6 (M + H)+ |
| 341 | 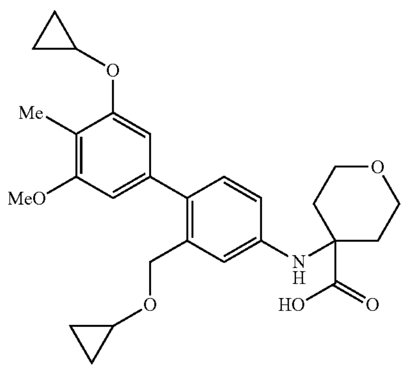 [SMILES: COc1cc(-c2ccc(NC3(C(=O)O)CCOCC3)cc2COC2CC2)cc(OC2CC2)c1C] | 468.2 (M + H)+ |
| 342 | 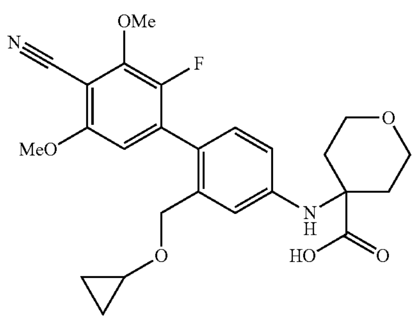 [SMILES: COc1cc(-c2ccc(NC3(C(=O)O)CCOCC3)cc2COC2CC2)c(F)c(OC)c1C#N] | 471.2 (M + H)+ |
| 343 | 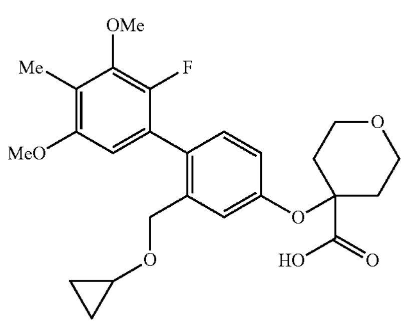 [SMILES: COc1cc(-c2ccc(OC3(C(=O)O)CCOCC3)cc2COC2CC2)c(F)c(OC)c1C] | 483.1 (M + Na)+ |

-continued
| Compound | Structure | LC-MS: m/z |
|---|---|---|
| 344 | 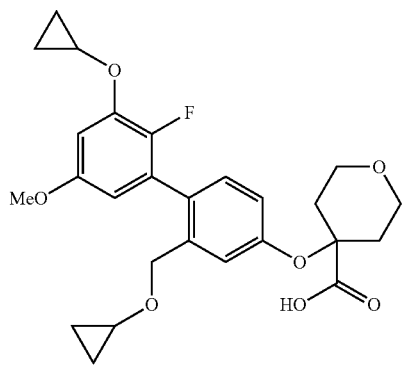 [SMILES: COc1cc(OC2CC2)c(F)c(-c2ccc(OC3(C(=O)O)CCOCC3)cc2COC2CC2)c1] | 495.0 (M + Na)+ |
| 345 | 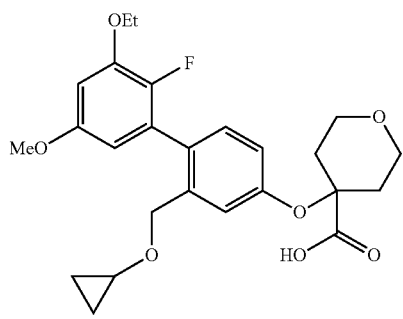 [SMILES: CCOc1cc(OC)cc(-c2ccc(OC3(C(=O)O)CCOCC3)cc2COC2CC2)c1F] | 483.1 (M + Na)+ |
| 346 | 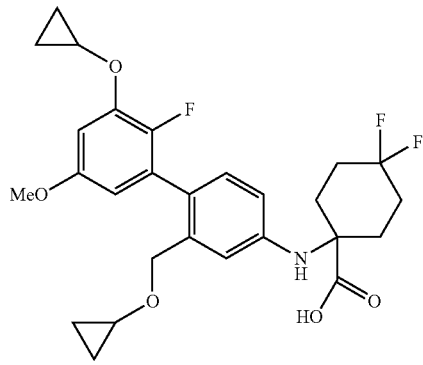 [SMILES: COc1cc(OC2CC2)c(F)c(-c2ccc(NC3(C(=O)O)CCC(F)(F)CC3)cc2COC2CC2)c1] | 506.6 (M + H)+ |
| 347 | 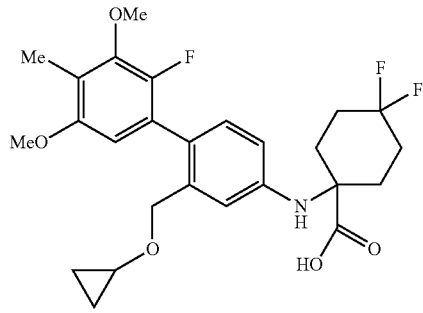 [SMILES: COc1cc(-c2ccc(NC3(C(=O)O)CCC(F)(F)CC3)cc2COC2CC2)c(F)c(OC)c1C] | 494.3 (M + H)+ |

-continued

| Compound | Structure | LC-MS: m/z |
|----------|-----------|------------|
| 348 | 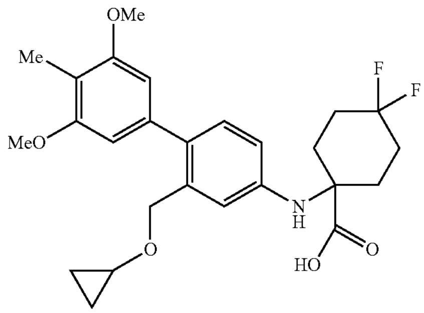 [SMILES: COc1cc(-c2ccc(NC3(C(=O)O)CCC(F)(F)CC3)cc2COC2CC2)cc(OC)c1C] | 476.3 (M + H)⁺ |
| 349 | 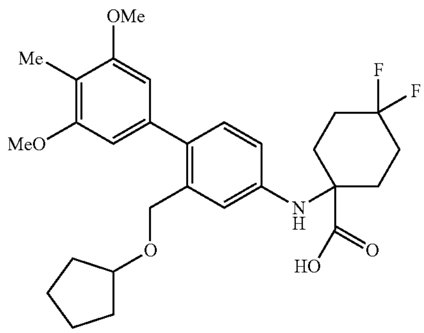 [SMILES: COc1cc(-c2ccc(NC3(C(=O)O)CCC(F)(F)CC3)cc2COC2CCCC2)cc(OC)c1C] | 504.6 (M + H)⁺ |
| 350 | 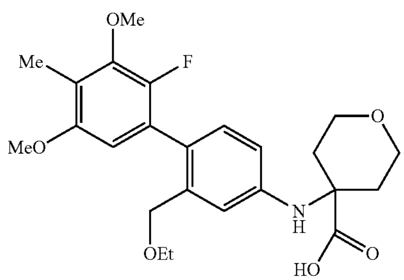 [SMILES: CCOCc1cc(NC2(C(=O)O)CCOCC2)ccc1-c1cc(OC)c(C)c(OC)c1F] | 448.5 (M + H)⁺ |
| 351 | 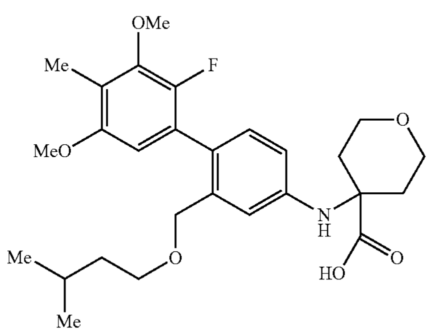 [SMILES: COc1cc(-c2ccc(NC3(C(=O)O)CCOCC3)cc2COCCC(C)C)c(F)c(OC)c1C] | 490.3 (M + H)⁺ |
| 352 | 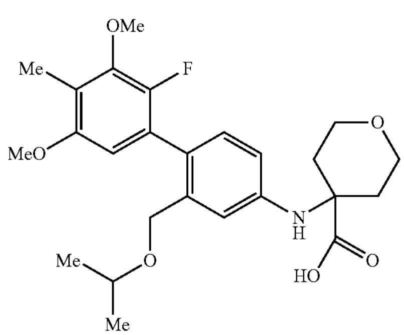 [SMILES: COc1cc(-c2ccc(NC3(C(=O)O)CCOCC3)cc2COC(C)C)c(F)c(OC)c1C] | 462.1 (M + H)⁺ |

-continued
| Compound | Structure | LC-MS: m/z |
|---|---|---|
| 353 | 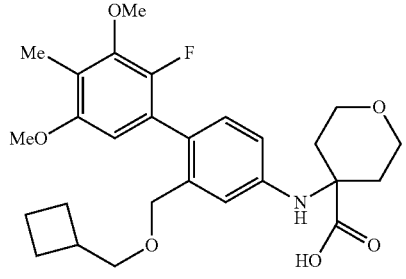 [SMILES: COc1cc(-c2ccc(NC3(C(=O)O)CCOCC3)cc2COCC2CCC2)c(F)c(OC)c1C] | 488.3 (M + H)+ |
| 354 | 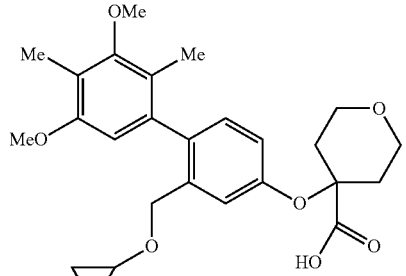 | 479.2 (M + Na)+ |
| 355 | 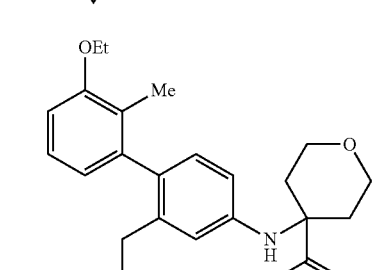 | 426.5 (M + H)+ |
| 356 | 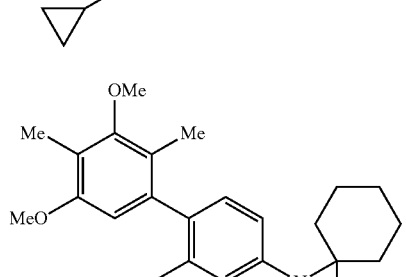 | 458.1 (M + H)+ |
| 357 | 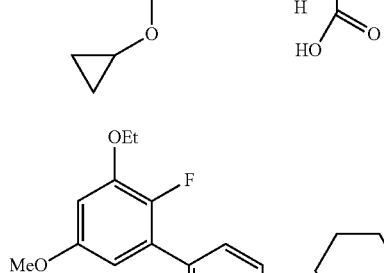 | 458.1 (M + H)+ |

| Compound | Structure | LC-MS: m/z |
|---|---|---|
| 358 | 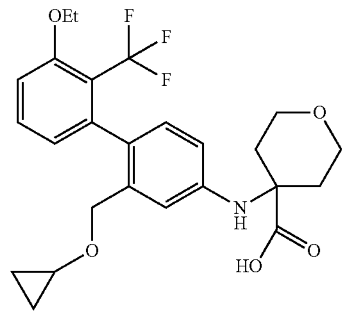 [SMILES: CCOc1cccc(-c2ccc(NC3(C(=O)O)CCOCC3)cc2COC2CC2)c1C(F)(F)F] | 480.1 (M + H)+ |
| 359 | 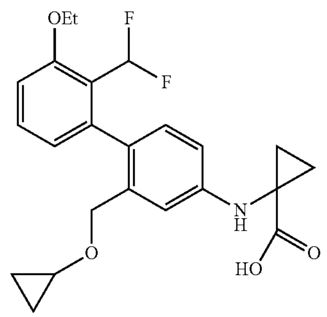 [SMILES: CCOc1cccc(-c2ccc(NC3(C(=O)O)CC3)cc2COC2CC2)c1C(F)F] | 440.1 (M + Na)+ |
| 360 | 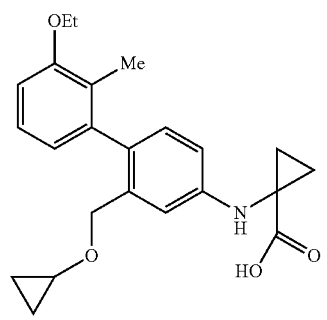 [SMILES: CCOc1cccc(-c2ccc(NC3(C(=O)O)CC3)cc2COC2CC2)c1C] | 404.1 (M + Na)+ |
| 361 | 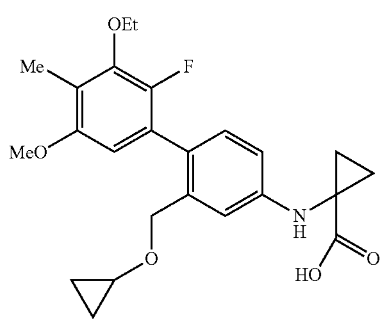 [SMILES: CCOc1c(C)c(OC)cc(-c2ccc(NC3(C(=O)O)CC3)cc2COC2CC2)c1F] | 430.1 (M + H)+ |
| 362 | 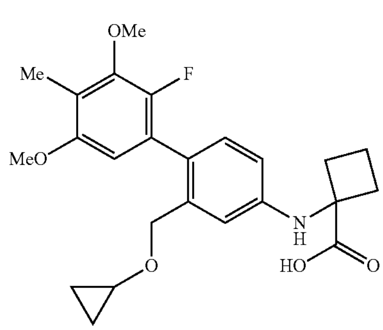 [SMILES: COc1cc(-c2ccc(NC3(C(=O)O)CCC3)cc2COC2CC2)c(F)c(OC)c1C] | 430.1 (M + H)+ |

-continued

| Compound | Structure | LC-MS: m/z |
|---|---|---|
| 363 | 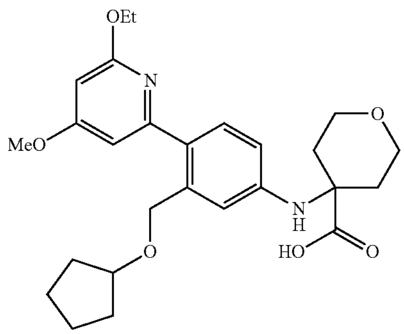 [SMILES: CCOc1cc(OC)cc(-c2ccc(NC3(C(=O)O)CCOCC3)cc2COC2CCCC2)n1] | 471.5 (M + H)+ |
| 364 | 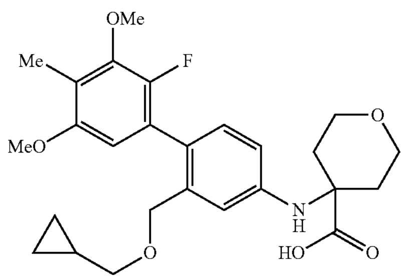 [SMILES: COc1cc(-c2ccc(NC3(C(=O)O)CCOCC3)cc2COCC2CC2)c(F)c(OC)c1C] | 474.6 (M + H)+ |
| 365 | 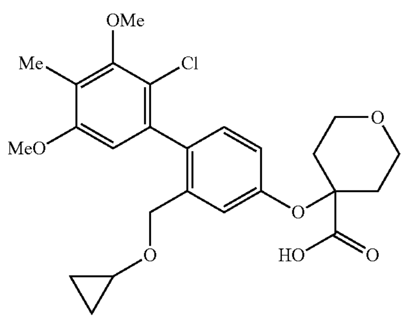 [SMILES: COc1cc(-c2ccc(OC3(C(=O)O)CCOCC3)cc2COC2CC2)c(Cl)c(OC)c1C] | 499.0 (M + Na)+ |
| 366 | 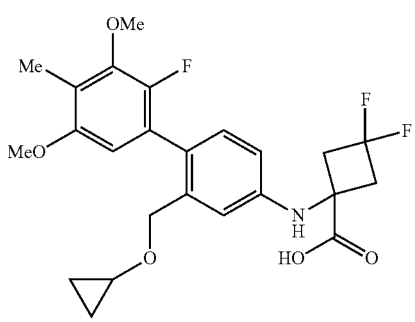 [SMILES: COc1cc(-c2ccc(NC3(C(=O)O)CC(F)(F)C3)cc2COC2CC2)c(F)c(OC)c1C] | 466.1 (M + H)+ |
| 367 | 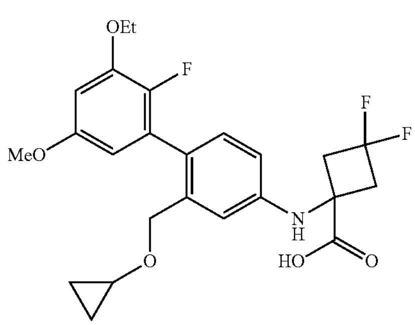 [SMILES: CCOc1cc(OC)cc(-c2ccc(NC3(C(=O)O)CC(F)(F)C3)cc2COC2CC2)c1F] | 466.1 (M + H)+ |

-continued
| Compound | Structure | LC-MS: m/z |
|---|---|---|
| 368 | 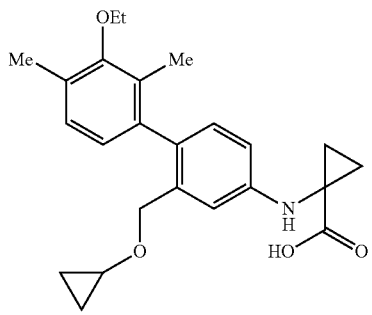 [SMILES: CCOc1c(C)ccc(-c2ccc(NC3(C(=O)O)CC3)cc2COC2CC2)c1C] | 396.1 (M + H)+ |
| 369 | 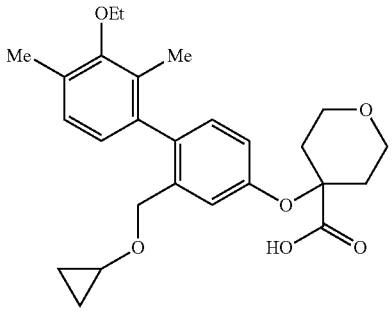 [SMILES: CCOc1c(C)ccc(-c2ccc(OC3(C(=O)O)CCOCC3)cc2COC2CC2)c1C] | 463.1 (M + Na)+ |
| 370 | 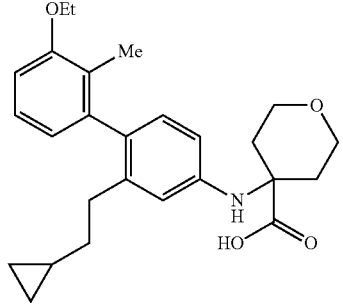 [SMILES: CCOc1cccc(-c2ccc(NC3(C(=O)O)CCOCC3)cc2CCC2CC2)c1C] | 424.1 (M + H)+ |
| 371 | 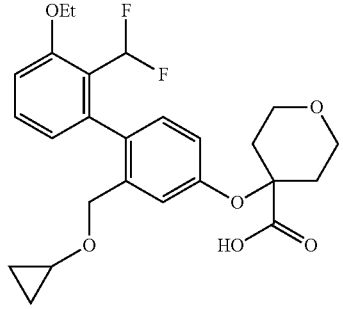 [SMILES: CCOc1cccc(-c2ccc(OC3(C(=O)O)CCOCC3)cc2COC2CC2)c1C(F)F] | 485.0 (M + Na)+ |

-continued

| Compound | Structure | LC-MS: m/z |
|---|---|---|
| 372 | 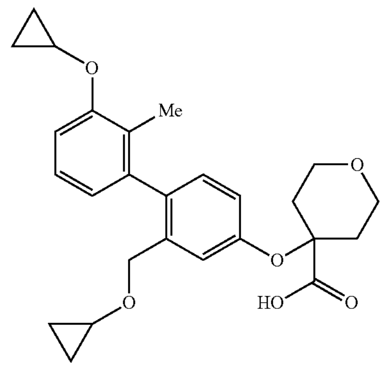 [SMILES: Cc1c(OC2CC2)cccc1-c1ccc(OC2(C(=O)O)CCOCC2)cc1COC1CC1] | 461.2 (M + Na)+ |
| 373 | 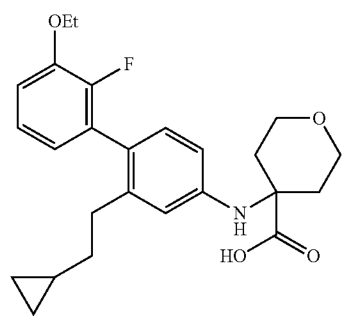 [SMILES: CCOc1cccc(-c2ccc(NC3(C(=O)O)CCOCC3)cc2CCC2CC2)c1F] | 428.0 (M + H)+ |
| 374 | 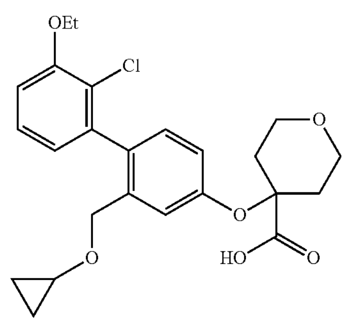 [SMILES: CCOc1cccc(-c2ccc(OC3(C(=O)O)CCOCC3)cc2COC2CC2)c1Cl] | 469.1 (M + Na)+ |
| 375 | 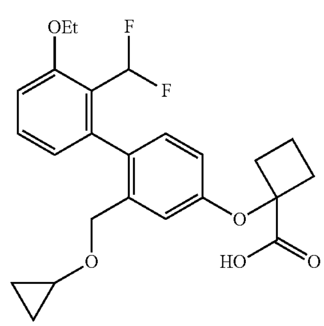 [SMILES: CCOc1cccc(-c2ccc(OC3(C(=O)O)CCC3)cc2COC2CC2)c1C(F)F] | 455.1 (M + Na)+ |

-continued

| Compound | Structure | LC-MS: m/z |
|---|---|---|
| 376 | 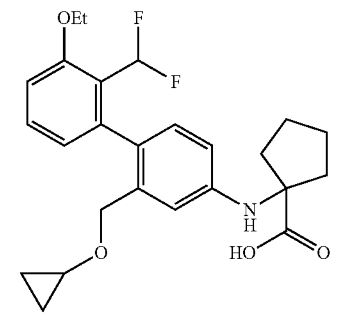 [SMILES: CCOc1cccc(-c2ccc(NC3(C(=O)O)CCCC3)cc2COC2CC2)c1C(F)F] | 446.1 (M + H)+ |
| 377 | 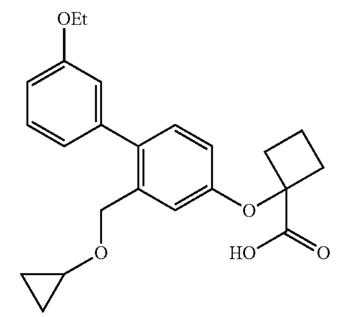 [SMILES: CCOc1cccc(-c2ccc(OC3(C(=O)O)CCC3)cc2COC2CC2)c1] | 405.1 (M + Na)+ |
| 378 | 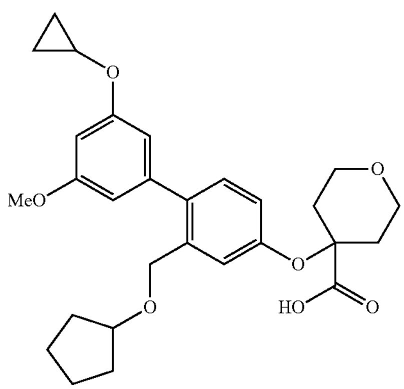 [SMILES: COc1cc(OC2CC2)cc(-c2ccc(OC3(C(=O)O)CCOCC3)cc2COC2CCCC2)c1] | 505.3 (M + Na)+ |
| 379 | 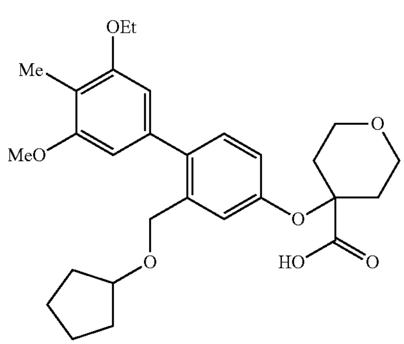 [SMILES: CCOc1cc(-c2ccc(OC3(C(=O)O)CCOCC3)cc2COC2CCCC2)cc(OC)c1C] | 502.4 (M + NH4)+ |

-continued

| Compound | Structure | LC-MS: m/z |
|---|---|---|
| 380 | 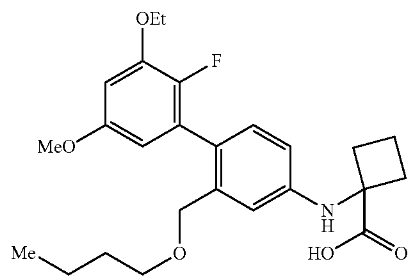 [SMILES: CCCCOCc1cc(NC2(C(=O)O)CCC2)ccc1-c1cc(OC)cc(OCC)c1F] | 446.0 (M + H)+ |
| 381 | 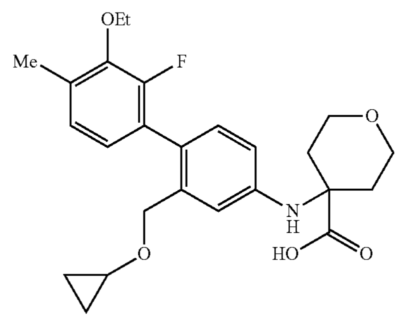 [SMILES: CCOc1c(C)ccc(-c2ccc(NC3(C(=O)O)CCOCC3)cc2COC2CC2)c1F] | 444.1 (M + H)+ |
| 382 | 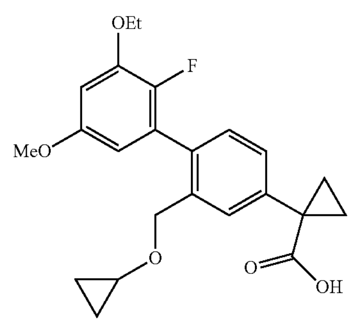 [SMILES: CCOc1cc(OC)cc(-c2ccc(C3(C(=O)O)CC3)cc2COC2CC2)c1F] | 418.5 (M + NH$_4$)+ |
| 383 | 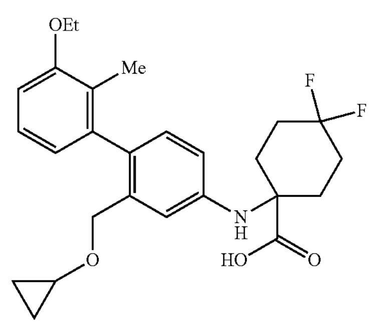 [SMILES: CCOc1cccc(-c2ccc(NC3(C(=O)O)CCC(F)(F)CC3)cc2COC2CC2)c1C] | 460.1 (M + H)+ |
| 384 | 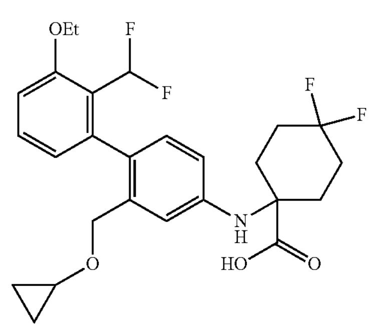 [SMILES: CCOc1cccc(-c2ccc(NC3(C(=O)O)CCC(F)(F)CC3)cc2COC2CC2)c1C(F)F] | 496.1 (M + H)+ |

-continued

| Compound | Structure | LC-MS: m/z |
|---|---|---|
| 385 | 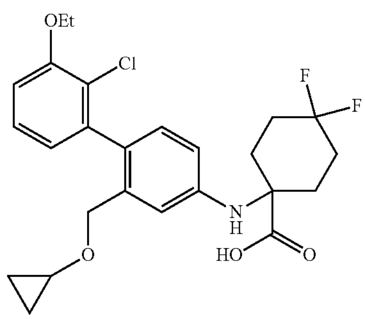 [SMILES: CCOc1cccc(-c2ccc(NC3(C(=O)O)CCC(F)(F)CC3)cc2COC2CC2)c1Cl] | 480.1 (M + H)+ |
| 386 | 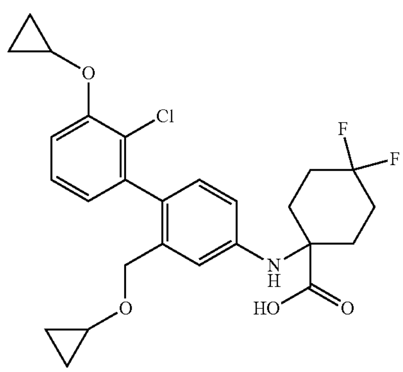 [SMILES: O=C(O)C1(Nc2ccc(-c3cccc(OC4CC4)c3Cl)c(COC3CC3)c2)CCC(F)(F)CC1] | 492.5 (M + H)+ |
| 387 | 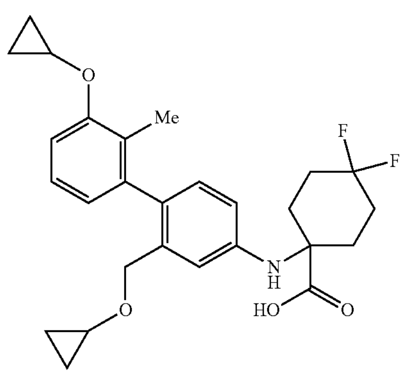 [SMILES: Cc1c(OC2CC2)cccc1-c1ccc(NC2(C(=O)O)CCC(F)(F)CC2)cc1COC1CC1] | 472.6 (M + H)+ |
| 388 | 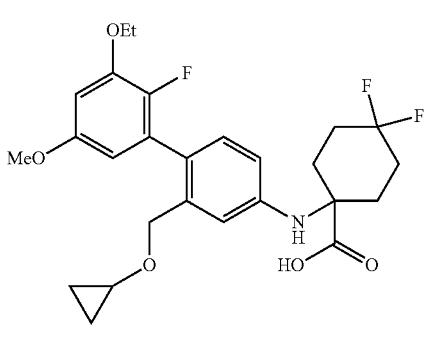 [SMILES: CCOc1cc(OC)cc(-c2ccc(NC3(C(=O)O)CCC(F)(F)CC3)cc2COC2CC2)c1F] | 494.2 (M + H)+ |

| Compound | Structure | LC-MS: m/z |
|---|---|---|
| 389 | 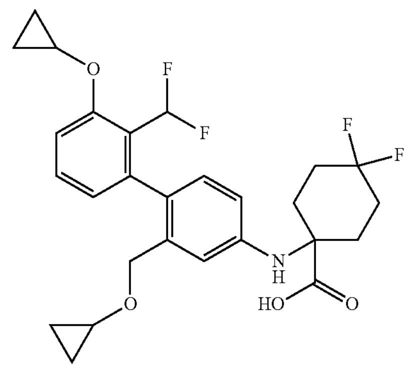 [SMILES: O=C(O)C1(Nc2ccc(-c3cccc(OC4CC4)c3C(F)F)c(COC3CC3)c2)CCC(F)(F)CC1] | 508.1 (M + H)+ |
| 390 | 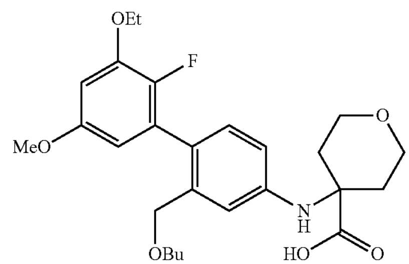 | 476.2 (M + H)+ |
| 391 | 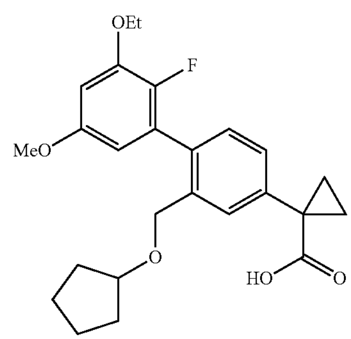 [SMILES: CCOc1cc(OC)cc(-c2ccc(C3(C(=O)O)CC3)cc2COC2CCCC2)c1F] | 446.4 (M + NH4)+ |
| 392 | 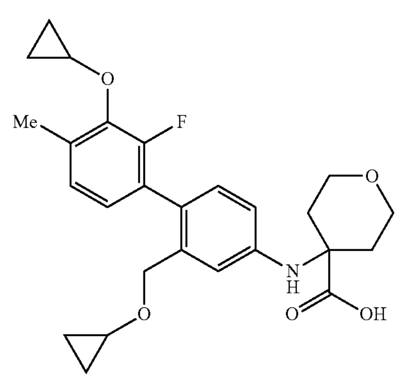 [SMILES: Cc1ccc(-c2ccc(NC3(C(=O)O)CCOCC3)cc2COC2CC2)c(F)c1OC1CC1] | 456.1 (M + H)+ |

-continued
| Compound | Structure | LC-MS: m/z |
|---|---|---|
| 393 | 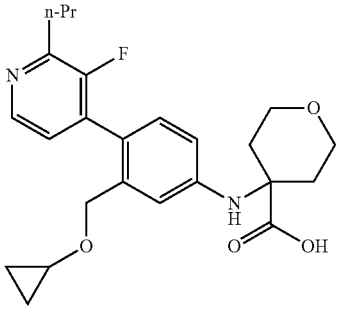 | 429.5 (M + H)+ |
| 394 | 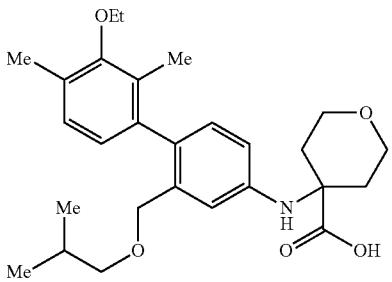 [SMILES: CCOc1c(C)ccc(-c2ccc(NC3(C(=O)O)CCOCC3)cc2COCC(C)C)c1C] | 456.6 (M + H)+ |
| 395 | 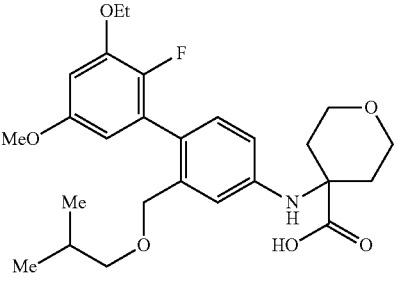 [SMILES: CCOc1cc(OC)cc(-c2ccc(NC3(C(=O)O)CCOCC3)cc2COCC(C)C)c1F] | 476.6 (M + H)+ |
| 396 | 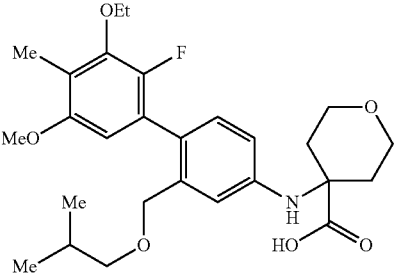 | 490.6 (M + H)+ |
| 397 | 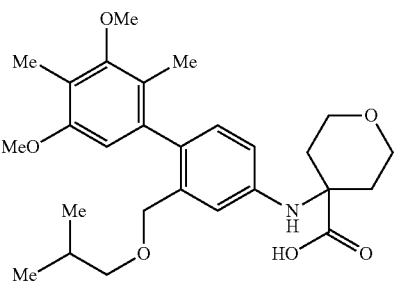 [SMILES: COc1cc(-c2ccc(NC3(C(=O)O)CCOCC3)cc2COCC(C)C)c(C)c(OC)c1C] | 472.6 (M + H)+ |

-continued

| Compound | Structure | LC-MS: m/z |
|---|---|---|
| 398 | 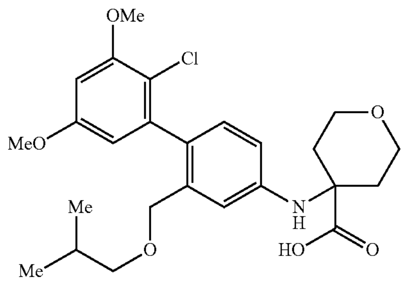 [SMILES: COc1cc(OC)c(Cl)c(-c2ccc(NC3(C(=O)O)CCOCC3)cc2COCC(C)C)c1] | 478.5 (M + H)+ |
| 399 | 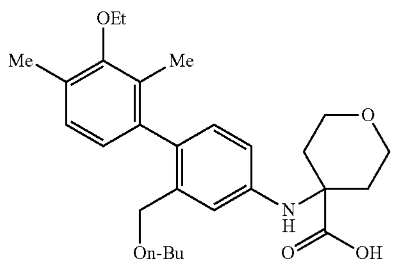 | 456.1 (M + H)+ |
| 400 | 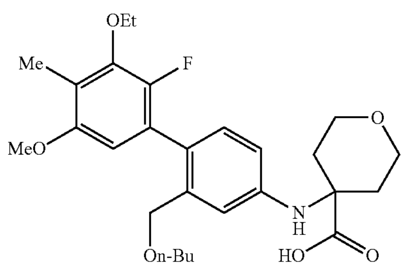 | 490.6 (M + H)+ |
| 401 | 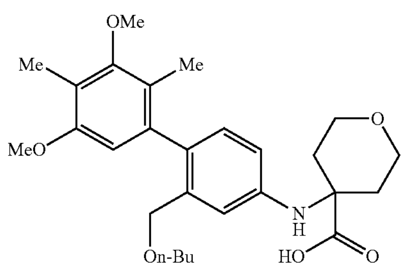 | 472.2 (M + H)+ |
| 402 | 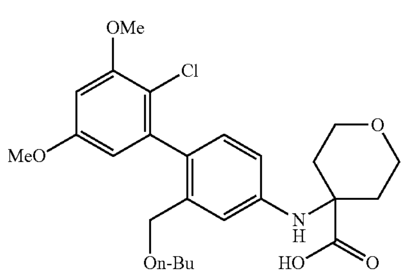 | 478.1 (M + H)+ |

-continued

| Compound | Structure | LC-MS: m/z |
|---|---|---|
| 403 | 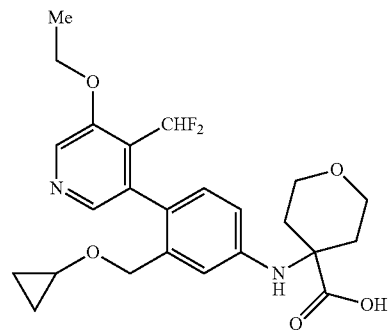 [SMILES: CCOc1cncc(-c2ccc(NC3(C(=O)O)CCOCC3)cc2COC2CC2)c1C(F)F] | 463.5 (M + H)+ |
| 404 | 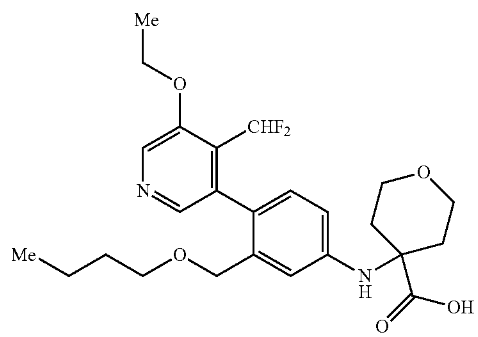 [SMILES: CCCCOCc1cc(NC2(C(=O)O)CCOCC2)ccc1-c1cncc(OCC)c1C(F)F] | 479.0 (M + H)+ |
| 405 | 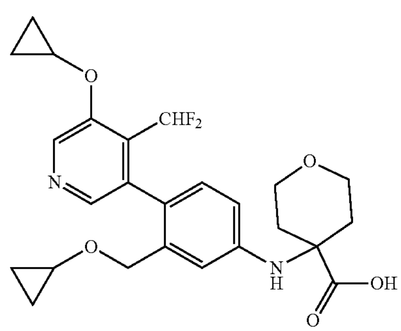 [SMILES: O=C(O)C1(Nc2ccc(-c3cncc(OC4CC4)c3C(F)F)c(COC3CC3)c2)CCOCC1] | 475.1 (M + H)+ |
| 406 | 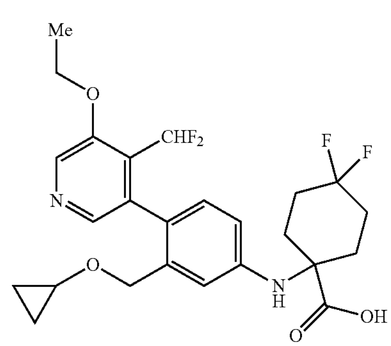 [SMILES: CCOc1cncc(-c2ccc(NC3(C(=O)O)CCC(F)(F)CC3)cc2COC2CC2)c1C(F)F] | 497.2 (M + H)+ |

-continued

| Compound | Structure | LC-MS: m/z |
|---|---|---|
| 407 | 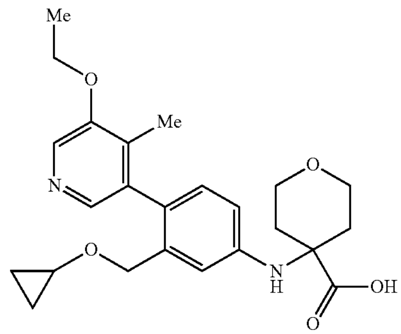 [SMILES: CCOc1cncc(-c2ccc(NC3(C(=O)O)CCOCC3)cc2COC2CC2)c1C] | 427.2 (M + H)+ |
| 408 | 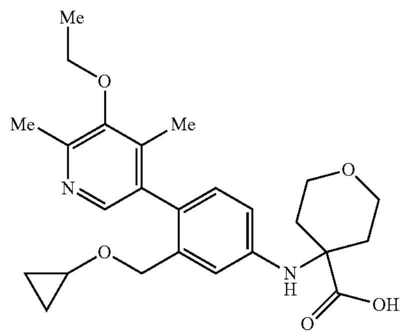 [SMILES: CCOc1c(C)ncc(-c2ccc(NC3(C(=O)O)CCOCC3)cc2COC2CC2)c1C] | 441.1 (M + H)+ |
| 409 | 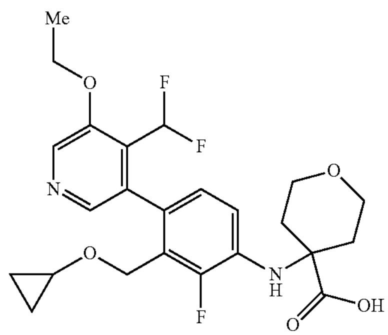 [SMILES: CCOc1cncc(-c2ccc(NC3(C(=O)O)CCOCC3)c(F)c2COC2CC2)c1C(F)F] | 481.0 (M + H)+ |
| 410 | 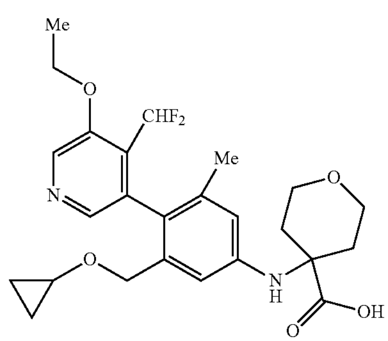 [SMILES: CCOc1cncc(-c2c(C)cc(NC3(C(=O)O)CCOCC3)cc2COC2CC2)c1C(F)F] | 477.2 (M + H)+ |

-continued
| Compound | Structure | LC-MS: m/z |
|---|---|---|
| 411 | 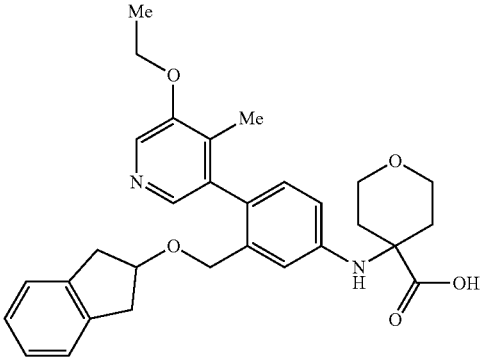 [SMILES: CCOc1cncc(-c2ccc(NC3(C(=O)O)CCOCC3)cc2COC2Cc3ccccc3C2)c1C] | 503.6 (M + H)+ |
| 412 | 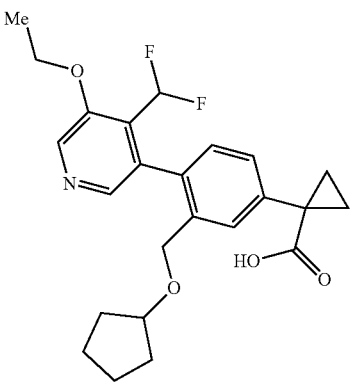 [SMILES: CCOc1cncc(-c2ccc(C3(C(=O)O)CC3)cc2COC2CCCC2)c1C(F)F] | 432.5 (M + H)+ |
| 413 | 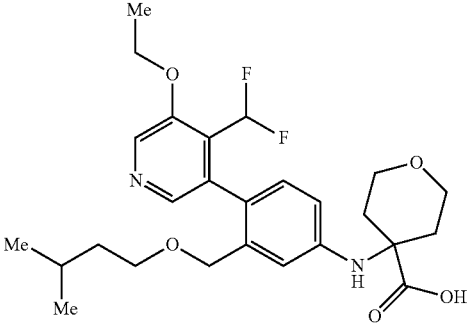 [SMILES: CCOc1cncc(-c2ccc(NC3(C(=O)O)CCOCC3)cc2COCCC(C)C)c1C(F)F] | 493.6 (M + H)+ |
| 414 | 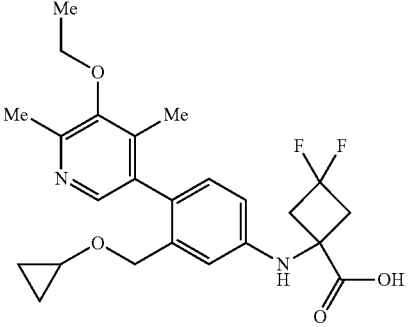 [SMILES: CCOc1c(C)ncc(-c2ccc(NC3(C(=O)O)CC(F)(F)C3)cc2COC2CC2)c1C] | 447.1 (M + H)+ |

-continued

| Compound | Structure | LC-MS: m/z |
|---|---|---|
| 415 | 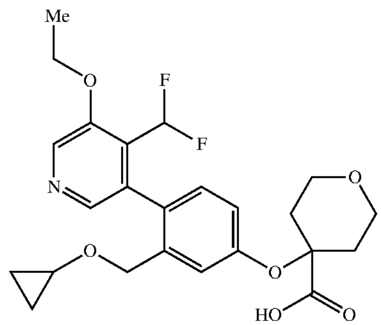 [SMILES: CCOc1cncc(-c2ccc(OC3(C(=O)O)CCOCC3)cc2COC2CC2)c1C(F)F] | 464.1 (M + H)+ |
| 416 | 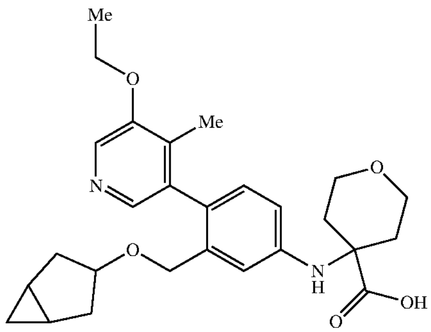 [SMILES: CCOc1cncc(-c2ccc(NC3(C(=O)O)CCOCC3)cc2COC2CC3CC3C2)c1C] | 467.5 (M + H)+ |
| 417 | 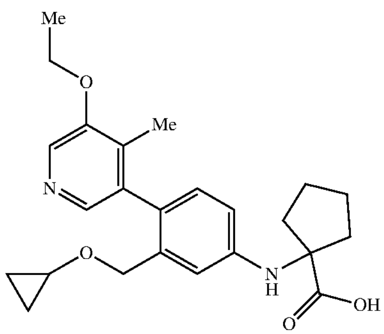 [SMILES: CCOc1cncc(-c2ccc(NC3(C(=O)O)CCCC3)cc2COC2CC2)c1C] | 411.5 (M + H)+ |

Biological Assays

In Vitro LPA1 Functional Antagonist Assay

CHO-K1 cells overexpressing human LPA1 were seeded in a total volume of 20 µL into black-walled, clear-bottom, Poly-D-lysine coated 384-well microplates and incubated at 37° C. for the appropriate time prior to testing. Assays were performed in 1× Dye Loading Buffer consisting of 1× Dye, 1× Additive A and 2.5 mM Probenecid in HBSS/20 mM Hepes. Probenicid was prepared fresh. Cells were loaded with dye prior to testing. Media was aspirated from cells and replaced with 20 µL Dye Loading Buffer. Cells were incubated for 30-60 minutes at 37° C. After dye loading, cells were removed from the incubator and 10 µL 3× test compound was added. Cells were incubated for 30 minutes at room temperature in the dark to equilibrate plate temperature followed by Oleoyl LPA challenge at $EC_{80}$. Compound antagonist activity was measured on a FLIPR Tetra (MSD). Calcium mobilization was monitored for 2 minutes and 10 µL Oleoyl LPA in HBSS/20 mM Hepes was added to the cells 5 seconds into the assay. For LPA $EC_{80}$ determination, after dye loading, cells were removed from the incubator and 10 µL HBSS/20 mM Hepes was added. 3× vehicle was included in the buffer. Cells were incubated for 30 minutes at room temperature in the dark to equilibrate plate temperature. Intermediate dilution of LPA stocks was performed to generate 4×LPA samples in assay buffer. LPA agonist activity was measured on a FLIPR Tetra (MSD). Calcium mobilization was monitored for 2 minutes and 10 µL 4×LPA sample in HBSS/20 mM Hepes was added to the cells 5 seconds into the assay. Compound activity was analyzed using CBIS data analysis suite (ChemInnovation, CA). Percentage inhibition is calculated using the following formula:

% Inhibition =

$100\% \times (1 - (\text{mean } RFU \text{ of test sample} - \text{mean } RFU \text{ of vehicle control})/$ $(\text{mean } RFU \text{ of } LPA \text{ control} - \text{mean } RFU \text{ of vehicle control})).$ Table B1 and Table B2 show the biological activity of compounds in in vitro LPA1 functional antagonist assay. Activity of the tested compounds provided in Table B1 is as follows: +++=IC$_{50}$<1 µM; ++=IC$_{50}$ 1 µM-10 µM; +=IC$_{50}$>10 µM. Activity of the tested compounds provided in Table B2 is in µM.

++=IC$_{50}$ 100 nM-1 µM; +=IC$_{50}$>1 µM. Activity of the tested compounds provided in Table B4 is in nM.

TABLE B1

| Compound | Activity |
|---|---|
| 101 | +++ |
| 102 | ++ |
| 103 | ++ |
| 104 | +++ |
| 105 | +++ |
| 109 | +++ |

TABLE B2

| Compound | IC$_{50}$ (µM) |
|---|---|
| 101 | 0.0272 |
| 102 | 2.49 |
| 103 | 1.54 |
| 104 | 0.162 |
| 105 | 0.0136 |
| 109 | 0.00268 |
| 185 | 0.00954 |
| 256 | 0.0103 |
| 280 | 0.0186 |
| 282 | 0.00888 |
| 283 | 0.0109 |
| 284 | 0.00397 |
| 285 | 0.00662 |
| 294 | 0.00715 |
| 295 | 0.00794 |
| 298 | 0.00264 |
| 355 | 0.00753 |

In Vitro LPA1 Calcium Flux Antagonist Assay—Bioduro Protocol

CHO-K1 cells overexpressing human LPA1 and G15a were seeded at a total volume of 20 µL (15000 cells/well) into Matrigel pre-coated 384-well plates (coming −3764) and incubated at 37° C. After overnight incubation, the cells were serum starved for 4 h. Assays were performed in dye loading buffer containing 1× Fluo-8 AM (AAT Bioquest, 21080) and 2.5 mM probenecid (Thermo Fisher, 36400) in HBSS/20 mM Hepes. After cell starvation, the medium was replaced with 20 µL of dye loading buffer and incubated at 37° C. for 30 min. Then 5 µL of 5× compound titrated in dye loading buffer was added to the cells and incubated for 30 min followed by LPA challenge at EC80. Calcium mobilization was measured on a FLIPR Tetra (MSD). For LPA EC80 determination, starved cells were incubated with 20 µL of dye loading buffer for 1 h, then 5 µL of 5×LPA titrated in dye loading buffer was added to the cells. Calcium signals induced by LPA was monitors on a FLIPR.

Percentage inhibition is calculated using the following formula:

% Inhibition =

$$100\% \times (1 - (\text{mean } RFU \text{ of test sample} - \text{mean } RFU \text{ of } DMSO)/(\text{mean } RFU \text{ of } LPA \text{ control} - \text{mean } RFU \text{ of } DMSO)).$$

Table B3 and Table B4 show the biological activity of compounds in in vitro LPA1 Calcium flux antagonist assay—Bioduro protocol. Activity of the tested compounds provided in Table B3 below as follows: +++=IC$_{50}$<100 nM;

TABLE B3

| Compound | Activity |
|---|---|
| 101 | ++ |
| 104 | ++ |
| 105 | ++ |
| 106 | + |
| 107 | + |
| 108 | + |
| 109 | +++ |
| 110 | ++ |
| 111 | +++ |
| 112 | ++ |
| 113 | + |
| 114 | ++ |
| 115 | + |
| 116 | + |
| 117 | +++ |
| 118 | +++ |
| 119 | +++ |
| 120 | +++ |
| 121 | +++ |
| 122 | ++ |
| 123 | +++ |
| 124 | +++ |
| 125 | ++ |
| 126 | +++ |
| 127 | +++ |
| 128 | +++ |
| 129 | +++ |
| 130 | ++ |
| 131 | ++ |
| 132 | +++ |
| 133 | +++ |
| 134 | +++ |
| 135 | +++ |
| 136 | + |
| 137 | +++ |
| 138 | ++ |
| 139 | ++ |
| 140 | +++ |
| 141 | +++ |
| 142 | + |
| 143 | +++ |
| 144 | +++ |
| 145 | ++ |
| 146 | +++ |
| 147 | +++ |
| 148 | +++ |
| 149 | +++ |
| 151 | + |
| 152 | ++ |
| 153 | + |
| 154 | ++ |
| 155 | ++ |
| 156 | ++ |
| 157 | ++ |
| 158 | +++ |
| 159 | + |
| 160 | ++ |
| 161 | ++ |
| 163 | ++ |
| 164 | + |
| 165 | +++ |
| 166 | +++ |
| 168 | +++ |
| 169 | + |
| 170 | + |
| 171 | + |
| 172 | +++ |
| 173 | ++ |
| 174 | +++ |
| 175 | ++ |
| 176 | ++ |
| 178 | + |
| 179 | +++ |
| 180 | +++ |

TABLE B3-continued

| Compound | Activity |
|---|---|
| 181 | +++ |
| 182 | +++ |
| 184 | +++ |
| 185 | +++ |
| 186 | +++ |
| 188 | + |
| 189 | +++ |
| 190 | +++ |
| 191 | +++ |
| 192 | +++ |
| 193 | +++ |
| 194 | +++ |
| 195 | + |
| 196 | +++ |
| 197 | +++ |
| 198 | ++ |
| 199 | + |
| 200 | ++ |
| 201 | +++ |
| 202 | + |
| 203 | +++ |
| 204 | ++ |
| 205 | + |
| 206 | ++ |
| 207 | +++ |
| 208 | +++ |
| 209 | +++ |
| 210 | + |
| 211 | + |
| 212 | +++ |
| 213 | +++ |
| 214 | +++ |
| 215 | +++ |
| 216 | +++ |
| 217 | ++ |
| 218 | + |
| 219 | +++ |
| 220 | ++ |
| 222 | ++ |
| 223 | +++ |
| 224 | ++ |
| 225 | ++ |
| 226 | +++ |
| 227 | +++ |
| 228 | +++ |
| 229 | +++ |
| 230 | ++ |
| 232 | ++ |
| 233 | ++ |
| 234 | + |
| 235 | ++ |
| 236 | + |
| 237 | +++ |
| 238 | ++ |
| 239 | ++ |
| 240 | +++ |
| 241 | ++ |
| 242 | ++ |
| 243 | ++ |
| 244 | +++ |
| 245 | +++ |
| 246 | +++ |
| 247 | + |
| 248 | +++ |
| 249 | +++ |
| 250 | +++ |
| 251 | +++ |
| 252 | +++ |
| 253 | +++ |
| 254 | ++ |
| 255 | + |
| 256 | +++ |
| 257 | +++ |
| 259 | +++ |
| 260 | ++ |
| 261 | +++ |
| 262 | +++ |
| 263 | +++ |

TABLE B3-continued

| Compound | Activity |
|---|---|
| 264 | +++ |
| 265 | +++ |
| 266 | ++ |
| 267 | +++ |
| 268 | ++ |
| 269 | ++ |
| 270 | +++ |
| 271 | +++ |
| 272 | +++ |
| 273 | +++ |
| 274 | +++ |
| 275 | ++ |
| 276 | +++ |
| 277 | +++ |
| 278 | +++ |
| 279 | +++ |
| 280 | +++ |
| 281 | ++ |
| 282 | +++ |
| 283 | +++ |
| 284 | +++ |
| 285 | +++ |
| 286 | +++ |
| 287 | +++ |
| 288 | +++ |
| 289 | +++ |
| 290 | +++ |
| 291 | +++ |
| 292 | ++ |
| 293 | +++ |
| 294 | +++ |
| 295 | +++ |
| 296 | +++ |
| 297 | ++ |
| 298 | +++ |
| 299 | +++ |
| 300 | +++ |
| 301 | +++ |
| 302 | ++ |
| 303 | +++ |
| 304 | + |
| 305 | + |
| 306 | ++ |
| 307 | +++ |
| 308 | +++ |
| 309 | +++ |
| 310 | +++ |
| 311 | ++ |
| 312 | +++ |
| 313 | +++ |
| 314 | +++ |
| 315 | +++ |
| 316 | + |
| 317 | +++ |
| 318 | +++ |
| 319 | +++ |
| 320 | +++ |
| 322 | +++ |
| 323 | ++ |
| 324 | + |
| 325 | +++ |
| 326 | ++ |
| 327 | ++ |
| 328 | + |
| 329 | +++ |
| 330 | +++ |
| 331 | +++ |
| 332 | +++ |
| 333 | +++ |
| 334 | +++ |
| 335 | +++ |
| 336 | +++ |
| 337 | ++ |
| 338 | +++ |
| 339 | +++ |
| 340 | +++ |
| 341 | ++ |
| 342 | +++ |

TABLE B3-continued

| Compound | Activity |
|---|---|
| 343 | + |
| 344 | ++ |
| 345 | ++ |
| 346 | +++ |
| 347 | +++ |
| 348 | +++ |
| 349 | +++ |
| 350 | + |
| 351 | +++ |
| 352 | +++ |
| 353 | +++ |
| 354 | +++ |
| 355 | +++ |
| 356 | +++ |
| 357 | +++ |
| 358 | +++ |
| 359 | +++ |
| 360 | +++ |
| 361 | +++ |
| 362 | ++ |
| 363 | + |
| 364 | +++ |
| 365 | +++ |
| 366 | +++ |
| 367 | +++ |
| 368 | +++ |
| 369 | +++ |
| 370 | +++ |
| 371 | +++ |
| 372 | +++ |
| 373 | +++ |
| 374 | +++ |
| 375 | +++ |
| 376 | +++ |
| 377 | + |
| 378 | ++ |
| 379 | +++ |
| 380 | +++ |
| 381 | +++ |
| 382 | + |
| 383 | +++ |
| 384 | +++ |
| 385 | +++ |
| 386 | +++ |
| 387 | +++ |
| 388 | +++ |
| 389 | +++ |
| 390 | +++ |
| 391 | ++ |
| 392 | +++ |
| 393 | + |
| 394 | +++ |
| 395 | +++ |
| 396 | +++ |
| 397 | +++ |
| 398 | ++ |
| 399 | +++ |
| 400 | +++ |
| 401 | +++ |
| 402 | +++ |
| 403 | +++ |
| 404 | +++ |
| 405 | +++ |
| 406 | +++ |
| 407 | +++ |
| 408 | ++ |
| 409 | ++ |
| 410 | ++ |
| 411 | +++ |
| 412 | ++ |
| 413 | +++ |
| 414 | ++ |
| 415 | +++ |
| 416 | +++ |
| 417 | +++ |

TABLE B4

| Compound | IC$_{50}$ (nM) |
|---|---|
| 101 | 340 |
| 104 | 628 |
| 105 | 245 |
| 106 | 3480 |
| 107 | 2580 |
| 108 | 1880 |
| 109 | 94.1 |
| 110 | 152 |
| 111 | 19.8 |
| 112 | 188 |
| 113 | 7130 |
| 114 | 248 |
| 115 | 6820 |
| 116 | 2160 |
| 117 | 60.5 |
| 118 | 96.4 |
| 119 | 35.6 |
| 120 | 57 |
| 121 | 13.5 |
| 122 | 112 |
| 123 | 14.8 |
| 124 | 91.6 |
| 125 | 116 |
| 126 | 32.1 |
| 127 | 16.3 |
| 128 | 31.4 |
| 129 | 17.2 |
| 130 | 191 |
| 131 | 190 |
| 132 | 20.1 |
| 133 | 82.9 |
| 134 | 90.6 |
| 135 | 27.8 |
| 136 | 885 |
| 137 | 45.2 |
| 138 | 174 |
| 139 | 353 |
| 140 | 28.8 |
| 141 | 24.5 |
| 142 | >10000 |
| 143 | 53.8 |
| 144 | 59.5 |
| 145 | 486 |
| 146 | 77.2 |
| 147 | 20.9 |
| 148 | 10.5 |
| 149 | 88 |
| 151 | 1580 |
| 152 | 390 |
| 153 | >10000 |
| 154 | 224 |
| 155 | 252 |
| 156 | 162 |
| 157 | 112 |
| 158 | 46.3 |
| 159 | >10000 |
| 160 | 666 |
| 161 | 976 |
| 163 | 382 |
| 164 | >10000 |
| 165 | 10.9 |
| 166 | 9.31 |
| 168 | 27.6 |
| 169 | >10000 |
| 170 | 1500 |
| 171 | >10000 |
| 172 | 82.1 |
| 173 | 314 |
| 174 | 29.3 |
| 175 | 175 |
| 176 | 883 |
| 178 | 1320 |
| 179 | 24.9 |
| 180 | 39.7 |
| 181 | 55.2 |
| 182 | 9.7 |
| 184 | 33.2 |
| 185 | 12.6 |

TABLE B4-continued

| Compound | IC$_{50}$ (nM) |
|---|---|
| 186 | 64.3 |
| 188 | 2730 |
| 189 | 52.5 |
| 190 | 27 |
| 191 | 34.3 |
| 192 | 15.1 |
| 193 | 31.9 |
| 194 | 79.8 |
| 195 | 760 |
| 196 | 30.1 |
| 197 | 12.5 |
| 198 | 232 |
| 199 | 3210 |
| 200 | 772 |
| 201 | 73.2 |
| 202 | >10000 |
| 203 | 26 |
| 204 | 163 |
| 205 | 1260 |
| 206 | 476 |
| 207 | 30.4 |
| 208 | 56.4 |
| 209 | 15.5 |
| 210 | >10000 |
| 211 | >10000 |
| 212 | 11.2 |
| 213 | 58.7 |
| 214 | 58.9 |
| 215 | 10.8 |
| 216 | 18.6 |
| 217 | 584 |
| 218 | >10000 |
| 219 | 58 |
| 220 | 81.6 |
| 222 | 167 |
| 223 | 4.76 |
| 224 | 158 |
| 225 | 320 |
| 226 | 22.2 |
| 227 | 25 |
| 228 | 2.63 |
| 229 | 5.28 |
| 230 | 139 |
| 232 | 756 |
| 233 | 914 |
| 234 | 5190 |
| 235 | 198 |
| 236 | 4710 |
| 237 | 63.6 |
| 238 | 268 |
| 239 | 970 |
| 240 | 23.4 |
| 241 | 87 |
| 242 | 266 |
| 243 | 82.9 |
| 244 | 2.73 |
| 245 | 23.2 |
| 246 | 24.3 |
| 247 | 1610 |
| 248 | 50.2 |
| 249 | 1.13 |
| 250 | 31.7 |
| 251 | 40.2 |
| 252 | 14.9 |
| 253 | 54.3 |
| 254 | 370 |
| 255 | 2390 |
| 256 | 16.5 |
| 257 | 8.41 |
| 259 | 81.3 |
| 260 | 174 |
| 261 | 51.9 |
| 262 | 30.8 |
| 263 | 60.4 |
| 264 | 5.42 |
| 265 | 12 |
| 266 | 142 |
| 267 | 68 |

TABLE B4-continued

| Compound | IC$_{50}$ (nM) |
|---|---|
| 268 | 648 |
| 269 | 259 |
| 270 | 79.8 |
| 271 | 21.4 |
| 272 | 6.96 |
| 273 | 17.1 |
| 274 | 28 |
| 275 | 229 |
| 276 | 25.4 |
| 277 | 72.7 |
| 278 | 36.6 |
| 279 | 4.19 |
| 280 | 8.12 |
| 281 | 110 |
| 282 | 25.7 |
| 283 | 11.5 |
| 284 | 11.9 |
| 285 | 13.9 |
| 286 | 9.87 |
| 287 | 2.46 |
| 288 | 11.9 |
| 289 | 51 |
| 290 | 15.8 |
| 291 | 173 |
| 292 | 117 |
| 293 | 5.72 |
| 294 | 5.85 |
| 295 | 3.31 |
| 296 | 2.4 |
| 297 | 137 |
| 298 | 0.763 |
| 299 | 38.4 |
| 300 | 35.3 |
| 301 | 12.5 |
| 302 | 85.2 |
| 303 | 12.3 |
| 304 | 5.64 |
| 305 | 711 |
| 306 | 165 |
| 307 | 58.4 |
| 308 | 23.6 |
| 309 | 37.7 |
| 310 | 6.93 |
| 311 | 148 |
| 312 | 5.44 |
| 313 | 5.93 |
| 314 | 37 |
| 315 | 24 |
| 316 | 1080 |
| 317 | 14 |
| 318 | 9.47 |
| 319 | 76.7 |
| 320 | 12.1 |
| 322 | 5.9 |
| 323 | 833 |
| 324 | >10000 |
| 325 | 59.6 |
| 326 | 124 |
| 327 | 412 |
| 328 | >10000 |
| 329 | 61.9 |
| 330 | 9.53 |
| 331 | 9.37 |
| 332 | 139 |
| 333 | 10.3 |
| 334 | 45.2 |
| 335 | 5.56 |
| 336 | 18.8 |
| 337 | 315 |
| 338 | 17.2 |
| 339 | 85.3 |
| 340 | 26.1 |
| 341 | 214 |
| 342 | 19.7 |
| 343 | 1130 |
| 344 | 106 |
| 345 | 144 |
| 346 | 7.24 |

TABLE B4-continued

| Compound | IC$_{50}$ (nM) |
|---|---|
| 347 | 23.5 |
| 348 | 69.5 |
| 349 | 14.2 |
| 350 | 4320 |
| 351 | 4.63 |
| 352 | 75 |
| 353 | 8.39 |
| 354 | 35.5 |
| 355 | 3.02 |
| 356 | 47.4 |
| 357 | 30.3 |
| 358 | 5.37 |
| 359 | 49.8 |
| 360 | 75.5 |
| 361 | 75.6 |
| 362 | 356 |
| 363 | 4850 |
| 364 | 82.9 |
| 365 | 18.7 |
| 366 | 55 |
| 367 | 33.2 |
| 368 | 40.7 |
| 369 | 44.8 |
| 370 | 1.95 |
| 371 | 22.3 |
| 372 | 57.4 |
| 373 | 1.2 |
| 374 | 14.6 |
| 375 | 24.3 |
| 376 | 1.03 |
| 377 | >10000 |
| 378 | 834 |
| 379 | 67.3 |
| 380 | 17.4 |
| 381 | 17.5 |
| 382 | >10000 |
| 383 | 0.847 |
| 384 | 0.803 |
| 385 | 0.633 |
| 386 | 3.84 |
| 387 | 4.39 |
| 388 | 6.2 |
| 389 | 0.772 |
| 390 | 0.658 |
| 391 | 471 |
| 392 | 9.44 |
| 393 | >10000 |
| 394 | 97.6 |
| 395 | 7.94 |
| 396 | 27.5 |
| 397 | 73 |
| 398 | 104 |
| 399 | 6.41 |
| 400 | 5.37 |
| 401 | 5.71 |
| 402 | 7.59 |
| 403 | 23.1 |
| 404 | 13 |
| 405 | 65 |
| 406 | 20 |
| 407 | 96.5 |
| 408 | 152 |
| 409 | 229 |
| 410 | 179 |
| 411 | 5.2 |
| 412 | 538 |
| 413 | 5.79 |
| 414 | 112 |
| 415 | 66.2 |
| 416 | 8.79 |
| 417 | 35.8 |

The invention claimed is:

1. A method for treating a disease, disorder, or condition selected from fibrosis, transplant rejection, cancer, osteoporosis, an inflammatory disorder, idiopathic pulmonary fibrosis (IPF), non-alcoholic steatohepatitis (NASH), non-alcoholic fatty liver disease (NAFLD), chronic kidney disease, diabetic kidney disease, systemic sclerosis, COVID-19, chronic obstructive pulmonary disease (COPD), neuroinflammation, multiple sclerosis, and Hermansky-Pudlak Syndrome, the method comprising administering to a patient in need thereof an effective amount of a compound selected from:

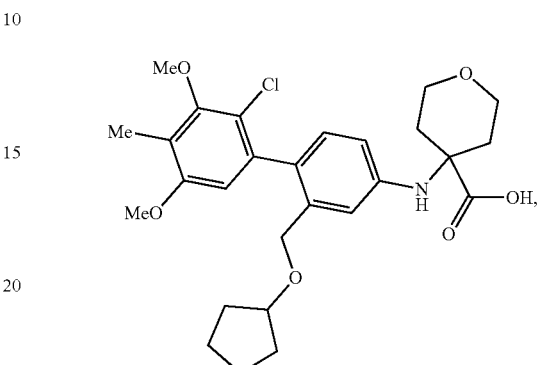

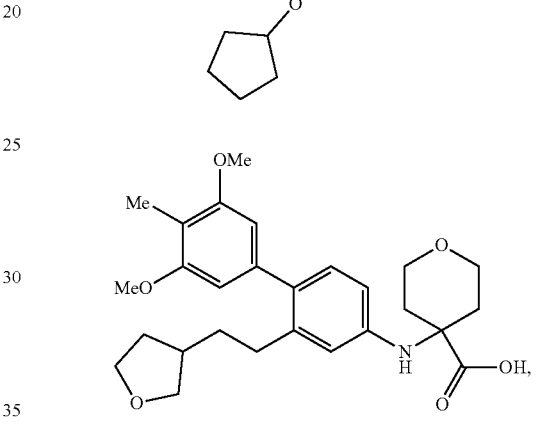

Enantiomer 1

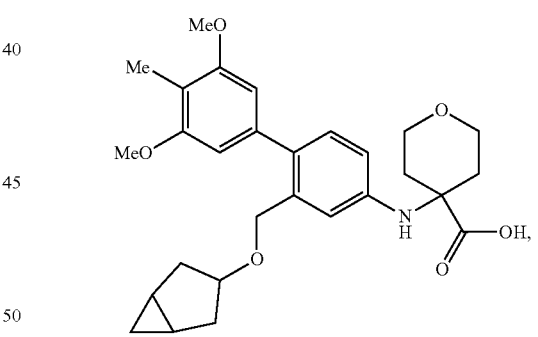

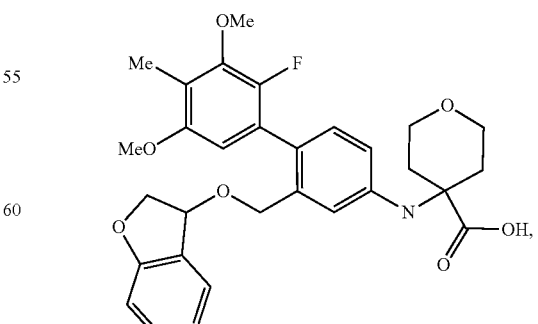

Enantiomer 1

-continued
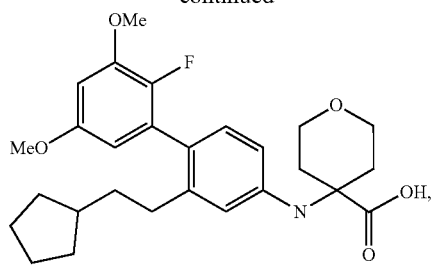
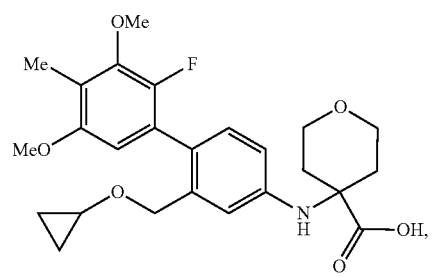
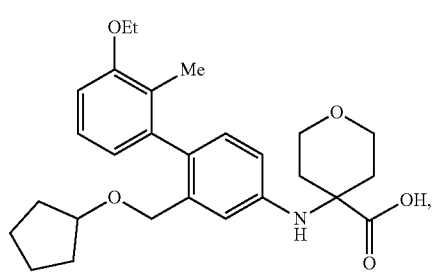
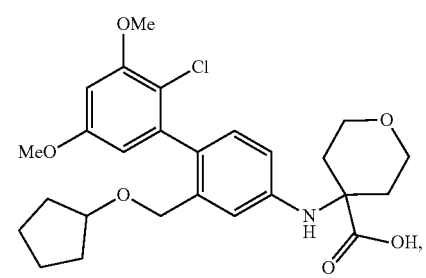
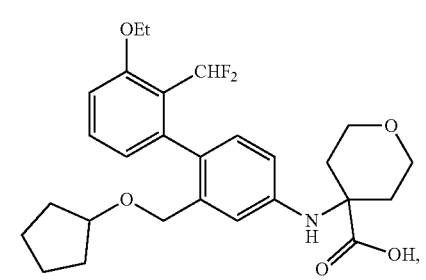
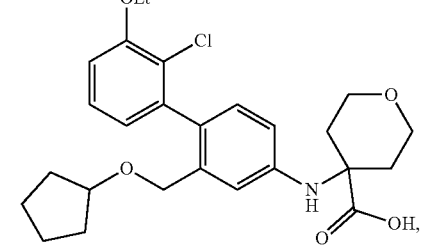
-continued
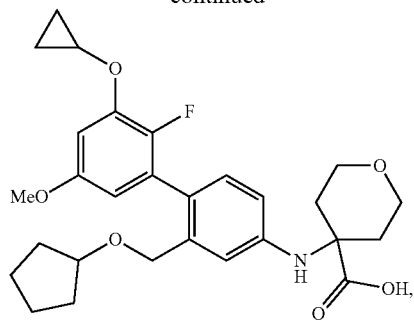
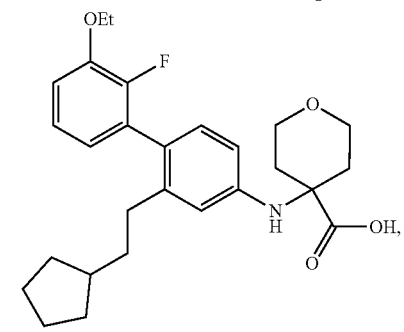
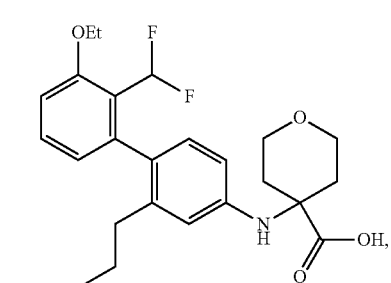
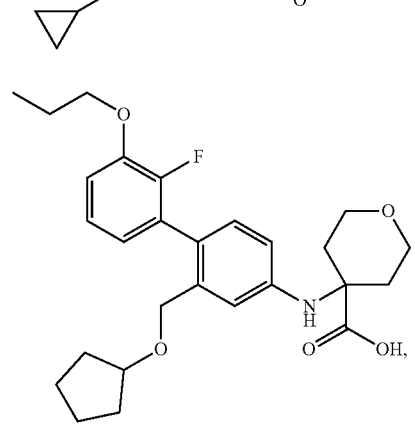
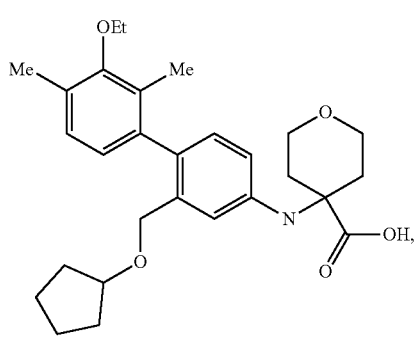

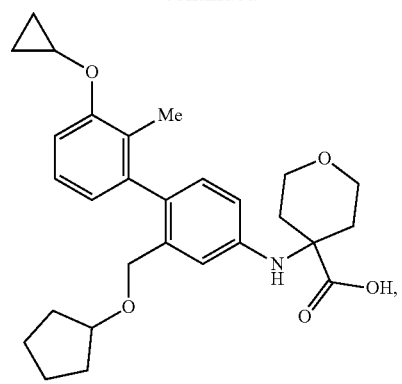
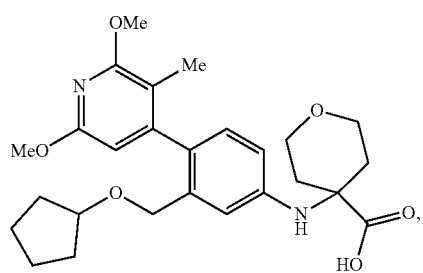
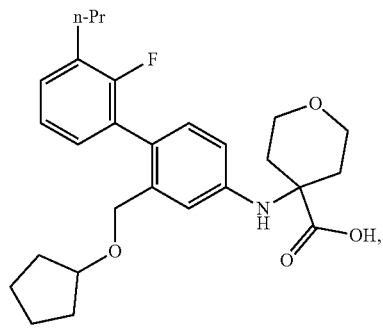
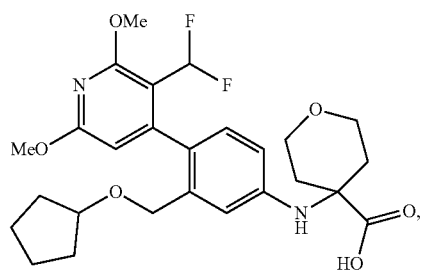
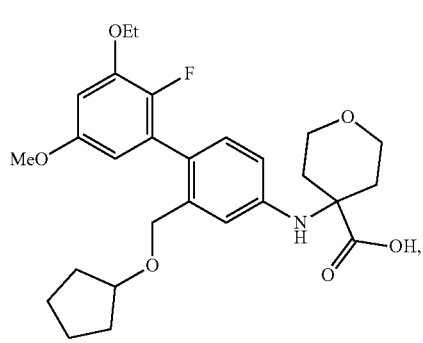
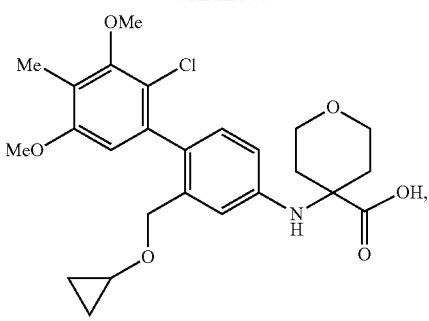
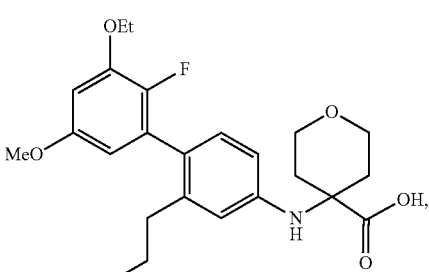
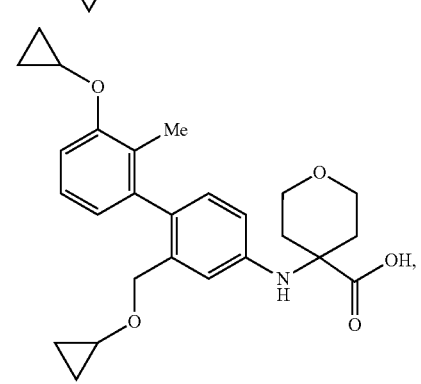
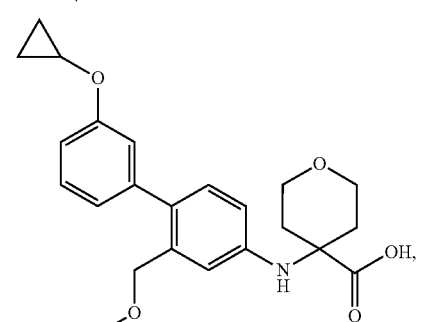
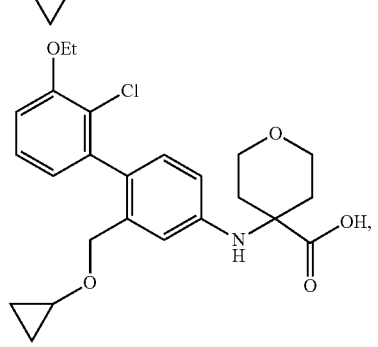

483
-continued
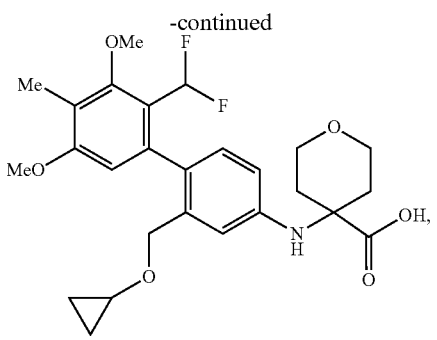
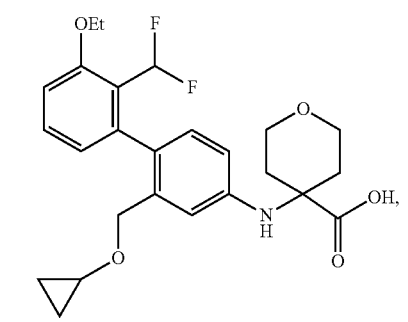
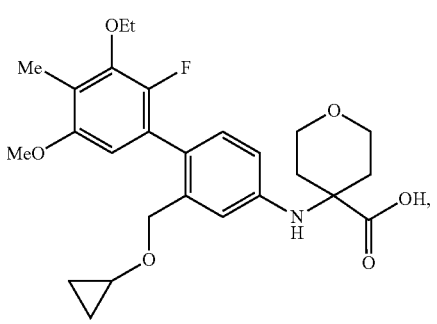
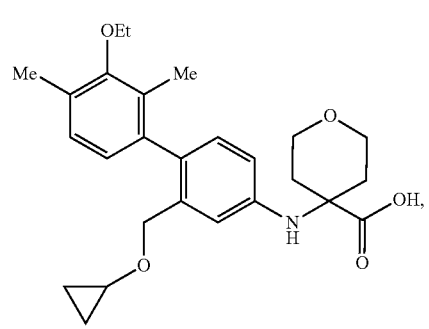
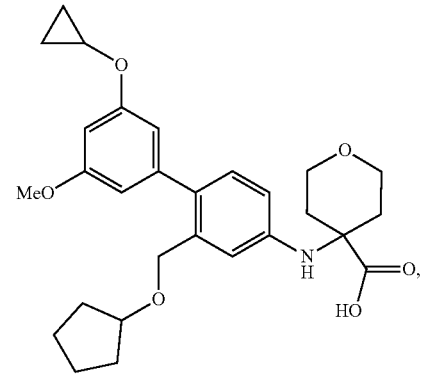
484
-continued
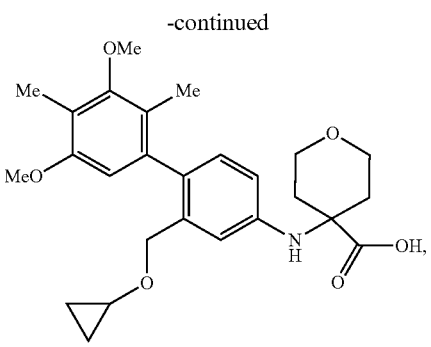
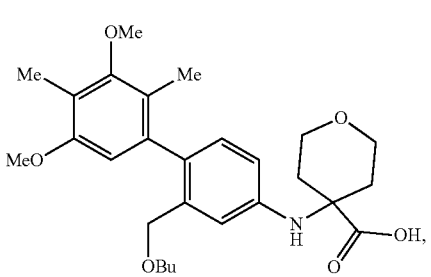
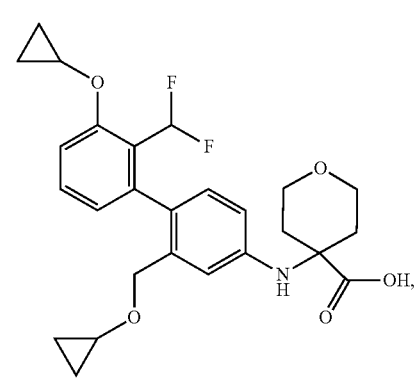
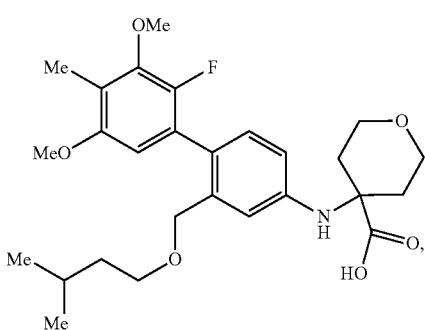
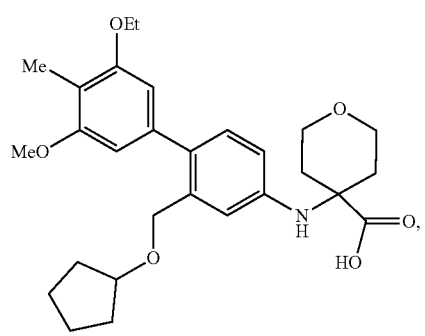

485
-continued
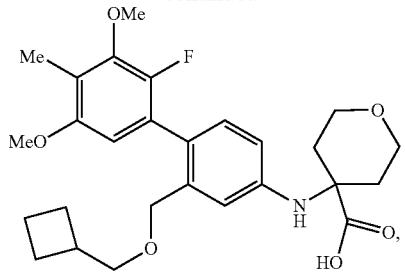
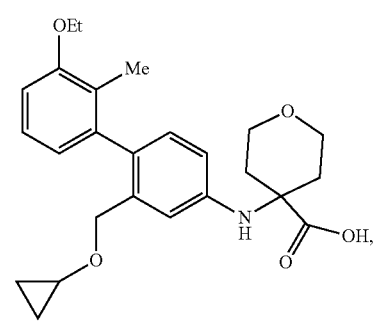
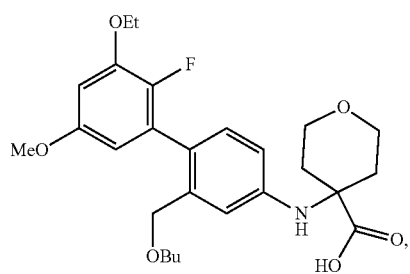
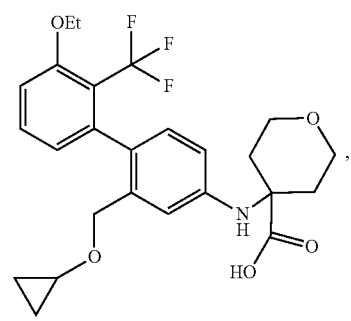
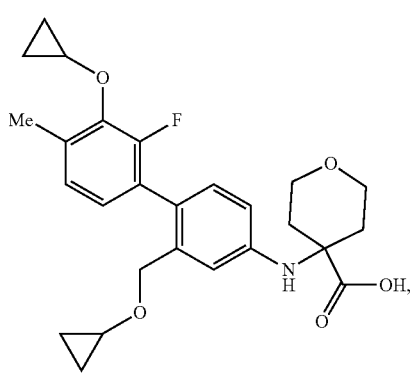
486
-continued
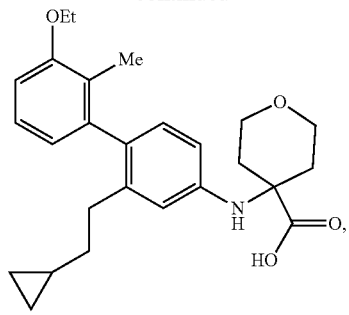
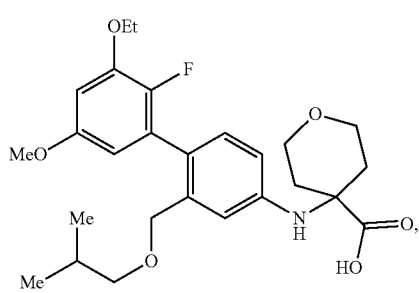
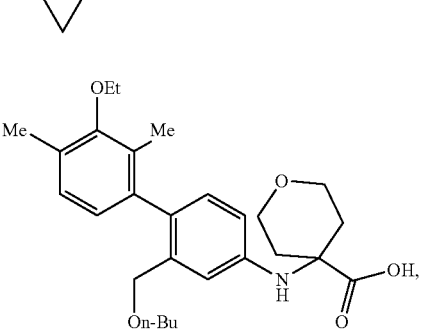
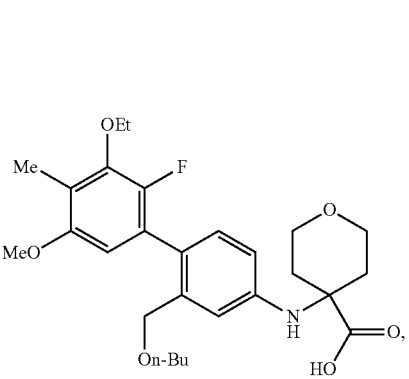

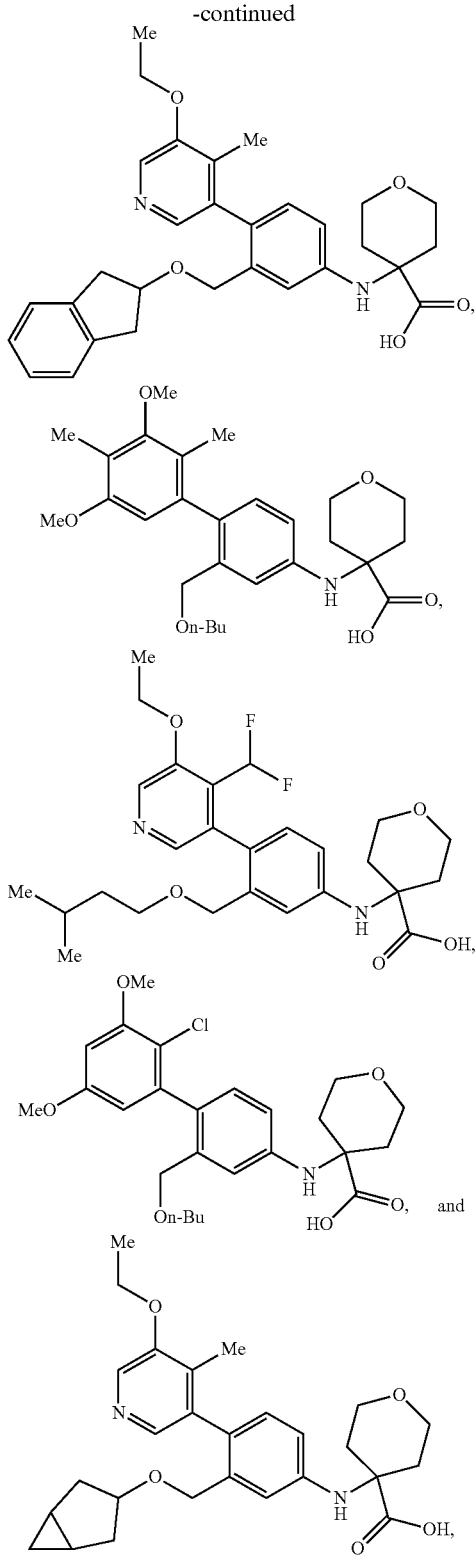

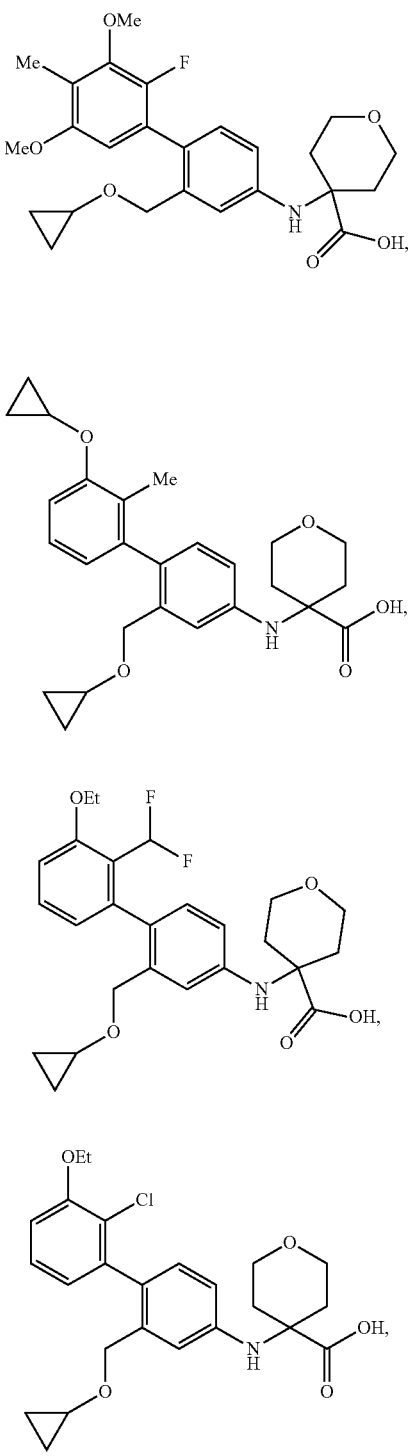

or a pharmaceutically acceptable salt thereof.

2. The method of claim 1, wherein the fibrosis is pulmonary fibrosis, liver fibrosis, renal fibrosis, cardiac fibrosis, dermal fibrosis, ocular fibrosis, or pancreatic fibrosis.

3. The method of claim 1, wherein the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral mucosa, nasal mucosa, ovary, pancreas, prostate, skin, spleen, small intestine, large intestine, stomach, testicle, or thyroid.

4. A method for treating pulmonary fibrosis, the method comprising administering to a patient in need thereof an effective amount of a compound selected from:

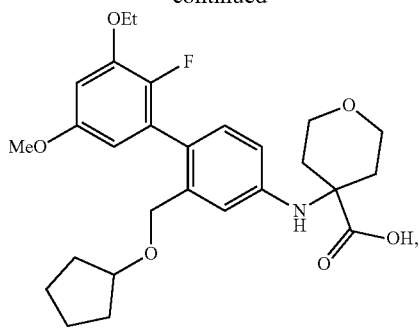

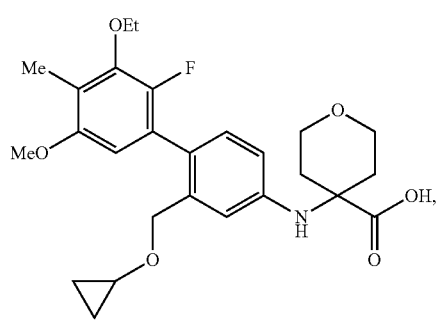

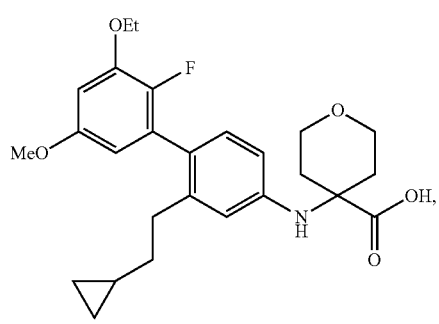

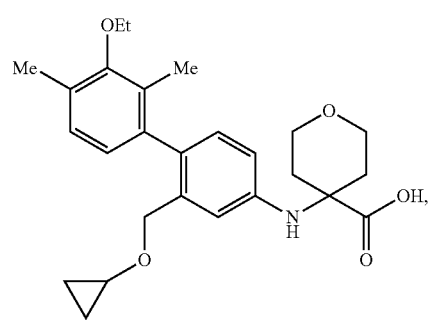

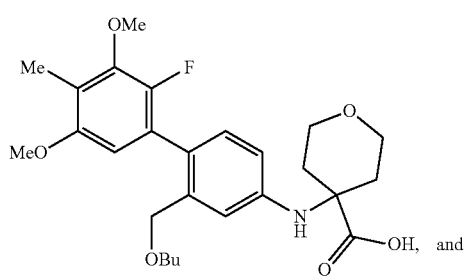

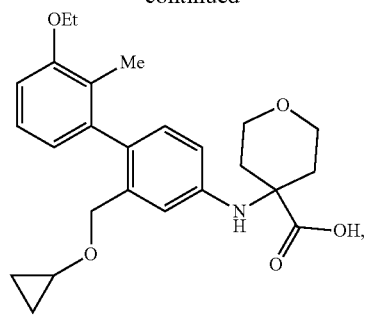

or a pharmaceutically acceptable salt thereof.

5. The method of claim 4, wherein the pulmonary fibrosis is idiopathic pulmonary fibrosis (IPF).

6. The method of claim 5, the method comprising administering to a patient in need thereof an effective amount of a compound which is:

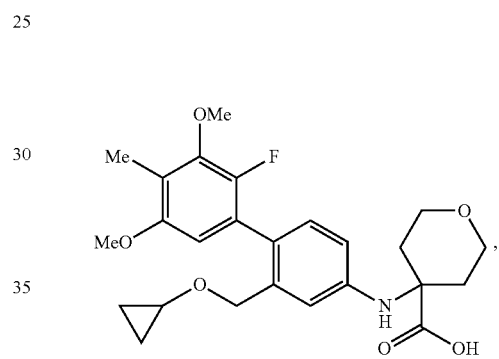

or a pharmaceutically acceptable salt thereof.

7. The method of claim 5, the method comprising administering to a patient in need thereof an effective amount of a compound which is:

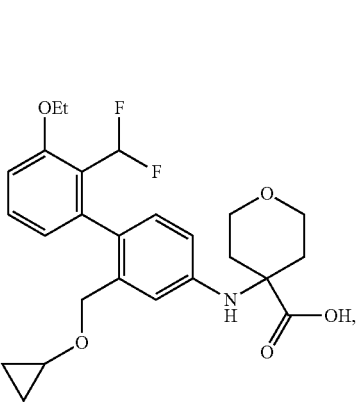 [SMILES: CCOc1cccc(-c2ccc(NC3(C(=O)O)CCOCC3)cc2COC2CC2)c1C(F)F]

or a pharmaceutically acceptable salt thereof.

8. The method of claim 5, the method comprising administering to a patient in need thereof a compound which is:

or a pharmaceutically acceptable salt thereof.

9. The method of claim 5, the method comprising administering to a patient in need thereof an effective amount of a compound which is:

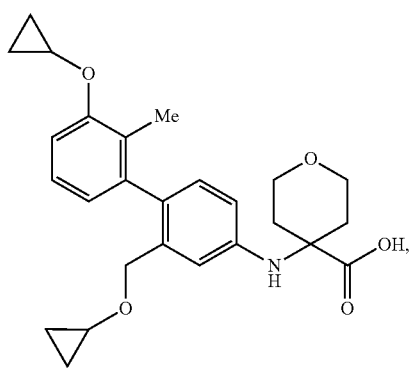 [SMILES: Cc1c(OC2CC2)cccc1-c1ccc(NC2(C(=O)O)CCOCC2)cc1COC1CC1]

or a pharmaceutically acceptable salt thereof.

10. The method of claim 5, the method comprising administering to a patient in need thereof an effective amount of a compound which is:

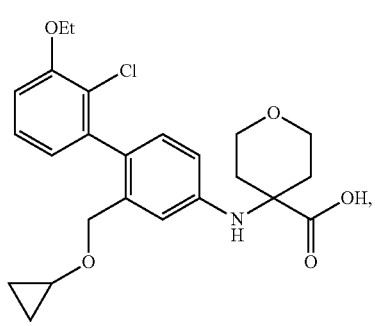 [SMILES: CCOc1cccc(-c2ccc(NC3(C(=O)O)CCOCC3)cc2COC2CC2)c1Cl]

or a pharmaceutically acceptable salt thereof.

11. The method of claim 5, the method comprising administering to a patient in need thereof an effective amount of a compound which is:

or a pharmaceutically acceptable salt thereof.

12. The method of claim 5, the method comprising administering to a patient in need thereof an effective amount of a compound which is:

or a pharmaceutically acceptable salt thereof.

13. The method of claim 5, the method comprising administering to a patient in need thereof an effective amount of a compound which is:

or a pharmaceutically acceptable salt thereof.

14. The method of claim 5, the method comprising administering to a patient in need thereof an effective amount of a compound which is:

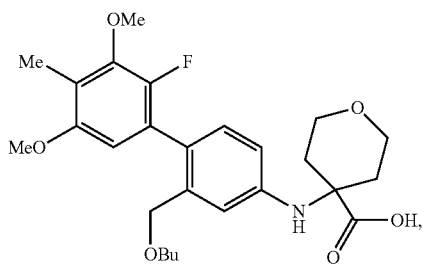
or a pharmaceutically acceptable salt thereof.
15. The method of claim 5, the method comprising administering to a patient in need thereof an effective amount of a compound which is:
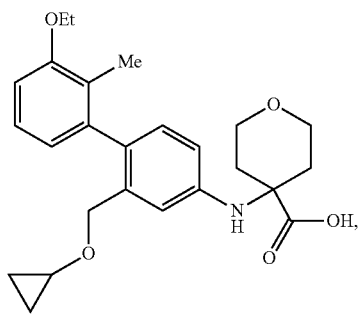 [SMILES: CCOc1cccc(-c2ccc(NC3(C(=O)O)CCOCC3)cc2COC2CC2)c1C]
or a pharmaceutically acceptable salt thereof.
* * * * *

UNITED STATES PATENT AND TRADEMARK OFFICE
CERTIFICATE OF CORRECTION

PATENT NO. : 12,428,375 B2
APPLICATION NO. : 18/534520
DATED : September 30, 2025
INVENTOR(S) : Wei Huang et al.

Page 1 of 3

It is certified that error appears in the above-identified patent and that said Letters Patent is hereby corrected as shown below:

In the Claims

In Claim 1, Column 478, Lines 53-65, please replace

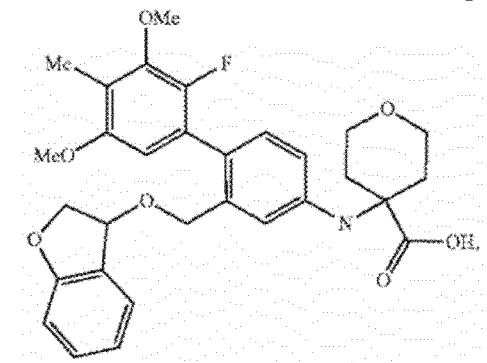

" with --

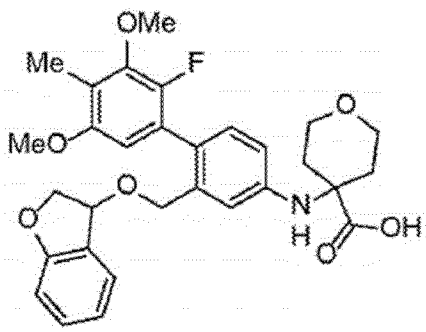

--.

In Claim 1, Column 479, Lines 1-11, please replace

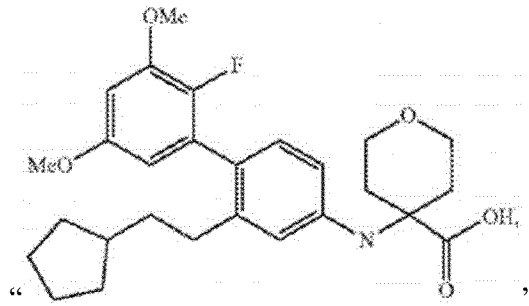

" with --

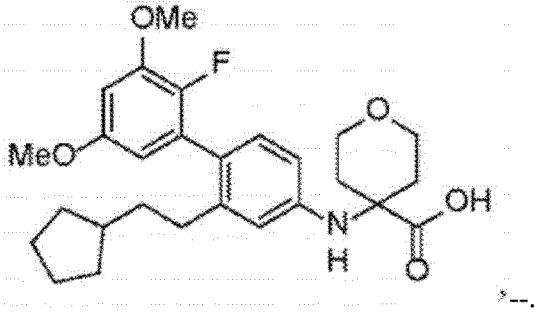

--.

Signed and Sealed this
Thirteenth Day of January, 2026

John A. Squires
*Director of the United States Patent and Trademark Office*

CERTIFICATE OF CORRECTION (continued)
U.S. Pat. No. 12,428,375 B2

Page 2 of 3

In Claim 1, Column 480, Lines 27-38, please replace

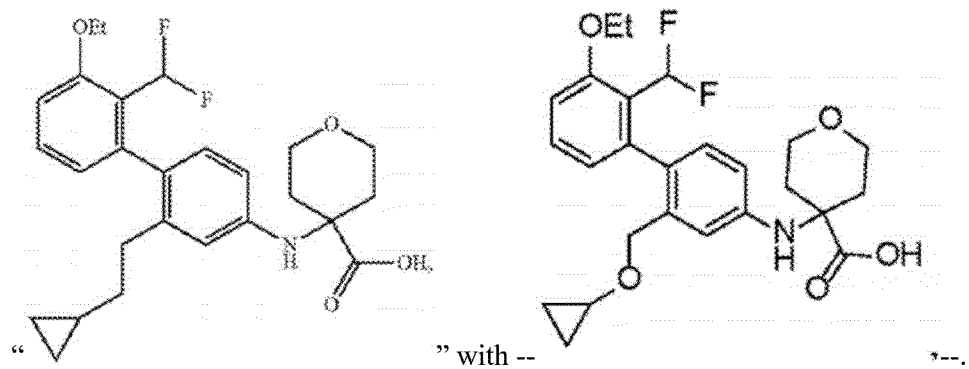

" with --             --.

In Claim 1, Column 480, Lines 54-66, please replace

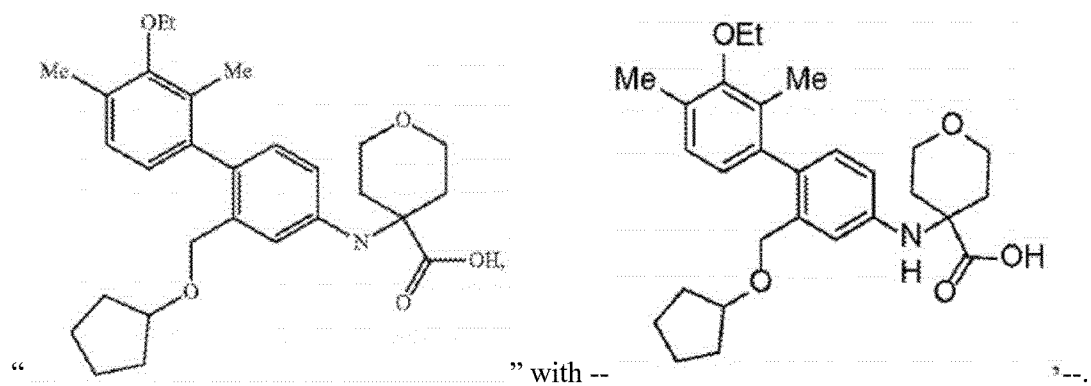

" with --             --.

In Claim 1, Column 483, Lines 15-26, please replace

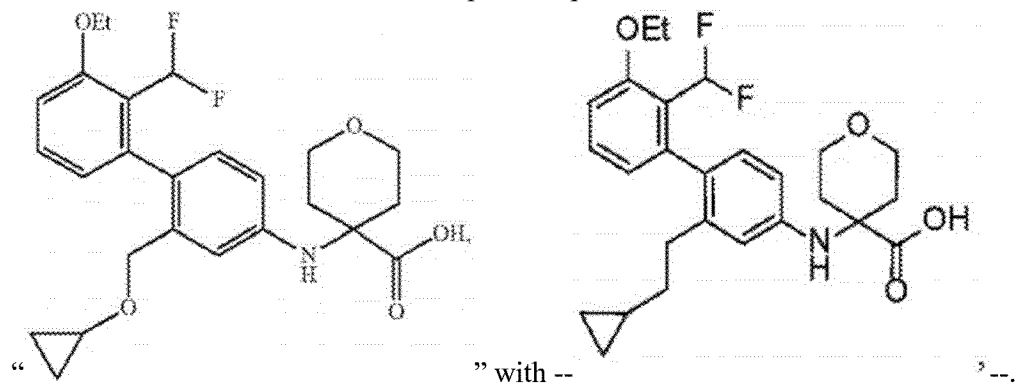

" with --             --.

CERTIFICATE OF CORRECTION (continued)
U.S. Pat. No. 12,428,375 B2

In Claim 1, Column 484, Lines 15-24, please replace

" 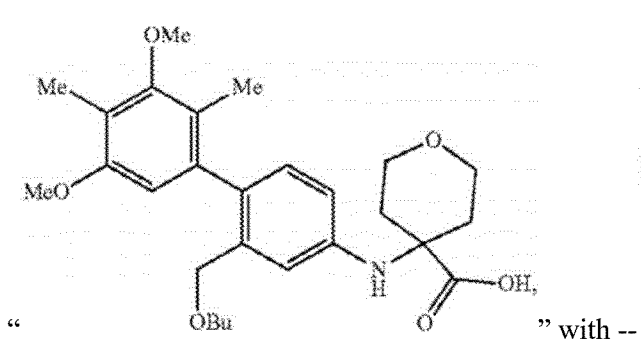 " with -- 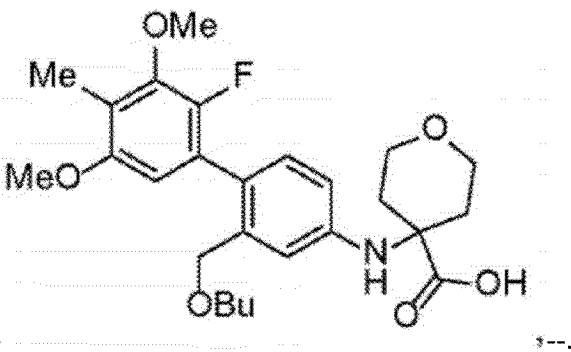 --.